United States Patent
Ahmed et al.

(10) Patent No.: US 7,465,726 B2
(45) Date of Patent: Dec. 16, 2008

(54) SUBSTITUTED PYRROLO[2.3-B]PYRIDINES

(75) Inventors: Saleh Ahmed, Oxford (GB); Oscar Barba, Oxford (GB); Jason Bloxham, Oxford (GB); Graham Dawson, Oxford (GB); William Gattrell, Oxford (GB); John Kitchin, Oxford (GB); Neil Anthony Pegg, Oxford (GB); Imaad Saba, Oxford (GB); Shazia Sadiq, Oxford (GB); Colin Peter Sambrook Smith, Oxford (GB); Don Smyth, Oxford (GB); Arno G. Steinig, Farmingdale, NY (US); Robin Wilkes, Oxford (GB); Bijoy Panicker, Farmingdale, NY (US); Paula Tavares, Farmingdale, NY (US); Matthew Cox, Farmingdale, NY (US); An-Hu Li, Farmingdale, NY (US); Hanqing Dong, Farmingdale, NY (US); Lifu Ma, Farmingdale, NY (US); Kenneth ('Ken') Foreman, Farmingdale, NY (US); Qinghua ('Felix') Weng, Farmingdale, NY (US); Kathryn Stolz, Farmingdale, NY (US)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

(21) Appl. No.: 11/194,158

(22) Filed: Aug. 1, 2005

(65) Prior Publication Data

US 2006/0211678 A1    Sep. 21, 2006

Related U.S. Application Data

(60) Provisional application No. 60/598,173, filed on Aug. 2, 2004, provisional application No. 60/698,516, filed on Jul. 12, 2005.

(51) Int. Cl.

| | |
|---|---|
| *A61K 31/437* | (2006.01) |
| *A61K 31/496* | (2006.01) |
| *A61K 31/5355* | (2006.01) |
| *A61K 31/541* | (2006.01) |
| *A61K 31/5513* | (2006.01) |
| *A61K 31/551* | (2006.01) |
| *C07D 471/04* | (2006.01) |
| *C07D 223/04* | (2006.01) |
| *C07D 243/08* | (2006.01) |
| *C07D 241/04* | (2006.01) |
| *C07D 413/10* | (2006.01) |
| *C07D 413/06* | (2006.01) |
| *C07D 413/08* | (2006.01) |
| *C07D 413/12* | (2006.01) |
| *C07D 413/14* | (2006.01) |
| *C07D 417/06* | (2006.01) |
| *C07D 417/14* | (2006.01) |
| *A61K 31/04* | (2006.01) |
| *A61K 31/519* | (2006.01) |
| *C07D 487/04* | (2006.01) |

(52) U.S. Cl. ............................ 514/228.2; 514/253.04; 514/235.5; 514/218; 514/217.04; 514/278; 514/300; 514/265.1; 546/113; 546/15; 546/117; 540/597; 540/575; 544/127; 544/61; 544/280

(58) Field of Classification Search ............... 546/113, 546/15, 117; 514/300, 278, 217.04, 218, 514/235.5, 253.04, 228.2; 544/127, 61; 540/575, 540/597

See application file for complete search history.

(56) References Cited

U.S. PATENT DOCUMENTS

| | | |
|---|---|---|
| 5,877,178 A | 3/1999 | Gangjee |
| 5,958,930 A | 9/1999 | Gangjee |
| 6,140,317 A | 10/2000 | Traxler |
| 6,140,332 A | 10/2000 | Traxler |
| 6,180,636 B1 | 1/2001 | Traxler |
| 6,180,643 B1 | 1/2001 | Zablocki |
| 6,187,778 B1 | 2/2001 | Dow |
| 6,232,320 B1 | 5/2001 | Stewart |
| 6,479,507 B2 | 11/2002 | Cheng |
| 6,537,999 B2 | 3/2003 | Gangjee |
| 6,541,481 B2 | 4/2003 | Kath |
| 6,579,882 B2 | 6/2003 | Stewart |
| 6,610,847 B2 | 8/2003 | Blumenkopf |
| 6,635,762 B1 | 10/2003 | Blumenkopf |
| 6,673,802 B2 | 1/2004 | Castelhano |

(Continued)

FOREIGN PATENT DOCUMENTS

WO    WO 97/28161    8/1997

(Continued)

OTHER PUBLICATIONS

Peng, T. et al (2003) J. Chem.Inf.Comput.Sci.:43:298-303.

(Continued)

*Primary Examiner*—Brenda L. Coleman
*Assistant Examiner*—Susanna Moore

(57) ABSTRACT

Compounds represented by Formula (I):

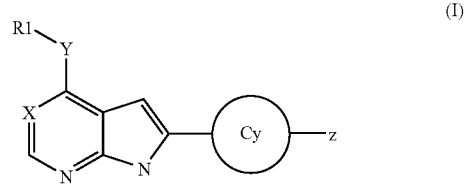

or stereoisomers or pharmaceutically acceptable salts thereof, are inhibitors of least two of the Abl, Aurora-A, Blk, c-Raf, cSRC, Src, PRK2, FGFR3, Flt3, Lck, Mek1, PDK-1, GSK3β, EGFR, p70S6K, BMX, SGK, CaMKII, Tie-2, IGF-1R, Ron, Ret, and KDR kinases in animals, including humans, for the treatment and/or prevention of various diseases and conditions such as cancer.

14 Claims, No Drawings

U.S. PATENT DOCUMENTS

| | | | |
|---|---|---|---|
| 6,680,324 B2 | 1/2004 | Castelhano |
| 6,696,455 B1 | 2/2004 | Gangjee |
| 6,686,366 B1 | 3/2004 | Castelhano |
| 6,713,474 B2 | 3/2004 | Hirst |
| 6,939,874 B2 | 9/2005 | Harmange |
| 7,115,617 B2 | 10/2006 | Buchanan |
| 7,244,733 B2 | 7/2007 | Hunt |
| 7,259,154 B2 | 8/2007 | Cox |
| 7,301,023 B2 | 11/2007 | Flanagan |
| 7,326,699 B2 | 2/2008 | Capraro |
| 7,335,667 B2 | 2/2008 | Rodgers |
| 2003/0036545 A1 | 2/2003 | Castelhano |
| 2003/0125343 A1 | 7/2003 | Gambacorti-Passerini |
| 2003/0199525 A1 | 10/2003 | Hirst |
| 2004/0138238 A1 | 7/2004 | Dhanoa |
| 2004/0214820 A1 | 10/2004 | Kleeman |
| 2005/0171128 A1 | 8/2005 | Blumenkopf |
| 2005/0250119 A1 | 11/2005 | Taing |
| 2005/0256140 A1 | 11/2005 | Luke |
| 2005/0267304 A1 | 12/2005 | Cox |
| 2006/0142330 A1 | 6/2006 | Bernotas |
| 2006/0148831 A1 | 7/2006 | Bernotas |
| 2006/0270665 A1 | 11/2006 | Wood |

FOREIGN PATENT DOCUMENTS

| | | |
|---|---|---|
| WO | WO 98/43973 | 10/1998 |
| WO | WO 99/62908 | 12/1999 |
| WO | WO 01/72751 | 10/2001 |

OTHER PUBLICATIONS

International Preliminary, date of issue, Feb. 6, 2007, Report I on Patentability in PCT/US2005/27274.
International Preliminary, date of issue, Mar. 1, 2006, Report II on Patentability in PCT/US2005/27274.
Written Opinion of the International Search Authority in PCT/US2005/27274.
International Search Report in PCT/US2005/27274, date of mailing, Oct. 20, 2006.

SUBSTITUTED PYRROLO[2,3-B]PYRIDINES

This claims the benefit of U.S. Ser. No. 60/598,173 filed Aug. 2, 2004 and U.S. Ser. No. 60/698,516 filed Jul. 12, 2005.

BACKGROUND OF THE INVENTION

The present invention is directed to novel pyrrolopyrimidine compounds, their salts, and compositions comprising them. In particular, the present invention is directed to novel aryl-amino substituted pyrrolopyrimidine compounds that inhibit the activity of at least two of the Abl, Aurora-A, Blk, c-Raf, cSRC, Src, PRK2, FGFR3, Flt3, Lck, Mek1, PDK-1, GSK3β, EGFR, p70S6K, BMX, SGK, CaMKII, Tie-2, Ret, IGF-1R, Ron, and KDR kinases in animals, including humans, for the treatment and/or prevention of various diseases and conditions such as cancer.

Cells may migrate and divide inappropriately if the signals for division or motility cannot be stopped. This might occur if the complex system of control proteins and messengers, which signal changes in the actin system, goes awry. One such control factor is the proto-oncogene protein Ab1, a tyrosine kinase. It is implicated in cancer, including leukemia. Accordingly, it is desirable to identify inhibitors of Ab1.

The Aurora kinase family is one regulator of chromosome segregation—regulating the structure and function of centrosomes and mitotic spindle. One member, the Aurora-A kinase, has been shown to play a role in tumorigenesis—being located at a chromosomal hot-spot, 20q13, frequently amplified in a variety of human cancers such as those of colon, ovary, breast and pancreas. It appears that overexpression of Aurora-A kinase alone is sufficient to cause aneupoidy in normal diploid epithelial cells. Over-expression of Aurora-A kinase in NIH3T3 cells results in centrosome aneupoidy. Thus, it is desirable to identify inhibitors of Aurora-A.

Shortly after birth, mice expressing an activated, mutant form of Blk form massive, monoclonal lymphomas and die. (S. V. Desiderio ath. Hughs Medical Institute). Thus, it is likely that Blk regulates cell proliferation. Further, experiments with Blk antisense appear to implicate Blk kinase with growth inhibition and apoptosis. (X. Yao and D. W. Scott, Proc. Nat. Acad. Sci., 90:7946-7950 (1993)). Thus, it is desirable to identify inhibitors of Blk.

C-Raf is an extracellular signal-regulated kinase and a downstream effector of Ras. It functions to suppress apoptosis and regulates cell differentiation. Thus, over-expression can lead to unwarranted suppression of apoptosis and unchecked cell differentiation. Thus, it is desirable to identify inhibitors of c-Raf.

The cytoplasmic tyrosine kinase cSRC, or c-Src, is involved in the signal transduction pathway and is elevated in breast cancer cell lines. Similarly, Src is involved in the regulation of cell growth and transformation. Thus over-expression of Src or cSRC can lead to excess proliferation. Thus, it is desirable to identify inhibitors of Src or c-SRC.

The Protein Kinase c-Related Kinase 2, or PRK2, mediates cytoskeletal organization. It has been implicated in promoting the PDK1-dependent activation of Akt, thereby regulating cell-cycle progression, cell growth, cell survival, cell motility and adhesion, translation of mRNA into protein, and angiogenesis. Thus, it is desirable to identify inhibitors of PRK2.

FGFR3 and Tie-2 are receptor tyrosine kinases that are believed to be important mediators of tumor angiogenesis. For example, FGFR3 mutations are often seen in bladder cancer cells. Tie-2 is a protein receptor found on cells lining blood vessels. When activated by growth factors secreted by tumor cells, Tie2 triggers vessel cell walls to part and grow new capillaries. Thus, it is desirable to identify inhibitors of FGFR3 or Tie-2. Flt3, also known as "vascular endothelial cell growth factor receptor 3" or VEGFR-3, is believed to assist in vascular development important to angiogenesis. Thus, it is desirable to identify inhibitors of Flt3.

Lck, along with fyn, is an Src kinase implicated in cancer, including breast and colon cancer. Accordingly, it is desirable to identify inhibitors of Lck.

Mek1 is a kinase in the Ras pathway strongly implicated in many cancers, including breast, colon, and ovarian cancer. Thus, it is desirable to identify inhibitors of Mek1.

PDK-1 is a kinase that activates the PI3K/PKB signalling pathway, which is often uncoupled and separate from the EGFR pathway. In particular, a PDK-1 phosphorylating step is essential to activation of PKB (D. R. Alessi et al., Curr. Biol., 7:261-269 (1997)). Additionally, PDK-1 activates other oncogene kinases such as PKA, ribosomal p90 S6 kinase (RSK), p70 S6 kinase (S6K), serum and glucocorticoid activated kinase (SGK), PKC-related kinase-2 (PRK-2) and MSK-1 (R. M. Biondi et al., Biochem. J., 372:1-13 (2003)). Thus, inhibition of PDK-1 can be multiply effective in treatment of cancer and tumors, including glioblastoma, melanoma, prostate, endometrial carcinoma, breast, ovarian, and non-small cell lung cancer (NSCLC), because PDK-1 regulates several oncogenic pathways. Accordingly, it is desirable to identify compounds that inhibit PDK-1.

GSK3β kinase is believed to play a strong part in cancers such as breast, ovarian, pancreatic, and prostate cancer. Thus, it is desirable to identify compounds that inhibit GSK3β.

Cell division involves signalling pathways from the cell exterior and interior. Signals travel the pathways and regulate the various activities of cell cycle control genes. Cancer cells have mis-regulation of such signal pathways and control genes—thereby leading to inappropriate or uncontrolled cell division. Over-expression of oncogenes (proteins that signal cells to proliferate) is one such mis-regulation. The Epidermal Growth Factor Receptor (EGFR) is one such oncogene, which is over-expressed in cancers such as brain, breast, gastrointestinal, lung, ovary and prostate cancers. There are selective EGFR inhibitors being investigated for use against cancer. For example, the 4-anilinoquinazoline compound Tarceva® inhibits only EGFR kinase with high potency, although it can inhibit the signal transduction of other receptor kinases that probably heterodimerize with the EGFR. Nevertheless, other compounds that inhibit EGFR remain needed.

The serine-threonine kinase p70S6K is at the end of one pathway that controls cell growth and is frequently activated in many tumors, including uterine, adenocarcinoma, myeloma, and prostate cancers. Thus, it is desirable to identify compounds that inhibit p70S6K.

BMX is a tyrosine kinase involved in interleukin-6 induced differentiation of prostate cancer cells. It plays a role in EGF-induced apoptosis of breast cancer cells, and is expressed in granocytes and myeloid leukemias, as well as other cancers. Thus, it is desirable to identify compounds that inhibit BMX.

The serum and glucocorticoid-induced protein kinase ("SGK") is a downstream target in the PI3K/Akt pathway, believed to play a part in cancers such as breast and prostate cancer. Thus, it is desirable to identify compounds that inhibit SGK.

Ca2+/calmodulin-dependent protein kinase II ("CaMKII") indirectly modulates Fas-mediated signalling in glioma. Therefore inhibition of CaMK II may be effective in the treatment of glioma. See, Bao Feng Yang et al., J. Biological Chemistry, 278:7043-7050 (2003). Thus, it is desirable to identify compounds that inhibit CaMKII.

Ret is a proto-oncogene implicated in many cancers such as thyroid cancer. Thus, it is desirable to identify compounds that inhibit Ret.

Endothelial-cell specific receptor protein tyrosine kinases such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas). Thus, it is desirable to identify compounds that inhibit KDR.

Ron (recepteur d'origine natais) is a receptor tyrosine kinase that is part of the MET proto-oncogene family. Inhibition of Ron has been shown to lead to a decrease in proliferation and induction of apoptosis. Thus, it is desirable to identify inhibitors of Ron.

IGF-1R (type 1 insulin-like growth factor receptor) performs important roles in cell division, development, and metabolism, and in its activated state, plays a role in oncogenesis and suppression of apoptosis. IGF-1R is known to be overexpressed in a number of cancer cell lines (IGF-1R overexpression is linked to acromegaly and to cancer of the prostate). By contrast, down-regulation of IGF-1R expression has been shown to result in the inhibition of tumorigenesis and an increased apoptosis of tumor cells. Thus, it is desirable to identify compounds that inhibit IGF-1R.

Some cancers develop resistance to certain kinase inhibitors over time and treatment. Resistance to a particular kinase inhibitor can be mediated by a loss of suppression of an enzyme at a branchpoint in the kinase pathway. The loss of suppression may lead to inappropriate activation of a parallel pathway from the original pathway. Thus, it is desirable to identify compounds that inhibit at least two kinases in order to provide compounds that are more efficacious than a very specific narrowly targeted compound that inhibits only one kinase. In particular, it is desirable to identify compounds that inhibit at least two of the Abl, Aurora-A, Blk, c-Raf, cSRC, Src, PRK2, FGFR3, Flt3, Lck, Mek1, PDK-1, GSK3β, EGFR, p70S6K, BMX, SGK, CaMKII, Tie-2, Ret, IGF-1R, Ron, and KDR kinases in animals, including humans, for the treatment and/or prevention of various diseases and conditions such as cancer.

U.S. Pat. No. 6,232,320, International Patent Publication Nos. WO 00/75145 and 99/62908 describes cell adhesion inhibiting antiinfammatory compounds. International Patent Publication No. 03/080064 describes kinase inhibitors. U.S. Pat. No. 6,713,474 describes pyrrolopyrimidines as therapeutic agents.

U.S. Pat. No. 6,541,481 describes substituted bicyclic derivatives useful as anticancer agents.

T. Peng et al., J. Chem. Inf. Comput. Sci.:43:298-303 (2003) describes 3D-QSAR and receptor modeling of tyrosine kinase inhyibitors with flexible atom receptor model (FLARM). International Patent Publication No. WO 98/43973 describes intermediate products and method for the production of pyrimidine derivatives. U.S. Pat. No. 6,610,847, International Patent Publication Nos. WO 99/65908 and WO 99/65909 describe pyrrolo[2,3-d]pyrimidine compounds. U.S. Pat. No. 6,635,762 describes monocyclic-7H-pyrrolo[2,3-d]pyrimidine compounds. International Patent Publication No. WO 02/30944 describes fluorescent nuceobase conjugates having anionic linkers. International Patent Publication No. WO 04/009600 describes 1-heterocycly-alkyl-3-sulfonylazaindole or azaindazole derivatives as 5-hydroxytryptamine-6 ligands. International Patent Publication No. WO04/007479 describes 3-guanidinocarbonyl-1-heteroaryl-indole derivatives. International Patent Publication No. WO 03/101990 describes 1-(aminoalkyl)-3-sulfonylazaindoles as 5-hydroxytryptamine-6 ligands.

International Patent Publication No. WO 02/096909 describes optical resolution of (1-benzyl-4-methylpiperidin-3-yl)-methylamine and the use thereof for the preparation of pyrrolo 2,3-pyrimidine derivatives as protein kinase inhibitors. International Patent Publication No. WO02/50306 describes processes for determining the biological activity of epidermal growth factor receptor tyrosine kinase inhibitors. International Patent Publication No. WO02/41882 describes combination comprising an agent decreasing VEGF activity and an agent decreasing EGF activity.

International Patent Publication No. WO 03/000187 describes novel pyrazolo- and pyrrolo-pyrimidines. International Patent Publication No. WO 02/057267, U.S. Pat. Nos. 6,686,366, 6,680,324, and 6,673,802 describe compounds specific to adenosine A1, A2A, and A3 receptors. International Patent Publication No. WO 01/47507 describes combinations of a receptor tyrosine kinase inhibitor with an organic compound capable of binding to α1-acidic glycoprotein. International Patent Publication No. WO 04/013141 describes condensed pyridines and pyrimidines with TIE2 (TEK) activity. International Patent Publication No. WO 04/014850 describes substituted aminopyrimidines as neurokinin antagonists.

International Patent Publication No. WO 03/000695 describes pyrrolopyrimidines as protein kinase inhibitors. U.S. Pat. No. 6,187,778 describes 4-aminopyrrole (3,4-d) pyrimidines as neuropeptide Y receptor antagonists. U.S. Pat. Nos. 6,140,317, 6,140,332, and 6,180,636 describe pyrrolopyrimidines. U.S. Pat. Nos. 6,696,455, 6,537,999 and 5,877,178 describe pyrimidine derivatives. U.S. Pat. No. 5,958,930 describes pyrrolo pyrimidine and furo pyrimidine derivatives.

International Patent Publication No. 03/000688 describes the preparation of azaindoles as protein kinase inhibitors. International Patent Publication Nos. WO 03/018021 and WO 03/018022 describe pyrimidines for treating IGF-1R related disorders, International Patent Publication No. WO 02/092599 describes pyrrolopyrimidines for the treatment of a disease that responds to an inhibition of the IGF-1R tyrosine kinase, International Patent Publication No. WO 01/72751 describes pyrrolopyrimidines as tyrosine kinase inhibitors. International Patent Publication No. WO 00/71129 describes pyrrolotriazine inhibitors of kinases. International Patent Publication No. WO 97/28161 describes pyrrolo[2,3-d]pyrimidines and their use as tyrosine kinase inhibitors.

Although the anticancer compounds described above have made a significant contribution to the art, there is a continuing need to improve anticancer pharmaceuticals with better selectivity or potency, reduced toxicity, or fewer side effects.

SUMMARY OF THE INVENTION

Compounds represented by Formula (I):

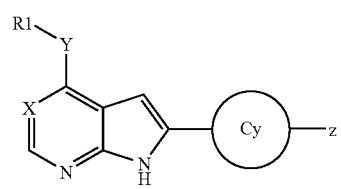

or stereoisomers or pharmaceutically acceptable salts thereof, are inhibitors of at least two of the Abl, Aurora-A, Blk, c-Raf, cSRC, Src, PRK2, FGFR3, Flt3, Lck, Mek1, PDK-1, GSK3β, EGFR, p70S6K, BMX, SGK, CaMKII, Tie-2, Ret, Ron, IGF-1R, and KDR kinases in animals, including humans, for the treatment and/or prevention of various diseases and conditions such as cancer

DETAILED DESCRIPTION OF THE INVENTION

The present invention relates to compounds of Formula I:

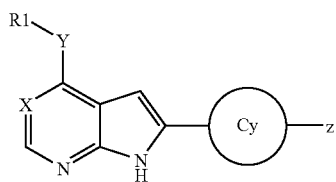
(I)

or a pharmaceutically acceptable salt thereof, wherein
X is N or C—CN;
Cy is

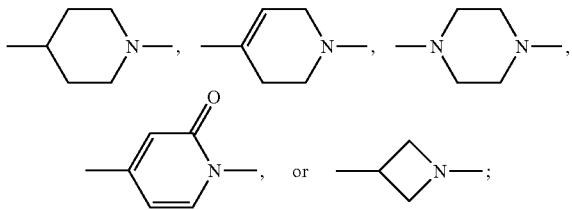

Z is hetaryl, —C$_{1-6}$alkyl-O—C$_{1-6}$alkyl-, —C$_{0-6}$alkyl-(heterocyclyl), —C$_{0-6}$alkyl-(hetaryl), —C(O)—C$_{0-6}$alkyl, —C(O)—C$_{0-6}$alkyl-O—C$_{0-6}$alkyl, —C(O)—C$_{0-6}$alkyl-O—C$_{1-6}$alkyl-O—C$_{0-6}$alkyl, —C(O)—C$_{0-6}$alkyl-N(C$_{0-6}$alkyl)(C$_{0-6}$alkyl), —C(O)—C$_{0-6}$alkyl-(heterocyclyl), —C(O)—C$_{0-6}$alkyl-(heterocyclyl)-C(O)—C$_{0-6}$alkyl, —C(O)—C$_{0-6}$alkyl-(hetaryl), —S(O)$_2$—C$_{0-6}$alkyl, —S(O)$_2$—N(C$_{0-6}$alkyl)(C$_{0-6}$alkyl), or —S(O)$_2$—(hetaryl), wherein any of the alkyl, heterocyclyl, or hetaryl optionally is substituted with 1-6 independent halo, OH, —C$_{0-6}$alkyl-O—C$_{0-6}$alkyl, —C$_{0-6}$alkyl-N(C$_{0-6}$alkyl)(C$_{0-6}$alkyl), —C(O)—C$_{0-6}$alkyl-N(C$_{0-6}$alkyl)(C$_{0-6}$alkyl), —C(O)—C$_{0-6}$alkyl-(heterocyclyl), or —C$_{0-6}$alkyl;
or Z is

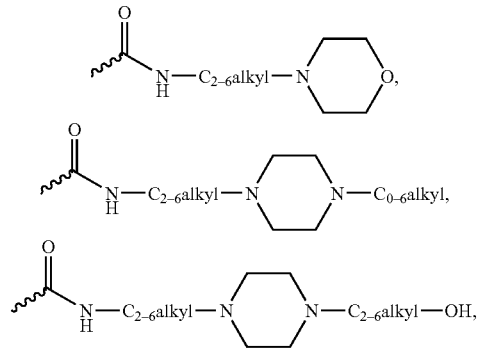

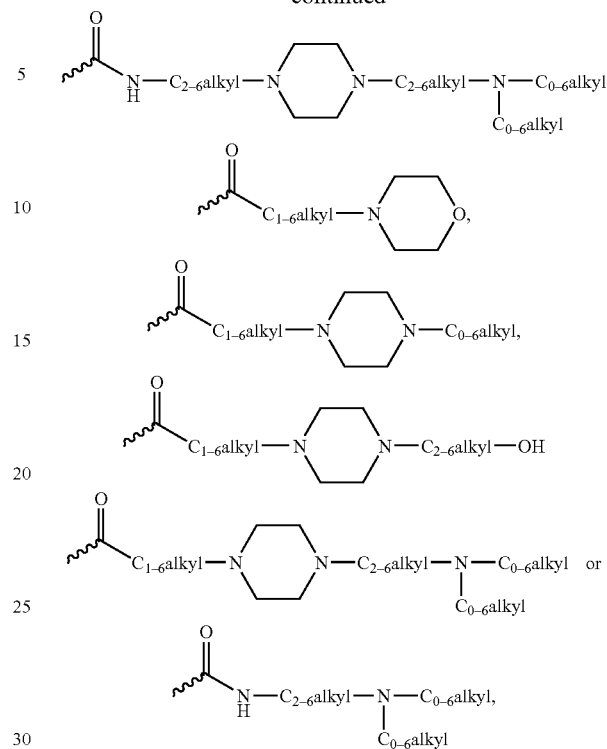

in which the wavy bond is the point of attachment, and wherein the piperazine or morpholine moieties are optionally substituted with 1-6 independent C$_{0-6}$alkyl groups;
Y is —(C$_{0-6}$alkyl)(C$_{0-6}$alkyl)-, —N(C$_{0-6}$alkyl)-, —N(C$_{0-6}$alkyl)-C$_{1-6}$alkyl-, O, S, >N—C$_{2-6}$alkyl-N—(C$_{0-6}$alkyl)(C$_{0-6}$alkyl), >N—C$_{2-6}$alkyl-O—C$_{0-6}$alkyl, >N—C$_{1-6}$alkyl-C(O)—NH—C$_{0-6}$alkyl, or >N—C$_{2-6}$alkyl-N—C(O)—C$_{1-6}$alkyl; and
R1 is aryl, hetaryl, or heterocyclyl, optionally substituted with 1-6 independent halo, —CN, —OH, —C$_{0-6}$alkyl, —C$_{3-10}$cycloalkyl, -haloC$_{1-6}$alkyl, —C$_{2-6}$alkynyl, —N(C$_{0-6}$alkyl)(C$_{0-6}$alkyl), —C(O)—C$_{0-6}$alkyl-N(C$_{0-6}$alkyl)(C$_{0-6}$alkyl), —C(O)—C$_{0-6}$alkyl-(heterocyclyl), —C$_{1-6}$alkyl-C(O)—C$_{0-6}$alkyl-N(C$_{0-6}$alkyl)(C$_{0-6}$alkyl), —O—C$_{0-6}$alkyl-(heterocyclyl), —C$_{0-6}$alkyl-O—C$_{0-6}$alkyl, —C$_{0-6}$alkyl-N(C$_{0-6}$alkyl)(C$_{0-6}$), —O—C$_{0-6}$alkyl-(hetaryl), —S(O)$_2$—N(C$_{0-6}$alkyl)(C$_{0-6}$alkyl), aryl, hetaryl, or heterocyclyl substituents, or substituted with an oxo (=O) using a bond from the aryl, hetaryl, or heterocyclyl ring, wherein any of the substituents optionally is substituted with 1-6 independent halo, CN, OH, —C$_{0-6}$alkyl-O—C$_{0-6}$alkyl, —C$_{0-6}$alkyl-N(C$_{0-6}$alkyl)(C$_{0-6}$alkyl), —C(O)—C$_{0-6}$alkyl-N(C$_{0-6}$alkyl)(C$_{0-6}$alkyl), —C(O)—C$_{0-6}$alkyl-(heterocyclyl), or C$_{0-6}$alkyl.
It is preferred that X is N.
It is preferred that Cy is

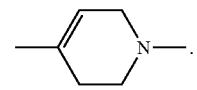

It is preferred that Y is —N(C$_{0-6}$alkyl)-.
Examples of R1 include, but are not limited to, the following groups, wherein the wavy bond is connected to Y:

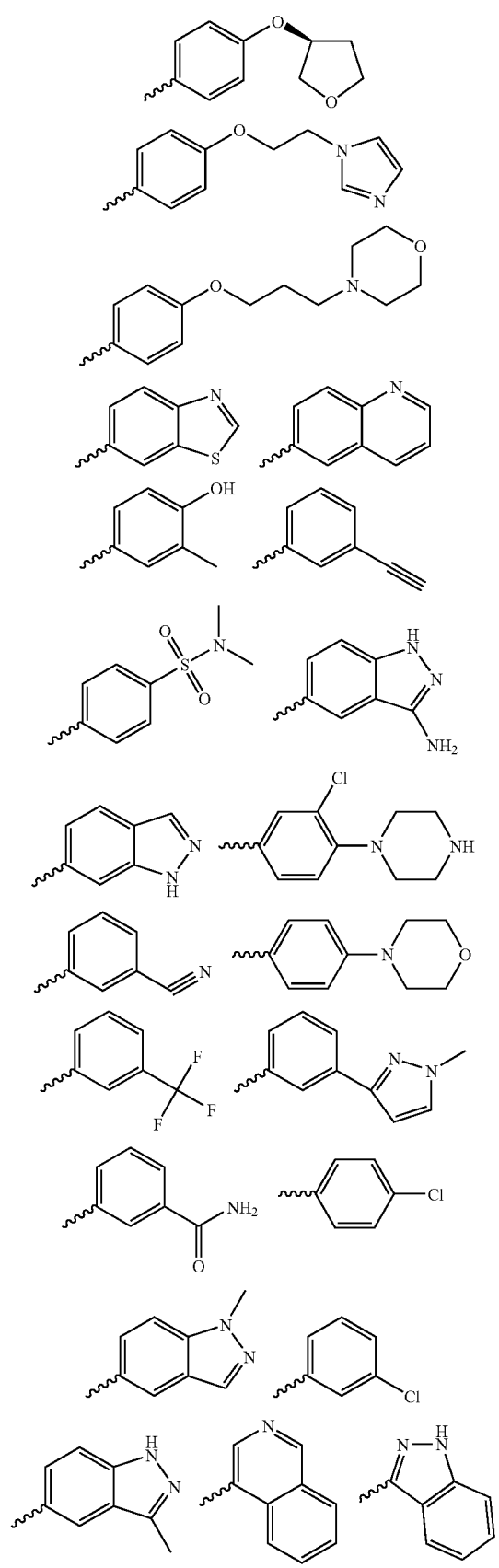
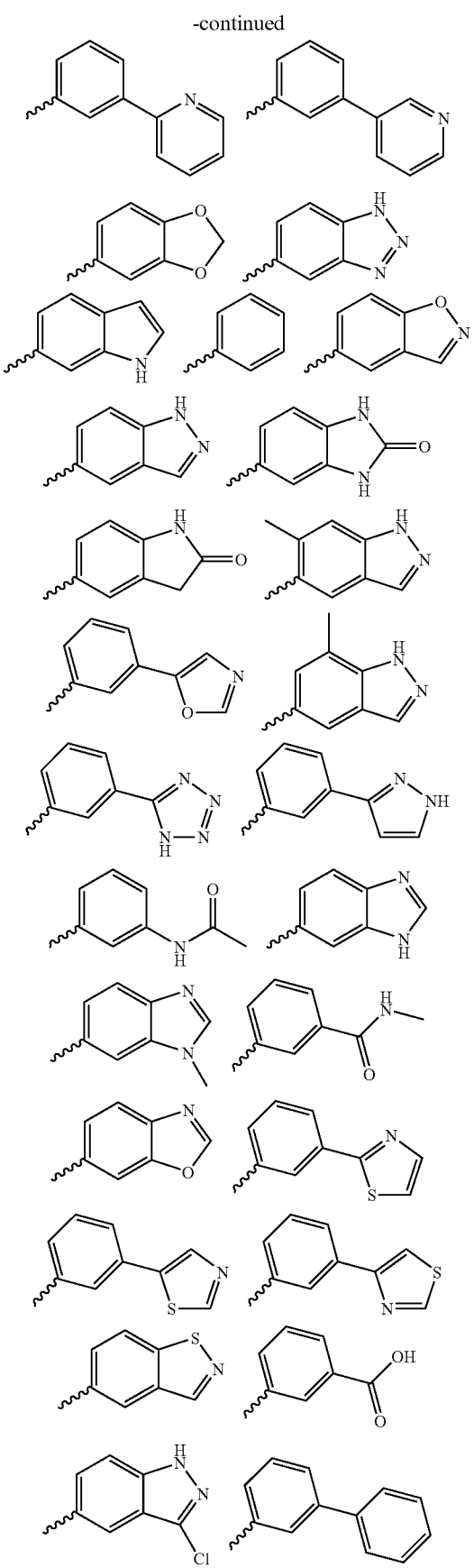
-continued

-continued
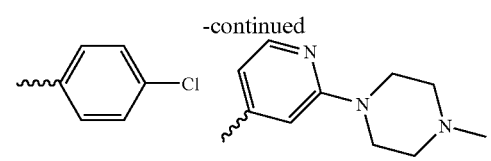
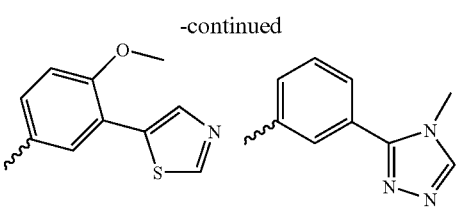
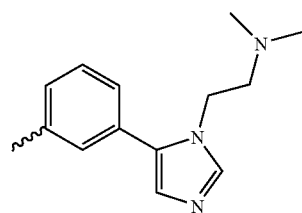
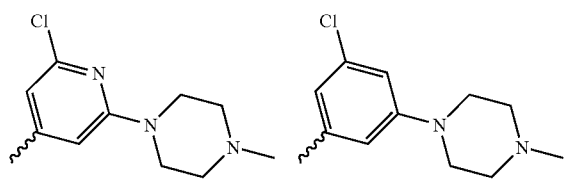
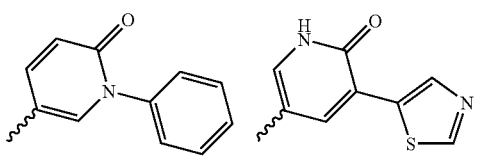
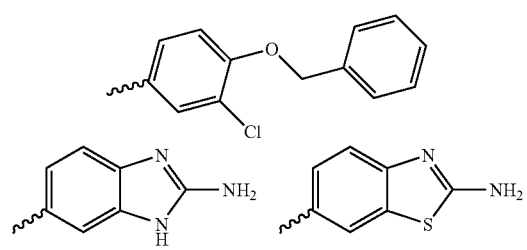
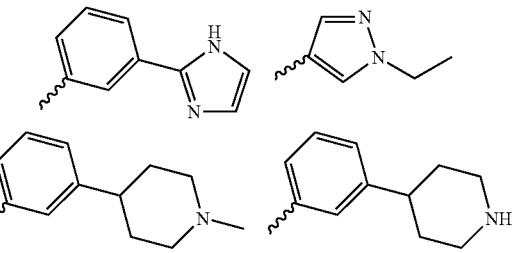
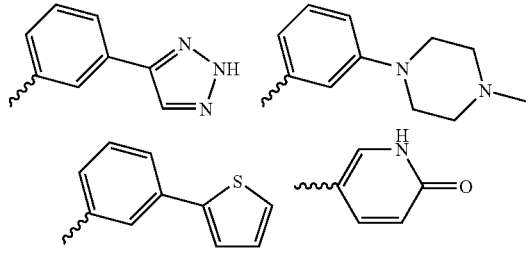
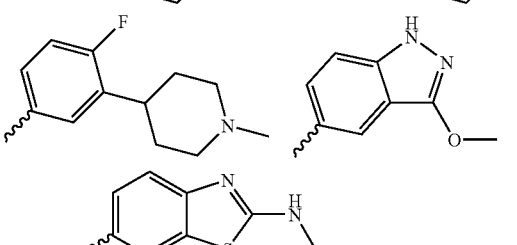
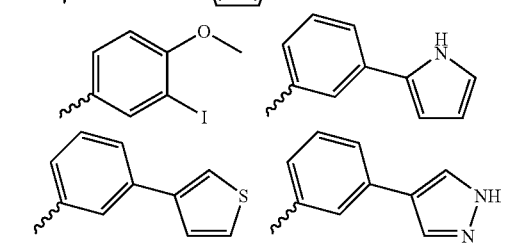
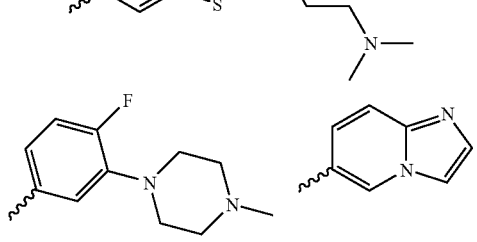
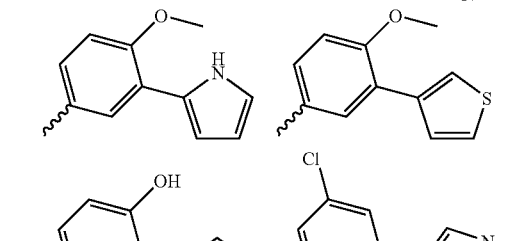
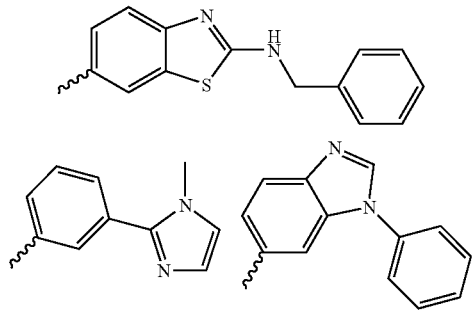
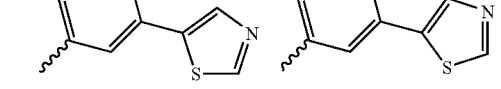

-continued
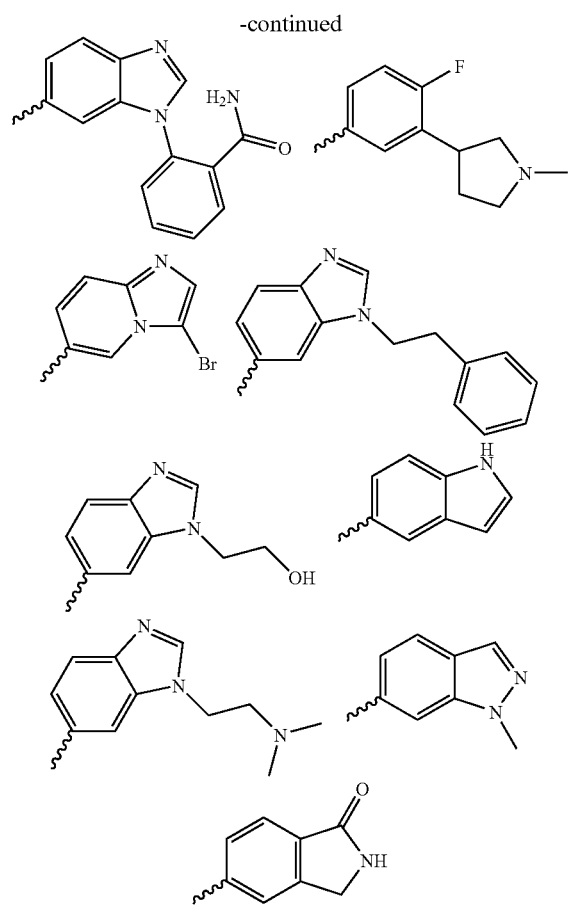
Examples of Z include, but are not limited to, the following groups, wherein the dotted line is connected to Cy:
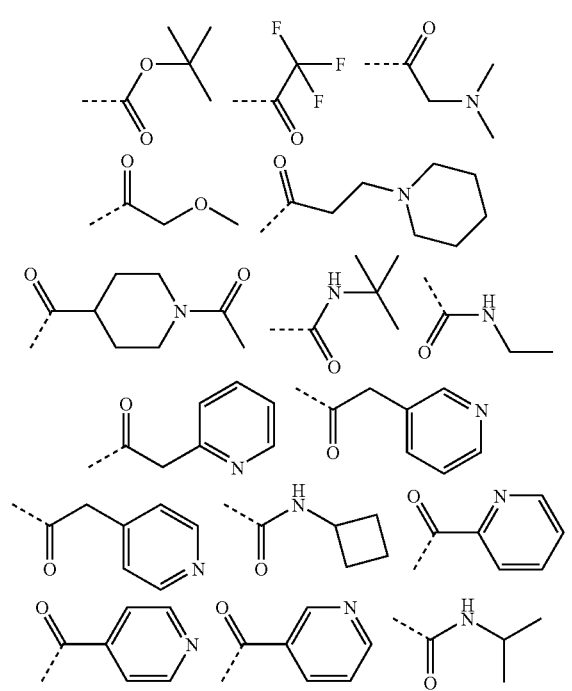
-continued
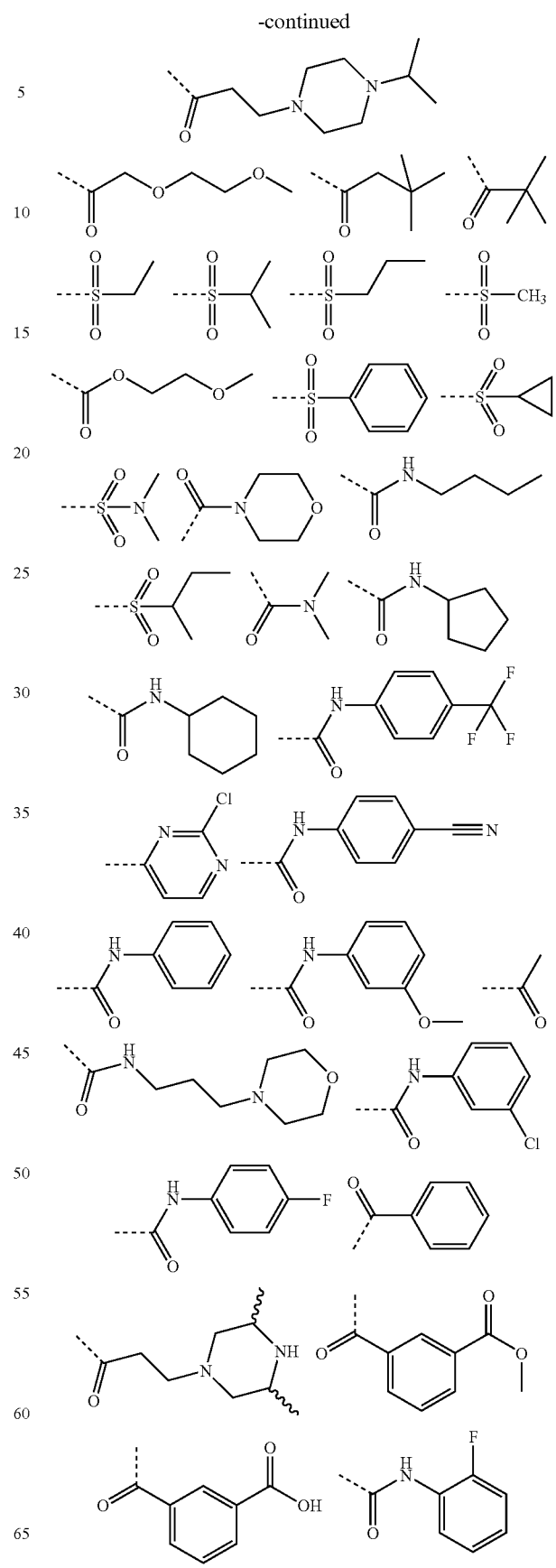

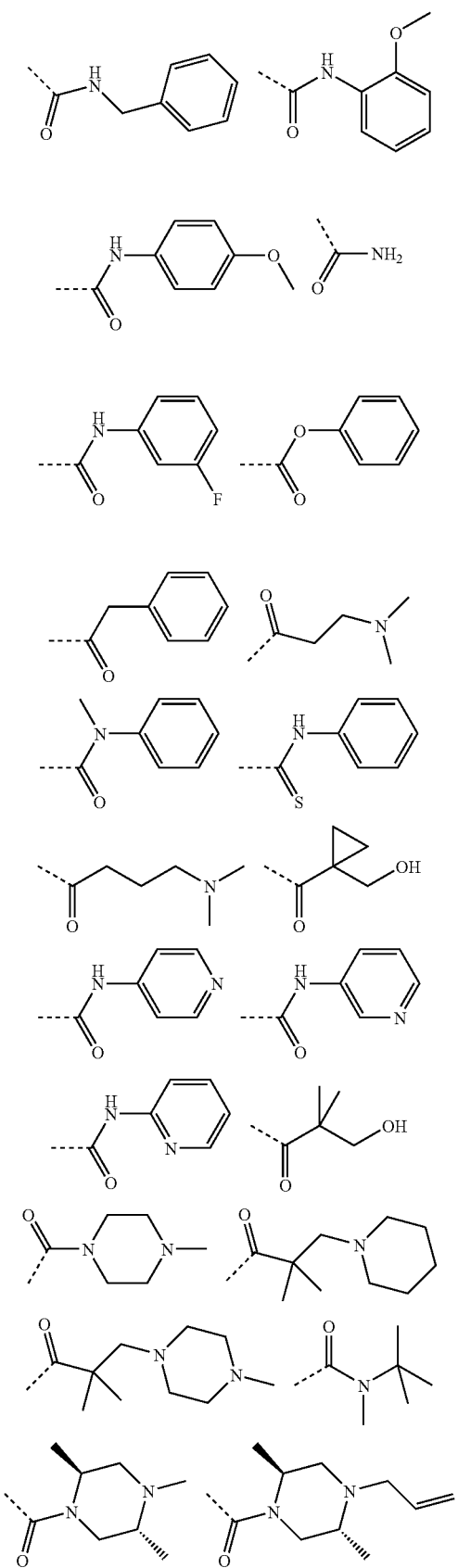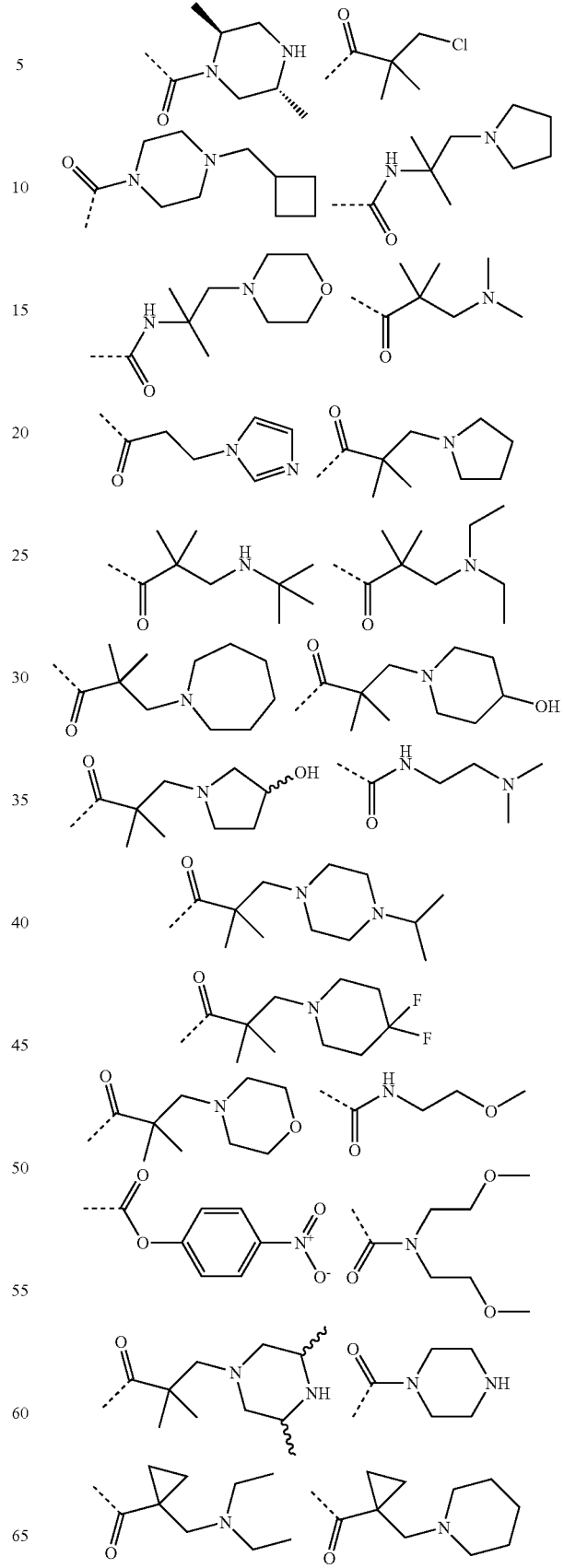

-continued
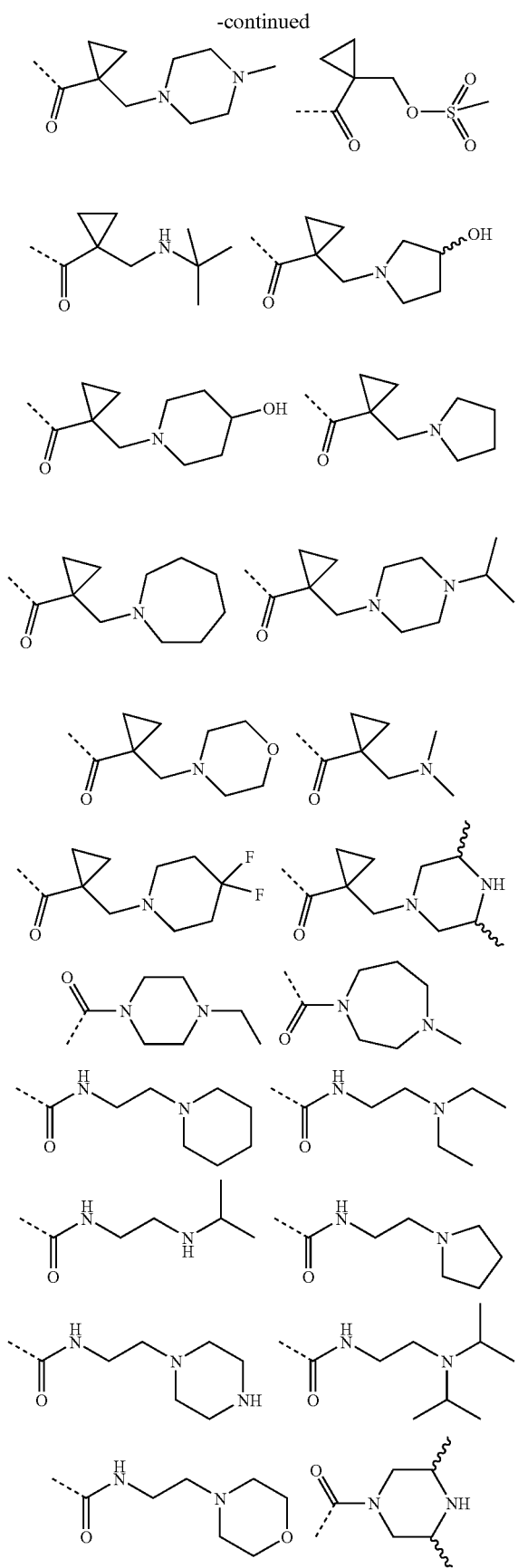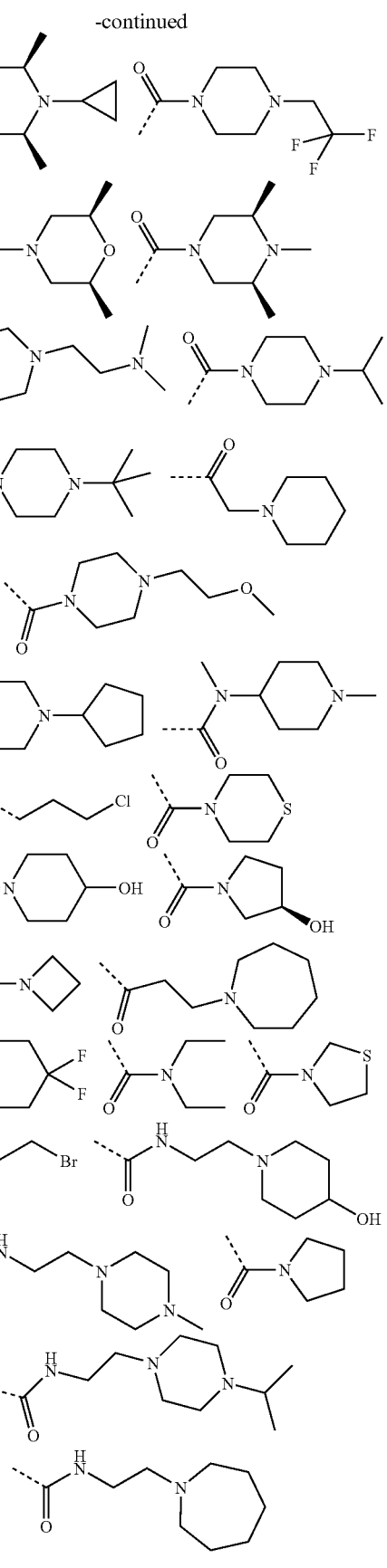

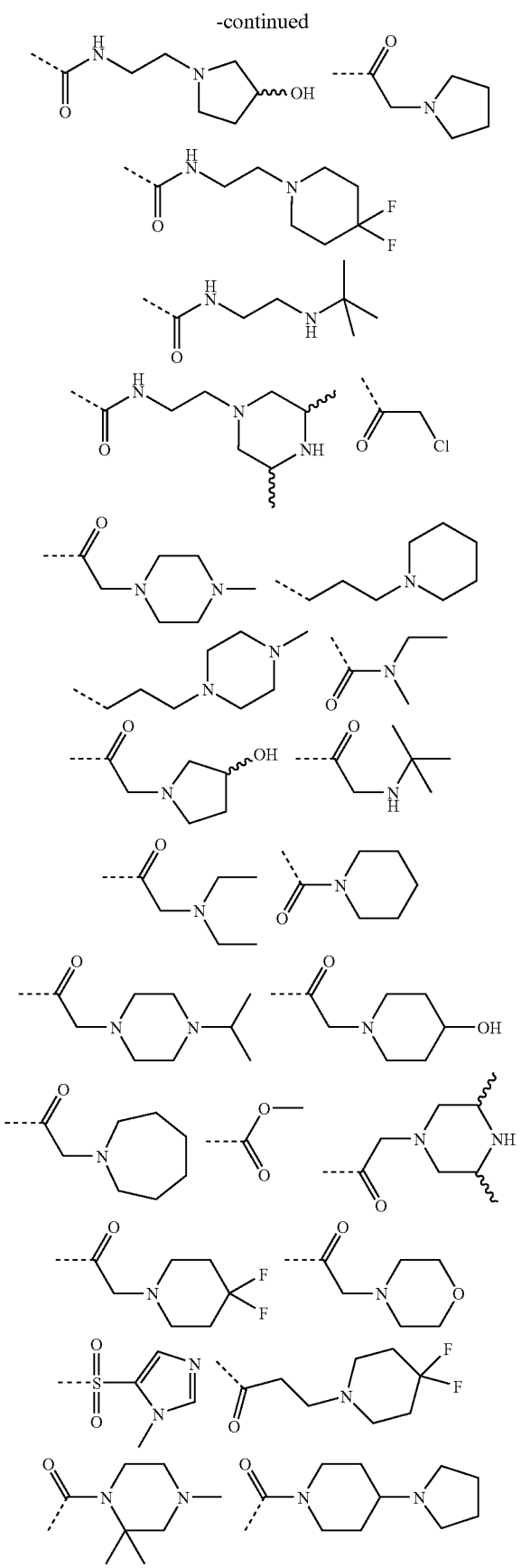
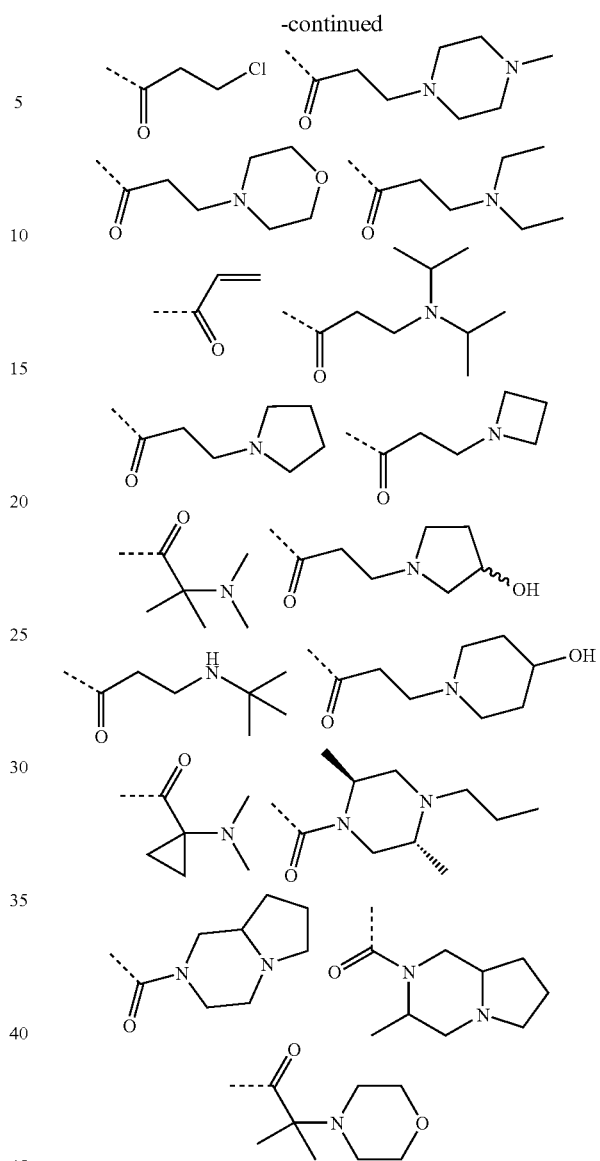

The molecular weight of the compound of Formula (I) is preferably less than 800, more preferably less than 600.

In the first aspect, the present invention is directed to a compound represented by Formula (I), or a stereoisomer, or a pharmaceutically acceptable salt thereof, wherein X is N and the other variables are as described above.

In an embodiment of the first aspect, the present invention is directed to a compound represented by Formula (I), or a stereoisomer, or a pharmaceutically acceptable salt thereof, wherein X is N, Cy is

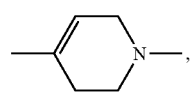

and the other variables are as described above.

In another embodiment of the first aspect, the present invention is directed to a compound represented by Formula (I), or a stereoisomer, or a pharmaceutically acceptable salt thereof, wherein X is N, Y is —N(C$_{0-6}$alkyl)-, and the other variables are as described above.

In a second aspect, the present invention is directed to a compound represented by:

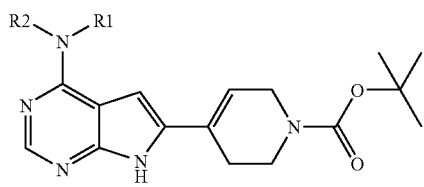

or a stereoisomer, or a pharmaceutically acceptable salt thereof, wherein R2 is —C$_{0-6}$alkyl, —C$_{2-6}$alkyl-N—(C$_{0-6}$alkyl)(C$_{0-6}$alkyl), —C$_{2-6}$alkyl-O—C$_{0-6}$alkyl, —C$_{1-6}$alkyl-C(O)—NH—C$_{0-6}$alkyl, or —C$_{2-6}$alkyl-N—C(O)—C$_{1-6}$alkyl; and the other variables are as described above for Formula (I).

In an embodiment of the second aspect, the present invention is directed to a compound represented by:


or a stereoisomer, or a pharmaceutically acceptable salt thereof wherein

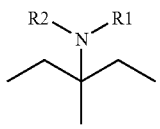

is selected from the following table:

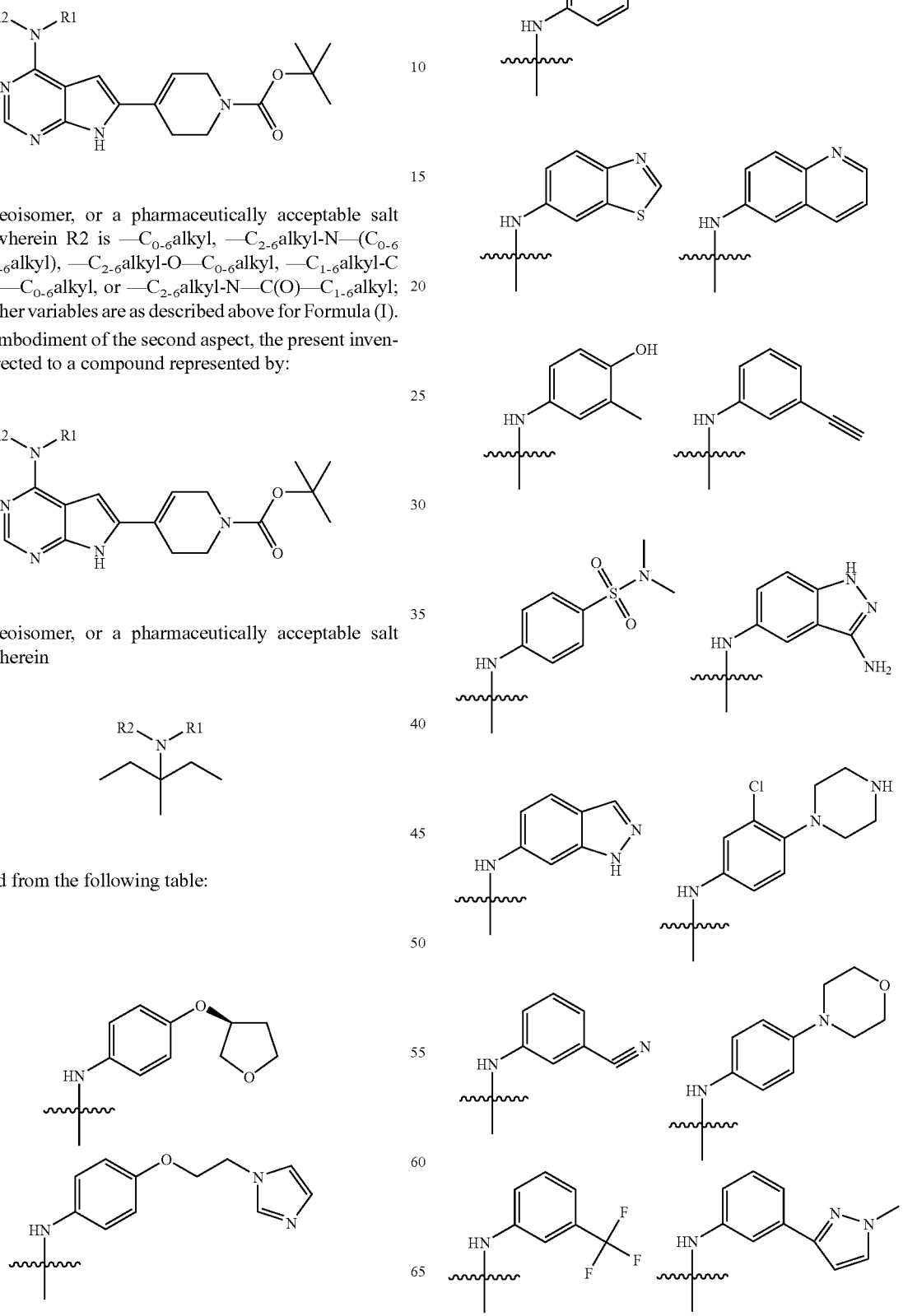

-continued
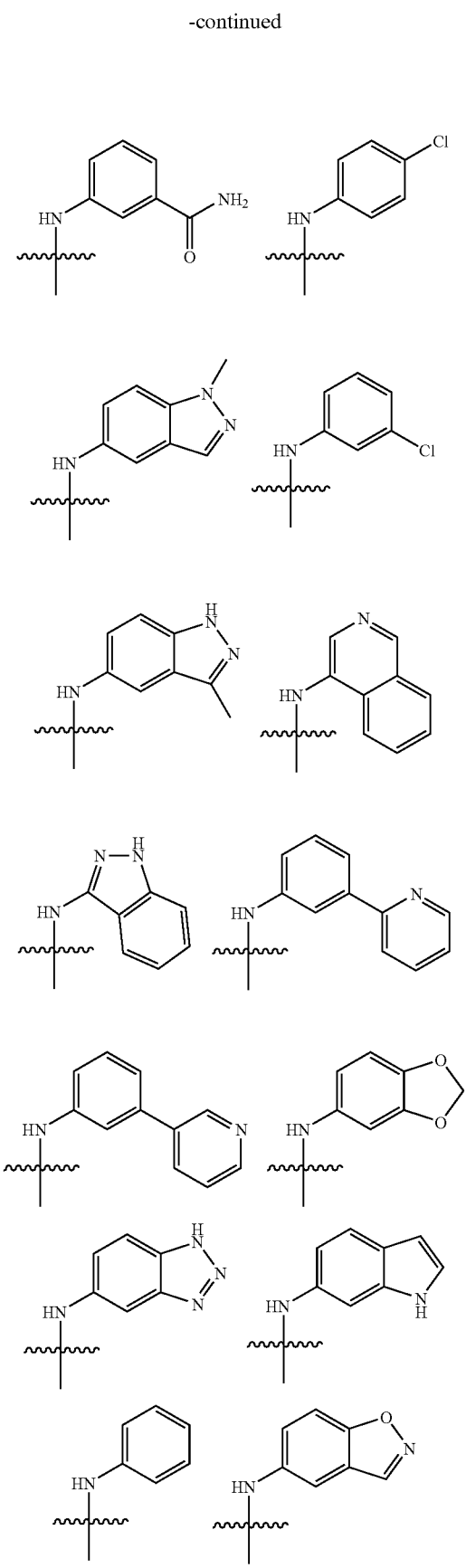
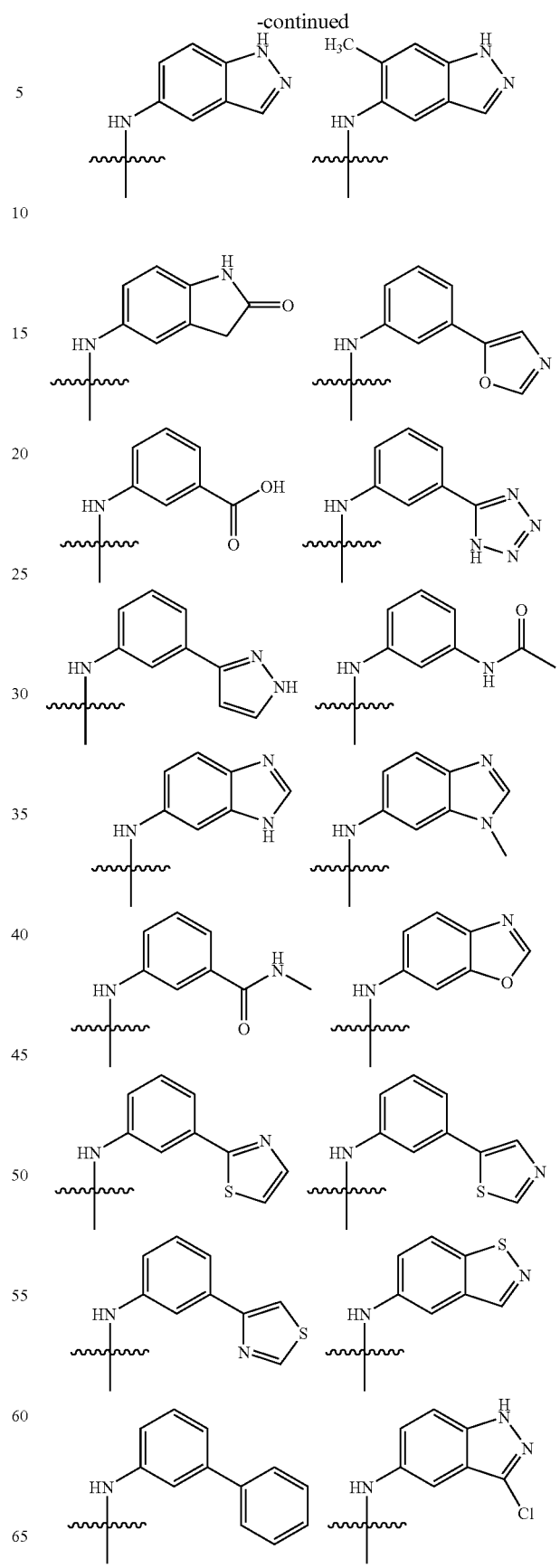

-continued
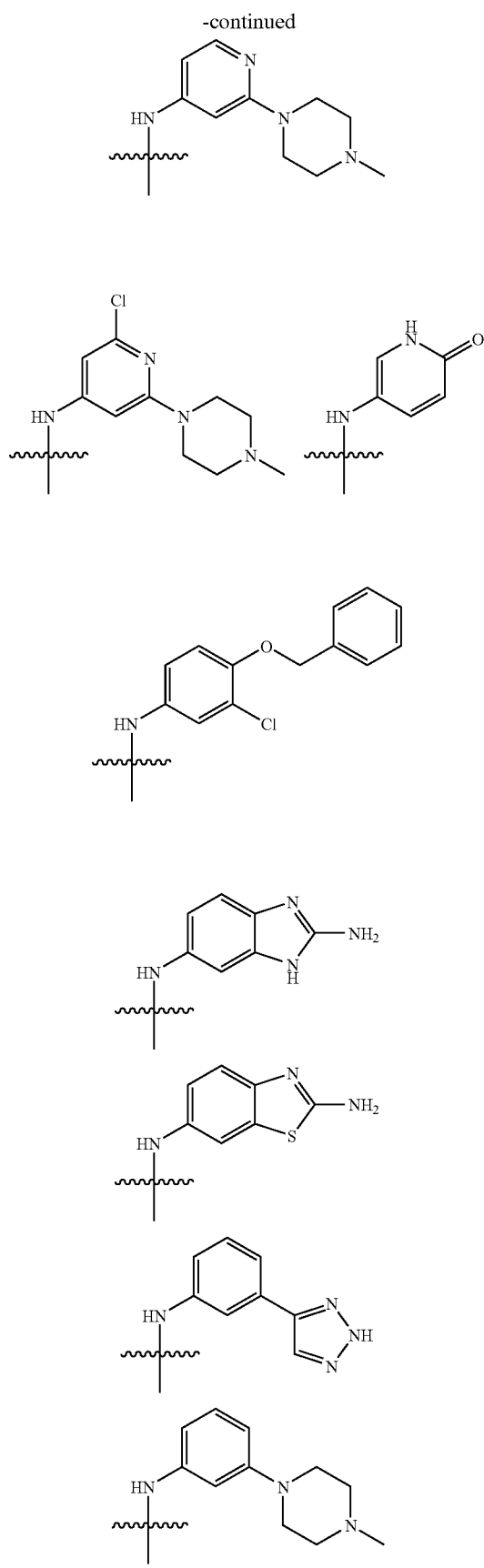
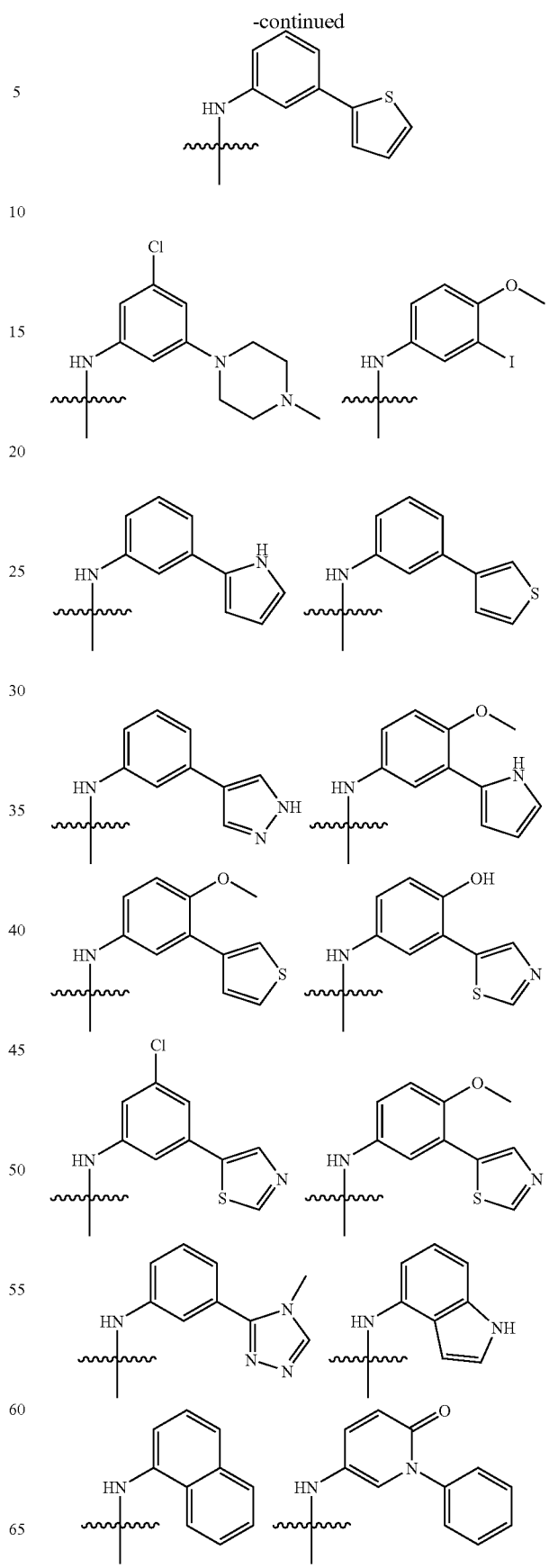

-continued
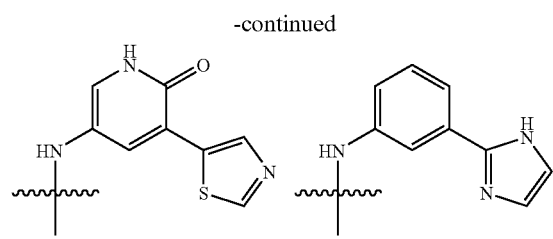
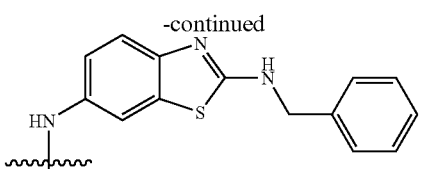
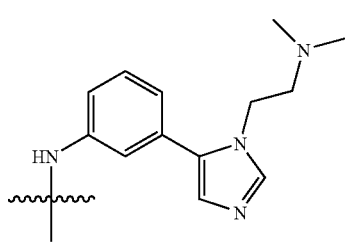
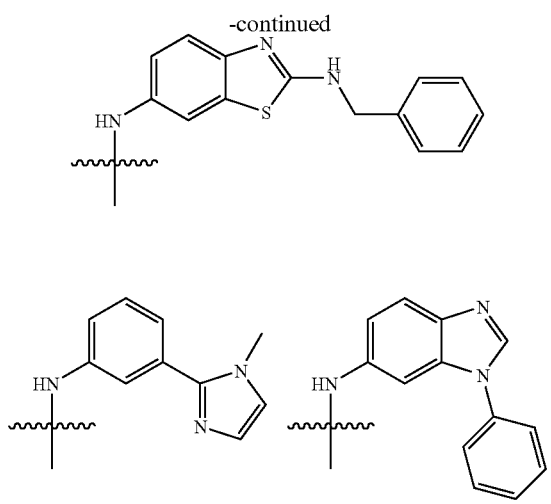
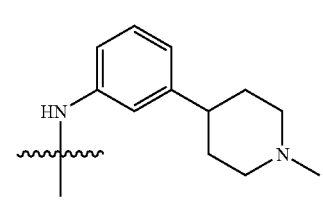
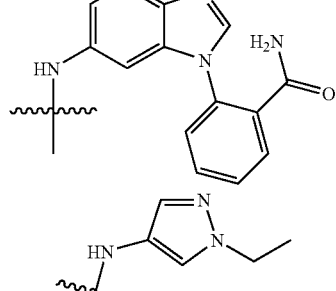
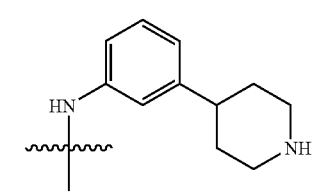
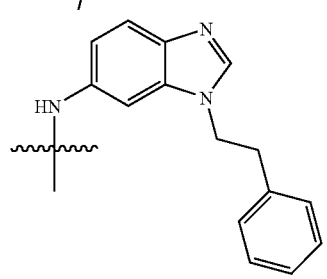
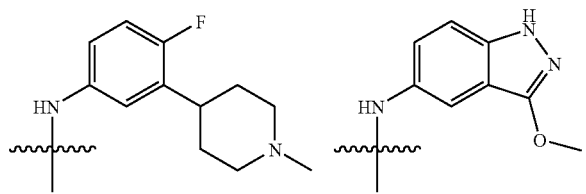
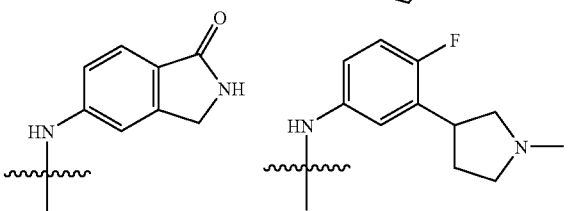
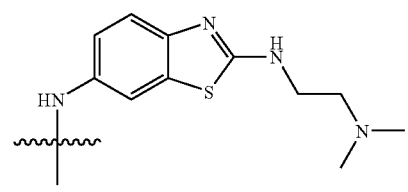
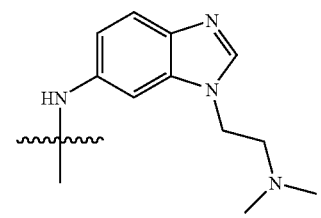
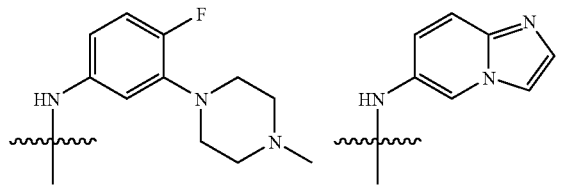
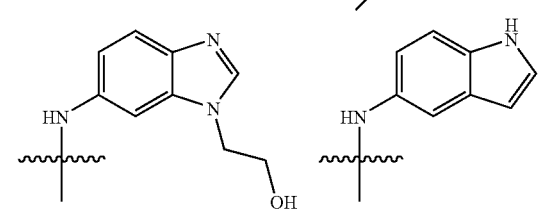

-continued

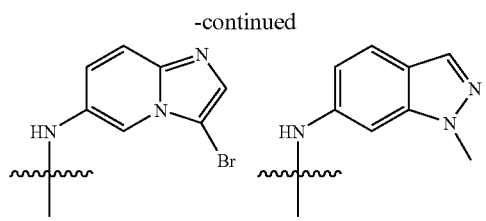

or a stereoisomer, or a pharmaceutically acceptable salt thereof.

In a third aspect, the present invention is directed to a compound represented by:

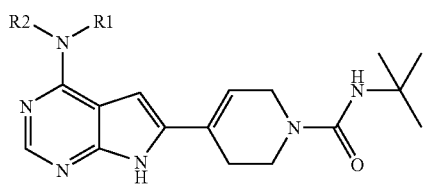

or a stereoisomer, or a pharmaceutically acceptable salt thereof, wherein R2 is —$C_{0-6}$alkyl, —$C_{2-6}$alkyl-N—($C_{0-6}$alkyl)($C_{0-6}$alkyl), —$C_{2-6}$alkyl-O—$C_{0-6}$alkyl, —$C_{1-6}$alkyl-C(O)—NH—$C_{0-6}$alkyl, or —$C_{2-6}$alkyl-N—C(O)—$C_{1-6}$alkyl; and the other variables are as described above for Formula (I).

In an embodiment of the third aspect, the present invention is directed to a compound represented by:

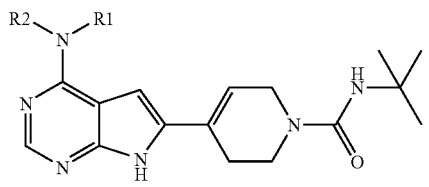

wherein

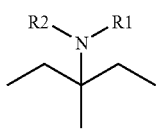

is selected from the following table:

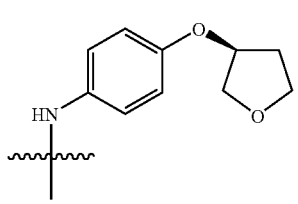

-continued

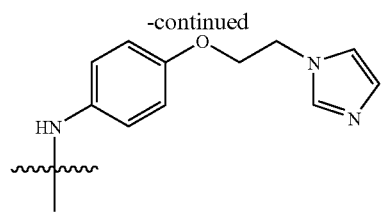

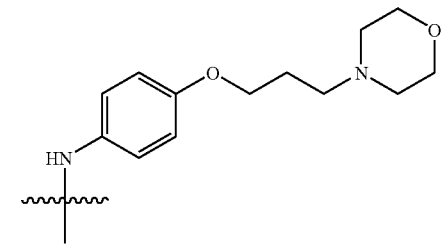

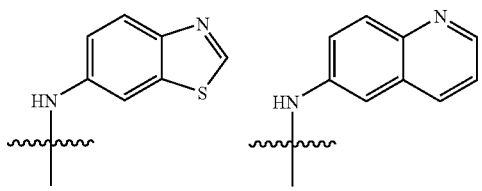

-continued

-continued
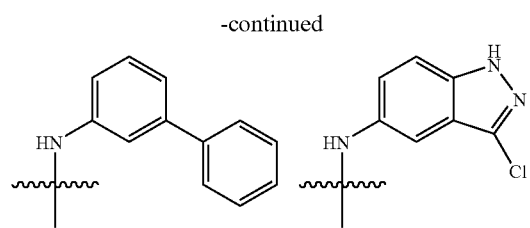
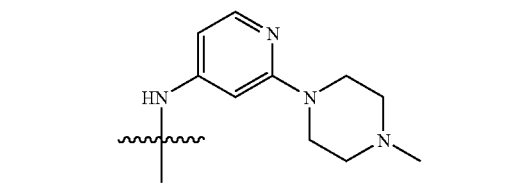
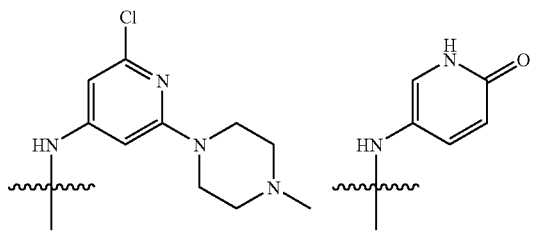
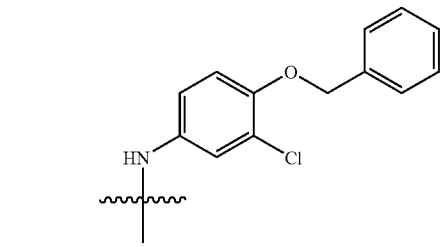
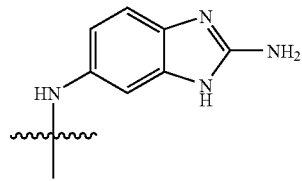
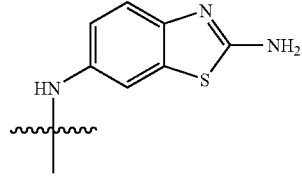
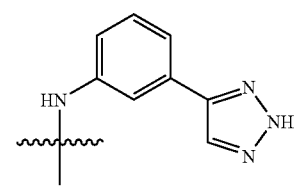
-continued
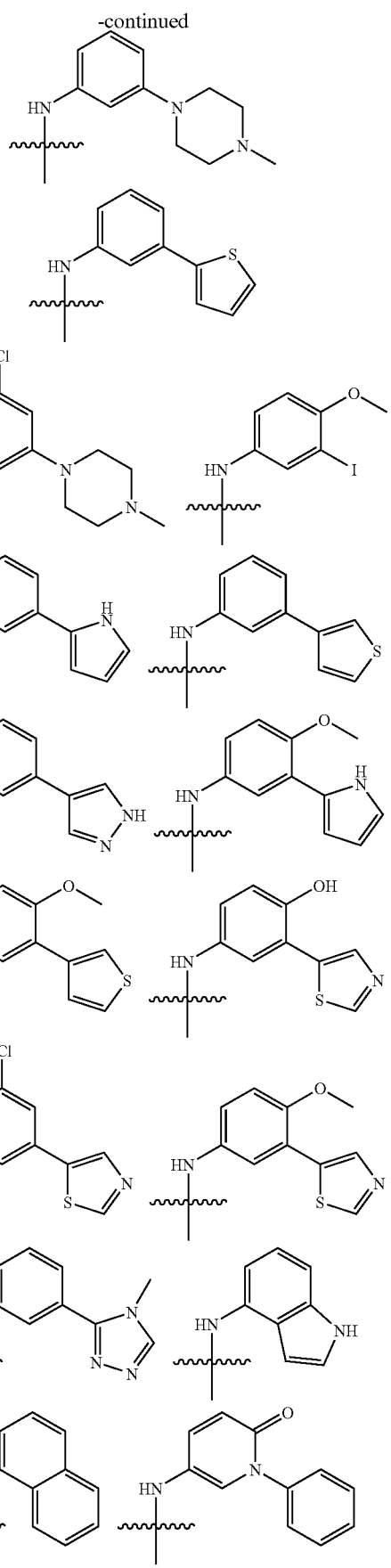

-continued
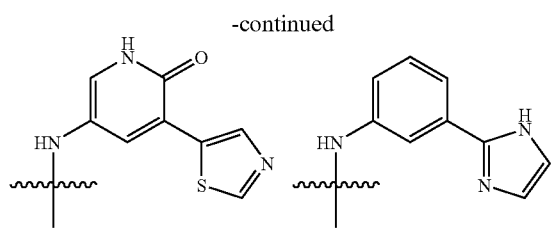 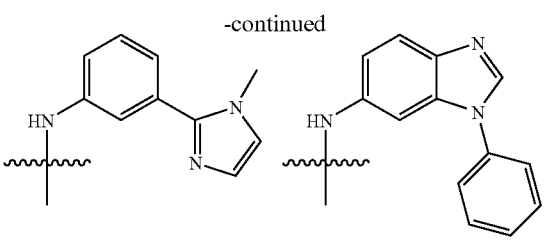
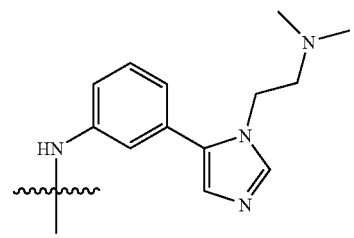 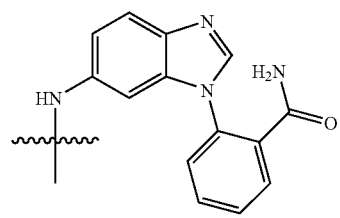
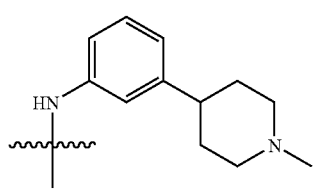
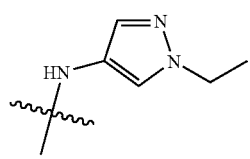
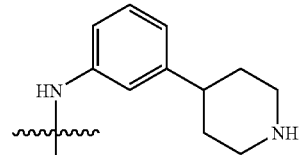 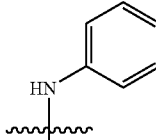 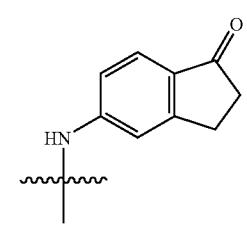
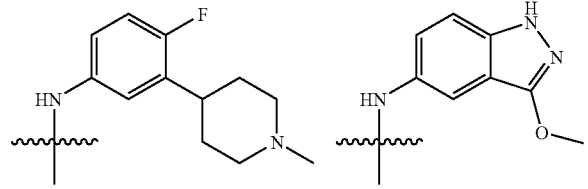
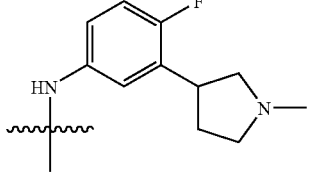
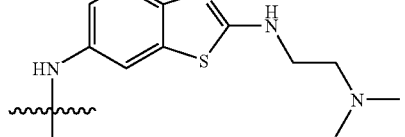
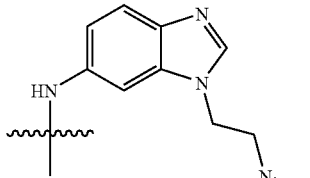
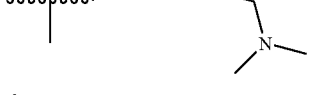
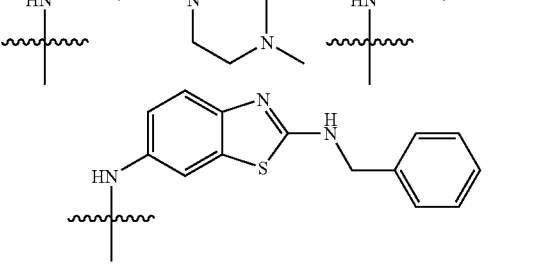
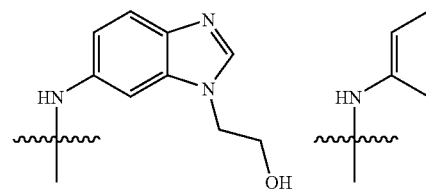 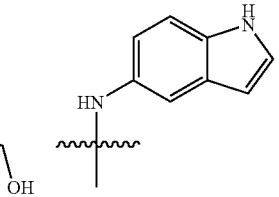

-continued

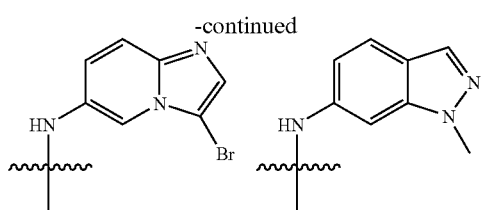

or a stereoisomer, or a pharmaceutically acceptable salt thereof.

In a fourth aspect, the present invention is directed to a compound represented by Formula (I), or a stereoisomer, or a pharmaceutically acceptable salt thereof, wherein Y—R1 is

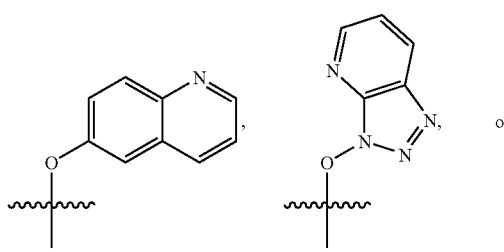

or

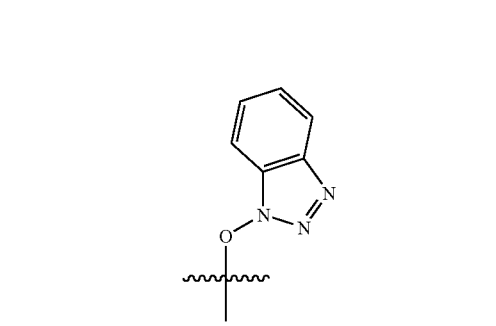

the other variables are as described above.

In a fifth aspect, the present invention is directed to a compound represented by Formula (I), or a stereoisomer, or a pharmaceutically acceptable salt thereof, wherein X is C—CN and the other variables are as described above.

In an embodiment of the fifth aspect, the present invention is directed to a compound represented by Formula (I), or a stereoisomer, or a pharmaceutically acceptable salt thereof, wherein X is C—CN, Cy is

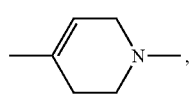

and the other variables are as described above.

In another embodiment of the fifth aspect, the present invention is directed to a compound represented by Formula (I), or a stereoisomer, or a pharmaceutically acceptable salt thereof, wherein X is C—CN, Y is —N($C_{0-6}$alkyl)-, and the other variables are as described above.

The compounds of the present invention include

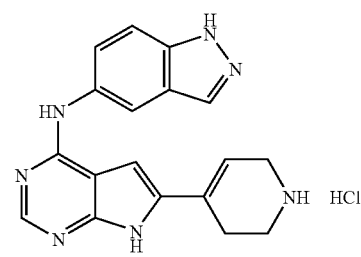

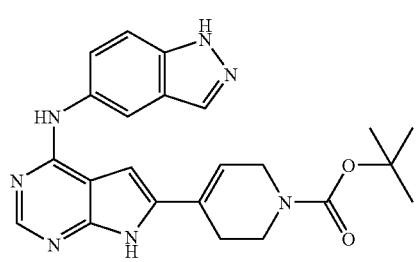

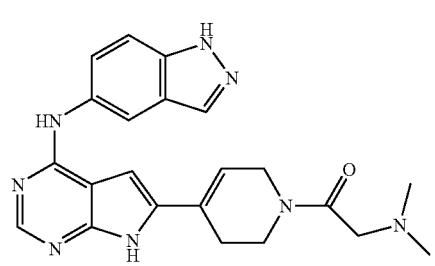

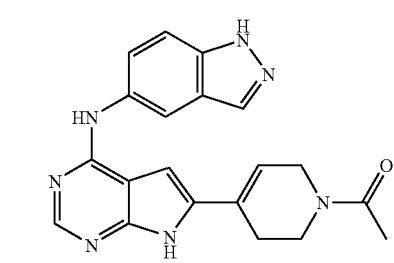

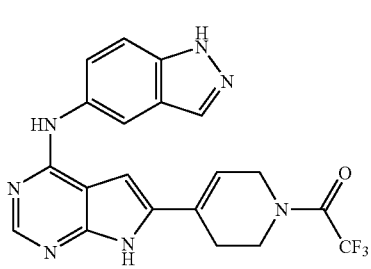

-continued
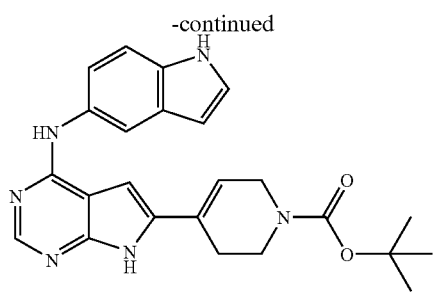
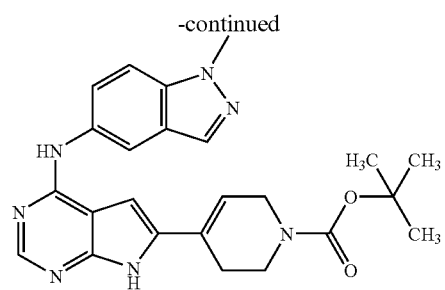
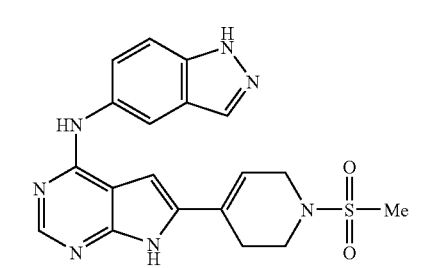
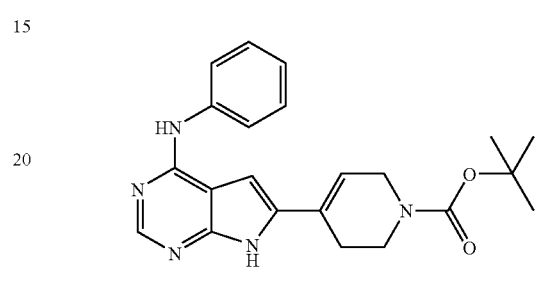
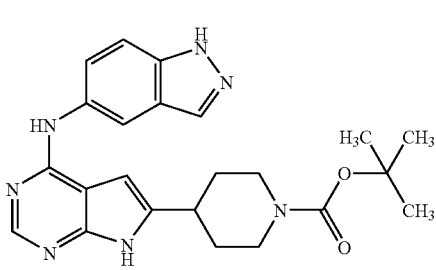
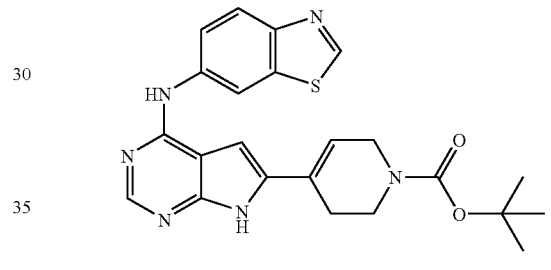
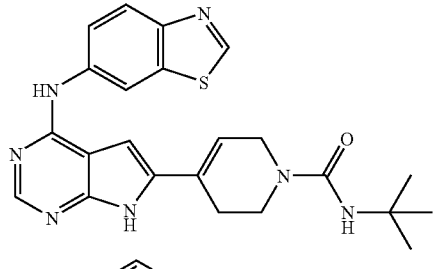
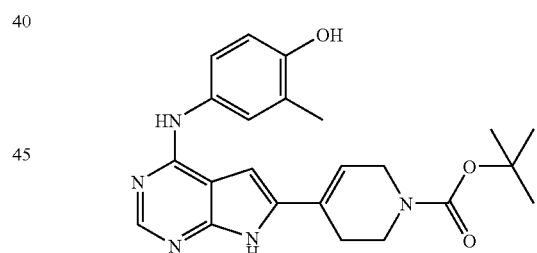
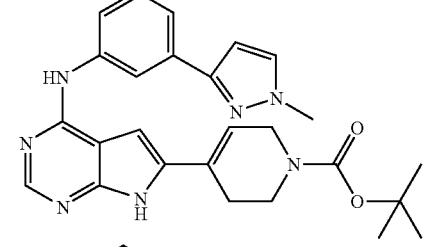
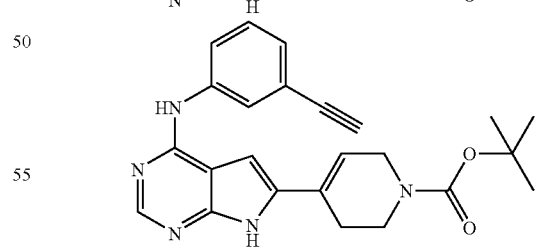
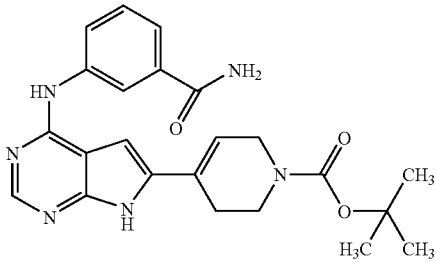
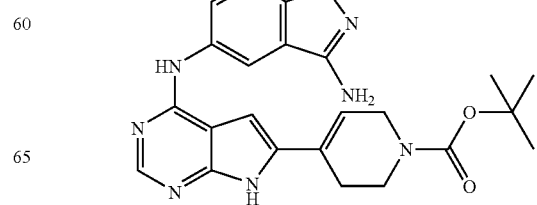

-continued
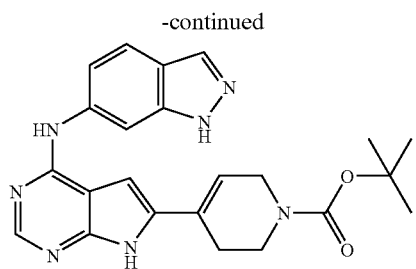
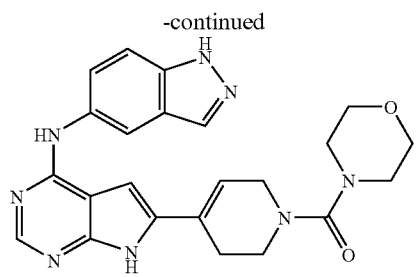
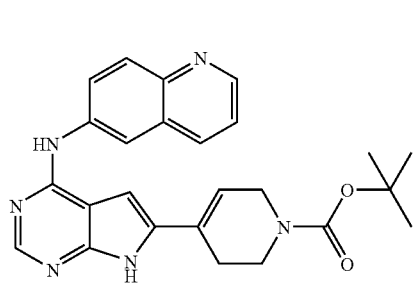
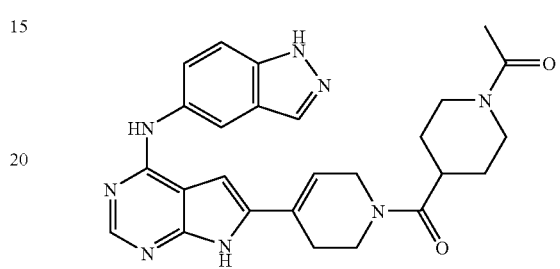
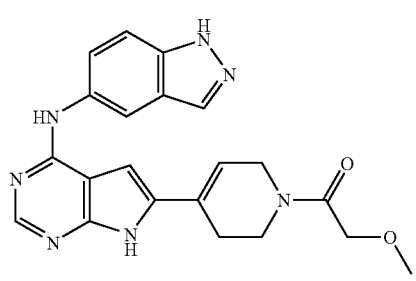
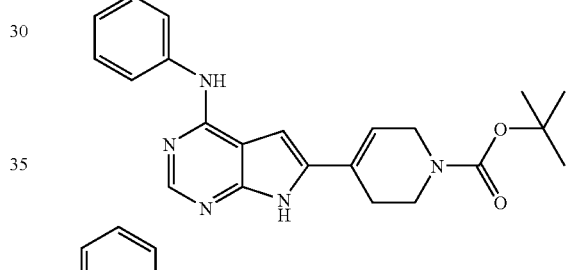
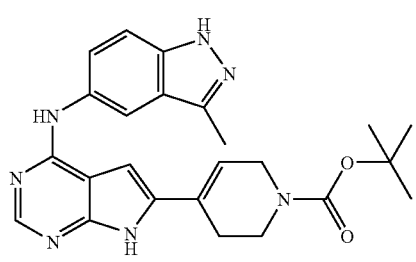
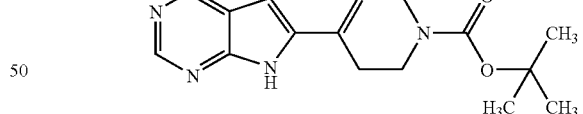
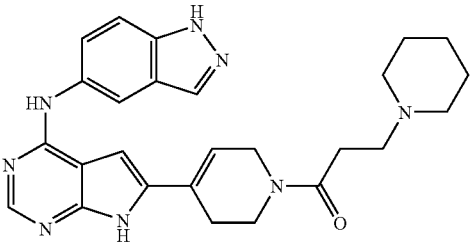
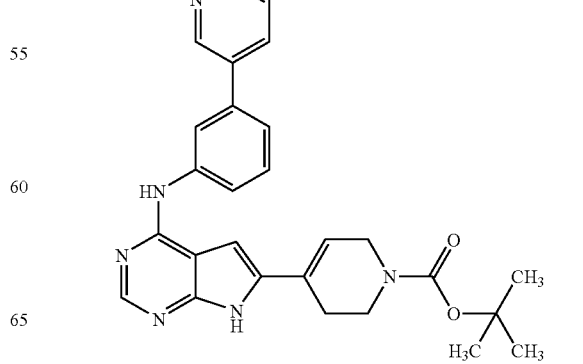

41
-continued
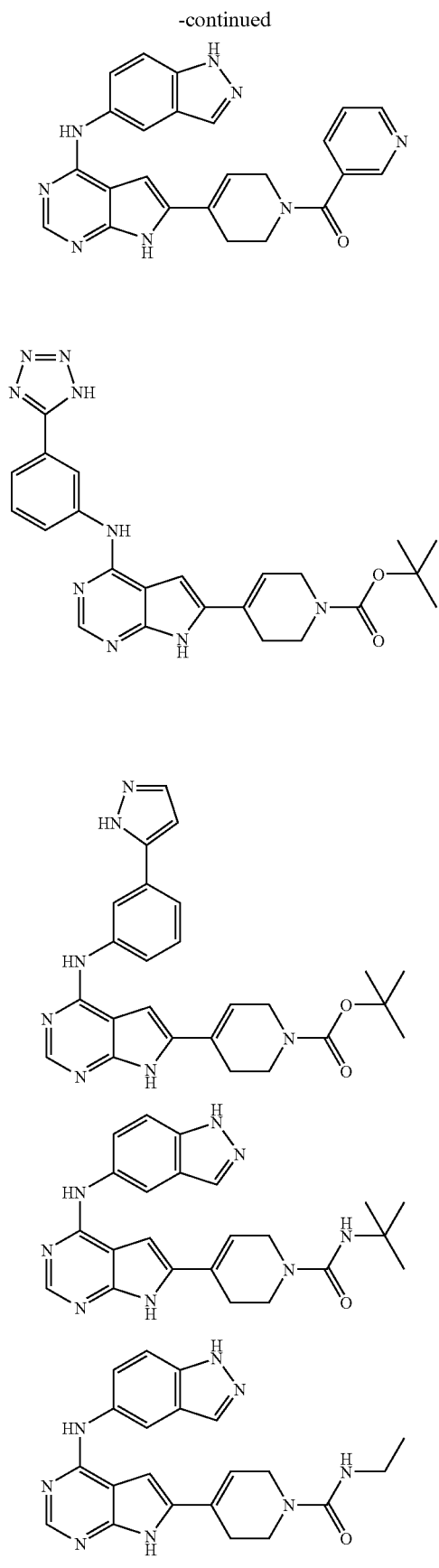
42
-continued
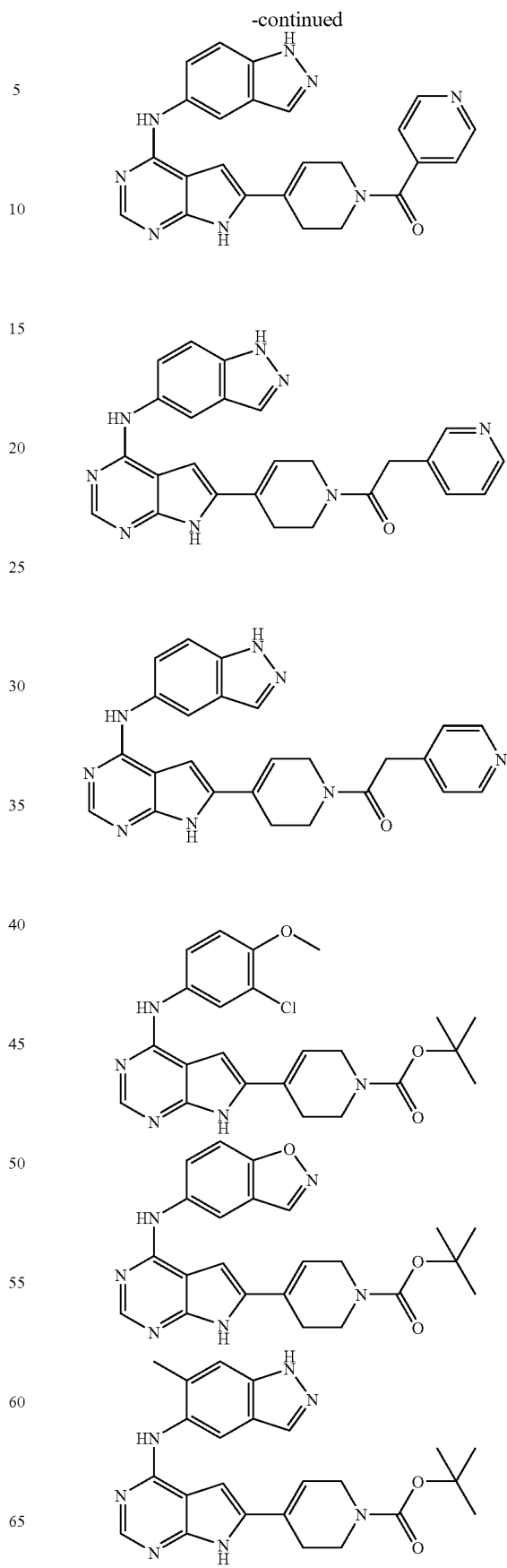

-continued
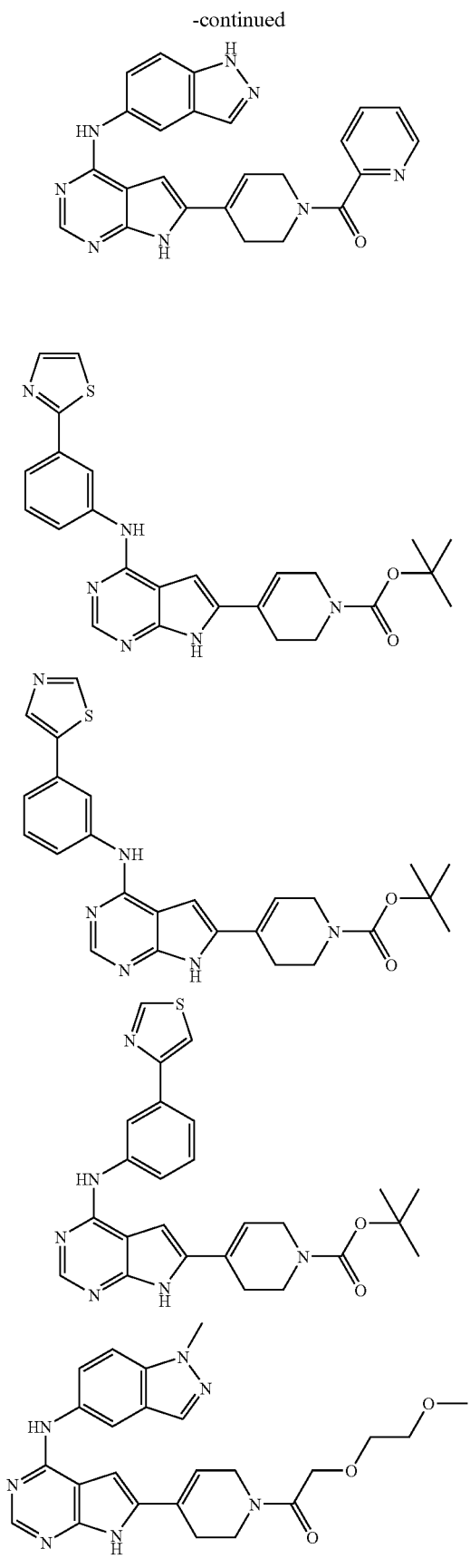
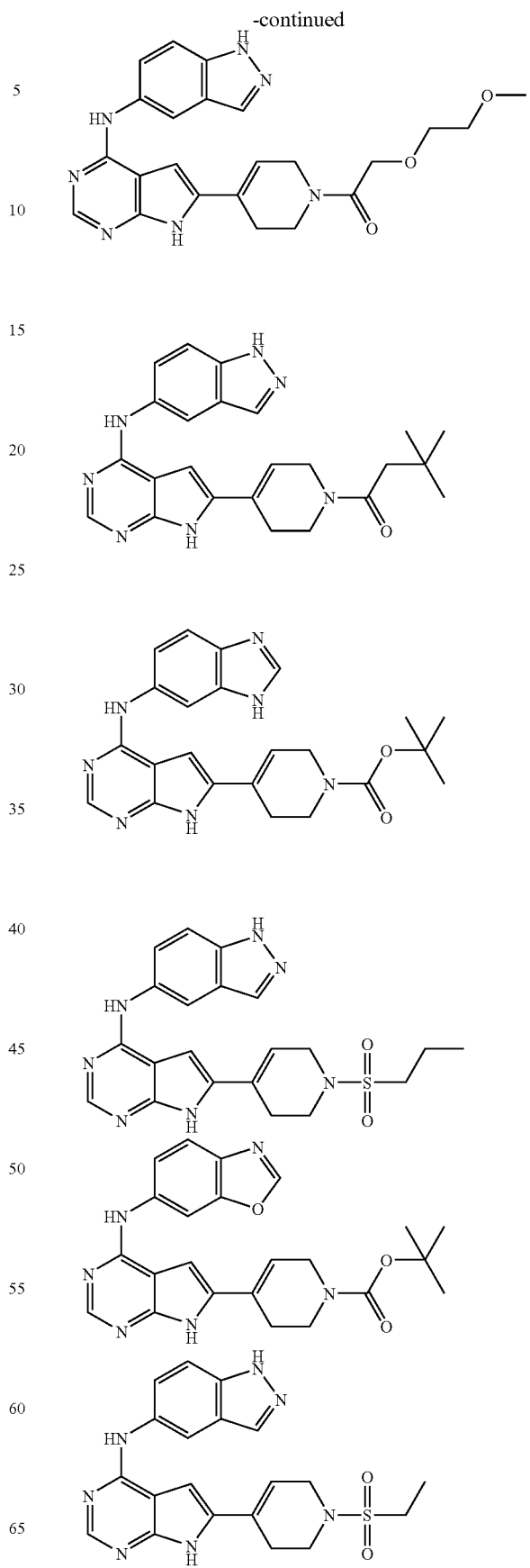

-continued
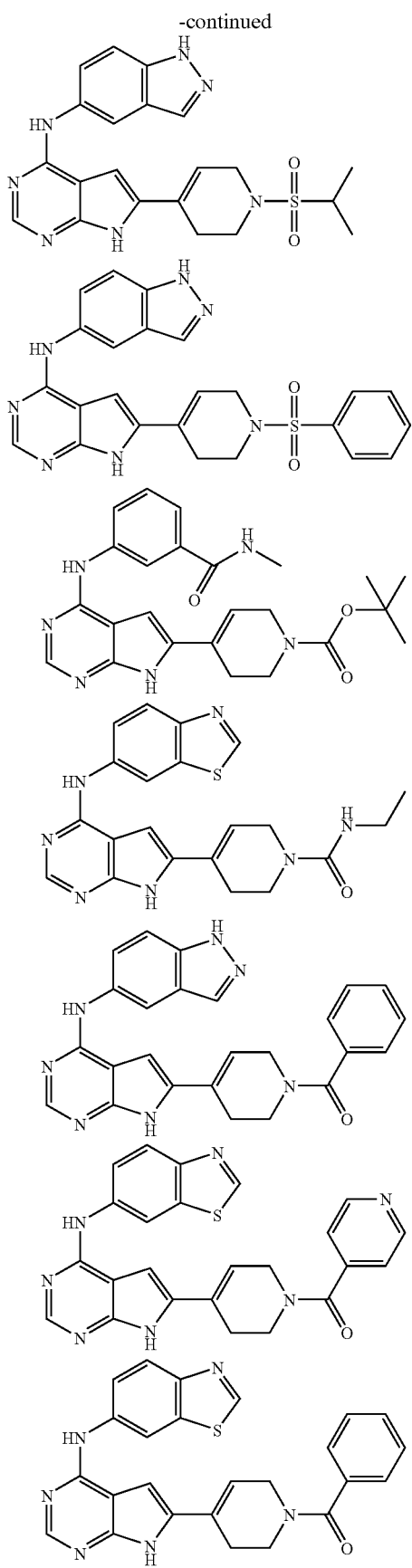
-continued
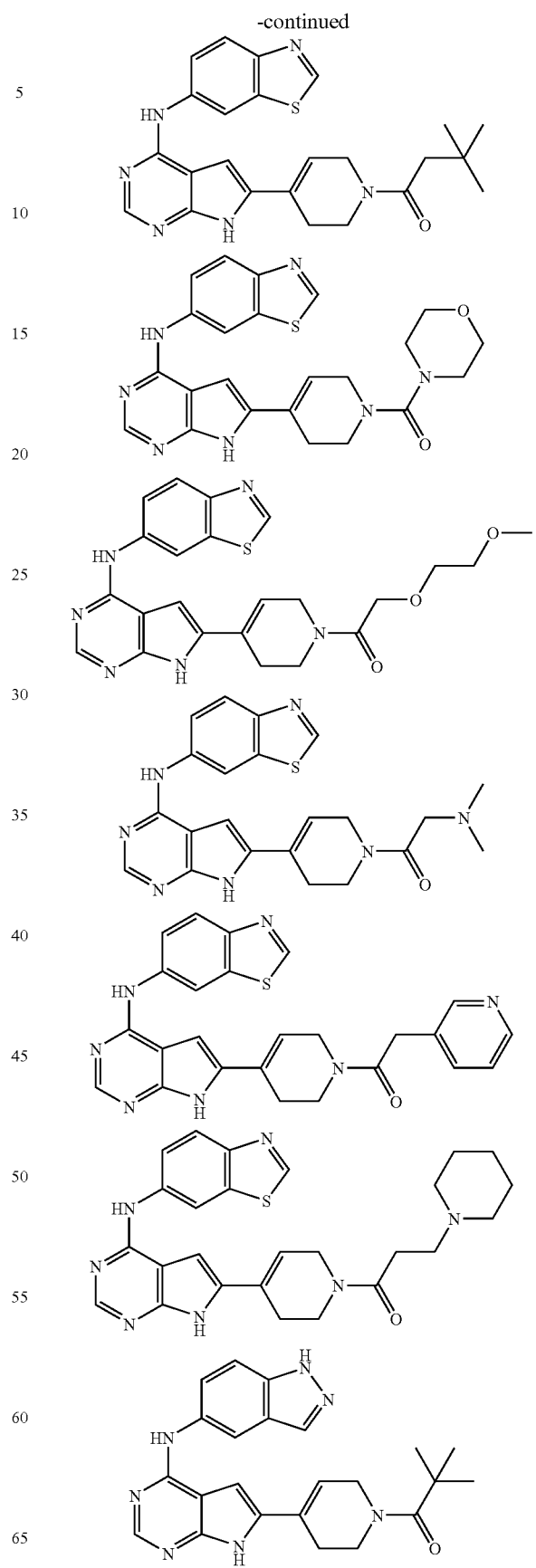

-continued
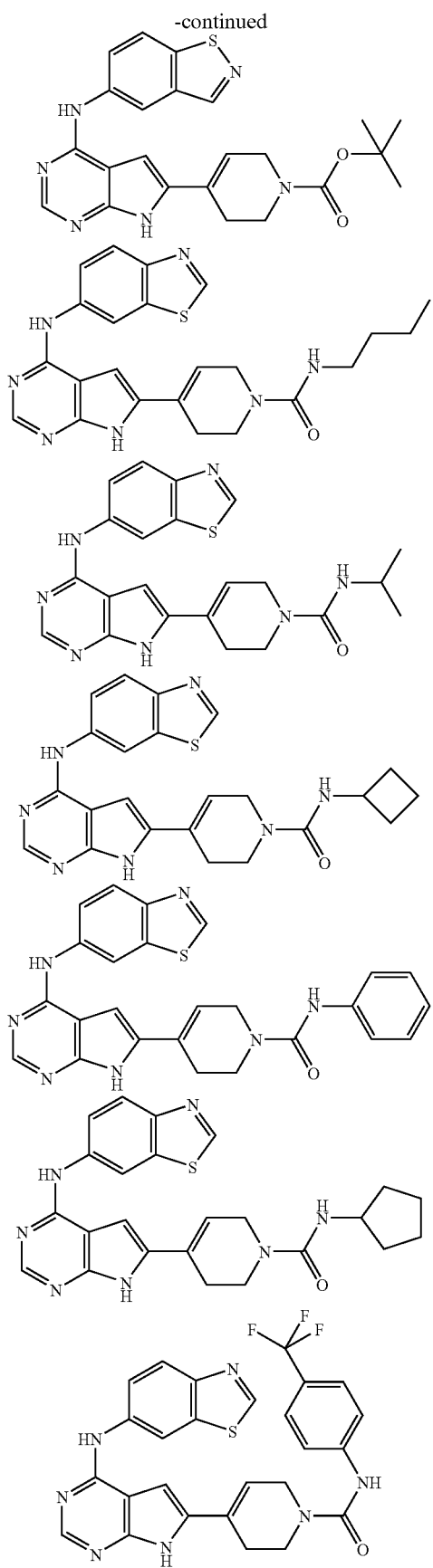
-continued
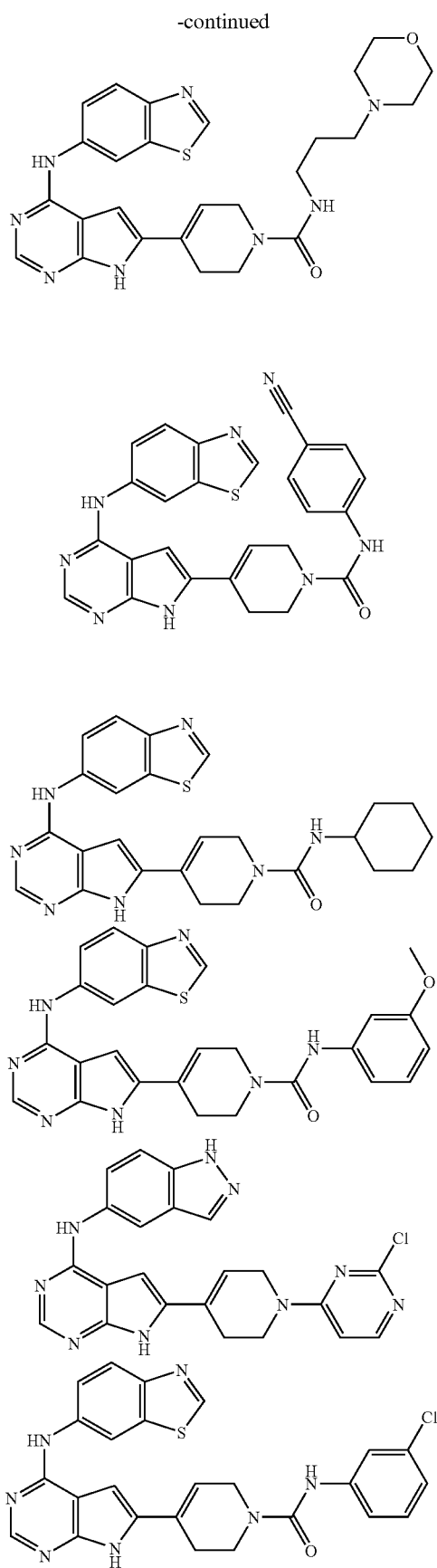

-continued
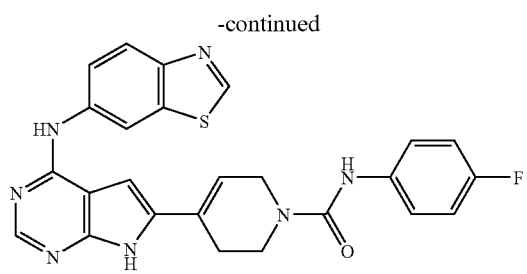
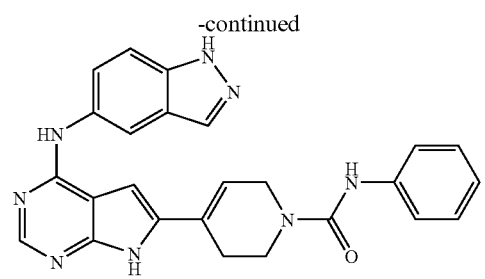
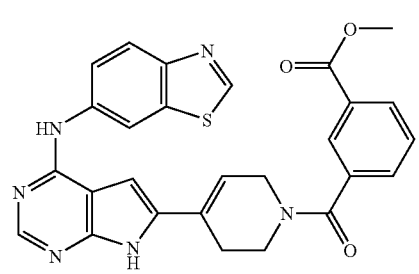
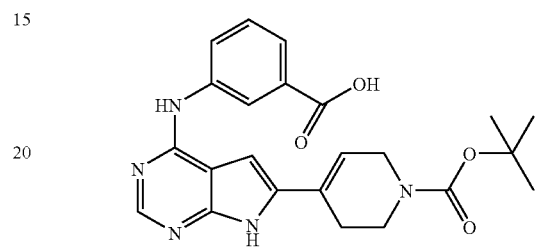
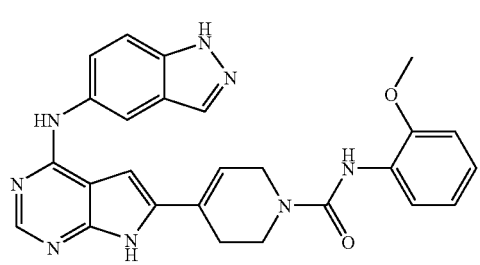
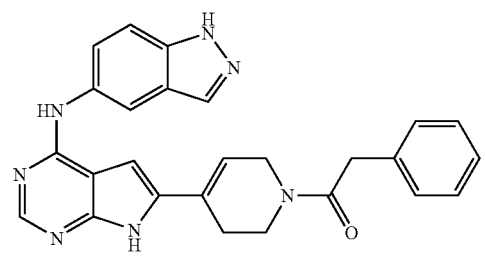
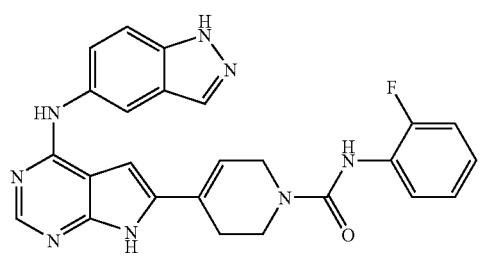
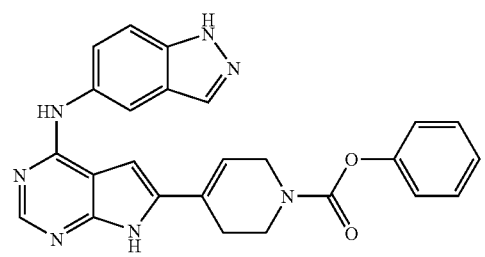
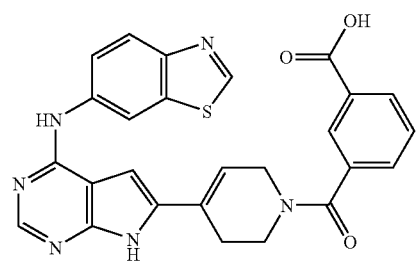
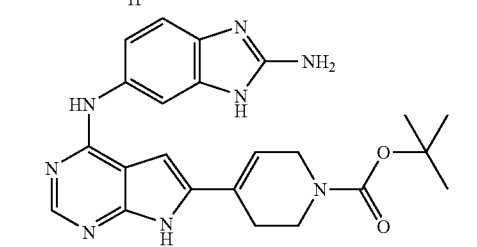
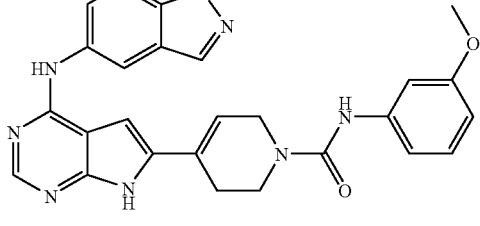
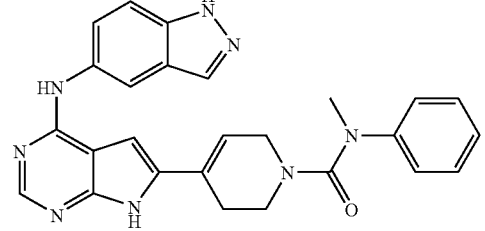

51
-continued
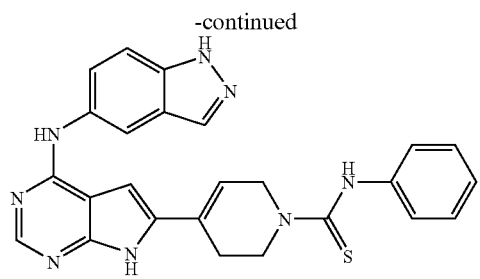
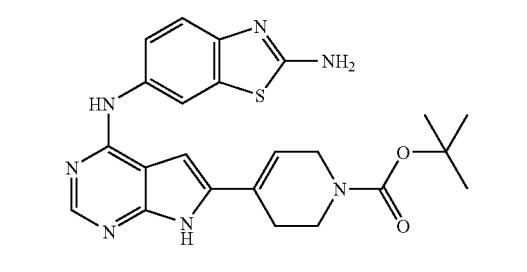
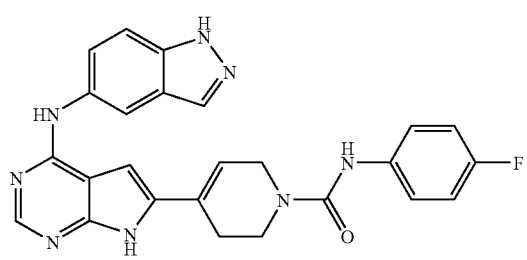
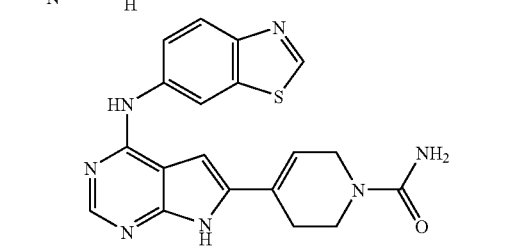
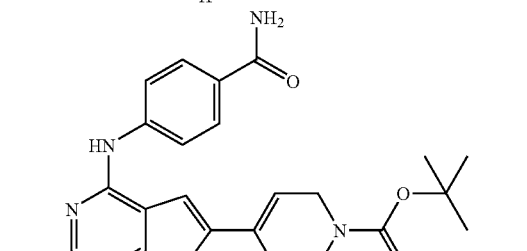
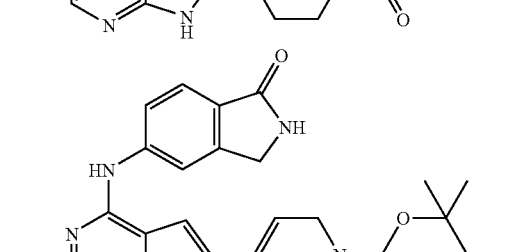
52
-continued
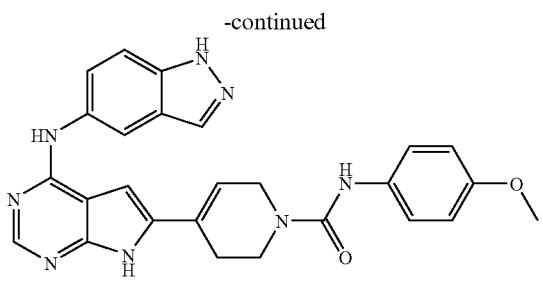
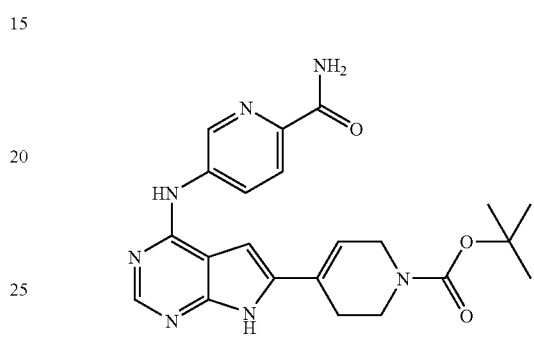
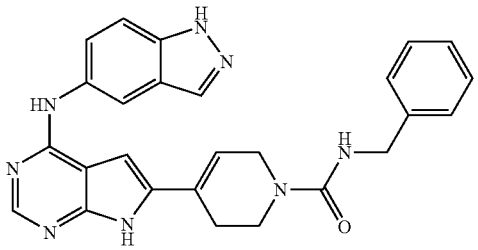
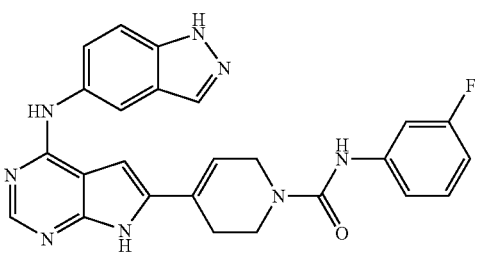
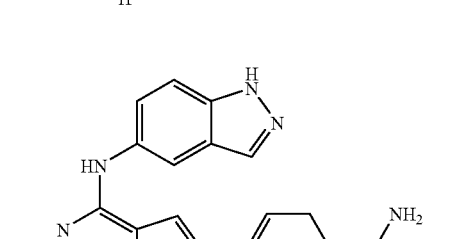
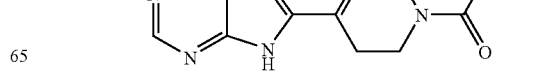

-continued
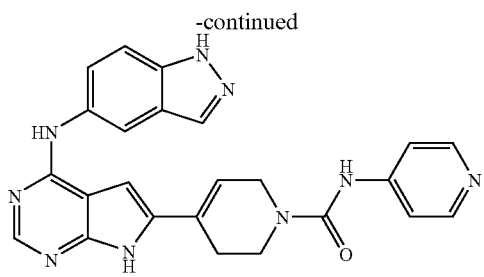
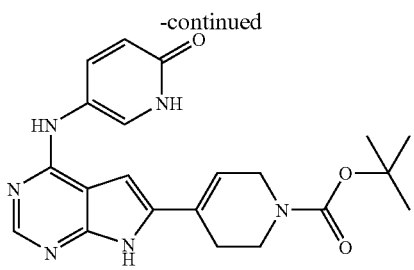
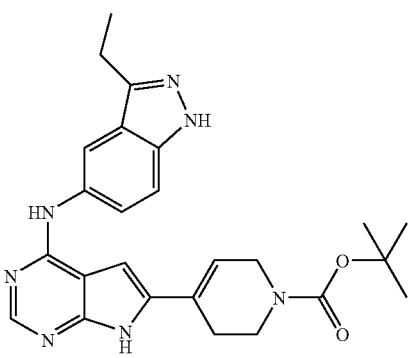
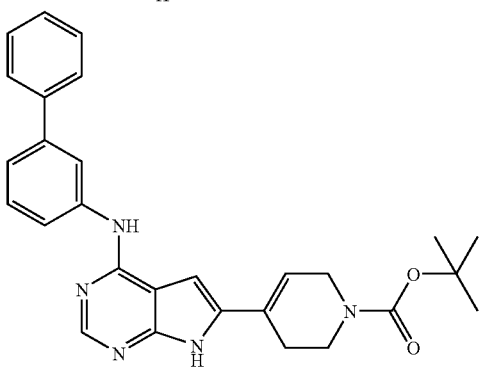
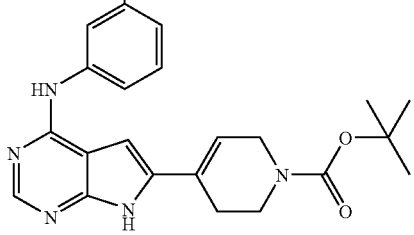
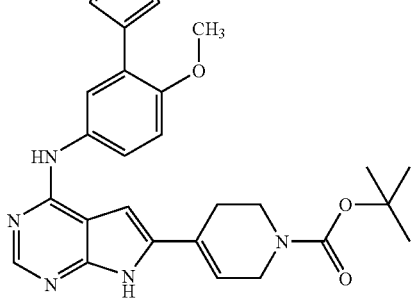

-continued
55
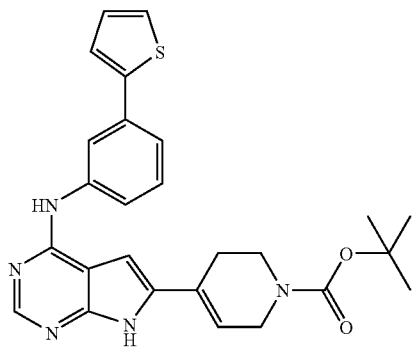
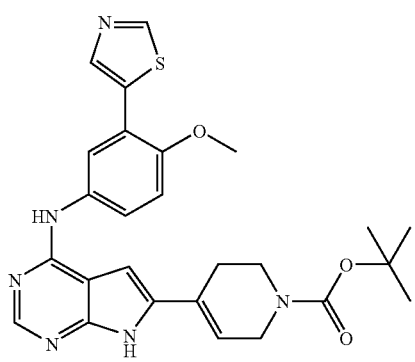
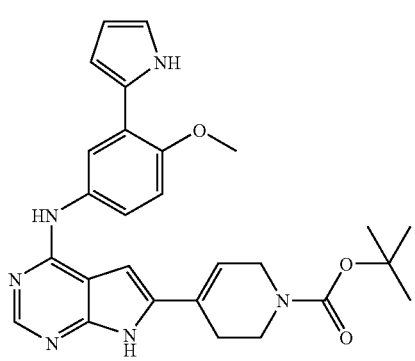
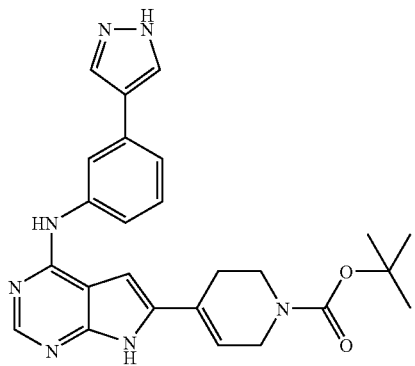
56
-continued
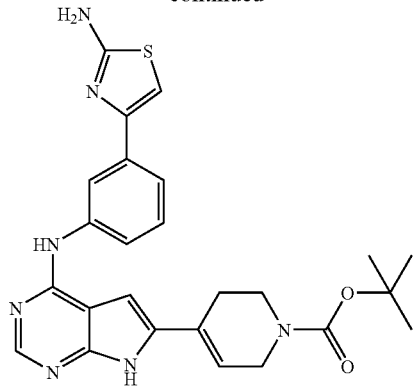
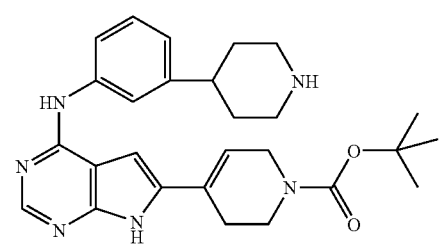
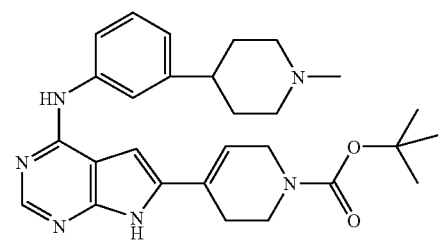
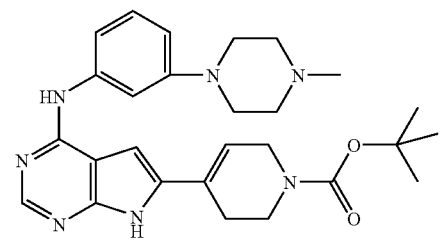

-continued
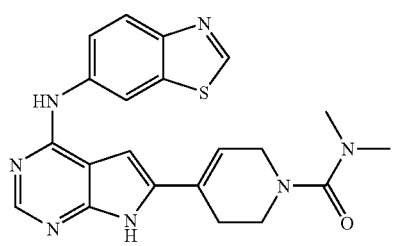
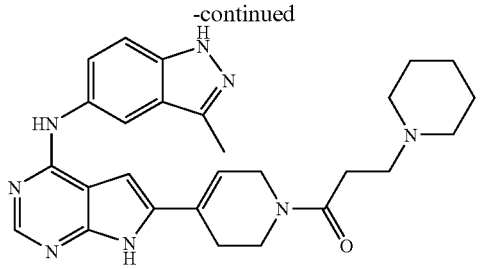
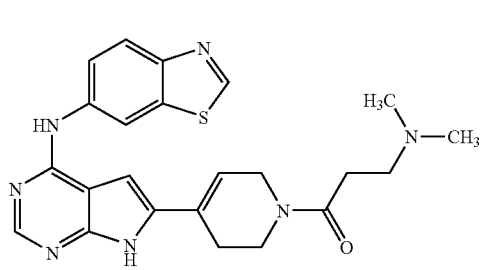
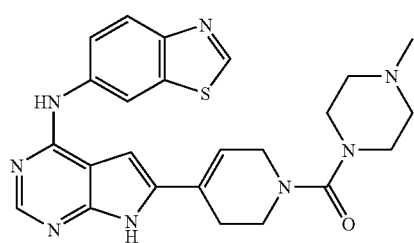
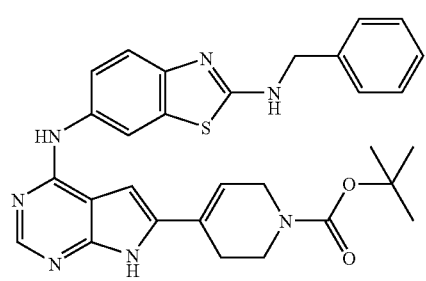
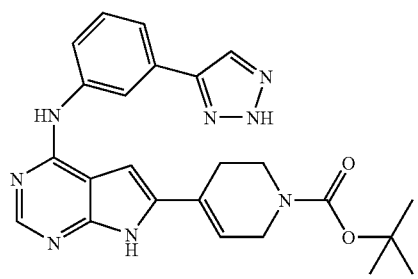
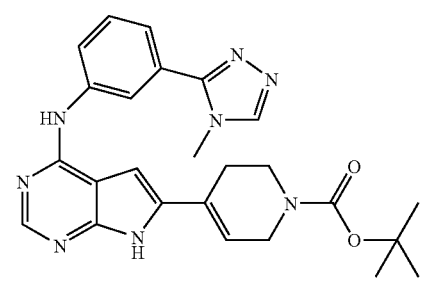
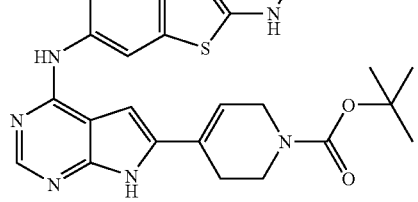
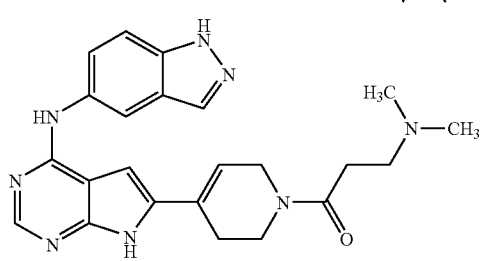
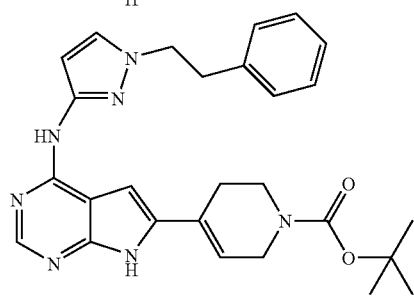

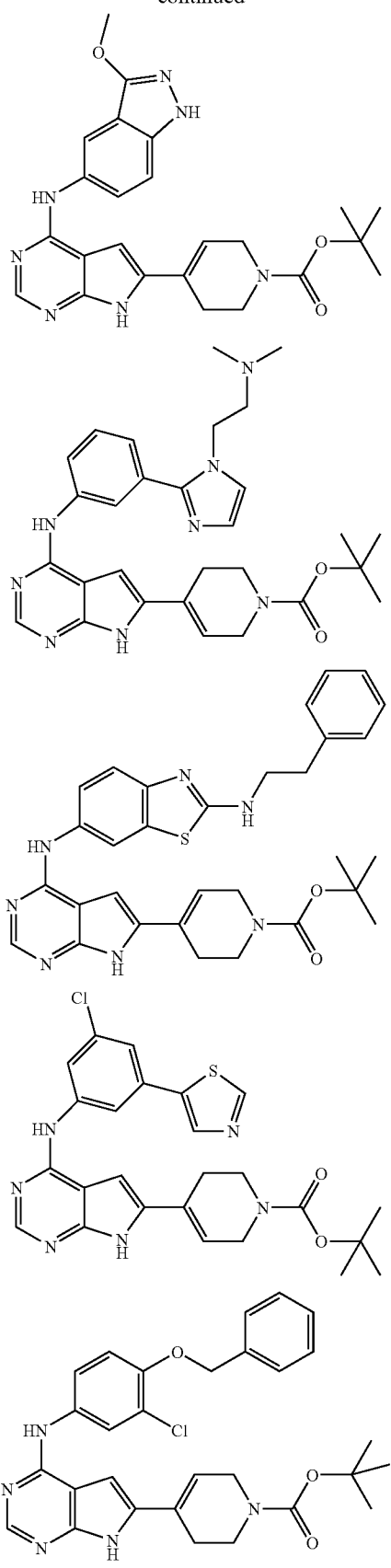
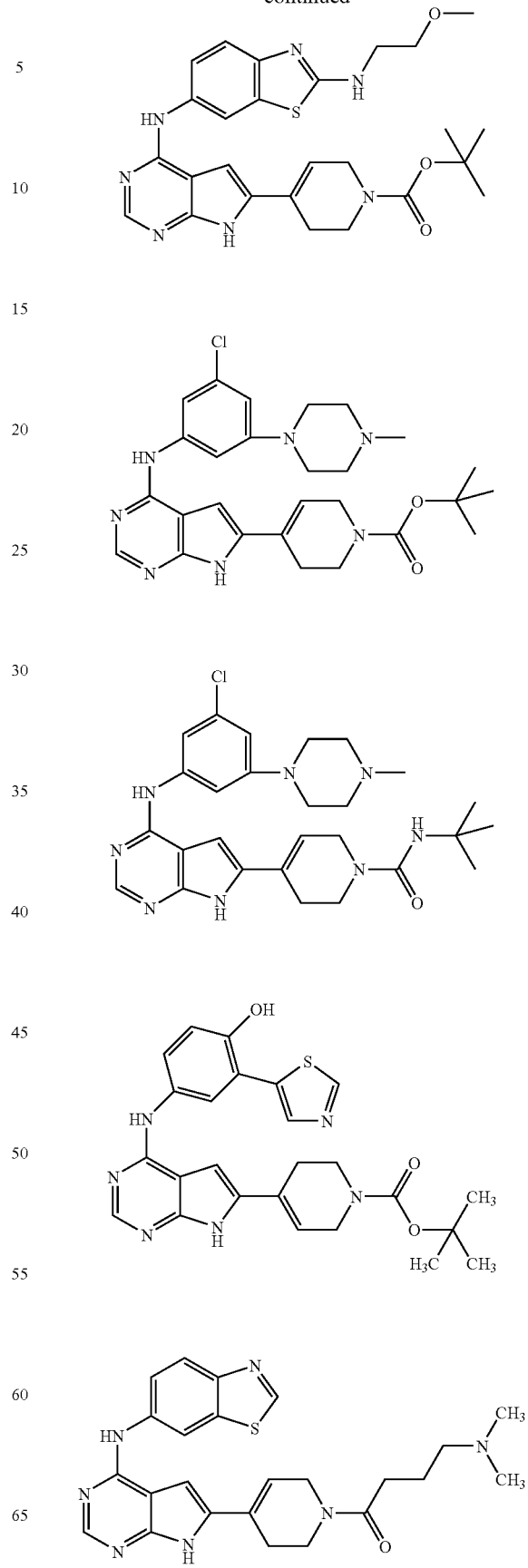

-continued
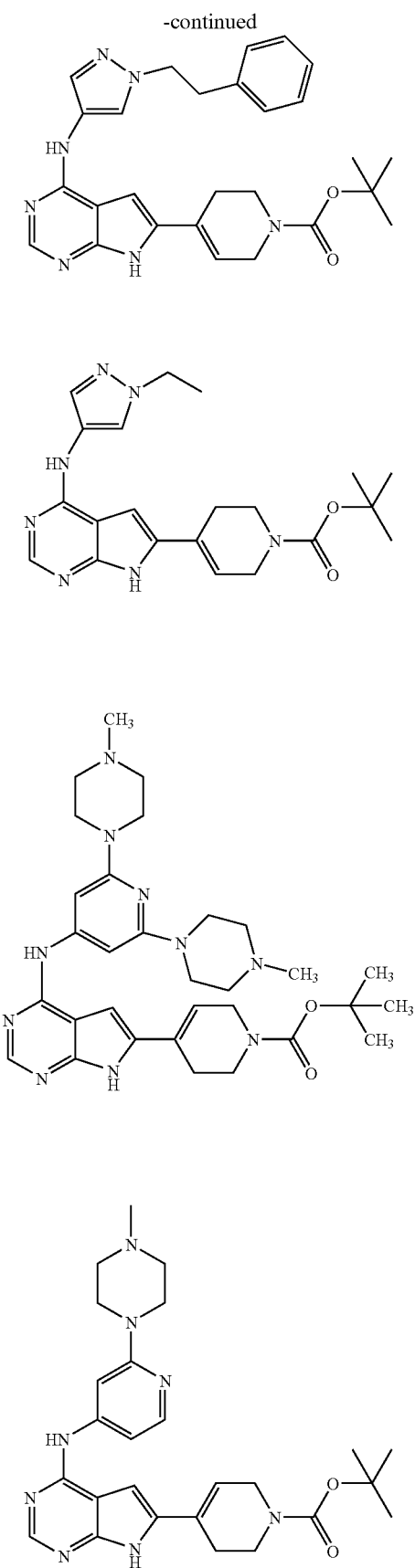
-continued
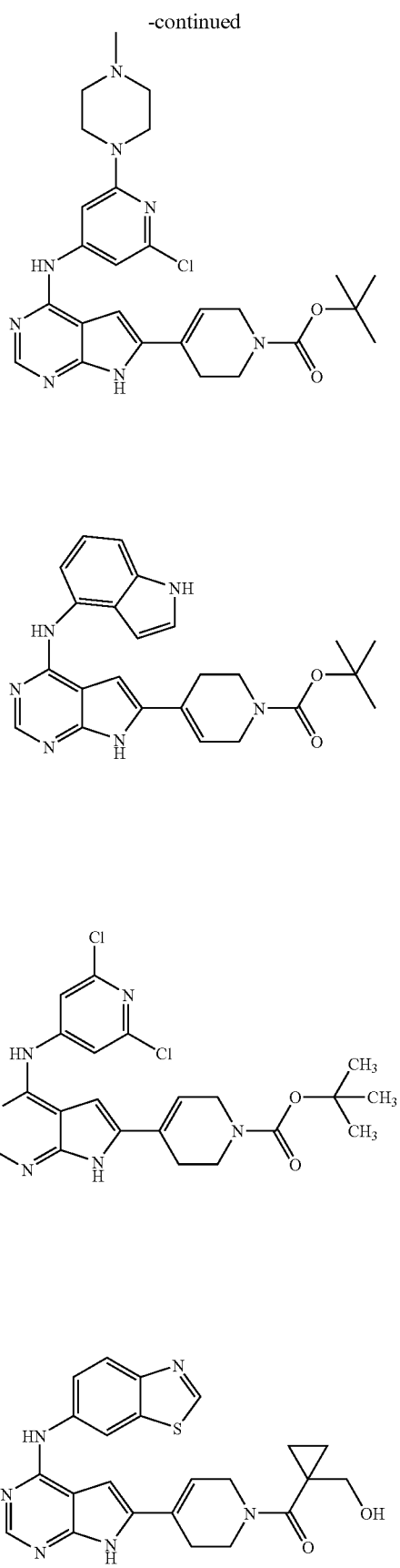

-continued
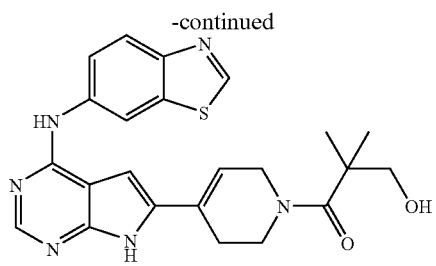
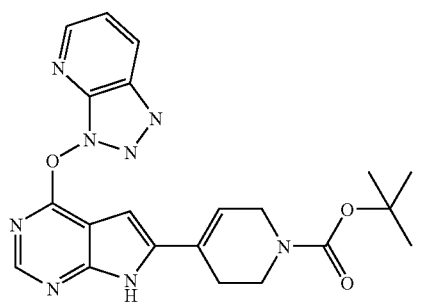
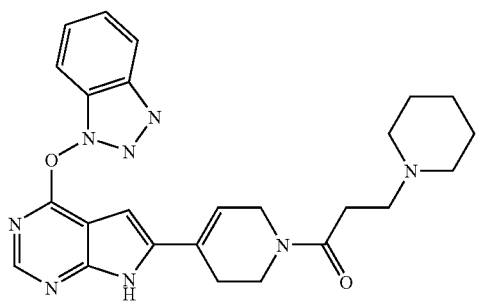
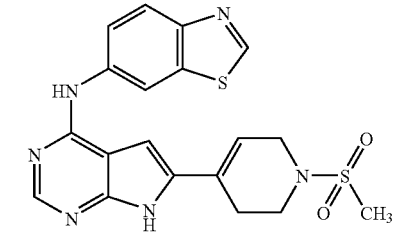
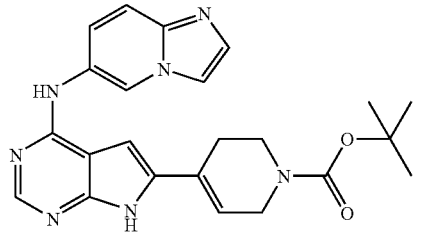
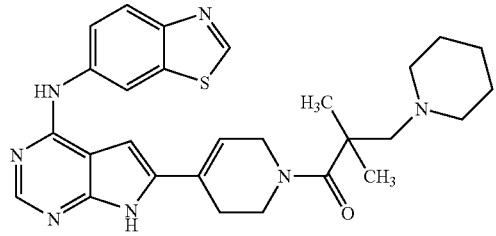
-continued
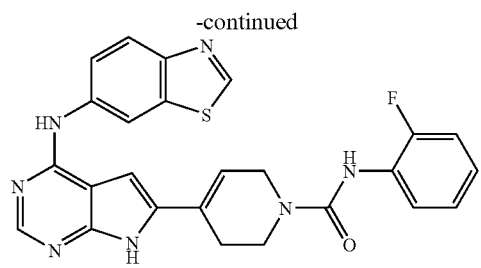
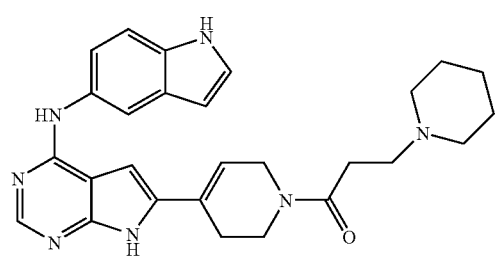
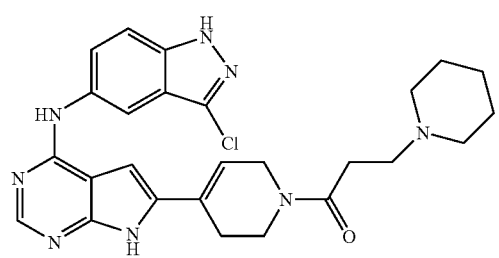
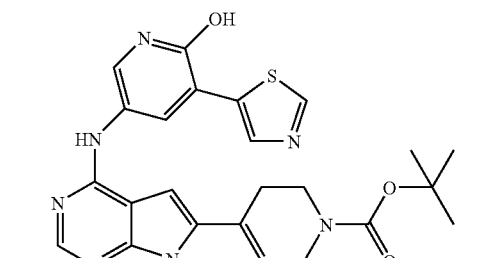
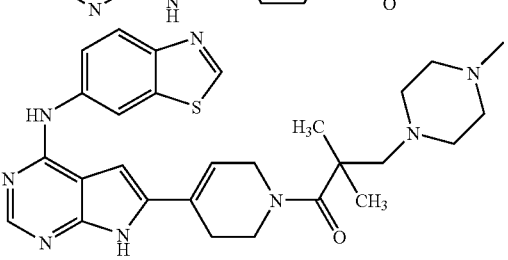
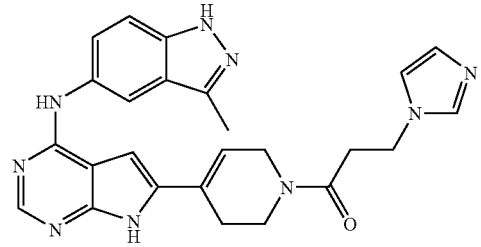

-continued
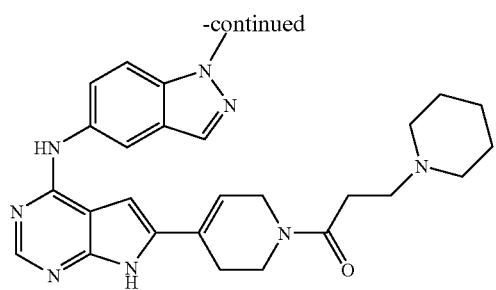
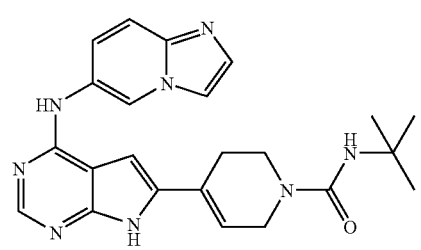
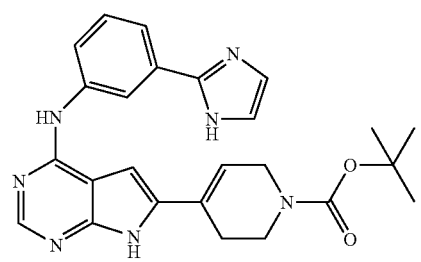
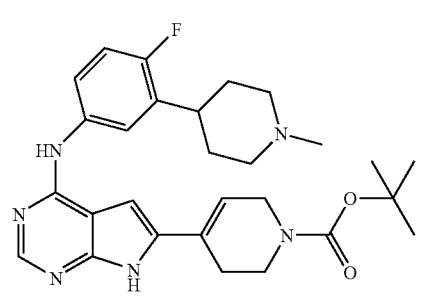
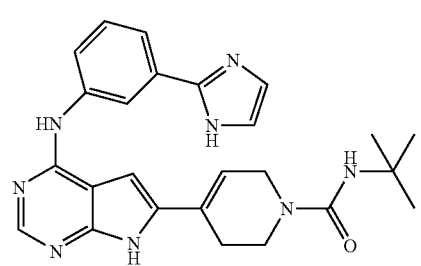
-continued
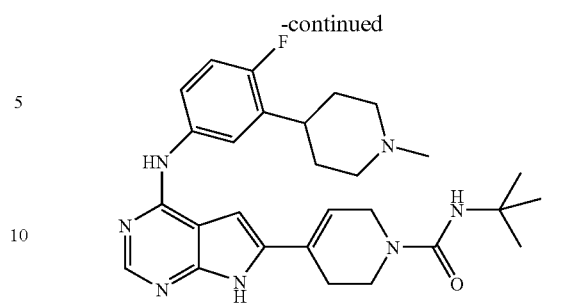
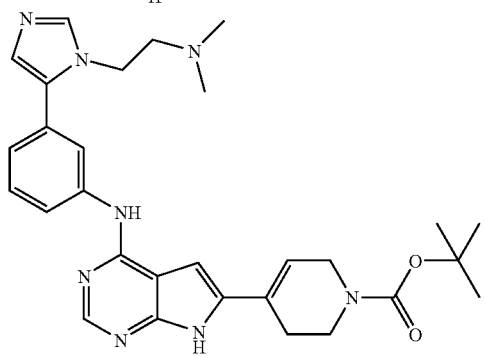
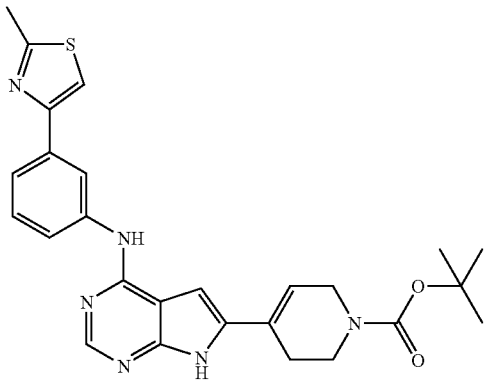
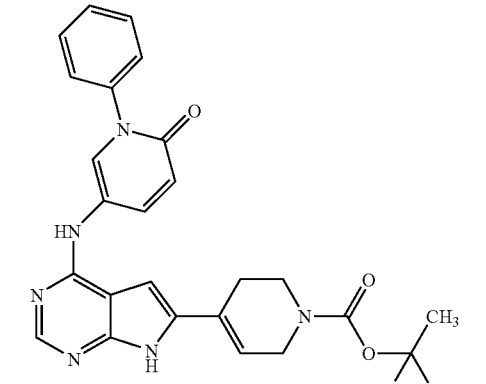
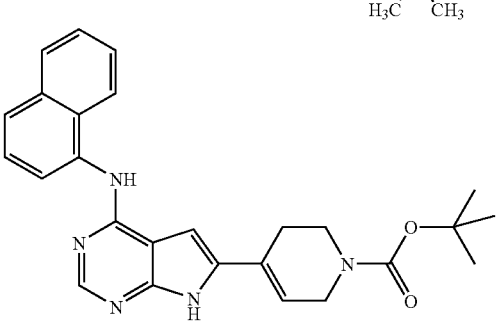

-continued
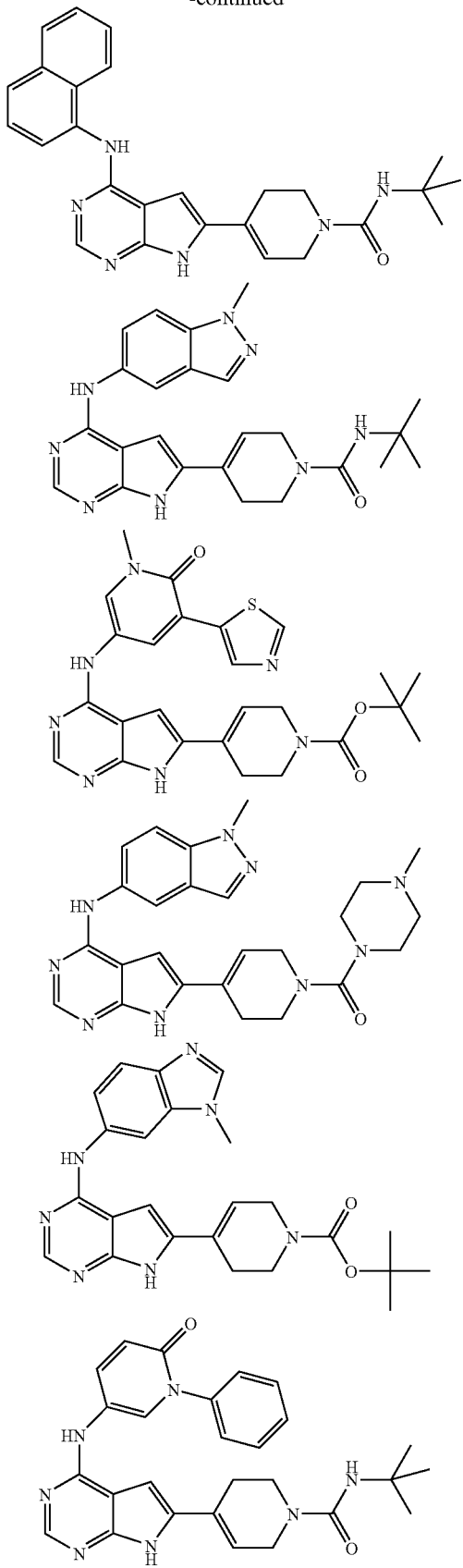
-continued
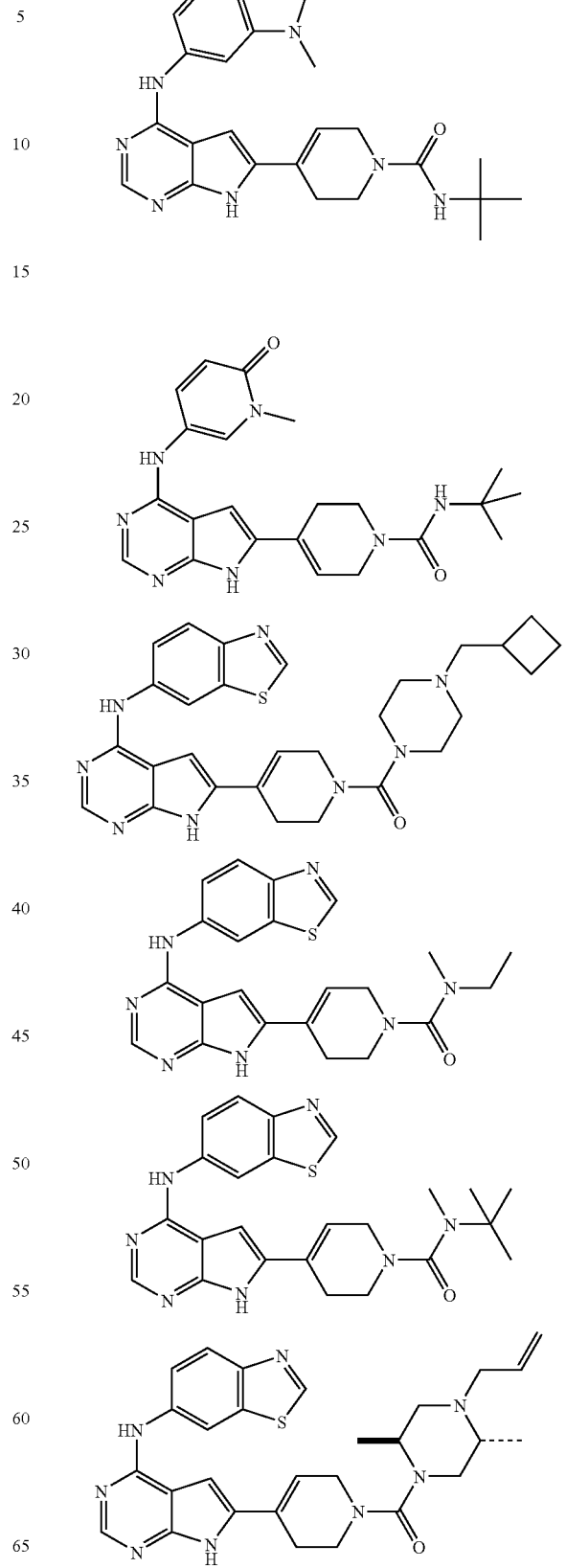

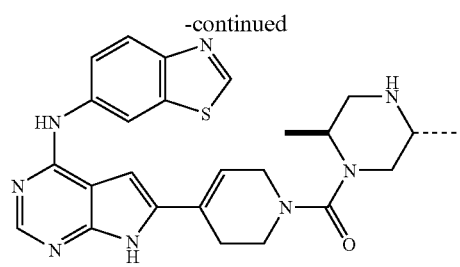
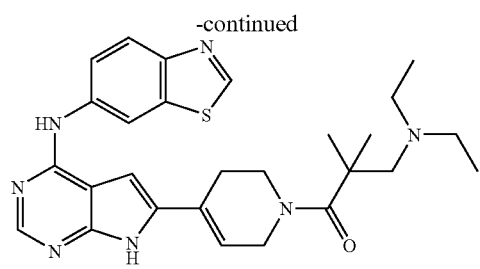
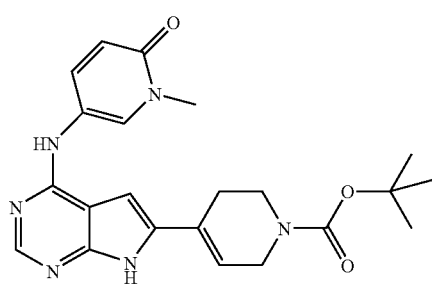
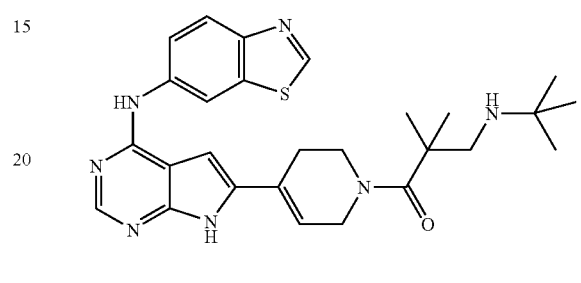
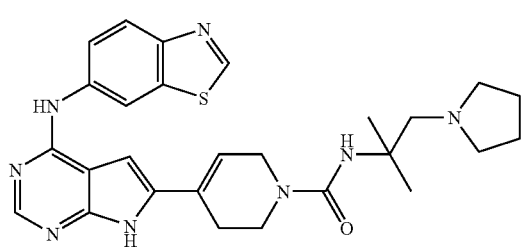
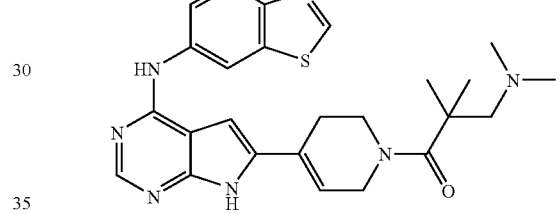
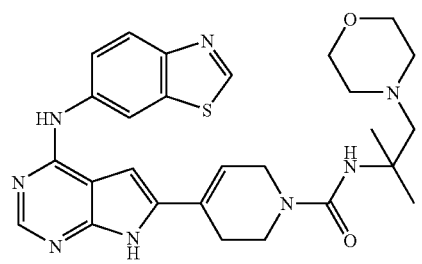
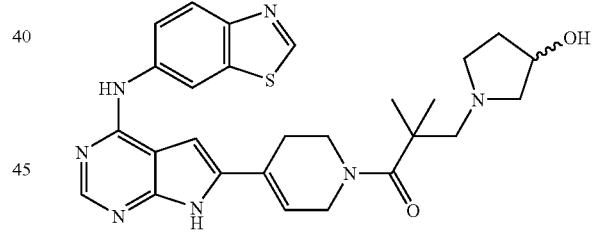
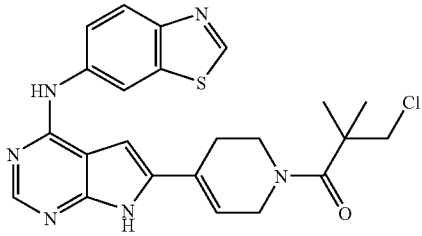
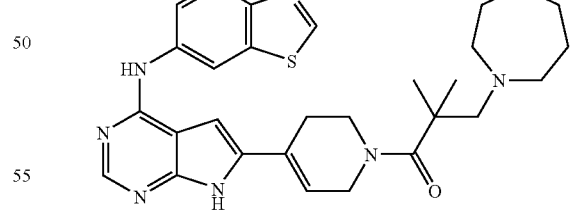
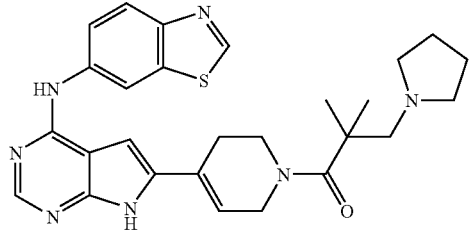
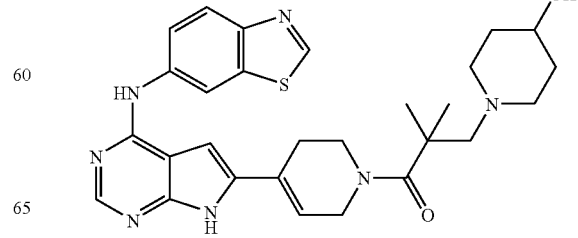

-continued
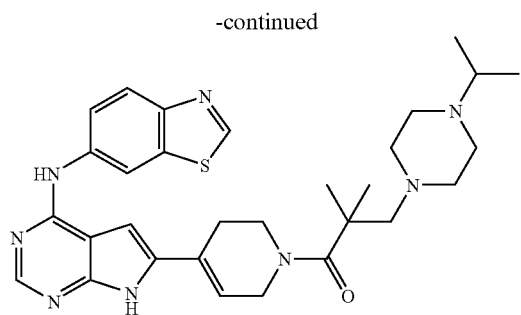
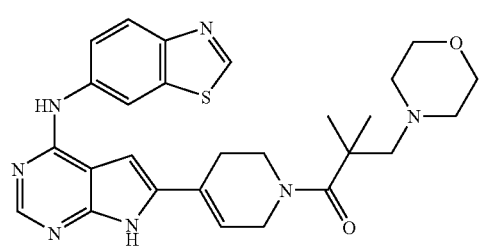
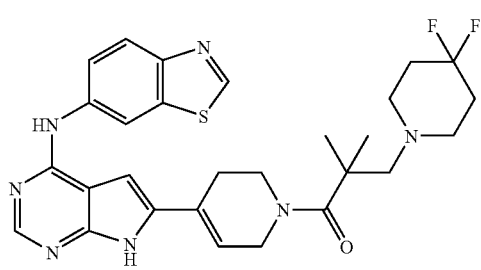

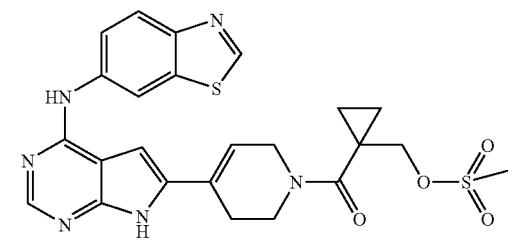
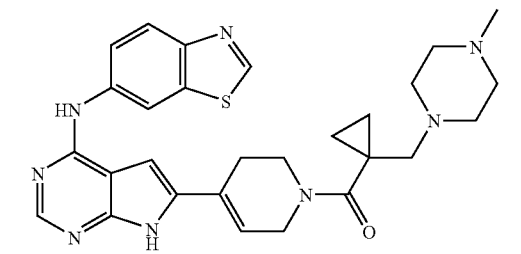
-continued
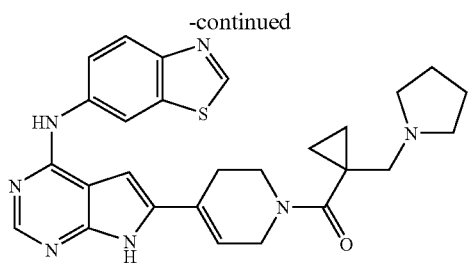
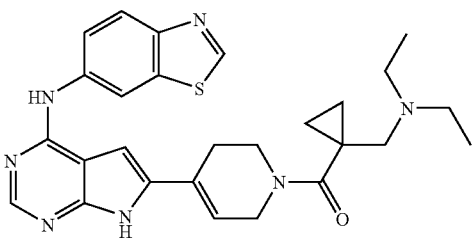
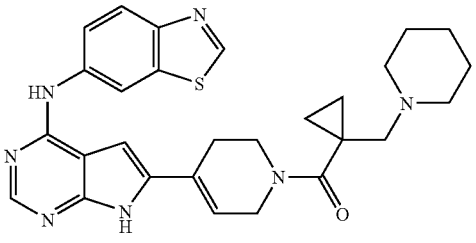
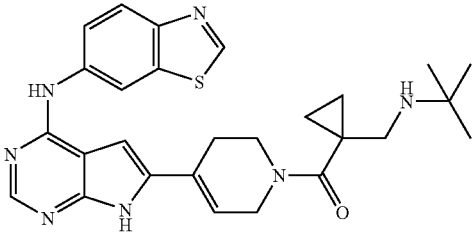
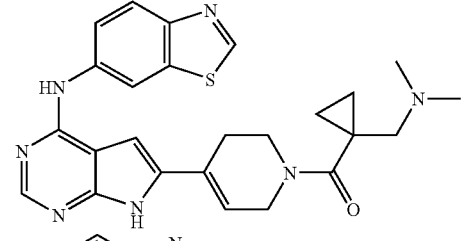
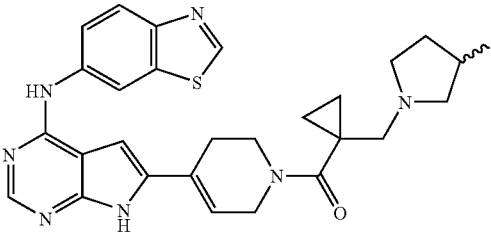

-continued
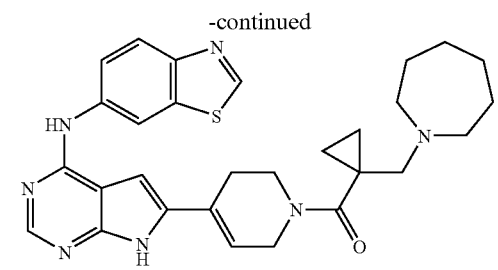
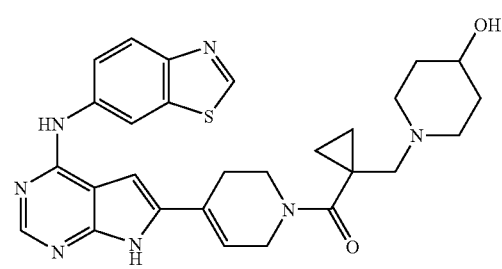
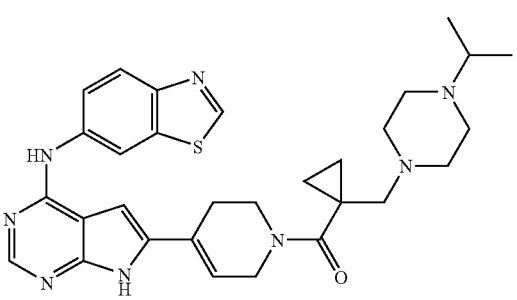
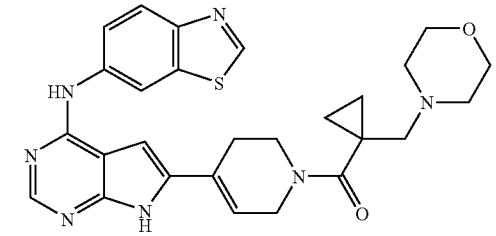
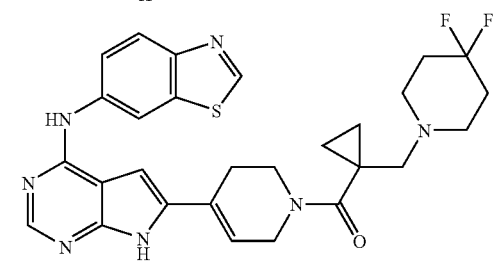
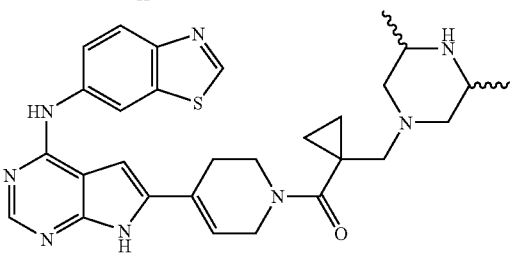
-continued
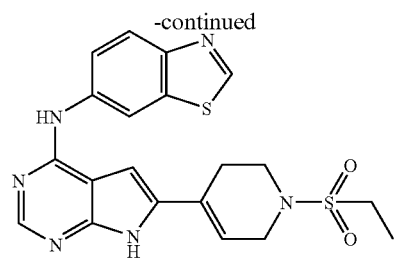
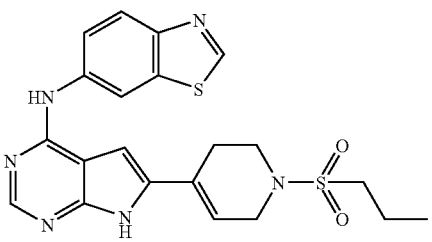
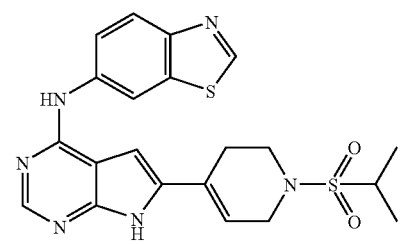
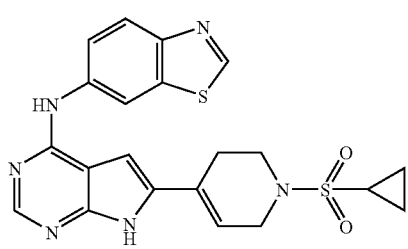
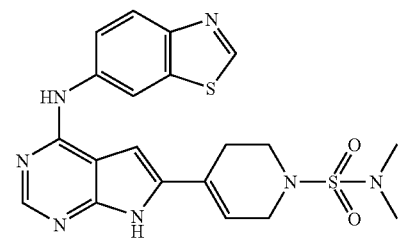
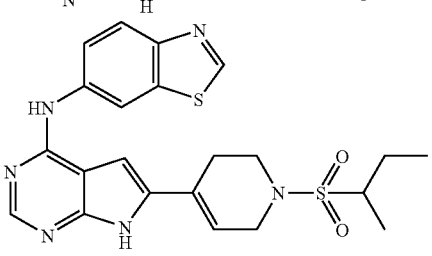

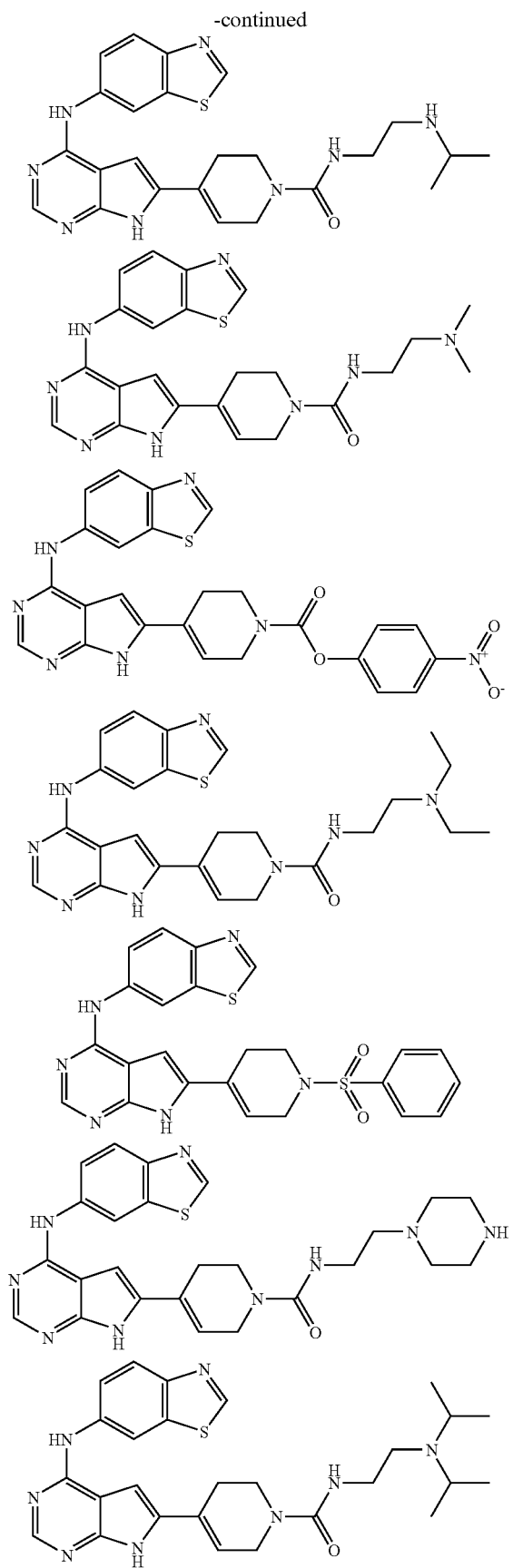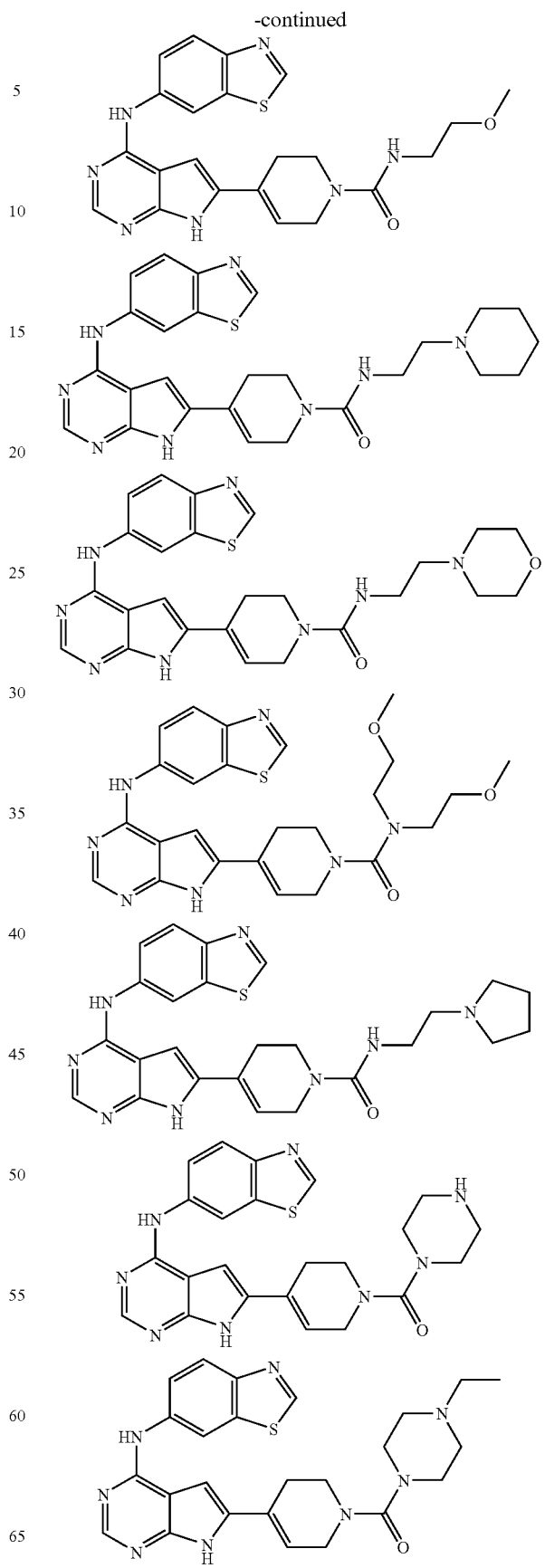

-continued
77
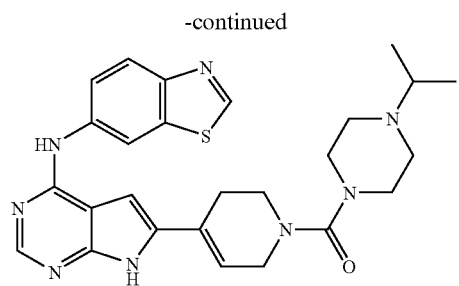
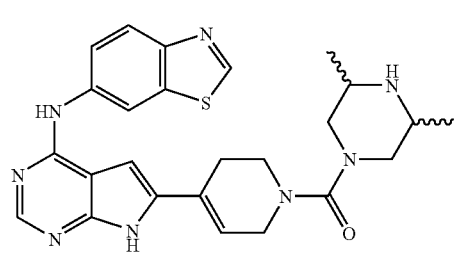
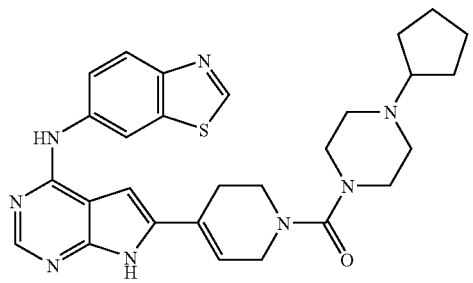
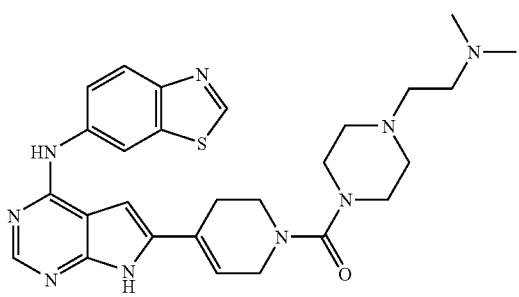
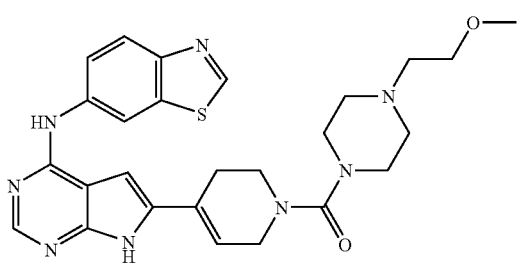
-continued
78
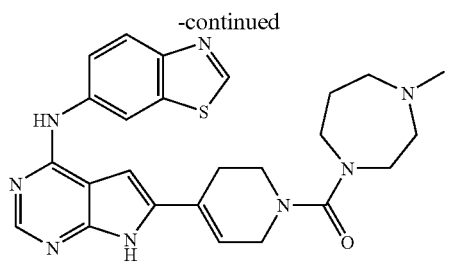
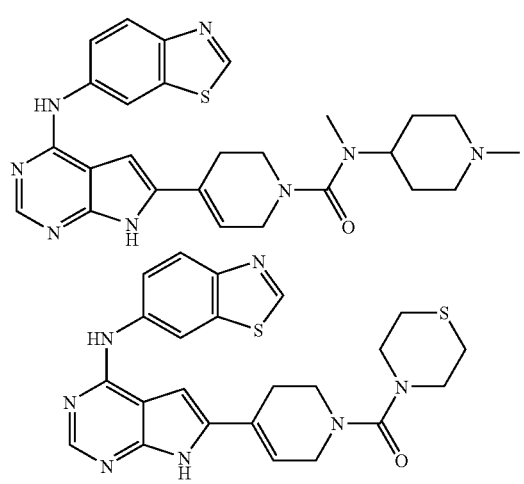

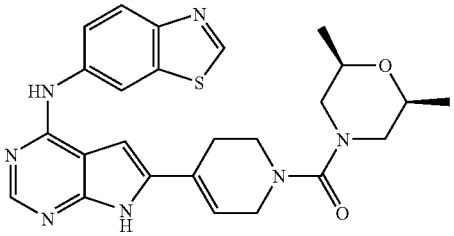
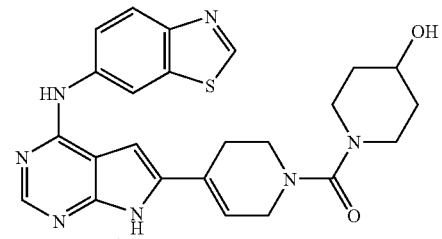
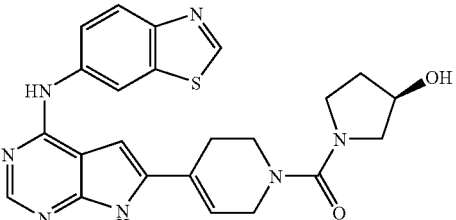
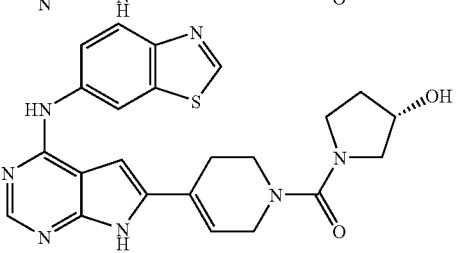

-continued
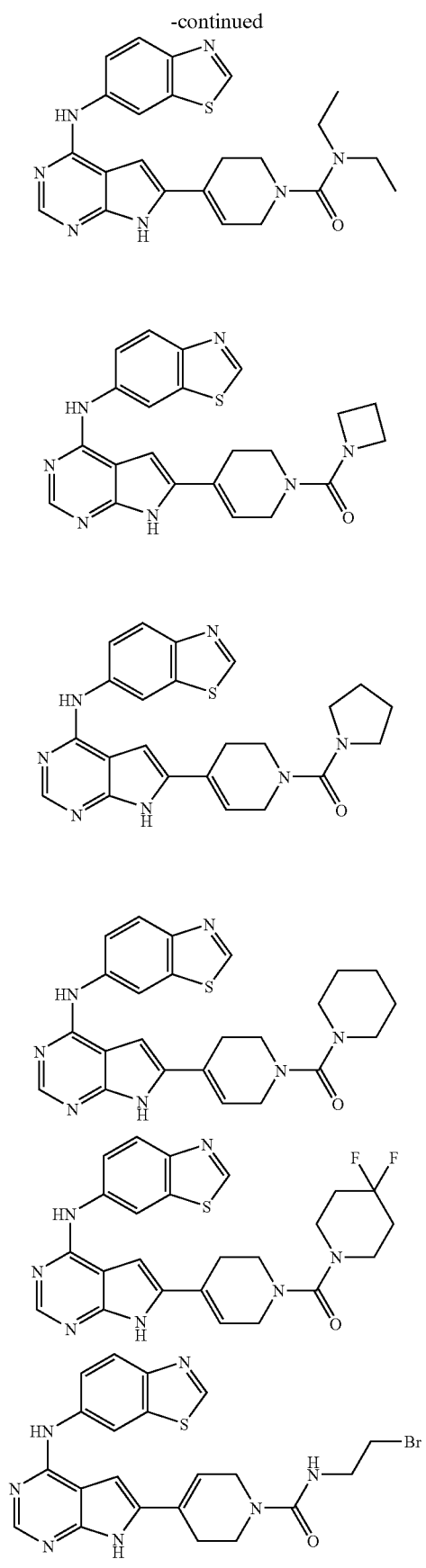
-continued
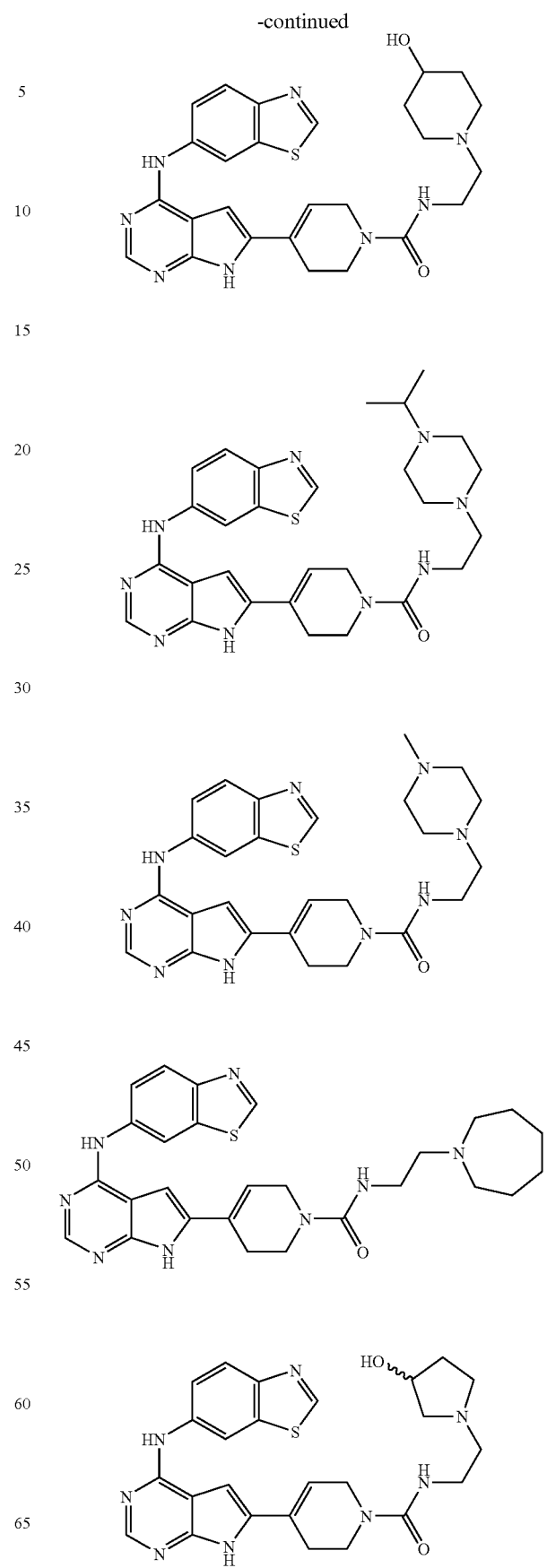

-continued
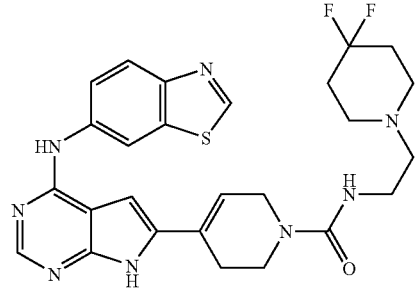
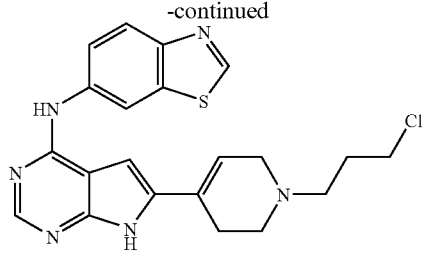
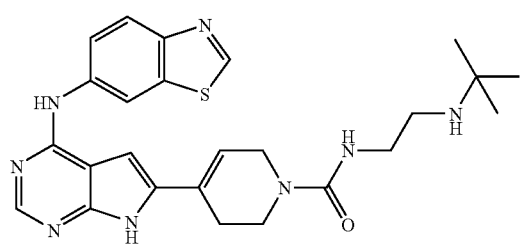
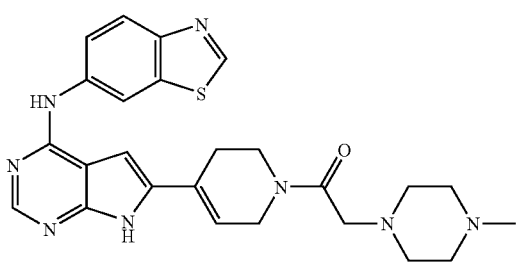
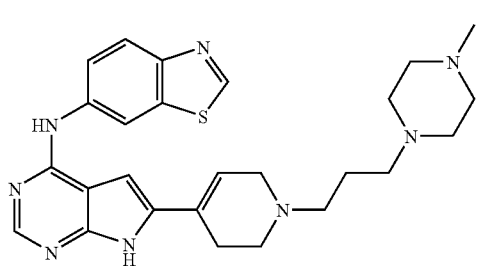
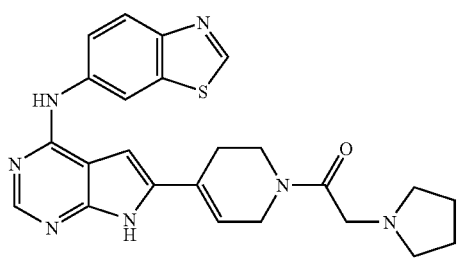
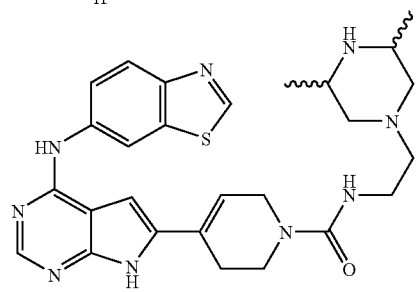
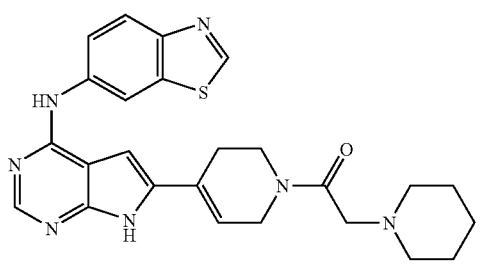
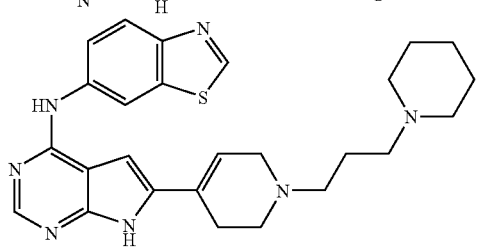
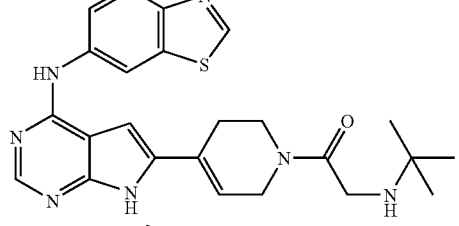
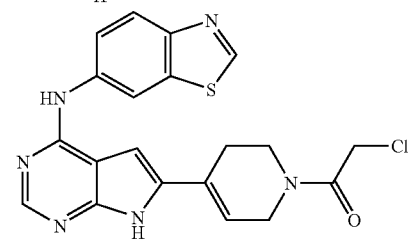
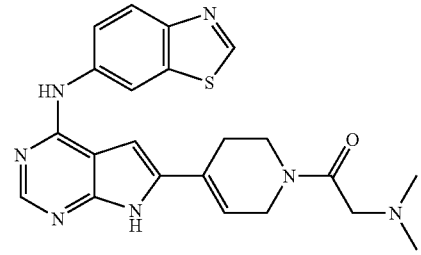

83
-continued
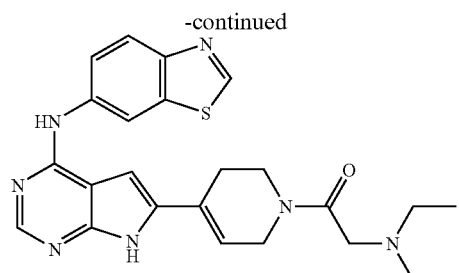
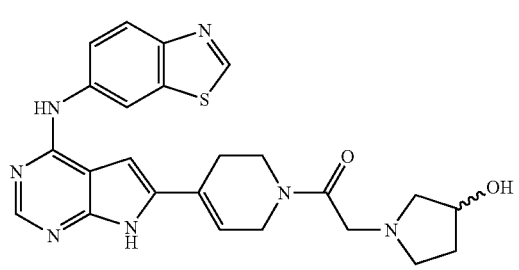
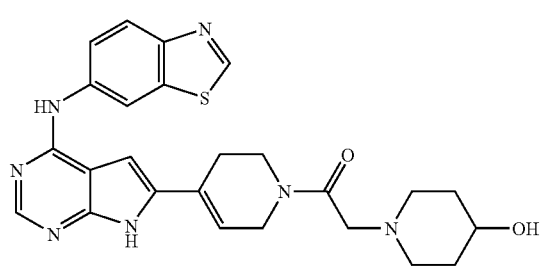
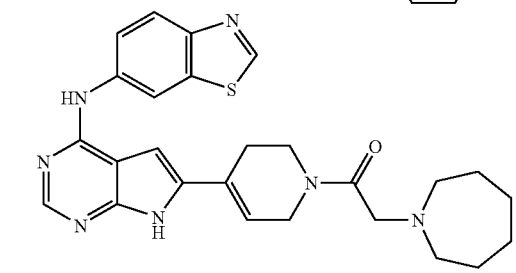
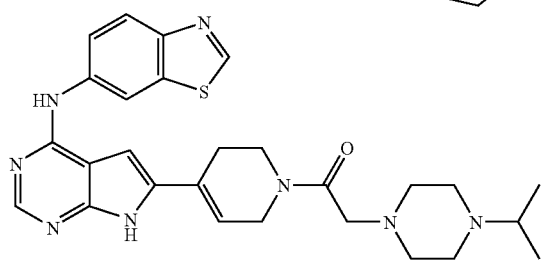
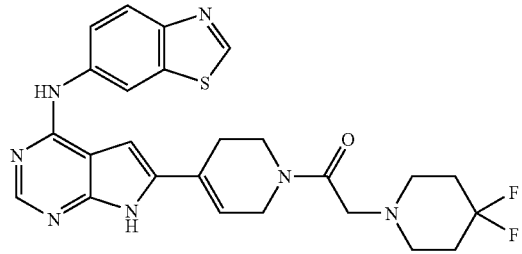
84
-continued
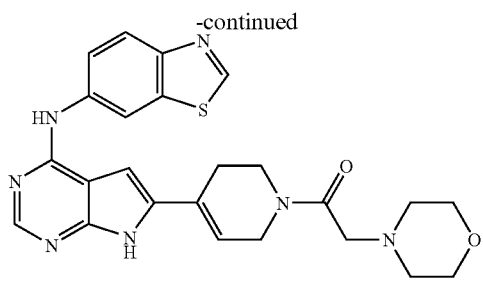
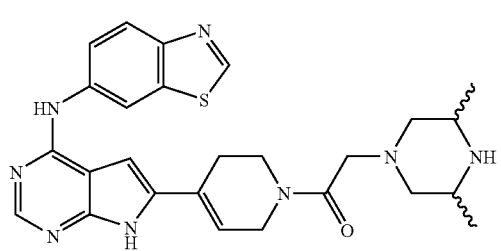
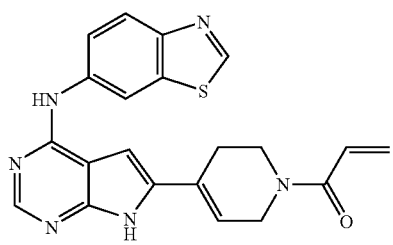
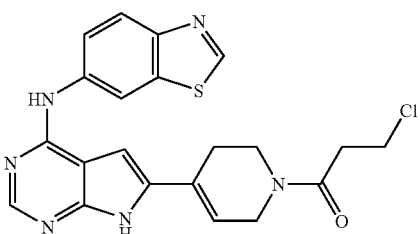
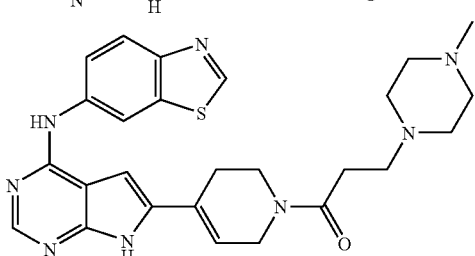
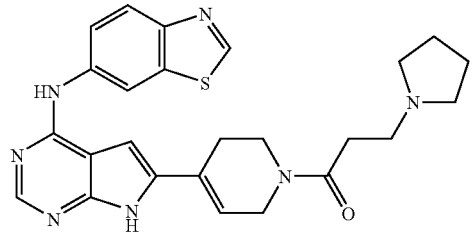

-continued
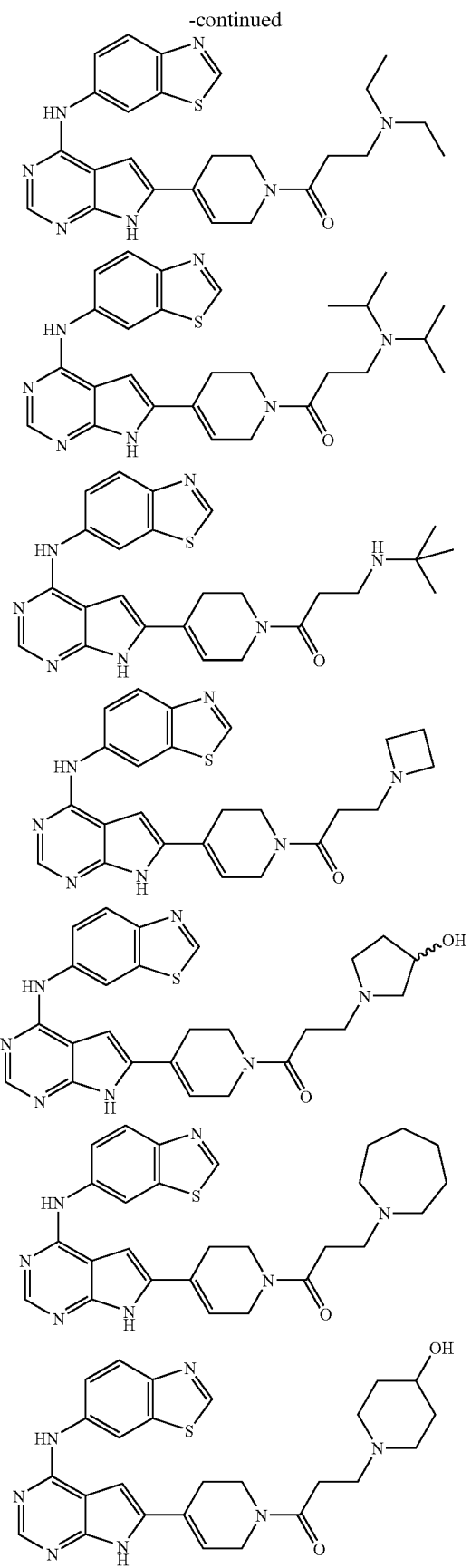
-continued
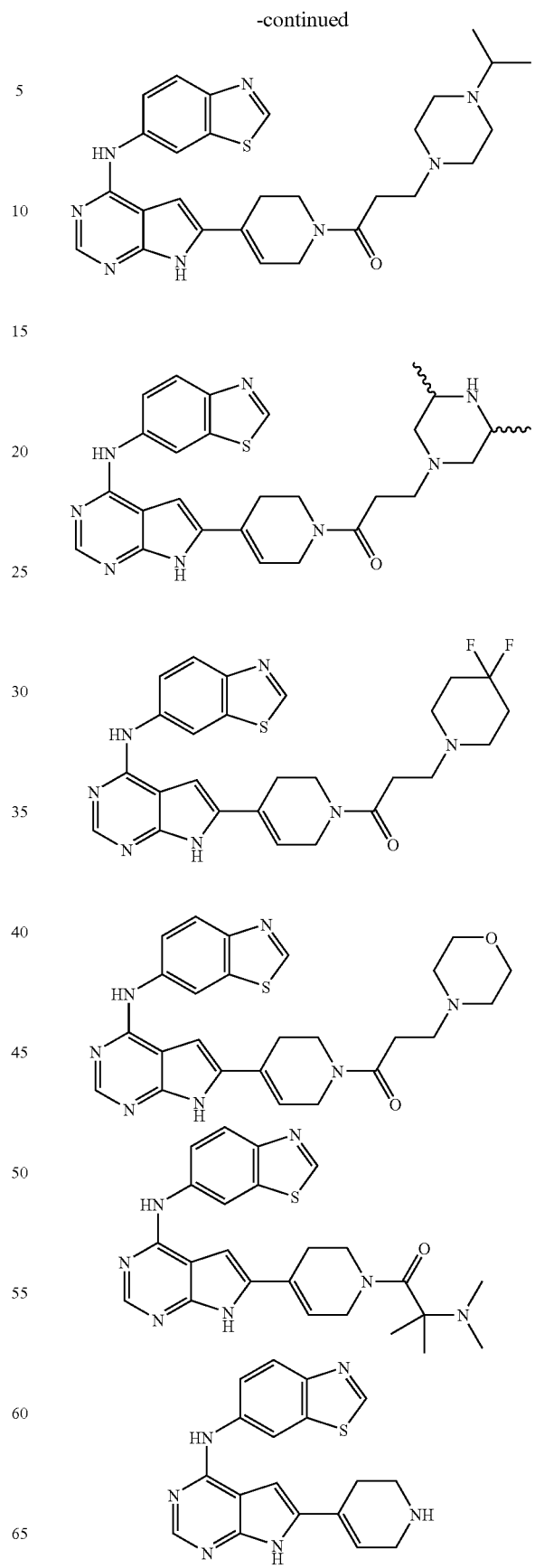

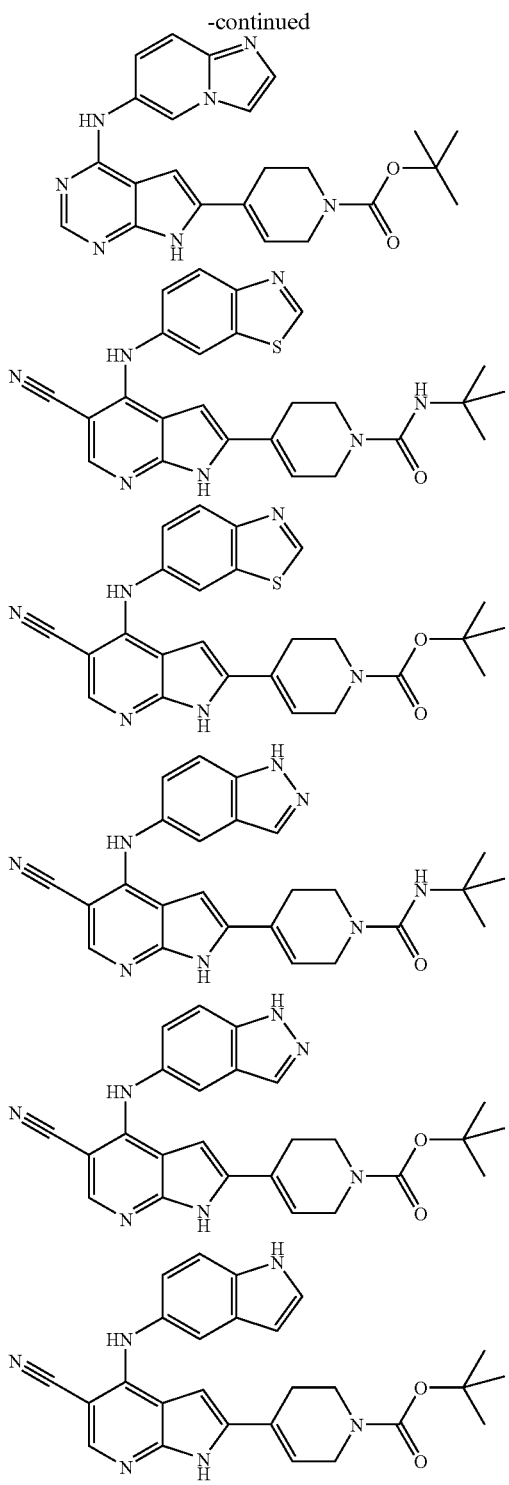

The compounds of the present invention include:
4-[4-(4-Fluoro-3-thiazol-5-ylphenylamino)-7H-pyrrolo[2,3-d]pyrimidin-6-yl]-3,6-dihydro-2H-pyridine-1-carboxylic acid tert-butyl ester;
4-[4-(4-Fluoro-3-thiazol-5-ylphenylamino)-7H-pyrrolo[2,3-d]pyrimidin-6-yl]-3,6-dihydro-2H-pyridine-1-carboxylic acid tert-butylamide;
4-{4-[4-Fluoro-3-(1H-imidazol-2-yl)-phenylamino]-7H-pyrrolo[2,3-d]-pyrimidin-6-yl}-3,6-dihydro-2H-pyridine-1-carboxylic acid tert-butyl ester;
4-{4-[4-Fluoro-3-(1H-imidazol-2-yl)-phenylamino]-7H-pyrrolo[2,3-d]-pyrimidin-6-yl}-3,6-dihydro-2H-pyridine-1-carboxylic acid tert-butylamide;
4-[4-(4-Fluoro-3-imidazol-1-ylphenylamino)-7H-pyrrolo[2,3-d]pyrimidin-6-yl]-3,6-dihydro-2H-pyridine-1-carboxylic acid tert-butyl ester;
4-[4-(4-Fluoro-3-imidazol-1-ylphenylamino)-7H-pyrrolo[2,3-d]pyrimidin-6-yl]-3,6-dihydro-2H-pyridine-1-carboxylic acid tert-butylamide;
4-{4-[4-Fluoro-3-(4-methylpiperazin-1-yl)-phenylamino]-7H-pyrrolo[2,3-d]pyrimidin-6-yl}-3,6-dihydro-2H-pyridine-1-carboxylic acid tert-butyl ester;
4-{4-[4-Fluoro-3-(4-methylpiperazin-1-yl)-phenylamino]-7H-pyrrolo[2,3-d]pyrimidin-6-yl}-3,6-dihydro-2H-pyridine-1-carboxylic acid tert-butylamide;
4-{4-[4-Fluoro-3-(1-methylazetidin-3-ylmethyl)-phenylamino]-7H-pyrrolo[2,3-d]pyrimidin-6-yl}-3,6-dihydro-2H-pyridine-1-carboxylic acid tert-butyl ester;
4-{4-[4-Fluoro-3-(1-methylazetidin-3-ylmethyl)-phenylamino]-7H-pyrrolo[2,3-d]pyrimidin-6-yl}-3,6-dihydro-2H-pyridine-1-carboxylic acid tert-butylamide;
4-{4-[4-Fluoro-3-(1-methylazetidin-3-yloxy)-phenylamino]-7H-pyrrolo[2,3-d]pyrimidin-6-yl}-3,6-dihydro-2H-pyridine-1-carboxylic acid tert-butyl ester;
4-{4-[4-Fluoro-3-(1-methylazetidin-3-yloxy)-phenylamino]-7H-pyrrolo[2,3-d]pyrimidin-6-yl}-3,6-dihydro-2H-pyridine-1-carboxylic acid tert-butyl ester;
4-{4-[4-Fluoro-3-(4-methylpiperazin-1-ylmethyl)-phenylamino]-7H-pyrrolo[2,3-d]pyrimidin-6-yl}-3,6-dihydro-2H-pyridine-1-carboxylic acid tert-butyl ester;
4-{4-[4-Fluoro-3-(4-methylpiperazin-1-ylmethyl)-phenylamino]-7H-pyrrolo[2,3-d]pyrimidin-6-yl}-3,6-dihydro-2H-pyridine-1-carboxylic acid tert-butylamide;
4-{4-[4-Fluoro-3-(1-methyl-1,2,3,6-tetrahydropyridin-4-yl)-phenylamino]-7H-pyrrolo[2,3-d]pyrimidin-6-yl}-3,6-dihydro-2H-pyridine-1-carboxylic acid tert-butyl ester;
4-{4-[4-Fluoro-3-(1-methyl-1,2,3,6-tetrahydropyridin-4-yl)-phenylamino]-7H-pyrrolo[2,3-d]pyrimidin-6-yl}-3,6-dihydro-2H-pyridine-1-carboxylic acid tert-butyl amide;
4-{4-[4-Fluoro-3-(1-methyl-2,5-dihydro-1H-pyrrol-3-yl)-phenylamino]-7H-pyrrolo[2,3-d]pyrimidin-6-yl}-3,6-dihydro-2H-pyridine-1-carboxylic acid tert-butyl ester;
4-{4-[4-Fluoro-3-(1-methyl-2,5-dihydro-1H-pyrrol-3-yl)-phenylamino]-7H-pyrrolo[2,3-d]pyrimidin-6-yl}-3,6-dihydro-2H-pyridine-1-carboxylic acid tert-butyl amide;
(S)-4-{4-[4-Fluoro-3-(1-methylpyrrolidin-3-yl)-phenylamino]-7H-pyrrolo[2,3-d]pyrimidin-6-yl}-3,6-dihydro-2H-pyridine-1-carboxylic acid tert-butyl ester;
(S)-4-{4-[4-Fluoro-3-(1-methylpyrrolidin-3-yl)-phenylamino]-7H-pyrrolo[2,3-d]pyrimidin-6-yl}-3,6-dihydro-2H-pyridine-1-carboxylic acid tert-butyl amide;
(R)-4-{4-[4-Fluoro-3-(1-methylpyrrolidin-3-yl)-phenylamino]-7H-pyrrolo[2,3-d]pyrimidin-6-yl}-3,6-dihydro-2H-pyridine-1-carboxylic acid tert-butyl ester;
(R)-4-{4-[4-Fluoro-3-(1-methylpyrrolidin-3-yl)-phenylamino]-7H-pyrrolo[2,3-d]pyrimidin-6-yl}-3,6-dihydro-2H-pyridine-1-carboxylic acid tert-butyl amide;

While the preferred groups for each variable have generally been listed above separately for each variable, preferred compounds of this invention include those in which several or each variable in Formula (I) is selected from the preferred, most preferred, especially or particularly listed groups for each variable. Therefore, this invention is intended to include all combinations of preferred, more preferred, most preferred, especially and particularly listed groups.

{4-[4-(Benzothiazol-6-ylamino)-7H-pyrrolo[2,3-d]pyrimidin-6-yl]-3,6-dihydro-2H-pyridin-1-yl}-(2,2,4-trimethylpiperazin-1-yl)-methanone;
{4-[4-(Benzothiazol-6-ylamino)-7H-pyrrolo[2,3-d]pyrimidin-6-yl]-3,6-dihydro-2H-pyridin-1-yl}-(2,4,5-trimethylpiperazin-1-yl)-methanone;
{4-[4-(Benzothiazol-6-ylamino)-7H-pyrrolo[2,3-d]pyrimidin-6-yl]-3,6-dihydro-2H-pyridin-1-yl}-(3,4,5-trimethylpiperazin-1-yl)-methanone;
{4-[4-(Benzothiazol-6-ylamino)-7H-pyrrolo[2,3-d]pyrimidin-6-yl]-3,6-dihydro-2H-pyridin-1-yl}-[4-(2,2,2-trifluoroethyl)-piperazin-1-yl]-methanone;
{4-[4-(Benzothiazol-6-ylamino)-7H-pyrrolo[2,3-d]pyrimidin-6-yl]-3,6-dihydro-2H-pyridin-1-yl}-(4-tert-butylpiperazin-1-yl)-methanone;
Benzothiazol-6-yl-[6-(3,6-dihydro-2H-[1,2']bipyridinyl-4-yl)-7H-pyrrolo[2,3-d]pyrimidin-4-yl]-amine;
Benzothiazol-6-yl-[6-(1-thiazol-2-yl-1,2,3,6-tetrahydropyridin-4-yl)-7H-pyrrolo[2,3-d]pyrimidin-4-yl]-amine;
Benzothiazol-6-yl-[6-(1-oxazol-2-yl-1,2,3,6-tetrahydropyridin-4-yl)-7H-pyrrolo[2,3-d]pyrimidin-4-yl]-amine;
4-[4-(3-Phenyl-3H-benzimidazol-5-ylamino)-7H-pyrrolo[2,3-d]pyrimidin-6-yl]-3,6-dihydro-2H-pyridine-1-carboxylic acid tert-butyl ester;
4-[4-(3-Phenyl-3H-benzimidazol-5-ylamino)-7H-pyrrolo[2,3-d]pyrimidin-6-yl]-3,6-dihydro-2H-pyridine-1-carboxylic acid tert-butylamide;
4-{4-[3-(2-Carbamoylphenyl)-3H-benzimidazol-5-ylamino]-7H-pyrrolo[2,3-d]pyrimidin-6-yl}-3,6-dihydro-2H-pyridine-1-carboxylic acid tert-butylamide;
4-{4-[3-(2-Carbamoylphenyl)-3H-benzimidazol-5-ylamino]-7H-pyrrolo[2,3-d]pyrimidin-6-yl}-3,6-dihydro-2H-pyridine-1-carboxylic acid tert-butyl ester;
4-{4-[3-(2-Aminoethyl)-3H-benzimidazol-5-ylamino]-7H-pyrrolo[2,3-d]pyrimidin-6-yl}-3,6-dihydro-2H-pyridine-1-carboxylic acid tert-butylamide;
4-{4-[3-(2-Aminoethyl)-3H-benzimidazol-5-ylamino]-7H-pyrrolo[2,3-d]pyrimidin-6-yl}-3,6-dihydro-2H-pyridine-1-carboxylic acid tert-butyl ester;
4-{4-[3-(2-Dimethylaminoethyl)-3H-benzimidazol-5-ylamino]-7H-pyrrolo[2,3-d]pyrimidin-6-yl}-3,6-dihydro-2H-pyridine-1-carboxylic acid tert-butylamide;
4-{4-[3-(2-Dimethylaminoethyl)-3H-benzimidazol-5-ylamino]-7H-pyrrolo[2,3-d]pyrimidin-6-yl}-3,6-dihydro-2H-pyridine-1-carboxylic acid tert-butyl ester;
4-{4-[3-(2-Acetylaminoethyl)-3H-benzimidazol-5-ylamino]-7H-pyrrolo[2,3-d]pyrimidin-6-yl}-3,6-dihydro-2H-pyridine-1-carboxylic acid tert-butylamide;
4-{4-[3-(2-Acetylaminoethyl)-3H-benzimidazol-5-ylamino]-7H-pyrrolo[2,3-d]pyrimidin-6-yl}-3,6-dihydro-2H-pyridine-1-carboxylic acid tert-butyl ester;
4-[4-(Imidazo[1,2-a]pyridin-6-ylamino)-7H-pyrrolo[2,3-d]pyrimidin-6-yl]-3,6-dihydro-2H-pyridine-1-carboxylic acid tert-butylamide;
4-[4-(Imidazo[1,2-a]pyridin-6-ylamino)-7H-pyrrolo[2,3-d]pyrimidin-6-yl]-3,6-dihydro-2H-pyridine-1-carboxylic acid tert-butyl ester;
4-[4-(3-Methylimidazo[1,2-a]pyridin-6-ylamino)-7H-pyrrolo[2,3-d]-pyrimidin-6-yl]-3,6-dihydro-2H-pyridine-1-carboxylic acid tert-butylamide;
4-[4-(3-Methylimidazo[1,2-a]pyridin-6-ylamino)-7H-pyrrolo[2,3-d]-pyrimidin-6-yl]-3,6-dihydro-2H-pyridine-1-carboxylic acid tert-butyl ester;
4-[4-(3-Phenylimidazo[1,2-a]pyridin-6-ylamino)-7H-pyrrolo[2,3-d]-pyrimidin-6-yl]-3,6-dihydro-2H-pyridine-1-carboxylic acid tert-butylamide;
4-[4-(3-Phenylimidazo[1,2-a]pyridin-6-ylamino)-7H-pyrrolo[2,3-d]-pyrimidin-6-yl]-3,6-dihydro-2H-pyridine-1-carboxylic acid tert-butyl ester;
4-{4-[3-(2-Carbamoylphenyl)-imidazo[1,2-a]pyridin-6-ylamino]-7H-pyrrolo[2,3-d]pyrimidin-6-yl}-3,6-dihydro-2H-pyridine-1-carboxylic acid tert-butylamide;
4-{4-[3-(2-Carbamoylphenyl)-imidazo[1,2-a]pyridin-6-ylamino]-7H-pyrrolo[2,3-d]pyrimidin-6-yl}-3,6-dihydro-2H-pyridine-1-carboxylic acid tert-butyl ester;
4-{4-[3-(2-Dimethylaminoethyl)-imidazo[1,2-a]pyridin-6-ylamino]-7H-pyrrolo[2,3-d]pyrimidin-6-yl}-3,6-dihydro-2H-pyridine-1-carboxylic acid tert-butylamide;
4-{4-[3-(2-Dimethylaminoethyl)-imidazo[1,2-a]pyridin-6-ylamino]-7H-pyrrolo[2,3-d]pyrimidin-6-yl}-3,6-dihydro-2H-pyridine-1-carboxylic acid tert-butyl ester;
4-{4-[3-(2-Acetylaminoethyl)-imidazo[1,2-a]pyridin-6-ylamino]-7H-pyrrolo[2,3-d]pyrimidin-6-yl}-3,6-dihydro-2H-pyridine-1-carboxylic acid tert-butylamide;
4-{4-[3-(2-Acetylaminoethyl)-imidazo[1,2-a]pyridin-6-ylamino]-7H-pyrrolo[2,3-d]pyrimidin-6-yl}-3,6-dihydro-2H-pyridine-1-carboxylic acid tert-butyl ester;
4-[4-(3-Dimethylaminomethylimidazo[1,2-a]pyridin-6-ylamino)-7H-pyrrolo[2,3-d]pyrimidin-6-yl]-3,6-dihydro-2H-pyridine-1-carboxylic acid tert-butylamide;
4-[4-(3-Dimethylaminomethylimidazo[1,2-a]pyridin-6-ylamino)-7H-pyrrolo[2,3-d]pyrimidin-6-yl]-3,6-dihydro-2H-pyridine-1-carboxylic acid tert-butyl ester;
4-[4-(7-Aminomethyl-1H-indazol-5-ylamino)-7H-pyrrolo[2,3-d]pyrimidin-6-yl]-3,6-dihydro-2H-pyridine-1-carboxylic acid tert-butylamide;
4-[4-(7-Aminomethyl-1H-indazol-5-ylamino)-7H-pyrrolo[2,3-d]pyrimidin-6-yl]-3,6-dihydro-2H-pyridine-1-carboxylic acid tert-butyl ester;
4-[4-(7-Aminomethyl-1-methyl-1H-indazol-5-ylamino)-7H-pyrrolo[2,3-d]pyrimidin-6-yl]-3,6-dihydro-2H-pyridine-1-carboxylic acid tert-butylamide;
4-[4-(7-Aminomethyl-1-methyl-1H-indazol-5-ylamino)-7H-pyrrolo[2,3-d]pyrimidin-6-yl]-3,6-dihydro-2H-pyridine-1-carboxylic acid tert-butyl ester;
4-[4-(7-Dimethylaminomethyl-1-methyl-1H-indazol-5-ylamino)-7H-pyrrolo[2,3-d]pyrimidin-6-yl]-3,6-dihydro-2H-pyridine-1-carboxylic acid tert-butylamide;
4-[4-(7-Dimethylaminomethyl-1-methyl-1H-indazol-5-ylamino)-7H-pyrrolo[2,3-d]pyrimidin-6-yl]-3,6-dihydro-2H-pyridine-1-carboxylic acid tert-butyl ester;
4-[4-(7-Dimethylaminomethyl-1H-indazol-5-ylamino)-7H-pyrrolo[2,3-d]pyrimidin-6-yl]-3,6-dihydro-2H-pyridine-1-carboxylic acid tert-butylamide;
4-[4-(7-Dimethylaminomethyl-1H-indazol-5-ylamino)-7H-pyrrolo[2,3-d]pyrimidin-6-yl]-3,6-dihydro-2H-pyridine-1-carboxylic acid tert-butyl ester;
4-{4-[7-(2-Dimethylaminoethyl)-1H-indazol-5-ylamino]-7H-pyrrolo[2,3-d]pyrimidin-6-yl}-3,6-dihydro-2H-pyridine-1-carboxylic acid tert-butylamide;
4-{4-[7-(2-Dimethylaminoethyl)-1H-indazol-5-ylamino]-7H-pyrrolo[2,3-d]pyrimidin-6-yl}-3,6-dihydro-2H-pyridine-1-carboxylic acid tert-butyl ester;
4-{4-[7-(2-Dimethylaminoethyl)-1-methyl-1H-indazol-5-ylamino]-7H-pyrrolo[2,3-d]pyrimidin-6-yl}-3,6-dihydro-2H-pyridine-1-carboxylic acid tert-butylamide;
4-{4-[7-(2-Dimethylaminoethyl)-1-methyl-1H-indazol-5-ylamino]-7H-pyrrolo[2,3-d]pyrimidin-6-yl}-3,6-dihydro-2H-pyridine-1-carboxylic acid tert-butyl ester;
4-[4-(Imidazo[1,5-a]pyridin-6-ylamino)-7H-pyrrolo[2,3-d]pyrimidin-6-yl]-3,6-dihydro-2H-pyridine-1-carboxylic acid tert-butylamide;

4-[4-(Imidazo[1,5-a]pyridin-6-ylamino)-7H-pyrrolo[2,3-d]pyrimidin-6-yl]-3,6-dihydro-2H-pyridine-1-carboxylic acid tert-butyl ester;
4-[4-(3-Methylimidazo[1,5-a]pyridin-6-ylamino)-7H-pyrrolo[2,3-d]-pyrimidin-6-yl]-3,6-dihydro-2H-pyridine-1-carboxylic acid tert-butylamide;
4-[4-(3-Methylimidazo[1,5-a]pyridin-6-ylamino)-7H-pyrrolo[2,3-d]-pyrimidin-6-yl]-3,6-dihydro-2H-pyridine-1-carboxylic acid tert-butyl ester;
4-[4-(1-Methylimidazo[1,5-a]pyridin-6-ylamino)-7H-pyrrolo[2,3-d]-pyrimidin-6-yl]-3,6-dihydro-2H-pyridine-1-carboxylic acid tert-butylamide;
4-[4-(1-Methylimidazo[1,5-a]pyridin-6-ylamino)-7H-pyrrolo[2,3-d]-pyrimidin-6-yl]-3,6-dihydro-2H-pyridine-1-carboxylic acid tert-butyl ester;
4-[4-(Imidazo[1,5-a]pyridin-7-ylamino)-7H-pyrrolo[2,3-d]pyrimidin-6-yl]-3,6-dihydro-2H-pyridine-1-carboxylic acid tert-butylamide;
4-[4-(Imidazo[1,5-a]pyridin-7-ylamino)-7H-pyrrolo[2,3-d]pyrimidin-6-yl]-3,6-dihydro-2H-pyridine-1-carboxylic acid tert-butyl ester;
4-[4-(3-Methylimidazo[1,5-a]pyridin-7-ylamino)-7H-pyrrolo[2,3-d]-pyrimidin-6-yl]-3,6-dihydro-2H-pyridine-1-carboxylic acid tert-butylamide;
4-[4-(3-Methylimidazo[1,5-a]pyridin-7-ylamino)-7H-pyrrolo[2,3-d]-pyrimidin-6-yl]-3,6-dihydro-2H-pyridine-1-carboxylic acid tert-butyl ester;
4-[4-(1-Methylimidazo[1,5-a]pyridin-7-ylamino)-7H-pyrrolo[2,3-d]-pyrimidin-6-yl]-3,6-dihydro-2H-pyridine-1-carboxylic acid tert-butylamide;
4-[4-(1-Methylimidazo[1,5-a]pyridin-7-ylamino)-7H-pyrrolo[2,3-d]-pyrimidin-6-yl]-3,6-dihydro-2H-pyridine-1-carboxylic acid tert-butyl ester;
4-[4-(Benzothiazol-6-ylamino)-7H-pyrrolo[2,3-d]pyrimidin-6-yl]-3,6-dihydro-2H-pyridine-1-carboxylic acid (2-hydroxy-1,1-dimethylethyl)-amide;
4-[4-(1-Methyl-1H-indazol-5-ylamino)-7H-pyrrolo[2,3-d]pyrimidin-6-yl]-3,6-dihydro-2H-pyridine-1-carboxylic acid (2-hydroxy-1,1-dimethylethyl)-amide;
4-[4-(Benzothiazol-6-ylamino)-7H-pyrrolo[2,3-d]pyrimidin-6-yl]-3,6-dihydro-2H-pyridine-1-carboxylic acid (2-methoxy-1,1-dimethylethyl)-amide;
4-[4-(1-Methyl-1H-indazol-5-ylamino)-7H-pyrrolo[2,3-d]pyrimidin-6-yl]-3,6-dihydro-2H-pyridine-1-carboxylic acid (2-methoxy-1,1-dimethylethyl)-amide;
4-[4-(Benzothiazol-6-ylamino)-7H-pyrrolo[2,3-d]pyrimidin-6-yl]-3,6-dihydro-2H-pyridine-1-carboxylic acid (2-dimethylamino-1,1-dimethylethyl)-amide;
4-[4-(1-Methyl-1H-indazol-5-ylamino)-7H-pyrrolo[2,3-d]pyrimidin-6-yl]-3,6-dihydro-2H-pyridine-1-carboxylic acid (2-dimethylamino-1,1-dimethylethyl)-amide;
4-[4-(Benzothiazol-6-ylamino)-7H-pyrrolo[2,3-d]pyrimidin-6-yl]-3,6-dihydro-2H-pyridine-1-carboxylic acid (1,1-dimethyl-2-pyrrolidin-1-ylethyl)-amide;
4-[4-(1-Methyl-1H-indazol-5-ylamino)-7H-pyrrolo[2,3-d]pyrimidin-6-yl]-3,6-dihydro-2H-pyridine-1-carboxylic acid (1,1-dimethyl-2-pyrrolidin-1-ylethyl)-amide;
4-[4-(Benzothiazol-6-ylamino)-7H-pyrrolo[2,3-d]pyrimidin-6-yl]-3,6-dihydro-2H-pyridine-1-carboxylic acid (1,1-dimethyl-2-morpholin-4-ylethyl)-amide;
4-[4-(1-Methyl-1H-indazol-5-ylamino)-7H-pyrrolo[2,3-d]pyrimidin-6-yl]-3,6-dihydro-2H-pyridine-1-carboxylic acid (1,1-dimethyl-2-morpholin-4-ylethyl)-amide;
4-[4-(1H-Indol-5-ylamino)-7H-pyrrolo[2,3-d]pyrimidin-6-yl]-3,6-dihydro-2H-pyridine-1-carboxylic acid tert-butylamide;
4-[4-(Quinolin-6-ylamino)-7H-pyrrolo[2,3-d]pyrimidin-6-yl]-3,6-dihydro-2H-pyridine-1-carboxylic acid tert-butylamide;
(Hexahydropyrrolo[1,2-a]pyrazin-2-yl)-{4-[4-(imidazo[1,2-a]pyridin-6-ylamino)-7H-pyrrolo[2,3-d]pyrimidin-6-yl]-3,6-dihydro-2H-pyridin-1-yl}-methanone;
(Hexahydropyrrolo[1,2-a]pyrazin-2-yl)-{4-[4-(3-methyl-3H-benzoimidazol-5-ylamino)-7H-pyrrolo[2,3-d]pyrimidin-6-yl]-3,6-dihydro-2H-pyridin-1-yl}-methanone;
(Hexahydropyrrolo[1,2-a]pyrazin-2-yl)-{4-[4-(1-methyl-1H-indazol-5-ylamino)-7H-pyrrolo[2,3-d]pyrimidin-6-yl]-3,6-dihydro-2H-pyridin-1-yl}-methanone;
{4-[4-(Benzothiazol-6-ylamino)-7H-pyrrolo[2,3-d]pyrimidin-6-yl]-3,6-dihydro-2H-pyridin-1-yl}-(hexahydropyrrolo[1,2-a]pyrazin-2-yl)-methanone.

As used herein, unless stated otherwise, "alkyl" as well as other groups having the prefix "alk" such as, for example, alkoxy, alkanyl, alkenyl, alkynyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains having at least one unsaturated carbon-carbon bond.

As used herein, for example, "$C_{0-4}$alkyl" is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

As used herein, the ">" symbol in front of a nitrogen atom refers to two bonds not to the same atom (not a double bond to the nitrogen).

The terms "cycloalkyl" and "carbocyclic ring" mean carbocycles containing no heteroatoms, and include mono-, bi-, and tricyclic saturated carbocycles, as well as fused and bridged systems. Such fused ring systems can include one ring that is partially or fully unsaturated, such as a benzene ring, to form fused ring systems, such as benzofused carbocycles. Cycloalkyl includes such fused ring systems as spirofused ring systems. Examples of cycloalkyl and carbocyclic rings include C3-10cycloalkyl groups, particularly C3-8cycloalkyl groups, such as cyclopropyl, cyclobutyl, cyclopentyl, cyclohexyl, and decahydronaphthalene, adamantane, indanyl, 1,2,3,4-tetrahydronaphthalene and the like.

The term "halogen" includes fluorine, chlorine, bromine, and iodine atoms.

The term "carbamoyl" unless specifically described otherwise means —C(O)—NH— or —NH—C(O)—.

The term "aryl" is well known to chemists. The preferred aryl groups are phenyl and naphthyl, more preferably phenyl.

The term "hetaryl" is well known to chemists. The term includes 5- or 6-membered heteroaryl rings containing 1-4 heteroatoms chosen from oxygen, sulfur, and nitrogen in which oxygen and sulfur are not next to each other. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The term "hetaryl" includes hetaryl rings with fused carbocyclic ring systems that are partially or fully unsaturated, such as a benzene ring, to form a benzofused hetaryl. For example, benzimidazole, benzoxazole, benzothiazole, benzofuran, quinoline, isoquinoline, quinoxaline, and the like. The term "hetaryl" also includes fused 5-6, 5-5, 6-6 ring systems, optionally possessing one nitrogen atom at a ring junction. Examples of such hetaryl rings include, but are not limited to, pyrrolopyrimidinyl, imidazo[1,2-a]pyridinyl, imidazo[2,1-b]thiazolyl, imidazo[4,5-b]pyridine, pyrrolo[2,1-f][1,2,4]triazinyl, and the like. Hetaryl groups may be attached to other groups through their carbon atoms or the heteroatom(s), if applicable. For example, pyrrole may be connected at the nitrogen atom or at any of the carbon atoms.

Unless otherwise stated, the terms "heterocyclic ring", "heterocyclyl" and "heterocycle" are equivalent, and include 4-10-membered, e.g. 5-membered, saturated or partially saturated rings containing 1-4 heteroatoms chosen from oxygen, sulfur, and nitrogen. The sulfur and oxygen heteroatoms are not directly attached to one another. Any nitrogen heteroatoms in the ring may optionally be substituted with $C_{1-4}$alkyl. Examples of heterocyclic rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, N-methylpiperidine, azepane, 1,4-diazapane, azocane, [1,3]dioxane, oxazolidine, piperazine, homopiperazine, morpholine, thiomorpholine, 1,2,3,6-tetrahydropyridine and the like. Other examples of heterocyclic rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocyclic rings. The term "heterocyclic" also includes fused ring systems and can include a carbocyclic ring that is partially or fully unsaturated, such as a benzene ring, to form benzofused heterocycles. For example, 3,4-dihydro-1,4-benzodioxine, tetrahydroquinoline, tetrahydroisoquinoline and the like.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula (I) is shown without a definitive stereochemistry at certain positions. The present invention includes all stereoisomers of Formula (I) and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of Formula (I) exists, the present invention includes any possible tautomers and pharmaceutically acceptable salts thereof, and mixtures thereof, except where specifically stated otherwise.

When the compound of Formula (I) and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The invention also encompasses a pharmaceutical composition that is comprised of a compound of Formula (I), or a pharmaceutically acceptable salt thereof, in combination with a pharmaceutically acceptable carrier.

Preferably the composition is comprised of a pharmaceutically acceptable carrier and a non-toxic therapeutically effective amount of a compound of Formula (I), or a pharmaceutically acceptable salt thereof.

Moreover, within this preferred embodiment, the invention encompasses a pharmaceutical composition for the treatment of disease by inhibiting glycogen phosphorylase, resulting in the prophylactic or therapeutic treatment of diabetes, hyperglycemia, hypercholesterolemia, hyperinsulinemia, hyperlipidemia, hypertension, atherosclerosis or tissue ischemia e.g. myocardial ischemia comprising a pharmaceutically acceptable carrier and a non-toxic therapeutically effective amount of compound of Formula (I), or a pharmaceutically acceptable salt thereof.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include arginine, betaine, caffeine, choline, N'N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

Since the compounds of Formula (I) are intended for pharmaceutical use they are preferably provided in substantially pure form, for example at least 60% pure, more suitably at least 75% pure especially at least 98% pure (% are on a weight for weight basis).

The pharmaceutical compositions of the present invention comprise a compound represented by Formula (I), or a pharmaceutically acceptable salt thereof, as an active ingredient, a pharmaceutically acceptable carrier and optionally other therapeutic ingredients or adjuvants. The compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The compositions are preferably suitable for oral administration. The pharmaceutical compositions may be conveniently presented in unit dosage form and prepared by any of the methods well known in the art of pharmacy.

In practice, the compounds of Formula (I), or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, sachets or tablets each containing a predetermined amount of the active ingredient. Further, the compositions can be presented as a powder, as granules, as a solution, as a suspension in an aqueous liquid, as a nonaqueous liquid, as an oil-in-water emulsion, or as a water-in-oil liquid emulsion. In addition to the common dosage forms set out above, the compounds of Formula (I), or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound of Formula (I) or a pharmaceutically acceptable salt thereof. The compounds of Formula (I), or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each sachet or capsule preferably contains from about 0.05 mg to about 5 g of the active ingredient.

For example, a formulation intended for oral administration to humans may contain from about 0.5 mg to about 5 g of active agent, compounded with an appropriate and convenient amount of carrier material, which may vary from about 5 to about 95% of the total composition. Unit dosage forms will generally contain from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound of Formula (I), or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of Formula (I), or a pharmaceutically acceptable salt thereof, may also be prepared in powder or liquid concentrate form.

Generally, dosage levels on the order of 0.01 mg/kg to about 150 mg/kg of body weight per day are useful in the treatment of the above-indicated conditions, or alternatively about 0.5 mg to about 7 g per patient per day. For example, lung cancer may be effectively treated by the administration of from about 0.01 to 50 mg of the compound per kilogram of body weight per day, or alternatively about 0.5 mg to about 3.5 g per patient per day. Similarly, breast cancer may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of Formula (I) and pharmaceutically acceptable salts thereof, may be used in the treatment of diseases or conditions in which the Abl, Aurora-A, Blk, c-Raf, cSRC, Src, PRK2, FGFR3, Flt3, Lck, Mek1, PDK-1, GSK3β, EGFR, p70S6K, BMX, SGK, CaMKII, Tie-2, Ret, Ron, IGF-1R, or KDR kinases plays a role.

Thus the invention also provides a method for the treatment of a disease or condition in which the Abl, Aurora-A, Blk, c-Raf, cSRC, Src, PRK2, FGFR3, Flt3, Lck, Mek1, PDK-1, GSK3#, EGFR, p70S6K, BMX, SGK, CaMKII, Tie-2, Ret, Ron, IGF-1R, or KDR kinases plays a role comprising a step of administering to a subject in need thereof an effective amount of a compound of Formula (I), or a pharmaceutically acceptable salt thereof.

Diseases or conditions in which the Abl, Aurora-A, Blk, c-Raf, cSRC, Src, PRK2, FGFR3, Flt3, Lck, Mek1, PDK-1, GSK3β, EGFR, p70S6K, BMX, SGK, CaMKII, Tie-2, Ret, Ron, IGF-1R, or KDR kinases plays a role include lung, breast, prostate, pancreatic, head and neck cancers, as well as leukemia.

The invention also provides a method for the treatment of cancers of the lung, breast, prostate, pancreas, head, neck or blood comprising a step of administering to a subject in need thereof an effective amount of a compound of Formula (I), or a pharmaceutically acceptable salt thereof.

The invention also provides a method for the treatment of lung cancer, breast cancer, prostate cancer, pancreatic cancer, head cancer, neck cancer, or leukemia in a human demonstrating such cancers comprising a step of administering to a subject in need thereof an effective amount of a compound of Formula (I), or a pharmaceutically acceptable salt thereof.

The invention also provides a method for the treatment of cancers of the lung, breast, prostate, pancreas, head, neck, or blood comprising a step of administering to a patient in need thereof an effective amount of a compound of Formula (I), or a pharmaceutically acceptable salt thereof.

The invention also provides the use of a compound of Formula (I), or a pharmaceutically acceptable salt thereof, in the treatment of a condition as defined above.

The invention also provides the use of a compound of Formula (I), or a pharmaceutically acceptable salt thereof, in the manufacture of a medicament for the treatment of a condition as defined above.

In the methods of the invention the term "treatment" includes both therapeutic and prophylactic treatment.

The compounds of Formula (I), or pharmaceutically acceptable salts thereof, may be administered alone or in combination with one or more other therapeutically active compounds. The other therapeutically active compounds may be for the treatment of the same disease or condition as the compounds of Formula (I) or a different disease or condition.

The therapeutically active compounds may be administered simultaneously, sequentially or separately.

The compounds of Formula (I) may be administered with other active compounds for the treatment of cancers of the lung, breast, prostate, pancreas, head, neck, or blood—for example AVASTIN, IRESSA, TARCEVA, ERBITUX, or cisplatin.

The compounds of Formula (I) may also be administered in combination with AVASTIN, IRESSA, TARCEVA, ERBITUX, or cisplatin.

The compounds of Formula (I) may exhibit advantageous properties compared to known kinase inhibitors, for example, the compounds may exhibit improved solubility thus improving absorption properties and bioavailability. Furthermore the compounds of Formula (I) may exhibit further advantageous properties such as reduced inhibition of cytochrome P450 enzymes, meaning that they are less likely to cause adverse drug-drug interactions than known kinase inhibitors.

EXPERIMENTAL

Scheme 1-Scheme 5, the EXAMPLES, and INTERMEDIATES serve to demonstrate how to synthesize compounds of this invention, but in no way limit the invention.

The following abbreviations are used:

| | |
|---|---|
| NMR | Nuclear magnetic resonance |
| LC/MS | Liquid chromatography mass spectrometry |
| LDA | Lithium diisopropylamide |
| DCM | Dichloromethane |
| THF | Tetrahydrofuran |
| MeCN | Acetonitrile |
| DMSO | Dimethylsulfoxide |
| BOC or Boc | t-butyloxycarbonyl |
| PyBrop | Bromotri(pyrrolidino)phosphonium hexafluorophosphate |
| DMF | N,N-dimethylformamide |
| PS-DIEA | Polymer supported diisopropylethylamine |
| EDCI or EDC | 1-(3-dimethylaminopropyl)-3-ethylcarbodiimide |
| HOBt | 1-hydroxybenzotriazole |
| DMAP | 4-dimethylaminopyridine |
| HATU | O-(7-azabenzotriazol-1-yl)-N,N,N',N'-tetra-methyluronium-hexafluorophosphate |
| Ex | Example |
| TLC | Thin layer chromatography |
| Min or mins | minute(s) |
| Hr, hrs, or h | hour(s) |
| RT, rt, or r.t | room temperature |
| Rt, or $t_R$ | Retention time |

DESCRIPTION OF THE CHEMISTRY

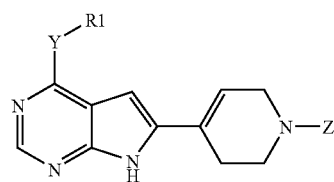

I-A

Compound of Formula I-A is equal to compound of Formula I wherein X=N,
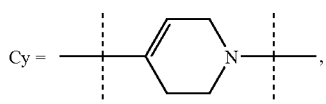
and Y, R1, and Z are as defined above for Formula (I).
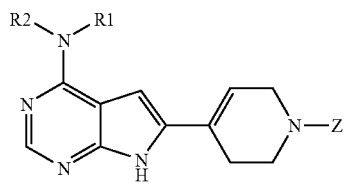
Compound of Formula I-B is equal to compound of Formula I wherein X=N,
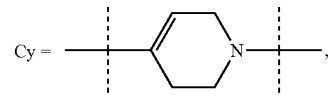
YR1=NR1R2, and R1, R2, and Z are as defined above for Formula (I).
Scheme 1 below describes how compounds of Formula I-A may be synthesized.
Scheme 1
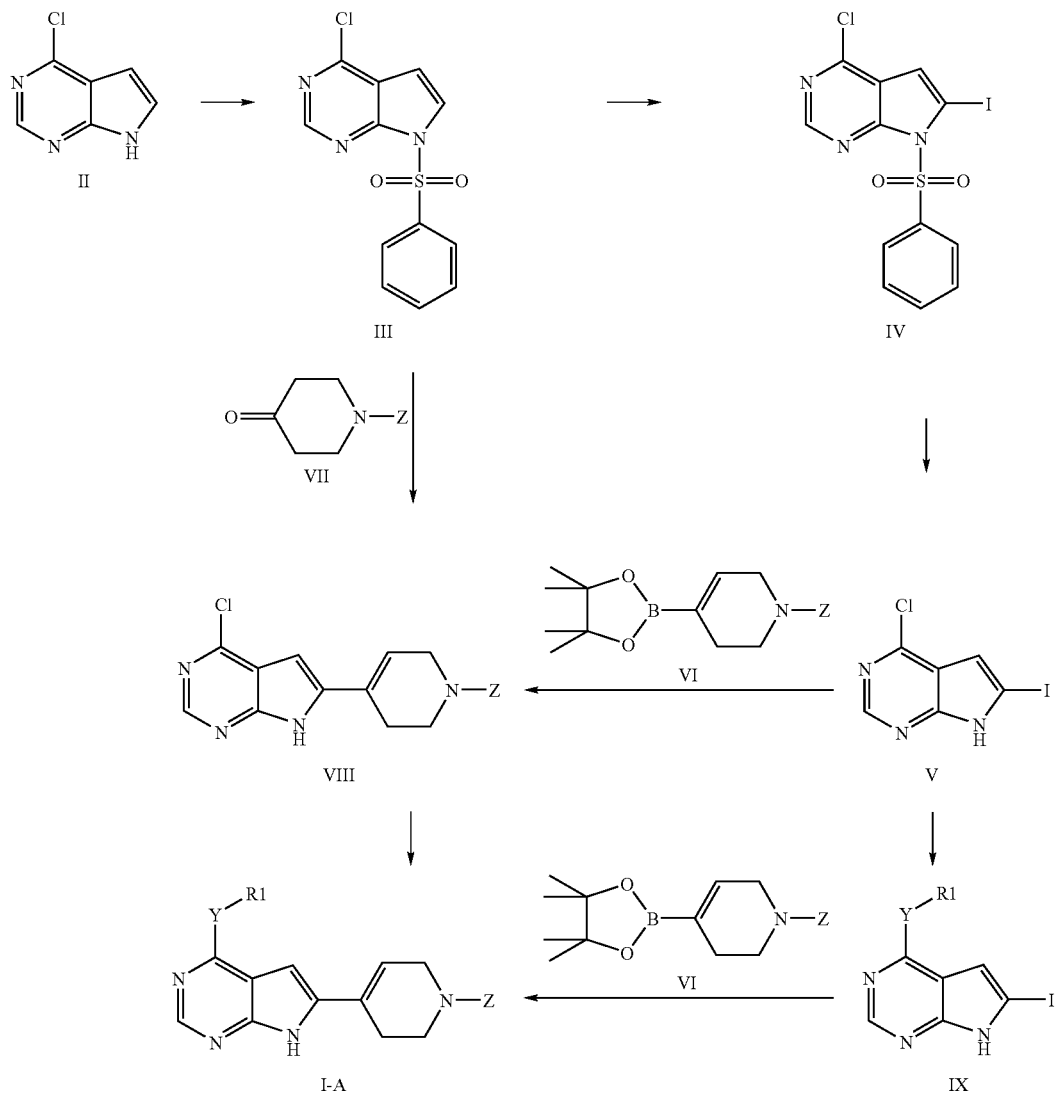

Compound of Formula II is commercially available or can be prepared by methods described in the literature (e.g., *J. Chem. Soc.* 1960, 131-138; *J. Heterocyclic Chem.* 1969, 6(2), 207-213). A benzenesulfonyl group is introduced under typical reaction conditions with typical bases and sulfonylating reagents in typical solvents to give compound of Formula III. Typical reagents and solvents include, but are not limited to, sodium hydride in DMF or THF, alkoxides such as potassium tert-butoxide in THF, a biphasic system consisting of aqueous NaOH and methylene chloride. Typical sulfonylating reagents are, e.g., benzenesulfonyl chloride or the corresponding anhydride. Typical conditions include, but are not limited to, −20° C. to RT, at atmospheric pressure, with equimolar amounts of base and sulfonylating reagent, although larger amounts can be used if desirable. Compounds of Formula III can be iodinated under typical metallation/iodination conditions to yield compounds of Formula IV. Typical conditions include, but are not limited to, adding a lithium amide base, such as LDA or LiTMP, to a cooled (about −78° C. to about 0° C.) solution of compound of Formula III in an ether-type solvent, such as THF, 2-methyl-THF, DME, and the like (optionally containing other solvents such as aliphatic or aromatic hydrocarbons), and reacting the resulting species with an iodine source such as $I_2$, ICl, or N-iodosuccinimide. Compounds of Formula V can be prepared from compounds of Formula IV by reacting with bases such as NaOH in alcoholic solvents such as MeOH at typical reaction temperatures from about −10° C. to about 40° C.

give compounds of Formula VIII directly. Displacement of the chloride of compounds of Formula VIII with HYR1 under typical chloride displacement conditions gives compounds of Formula I-A. Alternatively, the order of steps may be reversed: Compound of Formula V is first reacted with HYR1 under typical chloride displacement conditions to yield compounds of Formula IX, followed by palladium-mediated coupling with a boronate of Formula VI under typical Suzuki conditions as described above to give compounds of Formula I-A.

If deemed advantageous, the removal of the benzesulfonyl group may also be performed after chloride displacement and Suzuki coupling under substantially similar reaction conditions. Someone skilled in the art will realize that other groups may be used in place of the benzenesulfonyl group for the metalation/iodination reaction. Examples include, but are not limited to, toluenesulfonyl, tert-butoxycarbonyl, and tert-butylcarbamoyl. Furthermore, instead of introducing an iodine in the reaction from compound of Formula III to compound of Formula IV one may introduce a bromine using, e.g., bromine, $CBr_4$, or NBS under otherwise identical conditions and react the resulting compound in the same way as described above.

Further manipulation of the substituents Z may be desirable, and Scheme 2 below describes how compounds wherein Z=tert-butoxycarbonyl (Boc) may be used for that purpose.

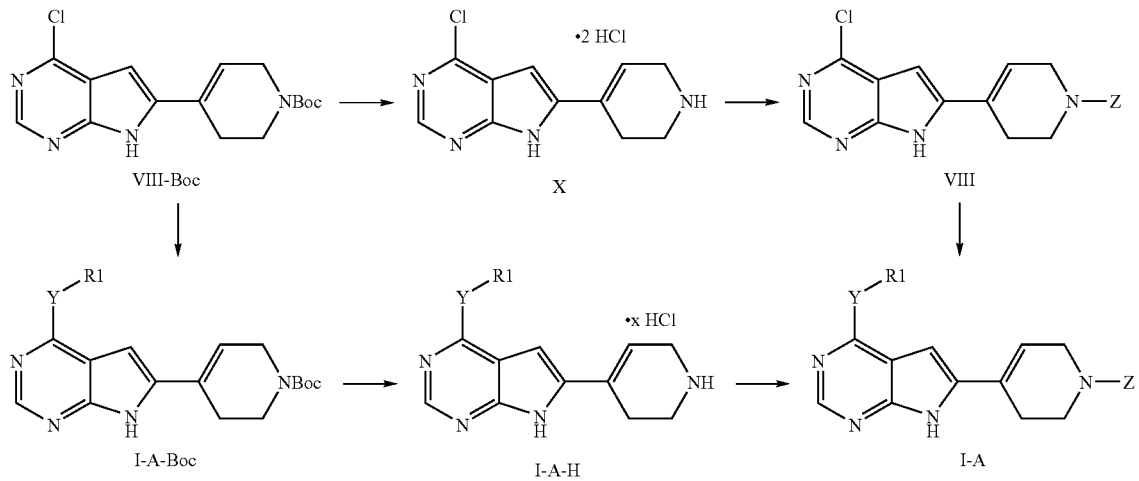

Scheme 2

Compounds of Formula VIII can be prepared by palladium-mediated coupling with a boronate of Formula VI under typical Suzuki conditions well known to someone skilled in the art. It will be appreciated that instead of the pinacol boronate shown, other boronate esters or the free boronic acids may also be used. Furthermore, reaction of the corresponding trialkyl tin derivatives of VI (i.e., compounds with, e.g., $Bu_3Sn$— in place of the pinacolboronate) under typical Stille coupling conditions may also be used to prepare compounds of Formula VIII from compounds of Formula V. In an alternative route, compound of Formula III can be reacted with a strong base such as LDA, lithium tetramethylpiperidide, or the like, in an ether-type solvent such as THF, DME, and the like, and then reacted with a protected 4-piperidone VII, to Compound of Formula I-A-Boc can be reacted with HCl in a typical solvent to give the hydrochloride salt of Formula I-A-H. Typical solvents include, but are not limited to, dioxane, MeOH, and water. Compounds of Formula I-A-H can be reacted with acids, anhydrides, acid halids, chloroformates, carbamoyl halides, sulfonyl halides, sulfamoyl halids, sulfonic anhydrides, and the like, under conditions described in the examples to give compounds of Formula I-A. Alternatively, a compound of Formula VII-Boc can be reacted with HCl as described above to give the hydrochloride salt of Formula X. Introduction of the Z substituents as described above to yield a compound of Formula VIII, followed by chloride displacement with HYR1 gives compounds of Formula I-A.

Someone skilled in the art will realize that acids other than HCl can be used for removal of the Boc group in compounds of Formula VIII-Boc and I-A-Boc.

When HYR1 is equal to HNR1R2, someone skilled in the art will recognize that a variety of typical reaction conditions, typical solvents, and typical additives are available for the conversion of VIII to I-B and of VIII-Boc to I-B-Boc, shown in Scheme 3.

Boc can directly be treated with suitable acids to remove the Boc group completely.

In some cases, compounds of Formula HNR1R2 are commercially available or synthesized according to literature procedures. In cases where neither is available, compounds of Formula HNR1R2 were synthesized via procedures described in the experimental section herein.

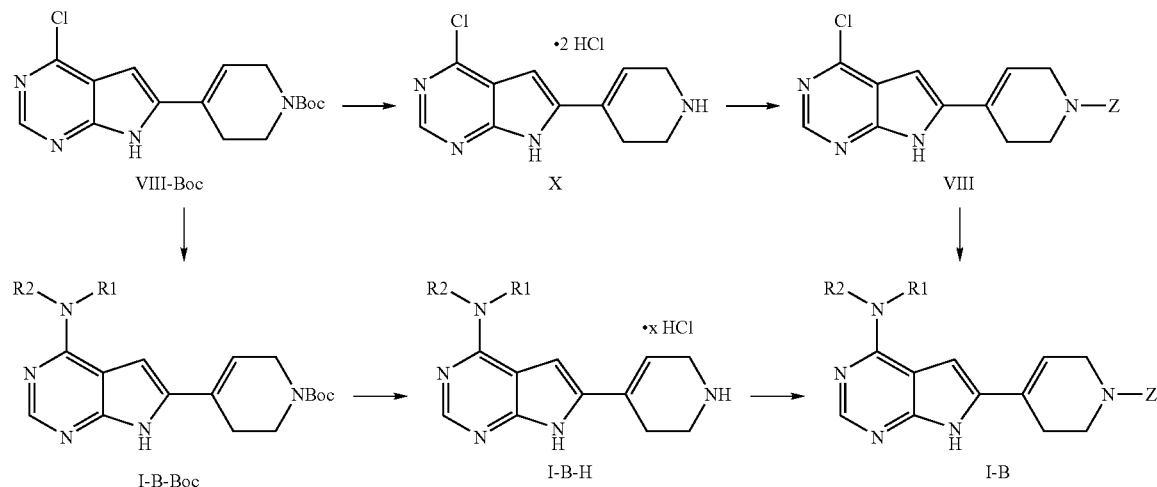

Generally, VIII or VIII-Boc are reacted with HNR1R2 in a suitable solvent. Typical solvents include, but are not limited to, alcohols such as ethanol, isopropyl alcohol, butanol, or trifluoroethanol (TFE); or polar solvents such as DMF, NMP, or DMSO. If deemed necessary, typical additives such as HCl and TFA may be added. The reaction is typically carried out at about 40° C. to about 150° C. If a relatively low boiling alcohol is used as solvent, it may be advisable to conduct the reaction in a pressure reactor. Alternatively, typical transition-metal mediated chloride displacement conditions well known to someone skilled in the art can be used. These conditions typically involve reacting VIII or VII-Boc with HNR1R2, a transition metal compound, a suitable ligand, and a base in a suitable solvent. Someone skilled in the art will recognize that especially when acidic additives are used, the Boc group may be partially or completely removed simultaneously, so that compounds of Formula I-B-H are solely obtained or in a mixture with compounds of Formula I-B-Boc. If one wishes to obtain compounds of Formula I-B-Boc, the reaction mixture containing compounds of Formula I-B-H (either exclusively or as mixture with compounds of Formula I-B-Boc) can directly be treated with a base such as triethylamine or diisopropylethylamine and di-tert-butyldicarbonate without the need for isolation. If one wishes to obtain compounds of Formula I-B-H, a mixture with compounds of Formula I-B-

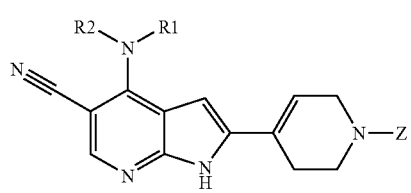

Compound of Formula I-C is equal to compound of Formula I wherein X=C—CN,

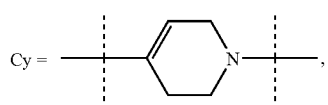

YR1=NR1R2, and R1, R2, and Z are as defined above for Formula (I).

Scheme 4 below describes how compounds of Formula I-C may be synthesized.

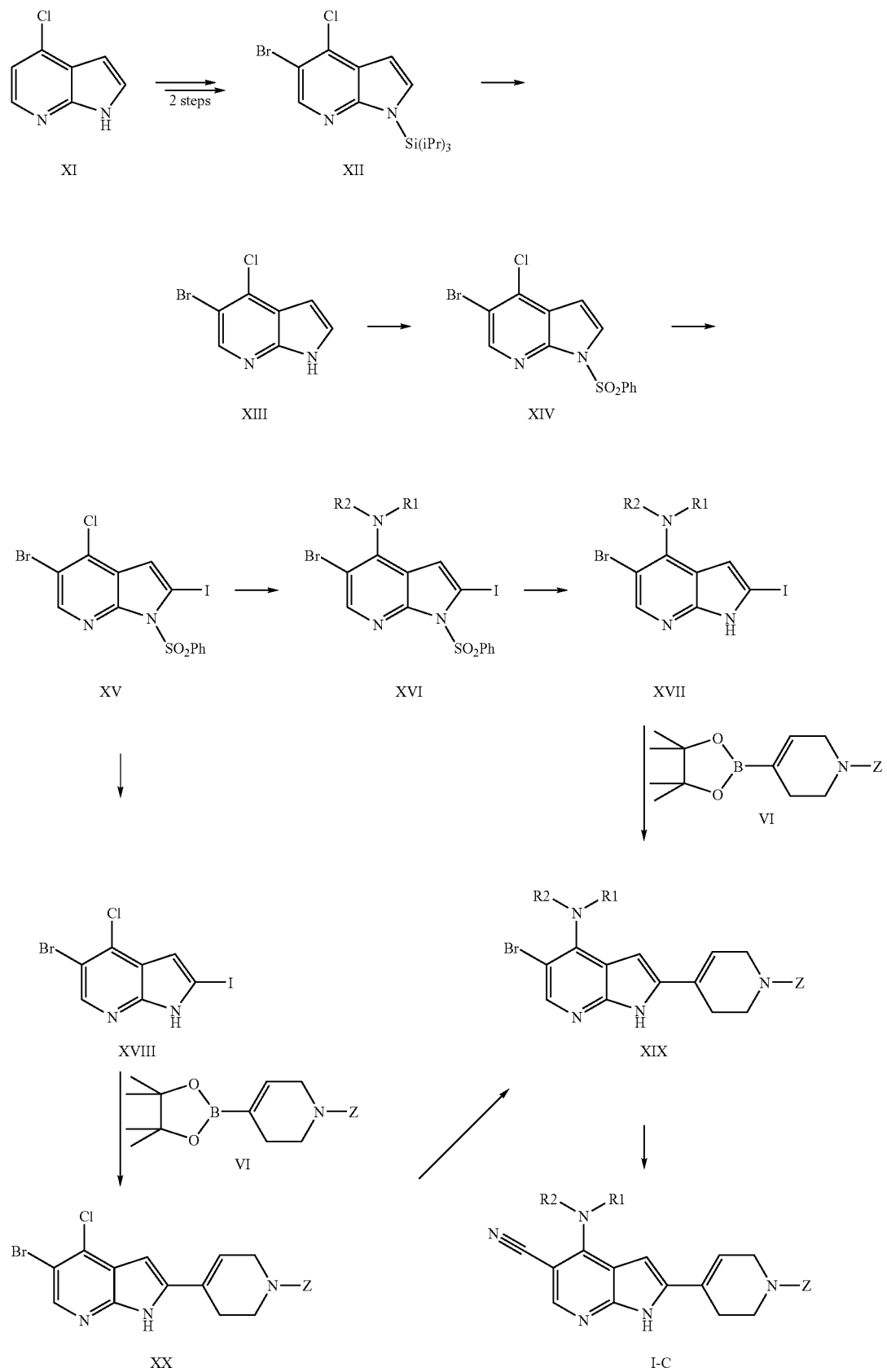
Scheme 4

The compound of Formula XII is known in the literature and may be prepared according to a published procedure (*Tetrahedron Lett.* 2004, 45, 2317-2319). Typical conditions for the removal of the triisopropylsilyl group to obtain compound of Formula XIII include, but are not limited to, treatment with tetrabutylammonium fluoride, or acids such as HCl or $H_2SO_4$ in alcoholic solvents. A compound of Formula XIV may be obtained from a compound of Formula XIII as described above for the conversion of a compound of Formula II to a compound of Formula III. A compound of Formula XV may be obtained from a compound of Formula XIV as described above for the conversion of a compound of Formula III to a compound of Formula IV. Compounds of Formula XVI can be obtained by reacting compound of Formula XV with HNR1R2 in a typical solvent under typical reaction conditions. Typical solvents include, but are not limited to, alcohols such as trifluoroethanol (TFE) with additives such as HCl and TFA. The reaction is typically carried out at about 40° C. to about 120° C. If the reaction temperature is higher than the boiling point of the reaction mixture, a pressure reactor should be used. The benzenesulfonyl group of compounds of Formula XVI can be removed to give compounds of Formula XVII under conditions described above for the conversion of a compound of Formula IV to a compound of Formula V. Compounds of Formula XIX can be prepared from compounds of Formula XVII by palladium-mediated coupling with a boronate of Formula VI under typical Suzuki conditions well known to someone skilled in the art. It will be appreciated that instead of the pinacol boronate shown, other boronate esters or the free boronic acids may also be used.

Furthermore, reaction of the corresponding trialkyl tin derivatives of VI (i.e., compounds with, e.g., $Bu_3Sn$— in place of the pinacolboronate) under typical Stille coupling conditions may also be used to prepare compounds of Formula XVII from compounds of Formula XVI. Alternatively, the benzesulfonyl group in compound of Formula XV may be removed first to yield compound of Formula XVIII, followed by coupling with a boronate of Formula VI to give compounds of Formula XX, and chloride displacement with HNR1R2 to give compounds of Formula XIX, under conditions described above. Finally, compounds of Formula I-C may be obtained from compounds of Formula XIX by transition metal-mediated conversion of the bromo to the cyano substituents. Typical conditions include, but are not limited to, reaction with $Pd_2dba_3$, dppf, and $Zn(CN)_2$ in DMF/water.

Someone skilled in the art will realize that other groups may be used in place of the benzenesulfonyl group for the metalation/iodination reaction. Examples include, but are not limited to, toluenesulfonyl, tert-butoxycarbonyl, and tert-butylcarbamoyl. Furthermore, if Z=Boc, the chloride displacement in compounds of Formula XX under the conditions described above may lead to removal of the Boc group to give a compound of Formula XIX wherein Z=H. Such a compound can be treated with a base such as triethylamine or diisopropylethylamine and di-tert-butyldicarbonate to obtain a compound of Formula XIX wherein Z=Boc, or with other appropriate reagents to introduce the desired Z substituent.

Further manipulation of the substituents Z may be desirable, and Scheme 5 below describes how compounds wherein Z=tert-butoxycarbonyl (Boc) may be used for that purpose.

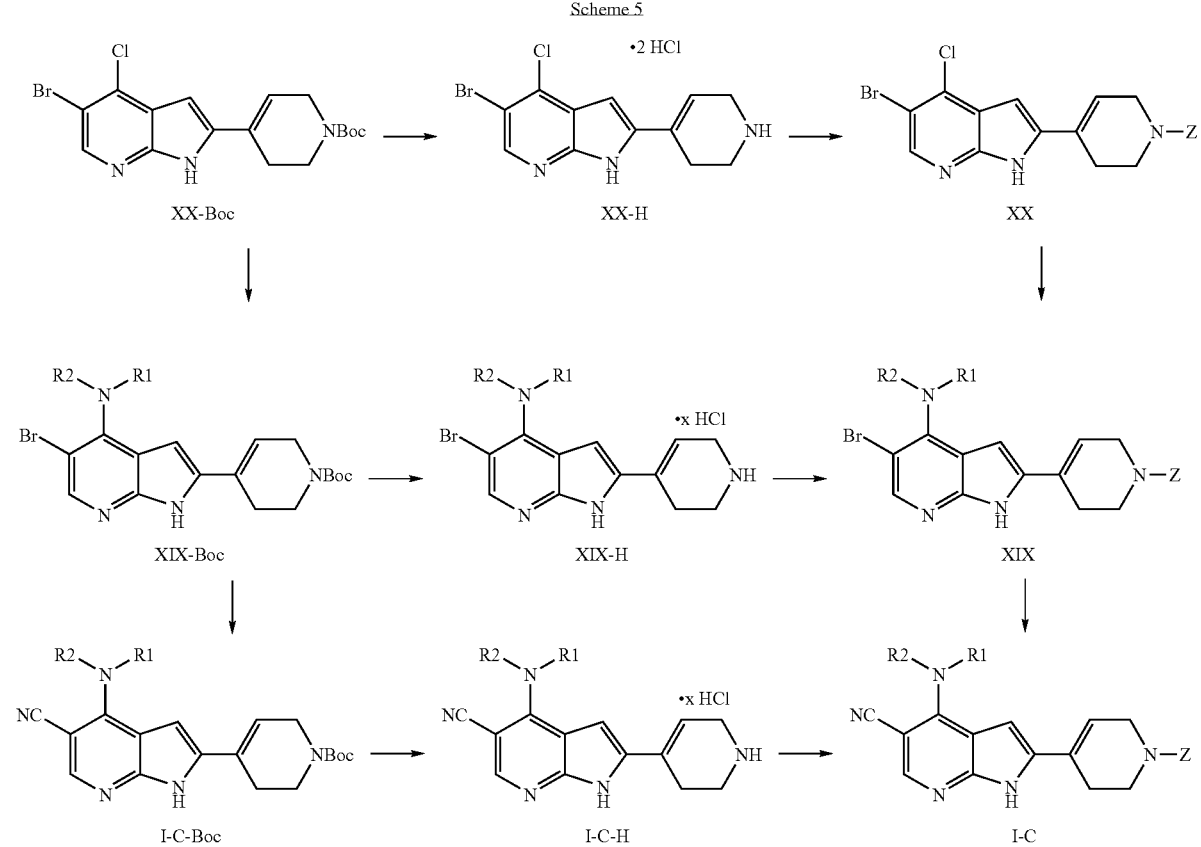

Scheme 5

Compounds of Formula XX-Boc, XIX-Boc, or I-C-Boc can be reacted with HCl in a typical solvent to give the hydrochloride salt of Formula XX-H, XIX-H, or I-C-H, respectively. Typical solvents include, but are not limited to, dioxane, MeOH, and water. Compounds of Formula XX-H, XIX-H, or I-C-H can be reacted with acids, anhydrides, acid halids, chloroformates, carbamoyl halides, sulfonyl halides, sulfamoyl halids, sulfonic anhydrides, and the like, under conditions described in the examples to give compounds of Formula XX, XIX, or I-C, respectively. Someone skilled in the art will realize that acids other than HCl can be used for removal of the Boc group in compounds of Formula XX-Boc, XIX-Boc, and I-C-Boc.

It would be appreciated by those skilled in the art that in some situations, a substituent that is identical or has the same reactivity to a functional group which has been modified in one of the following processes, will have to undergo protection followed by deprotection to afford the desired product and avoid undesired side reactions. Alternatively, another of the processes described within this invention may be employed in order to avoid competing functional groups. Examples of suitable protecting groups and methods for their addition and removal may be found in the following reference: "Protective Groups in Organic Syntheses", T. W. Greene and P. G. M. Wuts, John Wiley and Sons, 1989.

All melting points were determined with a Mel-Temp II apparatus and are uncorrected. Commercially available anhydrous solvents and HPLC-grade solvents were used without further purification. $^1$H NMR and $^{13}$C NMR spectra were recorded with Varian or Bruker instruments (400 MHz for $^1$H, 100.6 MHz for $^{13}$C) at rt with TMS or the residual solvent peak as internal standards. The line positions or multiplets are given in ppm (δ) and the coupling constants (J) are given as absolute values in Hertz, while the multiplicities in $^1$H NMR spectra are abbreviated as follows: s (singlet), d (doublet), t (triplet), q (quartet), quint (quintet), m (multiplet), m$_c$ (centered multiplet), br (broadened), AA'BB'. The signal multiplicities in $^{13}$C NMR spectra were determined using the DEPT135 pulse sequence and are abbreviated as follows: +(CH or CH$_3$), —(CH$_2$), C$_{quart}$ (C). LC/MS analysis was performed using a Gilson 215 autosampler and Gilson 819 autoinjector attached to a Hewlett Packard HP1100 and a Micromass ZQ2000 mass spectrometer. XTERRA MS C18 5µ 4.6×50 mm columns with detection at 254 nm and electrospray ionization in positive mode were used. For mass-directed purification (MDP), a Waters/MicromassZQ system was used.

The tables below list the mobile phase gradients (solvent A: acetonitrile; solvent B: 0.01% formic acid in HPLC water) and flow rates for the analytical HPLC programs.

| Time | A % | B % | Flow Rate (mL/min) MicromassZQ |
|---|---|---|---|
| Polar__5 min | | | |
| 0.00 | 5 | 95 | 1.3 |
| 3.00 | 90 | 10 | 1.3 |
| 3.50 | 90 | 10 | 1.3 |
| 4.00 | 5 | 95 | 1.3 |
| 5.00 | 5 | 95 | 1.3 |
| Polar__15 min | | | |
| 0.00 | 5 | 95 | 1.3 |
| 1.00 | 30 | 70 | 1.3 |
| 7.50 | 90 | 10 | 1.3 |

-continued

| Time | A % | B % | Flow Rate (mL/min) MicromassZQ |
|---|---|---|---|
| 10.00 | 100 | 0 | 1.3 |
| 13.00 | 5 | 95 | |
| 15.00 | 5 | 95 | 1.3 |
| Nonpolar__5 min | | | |
| 0.00 | 25 | 75 | 1.3 |
| 3.00 | 99 | 1 | 1.3 |
| 3.50 | 99 | 1 | 1.3 |
| 4.00 | 25 | 75 | 1.3 |
| 5.00 | 25 | 75 | 1.3 |
| Nonpolar__7 min | | | |
| 0.00 | 25 | 75 | 1.3 |
| 4.00 | 100 | 0 | 1.3 |
| 5.50 | 100 | 0 | 1.3 |
| 6.00 | 25 | 75 | 1.3 |
| 7.00 | 25 | 75 | 1.3 |
| Nonpolar__15 min | | | |
| 0.00 | 15 | 85 | 1.3 |
| 7.50 | 99 | 1 | 1.3 |
| 11.00 | 99 | 1 | 1.3 |
| 12.50 | 15 | 85 | 1.3 |
| 15.00 | 15 | 85 | 1.3 |

SYNTHESES OF EXAMPLES AND INTERMEDIATES

4-Chloro-7-(phenylsulfonyl)-7H-pyrrolo[2,3-d]pyrimidine (Compound of Formula II)

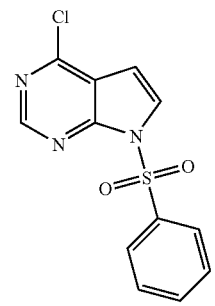

To a solution of 4-chloro-7H-pyrrolo[2,3-d]pyrimidine (10 g, 0.065 mol) in THF (300 mL) was added potassium tert-butoxide (9.15 g, 0.082 mol) at r.t. over 5 min. A slight exotherm was noticed and suspension was cooled with the aid of a water bath. Benzenesulfonyl chloride (10.5 mL, 0.082 mol) was then added drop-wise over a period of 10 min and the resulting suspension stirred for a further 3 h. Then water (20 mL) was added drop-wise and the solution was then stirred for 15 min. The solvent was evaporated under reduced pressure and the reaction mixture was eluted with ethyl acetate (1.2 l), washed with brine (2×100 mL), dried and concentrated. The resulting solid was triturated with ethyl acetate (50 mL) to afford 4-chloro-7-(phenylsulfonyl)-7H-pyrrolo[2,3-d]pyrimidine as an off-white solid. $^1$H NMR (CDCl$_3$, 400 MHz) δ 6.75 (1H, d), 7.55-7.625 (2H, t), 7.70 (1H, t), 7.82 (1H, d), 8.25 (1H, d) and 8.80 (1H, s).

4-Chloro-6-iodo-7-(phenylsulfonyl)-7H-pyrrolo[2,3-d]pyrimidine (Compound of Formula III)

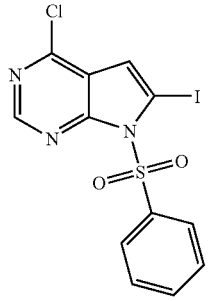

To a stirred solution of 4-chloro-7-(phenylsulfonyl)-7H-pyrrolo[2,3-d]-pyrimidine (5.0 g, 0.017 mol) in THF (200 mL) under inert atmosphere, at −78° C., was added 2.0 M LDA solution (9.8 mL, 0.0195 mol) over a period of 15 min. After 1 h a solution of iodine (4.97 g, 0.0196 mol) in THF (50 mL) was added dropwise over a period of 15 min. The resulting solution was stirred for a further 3 h. Water (10 mL) was then added and the mixture allowed to reach r.t. The mixture was diluted with DCM (1 l), washed with brine (2×100 mL), dried and concentrated under reduced pressure. The resulting solid was triturated with MeCN to afford the 4-chloro-6-iodo-7-(phenylsulfonyl)-7H-pyrrolo[2,3-d]pyrimidine. $^1$H NMR (CDCl$_3$, 400 MHz) 7.05 (1H, s), 7.50 (2H, t), 7.60 (1H, t), 8.20 (2H, d) and 8.65 (1H, br s).

4-Chloro-6-iodo-7H-pyrrolo[2,3-d]pyrimidine (Compound of Formula IV)

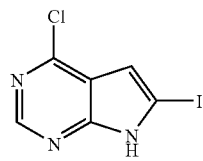

To a stirred solution of 4-chloro-6-iodo-7-(phenylsulfonyl)-7H-pyrrolo[2,3-d]pyrimidine (538 mg, 1.283 mmol) in THF (6.0 mL) was added 5 M sodium hydroxide methanolic solution (1.8 mL, 0.009 mmol). After 10 min the solvent was removed under reduced pressure, sat. ammonium chloride solution (5.0 mL) was added and the mixture evaporated to dryness. The resulting solid was triturated with water to afford 4-chloro-6-iodo-7H-pyrrolo[2,3-d]pyrimidine. 1H NMR (d$_6$-DMSO, 400 MHz) 6.90(1H, s) and 8.55 (1H, s).

tert-Butyl 4-(4-chloro-7H-pyrrolo[2,3-d]pyrimidin-6-yl)-3,6-dihydropyridine-1(2H)-carboxylate (Compound of Formula VIII-Boc)

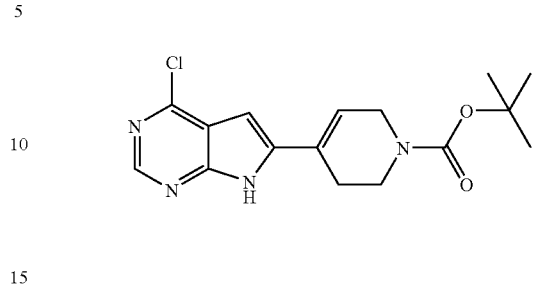

To a suspension of 4-chloro-6-iodo-7H-pyrrolo[2,3-d]pyrimidine (5.0 g, 0.018 mol) in 1,4-dioxane (120 mL) and water (30 mL) were added 4-(4,4,5,5-tetramethyl-[1,3,2]dioxaborolan-2-yl)-3,6-dihydro-2H-pyridine-1-carboxylic acid tert-butyl ester (5.97 g, 0.0193 mol), potassium carbonate (4.9 g, 0.036 mol) and PdCl$_2$(dppf).CH$_2$Cl$_2$ (0.73 g, 0.89 mmol). The flask was evacuated and refilled with N$_2$ (3×). The mixture was heated at 100° C. overnight. LC-MS showed the reaction was complete. The mixture was diluted with ethyl acetate (200 mL), then washed with brine (2×50 mL), and dried over anhydrous sodium sulfate. The filtrate was concentrated under reduced pressure to ≈100 mL, the resulting white precipitate was collected by filtration to give the first batch of the title compound. The filtrate was concentrated and the residue was purified by chromatography on silica gel, eluting with Hex:EtOAc=70:30→50:50 to give a white solid (containing pinacol), which was further crystallized with EtOAc/hexanes to give the second batch of the title compound as a white solid. LC-MS (ES, Pos.): 335/337 (3/1) [MH$^+$]. $^1$H NMR (CDCl$_3$, 400 MHz): δ=1.51 (s, 9H), 2.61 (m, 2H), 3.70 (m, 2H), 4.20 (m, 2H), 6.27 (s, 1H), 6.55 (s, 1H), 8.61 (s, 1H), 10.3 (brs, 1H).

Alternative synthesis: To a −78° C. solution of 4-chloro-7-phenylbenzenesulfonyl-7H-pyrrolo[2,3-d]pyrimidine (1.00 g, 3.41 mmol) in anhydrous THF (15 mL) was added LDA solution (1.5 M in cyclohexanes; 3.41 mL, 5.12 mmol) dropwise over 5 min. The mixture was left to stir for 1 h after which time 1-Boc-4-piperidone (0.82 g, 4.09 mmol) was added as a solution in THF (5 mL) and the mixture left to warm to rt over a weekend. The solution was diluted with EtOAc (150 mL) and partitioned over water. The organic layer was washed with brine, dried (MgSO$_4$), filtered and concentrated in vacuo. Purification by column chromatography on silica gel loading in DCM and eluting with 5:1 Hexanes:EtOAc stepwise to EtOAc yielded the title compound as an off-white powder.

General method for the reaction of amines with tert-butyl 4-(4-chloro-7H-pyrrolo[2,3-d]pyrimidin-6-yl)-3,6-dihydro-pyridine-1(2H)-carboxylate to generate compounds of Formula I-B-Boc:

Amine HNR1R2 (0.215 mmol) was added to a solution of tert-butyl 4-(4-chloro-7H-pyrrolo[2,3-d]pyrimidin-6-yl)-3,6-dihydropyridine-1(2H)-carboxylate (0.18 mmol) in butanol (4 mL). The reaction was heated to 95° C. for 2 h. If the reaction was incomplete the reaction temperature was increased to 105° C., and if required to 115° C., until all the starting material was consumed. The solvent was removed and the residue purified on silica gel by elution with dichloromethane:methanol to yield the product of Formula I-B-Boc. Alternatively, purification may be possible by HPLC, crystallization, or trituration.

The following EXAMPLES were prepared using the general method described above. In Table 1, reference is to formula I-B-Boc:

TABLE 1

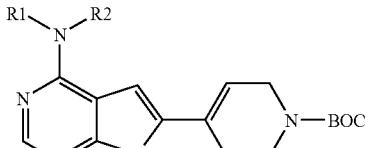

I-B-Boc

| EX. | R1\N/R2 | NMR | NMR Solvent | MH+ | HPLC Rt (min) |
|---|---|---|---|---|---|
| 1 | 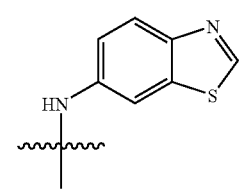 | 11.9 (NH, s), 9.6 (NH), 9.2 (H, s), 8.9 (H, s), 8.4 (H, s), 8.1 (H, m), 7.9 (H, d), 6.8 (H, s), 6.4 (H, brs), 4.1 (2H, brs), 3.6 (2H, brs), 2.5 (2H, brs), 1.4 (9H, s) | DMSO | 449 | 3.57 |
| 2 | 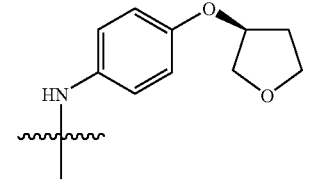 | 11.9 (NH, s), 9.2 (1H), 8.2 (1H), 7.8 (2H, d), 6.95 (2H, d), 6.7 (1H, s), 6.4 (1H, s), 5.0 (1H, m), 4.0 (2H, br.s), 3.9-3.7 (4H, m), 3.6 (2H, t), 2.5 (2H, br), 2.2 (1H, m), 2.0 (1H, m), 1.4 (9H, s) | DMSO | 478 | 3.22 |
| 3 | 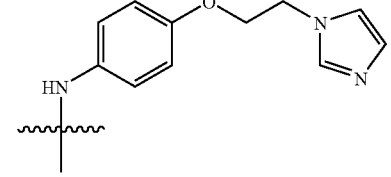 | 11.9 (NH, s), 9.2 (1H), 8.2 (1H), 7.8 (2H, d), 6.9 (2H, m), 7.25 (1H, m), 6.9 (2H, s), 6.7 (1H, s), 6.4 (1H, s), 4.4 (2H, t), 4.2 (2H, t), 4.0 (2H, s), 3.6 (1H, t), 2.5 (2H, br.s), 1.4 (9H, s) | DMSO | 502 | 2.77 |
| 4 | 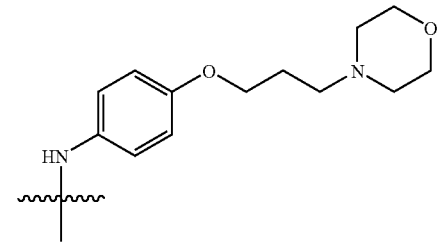 | 12.0 (NH, s), 9.2 (1H), 8.2 (1H), 7.7 (2H, d), 6.9 (2H, d), 6.7 (1H, s), 6.4 (1H, br.s), 4.0 (4H, m), 3.6 (6H, m), 2.5 (8H, m), 1.9 (2H, m) 1.4 (9H, s) | DMSO | 535 | 2.77 |
| 5 | 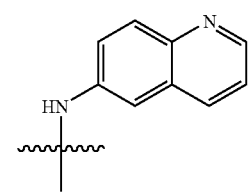 | 11.8 (NH, s), 9.6 (NH), 8.7 (H, m), 8.6 (H, s), 8.3 (H, s), 8.2 (H, m), 8.1 (H, m), 7.9 (H, m), 7.4 (H, m) 6.7 (H, s), 6.4 (H, s), 4.1 (2H, brs), 3.6 (2H, brs), 2.5 (2H, brs), 1.4 (9H, s) | DMSO | 442 | 3.47 |

TABLE 1-continued

I-B-Boc

| EX. | R1,R2-N group | NMR | NMR Solvent | MH+ | HPLC Rt (min) |
|---|---|---|---|---|---|
| 6 | HN-(4-hydroxy-3-methylphenyl) | 11.7 (NH, s), 9.0 (NH), 8.2 (H, s), 7.4 (2H, m) 6.8 (H, m), 6.7 (H, s), 6.4 (H, s), 4.1 (3H, brs), 3.6 (2H, brs), 2.5 (2H, brs), 2.2 (3H, s), 1.4 (9H, s) | DMSO | 421 | 3.29 |
| 7 | HN-(3-ethynylphenyl) | 11.9 (NH, s), 9.4 (NH), 8.4 (H, s), 8.2 (H, s), 7.9 (H, m), 7.4 (H, m), 7.2 (H, m), 6.8 (H, s), 6.4 (H, s), 4.1 (2H, brs), 3.6 (2H, brs), 2.5 (3H, brs), 1.4 (9H, s) | DMSO | 415 | 3.81 |
| 8 | HN-(4-(N,N-dimethylsulfamoyl)phenyl) | 11.8 (NH), 9.7 (NH), 8.3 (H, s), 8.1 (2H, m), 7.6 (2H, m), 6.8 (H, s) 6.4 (H, s), 4.1 (2H, brs), 3.6 (2H, brs), 2.6 (6H, s), 2.5 (2H, brs), 1.4 (9H, s) | DMSO | 498 | 3.87 |
| 9 | HN-(3-amino-1H-indazol-5-yl) | 11.9 (NH, s), 11.2 (NH, s), 9.2 (NH), 8.2 (H, s), 8.0 (H, s), 7.5 (H, m), 7.2 (H, m) 6.6 (H, s), 6.4 (H, s), 5.2 (NH2), 4.1 (2H, brs), 3.6 (2H, brs), 2.5 (2H, brs), 1.4 (9H, s) | DMSO | 447 | 3.57 |
| 10 | HN-(1H-indazol-6-yl) | 11.9 (NH, s), 11.1 (NH, s), 9.4 (NH), 8.6 (H, s), 8.4 (H, s), 8.0 (H, s), 7.7 (H, m), 7.4 (H, m), 6.9 (H, s), 6.4 (H, s), 4.1 (2H, brs), 3.6 (2H, brs), 2.5 (2H, brs), 1.4 (9H, s) | DMSO | 431 | 3.49 |

TABLE 1-continued
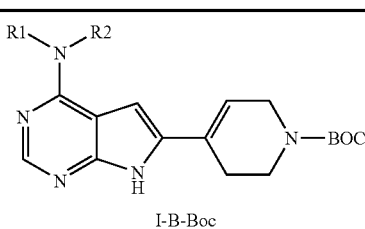
I-B-Boc
| EX. | R1\N/R2 | NMR | NMR Solvent | MH+ | HPLC Rt (min) |
|---|---|---|---|---|---|
| 11 | 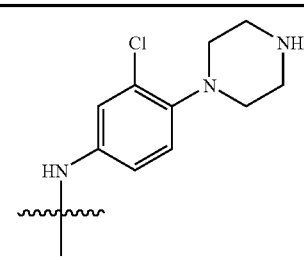 | 11.9 (NH, s), 9.3 (NH, s), 8.2 (H, s), 7.0 (H, m), 6.7 (2H, m), 6.5 (H, m), 6.4 (H, s), 5.1 (NH), 4.1 (2H, brs), 4.0 (4H, m), 3.6 (2H, brs), 3.0 (4H, m), 2.5 (2H, brs), 1.4 (9H, s) | DMSO | 510 | 3.42 |
| 12 | 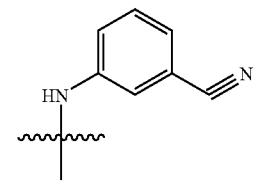 | 11.9 (NH, s), 9.6 (NH), 8.6 (H, s), 8.4 (H, s), 8.2 (H, m), 7.5 (2H, m), 6.8 (H, s), 6.4 (H, s), 4.1 (2H, brs), 3.6 (2H, brs), 2.5 (2H, brs), 1.4 (9H, s) | DMSO | 416 | 3.86 |
| 13 | 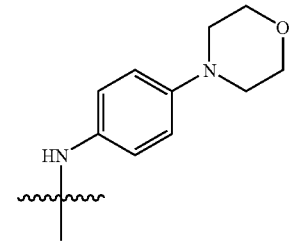 | 11.9 (NH, s), 9.2 (NH), 8.2 (H, s), 7.7 (2H, m), 7.0 (2H, m), 6.7 (H, s), 6.4 (H, s), 4.1 (2H, brs), 3.8 (4H, m), 3.6 (2H, brs), 3.1 (4H, m), 2.5 (2H, brs), 1.4 (9H, s) | DMSO | 477 | 3.34 |
| 14 | 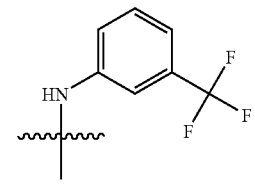 | 12.0 (NH, s), 9.6 (NH), 8.4 (2H, m), 8.2 (H, m), 7.6 (H, m), 7.4 (H, m), 6.8 (H, s), 6.4 (H, s), 4.1 (2H, brs), 3.6 (2H, brs), 2.5 (2H, brs), 1.4 (9H, s) | DMSO | 459 | 4.07 |
| 15 | 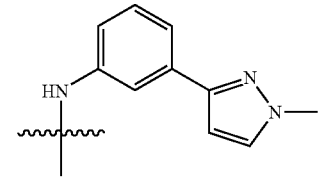 | 11.9 (NH, s), 9.4 (NH), 8.3 (H, s), 8.2 (H, s), 8.1 (H, m), 7.8 (H, s), 7.4 (2H, m), 6.9 (H, s), 6.7 (H, s) 6.4 (H, s), 4.1 (2H, brs), 3.9 (3H, s), 3.6 (2H, brs), 2.5 (2H, brs), 1.4 (9H, s) | DMSO | 471 | 3.47 |
| 16 | 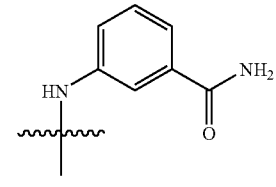 | 11.9 (NH, s), 9.5 (NH), 8.4 (2H, m), 8.2 (H, m), 7.9 (H, brs), 7.3-7.5 (3H, m), 6.8 (H, s), 6.4 (H, s), 4.1 (2H, brs), 3.6 (2H, brs), 2.5 (2H, brs), 1.4 (9H, s) | DMSO | 435 | 3.17 |

TABLE 1-continued

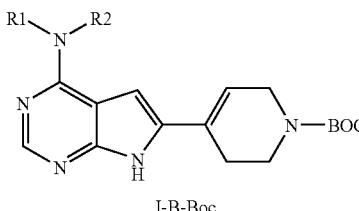

I-B-Boc

| EX. | R1,R2 group | NMR | NMR Solvent | MH+ | HPLC Rt (min) |
|---|---|---|---|---|---|
| 17 | 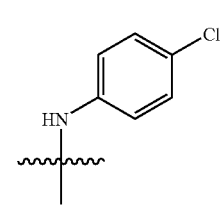 | 11.9 (NH, s), 9.4 (NH), 8.3 (H, s), 8.0 (2H, m), 7.4 (2H, m), 6.8 (H, s), 6.4 (H, s), 4.1 (2H, brs), 3.6 (2H, brs), 2.5 (2H, brs), 1.4 (9H, s) | DMSO | 426 | 3.86 |
| 18 | 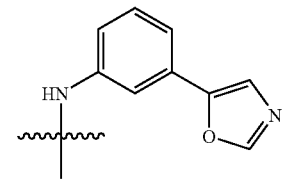 | 12.0 (NH, s), 9.5 (NH, s), 8.5 (1H, s), 8.35 (1H, s), 8.3 (1H, br m), 8.0 (1H, d), 7.7 (1H, s), 7.45 (1H, m), 7.4 (1H, m), 6.8 (1H, s), 6.4 (1H, br), 4.1 (2H, br s), 3.6 (2H, m), 2.5 (2H, obscured), 1.5 (9H, s) | DMSO | 459 | 3.31 |
| 19 | 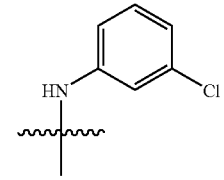 | 12.0 (NH, s), 9.5 (NH, s), 8.35 (H, s), 8.2 (1H, t), 7.8 (H, dd), 7.4 (H, t), 7.1 (H, dd), 6.8 (H, s), 6.4 (H, s), 4.1 (2H, br, s), 3.6 (2H, br, m), 2.5 (2H, obscured), 1.5 (9H, s) | DMSO | 426 | 3.92 |
| 20 | 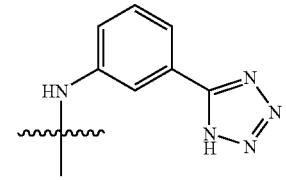 | 11.9 (NH, s), 11.0 (NH, 2), 9.6 (NH, s), 8.7 (1H, s), 8.4 (1H, s), 8.2 (1H, m), 7.7 (1H, m), 7.6 (1H, t), 6.9 (1H, s), 6.4 (1H, br s), 4.1 (2H, br s), 3.6 (2H, m), 2.5 (2H, obscured), 1.5 (9H, s) | DMSO | 458 | 3.14 |
| 21 | 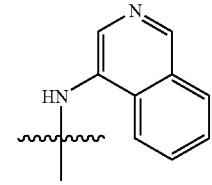 | 12.0 (NH, s), 9.8 (NH), 9.0 (H, s), 8.6 (3H, m), 8.3 (H, m), 8.1 (H, m), 7.6 (H, s), 7.1 (H, s), 6.8 (H, s), 4.1 (2H, brs), 3.6 (2H, brs), 2.5 (2H, brs), 1.4 (9H, s) | DMSO | 443 | 3.11 |
| 22 | 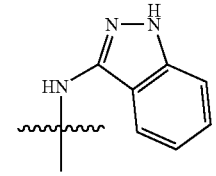 | 11.9 (NH, s), 11.0 (NH, s), 9.7 (NH), 8.1 (H, s), 7.6 (H, m), 7.5 (H, m), 7.4 (H, m), 7.0 (H, m), 6.6 (H, s), 6.4 (H, s), 4.1 (2H, brs), 3.6 (2H, brs), 2.5 (2H, brs), 1.4 (9H, s) | DMSO | 431 | 3.19 |

TABLE 1-continued

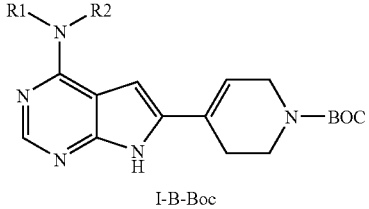

I-B-Boc

| EX. | R1,R2 group | NMR | NMR Solvent | MH+ | HPLC Rt (min) |
|---|---|---|---|---|---|
| 23 | 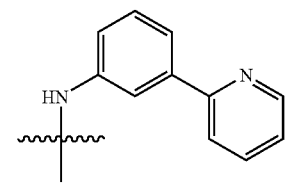 | 8.6 (H, d), 8.3 (H, s), 8.25 (H, s), 7.9 (3H, m), 7.8 (H, d), 7.5 (H, t), 7.4 (H, t), 6.7 (H, s), 6.3 (H, br.s), 4.2 (2H, br.s), 3.7 (2H, br.s), 2.6 (2H, br.s), 1.5 (9H, s) | CD$_3$OD | 469 | 3.27 |
| 24 | 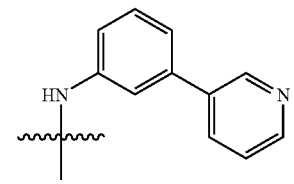 | 10.8 (NH, br.s), 8.9 (NH, s), 8.7 (H, d), 8.5 (H, s), 7.9 (2H, m), 7.7 (H, d), 7.6 (H, t), 7.4 (2H, d), 7.1 (H, s), 6.2 (H, NH, m), 4.2 (2H, br.s), 3.7 (2H, br.s), 2.6 (2H, br.s), 1.5 (9H, s) | CDCl$_3$ | 469 | 3.06 |
| 25 | 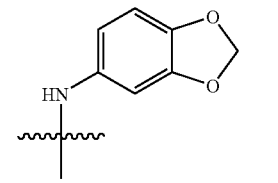 | 11.9 (NH, s), 9.9 (NH, s), 8.25 (H, s), 7.6 (H, d), 7.2 (H, dd), 6.9 (H, d), 6.75 (H, s), 6.4 (H, br, s), 6.0 (2H, s), 4.05 (2H, br, s), 3.6 (2H, br, m), 2.5 (2H, br, s), 1.5 (9H, s) | DMSO | 436 | 3.94 |
| 26 | 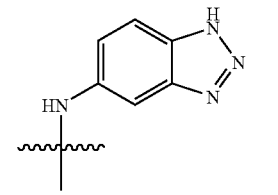 | 12.0 (NH, s), 9.6 (NH, s), 8.8 (H, s), 8.4 (H, s), 7.9 and 7.7 (2H, Abq), 6.9 (H, s), 6.4 (H, br, s), 4.1 (2H, br, s), 3.6 (2H, br, m), 2.5 (2H, obscured), 1.5 (9H, s) | DMSO | 433 | 3.69 |
| 27 | 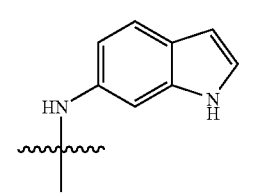 | 11.9 (NH, s), 11.0 (NH, s), 9.2 (NH, s), 8.3 (H, s), 8.2 (H, s), 7.5 (H, d), 7.3 (H, dd), 7.25 (H, t), 6.8 (H, s), 6.4 (2H, br, s), 4.1 (2H, br, s), 3.6 (2H, br, m), 2.5 (2H, br, s), 1.5 (9H, s) | DMSO | 431 | 4.07 |
| 28 | 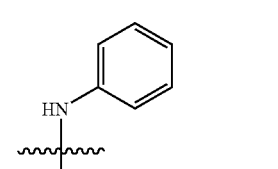 | 11.9 (NH, s), 9.3 (NH, s), 8.3 (H, s), 7.9 (2H, d), 7.35 (2H, t), 7.0 (H, t), 6.8 (H, s), 6.4 (H, br, s), 4.1 (2H, br, s), 3.6 (2H, br, m), 2.5 (2H, obscured), 1.5 (9H, s) | DMSO | 392 | 3.44 |

TABLE 1-continued

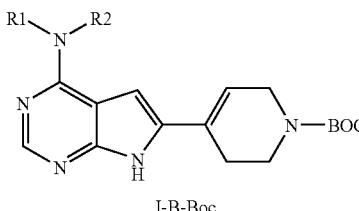

I-B-Boc

| EX. | R1\N\R2 | NMR | NMR Solvent | MH+ | HPLC Rt (min) |
|---|---|---|---|---|---|
| 29 | 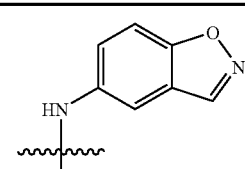 | 8.9 (H, s), 8.3 (H, s), 8.2 (H, s), 7.8 (H, d), 7.7 (H, d), 6.7 (H, s), 6.3 (H, br, s), 4.1 (2H, br, m), 3.7 (2H, br, m), 2.6 (2H, br, m), 1.5 (9H, s) | CD$_3$OD | 433 | 3.25 |
| 30 | 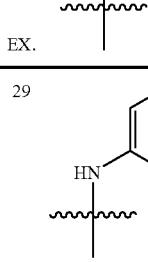 | 12.0 (NH, s), 9.4 (NH, s), 8.8 (NH, s), 8.2 (1H, s), 8.1 (1H, s), 7.8 (1H, m), 7.5 (1H, s), 7.3 (1H, m), 7.2 (1H, m), 6.6 (1H, s), 6.5 (1H, s), 6.3 (1H, s), 4.1 (2H, br s), 3.6 (2H, m), 2.5 (2H, obscured), 1.5 (9H, s) | DMSO | 458 | 3.19 |
| 31 | 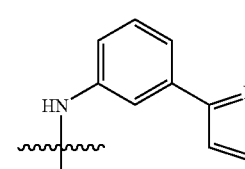 | 12.9 (NH, s), 11.8 (NH, s), 8.95 (NH, s), 8.1 (H, s), 8.0 (H, s), 7.7 (H, s), 7.45 (H, s), 6.3 (2H, br), 4.0 (2H, br), 3.5 (2H, m), 2.4 (2H, m), 2.3 (3H, s), 1.45 (9H, s) | DMSO | 446 | 2.95 |
| 32 | 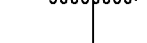 | 11.9 (NH, s), 10.3 (NH, s), 9.2 (NH, s), 8.2 (H, s), 7.8 (H, s), 7.5 (H, dd), 6.8 (H, d), 6.7 (H, s), 6.4 (H, br s), 4.05 (2H, br s), 3.6 (2H, m), 3.5 (2H, s), 2.5 (2H, br), 1.5 (9H, s) | DMSO | 447 | 2.92 |
| 33 | 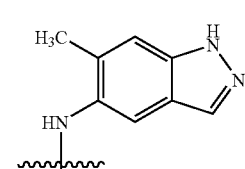 | 11.8 (NH, s), 9.9 (NH, s), 9.4 (NH, s), 8.3 (1H, s), 8.1 (1H, s), 7.6 (1H, m), 7.2 (2H, m), 6.9 (1H, s), 6.4 (1H, s), 4.1 (2H, br s), 3.6 (2H, m), 2.5 (2H, obscured), 2.1 (3H, s), 1.5 (9H, s | DMSO | 449 | 2.99 |
| 34 | 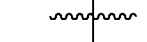 | 11.9 (NH, s), 9.9 (NH, s), 9.0 (1H, s), 8.9 (1H, s), 8.8 (1H, s), 8.5 (1H, s), 8.3 (1H, m), 8.1 (1H, m), 6.8 (1H, s), 6.4 (1H, s), 4.1 (2H, br s), 3.6 (2H, m), 2.5 (2H, obscured), 2.0 (3H, s), 1.5 (9H, s) | DMSO | 444 | 3.54 |

TABLE 1-continued

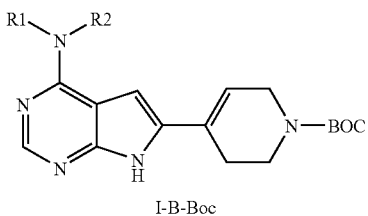

I-B-Boc

| EX. | 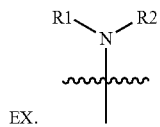 | NMR | NMR Solvent | MH+ | HPLC Rt (min) |
|---|---|---|---|---|---|
| 35 | | 12.35 (NH, s), 11.90 (NH, s), 9.32 (NH), 8.34 (H, s), 8.26 (H, s), 8.14 (H, s), 7.55 (H, d, J=8.8 Hz), 7.50 (H, dd, J=8.8, 1.6 Hz), 6.78 (H, s), 6.39 (H, s), 4.04 (2H, brs), 3.57 (2H, brs), 2.48 (2H, brs), 1.44 (9H, s) | DMSO | 432 | 2.72 |
| 36 | | 12.0 (NH, s), 9.5 (NH, s), 8.4 (1H, m), 8.2-8.3 (3H, m), 7.4 (2H, m), 6.8 (1H, s), 6.4 (1H, s), 4.1 (2H, br s), 3.6 (2H, m), 2.8 (3H, d), 2.5 (2H, obscured), 1.5 (9H, s) | DMSO | 449 | 3.17 |
| 37 | | 12.0 (NH, s), 9.6 (NH, s), 8.7 (2H, s), 8.4 (1H, s), 7.7 (2H, s), 6.8 (1H, s), 6.4 (1H, s), 4.1 (2H, br s), 3.6 (2H, m), 2.5 (2H, obscured), 1.5 (9H, s) | DMSO | 433 | 3.22 |
| 38 | | 11.9 (NH, s), 9.6 (NH, s), 8.5 (1H, s), 8.3 (1H, s), 8.2 (2H, d), 8.0 (1H, d), 7.8 (1H, d), 7.6 (1H, d), 7.5 (1H, m), 6.9 (1H, s), 6.4 (1H, s), 4.1 (2H, br s), 3.6 (2H, m), 2.5 (2H, obscured), 1.5 (9H, s) | DMSO | 475 | 3.57 |
| 39 | | 11.9 (NH, s), 9.5 (NH, s), 9.2 (1H, s), 8.5 (1H, s), 8.4 (1H, s), 8.1 (1H, s), 8.0 (1H, d), 7.6 (1H, d), 7.4 (1H, m), 6.9 (1H, s), 6.4 (1H, s), 4.1 (2H, br s), 3.6 (2H, m), 2.5 (2H, obscured), 1.5 (9H, s) | DMSO | 475 | 3.40 |
| 40 | | 11.8 (NH, s), 9.5 (NH, s), 9.1 (1H, s), 8.5 (1H, s), 8.4 (1H, s), 8.2 (1H, s), 8.0 (1H, d), 7.4 (1H, m), 7.4 (1H, m), 6.8 (1H, s), 6.4 (1H, s), 4.1 (2H, br s), 3.6 (2H, m), 2.5 (2H, obscured), 1.5 (9H, s) | DMSO | 475 | 3.44 |

TABLE 1-continued

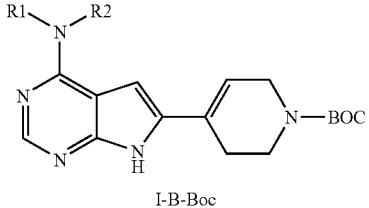

I-B-Boc

| EX. | R1,R2 group | NMR | NMR Solvent | MH+ | HPLC Rt (min) |
|---|---|---|---|---|---|
| 41 | 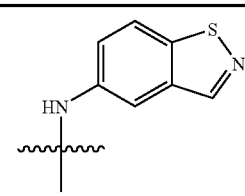 | 9.1 (1H, s), 8.4 (1H, d), 8.3 (1H, d), 8.2 (1H, s), 7.7 (1H, q), 6.8 (1H, s), 6.4 (1H, br s), 4.15 (2H, br s), 3.7 (2H, m), 2.55 (2H, br s), 1.5 (9H, s) | CD$_3$OD | 449 | 3.51 |
| 42 | 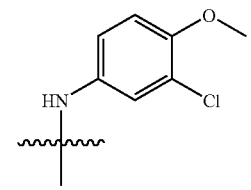 | Not recorded | | 456 | 3.27 |
| 43 | 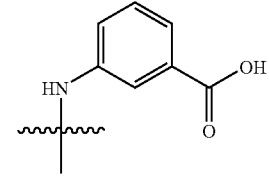 | Not recorded | | 436 | 2.84 |

Alternative Synthesis of 4-[4-(Benzothiazol-6-ylamino)-7H-pyrrolo[2,3-d]pyrimidin-6-yl]-3,6-dihydro-2H-pyridine-1-carboxylic acid tert-butyl ester

EXAMPLE 1

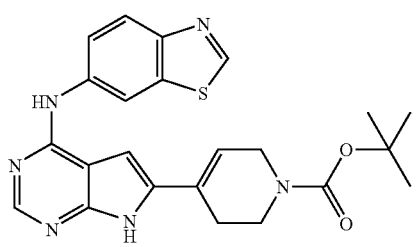

PdCl$_2$(dppf)$_2$·CH$_2$Cl$_2$ (8.2 mg, 0.010 mmol) was added into the mixture of benzothiazol-6-yl-(6-iodo-7H-pyrrolo[2,3-d]pyrimidin-4-yl)-amine (78.7 mg, 0.200 mmol), 4-(4,4,5,5-tetramethyl-[1,3,2]dioxaborolan-2-yl)-3,6-dihydro-2H-pyridine-1-carboxylic acid tert-butyl ester (68.0 mg, 0.220 mmol), and K$_2$CO$_3$ (55.3 mg, 2.00 mmol) in DMF:H$_2$O (2.5 mL:0.5 mL). The combined mixture was bubbled with N$_2$ for 5 min and was then heated at 100° C. under N$_2$ for 16 h. After that time, the mixture was concentrated in vacuo and purified by MS directed purification. One obtained the title compound as light brown solid. $^1$H NMR (CD$_3$OD, 400 MHz): δ 1.40 (s, 9H), 2.49 (brs, 2H), 3.57 (brs, 2H), 4.03 (brs, 2H), 6.20 (brs, 1H), 6.61 (s, 1H), 7.68 (dd, 1H, J=2.0 & 8.8 Hz), 7.90 (d, 1H, J=8.8 Hz), 8.19 (s, 1H), 8.64 (d, 1H, J=2.0 Hz), 9.02 (s, 1H). MS (ES+): m/z 449 (100) [MH+].

Benzothiazol-6-yl-(6-iodo-7H-pyrrolo[2,3-d]pyrimidin-4-yl)-amine (Compound of Formula IX Wherein R1=benzothiazol-6-yl and Y=NH)

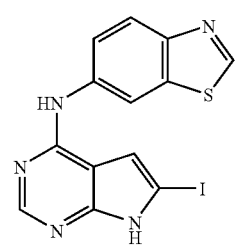

Following the General method for the reaction of amines with tert-butyl 4-(4-chloro-7H-pyrrolo[2,3-d]pyrimidin-6-yl)-3,6-dihydropyridine-1(2H)-carboxylate to generate compounds of Formula I-B-Boc, but using 4-chloro-6-iodo-7H-pyrrolo[2,3-d]pyrimidine and benzothiazol-6-ylamine, one obtained the title compound. MS (ES+): m/z 393.88 (100) [MH+].

EXAMPLE 44

4-[4-(1H-Indazol-5-ylamino)-7H-pyrrolo[2,3-d]pyrimidin-6-yl]-3,6-dihydro-2H-pyridine-1-carboxylic acid tert-butyl ester

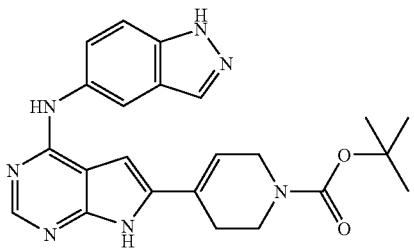

A mixture of 4-(4-chloro-7H-pyrrolo[2,3-d]pyrimidin-6-yl)-3,6-dihydro-2H-pyridine-1-carboxylic acid tert-butyl ester (136 mg, 0.41 mmol) and 5-aminoindazole (65 mg, 0.49 mmol) in n-BuOH (2 mL) were heated at 120° C. for 3 h, then cooled and the solvent removed in vacuo. The mixture was dissolved in DMSO/MeOH and purified by RP-HPLC (gradient 5 to 75% MeCN/H$_2$O over 15 min, 0.01% formic acid as buffer, flow rate 15 mL/min). Upon concentration of desired fractions, a white powder precipitated that was filtered, washed with ether and dried in vacuo to reveal the title compound. $^1$H NMR (400 MHz, DMSO-d$^6$): δ=1.42 (s, 9H), 2.44 (brs, 2H), 3.55 (brs, 2H), 4.03 (brs, 2H), 6.39 (brs, 1H), 6.76 (brs, 1H), 7.53-7.60 (m, 2H), 8.06 (s, 1H), 8.21-8.30 (m, 2H), 9.78 (brs, 1H), 12.08 (brs, 1H). MS (ES+): m/z 432.2 (20) [MH+].

General Method for Removal of the Boc Protecting Group:

Compound of Formula I-B-Boc (1 eq) was added to HCl in dioxane (4 M) (20 equiv) at rt. After 18 h the resultant solid was filtered off to yield the hydrochloride solid I-B-H.

EXAMPLE 45

(1H-Indazol-5-yl)-[6-(1,2,3,6-tetrahydropyridin-4-yl)-7H-pyrrolo[2,3-d]pyrimidin-4-yl]-amine

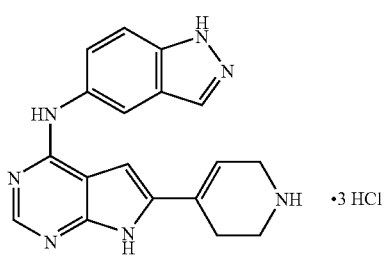

4-[4-(1H-Indazol-5-ylamino)-7H-pyrrolo[2,3-d]pyrimidin-6-yl]-3,6-dihydro-2H-pyridine-1-carboxylic acid tert-butyl ester (1 g, 2.32 mmol) was added to 4 M HCl in dioxane (16 mL) and stirred for 18 h. The solid was then filtered off, washed with ether and dried to yield the title compounds as an off-white solid. $^1$H NMR (d$_4$ MeOH, 400 MHz) 8.23 (1H, s), 8.2 (1H, s), 8.0 (1H, s), 7.8 (1H, d), 7.6 (1H, d), 6.85 (1H,br.s), 6.42 (1H, s), 4.0 (2H, s), 3.5 (2H, m), 2.85 (2H, br. s).

Alternative solvents for removal of the Boc group include, but are not limited to, MeOH and water, as demonstrated here with EXAMPLE 45: A suspension of tert-butyl 4-[4-(1H-indazol-5-ylamino)-7H-pyrrolo[2,3-d]pyrimidin-6-yl]-3,6-dihydro-2H-pyridine-1-carboxylate (670 mg, 1.55 mmol) in 4 N HCl (aq) (20 mL) was stirred at rt for 18 h. The precipitates were collected by filtration and washed with ether (3×10 mL) to afford (1H-indazol-5-yl)-[6-(1,2,3,6-tetrahydropyridin-4-yl)-7H-pyrrolo[2,3-d]pyrimidin-4-yl]amine as tri-HCl salt. $^1$H-NMR (DMSO-d$_6$, 400 MHz): δ=2.63 (m, 2H), 3.30 (m, 2H), 3.79 (m, 2H), 6.52 (s, br, 1H), 7.44 (dd, J=2.0, 8.8 Hz, 1H), 7.72 (d, J=8.8 Hz, 1H), 7.95 (s, 1H), 8.18 (d, J=1.2 Hz, 1H), 8.26 (s, 1H), 9.59 (s, 1H). MS (ES+): m/z 332.12 [MH+]. HPLC: t$_R$=0.44 and 1.37 min (ZQ2000, polar_5 min).

EXAMPLE 46

(1H-Indazol-5-yl)-[6-(1-methanesulfonyl-1,2,3,6-tetrahydropyridin-4-yl)-7H-pyrrolo[2,3-d]pyrimidin-4-yl]-amine

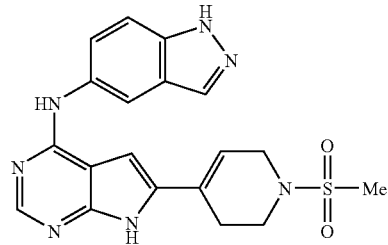

(1H-Indazol-5-yl)-[6-(1,2,3,6-tetrahydro-pyridin-4-yl)-7H-pyrrolo[2,3-d]pyrimidin-4-yl]-amine hydrochloride (80 mg, 0.217 mmol), Hunigs base (113 μL, 0.653 mmol) and methanesulfonyl chloride (17 μL, 0.2177 mmol) were combined in DMF at rt and stirred overnight. The reaction was concentrated in vacuo and residue purified on silica gel by elution with tetrahydrofuran:dichloromethane (3:2) to yield the title compound as white solid. $^1$H NMR (d$_6$-DMSO, 400 MHz) 9.4(1H, br. s), 8.4 (1H, s), 8.3(1H,s), 8.0(1H,s), 7.7(1H, d), 7.5(1H, d), 6.8(1H, s), 6.4(1H,s), 3.9(2H, s), 3.4(2H, m), 3.0(3H,s) and 2.6(2H, s); LC/MS: m/z 410 [M+H]+, Rt=2.82 min.

EXAMPLE 47

2-Dimethylamino-1-{4-[4-(1H-indazol-5-ylamino)-7H-pyrrolo[2,3-d]pyrimidin-6-yl]-3,6-dihydro-2H-pyridin-1-yl}-ethanone

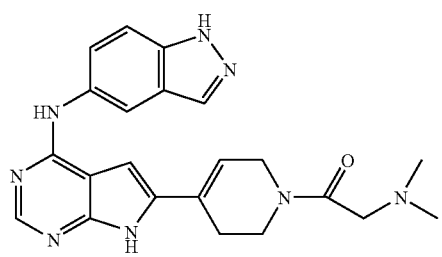

(1H-Indazol-5-yl)-[6-(1,2,3,6-tetrahydro-pyridin-4-yl)-7H-pyrrolo[2,3-d]pyrimidin-4-yl]-amine hydrochloride (80 mg, 0.217 mmol), N,N-dimethylglycine (22.4 mg, 0.277 mmol), PyBrop (101 mg, 0.217 mmol) and Hünigs base (113 µL, 0.653 mmol) were combined in DMF (3 mL) and stirred at rt for 37 h. The DMF was removed in vacuo and the residue was absorbed onto silica. Purification on silica gel by elution with tetrahydrofuran:methanol:conc ammonia (30:1:1) yielded a white solid. $^1$H NMR (d$_6$-DMSO, 400 MHz) Rotamers observed: 9.32 & 9.30 (1H, rotamers, 2s), 8.37 & 8.36 (1H, rotamers, 2s), 8.26 (1H, s), 8.0 (1H,s), 7.68 (2H,d), 7.53 (1H,d), 6.78 & 6.75 (1H, rotamers, 2s), 6.4 (1H, s), 4.3 (1H, s), 4.2(1H, s), 3.76 & 3.71 (2H, rotamers, 2t), 3.18 & 3.14 (2H, rotamers, 2s), 2.5 (2H, m), 2.23 & 2,21 (6H, rotamers, 2s); LC/MS: m/z 416 [M+H]$^+$, Rt=2.52 min.

EXAMPLE 48

1-{4-[4-(1H-Indazol-5-ylamino)-7H-pyrrolo[2,3-d]-pyrimidin-6-yl]-3,6-dihydro-2H-pyridin-1-yl}-ethanone

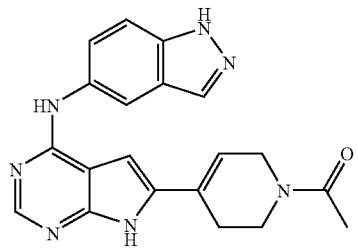

(1H-Indazol-5-yl)-[6-(1,2,3,6-tetrahydro-pyridin-4-yl)-7H-pyrrolo[2,3-d]pyrimidin-4-yl]-amine hydrochloride (60 mg, 0.137 mmol), HATU (63 mg, 0.164 mmol) and Hunigs base (100 µL, 0.576 mmol) were combined in DMF (4 mL) and stirred for 30 min. Acetic acid (8 µL, 0.168 mmol) was added and the solution was stirred overnight. Another portion of acetic acid (8 µL, 0.168 mmol) was added and the stirred for a further 4 h. The DMF was removed in vacuo and the residue was loaded onto silica. Purification on silica by elution with dichloromethane:methanol (95:5) yielded the title compound as a yellow solid. $^1$H NMR (400 MHz, DMSO-d$^6$): δ=2.03 & 2.07 (2s, rotamers, 3H), 2.44 & 2.53 (2s, rotamers, 2H), 3.62-3.67 (m, 2H), 4.11 & 4.18 (2s, rotamers, 2H), 6.39 (s, 1H), 6.72 & 6.76 (2s, rotamers, 1H), 7.50 (d, J=8.8 Hz, 1H), 7.63 (d, J=8.8 Hz, 1H), 8.03 (s, 1H), 8.24 (s, 1H), 8.33 (brs, 1H), 9.35 (brs, 1H), 11.90 (brs, 1H). MS (ES+): m/z 374.5 (100) [MH$^+$].

EXAMPLE 49

2,2,2-Trifluoro-1-{4-[4-(1H-indazol-5-ylamino)-7H-pyrrolo[2,3-d]pyrimidin-6-yl]-3,6-dihydro-2H-pyridin-1-yl}-ethanone

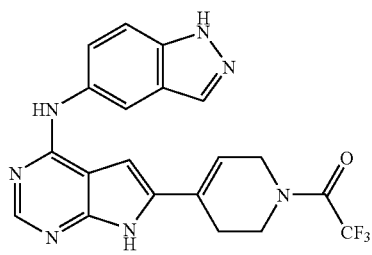

(1H-Indazol-5-yl)-[6-(1,2,3,6-tetrahydro-pyridin-4-yl)-7H-pyrrolo[2,3-d]pyrimidin-4-yl]-amine hydrochloride (150 mg, 0.34 mmol), Hunigs base (239 µL, 1.37 mmol) and trifluoroacetic anhydride (96 mL, 0.68 mmol) were combined in DMF (6 mL) and stirred overnight. Trifluoroacetic anhydride (96 mL, 0.68 mmol) was added and the mixture was stirred a further 2 h. The DMF was removed in vacuo and the residue was partioned between dichloromethane and 1 M HCl (aq). The organic layer was separated and dried over anhydrous magnesium sulphate, filtered and evaporated in vacuo. Purification on silica gel by elution with ethyl acetate yielded the title compound as a yellow solid. $^1$H NMR (400 MHz, DMSO-d$^6$): δ=2.58-2.64 (brm, 2H), 3.78-3.86 (m, 2H), 4.27 & 4.32 (2s, rotamers, 2H), 6.38 & 6.40 (2s, rotamers, 1H), 6.76 & 6.80 (2s, rotamers, 1H), 7.50 (d, J=8.8 Hz, 1H), 7.63 (d, J=8.8 Hz, 1H), 8.03 (s, 1H), 8.24 (s, 1H), 8.32-8.35 (m, 1H), 9.34 (s, 1H), 11.95 (s, 1H). MS (ES+): m/z 428.4 (100).

EXAMPLE 50

4-[4-(1H-Indol-5-ylamino)-7H-pyrrolo[2,3-d]pyrimidin-6-yl]-3,6-dihydro-2H-pyridine-1-carboxylic acid tert-butyl ester

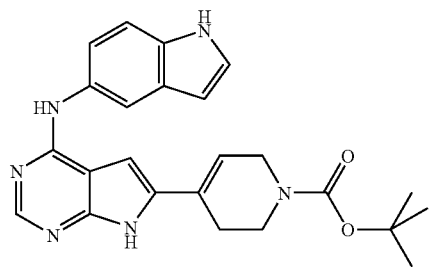

A suspension of 4-(4-chloro-7H-pyrrolo[2,3-d]pyrimidin-6-yl)-3,6-dihydro-2H-pyridine-1-carboxylic acid tert-butyl ester (606.0 mg, 1.810 mmol, 1 eq) and 5-aminoindole (548.9 mg, 4.153 mmol, 2.3 eq) in n-BuOH (30 mL) was stirred at 120° C. for 23 h, after which it was concentrated in vacuo, to a dark brown foam. The crude material (1.2974 g) was dissolved in mixtures of DCM and MeOH (DCM alone was insufficient), to which DiPEA (0.4 mL, 2 mmol, 1 eq) was added to ensure that material was free base and not HCl salt. The crude material was adsorbed onto Hydromatrix, dry loaded, and purified by chromatography on silica gel [Jones Flashmaster, 50 g/150 mL cartridge, eluting with MeOH:DCM 1%→5% →10%]. Trituration of combined and concentrated product fractions in DCM/sonication gave the title compound as white solid. $^1$H NMR (400 MHz, DMSOd$_6$): δ=1.43 (s, 9H), 2.44 (s, br, 2H), 3.55 (t, J=5.6 Hz, 2H), 4.03 (s, br, 2H), 6.35 (s, br, 1H), 6.40 (t, J=2.0 Hz, 1H), 6.67 (s, br, 1H), 7.29-7.41 (m, 3H), 8.03 (s, br, 1H), 8.19 (s, 1H), 9.14 (s, —NH), 10.99 (s, —NH), 11.81 (d, J=1.6 Hz, —NH). MS (ES+): m/z 431.04 (100) [MH$^+$]. HPLC: t$_R$=2.42 min (ZQ2000, polar__5 min).

Alternative preparation: 4-[7-Benzenesulfonyl-4-(1H-indol-5-ylamino)-7H-pyrrolo[2,3d]pyrimidin-6-yl]-3,6-dihydro-2H-pyridine-1-carboxylic acid tert-butyl ester (84 mg, 0.147 mmol) in THF (2 mL) was treated with a 5M solution of NaOH in MeOH (1 mL). After 10 min the reaction was evaporated to dryness and conc. NH₄Cl solution and water (enough to dissolve all inorganic salts) were added, the mixture was extracted with EtOAc (3×4 mL), the combined organic was washed with brine, dried over anhydrous magnesium sulphate, filtered, and concentrated to leave the title compound as pale pink solid.

4-[7-Benzenesulfonyl-4-(1H-indol-5-ylamino)-7H-pyrrolo[2,3-d]-pyrimidin-6-yl]-3,6-dihydro-2H-pyridine-1-carboxylic acid tert-butyl ester

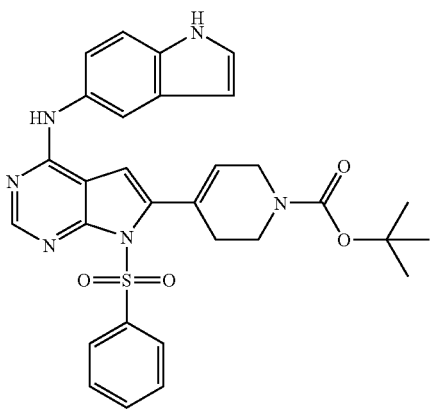

4-(7-Benzenesulfonyl-4-chloro-7H-pyrrolo[2,3-d]pyrimidin-6-yl)-3,6-dihydro-2H-pyridine-1-carboxylic acid tert-butyl ester (150 mg, 0.31 mmol) in butanol (5 mL) was treated with 5-aminoindole (50 mg, 0.38 mmol) and heated to 80° C. for 2 h and then 85° C. for 1 h. The mixture was evaporated to dryness and pre-absorbed onto silica. Purification on silica by elution with dichloromethane:methanol (97:3) yielded a slightly pink solid. ¹H NMR (d₆-DMSO, 400 MHz) 9.4(NH), 8.3(1H, s), 8.0(2H,d), 7.9(1H,s), 7.7(1H,m), 7.6(2H,m), 7.4 (2H,m), 7.2(1H,m), 6.8(1H, br.s), 6.4(1H, s), 6.0(1H,s), 4.1 (2H, m), 3.6(2H,m), 2.5(2H, m), and 1.5(9H, s); LC/MS: m/z 570 [M+H]⁺, Rt=4.07 min.

4-(7-Benzenesulfonyl-4-chloro-7H-pyrrolo[2,3-d]pyrimidin-6-yl)-3,6-dihydro-2H-pyridine-1-carboxylic acid tert-butyl ester

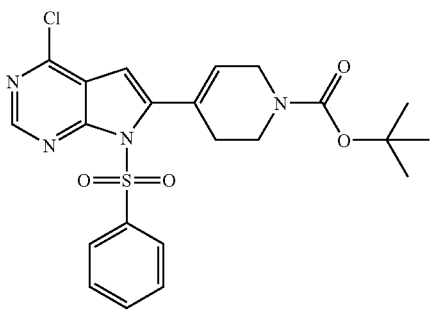

7-Benzenesulfonyl-4-chloro-6-iodo-7H-pyrrolo[2,3-d]pyrimidine (4.05 g, 9.65 mmol), 4-(4,4,5,5-tetramethyl-[1,3,2]dioxaborolan-2-yl)-3,6-dihydro-2H-pyridine-1-carboxylic acid tert-butyl ester (2.985 g, 9.65 mmol), potassium carbonate (2.935 g, 21.25 mmol) and dichlorobis(triphenylphosphine)-palladium(II) (678 mg, 0.96 mmol) were combined in dioxane/water (85 mL:21 mL) and heated to 90° C. for 2 h. After cooling the reaction mixture was extracted with ethyl acetate (3×50 mL), the organic layers were combined and washed with aqueous sodium bicarbonate, brine and finally water. The organic layer was dried over anhydrous magnesium sulphate, filtered and pre-absorbed onto silica in vacuo. Purification on silica gel by gradient elution with isohexane:ethyl acetate (6:1) finishing with isohexane:ethyl acetate (4:1) yielded a yellow solid. ¹H NMR (d₆-DMSO, 400 MHz) 8.8(1H, s), 8.0 (2H, d), 7.8(1H,m), 7.6(2H,m), 6.8(1H, s), 6.0(1H, s), 4.1(2H, br. s), 3.6(2H,m), 2.5(2H, br. s), and 1.5(9H, s); LC/MS: m/z 474 [M+H]⁺, Rt=4.42 min Functionalisation of (1H-Indazol-5-yl)-[6-(1,2,3,6-tetrahydropyridin-4-yl)-7H-pyrrolo[2,3-d]pyrimidin-4-yl]-amine hydrochloride (compound of Formula I-B-H wherein R2=H and R1=indazol-5-yl) to yield compounds of Formula I-B wherein R2=H, R1=indazol-5-yl, and Z is as defined previously:

Preferred method with Acid Chlorides, Chloroformates, Carbamoyl Chlorides, Sulfamoyl chlorides, Sulfonyl chlorides & Isocyanates.

To a solution of 1H-indazol-5-yl-[6-(1,2,3,6-tetrahydropyridin-4-yl)-7H-pyrrolo[2,3-d]pyrimidin-4-yl]-amine hydrochloride (40 mg, 0.11 mmol) in DMF (1.5 mL) was added diisopropylethylamine (57 µL, 3 eq., 0.33 mmol) at r.t., followed by the appropriate capping reagent (acid chloride, chloroformate, carbamoyl chloride, sulfamoyl chloride, sulfonyl chloride or isocyanate) (1 eq., 0.11 mmol). The reaction was stirred at r.t. overnight. After this time, the reaction was quenched with methanol (0.5 mL) and the solvent was evaporated under reduced pressure. The resultant residue was purified by mass-directed HPLC using water/acetonitrile mixtures optionally containing formic acid, trifluoroacetic acid, or ammonium carbonate to optimize separation.

(Alternative methods including the use of polymer-supported diisopropylethylamine (PS-DIEA) under the conditions outlined above, or use of the free base 1H-indazol-5-yl-[6-(1,2,3,6-tetrahydropyridin-4-yl)-7H-pyrrolo[2,3-d] pyrimidin-4-yl]-amine (prepared by stirring of 1H-indazol-5-yl-[6-(1,2,3,6-tetrahydropyridin-4-yl)-7H-pyrrolo[2,3-d] pyrimidin-4-yl]-amine hydrochloride with MP-Carbonate resin in methanol over 2 h at r.t.) with reduced amounts of diisopropylethylamine present (1 eq.) were also used to prepare some of the compounds described).

Preferred Method with Carboxylic Acids.

To a mixture of the appropriate carboxylic acid (1 eq., 0.1088 mmol), 1-ethyl-3-(3'-dimethylaminopropyl)carbodiimide hydrochloride (EDCI.HCl) (31.3 mg., 1.5 eq., 0.163 mmol), N-hydroxybenzotriazole monohydrate (HOBt.H₂O) (22.1 mg., 1.5 eq., 0.163 mmol) and a catalytic amount of 4-dimethylaminopyridine (DMAP) was added DMF (2 mL) followed by triethylamine (54 µL, 3.5 eq., 0.38 mmol). The solution was stirred at r.t. for 5 min before 1H-indazol-5-yl-[6-(1,2,3,6-tetrahydropyridin-4-yl)-7H-pyrrolo[2,3-d]-pyrimidin-4-yl]-amine hydrochloride (40 mg, 0.11 mmol) was added in a single portion. The reaction was stirred at r.t. overnight. After this time, the reaction was diluted with ethyl acetate (5 mL) and an aqueous solution of sodium bicarbonate (2 mL). The organic layer was collected and the aqueous layer extracted with ethyl acetate (2×5 mL). The combined organic layer was washed with water (2 mL), dried over anhydrous magnesium sulphate, filtered and the solvent was evaporated under reduced pressure. The resultant residue was purified by mass-directed HPLC. Alternatively, crude reaction mixtures were taken directly, the solvent was evaporated under reduced pressure and the residue was purified by mass-directed HPLC.

(An alternative method using the free base 1H-indazol-5-yl-[6-(1,2,3,6-tetrahydropyridin-4-yl)-7H-pyrrolo[2,3-d]pyrimidin-4-yl]-amine (prepared by stirring of 1H-indazol-5-yl-[6-(1,2,3,6-tetrahydropyridin-4-yl)-7H-pyrrolo[2,3-d]pyrimidin-4-yl]-amine hydrochloride with MP-Carbonate resin in methanol over 2 h at r.t.) with reduced amounts of triethylamine (1.5 eq.) was also used to prepare some of the compounds described).

Table 2: Examples of compounds prepared by functionalisation of (1H-indazol-5-yl)-[6-(1,2,3,6-tetrahydro-pyridin-4-yl)-7H-pyrrolo[2,3-d]pyrimidin-4-yl]-amine hydrochloride or (1H-indazol-5-yl)-[6-(1,2,3,6-tetrahydro-pyridin-4-yl)-7H-pyrrolo[2,3-d]pyrimidin-4-yl]-amine (prepared by stirring of (1H-indazol-5-yl)-[6-(1,2,3,6-tetrahydro-pyridin-4-yl)-7H-pyrrolo[2,3-d]pyrimidin-4-yl]-amine, as described above.

TABLE 2

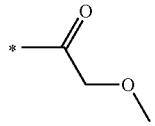

| EX. | Z | NMR | NMR Solvent | MH+ | HPLC Rt (Min) |
|---|---|---|---|---|---|
| 51 | 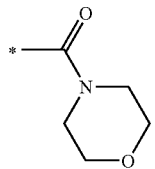 | 12.0 (1H, s), 9.4 (1H, s), 8.4 (2H, s), 8.2 (1H, s), 8.0 (1H, s), 7.7 (1H, d), 7.5 (1H, d), 6.8 (1H, d), 6.4 (1H, br.s), 4.2 (4H, m), 3.6 (2H, m), 3.3 (3H, s), 2.5 (2H, m. obscured) | DMSO | 404 | 2.81 |
| 52 | 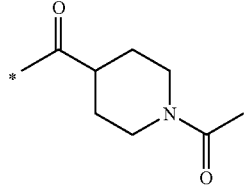 | 12.1 (1H, s), 9.3 (1H, s), 8.5 (1H, br.s), 8.4 (1H, s), 8.2 (1H, s), 8.0 (1H, s), 7.7 (1H, d), 7.5 (1H, d), 6.8 (1H, s), 6.4 (1H, br.s), 4.0 (2H, br.s), 3.6 (4H, m), 3.4 (2H, m, partially obscured), 3.2 (4H, m), 2.5 (2H, m, obscured) | DMSO | 445 | 2.64 |
| 53 | 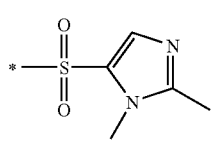 | 12.3 (1H, s), 9.4 (1H, s), 8.6 (1H, s), 8.4 (1H, d), 8.2 (1H, s), 8.0 (1H, s), 7.7 (1H, d), 7.5 (1H, d), 6.8 (1H, d), 6.4 (1H, br.s), 4.3 (2H, m), 4.2 (1H, br.s), 3.8 (3H, m), 3.2 (1H, m), 3.0 (1H, m), 2.6 (1H, m), 2.5 (2H, m, partially obscured), 2.0 (3H, s), 1.7 (2H | DMSO | 485 | 2.56 |
| 54 | 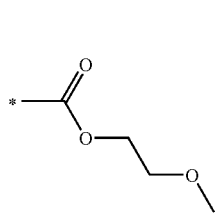 | 11.9 (1H, s), 9.4 (1H, s), 8.5 (1H, s), 8.4 (1H, s), 8.2 (1H, s), 8.0 (1H, s), 7.7 (1H, d), 7.5 (1H, d), 7.4 (1H, s), 6.8 (1H, s), 6.4 (1H, br.s), 3.8 (2H, br.s), 3.7 (3H, s), 3.4 (2H, m, partially obscured), 2.5 (2H, m, obscured), 2.3 (3H, s) | DMSO | 490 | 2.67 |
| 55 | | 11.8 (1H, s), 9.3 (1H, s), 8.4 (1H, s), 8.2 (1H, s), 8.0 (1H, s), 7.7 (1H, d), 7.5 (1H, d), 6.8 (1H, s), 6.4 (1H, br.s), 4.2 (2H, m), 4.1 (2H, m), 3.6 (2H, m), 3.5 (2H, m), 3.3 (3H, s), 2.5 (2H, m, obscured) | DMSO | 434 | 2.67 |

TABLE 2-continued

| EX. | Z | NMR | NMR Solvent | MH+ | HPLC Rt (Min) |
|---|---|---|---|---|---|
| 56 | *—C(=O)—O—CH₃ | 12.0 (1H, s), 9.4 (1H, s), 8.5 (1H, s), 8.4 (1H, s), 8.2 (1H, s), 8.0 (1H, s), 7.7 (1H, d), 7.5 (1H, d), 6.8 (1H, s), 6.4 (1H, br.s), 4.1 (2H, m), 3.6 3H, s + 2H, m), 2.5 (2H, m, obscured) | DMSO | 390 | 2.81 |
| 57 | *—S(=O)₂—N(CH₃)₂ | 11.7 (1H, s), 9.3 (1H, s), 8.6 (1H, s), 8.4 (1H, s), 8.2 (1H, s), 8.0 (1H, s), 7.7 (1H, d), 7.5 (1H, d), 6.8 (1H, s), 6.4 (1H, br.s), 3.9 (2H, m), 3.4 (2H, m), 2.8 (6H, s), 2.6 (2H, m) | DMSO | 439 | 2.86 |
| 58 | *—C(=O)—CH₂CH₂—(piperidinyl) | 11.8 (1H, s), 9.3 (1H, s), 8.4 (2H, br.s), 8.2 (1H, s), 8.0 (1H, s), 7.7 (1H, d), 7.5 (1H, d), 6.8 (1H, d), 6.4 (1H, br.s), 4.2 (1H, br.s), 4.1 (1H, br. s), 3.6 (2H, m), 2.6 (4H, m), 2.5 (2H, m, obscured), 2.4 (4H, m), 1.5 (4H, m), 1.4 (2H, m) | DMSO | 471 | 2.29 |
| 59 | *—C(=O)—CH₂CH₂CH₂—N(CH₃)₂ | 12.0 (1H, s), 9.4 (1H, s), 8.4 (2H, br.s), 8.2 (1H, s), 8.0 (1H, s), 7.7 (1H, d), 7.5 (1H, d), 6.8 (1H, d), 6.4 (1H, br.s), 4.2 (1H, br.s), 4.1 (1H, br. s), 3.7 (2H, m), 2.6 (2H, m, obscured), 2.4 (2H, m), 2.2 (2H, m), 2.1 (6H, 2 x s), 1.7 (2H, m) | DMSO | 445 | 2.37 |
| 60 | *—C(=O)—(3-pyridyl) | 11.8 (1H, s), 9.4 (1H, s), 8.7 (2H, s), 8.5 (1H, s), 8.4 (1H, s), 8.2 (1H, s), 8.0 (1H, s), 7.9 (1H, d), 7.7 (1H, d), 7.5 (2H, d), 6.8 (1H, s), 6.5 & 6.3 (1H, 2 x br.s, rotamers), 4.3 (1H, br.s), 4.2 & 3.9 (1H, 2 x m, rotamers), 3.6 (2H, m, partially obscured), 2.4 (2H, m). | DMSO | 437 | 2.51 |
| 61 | *—C(=O)—C₆H₅ | Not recorded | | 436 | 2.15 |
| 62 | *—C(=O)—C(CH₃)₃ | Not recorded | | 416 | 2.18 |

EXAMPLE 63

{6-[1-(2-Chloropyrimidin-4-yl)-1,2,3,6-tetrahydro-pyridin-4-yl]-7H-pyrrolo[2,3-d]pyrimidin-4-yl}-(1H-indazol-5-yl)-amine

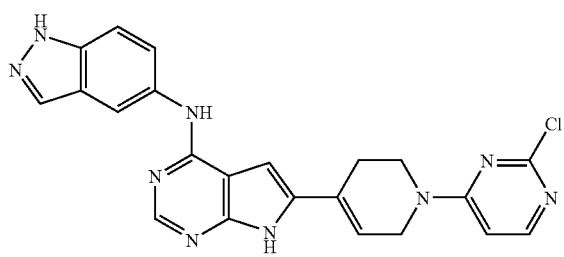

Following the Preferred method with Acid Chlorides, Chloroformates, Carbamoyl Chlorides, Sulfamoyl chlorides, Sulfonyl chlorides & Isocyanates, but using 2,4-dichloropyrimidine as capping reagent, one obtained the title compound. MS (ES+): m/z 444.03/446.06 (38/13) [MH$^+$]. HPLC: $t_R$=2.21 min (ZQ2000, polar_5 min).

Following the Preferred method with Acid Chlorides, Chloroformates, Carbamoyl Chlorides, Sulfamoyl chlorides, Sulfonyl chlorides & Isocyanates, using benzothiazol-6-yl-[6-(1,2,3,6-tetrahydropyridin-4-yl)-7H-pyrrolo[2,3-d]pyrimidin-4-yl]amine trihydrochloride and the appropriate capping reagent, one obtained the examples listed in TABLE 3.

TABLE 3

| EX. | Z | [MH$^+$] | HPLC $t_R$ (min) (ZQ2000, polar_5 min) |
|---|---|---|---|
| 64 | *C(O)-4-pyridyl | 454.08 | 2.23 |
| 65 | *C(O)-phenyl | 453.07 | 2.64 |
| 66 | *C(O)CH$_2$C(CH$_3$)$_3$ | 447.07 | 2.79 |
| 67 | *C(O)NH-n-butyl | 448.15 | 2.61 |
| 68 | *C(O)NH-cyclopentyl | 460.08 | 2.64 |
| 69 | *C(O)NH(CH$_2$)$_3$-morpholino | 519.10 | 1.83 |

TABLE 3-continued

| EX. | Z | [MH+] | HPLC $t_R$ (min) (ZQ2000, polar_5 min) |
|---|---|---|---|
| 70 | *—C(O)NH-cyclobutyl | 446.12 | 2.51 |
| 71 | *—C(O)NH-cyclohexyl | 474.11 | 2.77 |
| 72 | *—C(O)NH-(3-methoxyphenyl) | 498.12 | 2.71 |
| 73 | *—C(O)NH-(4-trifluoromethylphenyl) | 536.03 | 3.09 |
| 74 | *—C(O)NH-(4-cyanophenyl) | 493.06 | 2.71 |
| 75 | *—C(O)NH-(3-chlorophenyl) | 502.03 | 2.96 |

EXAMPLE 76
4-[4-(1H-Indazol-5-ylamino)-7H-pyrrolo-[2,3-d]-pyrimidin-6-y]-1-piperdin-1-carboxylic adic tert-butyl ester

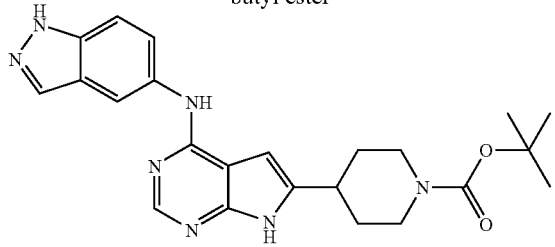

A rapidly stirred mixture of 4-[4-(1H-indazol-5-ylamino)-7H-pyrrolo[2,3-d]pyrimidin-6-yl]-3,6-dihydro-2H-pyridine-1-carboxylic acid tert-butyl ester (0.1 g) and 10% palladium on carbon (10 mg) was heated in ethanol (20 mL) at 100° C. under a 100 PSI hydrogen atmosphere for 6 h. After this time the mixture was cooled, filtered through celite and concentrated. Crystallisation from methanol/ethyl acetate afforded the title compound. 1H NMR (300 MHz, DMSO) δ=1.44 (9H, s), 1.55 (1H, m), 2.0 (2H, m), 2.89 (3H, m), 4.06 (2H, m), 6.46 (1H, s), 7.52 (1H, d), 7.66 (1H, d), 8.07 (1H, s), 8.12(1H, s) 18.8 (1H, s) and 9.15 (1H, s). MH+ 434.16.

EXAMPLE 77
4-[4-(1H-Indazol-5ylamino)-7H-pyrrolo[2,3-d]-pyrimidin-6-yl]-1-(2-methoxyethyl)-1H-pyridin-2-one

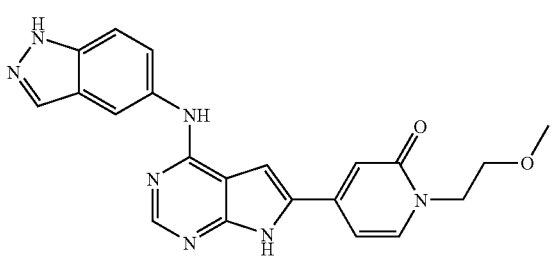

A mixture of (1H-indazol-5-yl)-(6-iodo-7H-pyrrolo[2,3-d]pyrimidin-4-yl)-amine (0.076 g), 1-(2-methoxy-ethyl)-2-oxo-1,2-dihydro-pyridine-4-boronic acid (36 mg), PdCl2(PPh3)2 (7 mg) end potassium carbonate (76 mg) in dioxane/wawr (4:1) (5 mL) was heated to 100° C. for 48 h. Purification via chromatograpby afforded tJm title compound as a pale yellow solid. δH 3.30 (3H, s), 3.62 (2H, t), 4.18 (2H, t), 5.99 (1H, dd), 6.89 (1H, d), (7.27 (1H, s), 7.57 (2H, d), 7.69 (2H, m), 8.09 (1H, s), 8.16 (1H, s), 8.18 (1H, s) and 9.67 (1H, s). MH+ 402.13.

A mixture of trifluoromethanesulfonic acid 1-(2-methoxy-ethyl)-2-oxo-1,2-dihydro-pyridin-4-yl ester (0.5 g, 1.66 mmol), bis-(pinacolato)di-boron (0.464 g, 1.83 mmol), potassium acetate (0.488 g, 4.98 mmol), PdCl2(dppf) (0.04 g, 0.05 mmol), dppf (0.028 g) in dioxane was heated at 80° C. for 24 h. The mixture was cooled, diluted with water (15 mL) and extracted with ethyl acetate (3×5 mL). The aqueous layer was concentrated and purification via elution through a silica plug afforded 1-(2-methoxy-ethyl)-2-oxo-1,2-dihydro-pyridine-4-boronic acid. MH+ 198.03.

A round bottom flask was charged with 4-hydroxy-1-(2-methoxy-ethyl)-1H-pyridin-2-one (5.39 mmol), DCM (15 mL) and triethylamine (1 mL, 7 mmol) and cooled to −78° C. Triflic anhydride (1 mL, 7 mmol) was added drop-wise, and after stirring for a further 20 min the cooling bath was removed and the mixture allowed to reach rt. After 1.5 h, the mixture was diluted with further DCM, washed with aqueous saturated sodium hydrogen carbonate solution, brine, dried and concentrated. Purification via flash chromatography afforded trifluoromethanesulfonic acid 1-(2-methoxy-ethyl)-2-oxo-1,2-dihydro-pyridin-4-yl ester (1.1 g) as a colourless oil. MH+ 301.98.

A mixture of 4-benzyloxy-1-(2-methoxy-ethyl)-1H-pyridin-2-one (1.4 g) and 10% palladium on carbon (100 mg) was stirred in ethyl acetate (50 mL) under a hydrogen atmosphere for 17 h. Then, the mixture was filtered through celite and concentrated to afford 4-hydroxy-1-(2-methoxy-ethyl)-1H-pyridin-2-one as a colourless solid. $\delta_H$ (300 MHz, CH3OD) 3.67 (2H, t), 4.10 (2H, t), 4.86 (3H, s), 5.85 (1H, d), 6.04 (1H, dd) and 7.48 (1H, d).

To admixture of 4-benzyloxy-2(1H)-pyridine (2 g, 9.94 mmol) and caesium carbonate (6.5 g, 19.88 mmol) in DMF (20 mL) was added 2-bromoethyl methyl ether (1.4 mL, 14.91 mmol). After stirring for 17 h the mixture was poured into water and extracted with ethyl acetate. The combined organics were washed with brine, dried and concentrated. Purification via flash chromatography afforded 4-benzyloxy-1-(2-methoxy-ethyl)-1H-pyridin-2-one. MH+ 201.96.

EXAMPLE 78

4-[4-(Quinolin-6-yloxy)-7H-pyrrolo[2,3-d]pyrimidin-6-yl]-3,6-dihydro-2H-pyridine-1-carboxylic acid tert-butyl ester

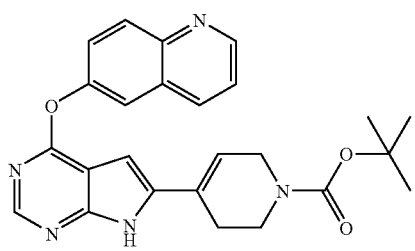

To a stirred suspension of sodium hydride (60% dispersion in mineral oil) (24 mg, 0.6 mmol) in anhydrous DMSO (4 mL) under argon, was added 6-hydroxyquinoline (239 mg, 1.65 mmol). The mixture was allowed to stir at rt for 1 h. To this mixture was added 1-[6-(1-tert-butoxycarbonyl-1,2,3,6-tetrahydropyridin-4-yl)-7H-pyrrolo[2,3-d]pyrimidin-4-yl]-4-aza-1-azonia-bicyclo[2.2.2]octane chloride (100 mg, 0.3 mmol) in DMSO (0.3 mL), and the mixture stirred for a further 16 h. TLC analysis showed no starting material so the mixture was neutralised with glacial acetic acid and basified with saturated aqueous sodium bicarbonate solution. The product was extracted in to EtOAc (3×50 mL), the organics dried with MgSO4, filtered and concentrated under reduced pressure. The resulting residue was purified on silica gel by elution with iso-hexane:ethyl acetate to yield the title compound. $^1$H NMR (DMSO, 400 MHz) 1.4 (9H, s), 2.5 (2H, broad), 3.6 (2H, broad), 4.1 (2H, broad), 6.5 (1H, m), 6.7 (1H, s), 7.6 (1H, m), 7.7 (1H, d), 7.9 (1H, s), 8.1 (1H, d), 8.3 (1H, s), 8.4 (1H, d), 8.9 (1H, s), 12.4 (NH, s). MH$^+$=444.24

1-[6-(1-tert-Butoxycarbonyl-1,2,3,6-tetrahydropyridin-4-yl)-7H-pyrrolo[2,3-d]pyrimidin-4-yl]-4-aza-1-azoniabicyclo[2.2.2]octane chloride

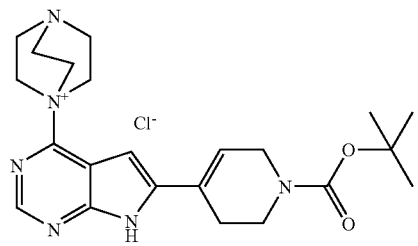

To a stirred solution of 1M tert-butyl 4-(4-chloro-7H-pyrrolo[2,3-d]-pyrimidin-6-yl)-3,6-dihydropyridine-1(2H)-carboxylate (200 mg, 0.6 mmol) in anhydrous DMSO (0.6 mL), was added 1,4-Diaza-bicyclo[2.2.2]octane (370 mg, 3.3 mmol). The mixture was stirred under argon at rt until TLC analysis showed no starting material was present. The resulting solution containing the title compound was used directly in the next step.

EXAMPLE 79

Benzothiazol-6-yl-[6-(1,2,3,6-tetrahydropyridin-4-yl)-7H-pyrrolo[2,3-d]pyrimidin-4-yl]amine trihydrochloride

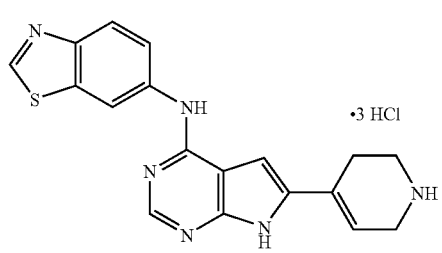

145

To a suspension of benzothiazol-6-yl-(6-iodo-7H-pyrrolo[2,3-d]pyrimidin-4-yl)-amine (4.05 g, 10.3 mmol) in 1,2-dimethoxyethane (125 mL) and water (25 mL) were added 4-(4,4,5,5-tetramethyl-[1,3,2]dioxaborolan-2-yl)-3,6-dihydro-2H-pyridine-1-carboxylic acid tert-butyl ester (3.50 g, 11.3 mmol), [1,1'-bis(diphenylphosphino)ferrocene]dichloro palladium(II), complex with dichloromethane (1:1) (420 mg, 0.51 mmol) and potassium carbonate (2.85 g, 20.6 mmol). The flask was evacuated and refilled with $N_2$ (3×). The mixture was heated at 80° C. overnight. The reaction mixture was diluted with EtOAc (200 mL) and water (50 mL) and filtered through a pad of celite. The organic phase was separated, and the aqueous phase was extracted with EtOAc (2×50 mL). The combined organic phases were washed with brine (100 mL), and dried over anhydrous sodium sulfate. Evaporation under reduced pressure afforded a brown solid. To a suspension of this crude material in methylene chloride (30 mL) was added 4M HCl/1,4-dioxane (30 mL), and the resulting mixture was stirred at rt overnight. The mixture was diluted with $CH_2Cl_2$ (30 mL), and the light-yellow solid was collected by filtration and dried in vacuo to give the title compound. LC-MS (ES, Pos.): 349 [MH$^+$]. $^1$H NMR (DMSO-$d_6$, 400 MHz): δ=2.51 (m, 2H), 3.34 (m, 2H), 3.81 (m, 2H), 6.52 (s, 1H), 7.09 (s, 1H), 7.73 (dd, J=8.7 Hz, 2.0 Hz, 1H), 8.22 (d, J=8.7 Hz, 1H), 8.36 (d, J=2.0 Hz, 1H), 8.51 (s, 1H), 9.46 (s, 1H).

Alternative preparation: A mixture of 4-(4-chloro-7H-pyrrolo[2,3-d]pyrimidin-6-yl)-3,6-dihydro-2H-pyridine-1-carboxylic acid tert-butyl ester (5.02 g, 15 mmol) and 1,3-benzothiazol-6-amine (2.25 g, 15 mmol) in 1-butanol (50 mL) was heated at 115° C. overnight, LC-MS showed the desired product and some de-Boc product. After the mixture was cooled to rt, it was diluted with hexane (50 mL), the gray solid was collected by filtration, a mixture of the desired product and some de-Boc product, which was directly used in the next step. To a suspension of this material in methylene chloride (30 mL) was added 4M HCl/1,4-dioxane (30 mL), the resulting mixture was stirred at rt for 5 h. The mixture was then diluted with $CH_2Cl_2$ (30 mL), and the light-yellow solid was collected by filtration and dried in vacuo.

EXAMPLE 80

3-{4-[4-(Benzothiazol-6-ylamino)-7H-pyrrolo[2,3-d]-pyrimidin-6-yl]-3,6-dihydro-2H-pyridine-1-carbonyl}-benzoic acid methyl ester

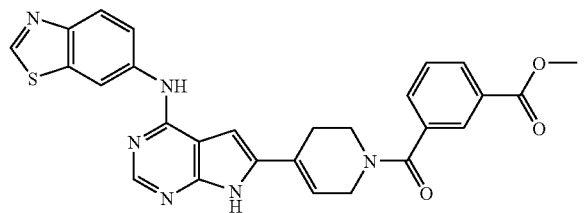

The title compound was obtained following the Preferred method with Acid Chlorides, Chloroformates, Carbamoyl Chlorides, Sulfamoyl chlorides, Sulfonyl chlorides & Isocyanates, using benzothiazol-6-yl-[6-(1,2,3,6-tetrahydropyridin-4-yl)-7H-pyrrolo[2,3-d]pyrimidin-4-yl]amine trihydrochloride and isophthalic acid monomethyl ester. $^1$H NMR (DMSO, 400 MHz): δ=9.6(1H,s), 9.25(1H,s), 8.9(1H,s), 8.3 (1H,s), 8.1-8.0(3H,m), 7.9(1H,d), 7.75 (1H, d), 7.65(1H, t), 6.85(1H, s), 6.5(1H, m), 6.3(1H, m), 4.3(1H, m), 4.1(1H, m), 3.9(3H, s), 3.6(1H, m), 2.6(1H, m). [MH$^+$—CH$_3$]=512.45.

146

EXAMPLE 81

3-{4-[4-(Benzothiazol-6-ylamino)-7H-pyrrolo[2,3-d]-pyrimidin-6-yl]-3,6-dihydro-2H-pyridine-1-carbonyl}-benzoic acid

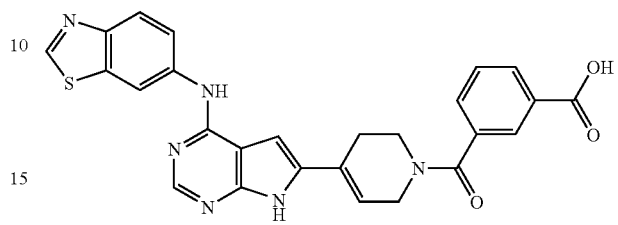

3-{4-[4-(Benzothiazol-6-ylamino)-7H-pyrrolo[2,3-d]pyrimidin-6-yl]-3,6-dihydro-2H-pyridine-1-carbonyl}-benzoic acid methyl ester (0.624 mmol) was suspended in a mixture of MeOH (6.0 mL) and water (2.0 mL). 2 M NaOH solution (1.0 mmol) was then added to the above suspension and the reaction temperature increased to 65° C. The resulting suspension was stirred for a further period of 16 h. The mixture was allowed to reach r.t and diluted with EtOAc (30 mL) and washed with 2M NaOH (2×20 mL). The aqueous phase was then acidified by careful addition of conc. HCl solution until pH≈1. The resulting brown precipitate was then filtered and dried under vacuum affording the title compound. $^1$H NMR (DMSO, 400 MHz): δ=9.45(1H,s), 8.7(1H,s), 8.15(1H, d), 8.1(1H,d), 8.0(1H,s), 7.8(1H,d), 7.7 (1H, d), 7.6(1H, t), 6.9(1H, s), 6.6(1H, m), 6.35(1H, m), 4.35(1H, m), 4.1(1H, m), 3.9(1H, m), 2.6(1H, m). [MH$^+$—CO$_2$]=498.25.

EXAMPLE 82

1-{4-[4-(1H-Indazol-5-ylamino)-7H-pyrrolo[2,3-d]-pyrimidin-6-yl]-3,6-dihydro-2H-pyridin-1-yl}-2-phenylethanone

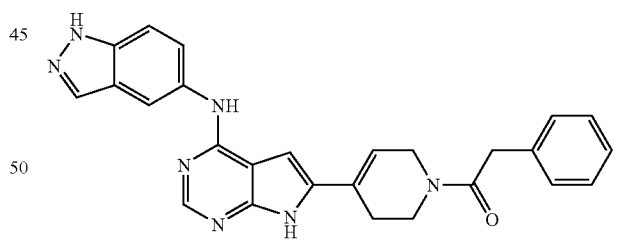

To a solution of (1H-indazol-5-yl)-[6-(1,2,3,6-tetrahydropyridin-4-yl)-7H-pyrrolo[2,3-d]pyrimidin-4-yl]amine trihydrochloride (73.6 mg, 0.2 mmol) and phenylacetyl chloride (31 mg, 0.2 mmol) in dichloromethane (1.5 mL) was added i-Pr$_2$NEt (0.1 mL). The resulting mixture was stirred at rt for 3 h. MeOH (0.3 mL) was added to quench the reaction. Solvents were removed and the residue was dissolved in DMF (≈2 mL), which was purified by mass-directed HPLC to obtain the title compound. $^1$H-NMR (DMSO-$d_6$, 400 MHz): δ=2.34 (m, 2H), 3.72 (t, J=5.6 Hz, 2H), 3.80 (d, J=17.6 Hz, 2H), 4.21 (d, J=35.6 Hz, 2H), 6.40 (s, 1H), 6.73 (d, J=38.4 Hz, 1H), 7.22-7.34 (m, 4H), 7.51 (d, J=8.8 Hz, 1H), 7.63 (m, 1H), 8.04 (s, 1H), 8.25 (d, J=4.4 Hz, 1H), 8.37 (t, J=7.2 Hz, 1H), 9.33 (d, J=13.6 Hz, 1H), 11.92 (d, J=14.8 Hz, 1H), 12.97 (s, 1H). MS (ES+): m/z 450.07 [MH⁺]. HPLC: $t_R$=2.17 min (ZQ2000, polar_5 min).

EXAMPLE 83

Phenyl 4-[4-(1H-indazol-5-ylamino)-7H-pyrrolo[2,3-d]pyrimidin-6-yl]-3,6-dihydro-2H-pyridine-1-carboxylate

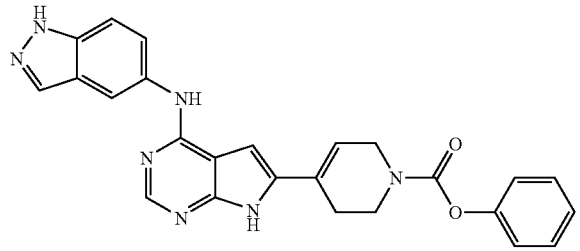

The title compound was obtained following the Preferred method with Acid Chlorides, Chloroformates, Carbamoyl Chlorides, Sulfamoyl chlorides, Sulfonyl chlorides & Isocyanates, using phenyl chloroformate. ¹H-NMR (DMSO-$d_6$, 400 MHz): δ=2.58-2.62 (m, 2H), 3.70 (m, 1H), 3.84 (m, 1H), 4.16 (m, 1H), 4.35 (m, 1H), 6.45 (s, 1H), 6.81 (s, 1H), 7.17 (d, J=8.4 Hz, 2H), 7.23 (t, J=6.8 Hz, 1H), 7.40 (t, J=7.2 Hz, 2H), 7.52 (d, J=8.8 Hz, 1H), 7.66 (d, J=7.2 Hz, 1H), 8.05 (s, 1H), 8.26 (s, 1H), 8.38 (s, 1H), 9.36 (s, 1H), 11.97 (s, 1H), 12.97 (s, 1H). MS (ES+): m/z 452.02 [MH⁺]. HPLC: $t_R$=2.38 min (ZQ2000, polar_5 min).

EXAMPLE 84

N-Methyl-N-phenyl 4-[4-(1H-indazol-5-ylamino)-7H-pyrrolo[2,3-d]pyrimidin-6-yl]-3,6-dihydro-2H-pyridine-1-carboxamide

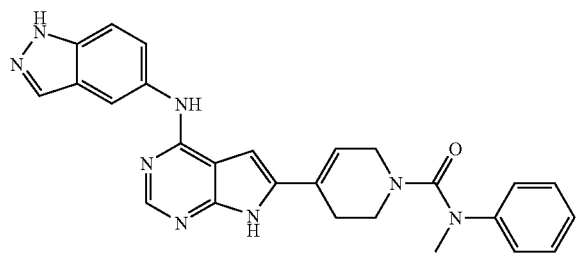

The title compound was obtained following the Preferred method with Acid Chlorides, Chloroformates, Carbamoyl Chlorides, Sulfamoyl chlorides, Sulfonyl chlorides & Isocyanates, using N-methyl-N-phenylcarbamoylchloride. ¹H-NMR (DMSO-$d_6$, 400 MHz): δ=2.20 (m, 2H), 3.13 (s, 3H), 3.78 (m, 2H), 6.28 (s, 1H), 6.66 (s, 1H), 7.14 (d, J=7.2 Hz, 1H), 7.18 (d, J=8.4 Hz, 2H), 7.38 (t, J=7.2 Hz, 2H), 7.50 (d, J=8.8 Hz, 1H), 7.64 (d, J=9.2 Hz, 1H), 8.04 (s, 1H), 8.24 (d, J=5.2 Hz, 1H), 8.36 (d, J=6.4 Hz, 1H), 9.29 (s, 1H), 11.85 (s, 1H), 12.96 (s, 1H). MS (ES+): m/z 465.04 [MH⁺]. HPLC: $t_R$=2.25 min (ZQ2000, polar_5 min).

EXAMPLE 85

4-[4-(1H-Indazol-5-ylamino)-7H-pyrrolo[2,3-d]pyrimidin-6-yl]-3,6-dihydro-2H-pyridine-1-carboxythioamide

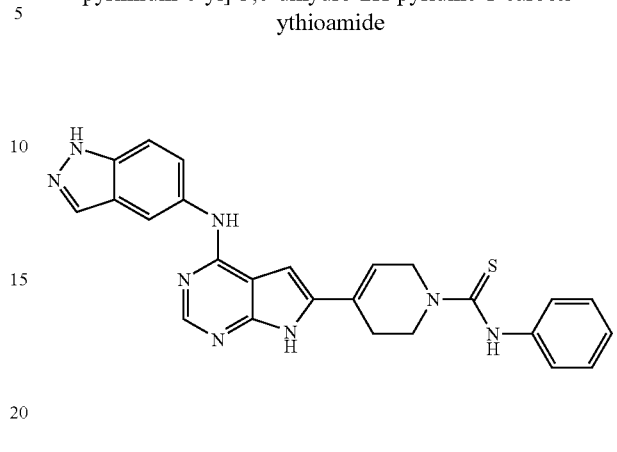

The title compound was obtained following the Preferred method with Acid Chlorides, Chloroformates, Carbamoyl Chlorides, Sulfamoyl chlorides, Sulfonyl chlorides & Isocyanates, using phenyl isothiocyanate. ¹H-NMR (DMSO-$d_6$, 400 MHz): δ=2.62 (m, 2H), 4.17 (t, J=6.0 Hz, 2H), 4.55 (m, 2H), 6.44 (s, 1H), 6.80 (s, 1H), 7.14 (m, 1H), 7.31-7.33 (m, 3H), 7.52 (d, J=8.8 Hz, 1H), 7.66 (d, J=8.8 Hz, 1H), 8.05 (s, 1H), 8.27 (d, J=1.2 Hz, 1H), 8.38 (d, J=6.8 Hz, 1H), 9.36 (s, 1H), 11.95 (s, 1H), 12.97 (s, 1H). MS (ES+): m/z 467.00 [MH⁺]. HPLC: $t_R$=2.33 min (ZQ2000, polar_5 min).

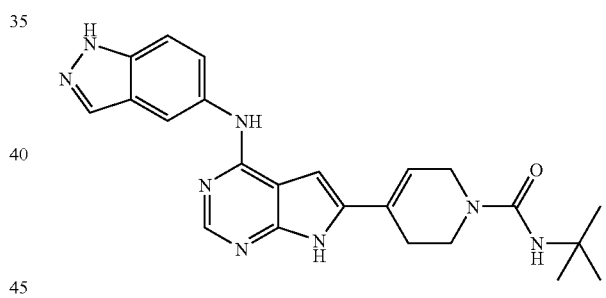

EXAMPLE 86 tert-Butyl 4-[4-(1H-indazol-5-ylamino)-7H-pyrrolo[2,3-d]pyrimidin-6-yl]-3,6-dihydro-2H-pyridine-1-carboxyamide The title compound was obtained following the Preferred method with Acid Chlorides, Chloroformates, Carbamoyl Chlorides, Sulfamoyl chlorides, Sulfonyl chlorides & Isocyanates, using tert-butyl isocyanate. ¹H-NMR (DMSO-$d_6$, 400 MHz): δ=1.28 (s, 9H), 2.44 (m, 2H), 3.52 (t, J=4.8 Hz, 2H), 3.99 (m, 2H), 5.79 (s, 1H), 6.40 (s, 1H), 6.74 (s, 1H), 7.52 (d, J=8.8 Hz, 1H), 7.66 (dd, J=1.6, 8.8 Hz, 1H), 8.05 (s, 1H), 8.25 (s, 1H), 8.37 (s, 1H), 9.32 (s, 1H), 11.90 (s, 1H), 12.97 (s, 1H). MS (ES+): m/z 431.04 [MH⁺]. HPLC: $t_R$=2.14 min (ZQ2000, polar_5 min).

EXAMPLE 87

Ethyl 4-[4-(1H-indazol-5-ylamino)-7H-pyrrolo[2,3-d]pyrimidin-6-yl]-3,6-dihydro-2H-pyridine-1-carboxyamide

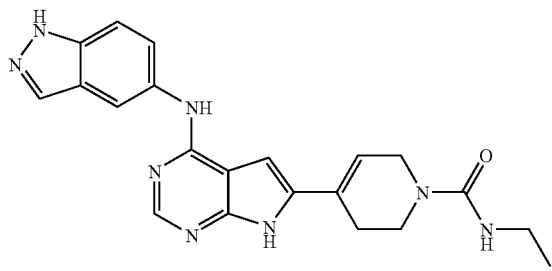

The title compound was obtained following the Preferred method with Acid Chlorides, Chloroformates, Carbamoyl Chlorides, Sulfamoyl chlorides, Sulfonyl chlorides & Isocyanates, using ethyl isocyanate. $^1$H-NMR (CD$_3$OD, 400 MHz): δ=1.14 (t, J=6.4 Hz, 3H), 2.54 (m, 2H), 3.23 (q, J=6.8 Hz, 2H), 3.65 (t, J=5.2 Hz, 2H), 4.11 (m, 2H), 6.40 (s, 1H), 6.68 (s, br, 1H), 7.47 (d, J=8.8 Hz, 1H), 7.76 (d, J=8.4 Hz, 1H), 7.98 (s, 1H), 8.12 (s, 1H), 8.17 (s, 1H). MS (ES+): m/z 403.05 [MH$^+$]. HPLC: t$_R$=1.86 min (ZQ2000, polar_5 min).

EXAMPLE 88

4-[4-(1H-Indazol-5-ylamino)-7H-pyrrolo[2,3-d]pyrimidin-6-yl]-3,6-dihydro-2H-pyridine-1-carboxylic acid (2-fluorophenyl)-amide

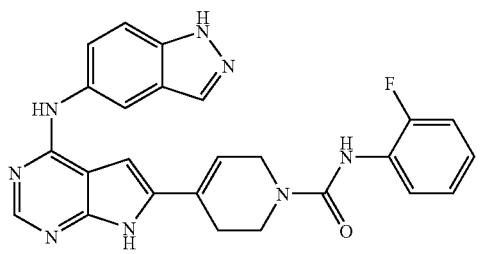

The title compound was obtained following the Preferred method with Acid Chlorides, Chloroformates, Carbamoyl Chlorides, Sulfamoyl chlorides, Sulfonyl chlorides & Isocyanates, using 2-fluorophenyl isocyanate. $^1$H NMR (400 MHz, DMSO-d$_6$): δ=2.53-2.59 (m, 2H), 3.70 (t, J=5.2 Hz, 2H), 4.19 (s, br, 2H), 6.45 (s, br, 1H), 6.78 (s, 1H), 7.10-7.16 (m, 2H), 7.17-7.23 (m, 1H), 7.42-7.49 (me, 1H), 7.52 (d, J=9.2 Hz, 1H), 7.66 (dd, J=8.8, 1.6 Hz, 1H), 8.05 (s, 1H), 8.26 (s, 1H), 8.34 (s, —NH), 8.37 (s, 1H), 9.33 (s, —NH), 11.93 (s, —NH), 12.96 (s, —NH). MS (ES+): m/z 469.02 (100) [MH$^+$]. HPLC: t$_R$=2.16 min (ZQ2000, polar_5 min).

EXAMPLE 89

4-[4-(1H-Indazol-5-ylamino)-7H-pyrrolo[2,3-d]pyrimidin-6-yl]-3,6-dihydro-2H-pyridine-1-carboxylic acid (3-fluorophenyl)-amide

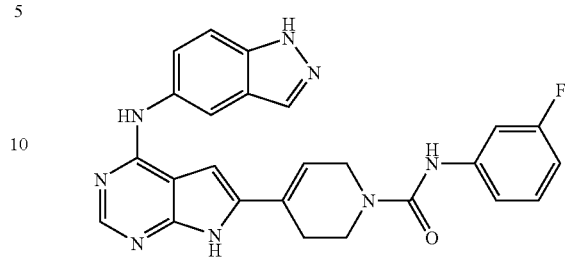

The title compound was obtained following the Preferred method with Acid Chlorides, Chloroformates, Carbamoyl Chlorides, Sulfamoyl chlorides, Sulfonyl chlorides & Isocyanates, using 3-fluorophenyl isocyanate. $^1$H NMR (400 MHz, DMSO-d$_6$): δ=2.44-2.56 (m, 2H), 3.70 (t, J=5.6 Hz, 2H), 4.21 (s, br, 2H), 6.46 (s, br, 1H), 6.70-6.80 (m, 2H), 7.22-7.32 (m, 2H), 7.44-7.55 (m, 2H), 7.65 (dd, J=8.8, 1.6 Hz, 1H), 8.05 (s, 1H), 8.26 (s, 1H), 8.36 (d, J=2.0 Hz, 1H), 8.75 (s, —NH), 9.33 (s, —NH), 11.92 (s, —NH), 12.96 (s, —NH). MS (ES+): m/z 469.02 (100) [MH$^+$]. HPLC: t$_R$=2.32 min (ZQ2000, polar_5 min).

EXAMPLE 90

4-[4-(1H-Indazol-5-ylamino)-7H-pyrrolo[2,3-d]pyrimidin-6-yl]-3,6-dihydro-2H-pyridine-1-carboxylic acid (4-fluorophenyl)-amide

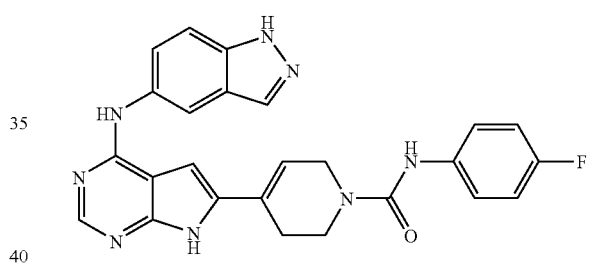

The title compound was obtained following the Preferred method with Acid Chlorides, Chloroformates, Carbamoyl Chlorides, Sulfamoyl chlorides, Sulfonyl chlorides & Isocyanates, using 4-fluorophenyl isocyanate. $^1$H NMR (400 MHz, DMSO-d$_6$): δ=2.44-2.56 (m, 2H), 3.67-3.72 (m$_c$, 2H), 4.19 (d, J=1.2 Hz, 2H), 6.46 (s, br, 1H), 6.77 (s, 1H), 7.08 (t, J=8.8 Hz, 2H), 7.47-7.54 (m, 3H), 7.66 (dd, J=8.8, 2.0 Hz, 1H), 8.05 (s, 1H), 8.26 (s, 1H), 8.36 (d, J=1.2 Hz, 1H), 8.57 (s, —NH), 9.33 (s, —NH), 12.96 (s, —NH). MS (ES+): m/z 469.02 (100) [MH$^+$]. HPLC: t$_R$=2.26 min (ZQ2000, polar_5 min).

EXAMPLE 91

4-[4-(1H-Indazol-5-ylamino)-7H-pyrrolo[2,3-d]pyrimidin-6-yl]-3,6-dihydro-2H-pyridine-1-carboxylic acid (2-methoxyphenyl)-amide

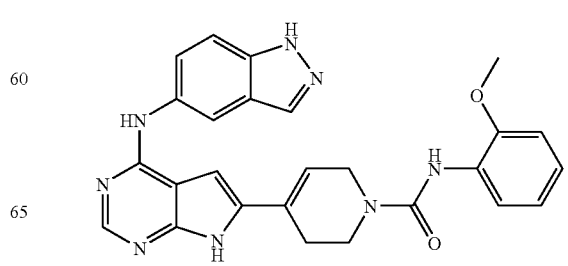

The title compound was obtained following the Preferred method with Acid Chlorides, Chloroformates, Carbamoyl Chlorides, Sulfamoyl chlorides, Sulfonyl chlorides & Isocyanates, using 2-methoxyphenyl isocyanate. $^1$H NMR (400 MHz, DMSO-d$_6$): δ=2.53-2.56 (m, 2H), 3.68 (t, J=5.2 Hz, 2H), 3.83 (s, 3H), 4.19 (s, br, 2H), 6.44 (s, br, 1H), 6.78 (s, 1H), 6.85-6.95 (m, 1H), 6.99-7.04 (m, 2H), 7.52 (d, J=9.2 Hz, 1H), 7.64-7.68 (m, 2H), 7.70 (s, —NH), 8.05 (s, 1H), 8.26 (s, 1H), 8.37 (s, 1H), 9.34 (s, —NH), 11.94 (s, —NH), 12.97 (s, —NH). MS (ES+): m/z 481.03 (100) [MH$^+$]. HPLC: t$_R$=2.23 min (ZQ2000, polar_5 min).

EXAMPLE 92

4-[4-(1H-Indazol-5-ylamino)-7H-pyrrolo[2,3-d]-pyrimidin-6-yl]-3,6-dihydro-2H-pyridine-1-carboxylic acid (3-methoxyphenyl)-amide

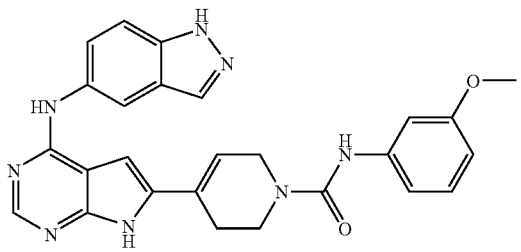

The title compound was obtained following the Preferred method with Acid Chlorides, Chloroformates, Carbamoyl Chlorides, Sulfamoyl chlorides, Sulfonyl chlorides & Isocyanates, using 3-methoxyphenyl isocyanate. $^1$H NMR (400 MHz, DMSO-d$_6$): δ=2.43-2.47 (m, 2H), 3.67-3.70 (m, 2H), 3.71 (s, 3H), 4.19 (s, br, 2H), 6.46 (s, br, 1H), 6.52 (ddd, J=7.6, 2.4, 1.6 Hz, 1H), 6.77 (s, 1H), 7.07-7.12 (m, 1H), 7.14 (dd, J=8.0, 7.6 Hz, 1H), 7.19 (t, J=2.0 Hz, 1H), 7.52 (d, J=8.8 Hz, 1H), 7.66 (dd, J=8.8, 1.6 Hz, 1H), 8.05 (s, 1H), 8.26 (s, 1H), 8.37 (s, 1H), 8.53 (s, —NH), 9.33 (s, —NH), 11.92 (s, —NH), 12.97 (s, —NH). MS (ES+): m/z 481.03 (100) [MH$^+$]. HPLC: t$_R$=2.23 min (ZQ2000, polar5 min).

EXAMPLE 93

4-[4-(1H-Indazol-5-ylamino)-7H-pyrrolo[2,3-d]-pyrimidin-6-yl]-3,6-dihydro-2H-pyridine-1-carboxylic acid (4-methoxyphenyl)-amide

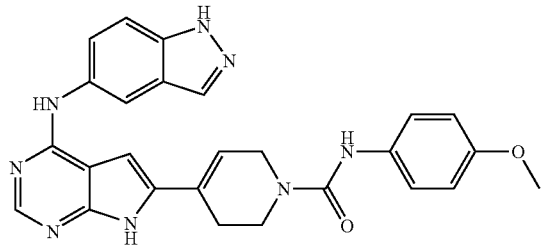

The title compound was obtained following the Preferred method with Acid Chlorides, Chloroformates, Carbamoyl Chlorides, Sulfamoyl chlorides, Sulfonyl chlorides & Isocyanates, using 4-methoxyphenyl isocyanate. $^1$H NMR (400 MHz, MeOH-d$_4$): δ=2.61 (s, br, 2H), 3.75-3.80 (m, 2H), 3.77 (s, 3H), 4.26 (s, br, 2H), 6.44 (s, br, 1H), 6.63-6.78 (s, br, 1H), 6.86 (dd, J=6.8, 2.0 Hz, 2H), 7.25 (dd, J=6.8, 2.0 Hz, 2H), 7.48 (dd, J=8.8, 2.4 Hz, 1H), 7.77 (d, J=8.8 Hz, 1H), 7.98 (d, J=2.4 Hz, 1H), 8.13 (s, 1H), 8.18 (s, 1H). MS (ES+): m/z 480.97 (100) [MH$^+$]. HPLC: t$_R$=2.13 min (ZQ2000, polar_5 min).

EXAMPLE 94

4-[4-(1H-Indazol-5-ylamino)-7H-pyrrolo[2,3-d]-pyrimidin-6-yl]-3,6-dihydro-2H-pyridine-1-carboxylic acid phenylamide

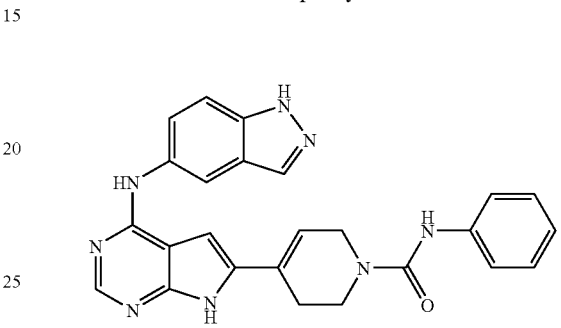

The title compound was obtained following the Preferred method with Acid Chlorides, Chloroformates, Carbamoyl Chlorides, Sulfamoyl chlorides, Sulfonyl chlorides & Isocyanates, using phenyl isocyanate. $^1$H NMR (400 MHz, DMSO-d$_6$): δ=2.43-2.57 (m, 2H), 3.69 (m, 2H), 4.21 (s, br, 2H), 6.51 (s, br, 1H), 6.75-6.84 (s, br, 1H), 6.95 (t, J=7.2 Hz, 1H), 7.24 (t, J=8.8 Hz, 2H), 7.49 (d, J=7.6 Hz, 2H), 7.51-7.57 (s, br, 1H), 7.60-7.67 (s, br, 1H), 8.08-8.20 (m, br, 1H+—NH), 8.25 (s, 1H), 8.55 (s, 1H), 13.01-13.31 (s, br, —NH). MS (ES+): m/z 451.01 (100) [MH$^+$]. HPLC: t$_R$=2.21 min (ZQ2000, polar_5 min).

EXAMPLE 95

4-[4-(1H-Indazol-5-ylamino)-7H-pyrrolo[2,3-d]-pyrimidin-6-yl]-3,6-dihydro-2H-pyridine-1-carboxylic acid benzylamide

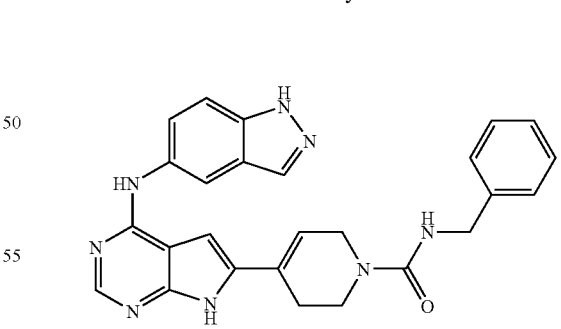

The title compound was obtained following the Preferred method with Acid Chlorides, Chloroformates, Carbamoyl Chlorides, Sulfamoyl chlorides, Sulfonyl chlorides & Isocyanates, using benzyl isocyanate. $^1$H NMR (400 MHz, DMSO-d$_6$): δ=2.44-2.53 (m, 2H), 3.60 (t, J=5.2 Hz, 2H), 4.07 (s, br, 2H), 4.28 (d, J=5.6 Hz, 2H), 6.42 (s, br, 1H), 6.75 (s, 1H), 7.14 (t, J=5.6 Hz, —NH), 7.18-7.23 (m, 1H), 7.25-7.34 (m, 4H), 7.51 (d, J=8.8 Hz, 1H), 7.65 (dd, J=9.2, 2.0 Hz, 1H), 8.04 (s, 1H), 8.25 (s, 1H), 8.36 (d, J=0.8 Hz, 1H), 9.31 (s, —NH), 11.88 (s, —NH), 12.96 (s, —NH). MS (ES+): m/z 465.04 (100) [MH+]. HPLC: $t_R$=2.20 min (ZQ2000, polar_5 min).

EXAMPLE 96

4-[4-(1H-Indazol-5-ylamino)-7H-pyrrolo[2,3-d]-pyrimidin-6-yl]-3,6-dihydro-2H-pyridine-1-carboxylic acid amide

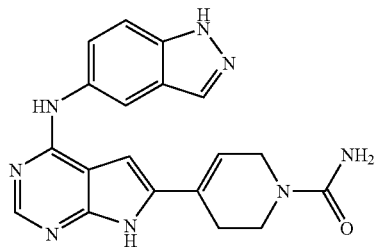

The title compound was obtained following the Preferred method with Acid Chlorides, Chloroformates, Carbamoyl Chlorides, Sulfamoyl chlorides, Sulfonyl chlorides & Isocyanates, using trimethylsilyl isocyanate. $^1$H NMR (400 MHz, DMSO-$d_6$): δ=2.33 (s, br, 2H), 3.53 (t, J=5.6 Hz, 2H), 4.00 (d, J=2.4 Hz, 2H), 6.03 (s, —NH$_2$), 6.39 (s, br, 1H), 6.75 (s, 1H), 7.51 (d, J=9.2 Hz, 1H), 7.65 (dd, J=8.8, 2.0 Hz, 1H), 8.04 (s, 1H), 8.25 (s, 1H), 8.36 (d, J=1.6 Hz, 1H), 9.30 (s, —NH), 11.88 (s, —NH), 12.96 (s, —NH). MS (ES+): m/z 375.13 (100) [MH+]. HPLC: $t_R$=1.76 min (ZQ2000, polar_5 min).

EXAMPLE 97

4-[4-(1H-Indazol-5-ylamino)-7H-pyrrolo[2,3-d]-pyrimidin-6-yl]-3,6-dihydro-2H-pyridine-1-carboxylic acid pyridin-3-ylamide

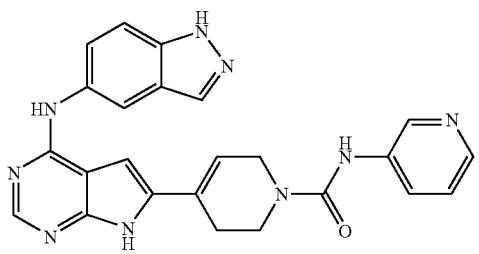

The title compound was obtained following the Preferred method with Acid Chlorides, Chloroformates, Carbamoyl Chlorides, Sulfamoyl chlorides, Sulfonyl chlorides & Isocyanates, using 3-pyridyl isocyanate. $^1$H NMR (400 MHz, DMSO-$d_6$): δ=2.48-2.57 (m, 2H), 3.75 (t, J=5.6 Hz, 2H), 4.27 (s, br, 2H), 6.54 (s, br, 1H), 6.79 (s, br, 1H), 7.50 (dd, J=8.8, 1.6 Hz, 1H), 7.67 (d, J=8.8 Hz, 1H), 7.76 (dd, J=8.8, 5.6 Hz, 1H), 8.08-8.13 (m, 1H), 8.15 (d, J=0.4 Hz, 1H), 8.26 (s, 1H), 8.30-8.37 (m, 1H), 8.41 (d, J=4.4 Hz, 1H), 8.99 (d, J=2.4 Hz, 1H), 9.33 (s, —NH), 10.87 (s, br, —NH), 12.68 (s, br, —NH), 13.06 (s, br, —NH). MS (ES+): m/z 452.02 (10) [MH+]. HPLC: $t_R$=1.75 min (ZQ2000, polar_5 min).

EXAMPLE 98

2-Pyridinyl 4-[4-(1H-indazol-5-ylamino)-7H-pyrrolo-[2,3-d]pyrimidin-6-yl]-3,6-dihydro-2H-pyridine-1-carboxyamide

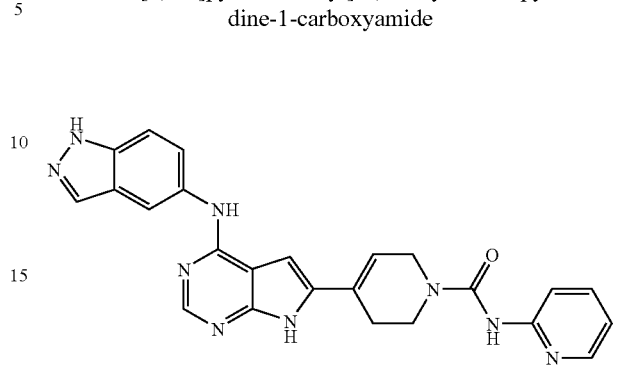

A solution of 2-aminopyridine (22.6 mg, 0.24 mmol) and diimidazol-1-ylmethanone (CDI, 39 mg, 0.24 mmol) in DMF (0.75 mL) was stirred at 50° C. for 1 h. After cooling to rt, i-Pr$_2$NEt (0.14 mL, 0.8 mmol) was added, followed by (1H-indazol-5-yl)-[6-(1,2,3,6-tetrahydropyridin-4-yl)-7H-pyrrolo[2,3-d]pyrimidin-4-yl]amine tri-HCl (88.1 mg, 0.2 mmol). The mixture was stirred at rt for 2 h and 50° C. for 3 h. The resulting mixture was filtered and submitted to mass-directed HPLC purification to yield the title compound. $^1$H-NMR(CD$_3$OD, 400 MHz): δ=2.66 (m, 2H), 3.88 (t, J=6.0 Hz, 2H), 4.37 (m, 2H), 6.45 (s, 1H), 6.71 (s, br, 1H), 7.38 (t, J=6.0 Hz, 1H), 7.48 (dd, J=2.0, 9.2 Hz, 1H), 7.66 (d, J=8.8 Hz, 1H), 7.76 (d, J=8.8 Hz, 1H), 7.98 (d, J=1.2 Hz, 1H), 8.16 (d, J=12.4 Hz, 1H), 8.22 (dt, J=1.6, 8.8 Hz, 1H). 8.29 (d, J=6.0 Hz, 1H). MS (ES+): m/z 451.95 [MH+]. HPLC: $t_R$=1.77 min (ZQ2000, polar_5 min).

EXAMPLE 99

4-Pyridinyl 4-[4-(1H-indazol-5-ylamino)-7H-pyrrolo-[2,3-d]pyrimidin-6-yl]-3,6-dihydro-2H-pyridine-1-carboxyamide

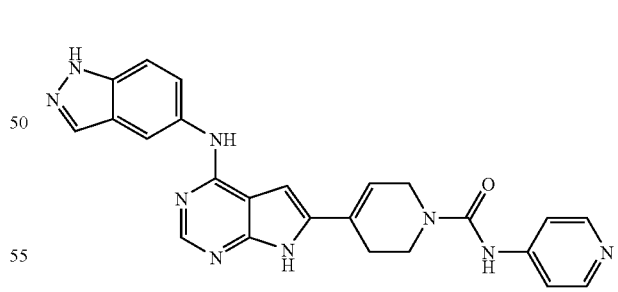

The title compound was prepared following the procedure for the corresponding 2-pyridyl compound, but using 4-aminopyridine. $^1$H-NMR(DMSO-$d_6$, 400 MHz): δ=3.72 (t, J=6.4 Hz, 2H), 4.22 (m, 2H), 6.46 (s, 1H), 6.68 (s, br, 1H), 6.78 (s, 1H), 7.51-7.53 (m, 2H), 7.55 (dd, J=1.6, 8.8 Hz, 1H), 8.05 (s, 1H), 8.26 (d, J=2.0 Hz, 1H), 8.30-8.33 (m, 2H), 8.36 (s, 1H), 8.99 (s, 1H), 9.34 (s, 1H), 11.94 (s, 1H), 12.97 (s, 1H). MS (ES+): m/z 452.02 [MH+]. HPLC: $t_R$=1.62 min (ZQ2000, polar_5 min).

EXAMPLE 100

1-{4-[4-(Benzothiazol-6-ylamino)-7H-pyrrolo[2,3-d]-pyrimidin-6-yl]-3,6-dihydro-2H-pyridin-1-yl}-2-pyridin-3-ylethanone

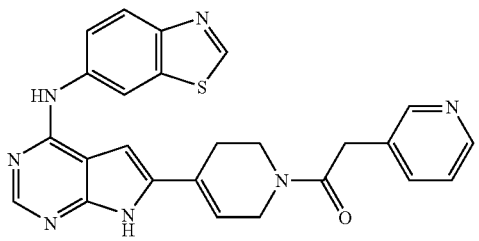

To a suspension of benzothiazol-6-yl-[6-(1,2,3,6-tetrahydropyridin-4-yl)-7H-pyrrolo[2,3-d]pyrimidin-4-yl]amine tri-HCl (137 mg, 0.300 mmol), 3-pyridinylacetic acid-HCl (78.1 mg, 0.450 mmol), and EDC (115 mg, 0.600 mmol) in DMF (1 mL) was added N,N-diisopropylethylamine (0.261 mL, 1.50 mmol). The mixture became a clear solution after being stirred for a few minutes and was stirred overnight. The products, which precipitated from the solution during the reaction, were collected by filtration, washed with dichloromethane (2×1 mL), and dried in vacuo to afford the title compound as a white solid. $^1$H-NMR (DMSO-d$_6$, 400 MHz): δ=2.73 (s, 2H), 2.89 (s, 2H), 3.78 (dt, J=4.0, 18.8 Hz, 2H), 3.86 (d, J=20 Hz, 2H), 4.19 (s, 1H), 4.33 (s, 1H), 6.45 (d, J=5.2 Hz, 1H), 6.84 (d, J=16.8 Hz, 1H), 7.33-7.36 (m, 1H), 7.65 (t, J=8.0 Hz, 1H), 7.87 (dt, J=2.0, 8.0 Hz, 1H), 7.95 (s, 1H), 8.04 (d, J=9.2 Hz, 1H), 8.34 (d, J=3.6 Hz, 1H), 8.44-8.48 (m, 1H), 8.92 (s, 1H), 9.24 (s, 1H), 9.62 (d, J=7.6 Hz, 1H). MS (ES+): m/z 467.94 [MH$^+$]. HPLC: t$_R$=1.98 min (ZQ2000, polar_5 min).

EXAMPLE 101

4-(4-(1,3-Benzothiazol-6-ylamino)-7H-pyrrolo[2,3-d]-pyrimidin-6-yl)-N-(4-fluorophenyl)-3,6-dihydro-pyridine-1(2H)-carboxamide

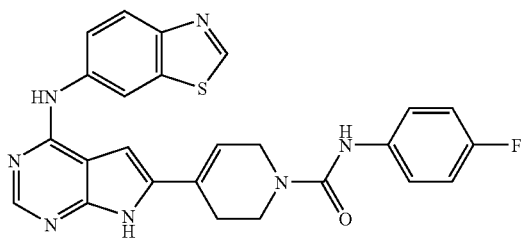

To a suspension of benzothiazol-6-yl-[6-(1,2,3,6-tetrahydropyridin-4-yl)-7H-pyrrolo[2,3-d]pyrimidin-4-yl]amine trihydrochloride (50.0 mg, 0.11 mmol) in DMF (1.5 mL) was added N,N-diisopropylethylamine (0.04 mL, 0.20 mmol). The reaction mixture stirred at −20° C. for 5 min prior to the addition of 4-fluorophenyl isocyanate (9.5 mg, 0.07 mmol) in DMF (0.5 mL). The mixture was left to stir at rt for 1 h. The mixture was concentrated in vacuo and purified via MDP, which afforded the title compound as a white solid. MS (ES+): m/z: 485.88 (100) [MH$^+$]. HPLC: t$_r$=2.73 min (ZQ2000: polar_5 min). $^1$H NMR (400 MHz, CDCl$_3$): δ=2.52-2.56 (m, 2H), 3.31 (s, 1H), 3.70 (t, 2H), 4.20 (s, 2H), 6.94 (m, 1H), 6.86 (d, J=0.8 Hz, 1H), 7.06-7.11 (m, 2H), 7.48-7.51 (m, 2H), 7.87 (dd, J=2.4, 8.8 Hz, 1H), 8.04 (d, J=8.8 Hz, 1H), 8.35 (s, 1H), 8.59 (s, 1H), 8.92 (d, J=2.0 Hz, 1H), 9.24 (s, 1H), 9.62 (s, 1H).

EXAMPLE 102

4-(4-(1,3-Benzothiazol-6-ylamino)-7H-pyrrolo[2,3-d]-pyrimidin-6-yl)-N-(2-fluorophenyl)-3,6-dihydro-pyridine-1(2H)-carboxamide

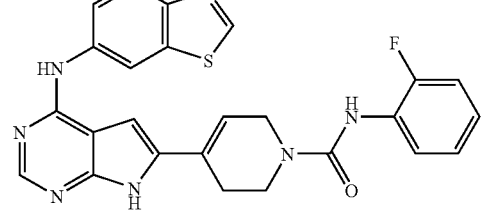

The procedure for EXAMPLE 101 was followed except for replacing 4-fluorophenyl isocyanate with 2-fluorophenyl isocyanate. $^1$H NMR (400 MHz, DMSO-d$_6$): δ=2.57 (s, br, 2H), 3.71 (t, J=5.2 Hz, 2H), 4.21 (s, br, 2H), 6.49 (s, br, 1H), 6.87 (d, J=2.0 Hz, 1H), 7.10-7.16 (m, 2H), 7.17-7.23 (m, 1H), 7.42-7.49 (m$_c$, 1H), 7.88 (dd, J=8.8, 2.0 Hz, 1H), 8.04 (d, J=8.8 Hz, 1H), 8.34 (s, br, —NH), 8.35 (s, 1H), 8.92 (d, J=2.0 Hz, 1H), 9.24 (s, 1H), 9.61 (s, —NH), 12.03 (s, —NH). MS (ES+): 485.98 (100) [MH$^+$]. HPLC: t$_R$=2.69 min (ZQ2000, polar_5 min).

EXAMPLE 103

4-[4-(Benzothiazol-6-ylamino)-7H-pyrrolo[2,3-d]-pyrimidin-6-yl]-3,6-dihydro-2H-pyridine-1-carboxylic acid phenylamide

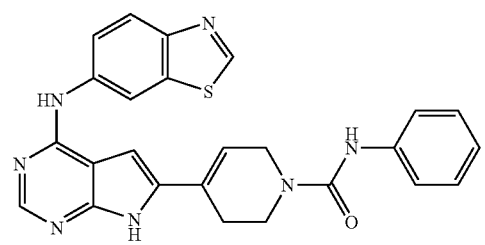

The procedure for EXAMPLE 101 was followed except for replacing 4-fluorophenyl isocyanate with phenyl isocyanate. $^1$H NMR (400 MHz, DMSO-d$_6$): δ=2.57 (s, br, 2H), 3.71 (t, J=5.2 Hz, 2H), 4.21 (d, J=1.6 Hz, 2H), 6.49 (s, br, 1H), 6.86 (d, J=2.0 Hz, 1H), 6.95 (m$_c$, 1H), 7.24 (m$_c$, 2H), 7.49 (dd, J=8.8, 1.2 Hz, 2H), 7.88 (dd, J=8.8, 2.4 Hz, 1H), 8.04 (d, J=8.8 Hz, 1H), 8.35 (s, 1H), 8.54 (s, —NH), 8.92 (d, J=2.4 Hz, 1H), 9.24 (s, 1H), 9.61 (s, —NH), 12.03 (d, J=2.0 Hz, —NH). MS (ES+): m/z 468.01 (100) [MH$^+$]. HPLC: t$_R$=2.70 min (ZQ2000, polar_5 min).

EXAMPLE 104

4-[4-(Benzothiazol-6-ylamino)-7H-pyrrolo[2,3-d]-pyrimidin-6-yl]-3,6-dihydro-2H-pyridine-1-carboxylic acid amide

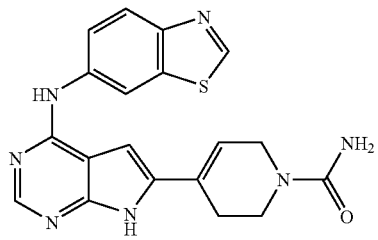

The procedure for EXAMPLE 101 was followed except for replacing 4-fluorophenyl isocyanate with trimethylsilyl isocyanate. $^1$H NMR (400 MHz, DMSO-d$_6$): δ=2.42-2.52 (m, 2H), 3.55 (t, J=5.6 Hz, 2H), 4.02 (d, J=2.0 Hz, 2H), 6.04 (s, —NH$_2$), 6.43 (s, br, 1H), 6.83 (d, J=2.0 Hz, 1H), 7.88 (dd, J=8.8, 2.4 Hz, 1H), 8.04 (d, J=8.8 Hz, 1H), 8.34 (s, 1H), 8.92 (d, J=2.4 Hz, 1H), 9.23 (s, 1H), 9.59 (s, —NH), 11.99 (s, —NH). MS (ES+): m/z 392.06 (100) [MH$^+$]. HPLC: t$_R$=2.10 min (ZQ2000, polar_5 min).

EXAMPLE 105

4-[4-(Benzothiazol-6-ylamino)-7H-pyrrolo[2,3-d]-pyrimidin-6-yl]-3,6-dihydro-2H-pyridine-1-carboxylic acid tert-butylamide

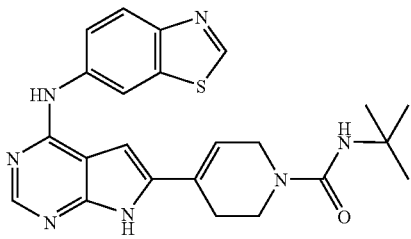

The procedure for EXAMPLE 101 was followed except for replacing 4-fluorophenyl isocyanate with tert-butyl isocyanate. Workup was carried out as follows: Residue was triturated in hot MeOH and was filtered. No solid was obtained but filtrate instantly precipitated. This off-white solid was filtered and again the filtrate was concentrated in vacuo, resuspended in MeOH, and filtered again (3×), until solid no longer precipitated from filtrate. Solid afforded the title compound, as an off-white solid. Mass directed purification (MDPS) of filtrate yielded a second batch of the title compound, as an off-white solid. $^1$H NMR (400 MHz, DMSO-d$_6$): 1.28 (s, 9H), 2.43-2.56 (m, 2H), 3.53 (t, J=5.6 Hz, 2H), 3.99 (d, J=2.0 Hz, 2H), 5.79 (s, —NH), 6.43 (s, br, 1H), 6.82 (d, J=1.2 Hz, 1H), 7.88 (dd, J=8.8, 2.0 Hz, 1H), 8.04 (d, J=8.8 Hz, 1H), 8.34 (s, 1H), 8.92 (d, J=2.0 Hz, 1H) 9.23 (s, 1H), 9.59 (s, —NH), 11.99 (s, —NH). MS (ES+): m/z 448.04 (100) [MH$^+$]. HPLC: t$_R$=2.63 min (ZQ2000, polar_5 min).

EXAMPLE 106

4-[4-(Benzothiazol-6-ylamino)-7H-pyrrolo[2,3-d]-pyrimidin-6-yl]-3,6-dihydro-2H-pyridine-1-carboxylic acid isopropylamide

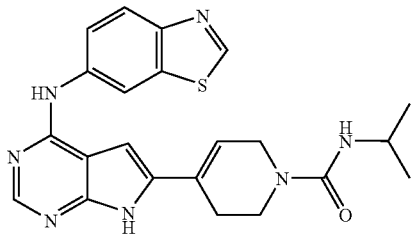

The procedure for EXAMPLE 101 was followed except for replacing 4-fluorophenyl isocyanate with isopropyl isocyanate. For purification, no chromatography was performed; material was triturated twice in MeOH to obtain the title compound as orange solid. $^1$H NMR (400 MHz, DMSO-d$_6$): δ=1.01 (d, J=6.8 Hz, 6H), 2.37-2.45 (m, 2H), 3.49 (t, J=5.6 Hz, 2H), 3.73 (dsept, J=6.8, 6.8 Hz, 1H), 3.94 (d, J=1.6 Hz, 2H), 6.20 (d, J=7.6 Hz, 1H), 6.44 (s, br, 1H), 6.83 (d, J=1.6 Hz, 1H), 7.88 (dd, J=8.8, 2.0 Hz, 1H), 8.04 (d, J=8.8 Hz, 1H), 8.34 (s, 1H), 8.92 (d, J=2.0 Hz, 1H), 9.23 (s, 1H), 9.58 (s, —NH), 11.98 (s, —NH). MS (ES+): m/z 434.04 (100) [MH$^+$]. HPLC: t$_R$=2.43 min (ZQ2000, polar_5 min).

EXAMPLE 107

4-(4-(1,3-Benzothiazol-6-ylamino)-7H-pyrrolo[2,3-d]-pyrimidin-6-yl)methylpiperazinyl-3,6-dihydropyridine-1(2H)-yl)-carboxamide

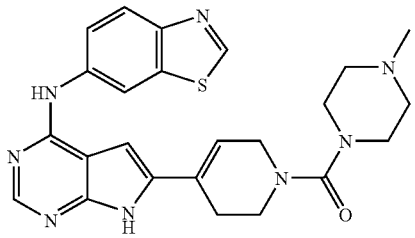

To a suspension of benzothiazol-6-yl-[6-(1,2,3,6-tetrahydropyridin-4-yl)-7H-pyrrolo[2,3-d]pyrimidin-4-yl]-amine tris-hydrochloride (200 mg, 0.44 mmol) in N,N-dimethylformamide (6 mL) was added N,N-diisopropylethylamine (0.5 mL, 3 mmol). The reaction mixture was stirred at 0° C. for 5 min prior to the addition of 4-methylpiperazine-1-carbonyl chloride hydrochloride (87 mg, 0.44 mmol). The resulting mixture was stirred at 0° C. for 1 h, diluted with water (50 mL), and the resulting precipitate was collected by filtration, washed with EtOAc (5 mL), and dried in vacuo to give the title compound. LC-MS (ES, Pos.): 474 [MH$^+$], and $^1$H NMR (DMSO-d$_6$, 400 MHz): δ=1.99 (s, 3H), 2.24 (m, 4H), 2.50 (m, 2H), 3.18 (m, 4H), 3.41 (m, 2H), 3.93 (m, 2H), 6.41 (s, 1H), 6.82 (s, 1H), 7.87 (d, J=8.8 Hz, 1H), 8.04 (d, J=8.8 Hz, 1H), 8.34 (s, 1H), 8.91 (s, 1H), 9.23 (s, 1H), 9.59 (s, 1H), 11.99 (s, 1H).

EXAMPLE 108

4-(4-(1,3-Benzothiazol-6-ylamino)-7H-pyrrolo[2,3-d]-pyrimidin-6-yl)-N,N-dimethyl-3,6-dihydropyridine-1 (2M)-carboxamide

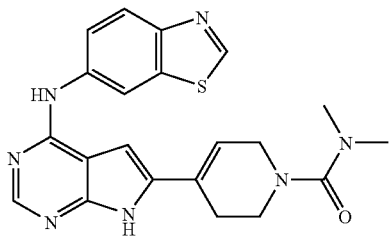

The procedure for EXAMPLE 101 was followed except for replacing 4-fluorophenyl isocyanate with N,N-dimethylcarbamoyl chloride. MS (ES+): m/z: 419.98 (100) [MH⁺]. HPLC: $t_r$=2.35 min (ZQ2000: polar_5 min). ¹H NMR (400 MHz, DMSO-$d_6$): δ=2.77 (s, 6H), 3.31-3.39 (m, 4H), 3.89 (d, J=2.4 Hz, 2H), 6.42 (s, 1H), 6.82 (d, J=2.0 Hz, 1H), 7.86-7.89 (dd, J=2.0, 9.2 Hz, 1H), 8.03 (d, J=9.2 Hz, 1H), 8.34 (s, 1H), 8.91 (d, J=2.0 Hz, 1H), 9.23 (s, 1H), 9.60 (s, 1H).

EXAMPLE 109

6-{1-[4-(Dimethylamino)butanoyl]-1,2,3,6-tetrahydropyridin-4-yl}-N-1,3-benzothiazol-6-yl-7H-pyrrolo[2,3-d]pyrimidin-4-amine

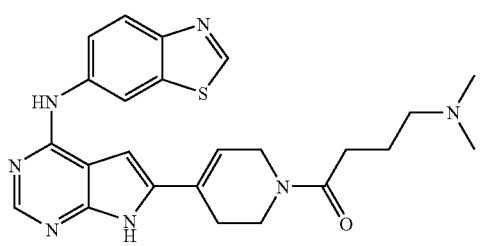

To a solution of benzothiazol-6-yl-[6-(1,2,3,6-tetrahydropyridin-4-yl)-7H-pyrrolo[2,3-d]pyrimidin-4-yl]-amine trihydrochloride (50.0 mg, 0.11 mmol) in DMF (3 mL) was added 4-(dimethylamino)butyric acid hydrochloride (17 mg, 0.13 mmol), TBTU (42 mg, 0.13 mmol) and N,N-diisopropylethylamine (0.11 mL). The reaction mixture was left to stir at rt over the weekend. The crude mixture was concentrated in vacuo and purified via MDP, which afforded the title compound as a tan solid. MS (ES+): m/z: 461.99 (100) [MH⁺]. HPLC: $t_r$=1.82 min (ZQ2000: polar_5 min). ¹H NMR (400 MHz, DMSO-$d_6$): δ=1.63-1.68 (m, 2H), 2.10 (s, 3H), 2.11 (s, 3H), 2.18-2.24 (m, 2H), 2.33-2.43 (m, 2H), 2.54-2.56 (m, 2H), 3.67-3.72 (m, 2H), 4.15 (bs, 1H), 4.21 (bs, 1H), 6.45 (s, 1H), 6.84 (d, J=6.4 Hz, 1H), 7.87 (dd, J=1.6, 8.8 Hz, 1H), 8.03 (d, J=8.8 Hz, 1H), 8.34 (s, 1H), 8.92 (s, 1H), 9.23 (s, 1H), 9.61 (s, 1H), 12.02 (d, J=11.2 Hz, 1H).

EXAMPLE 110

6-[1-(3-Hydroxy-2,2-dimethylpropanoyl)-1,2,3,6-tetrahydropyridin-4-yl]-N-1,3-benzothiazol-6-yl-7H-pyrrolo[2,3-d]pyrimidin-4-amine

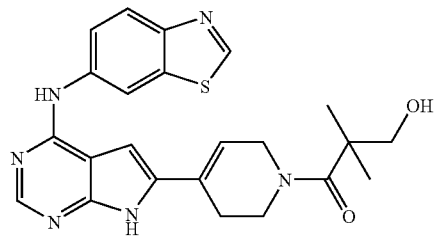

To a mixture of benzothiazol-6-yl-[6-(1,2,3,6-tetrahydropyridin-4-yl)-7H-pyrrolo[2,3-d]pyrimidin-4-yl]amine trihydrochloride (50.0 mg, 0.11 mmol) in DMF (3 mL) was added 2,2-dimethyl-3-hydroxypropionic acid (150 mg, 1.3 mmol), TBTU (42.0 mg, 0.13 mmol) and N,N-diisopropylethylamine (0.1 mL, 0.50 mmol). The reaction mixture stirred at rt for 16 h. The mixture was concentrated in vacuo and purified via MDP, which afforded the title compound as yellow solid. MS (ES+): m/z: 448.96 (100) [MH⁺]. HPLC: $t_r$=2.35 min (ZQ2000: polar_5 min). ¹H NMR (400 MHz, DMSO-$d_6$): δ=1.20 (s, 6H), 3.19 (s, 1H), 3.46 (s, 2H), 3.79-3.81 (m, 2H), 4.21 (s, 2H), 4.59 (bs, 1H), 6.43 (s, 1H), 6.84 (d, J=1.6 Hz, 1H), 7.87 (dd, J=1.6, 8.8 Hz, 1H), 8.03 (d, J=8.8 Hz, 1H), 8.34 (s, 1H), 8.91 (d, J=2.0 Hz, 1H), 9.23 (s, 1H), 9.62 (s, 1H), 12.03 (s, 1H).

EXAMPLE 111

6-[1-(2,2-Dimethyl-3-oxopropanoyl)-1,2,3,6-tetrahydropyridin-4-yl]-N-1,3-benzothiazol-6-yl-7H-pyrrolo[2,3-d]pyrimidin-4-amine

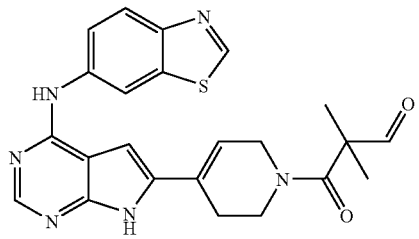

To a solution of 6-[1-(3-hydroxy-2,2-dimethylpropanoyl)-1,2,3,6-tetrahydropyridin-4-yl]-N-1,3-benzothiazol-6-yl-7H-pyrrolo[2,3-d]pyrimidin-4-amine (Example 110) (150 mg, 0.33 mmol) in DMSO (4 mL) was added EDC (190 mg, 1 mmol). The reaction mixture stirred at rt for 5 h. The mixture was taken up in a large amount of EtOAc and extracted with water. The combined organic extracts were dried over sodium sulfate and concentrated in vacuo, which afforded the title compound as a yellow solid. MS (ES+): m/z: 446.93 (100) [MH⁺]. HPLC: $t_r$=2.53 min (ZQ2000: polar_5 min). ¹H NMR (400 MHz, DMSO-$d_6$): δ=1.37 (s, 6H) 3.39-3.69 (m, 3H), 3.70-4.22 (m, 3H), 6.21 (bs, 1H), 6.82 (s, 1H), 6.84 (d, J=1.6 Hz, 1H), 7.87 (dd, J=1.6, 8.8 Hz, 1H), 8.03 (d, J=8.8 Hz, 1H), 8.34 (s, 1H), 8.91 (d, J=2.0 Hz, 1H), 9.23 (s, 1H), 9.62 (s, 1H), 12.03 (s, 1H).

EXAMPLE 112

6-{1-[4-(Dimethylamino)butanoyl]-1,2,3,6-tetrahydropyridin-4-yl}-N-1,3-benzothiazol-6-yl-7H-pyrrolo[2,3-d]pyrimidin-4-amine

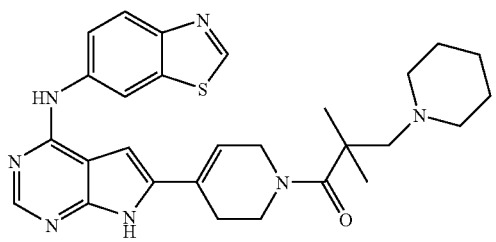

The procedure for EXAMPLE 109 was followed except for replacing 2,2-dimethyl-3-hydroxypropionic acid with 2,2-dimethyl-3-piperidin-1-ylpropanoic acid. The mixture was purified via MDP, which afforded the title compound as a yellow solid. MS (ES+): m/z: 516.06 (100) [MH$^+$]. HPLC: t$_r$=1.98 min (ZQ2000: polar_5 min). $^1$H NMR (400 MHz, DMSO-d$_6$): δ=1.21 (s, 6H), 1.26-1.28 (m, 2H), 1.37-1.41 (m, 5H), 2.30-2.34 (m, 5H), 2.47-2.49 (m, 2H), 3.75-3.77 (m, 2H), 4.26 (s, 2H), 6.44 (s, 1H), 6.82 (d, J=2.0 Hz, 1H), 7.87 (dd, J=2.4, 8.8 Hz, 1H), 8.03 (d, J=8.8 Hz, 1H), 8.34 (s, 1H), 8.91 (d, J=2.0 Hz, 1H), 9.23 (s, 1H), 9.59 (s, 1H), 12.01 (s, 1H).

2,2-Dimethyl-3-piperidin-1-ylpropanoic acid

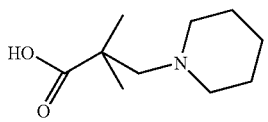

To a solution of benzyl-2,2-dimethyl-3-piperidin-1-ylpropanoate (117.0 mg, 0.42 mmol) in ethanol (5 mL) was slowly added 10% wt Palladium in carbon (50 mg, 0.05 mmol). The reaction mixture was left to stir at rt for 1 h under hydrogen. The mixture was filtered through Celite and concentrated in vacuo, which afforded the title compound as a yellow solid. $^1$H NMR (400 MHz, CDCl$_3$): δ=1.22 (s, 6H), 1.28-1.39 (bs, 2H), 1.74-1.79 (m, 4H), 2.76 (s, 2H), 2.79-3.08 (bs, 4H).

Benzyl-2,2-dimethyl-3-piperidin-1-ylpropanoate

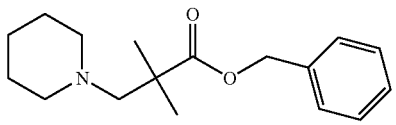

To a solution of benzyl-2,2-dimethyl-3-oxopropanoate (200 mg, 1.0 mmol) in DCM (30 mL) were added piperidine (0.10 mL, 1.1 mmol) and sodium triacetoxyborohydride (400 mg, 2.0 mmol). The reaction mixture was left to stir at rt for 16 h. The mixture was partitioned between DCM and water and treated with saturated NaHCO$_3$. The combined organic extracts were dried over Na$_2$SO$_4$ and concentrated in vacuo. Purification via silica gel chromatography (5% EtOAc in Hexane) afforded the title compound as a yellow oil. MS (ES+): m/z: 276.18 (100) [MH$^+$]. HPLC: t$_r$=1.97 min (ZQ2000: polar_5 min). $^1$H NMR (400 MHz, CDCl$_3$): δ=1.17 (s, 6H), 1.28-1.37 (m, 2H), 1.40-1.46 (m, 4H), 2.34-2.36 (m, 4H), 2.44 (s, 2H), 5.09 (s, 2H), 7.25-7.34 (m, 5H).

Benzyl-2,2-dimethyl-3-oxopropanoate

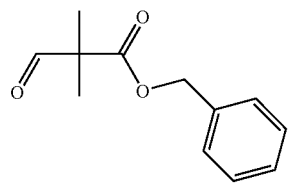

A mixture of DMSO (10 mL, 200 mmol) and DCM (0.2 mL) was added to a mixture of oxalyl chloride (8.1 mL, 0.096 mol) and DCM (350 mL) at −72° C. The resulting mixture was left to stir for 30 min at −72° C. To the mixture was added 1-benzyl-3-hydroxy-2,2-dimethylpropanoate (5 g, 19.2 mmol) in DCM (300 mL). The reaction mixture stirred at −72° C. for 30 min. The reaction was quenched with triethylamine (67 mL, 0.48 mol) and the reaction was allowed to slowly warm to rt. The mixture was partitioned between DCM and water, treated with saturated sodium bicarbonate and brine, dried over Na$_2$SO$_4$ and concentrated in vacuo, which afforded the title compound as a yellow oil. $^1$H NMR (400 MHz, CDCl$_3$): δ=1.35 (s, 6H), 5.11 (s, 2H), 7.31-7.39 (m, 5H), 9.68 (s, 1H).

1-Benzyl-3-hydroxy-2,2-dimethylpropanoate

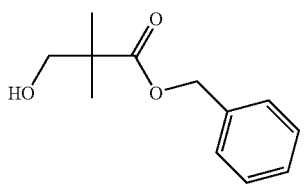

To a solution of 2,2-dimethyl-3-hydroxypropionic acid (10 g, 86.3 mmol) in methanol (55 mL) and water (6 mL) was added cesium carbonate (10 g, 30.0 mmol) as a 20% solution in water. The reaction mixture was left to stir at rt for 15 min. The mixture was concentrated in vacuo and the water was removed by making an azeotrope with toluene and concentrating it down. This process was repeated 3× and it yielded a white solid. The resulting solid was dissolved in DMF (55 mL) and benzyl bromide (8.20 mL, 68.9 mmol) was added. The reaction was left to stir at rt for 16 h. The mixture was partitioned between water and EtOAc. The organic layer was further partitioned between ethylacetate and sodium bicarbonate solution to remove excess acid. The organic extracts were dried over sodium sulfate, filtered and concentrated in vacuo, which afforded the product as a yellow oil. $^1$H NMR (400 MHz, CDCl$_3$): δ=1.21 (s, 6H), 2.77 (bs, 1H), 3.57 (s, 2H), 5.13 (s, 2H), 7.26-7.43 (m, 5H).

EXAMPLE 113

6-[1-(2,2-Dimethyl-4-methylpiperazin-1-ylpropanoyl)-1,2,3,6-tetrahydropyridin-4-yl]-N-1,3-benzothiazol-6-yl-7H-pyrrolo[2,3-d]pyrimidin-4-amine

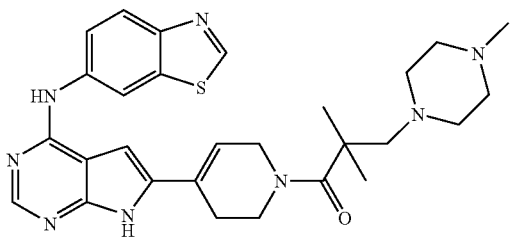

The procedure from EXAMPLE 110 was followed except for replacing 2,2-dimethyl-3-hydroxypropionic acid with 2,2-dimethyl-3-(4-methylpiperazin-1-yl)propanoic acid. The mixture was precipitated with water and the gravity filtration afforded the title compound as a tan solid. MS (ES+): m/z: 531.04 (10) [MH+]. HPLC: $t_r$=1.94 min (ZQ2000: polar_5 min). $^1$H NMR (400 MHz, DMSO-$d_6$): δ=1.21 (s, 6H), 2.04 (s, 3H), 2.06-2.20 (m, 4H), 2.23-2.38 (m, 4H), 2.51-2.52 (m, 4H), 3.75-3.77 (m, 2H), 4.23 (s, 2H), 6.44 (s, 1H), 6.82 (d, J=2.0 Hz, 1H), 7.87 (dd, J=2.4, 8.8 Hz, 1H), 8.03 (d, J=8.8 Hz, 1H), 8.33 (s, 1H), 8.91 (d, J=2.0 Hz, 1H), 9.22 (s, 1H), 9.58 (s, 1H), 12.01 (s, 1H).

2,2-Dimethyl-3-(4-methylpiperazin-1-yl)propanoic acid

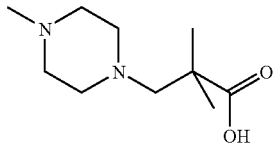

The procedure for 2,2-dimethyl-3-piperidin-1-ylpropanoic acid was followed except for replacing benzyl-2,2-dimethyl-3-piperidin-1-ylpropanoate with benzyl 2,2-dimethyl-3-(4-methylpiperazin-1-yl)propanoate. The compound was obtained as a yellow solid. $^1$H NMR (400 MHz, CDCl$_3$): δ=1.24 (s, 6H), 2.33 (s, 3H), 2.44-2.92 (m, 10H).

Benzyl 2,2-dimethyl-3-(4-methylpiperazin-1-yl)propanoate

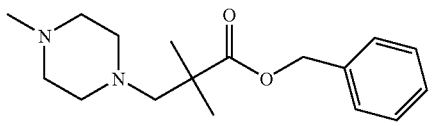

The procedure for benzyl-2,2-dimethyl-3-piperidin-1-ylpropanoate was followed except for replacing piperidine with 1-methylpiperazine. Purification via silica gel chromatography (5% EtOAc in hexane) afforded the title compound as a yellow oil. MS (ES+): m/z: 291.20 (100) [MH+]. HPLC: $t_r$=2.08 min (ZQ2000: polar_5 min). $^1$H NMR (400 MHz, CDCl$_3$): δ=1.18 (s, 6H), 2.09 (s, 3H), 2.23-2.33 (m, 4H), 2.39-2.50 (m, 6H), 5.11 (s, 2H) 7.31-7.36 (m, 5H)

General Procedure for Preparation of an α,α-dimethylpropane-1-one Library:

To a solution of benzothiazol-6-yl-[6-(1,2,3,6-tetrahydropyridin-4-yl)-7H-pyrrolo[2,3-d]pyrimidin-4-yl]-amine trishydrochloride (525.0 mg) in DMF (12 mL) and dichloromethane (1 mL) at 4° C. was added N,N-diisopropylethylamine (3 eq.) followed by 3-chloropivaloyl chloride (0.178 g, 1.0 eq). The resulting mixture was allowed to warm up to rt and left overnight before it was applied for next step reaction without any further purification. The mixture was divided into 13 aliquots, and 1 mg of KI, 5 eq. of N,N-diisopropylethylamine, and 10 eq. of corresponding amine were added. If an amine was used as hydrochloride, additional 2 eq. of N,N-diisopropylethylamine were added. The solutions were degassed with N$_2$ and heated at 80° C. for 96 h. The products were purified by preparative HPLC with water/acetonitrile/formic acid mixture and are assumed to be formate salts.

EXAMPLE 114

1-{4-[4-(Benzothiazol-6-ylamino)-7H-pyrrolo[2,3-d]-pyrimidin-6-yl]-3,6-dihydro-2H-pyridin-1-yl}-3-chloro-2,2-dimethylpropan-1-one

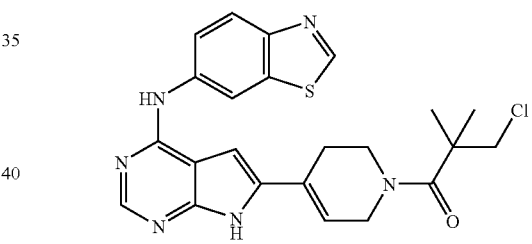

LC/MS: m/z 466.89/468.92 [MH+] (100/35), $t_R$=2.81 min (ZQ2000, polar_5 min).

EXAMPLE 115

1-{4-[4-(Benzothiazol-6-ylamino)-7H-pyrrolo[2,3-d]-pyrimidin-6-yl]-3,6-dihydro-2H-pyridin-1-yl}-2,2-dimethyl-3-pyrrolidin-1-ylpropan-1-one

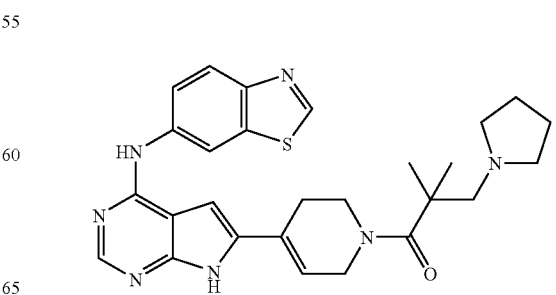

Following the general procedure, the title compound was isolated as yellow powder. ¹H NMR (400 MHz, DMSO-d₆): δ=12.01 (s, 1H), 9.60 (s, 1H), 9.23 (s, 1H), 8.91 (d, 1H, J=2.0 Hz), 8.32 (s, 1H), 8.21 (s, 2H), 8.05 (d, 1H, J=8.9 Hz), 7.88 (dd, 1H, J=2.0 Hz & 8.9 Hz), 6.83 (s, 1H), 6.43 (s, 1H), 4.24 (br s, 2H), 3.76 (t, 2H, J=5.7 Hz), 3.41 (m, 6H), 2.67 (s, 2H), 1.60 (m, 4H), 1.23 (br s, 6H). LC/MS: m/z 502.03 [MH⁺] (100), $t_R$=1.92 min (ZQ2000, polar_5 min).

EXAMPLE 116

1-{4-[4-(Benzothiazol-6-ylamino)-7H-pyrrolo[2,3-d]-pyrimidin-6-yl]-3,6-dihydro-2H-pyridin-1-yl}-3-diethylamino-2,2-dimethylpropan-1-one

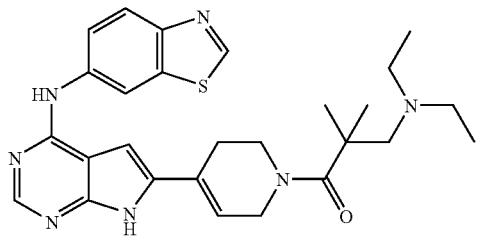

Following the general procedure, the title compound was isolated as yellow powder. ¹H NMR (400 MHz, DMSO-d₆): δ=11.94 (d, 1H, J=15.8 Hz), 9.48 (s, 1H), 9.17 (s, 1H), 8.85 (d, 1H, J=2.0 Hz), 8.25 (s, 1H), 8.13 (s, 2H), 7.96 (d, 1H, J=8.9 Hz), 7.79 (dd, 1H, J=2.0 Hz & 8.9 Hz), 6.76 (br s, 1H), 6.37 (br s, 1H), 4.21 (br s, 2H), 3.71 (t, 2H, J=5.3 Hz), 2.52 (br s, 2H), 2.40 (m, 6H), 1.14 (s, 6H), 0.82 (t, 6H, J=7.0 Hz). LC/MS: m/z 504.06 (95) [MH⁺], $t_R$=1.92 min (ZQ2000, polar_5 min).

EXAMPLE 117

1-{4-[4-(Benzothiazol-6-ylamino)-7H-pyrrolo[2,3-d]-pyrimidin-6-yl]-3,6-dihydro-2H-pyridin-1-yl}-3-tert-butylamino-2,2-dimethylpropan-1-one

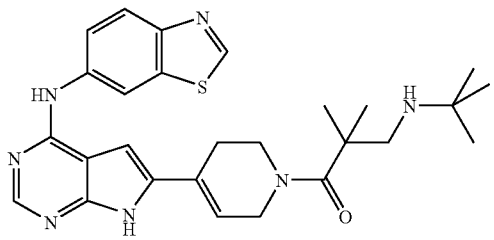

Following the general procedure, the title compound was isolated as yellow powder. ¹H NMR (400 MHz, DMSO-d₆): δ=11.98 (s, 1H), 9.56 (s, 1H), 9.19 (s, 1H), 8.85 (d, 1H, J=2.0 Hz), 8.24 (s, 1H), 8.15 (s, 2H), 7.97 (d, 1H, J=8.9 Hz), 7.79 (dd, 1H, J=2.0 Hz & 8.9 Hz), 6.78 (s, 1H), 6.37 (br s, 1H), 4.14 (s, 2H), 3.75 (t, 2H, J=5.4 Hz), 2.71 (s, 2H), 2.52 (br s, 2H), 1.26 (s, 6H), 1.09 (s, 9H). LC/MS: m/z 504.06 [MH⁺](95), $t_R$=1.99 min (ZQ2000, polar_5 min).

EXAMPLE 118

1-{4-[4-(Benzothiazol-6-ylamino)-7H-pyrrolo[2,3-d]-pyrimidin-6-yl]-3,6-dihydro-2H-pyridin-1-yl}-3-dimethylamino-2,2-dimethylpropan-1-one

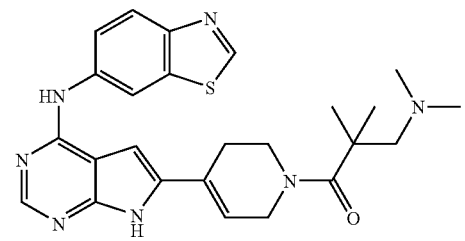

Following the general procedure, but saturating the reaction mixture with dimethylamine gas in a sealed tube and conducting the reaction at rt for 4 d, the title compound was isolated as yellow powder. LC/MS: m/z 476.06 [MH⁺](45), $t_R$=1.85 min (ZQ2000, polar_5 min).

EXAMPLE 119

1-{4-[4-(Benzothiazol-6-ylamino)-7H-pyrrolo[2,3-d]-pyrimidin-6-yl]-3,6-dihydro-2H-pyridin-1-yl}-3-(3-hydroxypyrrolidin-1-yl)-2,2-dimethylpropan-1-one

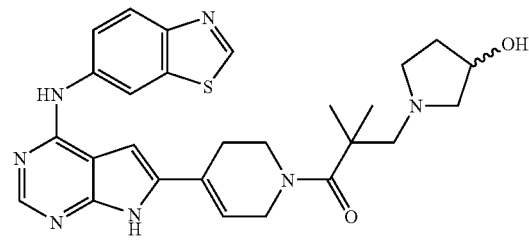

Following the general procedure, the title compound was isolated as yellow powder. ¹H NMR (400 MHz, DMSO-d₆): δ=11.95 (s, 1H), 9.54 (s, 1H), 9.17 (s, 1H), 8.85 (d, 1H, J=2.0 Hz), 8.24 (s, 1H), 8.16 (s, 2H), 7.97 (d, 1H, J=8.9 Hz), 7.78 (dd, 1H, J=2.0 Hz & 8.9 Hz), 6.77 (d, 1H), 6.37 (br s, 1H), 4.17 (br s, 2H), 4.01 (m, 1H), 3.71 (t, 2H, J=5.2 Hz), 3.15 (m, 1H), 2.74 (m, 1H), 2.52 (br s, 2H), 2.51 (m, 2H), 2.26 (dd, 1H, J=4.0 Hz & 9.6 Hz), 2.08 (s, 1H), 1.77 (m, 1H), 1.38 (m, 1H), 1.15 (s, 6H). LC/MS: m/z 518.02 [MH⁺] (50), $t_R$=1.87 min (ZQ2000, polar_5 min).

EXAMPLE 120

3-Azepan-1-yl-1-{4-[4-(benzothiazol-6-ylamino)-7H-pyrrolo[2,3-d]pyrimidin-6-yl]-3,6-dihydro-2H-pyridin-1-yl}-2,2-dimethylpropan-1-one

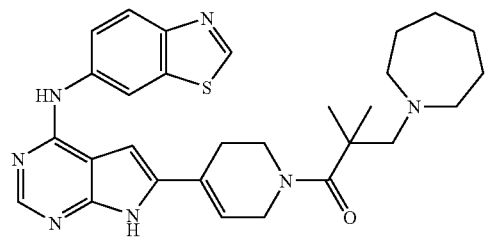

Following the general procedure, the title compound was isolated as yellow powder. ¹H NMR (400 MHz, DMSO-$d_6$): δ=11.96 (s, 1H), 9.53 (s, 1H), 9.19 (s, 1H), 8.85 (d, 1H, J=2.1 Hz), 8.27 (s, 1H), 8.09 (s, 2H), 7.97 (d, 1H, J=8.7 Hz), 7.80 (dd, 1H, J=2.1 Hz & 8.7 Hz), 6.77 (s, 1H), 6.37 (s, 1H), 4.20 (s, 2H), 3.73 (t, 2H, J=5.3 Hz), 3.29 (t, 1H, J=6.0 Hz), 3.22 (t, 1H, J=6.0 Hz), 2.74 (s, 2H), 2.68 (t, 4H, J=8.6 Hz), 1.48 (br s, 4H), 1.41 (br s, 4H), 1.15 (br s, 6H). LC/MS: m/z 530.03 [MH$^+$] (15), $t_R$=2.03 min (ZQ2000, polar_5 min).

EXAMPLE 121

1-{4-[4-(Benzothiazol-6-ylamino)-7H-pyrrolo[2,3-d]-pyrimidin-6-yl]-3,6-dihydro-2H-pyridin-1-yl}-3-(4-hydroxypiperidin-1-yl)-2,2-dimethylpropan-1-one

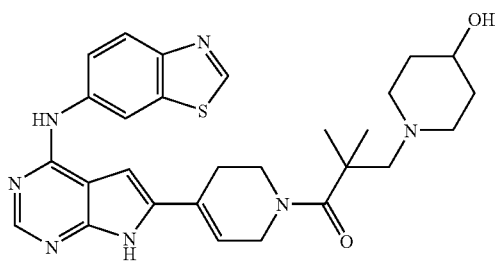

Following the general procedure, the title compound was isolated as yellow powder. ¹H NMR (400 MHz, DMSO-$d_6$): δ=11.97 (s, 1H), 9.53 (s, 1H), 9.17 (s, 1H), 8.84 (d, 1H, J=2.0 Hz), 8.28 (s, 1H), 8.10 (s, 2H), 7.98 (d, 1H, J=8.9 Hz), 7.83 (dd, 1H, J=2.0 Hz & 8.9 Hz), 6.67 (s, 1H), 6.36 (s, 1H), 4.19 (br s, 2H), 3.71 (t, 2H, J=5.5 Hz), 3.50 (m, 2H), 3.29 (m, 1H), 2.62 (m, 2H), 2.52 (m, 2H), 2.08 (t, 2H, J=9.4 Hz), 1.54 (m, 2H), 1.25 (m, 2H), 1.15 (s, 6H). LC/MS: m/z 532.05 [MH$^+$] (15), $t_R$=1.89 min (ZQ2000, polar_-5 min).

EXAMPLE 122

1-{4-[4-(Benzothiazol-6-ylamino)-7H-pyrrolo[2,3-d]-pyrimidin-6-yl]-3,6-dihydro-2H-pyridin-1-yl}-3-(4-isopropylpiperazin-1-yl)-2,2-dimethylpropan-1-one

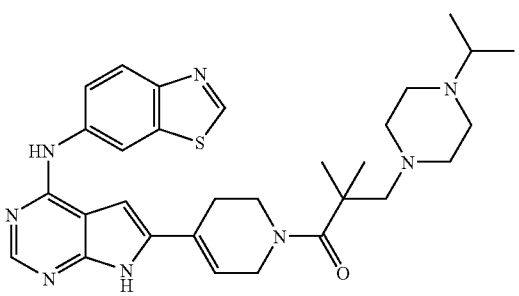

Following the general procedure, the title compound was isolated as yellow powder. ¹H NMR (400 MHz, DMSO-$d_6$): δ=11.95 (s, 1H), 9.53 (s, 1H), 9.18 (s, 1H), 8.85 (s, 1H), 8.27 (s, 1H), 8.13 (s, 2H), 7.97 (d, 1H, J=9.7 Hz), 7.80 (d, 1H, J=9.7 Hz), 6.76 (s, 1H), 6.37 (br s, 1H), 4.17 (br s, 2H), 3.68 (t, 2H, J=5.4 Hz), 3.35 (m, 4H), 2.31 (br s, 8H), 1.15 (s, 6H), 0.75 (d, 6H, J=6.4 Hz). LC/MS: m/z 559.10 [MH$^+$] (20), $t_R$=1.98 min (ZQ2000, polar_5 min).

EXAMPLE 123

1-{4-[4-(Benzothiazol-6-ylamino)-7H-pyrrolo[2,3-d]-pyrimidin-6-yl]-3,6-dihydro-2H-pyridin-1-yl}-2,2-dimethyl-3-morpholin-4-ylpropan-1-one

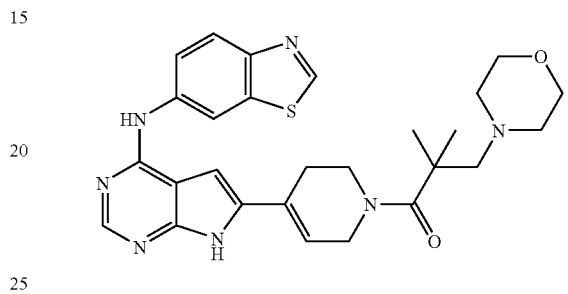

Following the general procedure, the title compound was isolated as yellow powder. ¹H NMR (400 MHz, DMSO-$d_6$): δ=11.96 (s, 1H), 9.54 (s, 1H), 9.17 (s, 1H), 8.85 (d, 1H, J=2.0 Hz), 8.31 (s, 1H), 8.01 (s, 2H), 7.97 (d, 1H, J=8.6 Hz), 7.81 (dd, 1H, J=2.0 Hz & 8.6 Hz), 6.76 (s, 1H), 6.38 (br s, 1H), 4.18 (br s, 2H), 3.69 (m, 6H), 3.38 (t, 2H, J=4.4 Hz), 2.52 (m, 2H), 2.32 (t, 2H, J=4.4 Hz), 2.17 (s, 2H), 1.15 (s, 6H). LC/MS: m/z 518.02 [MH$^+$] (100), $t_R$=1.91 min (ZQ2000, polar_-5 min)

EXAMPLE 124

1-{4-[4-(Benzothiazol-6-ylamino)-7H-pyrrolo[2,3-d]-pyrimidin-6-yl]-3,6-dihydro-2H-pyridin-1-yl}-3-(4,4-difluoropiperidin-1-yl)-2,2-dimethylpropan-1-one

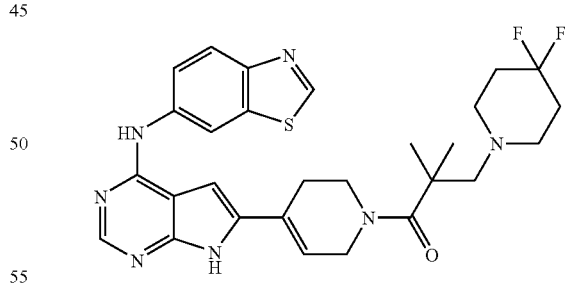

Following the general procedure, but using 4,4-difluoropiperidine hydrochloride and an additional 2 eq. of N,N-diisopropylethylamine, the title compound was isolated as yellow powder. ¹H NMR (400 MHz, DMSO-$d_6$): δ=11.96 (s, 1H), 9.54 (s, 1H), 9.16 (s, 1H), 8.84 (d, 1H, J=2.0 Hz), 8.24 (s, 1H), 8.11 (s, 2H), 7.97 (d, 1H, J=8.8 Hz), 7.80 (dd, 1H, J=2.0 Hz & 8.8 Hz), 6.77 (s, 1H), 6.38 (br s, 1H), 4.18 (br s, 2H), 3.66 (t, 2H, J=5.7 Hz), 3.10 (m, 4H), 2.52 (m, 2H), 1.77 (m, 2H), 1.07 (s, 6H), 1.04 (m, 4H). LC/MS: m/z 552.09 [MH$^+$] (10), $t_R$=1.99 min (ZQ2000, polar_5 min)

EXAMPLE 125

1-{4-[4-(Benzothiazol-6-ylamino)-7H-pyrrolo[2,3-d]-pyrimidin-6-yl]-3,6-dihydro-2H-pyridin-1-yl}-3-(3,5-dimethylpiperazin-1-yl)-2,2-dimethylpropan-1-one

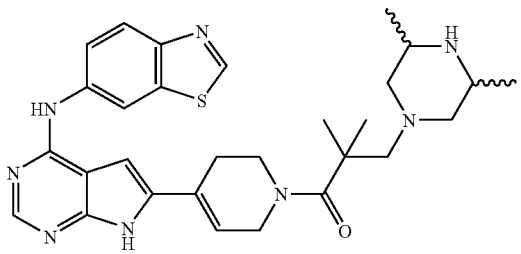

Following the general procedure, the title compound was isolated as yellow powder. $^1$H NMR (400 MHz, DMSO-d$_6$): δ=11.98 (s, 1H), 9.58 (s, 1H), 9.17 (s, 1H), 8.85 (d, 1H, J=2.0 Hz), 8.27 (s, 1H), 8.21 (s, 2H), 7.97 (d, 1H, J=8.9 Hz), 7.77 (dd, 1H, J=2.0 Hz & 8.9 Hz), 6.78 (d, 1H, J=4.1 Hz), 6.38 (br s, 1H), 4.19 (s, 2H), 3.69 (t, 2H, J=5.2 Hz), 2.84 (m, 4H), 2.64 (br s, 2H), 2.61 (br s, 2H), 2.52 (br s, 2H), 1.86 (t, 2H, J=11.0 Hz), 1.16 (s, 6H), 0.89 (d, 6H, J=6.3 Hz). LC/MS: m/z 545.07 [MH$^+$] (15), t$_R$=1.96 min (ZQ2000, polar_5 min).

EXAMPLE 126

1-{4-[4-(Benzothiazol-6-ylamino)-7H-pyrrolo[2,3-d]-pyrimidin-6-yl]-3,6-dihydro-2H-pyridin-1-yl}-2-(2-methoxyethoxy)-ethanone

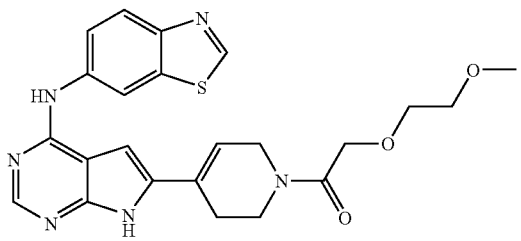

To a suspension of benzothiazol-6-yl-[6-(1,2,3,6-tetrahydropyridin-4-yl)-7H-pyrrolo[2,3-d]pyrimidin-4-yl]-amine tris-hydrochloride (138.0 mg, 0.2984 mmol), 1-hydroxybenzotriazole (40.8 mg, 0.302 mmol), and PS-Carbodiimide (1.37 mmol/g loading; 873 mg, 1.20 mmol) in anhydrous N,N-dimethylformamide (10 mL), N,N-diisopropylethylamine (260 µL, 1.5 mmol) was added. A small amount of sonication was used to get majority of solid into solution. 2-(2-Methoxyethoxy)acetic acid (45.7 mg, 0.334 mmol) in anhydrous DMF (1 mL) was added, and the reaction was vigorously shaken at rt for 5.5 h. An additional 0.2 eq of 2-(2-methoxyethoxy)acetic acid (8.1 mg, 0.060 mmol) in anhydrous N,N-dimethylformamide (0.5 mL) was added (after 7 h), and the reaction was shaken overnight at rt. The resin was filtered off (M-size frit) and rinsed several times with DMF. The filtrate was concentrated in vacuo at medium temp (bath temp: max 43° C.), redissolved in MeOH and DCM, and concentrated again under reduced pressure. The crude material was adsorbed onto Hydromatrix, dry loaded, and purified by chromatography on silica gel [Jones Flashmaster, 10 g/70 mL cartridge, eluting with MeOH:DCM 2%→5%→10%]. Fractions containing product were combined and concentrated in vacuo, affording the title compound, as an off-white solid. The material was further purified by trituration in MeOH/sonication, affording the title compound, as an off-white solid. $^1$H NMR (400 MHz, DMSO-d$_6$): δ=2.36-2.56 (s, br, rotamers, 2H), 3.19 (s, 3H), 2.38-2.45 (m, 2H), 3.49-3.55 (m, 2H), 3.58 & 3.64 (t, J=5.2 Hz, rotamers, 2H), 4.08 & 4.10 (s, br, rotamers, 2H), 4.14 & 4.18 (s, rotamers, 2H), 6.37 (s, br, 1H), 6.77 & 6.78 (s, rotamers, 1H), 7.80 (dd, J=8.8, 2.0 Hz, 1H), 7.97 (d, J=8.8 Hz, 1H), 8.28 (s, 1H), 8.85 (s, 1H), 9.17 (s, 1H), 9.54 (s, —NH), 11.95 (d, J=9.2 Hz, —NH). MS (ES+): m/z 465.01 (100) [MH$^+$]. HPLC: t$_R$=2.24 min (ZQ2000, polar_5 min).

EXAMPLE 127

4-[4-(Benzothiazol-6-ylamino)-7H-pyrrolo[2,3-d]-pyrimidin-6-yl]-3,6-dihydro-2H-pyridin-1-ylmorpholin-4-ylmethanone

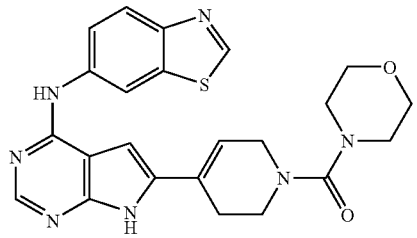

To a suspension of benzothiazol-6-yl-[6-(1,2,3,6-tetrahydropyridin-4-yl)-7H-pyrrolo[2,3-d]pyrimidin-4-yl]-amine tris-hydrochloride (200 mg, 0.44 mmol) in N,N-dimethylformamide (4 mL) was added N,N-diisopropylethylamine (0.5 mL, 3 mmol). The reaction mixture was stirred at 0° C. for 5 min prior to the addition of 4-chloro-carbonylmorpholine (65 mg, 0.44 mmol) in DMF (0.5 mL). The resulting mixture was stirred at 0° C. for 1 h, diluted with EtOAc (30 mL), washed with water (2×15 mL), brine (15 mL), and dried over anhydrous sodium sulfate. The filtrate was concentrated to 5 mL, and the resulting off-white solid was collected by filtration to give the title compound. LC-MS (ES, Pos.): 462 [MH$^+$], and $^1$H NMR (DMSO-d$_6$, 400 MHz): δ=2.53 (m, 2H), 3.17 (m, 4H), 3.43 (m, 2H), 3.60 (m, 4H), 3.96 (m, 2H), 6.42 (s, 1H), 6.82 (d, J=1.2 Hz, 1H), 7.88 (dd, J=8.8 Hz, 2.0 Hz, 1H), 8.04 (d, J=8.8 Hz, 1H), 8.34 (s, 1H), 8.91 (d, J=2.0 Hz, 1H), 9.23 (s, 1H), 9.60 (s, 1H), 12.0 (s, 1H).

EXAMPLE 128

{4-[4-(Benzothiazol-6-ylamino)-7H-pyrrolo[2,3-d]-pyrimidin-6-yl]-3,6-dihydro-2H-pyridin-1-yl}-(1-hydroxymethylcyclopropyl)-methanone

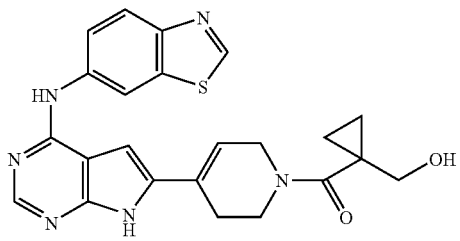

To a suspension of benzothiazol-6-yl-[6-(1,2,3,6-tetrahydropyridin-4-yl)-7H-pyrrolo[2,3-d]pyrimidin-4-yl]-amine tris-hydrochloride (230 mg, 0.50 mmol) in N,N-dimethylformamide (4 mL) were added N,N-diisopropylethylamine (0.7 mL, 4.0 mmol), 1-hydroxymethyl-cyclopropanecarboxylic acid (70 mg, 0.6 mmol) and 2-(1H-benzotriazol-1-yl)-1,1,3,3-tetramethyluronium tetrafluoroborate (190 mg, 0.6 mmol). The resulting mixture was stirred at rt overnight. The mixture was diluted with water (30 mL), and the precipitate was collected by filtration and dried in vacuum, giving the title compound as brown solid. LC-MS (ES, Pos.): 447 [MH$^+$]. $^1$H NMR (DMSO-d$_6$, 400 MHz): δ=0.74 (s, 2H), 0.77 (s, 2H), 2.51 (m, 2H), 3.50 (d, J=5.9 Hz, 2H), 3.85 (m, 2H), 4.20 (m, 2H), 4.90 (br s, 1H), 6.44 (s, 1H), 6.84 (s, 1H), 7.88 (dd, J=8.9 Hz, 2.1 Hz, 1H), 8.04 (d, J=8.9 Hz, 1H), 8.34 (s, 1H), 8.92 (d, J=2.1 Hz, 1H), 9.24 (s, 1H), 9.62 (s, 1H), 12.02 (s, 1H).

1-Hydroxymethylcyclopropanecarboxylic acid

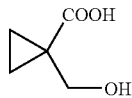

[Ref.: Estieu, K., et al. *Tetrahedron Letters*, 1996, 37(5), 623-624]: Ethyl α-bromocyclobutanecarboxylate (2.07 g, 10.0 mmol) was added to a solution of potassium hydroxide (2.80 g, 50.0 mmol) in water (50 mL), the resulting mixture was refluxed overnight. Evaporation under reduced pressure to remove most of water, the residue was acidified to pH=1 with 6N HCl, the white solid was filtered off. The filtrate was saturated with solid NaCl, extracted with EtOAc (3×20 mL), and the organic layers were combined and dried over anhydrous sodium sulfate. Evaporation afforded a light-yellow oil, which was purified by chromatography on silica gel, eluting with Hex:EtOAc=50:50→30:70→100% EtOAc to give the title compound as a colorless oil. $^1$H NMR (CDCl$_3$, 400 MHz): δ=0.98 (dd, J=7.1 Hz, 4.2 Hz, 2H), 1.38 (dd, J=7.1 Hz, 4.2 Hz, 2H), 3.65 (s, 2H).

EXAMPLE 129

{4-[4-(Benzothiazol-6-ylamino)-7H-pyrrolo[2,3-d]-pyrimidin-6-yl]-3,6-dihydro-2H-pyridin-1-yl}-(1-piperidin-1-ylmethylcyclopropyl)-methanone

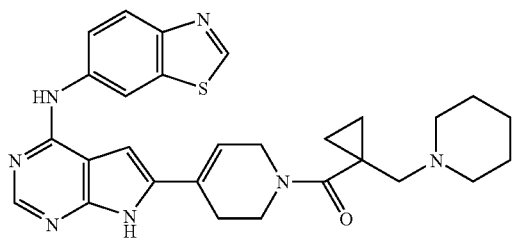

To a solution of {4-[4-(benzothiazol-6-ylamino)-7H-pyrrolo[2,3-d]pyrimidin-6-yl]-3,6-dihydro-2H-pyridin-1-yl}-(1-hydroxymethylcyclopropyl)-methanone (23.0 mg, 0.05 mmol) in N,N-dimethylformamide (1 mL) were added N,N-diisopropylethylamine (0.05 mL, 0.3 mmol) and methanesulfonic anhydride (11 mg, 0.06 mmol). The resulting mixture was stirred at rt overnight. LC-MS showed the reaction produced the desired product, but there was still 70% SM, another 1.2 eq. of methanesulfonic anhydride was added. 2 h later, LC-MS showed the reaction was complete. To the reaction mixture was added piperidine (0.05 mL, 0.5 mmol), and the resulting mixture was stirred at rt overnight. LC-MS showed the reaction was complete. The mixture was diluted with MeOH (1 mL) and purified by mass-directed purification to give the title compounds as an off-white solid. LC-MS (ES, Pos.): 514 [MH$^+$]. $^1$H NMR (CD$_3$OD, 400 MHz): δ=0.76 (s, 2H), 0.99 (s, 2H), 1.41-1.54 (m, 6H), 2.42-2.69 (m, 8H), 3.99 (m, 2H), 4.23 (m, 1H), 4.50 (m, 1H), 6.35 (s, 1H), 6.73 (s, 1H), 7.78 (dd, J=8.9 Hz, 2.1 Hz, 1H), 8.01 (d, J=8.9 Hz, 1H), 8.29 (s, 1H), 8.74 (d, J=2.1 Hz, 1H), 9.12 (s, 1H).

General Procedure for Preparation of an α-cyclopropyl-propane-1-one Library:

To the DMF solution of methanesulfonic acid 1-{4-[4-(benzothiazol-6-ylamino)-7H-pyrrolo[2,3-d]pyrimidin-6-yl]-3,6-dihydro-2H-pyridine-1-carbonyl}-cyclopropylmethyl ester (578.9 mg, divided into 13 aliquots for a 13-member library), prepared as described in the previous example, were added 10 eq. of N,N-diisopropylethylamine and 10 eq. of corresponding amine. If the amines were used as salts, additional DIPEA was used. The solutions were degassed with N$_2$ and left at rt for 96 h. The products were purified by preparative HPLC with water/acetonitrile/formic acid mixture and are assumed to be formate salts.

EXAMPLE 130

{4-[4-(Benzothiazol-6-ylamino)-7H-pyrrolo[2,3-d]-pyrimidin-6-yl]-3,6-dihydro-2H-pyridin-1-yl}-[1-(4-methylpiperazin-1-ylmethyl)-cyclopropyl]-methanone

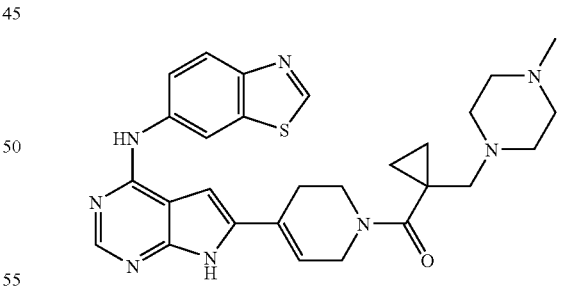

Following the general procedure, the title compound was isolated as yellow powder. $^1$H NMR (400 MHz, DMSO-d$_6$): δ=11.94 (s, 1H), 9.54 (s, 1H), 9.17 (s, 1H), 8.84 (d, 1H, J=2.0 Hz), 8.27 (s, 1H), 8.17 (s, 2H), 7.96 (d, 1H, J=8.9 Hz), 7.80 (dd, 1H, J=2.0 Hz & 8.9 Hz), 6.77 (s, 1H), 6.39 (s, 1H), 4.17 (br s, 2H), 3.74 (br s, 2H), 2.54 (br s, 2H), 2.43 (s, 2H), 2.13 (m, 4H), 2.02 (s, 3H), 0.79 (s, 2H), 0.59 (s, 2H). LC/MS: m/z 528.98 (10) [MH$^+$], t$_R$=1.90 min (ZQ2000, polar_5 min).

EXAMPLE 131

{4-[4-(Benzothiazol-6-ylamino)-7H-pyrrolo[2,3-d]-pyrimidin-6-yl]-3,6-dihydro-2H-pyridin-1-yl}-(1-pyrrolidin-1-ylmethylcyclopropyl)-methanone

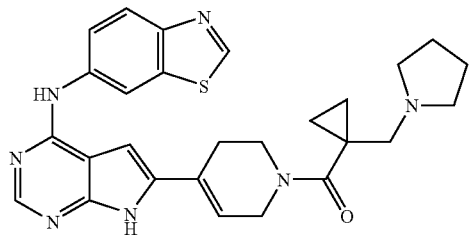

Following the general procedure, the title compound was isolated as yellow powder. $^1$H NMR (400 MHz, DMSO-d$_6$): δ=11.96 (s, 1H), 9.54 (s, 1H), 9.16 (s, 1H), 8.85 (d, 1H, J=2.0 Hz), 8.26 (s, 1H), 8.13 (s, 2H), 7.97 (d, 1H, J=8.9 Hz), 7.81 (dd, 1H, J=2.0 Hz & 8.9 Hz), 6.77 (s, 1H), 6.38 (s, 1H), 4.09 (br s, 2H), 3.74 (m, 2H), 2.53 (s, 2H), 2.52 (m, 2H), 2.47 (m, 2H), 1.55 (s, 4H), 1.05 (d, 2H, J=6.6 Hz), 0.79 (br s, 2H), 0.60 (dd, 2H, J=1.7 Hz & 6.6 Hz). LC/MS: m/z 499.57 [MH$^+$] (80), t$_R$=1.88 min (ZQ2000, polar_5 min).

EXAMPLE 132

{4-[4-(Benzothiazol-6-ylamino)-7H-pyrrolo[2,3-d]-pyrimidin-6-yl]-3,6-dihydro-2H-pyridin-1-yl}-(1-diethylaminomethylcyclopropyl)-methanone

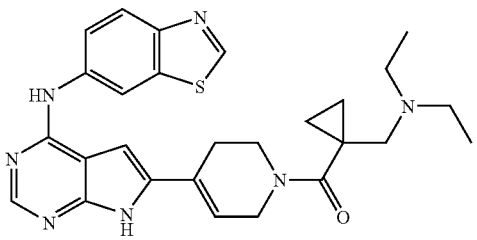

Following the general procedure, the title compound was isolated as yellow powder. $^1$H NMR (400 MHz, DMSO-d$_6$): δ=11.96 (s, 1H), 9.48 (s, 1H), 9.17 (s, 1H), 8.85 (d, 1H, J=2.0 Hz), 8.28 (s, 1H), 8.12 (s, 2H), 7.97 (d, 1H, J=8.9 Hz), 7.80 (dd, 1H, J=2.0 Hz & 8.9 Hz), 6.77 (s, 1H), 6.38 (br s, 1H), 4.06 (br s, 2H), 3.71 (t, 2H, J=5.3 Hz), 2.52 (br s, 2H), 2.51 (m, 4H), 1.08 (t, 2H, J=7.2 Hz), 0.82 (t, 6H, J=7.1 Hz), 0.78 (d, 2H, J=8.5 Hz), 0.60 (t, 2H, J=7.1 Hz). LC/MS: m/z 502.03 [MH$^+$] (100), t$_R$=1.93 min (ZQ2000, polar_5 min).

EXAMPLE 133

{4-[4-(Benzothiazol-6-ylamino)-7H-pyrrolo[2,3-d]-pyrimidin-6-yl]-3,6-dihydro-2H-pyridin-1-yl}-(1-piperidin-1-ylmethylcyclopropyl)-methanone

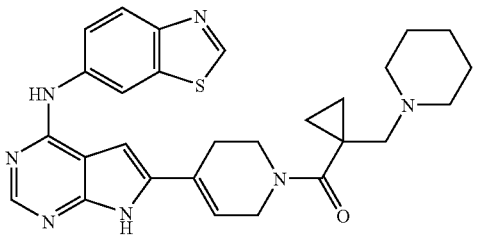

Following the general procedure, the title compound was isolated as yellow powder. $^1$H NMR (400 MHz, DMSO-d$_6$): δ=11.96 (s, 1H), 9.54 (s, 1H), 9.16 (s, 1H), 8.85 (s, 1H, J=2.0 Hz), 8.28 (s, 1H), 8.10 (s, 2H), 7.97 (d, 1H, J=8.9 Hz), 7.80 (dd, 1H, J=2.0 Hz & 8.9 Hz), 6.77 (s, 1H), 6.28 (s, 1H), 4.08 (m, 2H), 3.71 (m, 2H), 2.52 (m, 2H), 2.48 (m, 2H), 2.42 (br s, 4H), 1.34 (br s, 4H), 1.25 (br s, 2H), 0.80 (br s, 2H), 0.60 (dd, 2H, J=1.5 Hz & 6.2 Hz). LC/MS: m/z 514.04 [MH$^+$] (100), t$_R$=1.94 min (ZQ2000, polar_5 min).

EXAMPLE 134

{4-[4-(Benzothiazol-6-ylamino)-7H-pyrrolo[2,3-d]-pyrimidin-6-yl]-3,6-dihydro-2H-pyridin-1-yl}-[1-(tert-butylaminomethyl)-cyclopropyl]-methanone

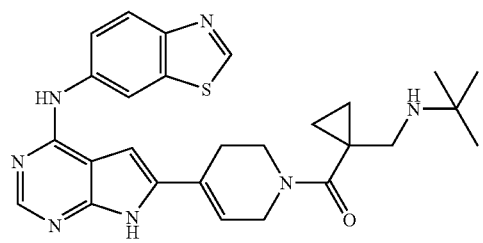

Following the general procedure, the title compound was isolated as yellow powder. $^1$H NMR (400 MHz, DMSO-d$_6$): δ=11.97 (s, 1H), 9.56 (s, 1H), 9.17 (s, 1H), 8.85 (d, 1H, J=2.0 Hz), 8.24 (s, 1H), 8.13 (s, 2H), 7.97 (d, 1H, J=8.9 Hz), 7.77 (dd, 1H, J=2.0 Hz & 8.9 Hz), 6.78 (s, 1H), 6.39 (br s, 1H), 4.19 (br s, 2H), 3.72 (br s, 2H), 2.74 (s, 2H), 2.52 (br s, 2H), 0.96 (s, 9H), 0.81 (t, 2H, J=6.9 Hz), 0.75 (t, 2H, J=6.9 Hz). LC/MS: m/z 501.98 [MH$^+$] (70), t$_R$=1.93 min (ZQ2000, polar_5 min).

EXAMPLE 135

{4-[4-(Benzothiazol-6-ylamino)-7H-pyrrolo[2,3-d]-pyrimidin-6-yl]-3,6-dihydro-2H-pyridin-1-yl)-(1-dimethylaminomethylcyclopropyl)-methanone

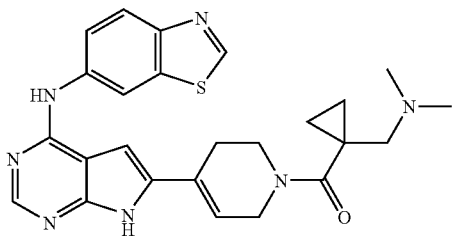

Following the general procedure, but using a sealed tube and saturating the reaction mixture with dimethylamine gas, the title compound was isolated as yellow powder. $^1$H NMR (400 MHz, DMSO-d$_6$): δ=11.94 (s, 1H), 9.55 (s, 1H), 9.19 (s, 1H), 8.84 (d, 1H, J=2.0 Hz), 8.27 (s, 1H), 8.15 (s, 2H), 7.96 (d, 1H, J=8.9 Hz), 7.68 (dd, 1H, J=2.0 Hz & 8.9 Hz), 6.78 (s, 1H), 6.31 (br s, 1H), 4.10 (br s, 2H), 3.78 (br s, 2H), 2.52 (br s, 2H), 2.42 (s, 2H), 2.10 (s, 6H), 0.81 (br s, 2H), 0.56 (t, 2H, J=4.5 Hz). LC/MS: m/z 474.11 [MH$^+$] (70), t$_R$=1.84 min (ZQ2000, polar_5 min).

EXAMPLE 136
{4-[4-(Benzothiazol-6-ylamino)-7H-pyrrolo[2,3-d]-pyrimidin-6-yl]-3,6-dihydro-2H-pyridin-1-yl}-[1-(3-hydroxypyrrolidin-1-ylmethyl)-cyclopropyl]-methanone

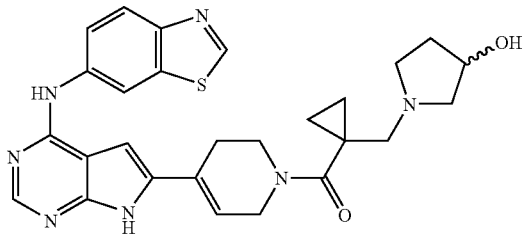

Following the general procedure, the title compound was isolated as yellow powder. $^1$H NMR (400 MHz, DMSO-$d_6$): δ=11.95 (s, 1H), 9.55 (s, 1H), 9.17 (s, 1H), 8.85 (d, 1H, J=2.0 Hz), 8.24 (s, 1H), 8.12 (s, 2H), 7.97 (d, 1H, J=8.9 Hz), 7.78 (dd, 1H, J=2.0 Hz & 8.9 Hz), 6.77 (d, 1H), 6.36 (br s, 1H), 4.07 (m, 2H), 3.72 (m, 2H), 2.78 (m, 2H), 2.54 (m, 2H), 2.52 (br s, 2H), 2.22 (dd, 1H, J=4.2 Hz & 9.7 Hz), 1.85 (m, 2H), 1.40 (m, 2H), 1.07 (d, 2H, J=6.6 Hz), 0.79 (br s, 2H), 0.60 (t, 2H, J=5.2 Hz). LC/MS: m/z 515.99 [MH$^+$] (75), $t_R$=1.84 min (ZQ2000, polar_5 min).

EXAMPLE 137
(1-Azepan-1-ylmethylcyclopropyl)-{4-[4-(benzothiazol-6-ylamino)-7H-pyrrolo[2,3-d]pyrimidin-6-yl]-3,6-dihydro-2H-pyridin-1-yl}-methanone

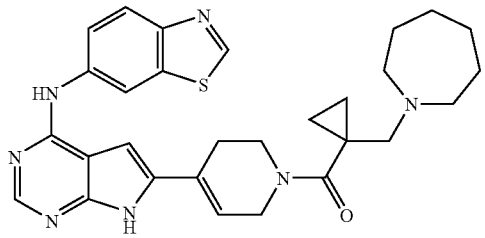

Following the general procedure, the title compound was isolated as yellow powder. $^1$H NMR (400 MHz, DMSO-$d_6$): δ=11.96 (s, 1H), 9.53 (s, 1H), 9.16 (s, 1H), 8.85 (d, 1H, J=2.1 Hz), 8.28 (s, 1H), 8.11 (s, 2H), 7.97 (d, 1H, J=8.7 Hz), 7.81 (dd, 1H, J=2.1 Hz & 8.7 Hz), 6.77 (s, 1H), 6.39 (s, 1H), 4.08 (br s, 2H), 3.73 (br s, 4H), 2.62 (m, 4H), 2.52 (br s, 2H), 1.43 (br s, 4H), 1.40 (br s, 4H), 0.80 (br s, 2H), 0.59 (t, 2H, J=5.6 Hz). LC/MS: m/z 528.13 [MH$^+$] (15), $t_R$=1.94 min (ZQ2000, polar_5 min).

EXAMPLE 138
{4-[4-(Benzothiazol-6-ylamino)-7H-pyrrolo[2,3-d]-pyrimidin-6-yl]-3,6-dihydro-2H-pyridin-1-yl}-[1-(4-hydroxypiperidin-1-ylmethyl)-cyclopropyl]-methanone

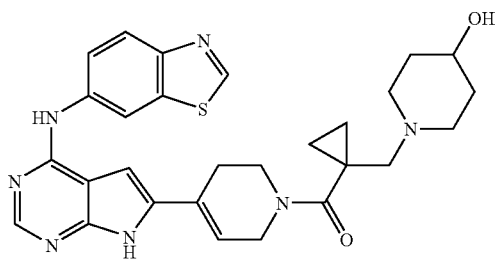

Following the general procedure, the title compound was isolated as yellow powder. $^1$H NMR (400 MHz, DMSO-$d_6$): δ=11.95 (s, 1H), 9.49 (s, 1H), 9.17 (s, 1H), 8.84 (d, 1H, J=2.0 Hz), 8.28 (s, 1H), 8.12 (s, 2H), 7.98 (d, 1H, J=8.9 Hz), 7.83 (dd, 1H, J=2.0 Hz & 8.9 Hz), 6.77 (s, 1H), 6.39 (s, 1H), 4.09 (br s, 2H), 3.71 (br s, 2H), 3.50 (m, 1H), 3.31 (m, 2H), 2.74 (br s, 2H), 2.52 (br s, 2H), 2.40 (s, 1H), 1.98 (t, 2H, J=9.9 Hz), 1.55 (m, 2H), 1.23 (m, 2H), 0.80 (br s, 2H), 0.58 (t, 2H, J=1.4 Hz). LC/MS: m/z 529.97 [MH$^+$] (20), $t_R$=1.86 min (ZQ2000, polar_5 min).

EXAMPLE 139
{4-[4-(Benzothiazol-6-ylamino)-7H-pyrrolo[2,3-d]-pyrimidin-6-yl]-3,6-dihydro-2H-pyridin-1-yl}-1-(4-isopropylpiperazin-1-ylmethyl)-cyclopropyl]-methanone

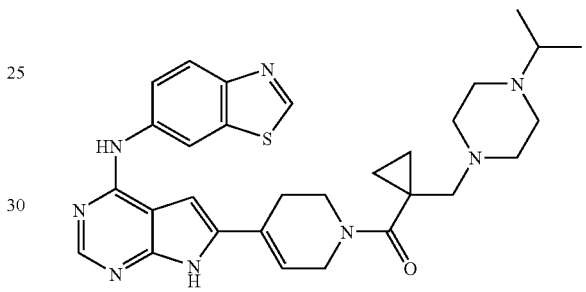

Following the general procedure, the title compound was isolated as yellow powder. $^1$H NMR (400 MHz, DMSO-$d_6$): δ=12.02 (s, 1H), 9.61 (s, 1H), 9.26 (s, 1H), 8.92 (d, 1H, J=2.0 Hz), 8.34 (s, 1H), 8.20 (s, 2H), 8.06 (d, 1H, J=8.9 Hz), 7.83 (dd, 1H, J=2.0 Hz & 8.9 Hz), 6.84 (s, 1H), 6.46 (br s, 1H), 4.14 (br s, 2H), 3.68 (m, 2H), 3.26 (m, 4H), 2.52 (br s, 2H), 2.49 (br s, 2H), 2.45 (br s, 4H), 2.17 (m, 1H), 0.91 (d, 6H, J=6.0 Hz), 0.88 (br s, 2H), 0.65 (t, 2H, J=4.8 Hz). LC/MS: m/z 557.02 [MH$^+$] (20), $t_R$=1.93 min (ZQ2000, polar_5 min).

EXAMPLE 140
{4-[4-(Benzothiazol-6-ylamino)-7H-pyrrolo[2,3-d]-pyrimidin-6-yl]-3,6-dihydro-2H-pyridin-1-yl}-(1-morpholin-4-ylmethylcyclopropyl)-methanone

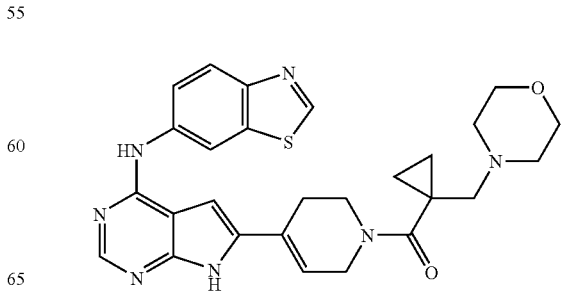

Following the general procedure, the title compound was isolated as yellow powder. ¹H NMR (400 MHz, DMSO-d₆): δ=11.96 (s, 1H), 9.54 (s, 1H), 9.17 (s, 1H), 8.85 (d, 1H, J=2.0 Hz), 8.31 (s, 1H), 8.09 (s, 2H), 7.97 (d, 1H, J=8.6 Hz), 7.81 (dd, 1H, J=2.0 Hz & 8.6 Hz), 6.73 (s, 1H), 6.33 (br s, 1H), 4.17 (br s, 2H), 3.72 (m, 2H), 3.42 (br s, 2H), 2.53 (br s, 2H), 2.35 (br s, 2H), 2.26 (br s, 6H), 0.81 (br s, 2H), 0.58 (t, 2H, J=5.9 Hz). LC/MS: m/z 515.99 [MH⁺] (50), $t_R$=1.87 min (ZQ2000, polar_5 min).

EXAMPLE 141

{4-[4-(Benzothiazol-6-ylamino)-7H-pyrrolo[2,3-d]-pyrimidin-6-yl]-3,6-dihydro-2H-pyridin-1-yl}-[1-(4,4-difluoropiperidin-1-ylmethyl)-cyclopropyl]-methanone

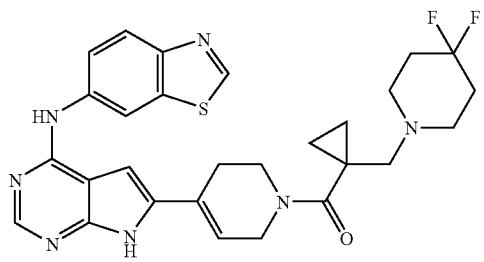

Following the general procedure, but using 4,4-difluoropiperidine hydrochloride and additional 2 eq. of N,N-diisopropylethylamine, the title compound was isolated as yellow powder. ¹H NMR (400 MHz, DMSO-d₆): δ=11.96 (s, 1H), 9.54 (s, 1H), 9.16 (s, 1H), 8.84 (d, 1H, J=2.0 Hz), 8.24 (s, 1H), 7.97 (d, 1H, J=8.8 Hz), 7.80 (dd, 1H, J=2.0 Hz & 8.8 Hz), 6.77 (s, 1H), 6.38 (br s, 1H), 4.18 (br s, 2H), 3.66 (t, 2H, J=5.7 Hz), 2.54 (br s, 6H), 1.78 (br s, 6H), 0.81 (s, 2H), 0.60 (t, 2H, J=5.4 Hz). LC/MS: m/z 550.01 [MH⁺] (30), $t_R$=2.01 min (ZQ2000, polar_5 min).

EXAMPLE 142

{4-[4-(Benzothiazol-6-ylamino)-7H-pyrrolo[2,3-d]-pyrimidin-6-yl]-3,6-dihydro-2H-pyridin-1-yl}-(1-{[(2-isopropylaminopropyl)-methylamino]-methyl}-cyclopropyl)-methanone

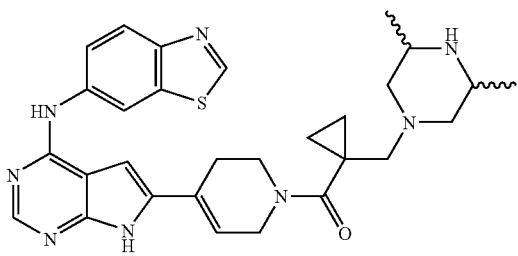

Following the general procedure, the title compound was isolated as yellow powder. ¹H NMR (400 MHz, DMSO-d₆): δ=11.97 (s, 1H), 9.57 (s, 1H), 9.17 (s, 1H), 8.85 (d, 1H, J=2.0 Hz), 8.27 (s, 1H), 8.21 (s, 2H), 7.97 (d, 1H, J=8.9 Hz), 7.77 (dd, 1H, J=2.0 Hz & 8.9 Hz), 6.78 (s, 1H), 6.38 (br s, 1H), 4.19 (s, 2H), 3.69 (m, 2H), 2.85 (m, 2H), 2.54 (m, 2H), 2.48 (br s, 2H), 1.61 (t, 2H, J=10.4 Hz), 0.89 (m, 6H), 0.81 (br s, 2H), 0.59 (br s, 2H). LC/MS: m/z 543.05 [MH⁺] (15), $t_R$=1.92 min (ZQ2000, polar_5 min).

General Procedure for the Preparation of a Urea Library

To a solution of benzothiazol-6-yl-[6-(1,2,3,6-tetrahydro-pyridin-4-yl)-7H-pyrrolo[2,3-d]pyrimidin-4-yl]-amine tris-hydrochloride (396 mg, in DMF (12 mL) and dichloromethane (1 mL) at 4° C. was added N,N-diisopropylethylamine followed by 4-nitrophenyl chloroformate (200 mg, 1.0 eq.). The resulting mixture was allowed to warm up to rt and left overnight. This solution of 4-[4-(benzothiazol-6-ylamino)-7H-pyrrolo[2,3-d]pyrimidin-6-yl]-3,6-dihydro-2H-pyridine-1-carboxylic acid 4-nitrophenyl ester was divided into 10 aliquots, and 5 eq. of N,N-diisopropylethylamine and 10 eq. of the corresponding amine were added. The solutions were degassed with N₂ and heated at 50° C. for 96 h. The products were purified by preparative HPLC with water/acetonitrile/formic acid mixtures and are assumed to be formate salts.

EXAMPLE 143

4-[4-(Benzothiazol-6-ylamino)-7H-pyrrolo[2,3-d]-pyrimidin-6-yl]-3,6-dihydro-2H-pyridine-1-carboxylic acid 4-nitrophenyl ester

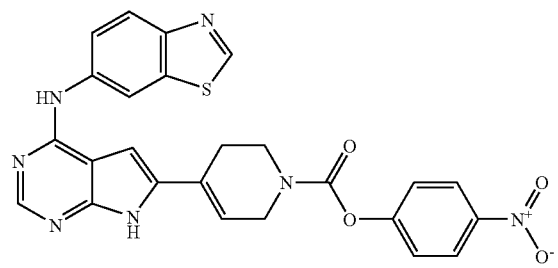

LC/MS: m/z 513.94 [MH⁺] (100), $t_R$=3.05 min (ZQ2000, polar_5 min).

EXAMPLE 144

4-[4-(Benzothiazol-6-ylamino)-7H-pyrrolo[2,3-d]-pyrimidin-6-yl]-3,6-dihydro-2H-pyridine-1-carboxylic acid (2-dimethylamino-ethyl)-amide

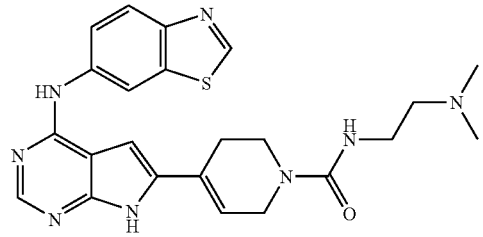

Following the general procedure, the title compound was isolated as yellow powder. ¹H NMR (400 MHz, DMSO-d₆): δ=11.99 (s, 1H), 9.60 (s, 1H), 9.24 (s, 1H), 8.91 (d, 1H, J=2.0

Hz), 8.34 (s, 1H), 8.24 (s, 2H), 8.04 (d, 1H, J=8.9 Hz), 7.87 (dd, 1H, J=2.0 Hz & 8.9 Hz), 6.84 (s, 1H), 6.43 (s, 1H), 4.02 (s, 2H), 3.55 (m, 2H), 3.43 (m, 2H), 3.29 (m, 2H), 2.33 (m, 2H), 2.19 (s, 6H). LC/MS: m/z 463.05 [MH+] (15), $t_R$=1.81 min (ZQ2000, polar__5 min).

EXAMPLE 145

4-[4-(Benzothiazol-6-ylamino)-7H-pyrrolo[2,3-d]-pyrimidin-6-yl]-3,6-dihydro-2H-pyridine-1-carboxylic acid (2-diethylaminoethyl)-amide

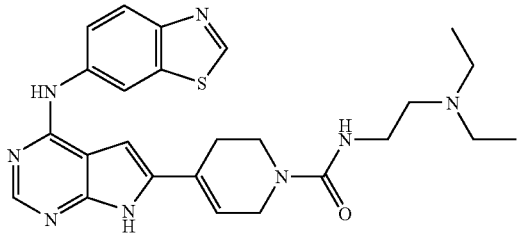

Following the general procedure, the title compound was isolated as yellow powder. $^1$H NMR (400 MHz, DMSO-$d_6$): δ=11.92 (s, 1H), 9.53 (s, 1H), 9.17 (s, 1H), 8.85 (d, 1H, J=2.0 Hz), 8.27 (s, 1H), 8.14 (s, 2H), 7.97 (d, 1H, J=8.9 Hz), 7.81 (dd, 1H, J=2.0 Hz & 8.9 Hz), 6.76 (s, 1H), 6.47 (t, 1H, J=5.3 Hz), 6.37 (br s, 1H), 3.95 (s, 2H), 3.48 (m, 2H), 3.40 (m, 4H), 3.10 (m, 2H), 2.51 (q, 4H, J=7.1 Hz), 0.93 (t, 6H, J=7.1 Hz). LC/MS: m/z 491.11 [MH+] (30), $t_R$=1.88 min (ZQ2000, polar__5 min).

EXAMPLE 146

4-[4-(Benzothiazol-6-ylamino)-7H-pyrrolo[2,3-d]-pyrimidin-6-yl]-3,6-dihydro-2H-pyridine-1-carboxylic acid (2-isopropylamino-ethyl)-amide

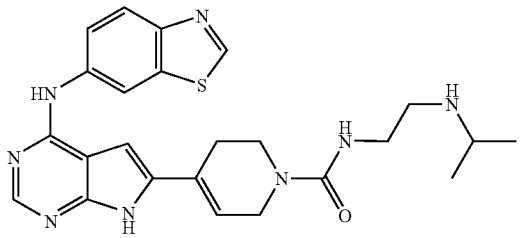

Following the general procedure, the title compound was isolated as yellow powder. $^1$H NMR (400 MHz, DMSO-$d_6$): δ=11.92 (s, 1H), 9.53 (s, 1H), 9.17 (s, 1H), 8.85 (d, 1H, J=2.0 Hz), 8.27 (s, 1H), 8.14 (s, 2H), 7.97 (d, 1H, J=8.9 Hz), 7.81 (dd, 1H, J=2.0 Hz & 8.9 Hz), 7.00 (t, 1H, J=4.7 Hz), 6.78 (s, 1H), 6.38 (br s, 1H), 4.07 (s, 2H), 3.52 (t, 2H, J=5.5 Hz), 3.26 (q, 2H, J=5.5 Hz), 3.16 (m, 1H), 2.86 (t, 2H, J=5.9 Hz), 2.69 (m, 2H), 1.14 (d, 6H, J=6.4 Hz). LC/MS: m/z 477.08 [MH+] (30), $t_R$=1.83 min (ZQ2000, polar__5 min).

EXAMPLE 147

4-[4-(Benzothiazol-6-ylamino)-7H-pyrrolo[2,3-d]-pyrimidin-6-yl]-3,6-dihydro-2H-pyridine-1-carboxylic acid (2-piperazin-1-ylethyl)-amide

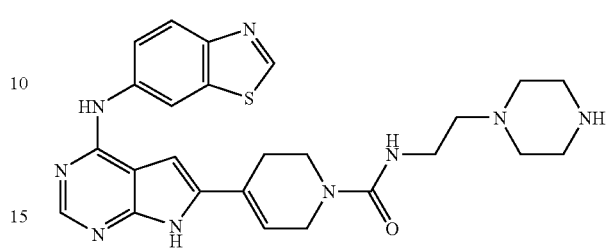

Following the general procedure, the title compound was isolated as yellow powder. $^1$H NMR (400 MHz, DMSO-$d_6$): δ=11.91 (s, 1H), 9.52 (s, 1H), 9.16 (s, 1H), 8.84 (d, 1H, J=2.0 Hz), 8.26 (s, 1H), 8.14 (s, 2H), 7.97 (d, 1H, J=8.9 Hz), 7.91 (s, 1H), 7.80 (dd, 1H, J=2.0 Hz & 8.9 Hz), 6.76 (s, 1H), 6.42 (t, 1H, J=5.3 Hz), 6.37 (br s, 1H), 3.94 (s, 2H), 3.48 (t, 2H, J=5.6 Hz), 3.28 (m, 4H), 3.11 (m, 2H), 2.91 (m, 2H), 2.51 (m, 2H), 2.33 (m, 2H), 2.27 (t, 2H, J=5.3 Hz). LC/MS: m/z 504.06 [MH+] (10), $t_R$=1.70 min (ZQ2000, polar__5 min).

EXAMPLE 148

4-[4-(Benzothiazol-6-ylamino)-7H-pyrrolo[2,3-d]-pyrimidin-6-yl]-3,6-dihydro-2H-pyridine-1-carboxylic acid (2-diisopropylamino-ethyl)-amide

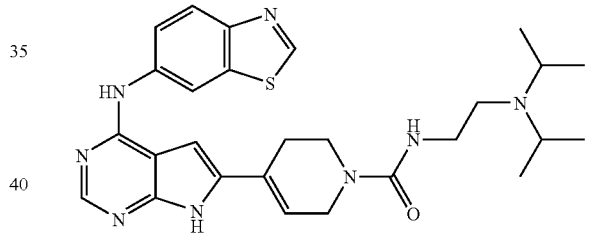

Following the general procedure, the title compound was isolated as yellow powder. $^1$H NMR (400 MHz, DMSO-$d_6$): δ=11.91 (s, 1H), 9.52 (s, 1H), 9.16 (s, 1H), 8.84 (d, 1H, J=2.0 Hz), 8.26 (s, 1H), 8.14 (s, 2H), 7.97 (d, 1H, J=8.9 Hz), 7.91 (s, 1H), 7.80 (dd, 1H, J=2.0 Hz & 8.9 Hz), 6.77 (s, 1H), 6.71 (br s, 1H), 6.37 (br s, 1H), 3.96 (s, 2H), 3.50 (t, 2H, J=5.4 Hz), 3.08 (m, 4H), 2.59 (t, 2H, J=7.2 Hz), 2.45 (br s, 2H), 0.99 (d, 12H, J=6.6 Hz). LC/MS: m/z 519.10 [MH+] (30), $t_R$=1.94 min (ZQ2000, polar__5 min).

EXAMPLE 149

4-[4-(Benzothiazol-6-ylamino)-7H-pyrrolo[2,3-d]-pyrimidin-6-yl]-3,6-dihydro-2H-pyridine-1-carboxylic acid (2-methoxyethyl)-amide

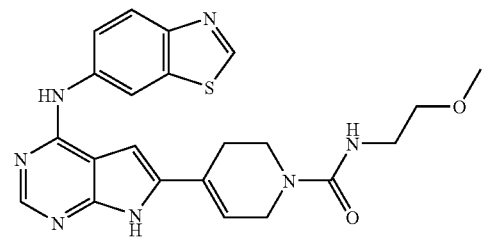

Following the general procedure, the title compound was isolated as yellow powder. $^1$H NMR (400 MHz, DMSO-d$_6$): δ=12.10 (s, 1H), 9.71 (s, 1H), 9.35 (s, 1H), 9.03 (d, 1H, J=2.0 Hz), 8.46 (s, 1H), 8.42 (s, 1H), 8.15 (d, 1H, J=8.9 Hz), 8.00 (dd, 1H, J=2.0 Hz & 8.9 Hz), 6.95 (s, 1H), 6.70 (t, 1H, J=5.6 Hz), 6.55 (br s, 1H), 4.14 (s, 2H), 3.68 (t, 2H, J=5.6 Hz), 3.47 (m, 2H), 3.37 (s, 3H), 3.34 (q, 2H, J=6.9 Hz), 2.61 (br s, 2H). LC/MS: m/z 450.04 [MH$^+$] (100), t$_R$=2.20 min (ZQ2000, polar_5 min).

EXAMPLE 150

4-[4-(Benzothiazol-6-ylamino)-7H-pyrrolo[2,3-d]-pyrimidin-6-yl]-3,6-dihydro-2H-pyridine-1-carboxylic acid bis-(2-methoxyethyl)-amide

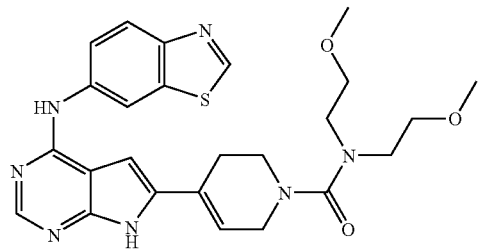

Following the general procedure, the title compound was isolated as yellow powder. $^1$H NMR (400 MHz, DMSO-d$_6$): δ=11.92 (s, 1H), 9.52 (s, 1H), 9.16 (s, 1H), 8.84 (d, 1H, J=2.0 Hz), 8.26 (s, 1H), 8.14 (s, 2H), 7.97 (d, 1H, J=8.9 Hz), 7.91 (s, 1H), 7.80 (dd, 1H, J=2.0 Hz & 8.9 Hz), 6.75 (s, 1H), 6.36 (br s, 1H), 3.81 (br s, 2H), 3.38 (t, 4H, J=6.1 Hz), 3.29 (m, 4H), 3.18 (s, 6H), 2.71 (s, 2H), 2.52 (br s, 2H). LC/MS: m/z 508.04 [MH$^+$] (100), t$_R$=2.39 min (ZQ2000, polar_5 min).

EXAMPLE 151

4-[4-(Benzothiazol-6-ylamino)-7H-pyrrolo[2,3-d]-pyrimidin-6-yl]-3,6-dihydro-2H-pyridine-1-carboxylic acid (2-piperidin-1-ylethyl)-amide

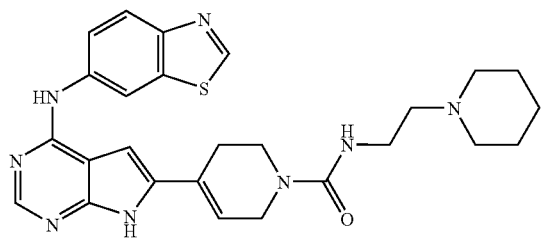

Following the general procedure, the title compound was isolated as yellow powder. $^1$H NMR (400 MHz, DMSO-d$_6$): δ=12.02 (s, 1H), 9.53 (s, 1H), 9.15 (s, 1H), 8.84 (d, 1H, J=2.0 Hz), 8.26 (s, 1H), 8.14 (s, 2H), 7.97 (d, 1H, J=8.9 Hz), 7.91 (s, 1H), 7.80 (dd, 1H, J=2.0 Hz & 8.9 Hz), 6.76 (s, 1H), 6.54 (t, 1H, J=5.2 Hz), 6.38 (br s, 1H), 3.95 (s, 2H), 3.49 (t, 2H, J=5.4 Hz), 3.17 (q, 2H, J=6.4 Hz), 2.55 (m, 6H), 2.51 (br s, 2H), 1.48 (m, 4H), 1.34 (m, 2H). LC/MS: m/z 503.10 [MH$^+$] (25), t$_R$=1.85 min (ZQ2000, polar_5 min).

EXAMPLE 152

4-[4-(Benzothiazol-6-ylamino)-7H-pyrrolo[2,3-d]-pyrimidin-6-yl]-3,6-dihydro-2H-pyridine-1-carboxylic acid (2-morpholin-4-ylethyl)-amide

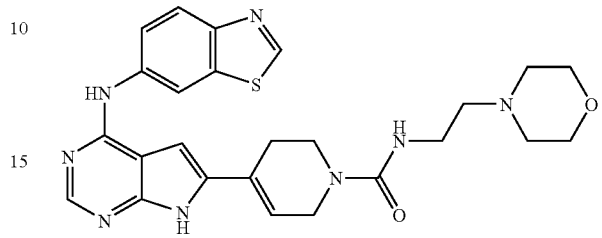

Following the general procedure, the title compound was isolated as yellow powder. $^1$H NMR (400 MHz, DMSO-d$_6$): δ=11.91 (s, 1H), 9.52 (s, 1H), 9.16 (s, 1H), 8.84 (d, 1H, J=2.0 Hz), 8.26 (s, 1H), 8.14 (s, 2H), 7.97 (d, 1H, J=8.9 Hz), 7.91 (s, 1H), 7.80 (dd, 1H, J=2.0 Hz & 8.9 Hz), 6.76 (s, 1H), 6.42 (t, 1H, J=5.5 Hz), 6.37 (br s, 1H), 3.95 (s, 2H), 3.48 (t, 2H, J=5.6 Hz), 3.49 (t, 6H, J=4.4 Hz), 3.11 (q, 2H, J=6.3 Hz), 2.49 (br s, 2H), 2.31 (m, 4H). LC/MS: m/z 505.07 [MH$^+$] (30), t$_R$=1.80 min (ZQ2000, polar_5 min).

EXAMPLE 153

4-[4-(Benzothiazol-6-ylamino)-7H-pyrrolo[2,3-d]-pyrimidin-6-yl]-3,6-dihydro-2H-pyridine-1-carboxylic acid (2-pyrrolidin-1-ylethyl)-amide

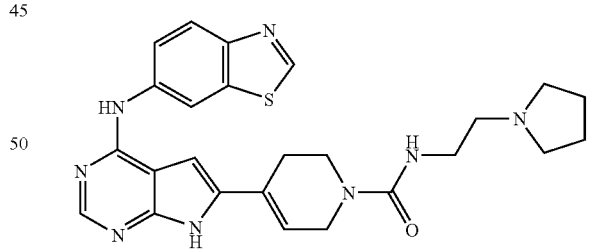

Following the general procedure, the title compound was isolated as yellow powder. $^1$H NMR (400 MHz, DMSO-d$_6$): δ=11.91 (s, 1H), 9.52 (s, 1H), 9.16 (s, 1H), 8.84 (d, 1H, J=2.0 Hz), 8.26 (s, 1H), 8.14 (s, 2H), 7.97 (d, 1H, J=8.9 Hz), 7.91 (s, 1H), 7.80 (dd, 1H, J=2.0 Hz & 8.9 Hz), 6.76 (s, 1H), 6.41 (t, 1H, J=5.4 Hz), 6.37 (br s, 1H), 3.94 (s, 2H), 3.50 (t, 2H, J=5.5 Hz), 3.18 (q, 2H, J=6.3 Hz), 2.67 (m, 6H), 2.48 (br s, 2H), 1.68 (t, 4H, J=3.2 Hz). LC/MS: m/z 489.03 [MH$^+$] (55), t$_R$=1.83 min (ZQ2000, polar_5 min).

The following examples were prepared following the same procedure:

EXAMPLE 154

{4-[4-(Benzothiazol-6-ylamino)-7H-pyrrolo[2,3-d]-pyrimidin-6-yl]-3,6-dihydro-2H-pyridin-1-yl}-piperazin-1-ylmethanone

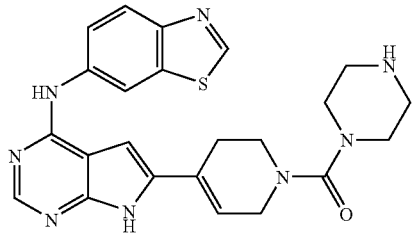

Following the general procedure, the title compound was isolated as yellow powder. $^1$H NMR (400 MHz, DMSO-d$_6$): δ=11.95 (s, 1H), 9.55 (s, 1H), 9.17 (s, 1H), 8.84 (d, 1H, J=2.0 Hz), 8.27 (s, 1H), 8.20 (s, 2H), 7.97 (d, 1H, J=8.9 Hz), 7.80 (dd, 1H, J=2.0 Hz & 8.9 Hz), 6.76 (s, 1H), 6.35 (s, 1H), 4.40 (br s, 4H), 3.89 (s, 2H), 3.36 (t, 2H, J=5.6 Hz), 3.17 (s, 3H), 2.85 (br s, 2H), 2.52 (br s, 2H). LC/MS: m/z 461.05 [MH$^+$] (40), t$_R$=1.77 min (ZQ2000, polar_5 min).

EXAMPLE 155

{4-[4-(Benzothiazol-6-ylamino)-7H-pyrrolo[2,3-d]-pyrimidin-6-yl]-3,6-dihydro-2H-pyridin-1-yl}-(4-ethylpiperazin-1-yl)-methanone

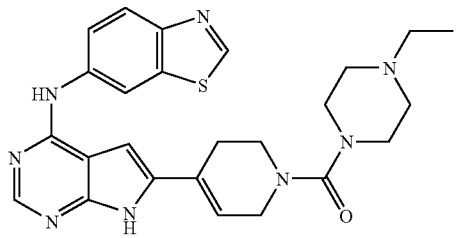

Following the general procedure, the title compound was isolated as yellow powder. $^1$H NMR (400 MHz, DMSO-d$_6$): δ=11.92 (s, 1H), 9.53 (s, 1H), 9.16 (s, 1H), 8.84 (d, 1H, J=2.0 Hz), 8.27 (s, 1H), 8.10 (s, 2H), 7.97 (d, 1H, J=8.9 Hz), 7.80 (dd, 1H, J=2.0 Hz & 8.9 Hz), 6.76 (s, 1H), 6.34 (s, 1H), 3.86 (br s, 2H), 3.34 (t, 2H, J=5.6 Hz), 3.11 (br s, 4H), 2.54 (br s, 2H), 2.30 (d, 4H, J=6.6 Hz), 2.29 (q, 2H, J=7.1 Hz), 0.94 (t, 3H, J=7.1 Hz). LC/MS: m/z 489.08 [MH$^+$] (30), t$_R$=1.81 min (ZQ2000, polar_5 min).

EXAMPLE 156

{4-[4-(Benzothiazol-6-ylamino)-7H-pyrrolo[2,3-d]-pyrimidin-6-yl]-3,6-dihydro-2H-pyridin-1-yl}-(4-isopropylpiperazin-1-yl)-methanone

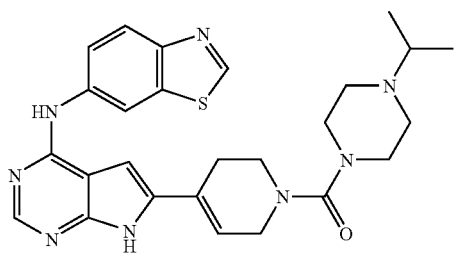

Following the general procedure, the title compound was isolated as yellow powder. $^1$H NMR (400 MHz, DMSO-d$_6$): δ=11.92 (s, 1H), 9.54 (s, 1H), 9.17 (s, 1H), 8.84 (d, 1H, J=2.0 Hz), 8.27 (s, 1H), 8.10 (s, 2H), 7.96 (d, 1H, J=8.9 Hz), 7.80 (dd, 1H, J=2.0 Hz & 8.9 Hz), 6.71 (s, 1H), 6.39 (s, 1H), 3.87 (br s, 4H), 3.34 (t, 4H, J=5.3 Hz), 3.11 (br s, 4H), 2.63 (m, 1H), 2.54 (br s, 2H), 0.92 (d, 6H, J=6.5 Hz). LC/MS: m/z 503.05 [MH$^+$] (50), t$_R$=1.85 min (ZQ2000, polar_5 min).

EXAMPLE 157

{4-[4-(Benzothiazol-6-ylamino)-7H-pyrrolo[2,3-d]-pyrimidin-6-yl]-3,6-dihydro-2H-pyridin-1-yl}-(3,5-dimethylpiperazin-1-yl)-methanone

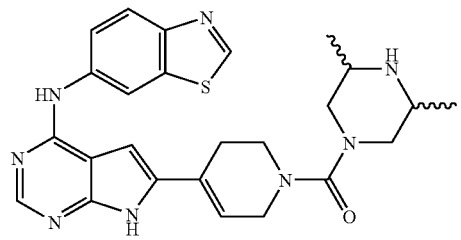

Following the general procedure, the title compound was isolated as yellow powder. $^1$H NMR (400 MHz, DMSO-d$_6$): δ=11.93 (s, 1H), 9.53 (s, 1H), 9.17 (s, 1H), 8.84 (d, 1H, J=2.0 Hz), 8.27 (s, 1H), 8.15 (s, 2H), 7.99 (d, 1H, J=8.9 Hz), 7.80 (dd, 1H, J=2.0 Hz & 8.9 Hz), 6.76 (s, 1H), 6.34 (s, 1H), 3.87 (br s, 2H), 3.65 (br s, 1H), 3.45 (s, 2H), 3.42 (s, 1H), 3.34 (t, 1H, J=5.6 Hz), 2.80 (m, 2H), 2.54 (br s, 2H), 2.38 (m, 2H), 0.96 (d, 6H, J=6.1 Hz). LC/MS: m/z 489.08 [MH$^+$] (30), t$_R$=1.82 min (ZQ2000, polar_5 min).

EXAMPLE 158

{4-[4-(Benzothiazol-6-ylamino)-7H-pyrrolo[2,3-d]-pyrimidin-6-yl]-3,6-dihydro-2H-pyridin-1-yl}-(4-cyclopentylpiperazin-1-yl)-methanone

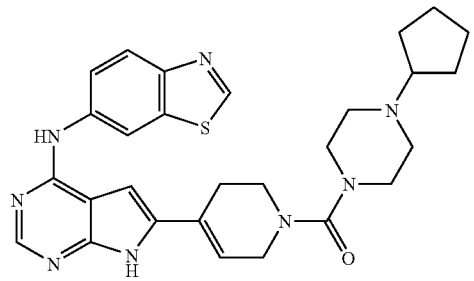

Following the general procedure, the title compound was isolated as yellow powder. $^1$H NMR (400 MHz, DMSO-d$_6$): δ=11.92 (s, 1H), 9.53 (s, 1H), 9.16 (s, 1H), 8.84 (d, 1H, J=2.0 Hz), 8.27 (s, 1H), 8.10 (s, 2H), 7.96 (d, 1H, J=8.9 Hz), 7.80 (dd, 1H, J=2.0 Hz & 8.9 Hz), 6.75 (s, 1H), 6.35 (s, 1H), 3.86 (br s, 2H), 3.33 (t, 2H, J=5.6 Hz), 3.10 (br s, 4H), 2.53 (br s, 2H), 2.43 (m, 1H), 2.36 (br s, 4H), 1.69 (m, 2H), 1.53 (m, 2H), 1.43 (m, 2H), 1.26 (m, 2H). LC/MS: m/z 529.08 [MH$^+$] (40), t$_R$=1.90 min (ZQ2000, polar_5 min).

EXAMPLE 159

{4-[4-(Benzothiazol-6-ylamino)-7H-pyrrolo[2,3-d]-pyrimidin-6-yl]-3,6-dihydro-2H-pyridin-1-yl}-(1-methylazepan-4-yl)-methanone

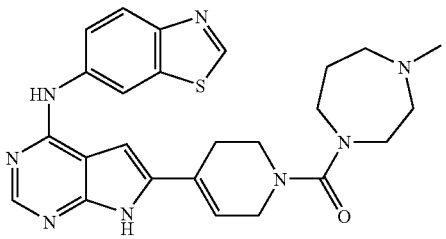

Following the general procedure, the title compound was isolated as yellow powder. $^1$H NMR (400 MHz, DMSO-d$_6$): δ=11.94 (s, 1H), 9.54 (s, 1H), 9.17 (s, 1H), 8.84 (d, 1H, J=2.0 Hz), 8.27 (s, 1H), 8.17 (s, 2H), 7.96 (d, 1H, J=8.9 Hz), 7.80 (dd, 1H, J=2.0 Hz & 8.9 Hz), 6.77 (s, 1H), 6.39 (s, 1H), 3.64 (br s, 2H), 3.36 (t, 6H, J=6.5 Hz), 2.66 (br s, 2H), 2.56 (m, 2H), 2.52 (br s, 2H), 2.28 (s, 3H), 1.79 (m, 2H). LC/MS: m/z 489.08 [MH$^+$] (20), t$_R$=1.81 min (ZQ2000, polar_5 min).

EXAMPLE 160

{4-[4-(Benzothiazol-6-ylamino)-7H-pyrrolo[2,3-d]-pyrimidin-6-yl]-3,6-dihydro-2H-pyridin-1-yl}-[4-(2-methoxyethyl)-piperazin-1-yl]-methanone

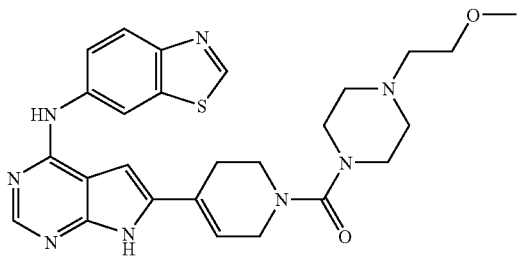

Following the general procedure, the title compound was isolated as yellow powder. $^1$H NMR (400 MHz, DMSO-d$_6$): δ=11.92 (s, 1H), 9.53 (s, 1H), 9.17 (s, 1H), 8.84 (s, 1H, J=2.0 Hz), 8.27 (s, 1H), 8.10 (s, 2H), 7.97 (d, 1H, J=8.9 Hz), 7.80 (dd, 1H, J=2.0 Hz & 8.9 Hz), 6.76 (s, 1H), 6.35 (s, 1H), 3.86 (br s, 2H), 3.37 (t, 2H, J=5.8 Hz), 3.34 (t, 2H, J=5.6 Hz), 3.17 (s, 3H), 3.10 (br s, 4H), 2.53 (br s, 2H), 2.41 (m, 2H), 2.37 (br s, 4H). LC/MS: m/z 519.10 [MH$^+$] (25), t$_R$=1.82 min (ZQ2000, polar_5 min).

EXAMPLE 161

{4-[4-(Benzothiazol-6-ylamino)-7H-pyrrolo[2,3-d]-pyrimidin-6-yl]-3,6-dihydro-2H-pyridin-1-yl}-[4-(2-dimethylaminoethyl)-piperazin-1-yl]-methanone

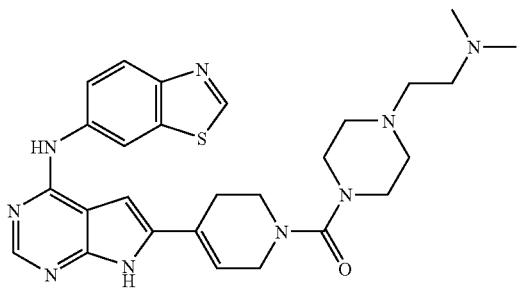

Following the general procedure, the title compound was isolated as yellow powder. $^1$H NMR (400 MHz, DMSO-d$_6$): δ=11.93 (s, 1H), 9.55 (s, 1H), 9.17 (s, 1H), 8.84 (d, 1H, J=2.0 Hz), 8.27 (s, 1H), 8.16 (s, 2H), 7.96 (d, 1H, J=8.9 Hz), 7.80 (dd, 1H, J=2.0 Hz & 8.9 Hz), 6.77 (s, 1H), 6.39 (s, 1H), 3.87 (br s, 2H), 3.34 (t, 2H, J=5.1 Hz), 3.11 (br s, 4H), 2.65 (t, 2H, J=6.3 Hz), 2.53 (br s, 2H), 2.43 (m, 2H), 2.37 (m, 4H), 2.35 (s, 6H). LC/MS: m/z 532.06 [MH$^+$] (35), t$_R$=1.82 min (ZQ2000, polar_5 min).

EXAMPLE 162

4-[4-(Benzothiazol-6-ylamino)-7H-pyrrolo[2,3-d]-pyrimidin-6-yl]-3,6-dihydro-2H-pyridine-1-carboxylic acid methyl-(1-methyl-piperidin-4-yl)-amide

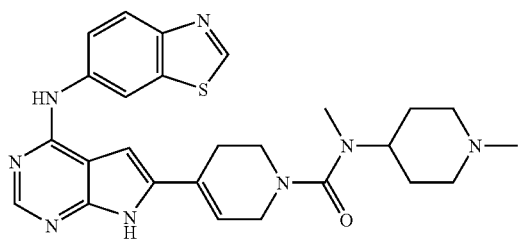

Following the general procedure, the title compound was isolated as yellow powder. $^1$H NMR (400 MHz, DMSO-d$_6$): δ=11.92 (s, 1H), 9.54 (s, 1H), 9.17 (s, 1H), 8.84 (d, 1H, J=2.0 Hz), 8.27 (s, 1H), 8.14 (s, 2H), 7.96 (d, 1H, J=8.9 Hz), 7.80 (dd, 1H, J=2.0 Hz & 8.9 Hz), 6.77 (s, 1H), 6.39 (s, 1H), 3.80 (br s, 2H), 3.42 (m, 3H), 3.30 (t, 2H, J=5.3 Hz), 2.80 (d, 2H, J=10.8 Hz), 2.63 (s, 3H), 2.52 (br s, 2H), 2.13 (s, 3H), 1.94 (t, 2H, J=11.8 Hz), 1.67 (m, 2H), 1.50 (d, 2H, J=10.8 Hz). LC/MS: m/z 503.11 [MH$^+$] (10), t$_R$=1.83 min (ZQ2000, polar_5 min).

EXAMPLE 163

{4-[4-(Benzothiazol-6-ylamino)-7H-pyrrolo[2,3-d]-pyrimidin-6-yl]-3,6-dihydro-2H-pyridin-1-yl}-thiomorpholin-4-ylmethanone

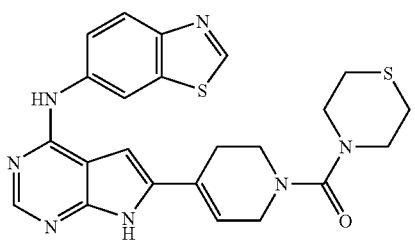

Following the general procedure, the title compound was isolated as yellow powder. $^1$H NMR (400 MHz, DMSO-d$_6$): δ=11.93 (s, 1H), 9.53 (s, 1H), 9.17 (s, 1H), 8.84 (d, 1H, J=2.0 Hz), 8.27 (s, 1H), 8.14 (s, 2H), 7.96 (d, 1H, J=8.9 Hz), 7.80 (dd, 1H, J=2.0 Hz & 8.9 Hz), 6.75 (s, 1H), 6.35 (s, 1H), 3.86 (br s, 2H), 3.35 (m, 4H), 2.56 (m, 4H), 2.52 (br s, 2H), 2.43 (m, 2H). LC/MS: m/z 478.02 [MH$^+$] (100), t$_R$=2.58 min (ZQ2000, polar_5 min).

EXAMPLE 164

{4-[4-(Benzothiazol-6-ylamino)-7H-pyrrolo[2,3-d]-pyrimidin-6-yl]-3,6-dihydro-2H-pyridin-1-yl}-(cis-2,6-dimethylmorpholin-4-yl)-methanone

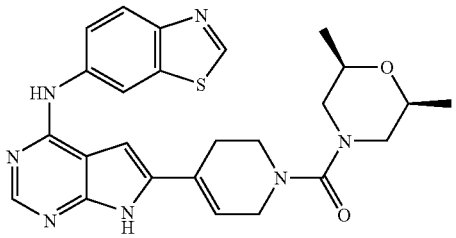

Following the general procedure, the title compound was isolated as yellow powder. $^1$H NMR (400 MHz, DMSO-d$_6$): δ=10.00 (s, 1H), 9.61 (s, 1H), 9.23 (s, 1H), 8.90 (d, 1H, J=2.0 Hz), 8.34 (s, 1H), 8.19 (s, 2H), 8.11 (d, 1H, J=8.9 Hz), 7.82 (dd, 1H, J=2.0 Hz & 8.9 Hz), 6.79 (s, 1H), 6.41 (s, 1H), 3.95 (br s, 2H), 3.45 (m, 4H), 2.54 (s, 2H), 2.49 (m, 2H), 2.08 (s, 2H), 1.08 (d, 6H, J=6.1 Hz). LC/MS: m/z 490.07 [MH$^+$] (100), t$_R$=2.52 min (ZQ2000, polar_5 min).

EXAMPLE 165

{4-[4-(Benzothiazol-6-ylamino)-7H-pyrrolo[2,3-d]-pyrimidin-6-yl]-3,6-dihydro-2H-pyridin-1-yl}-(4-hydroxypiperidin-1-yl)-methanone

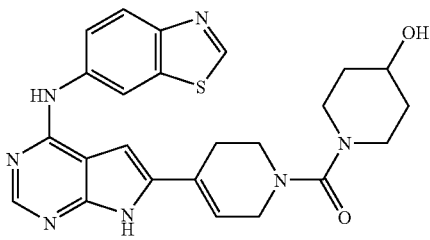

Following the general procedure, the title compound was isolated as yellow powder. $^1$H NMR (400 MHz, DMSO-d$_6$): δ=11.91 (s, 1H), 9.53 (s, 1H), 9.16 (s, 1H), 8.84 (d, 1H, J=2.0 Hz), 8.27 (s, 1H), 8.13 (s, 1H), 7.97 (d, 1H, J=8.9 Hz), 7.81 (dd, 1H, J=2.0 Hz & 8.9 Hz), 6.75 (d, 1H, J=1.8 Hz), 6.35 (s, 1H), 4.53 (br s, 1H), 3.85 (br s, 2H), 3.56 (m, 2H), 3.31 (m, 2H), 2.81 (m, 2H), 2.53 (br s, 2H), 1.67 (m, 2H), 1.28 (m, 2H). LC/MS: m/z 476.07 [MH$^+$] (100), t$_R$=2.16 min (ZQ2000, polar_5 min).

EXAMPLE 166

{4-[4-(Benzothiazol-6-ylamino)-7H-pyrrolo[2,3-d]-pyrimidin-6-yl]-3,6-dihydro-2H-pyridin-1-yl}-(3-hydroxypyrrolidin-1-yl)-methanone

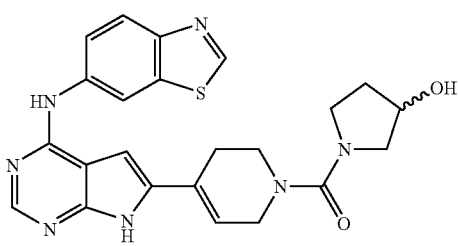

Following the general procedure, the title compound was isolated as yellow powder. $^1$H NMR (400 MHz, DMSO-d$_6$): δ=11.93 (s, 1H), 9.53 (s, 1H), 9.16 (s, 1H), 8.85 (d, 1H, J=2.0 Hz), 8.27 (s, 1H), 8.10 (s, 2H), 7.96 (d, 1H, J=8.9 Hz), 7.80 (dd, 1H, J=2.0 Hz & 8.9 Hz), 6.76 (s, 1H), 6.36 (s, 1H), 4.17 (br s, 1H), 3.86 (br s, 2H), 3.46 (m, 1H), 3.42 (m, 2H), 3.22 (m, 2H), 3.04 (d, 2H, J=10.9 Hz), 1.75 (m, 2H), 1.68 (m, 2H). LC/MS: m/z 462.04 [MH$^+$] (100), t$_R$=2.15 min (ZQ2000, polar_5 min).

EXAMPLE 167

4-[4-(Benzothiazol-6-ylamino)-7H-pyrrolo[2,3-d]-pyrimidin-6-yl]-3,6-dihydro-2H-pyridine-1-carboxylic acid diethylamide

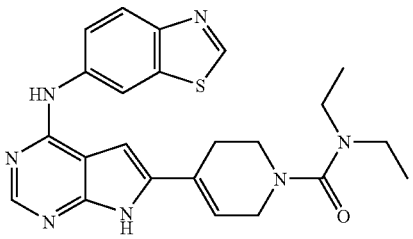

Following the general procedure, the title compound was isolated as yellow powder. $^1$H NMR (400 MHz, DMSO-d$_6$): δ=11.92 (s, 1H), 9.53 (s, 1H), 9.16 (s, 1H), 8.84 (d, 1H, J=2.0 Hz), 8.34 (s, 1H), 8.27 (s, 2H), 7.97 (d, 1H, J=8.9 Hz), 7.80 (dd, 1H, J=2.0 Hz & 8.9 Hz), 6.76 (s, 1H), 6.36 (s, 1H), 3.80 (br s, 2H), 3.31 (m, 2H), 3.08 (q, 4H, J=7.0 Hz), 2.47 (br s, 2H), 1.00 (t, 6H, J=7.0 Hz). LC/MS: m/z 448.08 [MH$^+$] (100), t$_R$=2.65 min (ZQ2000, polar_5 min).

EXAMPLE 168

Azetidin-1-yl-{4-[4-(benzothiazol-6-ylamino)-7H-pyrrolo[2,3-d]pyrimidin-6-yl]-3,6-dihydro-2H-pyridin-1-yl}-methanone

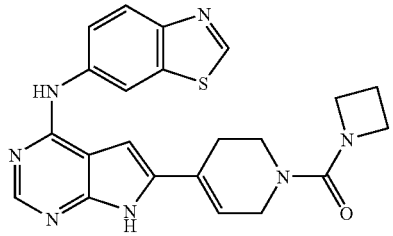

Following the general procedure, the title compound was isolated as yellow powder. $^1$H NMR (400 MHz, DMSO-d$_6$): δ=11.93 (s, 1H), 9.53 (s, 1H), 9.16 (s, 1H), 8.84 (d, 1H, J=2.0 Hz), 8.26 (s, 1H), 8.22 (s, 2H), 7.98 (d, 1H, J=8.9 Hz), 7.80 (dd, 1H, J=2.0 Hz & 8.9 Hz), 6.76 (s, 1H), 6.34 (s, 1H), 3.87 (m, 4H), 3.40 (t, 2H, J=5.6 Hz), 3.27 (br s, 2H), 2.54 (br s, 2H), 2.10 (m, 2H). LC/MS: m/z 432.03 [MH$^+$] (100), t$_R$=2.36 min (ZQ2000, polar_5 min).

EXAMPLE 169

{4-[4-(Benzothiazol-6-ylamino)-7H-pyrrolo[2,3-d]-pyrimidin-6-yl]-3,6-dihydro-2H-pyridin-1-yl}-pyrrolidin-1-ylmethanone

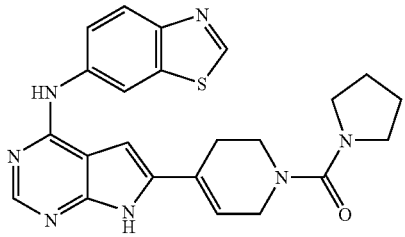

Following the general procedure, the title compound was isolated as yellow powder. $^1$H NMR (400 MHz, DMSO-d$_6$): δ=11.92 (s, 1H), 9.52 (s, 1H), 9.16 (s, 1H), 8.84 (d, 1H, J=2.0 Hz), 8.27 (s, 1H), 8.05 (s, 2H), 7.97 (d, 1H, J=8.9 Hz), 7.81 (dd, 1H, J=2.0 Hz & 8.9 Hz), 6.75 (s, 1H), 6.36 (s, 1H), 3.86 (br s, 2H), 3.36 (t, 2H, J=5.6 Hz), 3.24 (t, 4H, J=6.3 Hz), 2.52 (br s, 2H), 1.70 (m, 4H). LC/MS: m/z 446.06 [MH$^+$] (100), $t_R$=2.52 min (ZQ2000, polar__5 min).

EXAMPLE 170

{4-[4-(Benzothiazol-6-ylamino)-7H-pyrrolo[2,3-d]-pyrimidin-6-yl]-3,6-dihydro-2H-pyridin-1-yl}-(4,4-difluoropiperidin-1-yl)-methanone

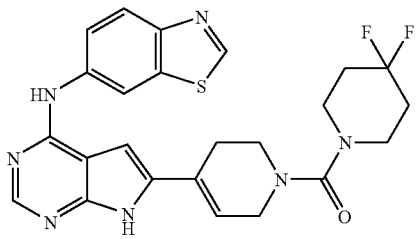

Following the general procedure, the title compound was isolated as yellow powder. $^1$H NMR (400 MHz, DMSO-d$_6$): δ=11.94 (s, 1H), 9.53 (s, 1H), 9.17 (s, 1H), 8.83 (d, 1H, J=2.0 Hz), 8.26 (s, 1H), 8.13 (s, 1H), 7.99 (d, 1H, J=8.9 Hz), 7.81 (dd, 1H, J=2.0 Hz & 8.9 Hz), 6.76 (d, 1H, J=1.8 Hz), 6.35 (s, 1H), 3.91 (br s, 2H), 3.37 (q, 2H, J=5.8 Hz), 3.22 (t, 4H, J=4.8 Hz), 2.52 (br s, 2H), 1.93 (m, 4H). LC/MS: m/z 496.02 [MH$^+$] (100), $t_R$=2.72 min (ZQ2000, polar__5 min).

EXAMPLE 171

{4-[4-(Benzothiazol-6-ylamino)-7H-pyrrolo[2,3-d]-pyrimidin-6-yl]-3,6-dihydro-2H-pyridin-1-yl}-(4-propylpiperazin-1-yl)-methanone

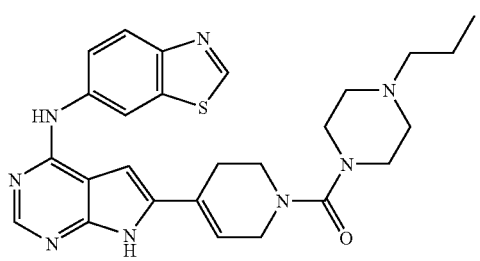

Following the general procedure, the title compound was isolated as yellow flakes. $^1$H NMR (400 MHz, DMSO-d$_6$): δ=11.92 (s, 1H), 9.53 (s, 1H), 9.16 (s, 1H), 8.84 (d, 1H, J=2.0 Hz), 8.27 (s, 1H), 8.10 (s, 2H), 7.97 (d, 1H, J=8.9 Hz), 7.80 (dd, 1H, J=2.0 Hz & 8.9 Hz), 6.76 (s, 1H), 6.34 (s, 1H), 3.86 (br s, 2H), 3.34 (m, 2H), 3.29 (m, 2H), 3.10 (br s, 4H), 2.54 (br s, 2H), 2.30 (br s, 2H), 2.18 (t, 2H, J=7.2 Hz), 1.35 (m, 2H), 0.79 (t, 3H, J=7.4 Hz). LC/MS: m/z 503.11 (65) [MH$^+$], $t_R$=1.89 (ZQ2000, polar__5 min).

EXAMPLE 172

{4-[4-(Benzothiazol-6-ylamino)-7H-pyrrolo[2,3-d]-pyrimidin-6-yl]-3,6-dihydro-2H-pyridin-1-yl}-(4-isobutylpiperazin-1-yl)-methanone

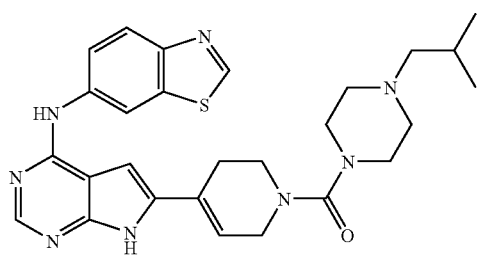

Following the general procedure, the title compound was isolated as yellow flakes. $^1$H NMR (400 MHz, DMSO-d$_6$): δ=12.02 (s, 1H), 9.76 (s, 1H), 9.35 (s, 1H), 9.07 (d, 1H, J=2.0 Hz), 8.58 (s, 1H), 8.35 (s, 1H), 8.20 (d, 1H, J=8.9 Hz), 8.04 (dd, 1H, J=2.0 Hz & 8.9 Hz), 6.91 (s, 1H), 6.57 (s, 1H), 4.10 (br s, 2H), 3.34 (m, 2H), 3.29 (m, 2H), 3.10 (br s, 4H), 2.54 (br s, 2H), 2.30 (br s, 2H), 2.21 (d, 2H, J=7.4 Hz), 1.90 (m, 1H), 1.02 (d, 6H, J=6.5 Hz). LC/MS: m/z 517.14 (30) [MH$^+$], $t_R$=1.90 (ZQ2000, polar__5 min).

EXAMPLE 173

{4-[4-(Benzothiazol-6-ylamino)-7H-pyrrolo[2,3-d]-pyrimidin-6-yl]-3,6-dihydro-2H-pyridin-1-yl}-[4-(1-ethylpropyl)-piperazin-1-yl]-methanone

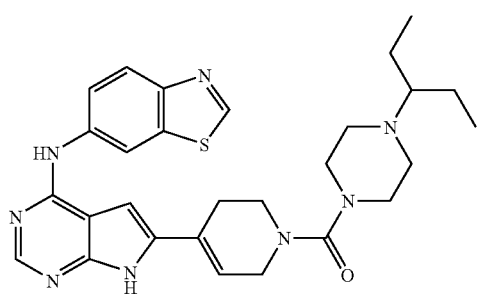

Following the general procedure, the title compound was isolated as yellow flakes. $^1$H NMR (400 MHz, DMSO-d$_6$): δ=11.92 (s, 1H), 9.53 (s, 1H), 9.16 (s, 1H), 8.84 (d, 1H, J=2.0 Hz), 8.27 (s, 1H), 8.10 (s, 1H), 7.97 (d, 1H, J=8.9 Hz), 7.80 (dd, 1H, J=2.0 Hz & 8.9 Hz), 6.76 (s, 1H), 6.34 (s, 1H), 3.86 (br s, 2H), 3.34 (m, 2H), 3.29 (m, 2H), 3.10 (br s, 4H), 2.54 (br s, 2H), 2.30 (br s, 2H), 2.36 (t, 1H, J=6.7 Hz), 1.68 (m, 2H), 1.48 (m, 2H), 1.08 (t, 6H, J=7.3 Hz). LC/MS: m/z 531.15 (35) [MH$^+$], $t_R$=1.95 (ZQ2000, polar__5 min).

EXAMPLE 174

{4-[4-(Benzothiazol-6-ylamino)-7H-pyrrolo[2,3-d]-pyrimidin-6-yl]-3,6-dihydro-2H-pyridin-1-yl}-(4-cyclobutylmethylpiperazin-1-yl)-methanone

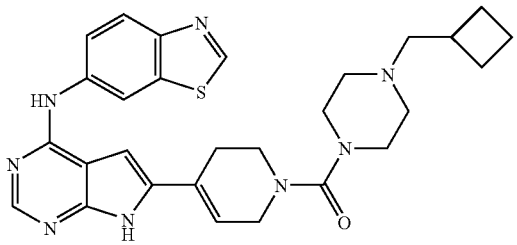

The reaction mixture derived from the preparation of {4-[4-(benzothiazol-6-ylamino)-7H-pyrrolo[2,3-d]pyrimidin-6-yl]-3,6-dihydro-2H-pyridin-1-yl}-piperazin-1-ylmethanone (EXAMPLE 154) was reacted with (bromomethyl)cyclobutane (90 mg, 5 eq.) in the presence of DIPEA at 60° C. for 72 h before the mixture was purified by HPLC, giving the title compound as yellow powder. $^1$H NMR (400 MHz, DMSO-d$_6$): δ=11.78 (s, 1H), 9.52 (s, 1H), 9.16 (s, 1H), 8.84 (d, 1H, J=2.0 Hz), 8.26 (s, 1H), 8.14 (s, 1H), 7.97 (d, 1H, J=8.9 Hz), 7.91 (s, 1H), 7.80 (dd, 1H, J=2.0 Hz & 8.9 Hz), 6.82 (d, 1H, J=1.7 Hz), 6.57 (br s, 1H), 3.94 (s, 2H), 3.46 (m, 4H), 3.36 (m, 4H), 3.18 (m, 4H), 2.54 (br s, 2H), 2.46 (m, 1H), 2.34 (m, 3H), 2.03 (m, 1H), 1.84 (m, 1H), 1.65 (m, 1H). LC/MS: m/z 529.17 (15) [MH$^+$], t$_R$=1.94 (ZQ2000, polar_5 min).

General Procedure for the Preparation of an Aminoethylurea Library Via Bromide Displacement:

To a solution of benzothiazol-6-yl-[6-(1,2,3,6-tetrahydro-pyridin-4-yl)-7H-pyrrolo[2,3-d]pyrimidin-4-yl]-amine trishydrochloride (303 mg) in DMF (8 mL) at 4° C. was added N,N-diisopropylethylamine followed by 2-bromoethyl isocyanate (100 mg). The resulting mixture was allowed to warming up to rt and left overnight. To this solution, divided into 8 aliquots, were added 10 eq. of N,N-diisopropylethylamine and 10 eq. of corresponding amine. If an amine was used as hydrochloride, additional 2 eq. of N,N-diisopropylethylamine were added. The above solutions were degassed with N$_2$ and heated at 40° C. for 72 h. The products were purified by preparative HPLC with water/acetonitrile /formic acid mixtures and are assumed to be formate salts.

EXAMPLE 175

4-[4-(Benzothiazol-6-ylamino)-7H-pyrrolo[2,3-d]-pyrimidin-6-yl]-3,6-dihydro-2H-pyridine-1-carboxylic acid (2-bromoethyl)-amide

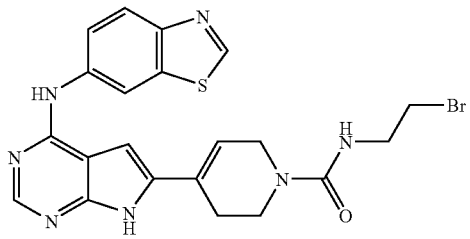

LC/MS: m/z 418.01 (40) [MH$^+$—Br], t$_R$=1.83 min (ZQ2000, polar_5 min).

EXAMPLE 176

4-[4-(Benzothiazol-6-ylamino)-7H-pyrrolo[2,3-d]-pyrimidin-6-yl]-3,6-dihydro-2H-pyridine-1-carboxylic acid[2-(4-methylpiperazin-1-yl)-ethyl]-amide

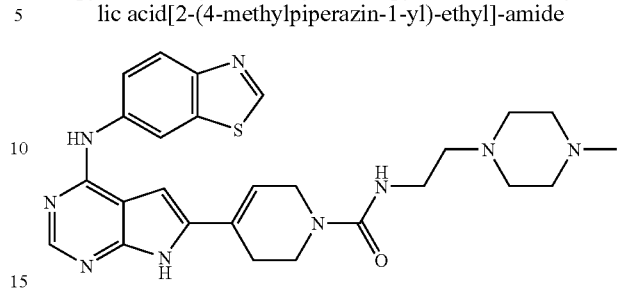

Following the general procedure, the title compound was isolated as yellow powder. $^1$H NMR (400 MHz, DMSO-d$_6$): δ=11.92 (s, 1H), 9.53 (s, 1H), 9.17 (s, 1H), 8.85 (d, 1H, J=2.0 Hz), 8.28 (s, 1H), 8.11 (s, 2H), 7.97 (d, 1H, J=8.9 Hz), 7.81 (dd, 1H, J=2.0 Hz & 8.9 Hz), 6.77 (s, 1H), 6.44 (t, 1H, J=5.3 Hz), 6.38 (s, 1H), 3.95 (br s, 4H), 3.45 (t, 4H, J=5.6 Hz), 3.11 (q, 4H, J=6.3 Hz), 2.43 (br s, 2H), 2.35 (t, 4H, J=7.1 Hz), 2.21 (s, 3H). LC/MS: m/z 518.09 [MH$^+$] (40), t$_R$=1.80 min (ZQ2000, polar_5 min).

EXAMPLE 177

4-[4-(Benzothiazol-6-ylamino)-7H-pyrrolo[2,3-d]-pyrimidin-6-yl]-3,6-dihydro-2H-pyridine-1-carboxylic acid (2-tert-butylaminoethyl)-amide

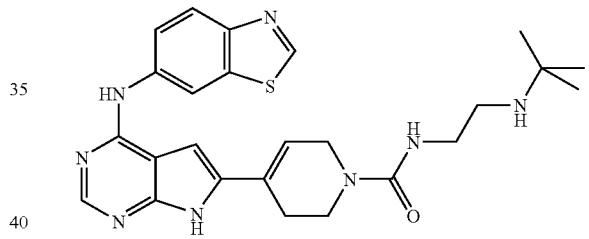

Following the general procedure, the title compound was isolated as yellow powder. $^1$H NMR (400 MHz, DMSO-d$_6$): δ=12.00 (s, 1H), 9.63 (s, 1H), 9.23 (s, 1H), 8.91 (d, 1H, J=2.0 Hz), 8.34 (s, 1H), 8.33 (s, 2H), 8.04 (d, 1H, J=8.9 Hz), 7.88 (dd, 1H, J=2.0 Hz & 8.9 Hz), 7.21 (br s, 1H), 6.85 (s, 1H), 6.45 (s, 1H), 4.06 (br s, 2H), 3.60 (m, 2H), 3.35 (q, 4H, J=5.3 Hz), 2.90 (t, 2H, J=6.1 Hz), 1.23 (s, 9H). LC/MS: m/z 491.11 [MH$^+$] (40), t$_R$=1.91 min (ZQ2000, polar_5 min).

EXAMPLE 178

4-[4-(Benzothiazol-6-ylamino)-7H-pyrrolo[2,3-d]-pyrimidin-6-yl]-3,6-dihydro-2H-pyridine-1-carboxylic acid[2-(3-hydroxypyrrolidin-1-yl)-ethyl]-amide

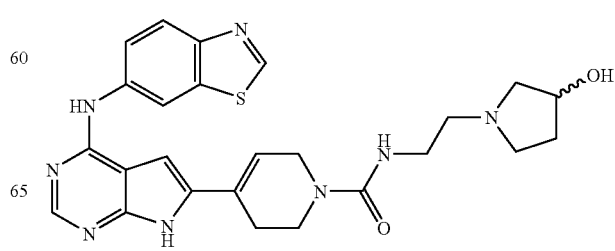

Following the general procedure, the title compound was isolated as yellow powder. $^1$H NMR (400 MHz, DMSO-$d_6$): δ=11.98 (s, 1H), 9.60 (s, 1H), 9.23 (s, 1H), 8.91 (d, 1H, J=2.0 Hz), 8.34 (s, 1H), 8.22 (s, 2H), 8.04 (d, 1H, J=8.9 Hz), 7.88 (dd, 1H, J=2.0 Hz & 8.9 Hz), 6.83 (s, 1H), 6.57 (t, 1H, J=5.3 Hz), 6.44 (s, 1H), 4.19 (m, 1H), 4.02 (br s, 2H), 3.56 (m, 1H), 3.19 (m, 2H), 2.80 (m, 1H), 2.70 (m, 1H), 2.56 (br s, 2H), 1.98 (m, 1H), 1.56 (m, 1H). LC/MS: m/z 505.07 [MH$^+$] (15), $t_R$=1.79 min (ZQ2000, polar_5 min).

EXAMPLE 179

4-[4-(Benzothiazol-6-ylamino)-7H-pyrrolo[2,3-d]-pyrimidin-6-yl]-3,6-dihydro-2H-pyridine-1-carboxylic acid (2-azepan-1-ylethyl)-amide

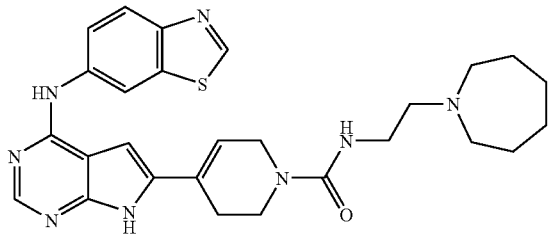

Following the general procedure, the title compound was isolated as yellow powder. $^1$H NMR (400 MHz, DMSO-$d_6$): δ=11.92 (s, 1H), 9.53 (s, 1H), 9.17 (s, 1H), 8.85 (d, 1H, J=2.0 Hz), 8.27 (s, 1H), 8.12 (s, 2H), 7.97 (d, 1H, J=8.9 Hz), 7.81 (dd, 1H, J=2.0 Hz & 8.9 Hz), 6.77 (s, 1H), 6.55 (t, 1H, J=5.0 Hz), 6.37 (s, 1H), 3.96 (br s, 2H), 3.50 (t, 2H, J=5.6 Hz), 3.15 (q, 4H, J=6.1 Hz), 2.77 (t, 4H, J=5.6 Hz), 2.67 (t, 2H, J=7.0 Hz), 1.57 (br s, 4H), 1.47 (br s, 4H). LC/MS: m/z 517.14 [MH$^+$] (40), $t_R$=1.94 min (ZQ2000, polar_5 min).

EXAMPLE 180

4-[4-(Benzothiazol-6-ylamino)-7H-pyrrolo[2,3-d]-pyrimidin-6-yl]-3,6-dihydro-2H-pyridine-1-carboxylic acid [2-(4-hydroxypiperidin-1-yl)-ethyl]-amide

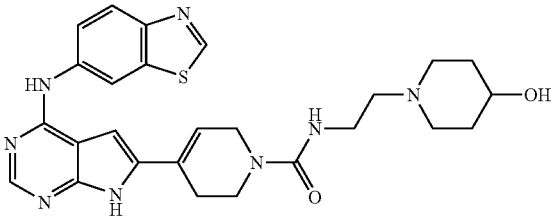

Following the general procedure, the title compound was isolated as yellow powder. $^1$H NMR (400 MHz, DMSO-$d_6$): δ=11.92 (s, 1H), 9.53 (s, 1H), 9.17 (s, 1H), 8.85 (d, 1H, J=2.0 Hz), 8.28 (s, 1H), 8.13 (s, 2H), 7.97 (d, 1H, J=8.9 Hz), 7.81 (dd, 1H, J=2.0 Hz & 8.9 Hz), 6.77 (s, 1H), 6.58 (t, 1H, J=5.0 Hz), 6.38 (s, 1H), 3.96 (br s, 2H), 3.50 (t, 4H, J=5.3 Hz), 3.17 (q, 2H, J=5.8 Hz), 2.86 (q, 2H, J=6.0 Hz), 2.55 (t, 2H, J=6.6 Hz), 2.42 (br s, 2H), 2.36 (m, 1H), 1.70 (m, 2H), 1.40 (m, 2H). LC/MS: m/z 519.14 [MH$^+$] (30), $t_R$=1.80 min (ZQ2000, polar_5 min).

EXAMPLE 181

4-[4-(Benzothiazol-6-ylamino)-7H-pyrrolo[2,3-d]-pyrimidin-6-yl]-3,6-dihydro-2H-pyridine-1-carboxylic acid [2-(4-isopropylpiperazin-1-yl)-ethyl]-amide

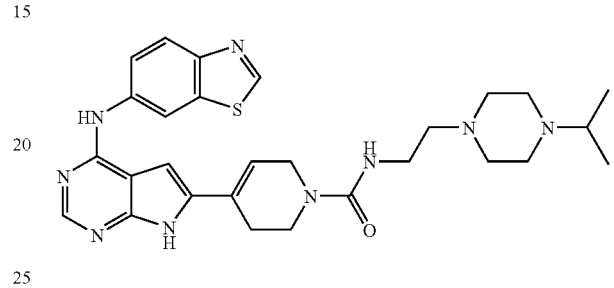

Following the general procedure, the title compound was isolated as yellow powder. $^1$H NMR (400 MHz, DMSO-$d_6$): δ=11.92 (s, 1H), 9.53 (s, 1H), 9.17 (s, 1H), 8.85 (d, 1H, J=2.0 Hz), 8.27 (s, 1H), 8.12 (s, 2H), 7.97 (d, 1H, J=8.9 Hz), 7.81 (dd, 1H, J=2.0 Hz & 8.9 Hz), 6.77 (s, 1H), 6.43 (t, 1H, J=5.3 Hz), 6.37 (s, 1H), 3.95 (br s, 4H), 3.48 (t, 4H, J=5.6 Hz), 3.12 (q, 4H, J=6.3 Hz), 2.64 (m, 1H), 2.52 (br s, 2H), 2.41 (m, 2H), 2.33 (t, 2H, J=7.3 Hz), 0.91 (d, 6H, J=6.6 Hz). LC/MS: m/z 546.20 [MH$^+$] (20), $t_R$=1.80 min (ZQ2000, polar_5 min).

EXAMPLE 182

4-[4-(Benzothiazol-6-ylamino)-7H-pyrrolo[2,3-d]-pyrimidin-6-yl]-3,6-dihydro-2H-pyridine-1-carboxylic acid [2-(4,4-difluoropiperidin-1-yl)-ethyl]-amide

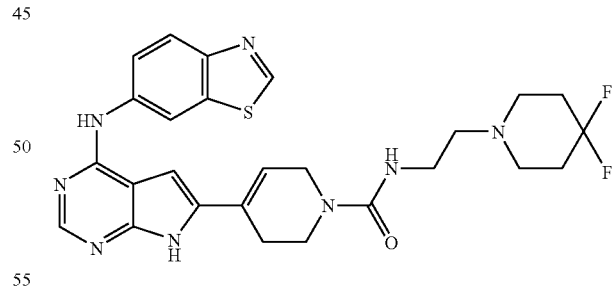

Following the general procedure, but using 4,4-difluoropiperidine hydrochloride and an additional 2 eq. of N,N-diisopropylethylamine, the title compound was isolated as yellow powder. $^1$H NMR (400 MHz, DMSO-$d_6$): δ=11.92 (s, 1H), 9.52 (s, 1H), 9.17 (s, 1H), 8.85 (d, 1H, J=2.0 Hz), 8.28 (s, 1H), 8.02 (s, 2H), 7.97 (d, 1H, J=8.9 Hz), 7.81 (dd, 1H, J=2.0 Hz & 8.9 Hz), 6.77 (s, 1H), 6.43 (t, 1H, J=5.3 Hz), 6.37 (s, 1H), 3.95 (br s, 2H), 3.49 (t, 2H, J=5.3 Hz), 3.11 (q, 4H, J=6.3 Hz), 2.52 (br s, 2H), 2.38 (t, 4H, J=7.1 Hz), 1.86 (m, 4H). LC/MS: m/z 539.08 [MH$^+$] (40), $t_R$=1.94 min (ZQ2000, polar_r5 min).

EXAMPLE 183

4-[4-(Benzothiazol-6-ylamino)-7H-pyrrolo[2,3-d]-pyrimidin-6-yl]-3,6-dihydro-2H-pyridine-1-carboxylic acid [2-(3,5-dimethylpiperazin-1-yl)-ethyl]-amide

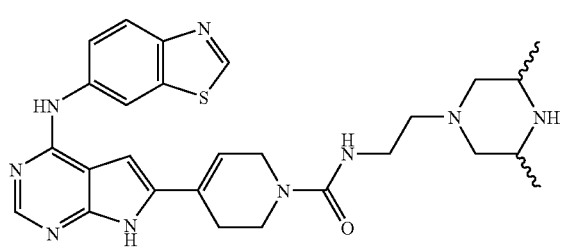

Following the general procedure, the title compound was isolated as yellow powder. $^1$H NMR (400 MHz, DMSO-$d_6$): δ=11.93 (s, 1H), 9.55 (s, 1H), 9.17 (s, 1H), 8.85 (d, 1H, J=2.0 Hz), 8.28 (s, 1H), 8.11 (s, 2H), 7.97 (d, 1H, J=8.9 Hz), 7.81 (dd, 1H, J=2.0 Hz & 8.9 Hz), 6.77 (s, 1H), 6.42 (t, 1H, J=5.2 Hz), 6.37 (s, 1H), 3.94 (br s, 2H), 3.49 (t, 2H, J=5.6 Hz), 3.11 (q, 2H, J=6.3 Hz), 3.00 (m, 2H), 2.85 (m, 2H), 2.41 (br s, 2H), 2.33 (t, 2H, J=6.8 Hz), 1.76 (t, 2H, J=11.4 Hz), 1.03 (d, 6H, J=6.3 Hz). LC/MS: m/z 532.15 [MH$^+$] (60), $t_R$=1.77 min (ZQ2000, polar_5 min).

General Procedure for 3-Aminopropyl Derivatives

To a solution of benzothiazol-6-yl-[6-(1,2,3,6-tetrahydro-pyridin-4-yl)-7H-pyrrolo[2,3-d]pyrimidin-4-yl]-amine tris-hydrochloride (65.3 mg) in DMF (4 mL) at rt were added N,N-diisopropylethylamine (5 eq.) followed by 1-chloro-3-iodopropane (30.0 mg). The resulting mixture was left at rt for 5 d. To this solution, containing benzothiazol-6-yl-{6-[1-(3-chloropropyl)-1,2,3,6-tetrahydropyridin-4-yl]-7H-pyrrolo [2,3-d]pyrimidin-4-yl}-amine, divided into 2 aliquots, were added 1 mg of KI, 5 eq. N,N-diisopropylethylamine, and 5 eq. of the corresponding amine. The above solutions were degassed with $N_2$ and heated at 60° C. for 2 d. The products were purified by preparative HPLC with water/acetonitrile/formic acid mixtures and are assumed to be formate salts.

EXAMPLE 184

Benzothiazol-6-yl-{6-[1-(3-chloropropyl)-1,2,3,6-tetrahydropyridin-4-yl]-7H-pyrrolo[2,3-d]pyrimidin-4-yl}-amine

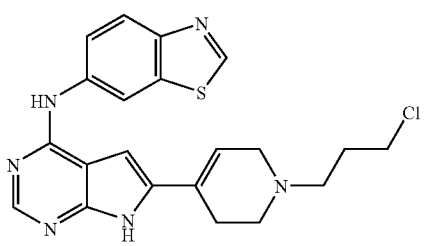

LC/MS: m/z 424.95 [MH$^+$] (20), $t_R$=1.86 min (ZQ2000, polar_5 min).

EXAMPLE 185

Benzothiazol-6-yl-(6-{1-[3-(4-methylpiperazin-1-yl)-propyl]-1,2,3,6-tetrahydropyridin-4-yl}-7H-pyrrolo[2,3-d]pyrimidin-4-yl)-amine

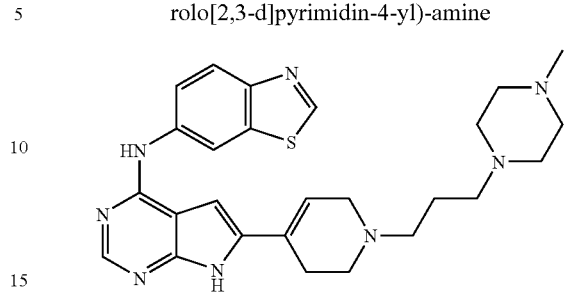

Following the general procedure, the title compound was isolated as yellow powder. $^1$H NMR (400 MHz, DMSO-$d_6$): δ=11.94 (s, 1H), 9.56 (s, 1H), 9.19 (s, 1H), 8.85 (d, 1H, J=2.0 Hz), 8.29 (s, 1H), 8.08 (s, 2H), 7.97 (d, 1H, J=8.9 Hz), 7.80 (dd, 1H, J=2.0 Hz & 8.9 Hz), 6.72 (d, 1H), 6.29 (s, 1H), 3.21 (br s, 4H), 2.81 (t, 2H, J=6.9 Hz), 2.66 (m, 4H), 2.56 (t, 2H, J=7.4 Hz), 2.52 (m, 4H), 2.36 (s, 3H), 1.69 (m, 2H). LC/MS: m/z 489.03 [MH$^+$] (20), $t_R$=1.53 min (ZQ2000, polar_5 min).

EXAMPLE 186

Benzothiazol-6-yl-{6-[1-(3-piperidin-1-ylpropyl)-1,2,3,6-tetrahydropyridin-4-yl]-7H-pyrrolo[2,3-d]pyrimidin-4-yl}-amine

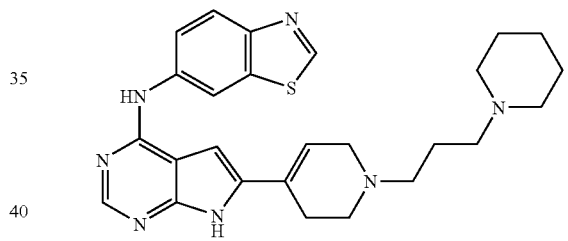

Following the general procedure, the title compound was isolated as yellow powder. $^1$H NMR (400 MHz, DMSO-$d_6$): δ=11.91 (s, 1H), 9.55 (s, 1H), 9.16 (s, 1H), 8.84 (d, 1H, J=2.0 Hz), 8.27 (s, 1H), 8.08 (s, 2H), 7.97 (d, 1H, J=8.9 Hz), 7.65 (dd, 1H, J=2.0 Hz & 8.9 Hz), 6.74 (d, 1H), 6.32 (s, 1H), 3.20 (br s, 2H), 3.03 (br s, 4H), 2.90 (t, 2H, J=7.6 Hz), 2.67 (t, 2H, J=5.6 Hz), 2.52 (m, 4H), 1.79 (m, 2H), 1.59 (m, 4H), 1.44 (m, 2H). LC/MS: m/z 474.04 [MH$^+$] (30), $t_R$=1.55 min (ZQ2000, polar_5 min).

EXAMPLE 187

4-[4-(1-Ethyl-1H-pyrazol-4-ylamino)-7H-pyrrolo[2,3-d]pyrimidin-6-yl]-3,6-dihydro-2H-pyridine-1-carboxylic acid tert-butyl ester

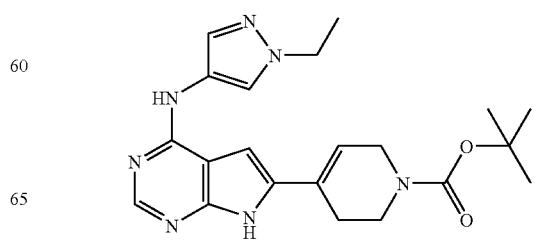

A mixture of 4-(4-chloro-7H-pyrrolo[2,3-d]pyrimidin-6-yl)-3,6-dihydro-2H-pyridine-1-carboxylic acid tert-butyl ester (110 mg, 0.33 mmol) and 1-ethyl-4-amino-1H-pyrazole (44 mg, 0.39 mmol) in 1-butanol (3 mL) was heated at 120° C. overnight, LC-MS showed the desired product and some de-Boc product. After the mixture was cooled to rt, it was diluted with methylene chloride (3 ml), then N,N-diisopropylethylamine (0.11 mL, 0.66 mmol) and di-tert-butyldicarbonate (72 mg, 0.33 mmol) were added, the resulting mixture was stirred at rt for 30 min. The mixture was diluted with EtOAc (30 mL), then washed with brine (20 mL), and dried over anhydrous sodium sulfate. The solvent was evaporated under reduced pressure, and the residue was crystallized with EtOAc to give the title compound as an off-white solid. LC-MS (ES, Pos.): 410 [MH$^+$]. $^1$H NMR (CDCl$_3$, 400 MHz): δ=1.51 (s, 9H), 1.56 (t, J=7.3 Hz, 3H), 2.50 (m, 2H), 3.66 (m, 2H), 4.16 (m, 2H), 4.22 (q, J=7.3 Hz, 2H), 6.04 (s, 1H), 6.17 (s, 1H), 6.57 (s, 1H), 7.56 (s, 1H), 7.95 (s, 1H), 8.38 (s, 1H), 10.96 (br s, 1H).

4-Amino-1-ethyl-1H-pyrazole

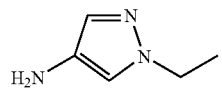

To a solution of 1-ethyl-4-nitro-1H-pyrazole (59 mg, 0.42 mmol) in ethyl acetate (2 mL) and ethanol (2 mL) was added 10% Pd—C (20 mg), and the resulting mixture was stirred under hydrogen atmosphere overnight. TLC showed the reaction was complete. The catalyst was removed by filtration through a pad of celite, and the filtrate was concentrated under reduced pressure to give the title compound as red oil. $^1$H NMR (CDCl$_3$, 400 MHz): δ=1.43 (t, J=7.3 Hz, 3H), 2.90 (br s, 2H), 4.05 (q, J=7.3 Hz, 2H), 7.02 (d, J=0.8 Hz, 1H), 7.15 (d, J=0.8 Hz, 1H).

1-Ethyl-4-nitro-1H-pyrazole

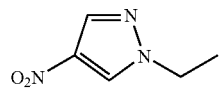

To a solution of 4-nitro-1H-pyrazole (226 mg, 2.0 mmol) in N,N-dimethylformamide (3 mL) were added potassium carbonate (0.33 g, 2.4 mmol) and iodoethane (0.37 g, 2.4 mmol). The resulting mixture was stirred at rt overnight. TLC showed the reaction was complete. The mixture was diluted with EtOAc (40 mL), then washed with water (2×20 mL), brine (20 mL), and dried over anhydrous sodium sulfate. The crude material was purified by chromatography on silica gel, eluting with Hex:EtOAc=70:30 to give the title compound as a white solid. $^1$H NMR (CDCl$_3$, 400 MHz): δ=1.55 (t, J=7.3 Hz, 3H), 4.22 (q, J=7.3 Hz, 2H), 8.07 (s, 1H), 8.14 (s, 1H).

EXAMPLE 188

4-[4-(1-Phenethyl-1H-pyrazol-3-ylamino)-7H-pyrrolo[2,3-d]pyrimidin-6-yl]-3,6-dihydro-2H-pyridine-1-carboxylic acid tert-butyl ester

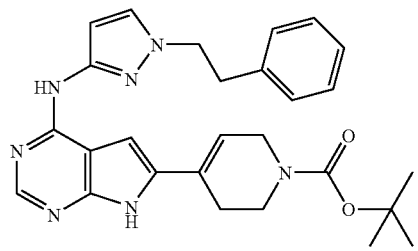

A mixture of 4-(4-chloro-7H-pyrrolo[2,3-d]pyrimidin-6-yl)-3,6-dihydro-2H-pyridine-1-carboxylic acid tert-butyl ester (110 mg, 0.33 mmol) and 3-amino-1-phenethyl-1H-pyrazole (74 mg, 0.39 mmol) in 1-butanol (3 mL) was heated at 120° C. overnight, LC-MS showed the reaction was complete. The mixture was concentrated, then dissolved in MeOH-DMSO, and purified by MSDP (using water/acetonitrile/HCOOH mixtures) to give the title compound as a brown solid. LC-MS (ES, Pos.): 486 [MH$^+$]. $^1$H NMR (CD$_3$OD, 400 MHz): δ=1.49 (s, 9H), 2.54 (m, 2H), 3.16 (t, J=7.1 Hz, 2H), 3.65 (m, 2H), 4.12 (m, 2H), 4.32 (t, J=7.1 Hz, 2H), 6.27 (s, 1H), 6.48 (d, J=2.3 Hz, 1H), 6.53 (s, 1H), 7.14-7.28 (m, 5H), 7.36 (d, J=2.3 Hz, 1H), 8.21 (s, 1H).

3-Amino-1-phenethyl-1H-pyrazole

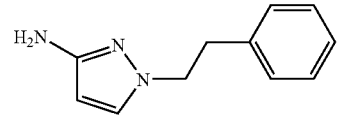

To a solution of 3-nitro-1-phenethyl-1H-pyrazole (90 mg, 0.41 mmol) in ethyl acetate (2 mL) and ethanol (2 mL) was added 10% Pd—C (20 mg), the resulting mixture was stirred under hydrogen atmosphere overnight. TLC showed the reaction was complete. The catalyst was removed by filtration through a pad of celite, and the filtrate was concentrated under reduced pressure to give the title compound as colorless oil. LC-MS (ES, Pos.): 188 [MH$^+$]. $^1$H NMR (CDCl$_3$, 400 MHz): δ=3.10 (t, J=7.2 Hz, 2H), 3.64 (br s, 2H), 4.12 (t, J=7.2 Hz, 2H), 5.51 (d, J=2.3 Hz, 1H), 6.91 (d, J=2.3 Hz, 1H), 7.08-7.11 (m, 2H), 7.20-7.30 (m, 3H).

3-Nitro-1-phenethyl-1H-pyrazole

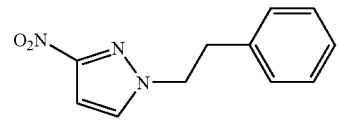

To a solution of 3-nitro-1H-pyrazole (226 mg, 2.0 mmol) in N,N-dimethylformamide (3 mL) were added potassium carbonate (0.33 g, 2.4 mmol) and 1-bromo-2-phenylethane (0.44 g, 2.4 mmol). The resulting mixture was stirred at rt overnight. TLC showed the reaction was complete. The mixture was diluted with EtOAc (40 mL), then washed with water (2×20 mL), brine (20 mL), and dried over anhydrous sodium sulfate. The crude material was purified by chromatography on silica gel, eluting with Hex:EtOAc=80:20→70:30 to give the title compound as a white solid. NOE experiment confirmed the structure. $^1$H NMR (CDCl$_3$, 400 MHz): δ=3.22 (t, J=7.1 Hz, 2H), 4.43 (t, J=7.1 Hz, 2H), 6.79 (d, J=2.5 Hz, 1H), 7.06-7.09 (m, 2H), 7.12 (d, J=2.5 Hz, 1H), 7.23-7.32 (m, 3H).

3-Nitro-1H-pyrazole

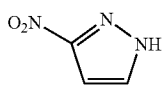

[Ref.: Janssen, J. W. A. M. and Habraken, C. L., *J. Org. Chem.*, 1971, 36, 3081.] A solution of 1-nitro-1H-pyrazole (3.0 g, 0.026 mol) in anisole (200 mL) was heated at 145° C. overnight. The mixture was cooled to rt, the white solid was collected by filtration and washed with hexanes. The mother liquid was diluted with hexanes (500 mL) and cooled to −20° C., and the resulting off-white solid was collected and combined with the previous solid. LC-MS (ES, Pos.): 114 [MH$^+$]. $^1$H NMR (DMSO-d$_6$, 400 MHz): δ=7.04 (d, J=2.5 Hz, 1H), 8.04 (d, J=2.5 Hz, 1H), 13.96 (br s, 1H).

EXAMPLE 189

4-[4-(1-Phenethyl-1H-pyrazol-4-ylamino)-7H-pyrrolo[2,3-d]pyrimidin-6-yl]-3,6-dihydro-2H-pyridine-1-carboxylic acid tert-butyl ester

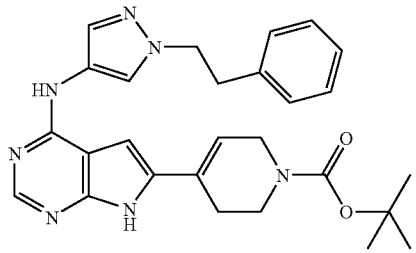

A mixture of 4-(4-chloro-7H-pyrrolo[2,3-d]pyrimidin-6-yl)-3,6-dihydro-2H-pyridine-1-carboxylic acid tert-butyl ester (110 mg, 0.33 mmol) and 4-amino-1-phenethyl-1H-pyrazole (74 mg, 0.39 mmol) in 1-butanol (3 mL) was heated at 120° C. overnight, LC-MS showed the desired product and some de-Boc product (ca. 1:1 ratio). After the mixture was cooled to rt, it was diluted with methylene chloride (3 mL), then N,N-diisopropylethylamine (0.11 mL, 0.66 mmol) and di-tert-butyldicarbonate (72 mg, 0.33 mmol) were added, the resulting mixture was stirred at rt for 30 min. The mixture was diluted with EtOAc (30 mL), then washed with brine (20 mL), and dried over anhydrous sodium sulfate. The solvent was evaporated under reduced pressure, and the residue was crystallized with EtOAc to give the title compound as an off-white solid. LC-MS (ES, Pos.): 486 [MH$^+$]. $^1$H NMR (CDCl$_3$, 400 MHz): δ=1.50 (s, 9H), 2.50 (m, 2H), 3.23 (t, J=7.3 Hz, 2H), 3.66 (m, 2H), 4.17 (m, 2H), 4.38 (t, J=7.3 Hz, 2H), 6.08 (s, 1H), 6.17 (s, 1H), 6.55 (s, 1H), 7.17-7.32 (m, 5H), 7.60 (s, 1H), 7.80 (s, 1H), 8.37 (s, 1H), 10.99 (br s, 1H).

4-Amino-1-phenethyl-1H-pyrazole

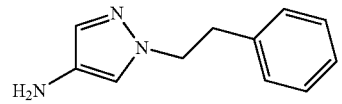

To a solution of 4-nitro-1-phenethyl-1H-pyrazole (90 mg, 0.41 mmol) in ethyl acetate (2 mL) and ethanol (2 mL) was added 10% Pd—C (20 mg), and the resulting mixture was stirred under hydrogen atmosphere overnight. TLC showed the reaction was complete. The catalyst was removed by filtration through a pad of celite, and the filtrate was concentrated under reduced pressure to give the title compound as red oil. $^1$H NMR (CDCl$_3$, 400 MHz): δ=2.36 (br s, 2H), 3.11 (t, J=7.5 Hz, 2H), 4.21 (t, J=7.5 Hz, 2H), 6.83 (d, J=0.8 Hz, 1H), 7.10-7.12 (m, 2H), 7.18 (d, J=0.8 Hz, 1H), 7.20-7.28 (m, 3H).

4-Nitro-1-phenethyl-1H-pyrazole

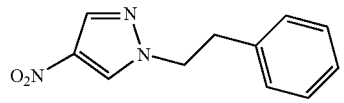

To a solution of 4-nitro-1H-pyrazole (226 mg, 2.0 mmol) in N,N-dimethylformamide (3 mL) were added potassium carbonate (0.33 g, 2.4 mmol) and 1-bromo-2-phenylethane (0.44 g, 2.4 mmol). The resulting mixture was stirred at rt overnight. TLC showed the reaction was complete. The mixture was diluted with EtOAc (40 mL), then washed with water (2×20 mL), brine (20 mL), and dried over anhydrous sodium sulfate. The crude material was purified by chromatography on silica gel, eluting with Hex:EtOAc=80:20→70:30 to give the title compound as a white solid. $^1$H NMR (CDCl$_3$, 400 MHz): δ=3.20 (t, J=7.0 Hz, 2H), 4.37 (t, J=7.0 Hz, 2H), 7.04-7.07 (m, 2H), 7.25-7.32 (m, 3H), 7.81 (s, 1H), 8.09 (s, 1H).

4-Nitro-1H-pyrazole

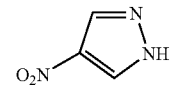

[Ref: Huettel, R. and Buechele, F., *Chem. Ber.* 1955, 88, 1586-1590] 1-Nitro-1H-pyrazole (2.2 g, 0.019 mol) was dissolved in sulfuric acid (10 mL) at −10° C., and the resulting mixture was slowly warmed to rt overnight. The solution was added to ice (100 g) dropwise, and the resulting white solid was collected by filtration and washed with water. The aqueous phase was extracted with EtOAc (3×30 mL), the combined organic phases were washed with brine (2×30 mL), and dried over anhydrous sodium sulfate. Evaporation under reduced pressure provided an off-white solid, which was combined with the first solid and dried in vacuo to provide the title compound. LC-MS (ES, Pos.): 114 [MH⁺]. ¹H NMR (DMSO-d₆, 400 MHz): δ=8.27 (s, 1H), 8.90 (s, 1H), 13.96 (br s, 1H).

EXAMPLE 190

4-[4-(Biphenyl-3-ylamino)-7H-pyrrolo[2,3-d]pyrimidin-6-yl]-3,6-dihydro-2H-pyridine-1-carboxylic acid tert-butyl ester

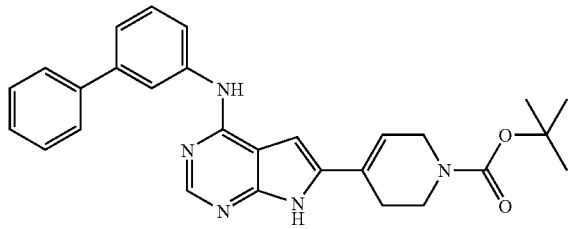

A mixture of 4-(4-chloro-7H-pyrrolo[2,3-d]pyrimidin-6-yl)-3,6-dihydro-2H-pyridine-1-carboxylic acid tert-butyl ester (60.0 mg, 0.179 mmol) and biphenyl-3-ylamine (30.5 mmol, 0.180 mmol) in nBuOH (3 mL) was heated to 80° C. (bath temp.) for 17 h. The solvent was evaporated, water/NaHCO₃ solution was added, the mixture was extracted with CH₂Cl₂ (3×20 mL), and the combined extracts were washed with brine and dried over MgSO₄. MgSO₄ was filtered off, the filtrate was concentrated, and the residue was chromatographed on silica gel [Jones Flashmaster, 5 g/25 mL cartridge, eluting with CH₂Cl₂ (1-9)→1% MeOH in CH₂Cl₂ (10-19) →2% MeOH in CH₂Cl₂ (20-30)]. Fr.17-26 were combined and dried in vacuo overnight. One obtained the title compound as off-white solid. MS (ES+): m/z 468.1 (100) [MH⁺]. HPLC: t_R=3.2 min (ZQ2000, nonpolar_5 min). ¹H NMR (CDCl₃, 400 MHz): δ=1.50 (s, 9H), 2.44-2.55 (brs, 2H), 3.61-3.71 (m, 2H), 4.13-4.22 (m, 2H), 6.15 (s, 1H), 6.24 (s, 1H), 7.11 (brs, 1H), 7.37 (t, J=7.4 Hz, 1H), 7.40-7.52 (m, 4H), 7.60-7.67 (m, 3H), 7.80 (t, J=1.6 Hz, 1H), 8.43 (s, 1H), 11.83 (brs, 1H).

EXAMPLE 191

4-[4-(3-Chloro-1H-indazol-5-ylamino)-7H-pyrrolo[2,3-d]pyrimidin-6-yl]-3,6-dihydro-2H-pyridine-1-carboxylic acid tert-butyl ester

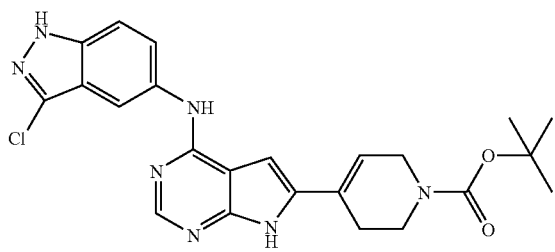

A mixture of 4-(4-chloro-7H-pyrrolo[2,3-d]pyrimidin-6-yl)-3,6-dihydro-2H-pyridine-1-carboxylic acid tert-butyl ester (49.6 mg, 0.148 mmol) and 5-amino-3-chloroindazole (26.5 mg, 0.155 mmol) in isopropyl alcohol (2.5 mL, 0.033 mol) in a sealed tube was heated to 90° C. (bath temp.) for 3.5 h. The bath temperature was increased to 105° C., and heating was continued overnight. The bath temperature was increased to 120° C., and heating was continued for 5 d. LC/MS at that time indicated loss of Boc group, i.e., (3-chloro-1H-indazol-5-yl)-[6-(1,2,3,6-tetrahydropyridin-4-yl)-7H-pyrrolo[2,3-d]pyrimidin-4-yl]-amine, C₁₈H₁₆ClN₇, MW=365.83. Solvents were evaporated. The reddish residue was suspended in N,N-dimethylformamide (3 mL). N,N-diisopropylethylamine (52 µL, 0.30 mmol) and di-tert-butyldicarbonate (33 mg, 0.15 mmol) were added, and the mixture was stirred at rt for 2 h. DMF was evaporated, water and CH₂Cl₂ were added, and the insoluble brown material was filtered off and washed with CH₂Cl₂ and water. The layers of the filtrate were separated; the organic layer was washed with water (2×) and brine and dried over MgSO₄. The drying agent was filtered off, and the filtrate was concentrated, redissolved in MeOH, passed a through 0.45 µm filter, and purified by MDP. One obtained the title compound as light tan solid. MS (ES+): m/z 465.9/467.9 (100/38) [MH⁺]. HPLC: t_R=2.7 min (ZQ2000, polar_5 min). ¹H NMR (DMSO-d₆, 400 MHz): δ=1.43 (s, 9H), 2.37-2.44 (brs, 2H), 3.51-3.58 (m_c, 2H), 3.99-4.07 (m, 2H), 6.36 (s, 1H), 6.54 (s, 1H), 7.49 (d, J=8.8 Hz, 1H), 7.55 (d, J=8.8 Hz, 1H), 8.05 (s, 1H), 8.12 (s, 1H), 9.21 (s, 1H), 11.88 (brs, 1H), 13.43 (brs, 1H).

Alternative synthesis: To a suspension of (3-chloro-1H-indazol-5-yl)-[6-(1,2,3,6-tetrahydropyridin-4-yl)-7H-pyrrolo[2,3-d]pyrimidin-4-yl]-amine trifluoroacetate (179.8 mg, 0.2457 mmol, 1 eq) and di-tert-butyldicarbonate (63.1 mg, 0.286 mmol, 1.16 eq) in anhydrous DCM (3 mL), Hünig's base (300 µL, 2 mmol, 7 eq) was added. Addition of anhydrous DMF (1 mL) aided solubility. The reaction was stirred at rt for 2 h and concentrated in vacuo. The crude material was adsorbed onto Hydromatrix, dry loaded, and purified by chromatography on silica gel [Jones Flashmaster, 10 g/70 mL cartridge, eluting with MeOH:DCM 1%→2%→5%→7%]. Fractions 35-53 were combined and concentrated in vacuo. The material was purified on the Mass Directed Purification System (MDPS), yielding the title compound as a white solid. ¹H NMR (400 MHz, MeOH-d₄): δ=1.50 (s, 9H), 2.49 (s, br, 2H), 3.64 (s, br, 2H), 4.12 (s, br, 2H), 6.27 (s, br, 1H), 6.39 (s, br, 1H), 7.56 (s, 2H), 8.06 (s, 1H), 8.14 (s, 1H). MS (ES+): m/z 465.95/467.97 [MH⁺]. HPLC: t_R=2.67 min (ZQ2000, polar_5 min).

(3-Chloro-1H-indazol-5-yl)-[6-(1,2,3,6-tetrahydropyridin-4-yl)-7H-pyrrolo[2,3-d]pyrimidin-4-yl]-amine trifluoroacetate

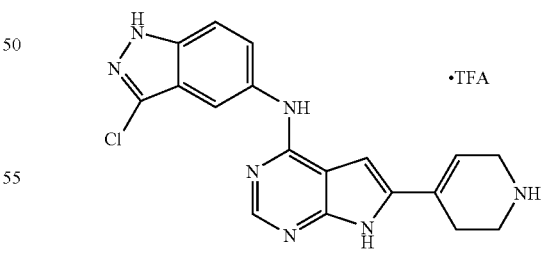

Into a 10 mL sealed tube, to a suspension/solution of 4-(4-chloro-7H-pyrrolo[2,3-d]pyrimidin-6-yl)-3,6-dihydro-2H-pyridine-1-carboxylic acid tert-butyl ester (85.3 mg, 0.229 mmol, 1 eq) and 5-amino-3-chloroindazole (3) (43.3 mg, 0.258 mmol, 1.13 eq) in 2,2,2-trifluoroethanol (TFE) (6 mL), trifluoroacetic acid (TFA) (88 µL, 1.1 mmol, 5 eq) was added and the reaction was allowed to stir for 5 d at 100° C. The reaction was cooled to rt and concentrated under reduced pressure. Purification of the crude material most likely to have been problematic-N-BOC protection carried out for easier purification by chromatography on silica gel. MS (ES+): m/z 365.98/367.98 (30/10) [MH⁺]. HPLC: $t_R$=0.48 & 1.57 min (ZQ2000, polar__5 min).

5-amino-3-chloroindazole

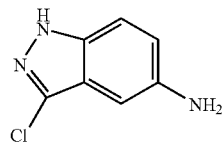

A mixture of 5-aminoindazole (1.373 g, 10.00 mmol) and N-chlorosuccinimide (1.381 g, 10.14 mmol) in methylene chloride (50 mL) was sonicated at rt for 30 min. The brown mixture was then stirred overnight at rt. The suspension was diluted with CH₂Cl₂ to ≈100 mL, water and aq. K₂CO₃ solution were added, and the insoluble brown material was filtered off and washed with CH₂Cl₂ and water. The layers of the filtrate were separated; the organic layer was washed with water (3×) and brine and dried over MgSO₄. The dried solution was filtered through a pad of silica gel, washing with 5% MeOH in CH₂Cl₂ until no more product eluted as indicated by TLC. Concentrating and drying in vacuo gave the title compound as yellow solid. MS (ES+): m/z 168.2/170.2 (100/37) [MH⁺]. HPLC: $t_R$=2.1 min (ZQ2000, polar__5 min). ¹H NMR (CDCl₃, 400 MHz): δ=5.06 (s, 2H), 6.96 (d, J=8.5 Hz, 1H), 7.27 (d, J=8.5 Hz, 1H), 7.78 (s, 1H), 12.95 (brs, 1H).

EXAMPLE 192

1-{4-[4-(3-Chloro-1H-indazol-5-ylamino)-7H-pyrrolo[2,3-d]pyrimidin-6-yl]-3,6-dihydro-2H-pyridin-1-yl}-3-piperidin-1-yl-propan-1-one

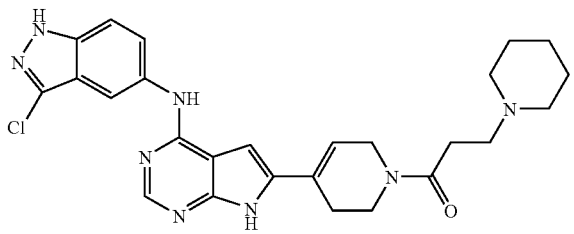

To a suspension of (3-chloro-1H-indazol-5-yl)-[6-(1,2,3,6-tetrahydropyridin-4-yl)-7H-pyrrolo[2,3-d]pyrimidin-4-yl]-amine tris-hydrochloride (46.9 mg, 0.0967 mmol, 1 eq), 1-piperidinepropanoic acid (40.5 mg, 0.255 mmol, 2.6 eq), N-(3-dimethylaminopropyl)-N'-ethylcarbodiimide hydrochloride (EDC) (56.2 mg, 0.293 mmol, 3 eq), and 1-hydroxybenzotriazole (HOBt) (13.9 mg, 0.103 mmol, 1 eq) in anhydrous DMF (5 mL), DiPEA (85 µL, 0.48 mmol, 5 eq) was added under an atmosphere of N₂ The reaction was stirred at rt for 18 h, after which all solvent was evaporated under reduced pressure. The crude material was adsorbed onto Hydromatrix, dry loaded, and purified by chromatography on silica gel [Jones Flashmaster, 5 g/25 mL cartridge, eluting with MeOH:DCM 5%→7N NH₃/MeOH:DCM 2%→5%→8%→15%]. Fractions 25-39 were combined and concentrated in vacuo, yielding the desired amide, but which contained a considerable amount of 1-(3-dimethylaminopropyl)-3-ethylurea. The yellow solid was triturated in hot MeOH/sonication, giving the title compound as an off-white solid. ¹H NMR (400 MHz, CDCl₃): δ=1.26 (s, br, 2H), 1.63 (m, 4H), 2.37-2.56 (m, 6H), 2.56-2.68 (m, 2H), 2.68-2.80 (m, 2H), 3.68 & 3.76 (t, J=5.6 Hz, rotamers, 2H), 4.22 & 4.25 (s, br, rotamers, 2H), 5.92 & 5.98 (s, rotamers, 1H), 6.18 & 6.22 (s, br, rotamers, 1H), 7.49 (d, J=8.8 Hz, 1H), 7.79 (dd, J=8.8, 1.6 Hz, 1H), 8.13 (s, 1H), 8.26 (s, 1H). MS (ES+): m/z 505.00/506.99 (27/10) [MH⁺]; m/z 407.96/409.98 (100/36) [MH⁺—C₆H₁₄N]. HPLC: $t_R$=1.75 min (ZQ2000, polar__5 min).

(3-Chloro-1H-indazol-5-yl)-[6-(1,2,3,6-tetrahydropyridin-4-yl)-7H-pyrrolo[2,3-d]pyrimidin-4-yl]-amine tris-hydrochloride

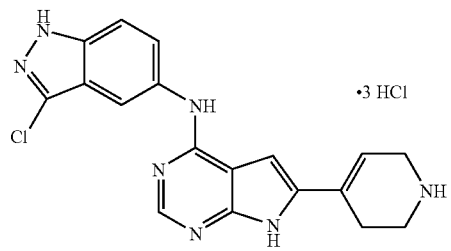

A suspension of 4-[4-(3-chloro-1H-indazol-5-ylamino)-7H-pyrrolo[2,3-d]pyrimidin-6-yl]-3,6-dihydro-2H-pyridine-1-carboxylic acid tert-butyl ester (45.4 mg, 0.0945 mmol, 1 eq) in 4.0 M of HCl in 1,4-dioxane (3.25 mL, 140 eq) was allowed to stir at rt for 2 h. The reaction was concentrated in vacuo to dryness, affording the title compound, as a yellow solid. ¹H NMR (400 MHz, MeOH-d₄): δ=2.83 (s, br, 2H), 3.52 (t, J=6.0 Hz, 2H), 3.95 (s, br, 2H), 6.44 (s, 1H), 6.83 (s, br, 1H), 7.56 (d, J=8.8 Hz, 1H), 7.75 (dd, J=8.8, 0.8 Hz, 1H), 8.19 (s, 1H), 8.28 (d, J=0.8 Hz, 1H). MS (ES+): m/z 365.98/368.00 (20/8) [MH⁺]. HPLC: $t_R$=0.48 & 1.56 min (ZQ2000, polar__5 min).

General Procedure for Preparation of a 3,6-dihydro-2H-pyridin-1-yl-Ethanone Library:

To a solution of benzothiazol-6-yl-[6-(1,2,3,6-tetrahydropyridin-4-yl)-7H-pyrrolo[2,3-d]pyrimidin-4-yl]-amine tris-hydrochloride (525 mg, 1.15 mmol) in DMF (12 mL) and dichloromethane (1 mL) at 4° C. was added N,N-diisopropylethylamine (0.7 g, 6.0 mmol) followed by chloroacetyl chloride (130 mg, 1.15 mmol). The resulting solution was allowed to warm up to rt and stirred overnight. This solution containing 1-{4-[4-(benzothiazol-6-ylamino)-7H-pyrrolo[2,3-d]pyrimidin-6-yl]-3,6-dihydro-2H-pyridin-1-yl}-2-chloroethanone was divided into 13 aliquots to synthesize a 13-membered library, and 1 mg of KI, 5 eq. DIPEA, and 5 eq. of the amines were added. If the amines were used as salts, additional DIPEA was used. The above solutions were degassed with N₂ and heated at 50° C. for 12 h. The products were purified by preparative HPLC with water/acetonitrile/formic acid mixtures and are assumed to be formate salts.

EXAMPLE 193

1-{4-[4-(Benzothiazol-6-ylamino)-7H-pyrrolo[2,3-d]-pyrimidin-6-yl]-3,6-dihydro-2H-pyridin-1-yl}-2-chloroethanone

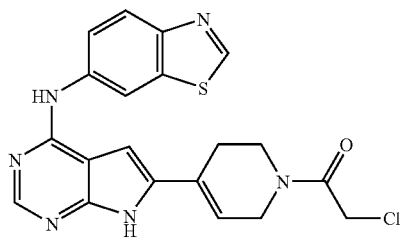

MS: m/z 424.9/426.9 (100/45) [MH$^+$]; HPLC: t$_R$=2.45 min (ZQ2000, polar__5 min).

EXAMPLE 194

1-{4-[4-(Benzothiazol-6-ylamino)-7H-pyrrolo[2,3-d]-pyrimidin-6-yl]-3,6-dihydro-2H-pyridin-1-yl}-2-(4-methylpiperazin-1-yl)-ethanone

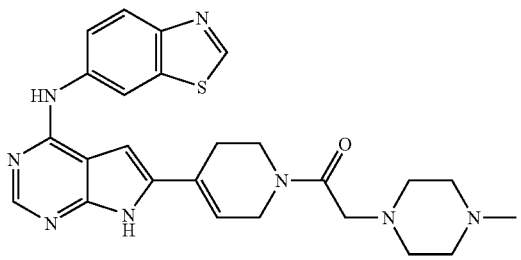

Following the general procedure, the title compound was isolated as yellow powder. $^1$H NMR (400 MHz, DMSO-d$_6$): δ=11.96 (d, 1H, J=10.3 Hz), 9.55 (br s, 1H), 9.17 (s, 1H), 8.85 (d, 1H, J=2.0 Hz), 8.27 (s, 1H), 8.12 (s, 2H), 7.97 (d, 1H, J=8.9 Hz), 7.80 (dd, 1H, J=2.1 Hz & 8.9 Hz), 6.78 (1H, d), 6.37 (s, 1H), 4.25 (s, 1H), 4.08 (s, 2H), 3.68 (t, 1H, J=5.4 Hz), 3.64 (t, 1H, J=5.4 Hz), 3.18 (d, 2H, J=6.4 Hz), 2.53 (br s, 2H), 2.41 (m, 7H), 2.16 (s, 3H). MS: m/z 489.04 (35) [MH$^+$]. HPLC: t$_R$=1.81 min (ZQ2000, polar__5 min).

EXAMPLE 195

1-{4-[4-(Benzothiazol-6-ylamino)-7H-pyrrolo[2,3-d]-pyrimidin-6-yl]-3,6-dihydro-2H-pyridin-1-yl}-2-pyrrolidin-1-ylethanone

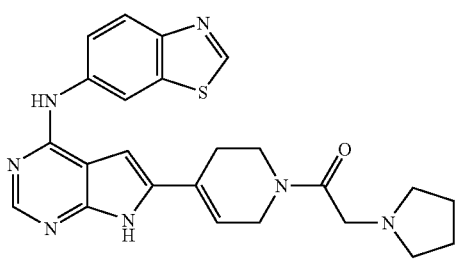

Following the general procedure, the title compound was isolated as yellow powder. $^1$H NMR (400 MHz, DMSO-d$_6$): δ=11.96 (d, 1H, J=17.2 Hz), 9.55 (d, 1H, J=5.3 Hz), 9.17 (s, 1H), 8.90 (s, 1H), 8.26 (s, 1H), 8.13 (s, 2H), 7.97 (d, 1H, J=8.9 Hz), 7.80 (d, 1H, J=8.9 Hz), 6.78 (d, 1H, J=8.9 Hz), 6.37 (d, 1H, J=3.1 Hz), 4.21 (s, 1H), 4.09 (s, 1H), 3.66 (t, 2H, J=5.4 Hz), 3.48 (d, 2H, J=6.2 Hz), 2.60 (m, 5H), 2.51 (br s, 1H), 1.68 (d, 4H, J=2.5 Hz). MS: m/z 460.02 (70) [MH$^+$]. HPLC: t$_R$=1.82 min (ZQ2000, polar__5 min).

EXAMPLE 196

1-{4-[4-(Benzothiazol-6-ylamino)-7H-pyrrolo[2,3-d]-pyrimidin-6-yl]-3,6-dihydro-2H-pyridin-1-yl}-2-diethylaminoethanone

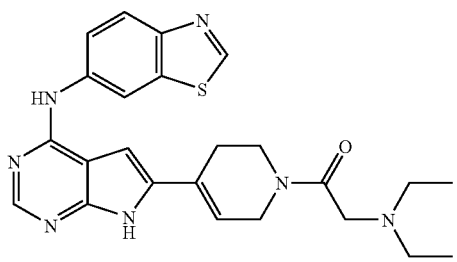

Following the general procedure, the title compound was isolated as yellow powder. $^1$H NMR (400 MHz, DMSO-d$_6$): δ=11.98 (d, 1H, J=15.8 Hz), 9.54 (d, 1H, J=12.7 Hz), 9.18 (s, 1H), 8.85 (d, 1H, J=2.0 Hz), 8.24 (s, 1H), 8.12 (s, 2H), 7.97 (d, 1H, J=8.9 Hz), 7.82 (d, 1H, J=8.9 Hz), 6.79 (d, 1H), 6.34 (s, 1H), 4.27 (s, 1H), 4.15 (s, 1H), 3.68 (m, 2H), 3.46 (d, 2H, J=11.1 Hz), 2.53 (m, 6H), 0.96 (t, 6H, J=7.1 Hz). MS: m/z 462.04 (80) [MH$^+$]. HPLC: t$_R$=1.84 min (ZQ2000, polar__5 min).

EXAMPLE 197

1-{4-[4-(Benzothiazol-6-ylamino)-7H-pyrrolo[2,3-d]-pyrimidin-6-yl]-3,6-dihydro-2H-pyridin-1-yl}-2-piperidin-1-ylethanone

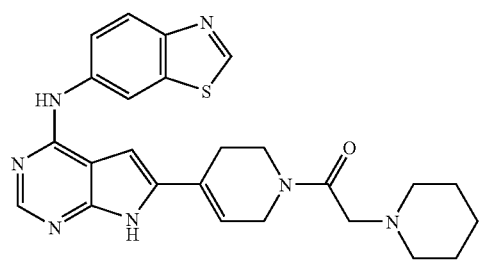

Following the general procedure, the title compound was isolated as yellow powder. $^1$H NMR (400 MHz, DMSO-d$_6$): δ=11.95 (d, 1H, J=19.3 Hz), 9.50 (br s, 1H), 9.13 (s, 1H), 8.81 (s, 1H, J=2.0 Hz), 8.21 (s, 1H), 8.08 (d, 2H), 8.00 (d, 1H, J=8.9 Hz), 7.78 (dd, 1H, J=2.0 Hz & 8.9 Hz), 6.75 (s, 1H), 6.34 (s, 1H), 4.22 (s, 1H), 4.04 (s, 1H), 3.65 (t, 1H, J=5.3 Hz), 3.60 (t, 1H, J=5.3 Hz), 3.17 (d, 2H, J=7.9 Hz), 2.51 (br s, 1H), 2.36 (m, 4H), 1.42 (m, 3H), 1.29 (m, 2H), 1.07 (d, 2H, J=6.6 Hz). MS: m/z 474.04 (100) [MH$^+$]. HPLC: t$_R$=1.86 min (ZQ2000, polar__5 min).

EXAMPLE 198

1-{4-[4-(Benzothiazol-6-ylamino)-7H-pyrrolo[2,3-d]-pyrimidin-6-yl]-3,6-dihydro-2H-pyridin-1-yl}-2-tert-butylaminoethanone

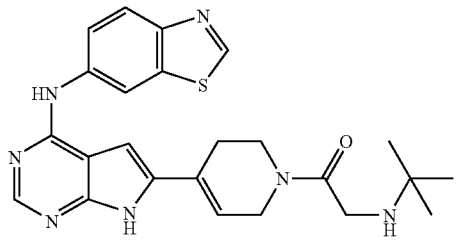

Following the general procedure, the title compound was isolated as yellow powder. $^1$H NMR (400 MHz, DMSO-$d_6$): δ=11.99 (d, 1H, J=19.2 Hz), 9.63 (s, 1H), 9.17 (s, 1H), 8.84 (t, 1H), 8.27 (d, 1H, J=2.7 Hz), 8.17 (s, 2H), 8.00 (d, 1H, J=8.8 Hz), 7.81 (dd, 1H, J=2.1 Hz & 8.8 Hz), 6.80 (d, 1H, J=7.9 Hz), 6.40 (br s, 1H), 4.18 (s, 1H), 4.13 (s, 1H), 3.72 (m, 2H), 3.63 (t, 1H, J=5.4 Hz), 2.55 (br s, 1H), 1.13 (s, 9H), 2.75 (br s, 1H), 2.60 (m, 2H), 1.41 (s, 9H). MS: m/z 462.04 (80) [MH$^+$]. HPLC: $t_R$=1.87 min (ZQ2000, polar_5 min).

EXAMPLE 199

1-{4-[4-(Benzothiazol-6-ylamino)-7H-pyrrolo[2,3-d]-pyrimidin-6-yl]-3,6-dihydro-2H-pyridin-1-yl}-2-dimethylaminoethanone

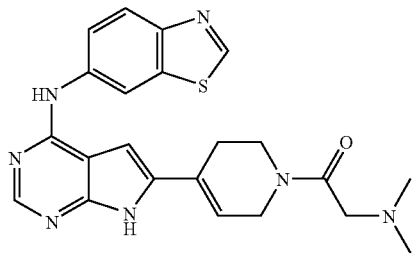

Following the general procedure, but saturating the reaction solution with dimethylamine gas in a sealed tube and reacting it at rt for two days, the title compound was isolated as yellow powder. $^1$H NMR (400 MHz, DMSO-$d_6$): δ=11.94 (d, 1H, J=7.8 Hz), 9.53 (d, 1H, J=7.2 Hz), 9.21 (s, 1H), 8.84 (s, 1H), 8.27 (s, 1H), 8.15 (s, 2H), 7.96 (d, 1H, J=8.9 Hz), 7.68 (dd, 1H, J=2.0 Hz & 8.9 Hz), 6.77 (d, 1H, J=6.4 Hz), 6.36 (d, 1H, J=3.5 Hz), 4.25 (br s, 1H), 4.07 (br s, 1H), 3.55 (m, 3H), 2.51 (br s, 1H), 2.15 (d, 6H, J=6.4 Hz). MS: m/z 434.00 (30) [MH$^+$]. HPLC: $t_R$=1.79 min (ZQ2000, polar_5 min).

EXAMPLE 200

1-{4-[4-(Benzothiazol-6-ylamino)-7H-pyrrolo[2,3-d]-pyrimidin-6-yl]-3,6-dihydro-2H-pyridin-1-yl}-2-(3-hydroxypyrrolidin-1-yl)-ethanone

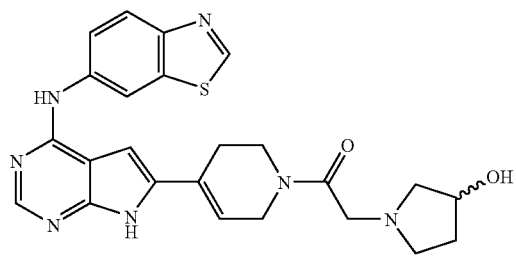

Following the general procedure, the title compound was isolated as yellow powder. $^1$H NMR (400 MHz, DMSO-$d_6$): δ=11.98 (d, 1H, J=18.3 Hz), 9.55 (s, 1H), 9.16 (s, 1H), 8.85 (d, 1H, J=1.7 Hz), 8.40 (s, 1H), 8.14 (s, 2H), 7.94 (d, 1H, J=8.6 Hz), 7.81 (dd, 1H, J=1.9 Hz & 8.6 Hz), 6.78 (d, 1H, J=7.2 Hz), 6.21 (br s, 1H), 4.21 (br s, 1H), 4.14 (br s, 1H), 4.08 (s, 1H), 3.70 (m, 2H), 3.35 (m, 2H), 2.82 (m, 2H), 2.63 (m, 2H), 2.45 (m, 1H), 2.42 (m, 2H), 1.88 (m, 1H), 1.50 (m, 1H). MS: m/z 476.00 (60) [MH$^+$]. HPLC: $t_R$=1.78 min (ZQ2000, polar_5 min).

EXAMPLE 201

2-Azepan-1-yl-1-{4-[4-(benzothiazol-6-ylamino)-7H-pyrrolo[2,3-d]pyrimidin-6-yl]-3,6-dihydro-2H-pyridin-1-yl}-ethanone

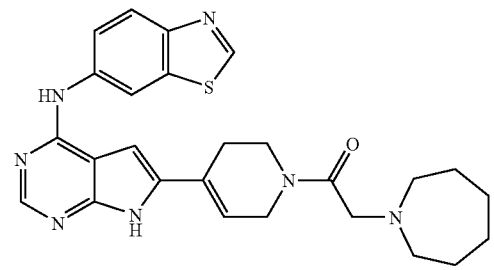

Following the general procedure, the title compound was isolated as yellow powder. $^1$H NMR (400 MHz, DMSO-$d_6$): δ=12.06 (s, 1H), 9.54 (d, 1H, J=3.7 Hz), 9.17 (s, 1H), 8.84 (d, 1H, J=2.0 Hz), 8.31 (s, 1H), 8.12 (s, 2H), 7.97 (d, 1H, J=8.7 Hz), 7.80 (dd, 1H, J=2.0 Hz & 9.2 Hz), 6.78 (s, 1H), 6.38 (s, 1H), 4.27 (s, 1H), 4.07 (s, 1H), 3.69 (t, 2H, J=5.6 Hz), 3.65 (t, 1H, J=5.6 Hz), 3.38 (s, 2H), 2.62 (m, 4H), 2.55 (m, 1H), 1.50 (m, 8H). LC/MS: m/z 488.07 (25) [MH$^+$], $t_R$=1.91 min (ZQ2000, polar_5 min).

EXAMPLE 202

1-{4-[4-(Benzothiazol-6-ylamino)-7H-pyrrolo[2,3-d]-pyrimidin-6-yl]-3,6-dihydro-2H-pyridin-1-yl}-2-(4-hydroxypiperidin-yl-ethanone

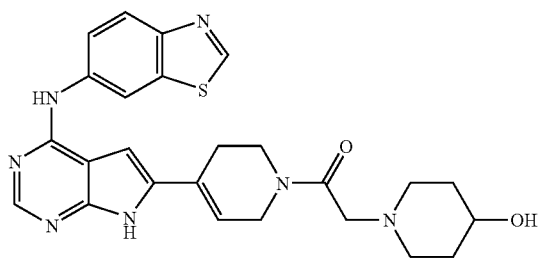

Following the general procedure, the title compound was isolated as yellow powder. $^1$H NMR (400 MHz, DMSO-$d_6$): δ=11.97 (d, 1H, J=15.3 Hz), 9.53 (s, 1H), 9.16 (s, 1H), 8.85 (s, 1H), 8.27 (d, 1H, J=1.5 Hz), 8.09 (s, 2H), 7.97 (d, 1H, J=8.9 Hz), 7.81 (dd, 1H, J=1.5 Hz & 8.9 Hz), 6.79 (s, 1H), 6.38 (s, 1H), 4.22 (br s, 1H), 4.09 (br s, 1H), 3.66 (m, 2H), 3.44 (m, 2H), 3.36 (s, 1H), 2.74 (m, 3H), 2.54 (m, 1H), 2.35 (m, 1H), 2.22 (m, 2H), 1.70 (m, 2H), 1.39 (m, 2H). LC/MS: m/z 490.03 (45) [MH$^+$], $t_R$=1.77 min (ZQ2000, polar_5 min).

EXAMPLE 203

1-{4-[4-(Benzothiazol-6-ylamino)-7H-pyrrolo[2,3-d]-pyrimidin-6-yl]-3,6-dihydro-2H-pyridin-1-yl-2-(4-isopropylpiperazin-1-yl)-ethanone

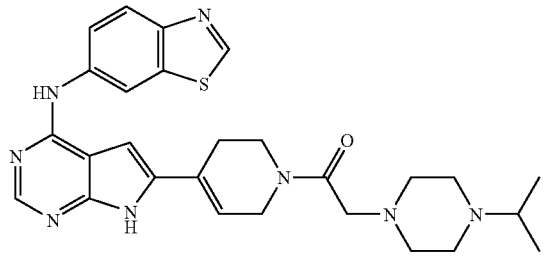

Following the general procedure, the title compound was isolated as yellow powder. $^1$H NMR (400 MHz, DMSO-d$_6$): δ=11.96 (d, 1H, J=19.8 Hz), 9.54 (d, 1H, J=4.6 Hz), 9.17 (s, 1H), 8.85 (s, 1H), 8.36 (s, 1H), 8.10 (s, 2H), 7.97 (d, 1H, J=9.7 Hz), 7.80 (dd, 1H, J=2.0 Hz & 9.7 Hz), 6.75 (s, 1H), 6.37 (br s, 1H), 4.25 (br s, 2H), 4.15 (br s, 2H), 3.70 (t, 2H, J=5.2 Hz), 3.62 (t, 1H, J=5.2 Hz), 3.18 (d, 4H, J=6.4 Hz), 2.67 (m, 2H), 2.52 (m, 4H), 0.91 (d, 6H, J=6.5 Hz). LC/MS: m/z 517.07 (95) [MH$^+$], $t_R$=1.84 min (ZQ2000, polar__5 min).

EXAMPLE 204

1-{4-[4-(Benzothiazol-6-ylamino)-7H-pyrrolo[2,3-d]-pyrimidin-6-yl]-3,6-dihydro-2H-pyridin-1-yl}-2-morpholin-4-ylethanone

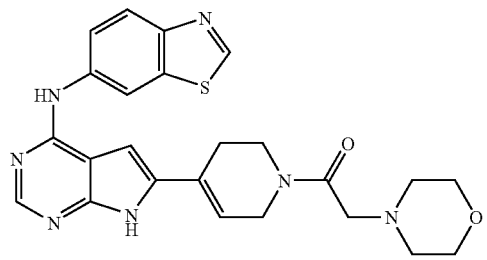

Following the general procedure, the title compound was isolated as yellow powder. $^1$H NMR (400 MHz, DMSO-d$_6$): δ=11.98 (d, 1H, J=14.6 Hz), 9.61 (s, 1H), 9.17 (s, 1H), 8.85 (d, 1H, J=2.0 Hz), 8.31 (s, 1H), 8.11 (s, 2H), 7.97 (d, 1H, J=8.6 Hz), 7.81 (dd, 1H, J=2.0 Hz & 8.6 Hz), 6.78 (s, 1H), 6.38 (br s, 1H), 4.26 (br s, 1H), 4.08 (br s, 1H), 3.70 (t, 2H, J=5.2 Hz), 3.62 (t, 2H, J=5.2 Hz), 3.51 (m, 4H), 3.17 (d, 2H, J=11.6 Hz), 2.52 (m, 1H), 2.29 (br s, 3H). LC/MS: m/z 476.00 (95) [MH$^+$], $t_R$=1.81 min (ZQ2000, polar__5 min).

EXAMPLE 205

1-{4-[4-(Benzothiazol-6-ylamino)-7H-pyrrolo[2,3-d]-pyrimidin-6-yl]-3,6-dihydro-2H-pyridin-1-yl}-2-(4,4-difluoropiperidin-1-yl)-ethanone

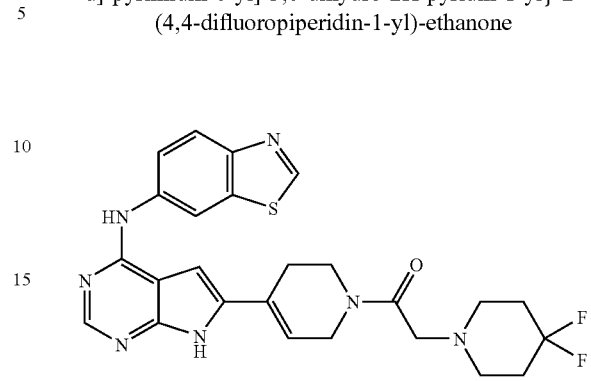

Following the general procedure, but using 4,4-difluoropiperidine hydrochloride and additional 2 equiv. of DIPEA, the title compound was isolated as yellow powder. $^1$H NMR (400 MHz, DMSO-d$_6$): δ=11.98 (d, 1H, J=14.3 Hz), 9.54 (d, 1H, J=3.6 Hz), 9.16 (s, 1H), 8.85 (d, 1H, J=2.0 Hz), 8.27 (s, 1H), 8.11 (s, 2H), 7.97 (d, 1H, J=8.8 Hz), 7.80 (dd, 1H, J=2.0 Hz & 8.8 Hz), 6.78 (s, 1H), 6.32 (br s, 1H), 4.22(br s, 1H), 4.08 (br s, 1H), 3.66 (t, 2H, J=5.7 Hz), 3.54 (t, 1H, J=5.7 Hz), 3.45 (m, 1H), 3.27 (d, 2H, J=9.5 Hz), 2.53 (br s, 4H), 1.87 (m, 4H). LC/MS: m/z 509.99 (40) [MH$^+$], $t_R$=1.98 min (ZQ2000, polar__5 min).

EXAMPLE 206

1-{4-[4-(Benzothiazol-6-ylamino)-7H-pyrrolo[2,3-d]-pyrimidin-6-yl]-3,6-dihydro-2H-pyridin-1-yl}-2-(3,5-dimethylpiperazin-1-yl)-ethanone

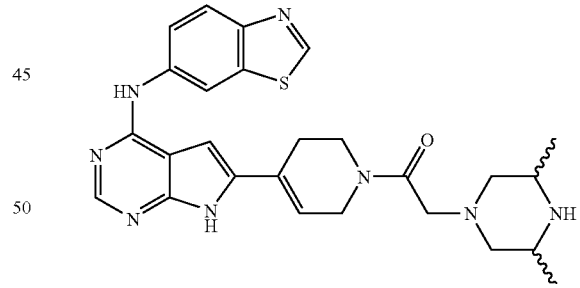

Following the general procedure, the title compound was isolated as yellow powder. Its structure has been confirmed by 2D ROESY NMR experiments. It's derived from cis/trans 2,6-dimethylpiperazine, with predominantly cis isomer. $^1$H NMR (400 MHz, DMSO-d$_6$): δ=11.98 (d, 1H, J=17.2 Hz), 9.56 (s, 1H), 9.16 (s, 1H), 8.85 (d, 1H, J=2.1 Hz), 8.27 (s, 1H), 8.20 (s, 2H), 7.96 (d, 1H, J=8.9 Hz), 7.75 (dd, 1H, J=2.1 Hz & 8.9 Hz), 6.78 (d, 1H, J=4.1 Hz), 6.36 (br s, 1H), 4.20 (s, 1H), 4.15 (s, 1H), 3.64 (q, 2H, J=5.5 Hz), 3.51 (s, 2H), 3.22 (br s, 2H), 2.97 (m, 2H), 2.73 (m, 2H), 2.51 (br s, 1H), 1.91 (m, 1H), 1.01 (m, 6H). LC/MS: m/z 503.05 (30) [MH⁺], $t_R$=1.83 min (ZQ2000, polar_5 min).

General Procedure for Preparation of a 3,6-dihydro-2H-pyridin-1-yl-propanone Library:

To a solution of benzothiazol-6-yl-[6-(1,2,3,6-tetrahydro-pyridin-4-yl)-7H-pyrrolo[2,3-d]pyrimidin-4-yl]-amine tris-hydrochloride (187 mg, 0.408 mmol) in DMF (12 mL) and dichloromethane (1 mL) at 4° C. was added N,N-diisopropylethylamine (0.3 g, 2.0 mmol), followed by 3-chloropropanoyl chloride (52 mg, 0.41 mmol). The resulting mixture was allowed to warm up to rt and stirred overnight. This solution containing 1-{4-[4-(benzothiazol-6-ylamino)-7H-pyrrolo[2,3-d]pyrimidin-6-yl]-3,6-dihydro-2H-pyridin-1-yl}-3-chloropropan-1-one and 1-{4-[4-(benzothiazol-6-ylamino)-7H-pyrrolo[2,3-d]pyrimidin-6-yl]-3,6-dihydro-2H-pyridin-1-yl}-propenone was divided into 13 aliquots to synthesize a 13-membered library, and 1 mg of KI, 5 eq. DIPEA, and 5 eq. of the amines were added. If the amines were used as salts, additional DIPEA was used. The solutions were degassed with N₂ and heated at 70° C. for 48 h. The products were purified by preparative HPLC with water/acetonitrile/formic acid mixture and are assumed to be formate salts.

EXAMPLE 207

1-{4-[4-(Benzothiazol-6-ylamino)-7H-pyrrolo[2,3-d]-pyrimidin-6-yl]-3,6-dihydro-2H-pyridin-1-yl}-3-chloropropan-1-one

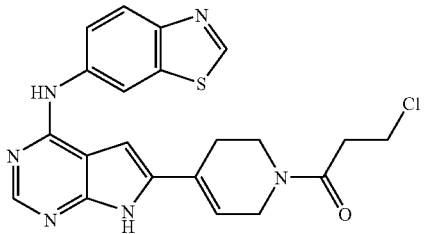

HPLC purification of the reaction mixture gave the title compound as yellow powder. ¹H NMR (400 MHz, DMSO-d₆): δ=11.99 (d, 1H, J=17.2 Hz), 9.55 (s, 1H), 9.17 (s, 1H), 8.84 (s, 1H), 8.28 (s, 1H), 7.97 (d, 1H, J=8.9 Hz), 7.79 (d, 1H, J=11.8 Hz), 6.78 (1H, d, J=6.3 Hz), 6.38 (s, 1H), 4.18 (d, 2H, J=17.2 Hz), 3.81 (q, 2H, J=6.6 Hz), 3.64 (m, 2H, J=5.5 Hz), 2.90 (t, 1H, J=6.6 Hz), 2.84 (t, 1H, J=6.6 Hz), 2.51 (s, 1H). LC/MS: m/z 438.98/440.94 (100/40) [MH⁺], $t_R$=2.52 min (ZQ2000, polar_5 min).

EXAMPLE 208

1-{4-[4-(Benzothiazol-6-ylamino)-7H-pyrrolo[2,3-d]-pyrimidin-6-yl]-3,6-dihydro-2H-pyridin-1-yl}-propenone

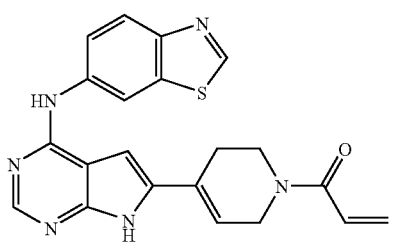

HPLC purification of the reaction mixture gave the title compound as yellow powder. ¹H NMR (400 MHz, DMSO-d₆): δ=11.96 (d, 1H, J=17.2 Hz), 9.55 (s, 1H), 9.20 (s, 1H), 9.16 (s, 1H), 8.28 (d, 2H, J=6.5 Hz), 7.97 (d, 1H, J=8.9 Hz), 7.81 (d, 1H, J=11.8 Hz), 6.88 (m, 1H), 6.78 (m, 1H), 6.38 (s, 1H), 6.09 (d, 1H, J=16.2 Hz), 4.27 (s, 1H), 4.16 (s, 1H), 3.72 (m, 3H), 2.95 (t, 1H, J=6.6 Hz). LC/MS: m/z 402.98 (100) [MH⁺], $t_R$=2.30 min (ZQ2000, polar_5 min).

EXAMPLE 209

1-{4-[4-(Benzothiazol-6-ylamino)-7H-pyrrolo[2,3-d]-pyrimidin-6-yl]-3,6-dihydro-2H-pyridin-1-yl}-3-(4-methylpiperazin-1-yl)-propan-1-one

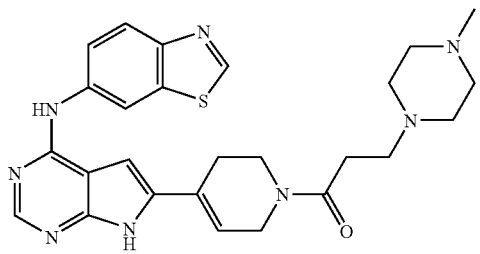

Following the general procedure, the title compound was isolated as yellow powder. ¹H NMR (400 MHz, DMSO-d₆): δ=12.30 (1H, d, J=17.2 Hz), 9.61 (s, 1H), 9.27 (s, 1H), 8.92 (s, 1H), 8.34 (s, 1H), 8.04 (d, 1H, J=8.9 Hz), 7.88 (d, 1H, J=8.9 Hz), 6.84 (1H, d, J=6.4 Hz), 6.44 (s, 1H), 4.24 (1H, s), 4.14 (1H, s), 3.77 (t, 2H, J=6.6 Hz), 3.30 (m, 10H), 2.93 (s, 1H, J=6.6 Hz), 2.89 (s, 1H), 2.74 (s, 1H), 2.73 (d, 1H, J=0.5 Hz), 2.14 (t, 3H, J=8.1 Hz). LC/MS: m/z 503.01 (30) [MH⁺], $t_R$=1.79 min (ZQ2000, polar_5 min).

EXAMPLE 210

1-{4-[4-(Benzothiazol-6-ylamino)-7H-pyrrolo[2,3-d]-pyrimidin-6-yl]-3,6-dihydro-2H-pyridin-1-yl}-3-pyrrolidin-1-ylpropan-1-one

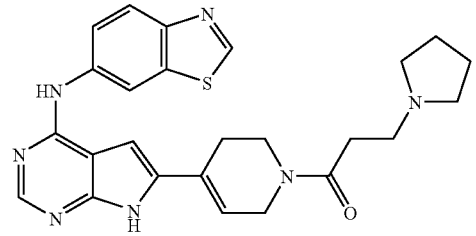

Following the general procedure, the title compound was isolated as yellow powder. ¹H NMR (400 MHz, DMSO-d₆): δ=12.34 (d, 1H, J=17.2 Hz), 9.61 (s, 1H), 9.23 (s, 1H), 8.91 (s, 1H), 8.34 (s, 1H), 8.03 (d, 1H, J=8.8 Hz), 7.87 (d, 1H, J=8.9 Hz), 6.84 (1H, d, J=7.0 Hz), 6.44 (s, 1H), 4.23 (1H, s), 4.13 (1H, s), 3.71 (t, 2H, J=5.5 Hz), 3.32 (s, 6H), 2.60 (m, 3H), 2.14 (d, 1H, J=5.2 Hz), 1.66 (m, 4H). LC/MS: m/z 473.94 (70) [MH⁺], $t_R$=1.82 min (ZQ2000, polar_5 min).

EXAMPLE 211

1-{4-[4-(Benzothiazol-6-ylamino)-7H-pyrrolo[2,3-d]-pyrimidin-6-yl]-3,6-dihydro-2H-pyridin-1-yl}-3-diethylaminopropan-1-one

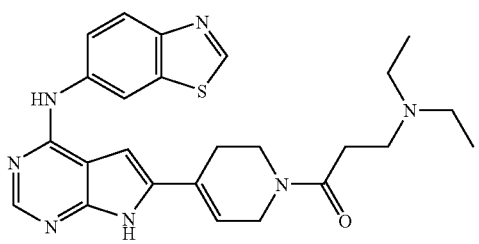

Following the general procedure, the title compound was isolated as yellow powder. $^1$H NMR (400 MHz, DMSO-$d_6$): δ=12.30 (d, 1H, J=17.2 Hz), 9.60 (s, 1H), 9.24 (s, 1H), 8.91 (s, 1H), 8.34 (s, 1H), 8.03 (d, 1H, J=8.9 Hz), 7.87 (d, 1H, J=8.9 Hz), 6.83 (d, 1H, J=6.4 Hz), 6.44 (s, 1H), 4.24 (s, 1H), 4.14 (s, 1H), 3.71 (t, 2H, J=5.5 Hz), 3.32 (s, 2H), 2.65 (m, 2H), 2.54 (br s, 1H), 2.51 (m, 1H), 2.47 (m, 4H), 0.93 (q, 6H, J=7.90 Hz). LC/MS: m/z 475.96 (70) [MH$^+$], $t_R$=1.85 min (ZQ2000, polar_5 min).

EXAMPLE 212

1-{4-[4-(Benzothiazol-6-ylamino)-7H-pyrrolo[2,3-d]-pyrimidin-6-yl]-3,6-dihydro-2H-pyridin-1-yl}-3-diisopropylaminopropan-1-one

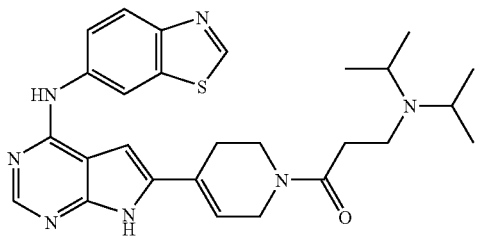

The general procedure was followed, except that 10 eq. of diisopropylamine were used and that the reaction was heated for 5 d. LC/MS: m/z 504.04 (15) [MH$^+$], $t_R$=1.91 (ZQ2000, polar_5 min).

EXAMPLE 213

1-{4-[4-(Benzothiazol-6-ylamino)-7H-pyrrolo[2,3-d]-pyrimidin-6-yl]-3,6-dihydro-2H-pyridin-1-yl}-3-tert-butylaminopropan-1-one

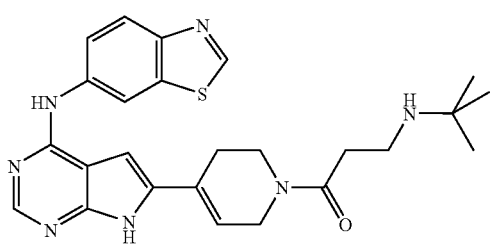

Following the general procedure, but using 10 eq. of tert-butylamine, the title compound was isolated as yellow powder. $^1$H NMR (400 MHz, DMSO-$d_6$): δ=12.21 (d, 1H, J=17.2 Hz), 9.79 (s, 1H), 9.41 (s, 1H), 9.07 (d, 1H, J=2.0 Hz), 8.50 (d, 1H, J=1.5 Hz), 8.43 (s, 4H), 8.21 (d, 1H, J=5.7 Hz), 8.04 (dd, 1H, J=2.1 Hz & 8.8 Hz), 7.99 (d, 1H, 1.5 Hz), 7.68 (br s, 1H), 7.02 (d, 1H, J=4.8 Hz), 6.60 (br s, 1H), 4.36 (1H, s), 3.94 (t, 1H, J=5.7 Hz), 3.83 (t, 1H, J=5.7 Hz), 3.21 (t, 2H, J=6.3 Hz), 2.99 (t, 1H, J=10.8), 2.90 (s, 1H, J=10.8 Hz), 2.75 (br s, 1H), 2.60 (m, 2H), 1.41 (s, 9H). LC/MS: m/z 476.00 (100) [MH$^+$], $t_R$=1.89 min (ZQ2000, polar_5 min).

EXAMPLE 214

3-Azetidin-1-yl-1-{4-[4-(benzothiazol-6-ylamino)-7H-pyrrolo[2,3-d]pyrimidin-6-yl]-3,6-dihydro-2H-pyridin-1-yl}-propan-1-one

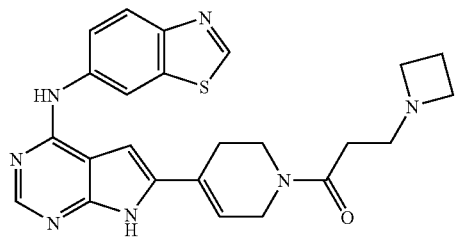

Following the general procedure, the title compound was isolated as yellow powder. $^1$H NMR (400 MHz, DMSO-$d_6$): δ=12.01 (d, 1H, J=17.2 Hz), 9.85 (s, 1H), 9.21 (s, 1H), 8.90 (s, 1H), 8.29 (d, 1H, J=1.0 Hz), 8.23 (s, 2H), 7.97 (d, 1H, J=5.7 Hz), 7.81 (dd, 1H, J=2.1 Hz & 8.8 Hz), 6.80 (d, 1H, J=5.4 Hz), 6.40 (br s, 1H), 4.16 (d, 1H, J=10.1 Hz), 3.68 (t, 1H, J=5.1 Hz), 3.63 (t, 1H, J=4.9 Hz), 3.01 (t, 1H, J=8.3 Hz), 2.85 (m, 2H), 2.34 (t, 4H, J=6.6 Hz), 2.13 (m, 2H), 2.09 (t, 2H, J=4.2 Hz), 1.67 (t, 2H, J=7.2 Hz). LC/MS: m/z 126.01 (100%), 320.02 (50%), 332.01 (90%) [MH$^+$—H$_2$NCOCH$_2$CH$_2$N(CH$_2$)$_3$], 390.98 (35) [MH$^+$—CH$_2$N(CH$_2$)$_3^+$], $t_R$=1.62 min (ZQ2000, polar_-5 min).

EXAMPLE 215

1-{4-[4-(Benzothiazol-6-ylamino)-7H-pyrrolo[2,3-d]-pyrimidin-6-yl]-3,6-dihydro-2H-pyridin-1-yl}-3-(3-hydroxypyrrolidin-1-yl)-propan-1-one

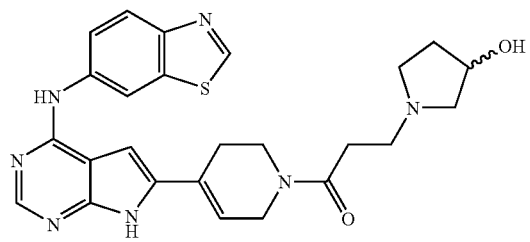

Following the general procedure, the title compound was isolated as yellow powder. $^1$H NMR (400 MHz, DMSO-$d_6$): δ=11.84 (d, 1H, J=14.3 Hz), 9.42 (s, 1H), 9.03 (s, 1H), 8.76 (s, 1H), 8.15 (s, 1H), 8.01 (s, 4H), 7.87 (d, 1H, J=8.6 Hz), 7.67 (dd, 1H, J=1.9 Hz & 10.9 Hz), 6.65 (d, 1H, J=8.1 Hz), 6.21 (br s, 1H), 4.09 (br s, 2H), 3.96 (br s, 1H), 3.51 (m, 4H), 2.81 (m, 1H), 2.75 (m, 2H), 2.54 (m, 3H), 2.44 (m, 3H), 2.11 (s, 1H), 1.82 (m, 1H). LC/MS: m/z 490.00 (50) [MH$^+$], $t_R$=1.79 min (ZQ2000, polar_5 min).

EXAMPLE 216

3-Azepan-1-yl-1-{4-[4-(benzothiazol-6-ylamino)-7H-pyrrolo[2,3-d]pyrimidin-6-yl]-3,6-dihydro-2H-pyridin-1-yl}-propan-1-one

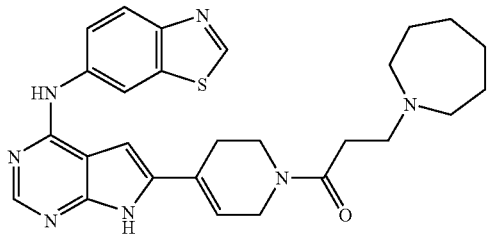

Following the general procedure, the title compound was isolated as yellow powder. $^1$H NMR (400 MHz, DMSO-d$_6$): δ=12.06 (d, 1H, J=16.8 Hz), 9.62 (s, 1H), 9.24 (s, 1H), 8.92 (s, 1H), 8.35 (s, 1H), 8.25 (s, 3H), 8.04 (d, 1H, J=8.7 Hz), 7.88 (d, 1H, J=9.2 Hz), 6.85 (d, 1H, J=5.1 Hz), 6.45 (s, 1H), 4.91 (s, 1H), 4.55 (s, 1H), 3.74 (t, 2H, J=9.6 Hz), 2.90 (m, 2H), 2.70 (m, 3H), 2.68 (m, 1H), 1.57 (m, 12H). LC/MS: m/z 502.03 (10) [MH$^+$], t$_R$=1.91 min (ZQ2000, polar__5 min).

EXAMPLE 217

1-{4-[4-(Benzothiazol-6-ylamino)-7H-pyrrolo[2,3-d]-pyrimidin-6-yl]-3,6-dihydro-2H-pyridin-1-yl}-3-(4-hydroxypiperidin-1-yl)-propan-1-one

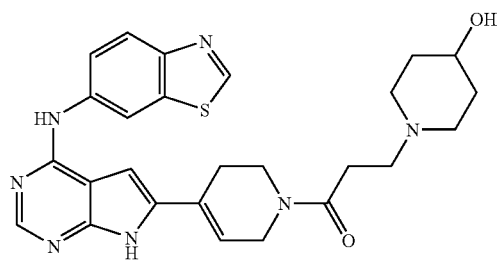

Following the general procedure, the title compound was isolated as yellow powder. $^1$H NMR (400 MHz, DMSO-d$_6$): δ=12.00 (d, 1H, J=18.3 Hz), 9.61 (s, 1H), 9.17 (s, 1H), 8.85 (s, 1H), 8.28 (d, 1H, J=1.5 Hz), 8.12 (s, 3H), 7.97 (d, 1H, J=8.9 Hz), 7.81 (dd, 1H, J=2.1 Hz & 8.9 Hz), 6.77 (d, 1H, J=5.8 Hz), 6.37 (d, 1H, J=2.1 Hz), 4.30 (br s, 1H), 4.17 (br s, 1H), 3.63 (d, 2H, J=3.9 Hz), 3.36 (m, 1H), 2.78 (m, 4H), 2.59 (m, 4H), 2.54 (m, 2H), 2.20 (m, 2H), 1.66 (m, 2H). LC/MS: m/z 503.99 (20) [MH$^+$], t$_R$=1.79 min (ZQ2000, polar__5 min).

EXAMPLE 218

1-{4-[4-(Benzothiazol-6-ylamino)-7H-pyrrolo[2,3-d]-pyrimidin-6-yl]-3,6-dihydro-2H-pyridin-1-yl}-3-(4-isopropylpiperazin-1-yl)-propan-1-one

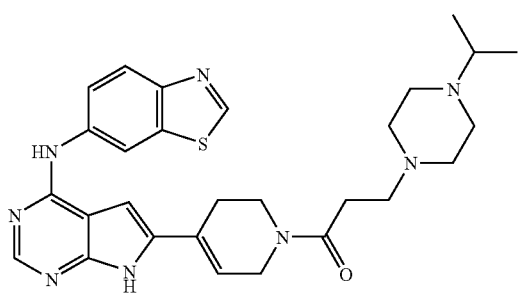

Following the general procedure, the title compound was isolated as yellow powder. $^1$H NMR (400 MHz, DMSO-d$_6$): δ=12.07 (d, 1H, J=18.3 Hz), 9.63 (s, 1H), 9.23 (s, 1H), 8.92 (s, 1H), 8.34 (s, 1H), 8.19 (s, 2H), 8.04 (d, 1H, J=8.9 Hz), 7.78 (d, 1H, J=15.2 Hz), 6.84 (d, 1H, J=5.3 Hz), 6.45 (br s, 1H), 4.27 (br s, 2H), 4.24 (br s, 2H), 3.78 (t, 6H, J=5.9 Hz), 2.67 (m, 1H), 2.58 (m, 8H), 0.97 (t, 6H, J=6.2 Hz). LC/MS: m/z 531.04 (20) [MH$^+$], t$_R$=1.81 min (ZQ2000, polar__5 min).

EXAMPLE 219

1-{4-[4-(Benzothiazol-6-ylamino)-7H-pyrrolo[2,3-d]-pyrimidin-6-yl]-3,6-dihydro-2H-pyridin-1-yl}-3-morpholin-4-ylpropan-1-one

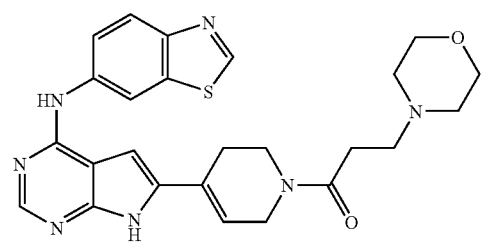

Following the general procedure, the title compound was isolated as yellow powder. $^1$H NMR (400 MHz, DMSO-d$_6$): δ=12.01 (d, 1H, J=14.6 Hz), 9.60 (s, 1H), 9.17 (s, 1H), 8.83 (s, 1H), 8.28 (d, 1H, J=1.2 Hz), 8.11 (s, 2H), 7.99 (d, 1H, J=8.6 Hz), 7.81 (dd, 1H, J=1.7 Hz & 9.3 Hz), 6.77 (d, 1H, J=6.3 Hz), 6.38 (br s, 1H), 4.20 (br s, 1H), 3.99 (br s, 1H), 3.63 (t, 4H, J=5.2 Hz), 3.50 (t, 4H, J=4.3 Hz), 2.52 (m, 4H), 2.27 (m, 4H). LC/MS: m/z 489.96 (70) [MH$^+$], t$_R$=1.81 min (ZQ2000, polar__5 min).

EXAMPLE 220

1-{4-[4-(Benzothiazol-6-ylamino)-7H-pyrrolo[2,3-d]-pyrimidin-6-yl]-3,6-dihydro-2H-pyridin-1-yl}-3-(4,4-difluoropiperidin-1-yl)-propan-1-one

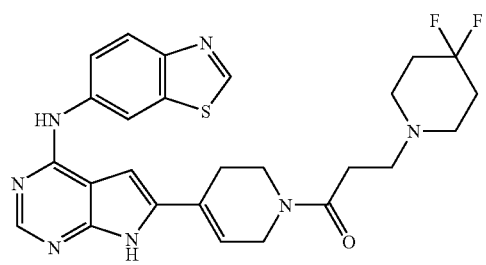

Following the general procedure, but using 4,4-difluoropiperidine hydrochloride and additional 2 equiv. of DIPEA, the title compound was isolated as yellow powder. $^1$H NMR (400 MHz, DMSO-d$_6$): δ=11.97 (d, 1H, J=14.3 Hz), 9.56 (s, 1H), 9.18 (s, 1H), 8.86 (d, 1H, J=2.1 Hz), 8.27 (d, 1H, J=1.4 Hz), 8.11 (s, 2H), 7.97 (s, 1H), 7.85 (dd, 1H, J=2.1 Hz & 8.9 Hz), 6.79 (d, 1H, J=6.3 Hz), 6.39 (br s, 1H), 4.19 (br s, 1H), 4.09 (br s, 1H), 3.79 (t, 2H, J=5.7 Hz), 3.41 (m, 6H), 2.48 (m, 2H), 1.92 (m, 6H). LC/MS: m/z 523.96 (30) [MH$^+$], t$_R$=1.93 min (ZQ2000, polar__5 min).

EXAMPLE 221

1-{4-[4-(Benzothiazol-6-ylamino)-7H-pyrrolo[2,3-d]-pyrimidin-6-yl]-3,6-dihydro-2H-pyridin-1-yl}-3-(3,5-dimethylpiperazin-1-yl)-propan-1-one

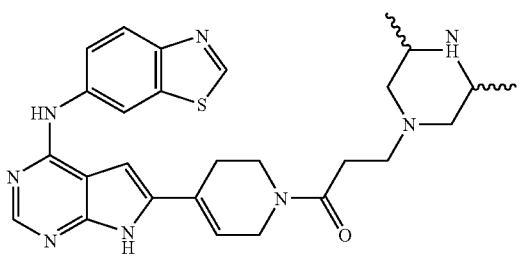

Following the general procedure, the title compound was isolated as yellow powder. Its structure has been confirmed by 2D ROESY NMR experiments. It's derived from cis/trans 2,6-dimethylpiperazine, with predominantly cis isomer. $^1$H NMR (400 MHz, DMSO-$d_6$): δ=11.92 (d, 1H, J=17.2 Hz), 9.62 (s, 1H), 9.08 (s, 1H), 8.72 (s, 1H), 8.08 (s, 1H), 7.98 (d, 2H), 7.89 (d, 1H, J=8.9 Hz), 7.68 (d, 1H, J=8.9 Hz), 6.65 (1H, d, J=5.4 Hz), 6.26 (s, 1H), 4.05 (2H, s), 3.95 (2H, s), 3.51 (s, 4H), 2.76 (m, 1H), 2.47 (s, 1H), 2.43 (m, 1H), 1.91 (br s, 1H), 1.64 (br s, 1H), 1.48 (m, 3H), 0.74 (t, 6H, J=6.0 Hz). LC/MS: m/z 516.00 (30) [MH$^+$], $t_R$=1.99 min (ZQ2000, polar_5 min).

EXAMPLE 222

1-4-[4-(Benzothiazol-6-ylamino)-7H-pyrrolo[2,3-d]-pyrimidin-6-yl]-3,6-dihydro-2H-pyridin-1-yl-3-piperidin-1-ylpropan-1-one

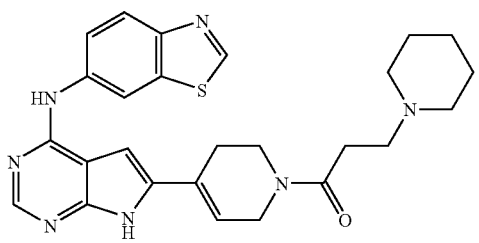

To a suspension/solution of benzothiazol-6-yl-[6-(1,2,3,6-tetrahydropyridin-4-yl)-7H-pyrrolo[2,3-d]pyrimidin-4-yl]-amine tris-hydrochloride (100.9 mg, 0.220 mmol, 1 eq), 1-piperidinepropanoic acid (87.9 mg, 0.554 mmol, 2.5 eq), EDC (130.8 mg, 0.682 mmol, 3 eq), and HOBt (30.3 mg, 0.224 mmol, 1 eq) in anhydrous DMF (6 mL), DiPEA (192 µL, 1.1 mmol, 5 eq) was added at rt, under an atmosphere of $N_2$. The reaction mixture was stirred at rt for 15 h and was concentrated under reduced pressure. The residue was dissolved in a 5% MeOH:DCM mixture and washed with NaHCO$_3$ (1×) and brine (1×), dried over anhydrous Na$_2$SO$_4$, filtered, and concentrated in vacuo. The crude material was adsorbed onto Hydromatrix, dry loaded, and purified by chromatography on silica gel [Jones Flashmaster, 5 g/25 mL cartridge, eluting with MeOH:DCM 5%→10%→7N NH$_3$/MeOH:DCM 5%]. Fractions containing product were combined and concentrated in vacuo. Further purification of the yellow solid thus obtained by trituration in hot DCM/sonication gave the title compound as light tan solid. $^1$H NMR (400 MHz, MeOH-$d_4$): δ=1.45-1.58 (s, br, 2H), 1.60-1.72 (m, 4H), 2.49-2.85 (m, 10H), 3.81 & 3.85 (t, J=5.6 Hz, rotamers, 2H), 4.27 & 4.32 (s, br, rotamers, 2H), 6.34 (d, J=1.2 Hz, 1H), 6.74 & 6.76 (s, rotamers, 1H), 7.78 & 7.80 (dd, J=8.8, 2.8 Hz, rotamers, 1H), 8.02 (d, J=8.8 Hz, 1H), 8.29 & 8.30 (s, rotamers, 1H), 8.75 & 8.76 (d, J=2.0 Hz, rotamers, 1H), 9.13 (s, 1H). MS (ES+): m/z 487.97 (75) [MH$^+$]. HPLC: $t_R$=1.89 min (ZQ2000, polar_5 min).

EXAMPLE 223

1-4-[4-(Benzothiazol-6-ylamino)-7H-pyrrolo[2,3-d]-pyrimidin-6-yl]-3,6-dihydro-2H-pyridin-1-yl-3-dimethylaminopropan-1-one

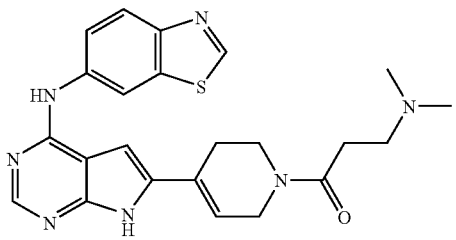

The title compound was obtained following the procedure for 1-4-[4-(benzothiazol-6-ylamino)-7H-pyrrolo[2,3-d]pyrimidin-6-yl]-3,6-dihydro-2H-pyridin-1-yl-3-piperidin-1-yl-propan-1-one, using 3-dimethylaminopropionic acid, as brown solid. $^1$H NMR (400 MHz, MeOH-$d_4$): δ=2.33 & 2.35 (s, rotamers, 6H), 2.62 (s, br, 2H), 2.67-2.73 (m, 4H), 3.83 & 3.86 (t, J=5.6 Hz, rotamers, 2H), 4.29 & 4.33 (s, br, rotamers, 2H), 6.36 (d, J=1.6 Hz, 1H), 6.75 & 6.77 (s, rotamers, 1H), 7.79 & 7.81 (dd, J=8.8, 2.8 Hz, rotamers, 1H), 8.04 (d, J=8.8 Hz, 1H), 8.31 & 8.32 (s, rotamers, 1H), 8.77 & 8.78 (d, J=2.0 Hz, rotamers, 1H), 9.15 (s, 1H). MS (ES+): m/z 448.00 (12) [MH$^+$]. HPLC: $t_R$=2.00 min (ZQ2000, polar_5 min).

EXAMPLE 224

Benzothiazol-6-yl-[6-(1-methanesulfonyl-1,2,3,6-tetrahydropyridin-4-yl)-7H-pyrrolo[2,3-d]pyrimidin-4-yl]amine

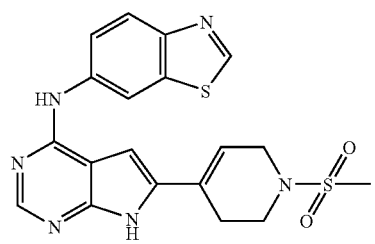

To a solution of benzothiazol-6-yl-[6-(1,2,3,6-tetrahydropyridin-4-yl)-7H-pyrrolo[2,3-d]pyrimidin-4-yl]amine trihydrochloride (100 mg, 0.2 mmol) in DMF (5 mL) was added N,N-diisopropylethylamine (0.4 mL, 2.0 mmol) and methanesulfonic anhydride (42 mg, 0.24 mmol). The reaction mixture was left to stir at rt for 1 h. The mixture was concentrated in vacuo and purified via MDP, which afforded the title compound as a tan solid. MS (ES+): m/z: 426.98 (100) [MH$^+$]. HPLC: t$_r$=2.44 min (ZQ2000: polar_5 min). $^1$H NMR (400 MHz, CDCl$_3$): δ=2.64 (m, 2H), 3.13-3.20 (m, 3H), 3.91 (s, 2H), 6.47 (s, 1H), 6.87 (s, 1H), 7.87 (dd, J=1.6, 8.8 Hz, 1H), 8.02 (d, J=8.8 Hz, 1H), 8.35 (s, 1H), 8.92 (d, J=2.0 Hz, 1H), 9.23 (s, 1H), 9.64 (s, 1H), 12.04 (s, 1H).

General Procedure for Preparation of a Sulfonamide Library

To a solution of benzothiazol-6-yl-[6-(1,2,3,6-tetrahydropyridin-4-yl)-7H-pyrrolo[2,3-d]pyrimidin-4-yl]-amine trishydrochloride (25.3 mg, 0.069 mmol) in DMF (0.5 mL) at 4° C. was added N,N-diisopropylethylamine (40 mg, 5 eq.) followed by the corresponding sulfonyl chloride (1 eq.). The resulting mixture was allowed to warming up to rt and stirred for 3 h. The products were purified by preparative HPLC with water/acetonitrile /formic acid mixtures and are assumed to be formate salts.

EXAMPLE 225

Benzothiazol-6-yl-[6-(1-ethanesulfonyl-1,2,3,6-tetrahydropyridin-4-yl)-7H-pyrrolo[2,3-d]pyrimidin-4-yl]-amine

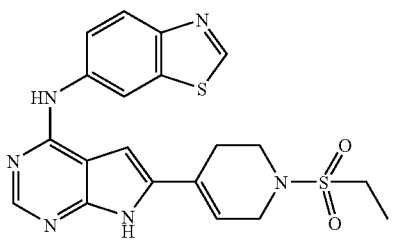

Following the general procedure, the title compound was isolated as tan powder. $^1$H NMR (400 MHz, DMSO-d$_6$): δ=11.97 (s, 1H), 9.56 (s, 1H), 9.17 (s, 1H), 8.85 (d, 1H, J=2.1 Hz), 8.28 (s, 1H), 7.99 (d, 1H, J=8.9 Hz), 7.80 (dd, 1H, J=2.1 Hz & 8.9 Hz), 6.87 (s, 1H), 6.40 (s, 1H), 3.91 (br s, 2H), 3.43 (t, 2H, J=5.7 Hz), 3.07 (q, 2H, J=4.3 Hz), 2.54 (br s, 2H), 1.19 (t, 3H, J=5.7 Hz). LC/MS: m/z 440.92 [MH$^+$] (100), t$_R$=2.57 min (ZQ2000, polar_5 min).

EXAMPLE 226

Benzothiazol-6-yl-{6-[1-(propane-1-sulfonyl)-1,2,3, 6-tetrahydropyridin-4-yl]-7H-pyrrolo[2,3-d]pyrimidin-4-yl}-amine

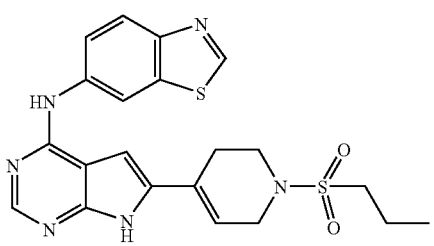

Following the general procedure, the title compound was isolated as tan powder. $^1$H NMR (400 MHz, DMSO-d$_6$): δ=12.02 (s, 1H), 9.56 (s, 1H), 9.19 (s, 1H), 8.86 (d, 1H, J=2.1 Hz), 8.28 (s, 1H), 7.99 (d, 1H, J=8.9 Hz), 7.80 (dd, 1H, J=2.1 Hz & 8.9 Hz), 6.79 (s, 1H), 6.40 (s, 1H), 3.90 (br s, 2H), 3.42 (t, 2H, J=5.7 Hz), 3.04 (t, 2H, J=5.7 Hz), 2.53 (br s, 2H), 1.64 (m, 2H), 0.93 (t, 3H, J=7.4 Hz). LC/MS: m/z 454.96 [MH$^+$] (100), t$_R$=2.72 min (ZQ2000, polar_5 min).

EXAMPLE 227

Benzothiazol-6-yl-{6-[1-(propane-2-sulfonyl)-1,2,3, 6-tetrahydropyridin-4-yl]-7H-pyrrolo[2,3-d]pyrimidin-4-yl}-amine

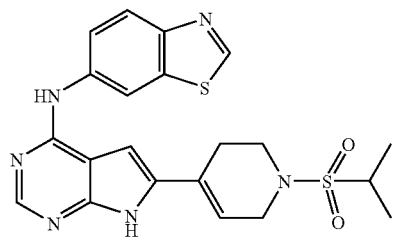

Following the general procedure, the title compound was isolated as tan powder. $^1$H NMR (400 MHz, DMSO-d$_6$): δ=11.97 (s, 1H), 9.56 (s, 1H), 9.18 (s, 1H), 8.85 (d, 1H, J=2.1 Hz), 8.29 (s, 1H), 7.97 (d, 1H, J=8.9 Hz), 7.81 (dd, 1H, J=2.1 Hz & 8.9 Hz), 6.79 (s, 1H), 6.39 (s, 1H), 3.95 (br s, 2H), 3.51 (t, 2H, J=5.5 Hz), 3.38 (m, 1H), 2.51 (br s, 2H), 1.18 (d, 6H, J=6.8 Hz). LC/MS: m/z 454.95 [MH$^+$] (100), t$_R$=2.68 min (ZQ2000, polar_5 min).

EXAMPLE 228

Benzothiazol-6-yl-[6-(1-cyclopropanesulfonyl-1,2,3, 6-tetrahydropyridin-4-yl)-7H-pyrrolo[2,3-d]pyrimidin-4-yl]-amine

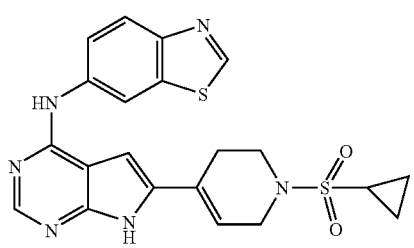

Following the general procedure, the title compound was isolated as tan powder. $^1$H NMR (400 MHz, DMSO-d$_6$): δ=11.93 (s, 1H), 9.56 (s, 1H), 9.17 (s, 1H), 8.85 (d, 1H, J=2.0 Hz), 8.28 (s, 1H), 7.97 (d, 1H, J=8.9 Hz), 7.78 (dd, 1H, J=2.0 Hz & 8.9 Hz), 6.80 (s, 1H), 6.41 (s, 1H), 3.93 (br s, 2H), 3.41 (t, 2H, J=5.6 Hz), 2.62 (m, 1H), 2.57 (br s, 2H), 0.92 (m, 4H). LC/MS: m/z 452.94 [MH$^+$] (100), t$_R$=2.64 min (ZQ2000, polar_5 min).

EXAMPLE 229

4-[4-(Benzothiazol-6-ylamino)-7H-pyrrolo[2,3-d]-pyrimidin-6-yl]-3,6-dihydro-2H-pyridine-1-sulfonic acid dimethylamide

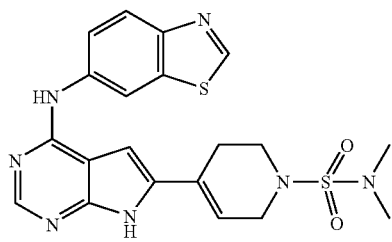

Following the general procedure, the title compound was isolated as tan powder. $^1$H NMR (400 MHz, DMSO-d$_6$): δ=11.97 (s, 1H), 9.56 (s, 1H), 9.17 (s, 1H), 8.86 (d, 1H, J=2.1 Hz), 8.27 (s, 1H), 7.97 (d, 1H, J=8.9 Hz), 7.78 (dd, 1H, J=2.1 Hz & 8.9 Hz), 6.79 (s, 1H), 6.38 (s, 1H), 3.87 (br s, 2H), 3.39 (t, 2H, J=5.7 Hz), 2.78 (s, 6H), 2.52 (br s, 2H). LC/MS: m/z 455.97 [MH$^+$] (100), $t_R$=2.66 min (ZQ2000, polar_5 min).

EXAMPLE 230

Benzothiazol-6-yl-{6-[1-(butane-2-sulfonyl)-1,2,3,6-tetrahydropyridin-4-yl]-7H-pyrrolo[2,3-d]pyrimidin-4-yl}-amine

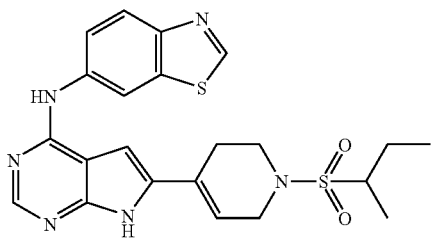

Following the general procedure, the title compound was isolated as tan powder. $^1$H NMR (400 MHz, DMSO-d$_6$): δ=11.97 (s, 1H), 9.60 (s, 1H), 9.18 (s, 1H), 8.85 d, 1H, J=2.1 Hz), 8.27 (s, 1H), 7.97 (d, 1H, J=8.9 Hz), 7.81 (dd, 1H, J=2.1 Hz & 8.9 Hz), 6.79 (s, 1H), 6.39 (s, 1H), 3.95 (br s, 2H), 3.51 (m, 2H), 3.19 (m, 1H), 2.53 (br s, 2H), 1.83 (m, 1H), 1.39 (m, 1H), 1.17 (d, 3H, J=6.8 Hz), 0.89 (t, 3H, J=7.5 Hz). LC/MS: m/z 468.98 [MH$^+$] (100), $t_R$=2.84 min (ZQ2000, polar_5 min).

EXAMPLE 231

[6-(1-Benzenesulfonyl-1,2,3,6-tetrahydropyridin-4-yl)-7H-pyrrolo[2,3-d]pyrimidin-4-yl]-benzothiazol-6-ylamine

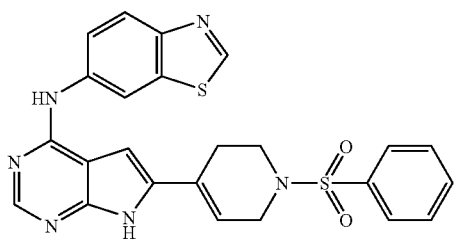

Following the general procedure, the title compound was isolated as tan powder. $^1$H NMR (400 MHz, DMSO-d$_6$): δ=11.98 (s, 1H), 9.54 (s, 1H), 9.16 (s, 1H), 8.84 (d, 1H, J=2.1 Hz), 8.29 (s, 1H), 7.96 (d, 1H, J=8.9 Hz), 7.81 (dd, 1H, J=2.1 Hz & 8.9 Hz), 7.76 (dd, 2H, J=1.5 Hz & 7.8 Hz), 7.67 (m, 1H), 7.59 (dd, J=7.8 Hz & 7.8 Hz), 6.74 (s, 1H), 6.31 (s, 1H), 3.68 (br s, 2H), 3.17 (t, 2H, J=5.7 Hz), 2.54 (br s, 2H). LC/MS: m/z 488.88 [MH$^+$] (100), $t_R$=2.97 min (ZQ2000, polar_5 min).

EXAMPLE 232

1-4-[4-(1H-Indol-5-ylamino)-7H-pyrrolo[2,3-d]-pyrimidin-6-yl]-3,6-dihydro-2H-pyridin-1-yl-3-piperidin-1-ylpropan-1-one

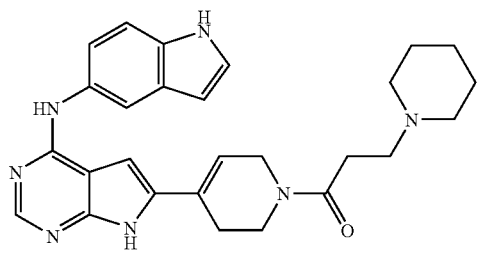

A mixture of 1-[4-(4-chloro-7H-pyrrolo[2,3-d]pyrimidin-6-yl)-3,6-dihydro-2H-pyridin-1-yl]-3-piperidin-1-ylpropan-1-one (67.7 mg, 0.114 mmol, 1 eq), 5-aminoindole (18.0 mg, 0.136 mmol, 1.2 eq), and TFA (45 μL, 0.58 mmol, 5 eq) in TFE (1.2 mL), in a sealed tube, was heated at 100° C. for 5 d and concentrated under reduced pressure. The crude material was adsorbed onto Hydromatrix, dry loaded, and purified by chromatography on silica gel [Jones Flashmaster, 5 g/25 mL cartridge, eluting with MeOH:DCM 5%→7N NH$_3$/MeOH:DCM 2%→6%]. Fractions containing product were combined, concentrated in vacuo, and purified by HPLC to give the title compound as a yellow solid. $^1$H NMR (400 MHz, CDCl$_3$): δ=1.46 (s, br, 2H), 1.60 (sextet, J=5.6 Hz, 4H), 2.22 & 2.29 (s, br, rotamers, 2H), 2.44 (s, br, 4H), 2.51-2.61 (m, 2H), 2.63-2.70 (m, 2H), 3.58 & 3.68 (t, J=5.6 Hz, rotamers, 2H), 4.16 & 4.21 (s, br, rotamers, 2H), 5.50 & 5.51 (s, br, rotamers, 1H), 6.05 & 6.10 (s, br, rotamers, 1H), 6.54 (t, J=3.2 Hz, 1H), 7.19 & 7.21 (dt, J=8.4, 2.0 Hz, 1H), 7.29 (d, J=3.2 Hz, 1H), 7.43 (d, J=8.4 Hz, 1H), 7.67 (d, J=2.0 Hz, 1H), 8.21 (s, 1H). MS(100) [MH$^+$]. HPLC: $t_R$=1.72 min (ZQ2000, polar_5 min).

1-[4-(4-Chloro-7H-pyrrolo[2,3-d]pyrimidin-6-yl)-3,6-dihydro-2H-pyridin-1-yl]-3-piperidin-1-ylpropan-1-one

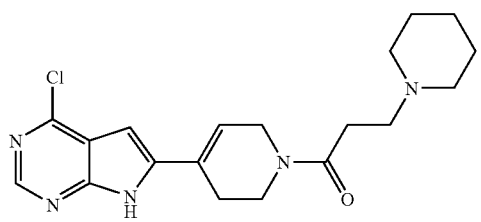

To a suspension/solution of 4-chloro-6-(1,2,3,6-tetrahydropyridin-4-yl)-7H-pyrrolo[2,3-d]pyrimidine bis-hydrochloride (19.1 mg, 0.0621 mmol, 1 eq), 1-piperidinepropanoic acid (24.5 mg, 0.156 mmol, 2.5 eq), 1-hydroxybenzotriazole (HOBt) (8.5 mg, 0.063 mmol, 1 eq), and N-(3-dimethylaminopropyl)-N'-ethylcarbodiimide hydrochloride (EDC) (36.3 mg, 0.189 mmol, 3 eq) in anhydrous DMF (1.3 mL), DiPEA (64 µL, 0.37 mmol, 6 eq) was added and the reaction was stirred at rt, under $N_2$, for 16 h. Solvent was concentrated in vacuo and the residue was dissolved in DCM, washed with $NaHCO_3$ (2×) and brine (1×), dried over anhydrous $Na_2SO_4$, filtered, and concentrated under reduced pressure. The crude material was purified on MDPS giving the title compound as a yellow solid. $^1$H NMR (400 MHz, MeOH-$d_4$): δ=1.45-1.56 (s, br, 2H), 1.64 (sextet, J=5.6 Hz, 4H), 2.46-2.78 (m, 10H), 3.81 & 3.84 (t, J=5.6 Hz, rotamers, 2H), 4.29 & 4.33 (d, J=2.0 Hz, rotamers, 2H), 6.48 (s, br, 1H), 6.62 & 6.63 (s, rotamers, 1H), 8.50 (d, 1H). MS (ES+): m/z 373.99/376.00 (100/36) [MH$^+$]. HPLC: $t_R$=1.86 min (ZQ2000, polar_5 min).

Alternative preparation: To a suspension/solution of 4-chloro-6-(1,2,3,6-tetrahydropyridin-4-yl)-7H-pyrrolo[2,3-d]pyrimidine bis-hydrochloride (495.4 mg, 1.610 mmol, 1 eq), 1-piperidinepropanoic acid (335.4 mg, 2.133 mmol, 1.3 eq), and TBTU (624.4 mg, 1.945 mmol, 1.2 eq) in anhydrous DMF (15 mL), DiPEA (1.4 mL, 8 mmol, 5 eq) was added at rt, under $N_2$, and stirred for 2 h. The solvent was evaporated under reduced pressure. The crude material was adsorbed onto Hydromatrix, dry loaded, and purified by chromatography on silica gel [Jones Flashmaster, 50 g/150 mL cartridge, eluting with MeOH:DCM 2%→5%→10%→7N $NH_3$/MeOH:DCM 2%→5%]. Fractions containing product were combined and concentrated in vacuo, affording the title compound as a yellow solid.

4-Chloro-6-(1,2,3,6-tetrahydropyridin-4-yl)-7H-pyrrolo[2,3-d]pyrimidine bis-hydrochloride

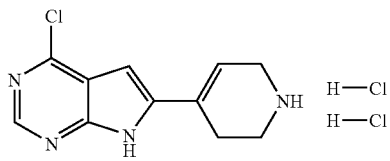

To 4-(4-chloro-7H-pyrrolo[2,3-d]pyrimidin-6-yl)-3,6-dihydro-2H-pyridine-1-carboxylic acid tert-butyl ester (601.6 mg, 1.797 mmol, 1 eq), a 4.0 M solution of HCl in 1,4-dioxane (15 mL, 33 eq) was added and the reaction was stirred at rt for 18 h. The solid was then filtered off, washed several times with ether, and dried under vacuum pressure, yielding the title compound as a yellow solid. $^1$H NMR (400 MHz, DMSOd$_6$): δ=2.77 (s, 2H), 3.33 (d, J=4.8 Hz, 2H), 3.83 (s, br, 2H), 5.27-5.65 (s, br, —NH+H$_2$O), 6.60 (s, 1H), 6.71 (d, J=1.6 Hz, 1H), 8.59 (s, 1H), 9.30 (s, br, —NH), 12.85 (s, H+). MS (ES+): m/z 235.09/237.11 (3) [MH$^+$]; 206.12/208.14 (100) [MH$^+$—CH$_3$N]. HPLC: $t_R$=1.52 min (ZQ2000, polar_5 min).

EXAMPLE 233

1-4-[4-(Benzotriazol-1-yloxy)-7H-pyrrolo[2,3-d]-pyrimidin-6-yl]-3,6-dihydro-2H-pyridin-1-yl-3-piperidin-1-ylpropan-1-one

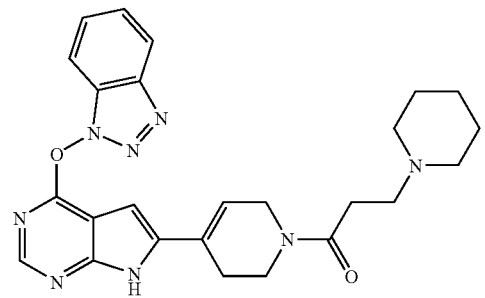

The title compound was also isolated from the TBTU-coupling reaction mixture from the preparation of 1-[4-(4-chloro-7H-pyrrolo[2,3-d]pyrimidin-6-yl)-3,6-dihydro-2H-pyridin-1-yl]-3-piperidin-1-yl-propan-1-one, after concentration in vacuo at ≈50° C. bath temp., and purified by HPLC, yielding a yellow solid. $^1$H NMR (400 MHz, CDCl$_3$): δ=1.45 (s, br, 2H), 1.61 (pentet, J=5.6 Hz, 4H), 2.50 (s, br, 4H), 2.55-2.73 (m, 4H), 2.74-2.84 (m, 2H), 3.73 & 3.84 (t, J=5.6 Hz, rotamers, 2H), 4.20 & 4.30 (s, br, rotamers, 2H), 6.34 & 6.41 (s, br, rotamers, 1H), 6.49 & 6.54 (s, rotamers, 1H), 7.44-7.51 (m, 2H), 7.52-7.58 (m, 1H), 8.15 (d, J=8.4 Hz, 1H), 8.27 (s, 1H). MS (ES+): m/z 473.03 (100) [MH$^+$]. HPLC: $t_R$=2.08 min (ZQ2000, polar_5 min).

EXAMPLE 234

4-[4-([1,2,3]Triazolo[4,5-b]pyridin-3-yloxy)-7H-pyrrolo[2,3-d]pyrimidin-6-yl]-3,6-dihydro-2H-pyridine-1-carboxylic acid tert-butyl ester

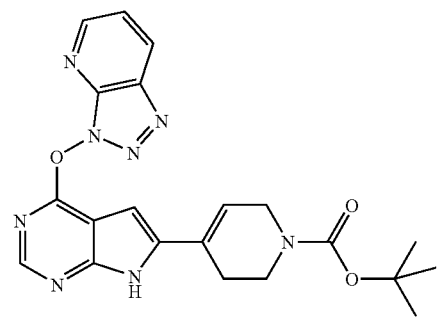

A solution of 4-(4-chloro-7H-pyrrolo[2,3-d]pyrimidin-6-yl)-3,6-dihydro-2H-pyridine-1-carboxylic acid tert-butyl ester (11.5 mg, 0.0343 mmol, 1 eq) and 1-hydroxy-7-azabenzotriazole (HOAt) (5.6 mg, 0.041 mmol, 1.2 eq) in n-butanol (1 mL) was stirred at 80° C. for 15 h. Solid that had formed during the course of the reaction was filtered over a Hirsh funnel and washed with minimal n-butanol. The filtrate was concentrated in vacuo. To a solution of the solid (3-[6-(1,2,3,6-tetrahydropyridin-4-yl)-7H-pyrrolo[2,3-d]pyrimidin-4-yloxy]-3H-[1,2,3]triazolo[4,5-b]pyridine) (6.4 mg, 0.015 mmol, 1 eq) in DMSO (1 mL), di-tert-butyldicarbonate (5.0 mg, 0.023 mmol, 1.5 eq) and DiPEA (20 µL, 0.1 mmol, 7 eq)

were added and the reaction was stirred at rt for 2 h. This solution was combined with the concentrated filtrate and purified on the MDPS yielding the title compound. $^1$H NMR (400 MHz, MeOH-d$_4$): δ=1.51 (s, 9H), 2.64 (s, br, 2H), 3.70 (s, br, 2H), 4.17 (s, br, 2H), 6.46 (s, br, 1H), 6.74 (s, 1H), 7.61 (dd, J=8.4, 4.4 Hz, 1H), 8.13 (s, 1H), 8.61 (d, J=8.0 Hz, 1H), 8.74 (d, J=4.4 Hz, 1H). MS (ES+): m/z 435.00 (62) [MH$^+$]. HPLC: t$_R$=3.36 min (ZQ2000, polar_5 min).

3-[6-(1,2,3,6-Tetrahydropyridin-4-yl)-7H-pyrrolo[2,3-d]pyrimidin-4-yloxy]-3H-[1,2,3]triazolo[4,5-b]pyridine

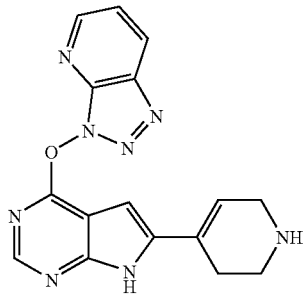

$^1$H NMR (400 MHz, DMSO-d$_6$): δ=2.81 (s, br, 2H), 3.35-3.45 (m, 2H+H$_2$O), 3.85 (s, br, 2H), 6.63 (s, 1H), 6.96 (d, J=1.6 Hz, 1H), 7.67 (dd, J=8.0, 8.4 Hz, 1H), 8.26 (s, 1H), 8.75-8.82 (m, 2H), 9.41 (s, br, —NH), 13.01 (s, —NH). MS (ES+): m/z 335.04 (2) [MH$^+$]. HPLC: t$_R$=1.73 min (ZQ2000, polar5 min).

General Procedure for Coupling of Aminopyridines with 4-(4-chloro-7H-pyrrolo[2,3-d]pyrimidin-6-yl)-3,6-dihydro-2H-pyridine-1-carboxylic Acid tert-butyl ester

EXAMPLES 235-237

To a mixture of 4-(4-chloro-7H-pyrrolo[2,3-d]pyrimidin-6-yl)-3,6-dihydro-2H-pyridine-1-carboxylic acid tert-butyl ester (134 mg, 0.4 mmol), substituted-4-aminopyridine (0.6 mmol), (R)-(+)-2,2'-bis(diphenylphosphino)-1,1'-binaphthyl (75 mg, 0.04 mmol) and sodium t-butoxide (77 mg, 0.8 mmol) was added degassed DMF (3 mL), and the reaction was heated overnight at 70° C. under N$_2$. The reaction was cooled to RT, filtered and purified through mass directed HPLC purification system. The product obtained was further purified by preparative TLC using DCM:methanol mixture as eluent to afford pure product.

EXAMPLE 235

4-{4-[2-(4-Methylpiperazin-1-yl)-pyridin-4-ylamino]-7H-pyrrolo[2,3-d]pyrimidin-6-yl}-3,6-dihydro-2H-pyridine-1-carboxylic acid tert-butyl ester

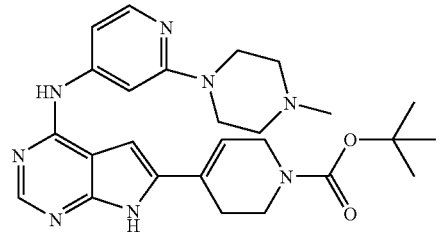

Following the general procedure described above, and employing 2-(4-methylpiperazin-1-yl)-pyridin-4-ylamine, the reaction afforded 4-{4-[2-(4-methylpiperazin-1-yl)-pyridin-4-ylamino]-7H-pyrrolo[2,3-d]pyrimidin-6-yl}-3,6-dihydro-2H-pyridine-1-carboxylic acid tert-butyl ester. $^1$H NMR (400 MHz, CD$_3$OD): δ=8.21-8.26 (m, 1H), 7.82-7.86 (m, 1H), 7.46 (d, J=7.1 Hz, 1H), 7.09-7.11 (m, 1H), 6.64 (s, 1H), 6.38-6.43 (m, 1H), 6.19 (bs, 1H), 4.01 (bs, 1H), 3.52-3.57 (m, 2H), 3.40-3.44 (m, 4H), 3.17-3.20 (m, 1H), 2.46-2.51 (m, 6H), 2.26 (s, 3H), 1.39 (s, 9H); MS (ES+): m/z 491.11 (100) [MH$^+$]; HPLC: t$_R$=1.90 min (ZQ2000, polar_5 min).

2-(4-Methylpiperazin-1-yl)-pyridin-4-ylamine

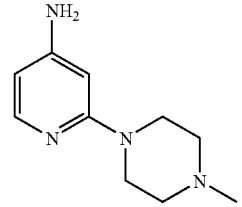

To a mixture of 1-methyl-4-(4-nitropyridin-2-yl)-piperidine (450 mg, 2.024 mmol), iron powder (1.130 g, 20.2 mmol), ethanol (8 mL) and water (2 mL) was added concentrated HCl (0.055 mL, 0.6 mmol) and the mixture was heated to reflux for 3 h. The reaction mixture was cooled to RT, filtered, filter cake washed with ethanol and the filtrate was evaporated. To the residue, aqueous saturated sodium bicarbonate solution (5 mL) and water (20 mL) were added and extracted with DCM (3×40 mL). The DCM extract was washed with brine, dried over anhydrous sodium sulphate and evaporated to afford the title compound as a reddish pink solid. MS (ES+): m/z 193.27 (100) [MH$^+$]; HPLC: t$_R$=0.32 min (ZQ2000, polar_5 min).

1-Methyl-4-(4-nitropyridin-2-yl)-piperazine

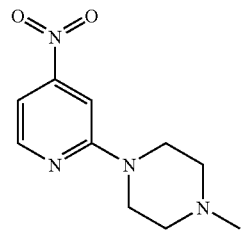

To a solution of 2-chloro-4-nitropyridine (793 mg, 5 mmol) in pyridine (10 mL) was added 1-methylpipeazine (0.555 mL, 5 mmol) and the mixture was heated to 90° C. overnight. The reaction mixture was evaporated under reduced pressure, water was added to the residue followed by saturated aqueous sodium bicarbonate (3 mL) and extracted with DCM (4×50 mL). The combined DCM layer was washed with brine, dried over anhydrous sodium sulfate and evaporated under reduced pressure. The crude product was purified by chromatography on silica gel [Jones Flashmaster, 70 g/150 mL cartridge, eluting with DCM:Methanol 100:0→98:2], yielding the title compound as orange-yellow solid (311 mg, 28%). $^1$H NMR (400 MHz, CDCl$_3$): δ=8.36 (dd, J=5.3, 0.36 Hz, 1H), 7.32 (d, J=1.6 Hz, 1H), 7.24 (dd, J=5.4, 1.8 Hz, 1H), 3.67 (t, J=5.3 Hz, 4H), 2.53 (t, J=5.2 Hz, 4H), 2.36 (s, 3H); MS (ES+): m/z 223.21 (100) [MH$^+$]; HPLC: $t_R$=0.49 & 1.37 min (ZQ2000, polar_5 min).

EXAMPLE 236

4-{4-[2-Chloro-6-(4-methylpiperazin-1-yl)-pyridin-4-ylamino]-7H-pyrrolo[2,3-d]pyrimidin-6-yl}-3,6-dihydro-2H-pyridine-1-carboxylic acid tert-butyl ester

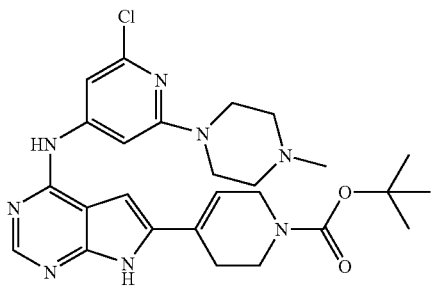

Following the general procedure described above, and employing 2-chloro-6-(4-methylpiperazin-1-yl)-pyridin-4-ylamine, the reaction afforded the title compound. $^1$H NMR (400 MHz, CD$_3$OD): δ=8.23-8.27 (m, 1H), 7.21-7.24 (m, 2H), 6.87 (s, 1H), 6.42 (s, 1H), 6.20 (bs, 1H), 4.02 (bs, 1H), 3.50-3.60 (m, 2H), 3.41-3.47 (m, 4H), 3.19-3.21 (m, 1H), 2.42-2.47 (m, 6H), 2.25 (s, 3H), 1.40 (s, 9H); MS (ES+): m/z 525.04 (100) [MH$^+$]; HPLC: $t_R$=2.31 min (ZQ2000, polar_5 min).

2-Chloro-6-(4-methylpiperazin-1-yl)-pyridin-4-ylamine & 2,6-Bis-(4-methylpiperazin-1-yl)-pyridin-4-ylamine

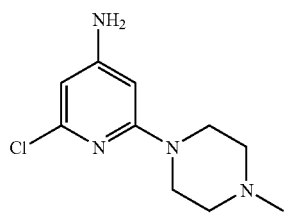

and

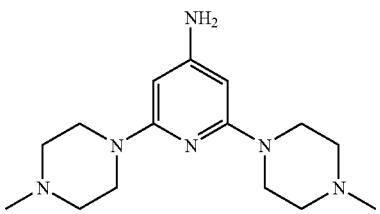

A mixture of 4-amino-2,6-dichloropyridine (1.00 g, 6.14 mmol) and 1-methylpiperazine (0.68 mL, 6.1 mmol) in pyridine (10 mL) was heated at 150° C. for 3 d under N$_2$. The reaction mixture was evaporated under reduced pressure, and to the residue water was added followed by saturated aqueous sodium bicarbonate (5 mL) and extracted with DCM (4×50 mL). The combined DCM layer was washed with brine, dried over anhydrous sodium sulfate and evaporated under reduced pressure. The crude product was purified by chromatography on silica gel [Jones Flashmaster, 70 g/150 mL cartridge, eluting with DCM:2N NH$_3$ in methanol [100:0→75:25], yielding the title compounds. 2-Chloro-6-(4-methylpiperazin-1-yl)-pyridin-4-ylamine: MS (ES+): m/z 227.18 (100) [MH$^+$]; HPLC: $t_R$=0.48 & 1.07 min (ZQ2000, polar_5 min). 2,6-Bis-(4-methylpiperazin-1-yl)-pyridin-4-ylamine: MS (ES+): m/z 291.21 (100) [MH$^+$]; HPLC: $t_R$=0.31 min (ZQ2000, polar_5 min).

EXAMPLE 237

4-{4-[2,6-Bis-(4-methylpiperazin-1-yl)-pyridin-4-ylamino]-7H-pyrrolo[2,3-d]pyrimidin-6-yl}-3,6-dihydro-2H-pyridine-1-carboxylic acid tert-butyl ester

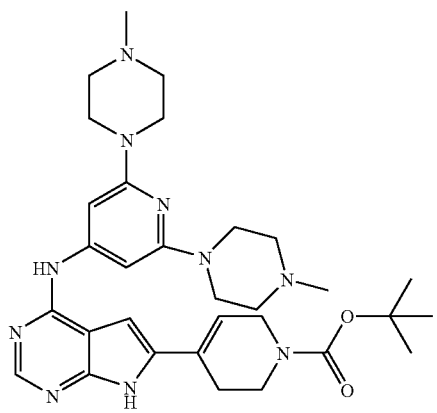

Following the general procedure described above, and employing 2,6-bis-(4-methylpiperazin-1-yl)-pyridin-4-ylamine, the reaction afforded the title compound. $^1$H NMR (400 MHz, CD$_3$OD+CDCl$_3$): δ=8.27-8.31 (m, 1H), 6.48-6.55 (m, 3H), 6.19 (bs, 1H), 4.09 (bs, 2H), 3.60 (t, J=5.6 Hz, 2H), 3.47-3.51 (m, 8H), 2.50-2.54 (m, 10H), 2.30 (s, 6H), 1.45 (s, 9H); MS (ES+): m/z 589.13 (100) [MH$^+$]; HPLC: $t_R$=1.84 min (ZQ2000, polar_5 min).

EXAMPLE 238

4-[4-(6-Carbamoylpyridin-3-ylamino)-7H-pyrrolo[2,3-d]pyrimidin-6-yl]-3,6-dihydro-2H-pyridine-1-carboxylic acid tert-butyl ester

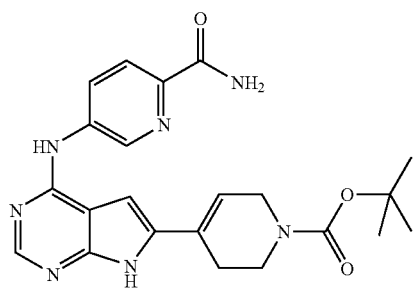

Into the DMF (1 mL) solution of 4-(4-chloro-7H-pyrrolo[2,3-d]pyrimidin-6-yl)-3,6-dihydro-2H-pyridine-1-carboxylic acid tert-butyl ester (122 mg, 0.363 mmol) was added t-BuOK (1M in t-BuOH, 0.726 mL, 0.726 mmol) dropwise at RT under $N_2$ over 5 min. The mixture was then put in an ice/water bath and stirred for 10 min. After that time, the DMF (1 mL) solution of 5-aminopyridine-2-carboxylic acid amide (99.5 mg, 0.726 mmol) was added into the above mixture dropwise. The reaction mixture was warmed to RT. $Pd_2(dba)_3 \cdot CHCl_3$ (9.4 mg, 2.5% eq.) and R(+)-BINAP (22.6 mg, 0.1 eq.) were added, and the mixture was heated at 100° C. for 24 h. The mixture was filtered and the filtrate was concentrated in vacuo. The crude was submitted to MS directed purification. A brown oil was obtained that was purified further by HPLC to obtain the title compound as an off-white solid. $^1$H NMR (DMSO-$d_6$, 400 MHz): δ=1.50 (s, 9H), 2.50 (m, 2H), 3.64 (t, 2H, J=5.6 Hz), 4.12 (brs, 2H), 6.50 (brs, 1H), 6.88 (s, 1H), 7.53 (d, 1H, J=4.2 Hz), 8.04-8.05 (m, 1H), 8.08 (d, 1H, J=8.8 Hz), 8.44 (s, 1H), 8.68 (dd, 1H, J=2.4 & 8.4 Hz), 9.12 (d, 1H, J=2.4 Hz), 9.91 (s, 1H), 12.18 (s, 1H). MS (ES+): m/z 436.10 (100) [MH$^+$]. HPLC: $t_R$=2.75 min (ZQ2000, polar_5 min).

5-Aminopyridine-2-carboxylic acid amide

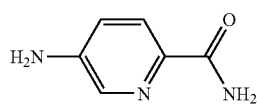

MeOH (30 mL) was added into the mixture of 5-aminopyridine-2-carbonitrile (1191 mg, 10.00 mmol), NaBO$_3$·H$_2$O (2995 mg, 30.00 mmol), and H$_2$O (30 mL), and the mixture was then heated at 50° C. for 16 h. The mixture was then concentrated in vacuo, then treated with water (30 mL), and extracted with EtOAc (4×50 mL). The combined extracts were dried over MgSO$_4$, filtered, and concentrated in vacuo to obtain a yellow solid. The solid was triturated with 40 mL of 40% EtOAc/hexane to yield the title compound as yellow solid. $^1$H NMR (DMSO-$d_6$, 400 MHz): δ=5.86 (s, 2H), 6.89 (dd, 1H, J=2.4 & 8.4 Hz), 7.07 (brs, 1H), 7.59 (brs, 1H), 7.64 (d, 1H, J=8.4 Hz), 7.83 (d, 1H, J=2.4 Hz). MS (ES+): m/z 138.18 (100) [MH$^+$]. HPLC: $t_R$=0.75 min (ZQ2000, polar_5 min).

EXAMPLE 239

4-[4-(6-Methoxypyridin-3-ylamino)-7H-pyrrolo[2,3-d]pyrimidin-6-yl]-3,6-dihydro-2H-pyridine-1-carboxylic acid tert-butyl ester

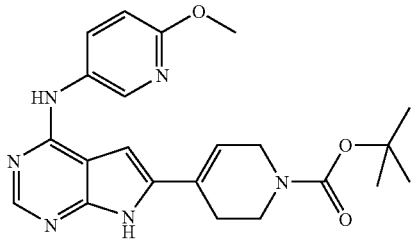

The title compound was obtained following the procedure for the synthesis of 4-[4-(6-carbamoylpyridin-3-ylamino)-7H-pyrrolo[2,3-d]pyrimidin-6-yl]-3,6-dihydro-2H-pyridine-1-carboxylic acid tert-butyl ester, but using 6-methoxypyridin-3-ylamine in place of 5-aminopyridine-2-carboxylic acid amide. $^1$H NMR (CD$_3$OD, 400 MHz): δ=1.40 (s, 9H), 2.47 (m, 2H), 3.57 (m, 2H), 4.00 (m, 2H), 6.19 (brs, 1H), 6.50 (s, 1H), 6.74 (s, 1H, d, 1H, J=9.2 Hz), 7.48 (dd, 1H, J=2.8 Hz & 8.8 Hz), 8.04-8.05 (m, 1H), 8.07 (s, 1H), 8.31 (d, 1H, J=3.2 Hz). MS (ES+): m/z 423.08 (100) [MH$^+$]. HPLC: $t_R$=2.86 min (ZQ2000, polar_5 min).

EXAMPLE 240

4-[4-(6-Oxo-1,6-dihydropyridin-3-ylamino)-7H-pyrrolo[2,3-d]pyrimidin-6-yl]-3,6-dihydro-2H-pyridine-1-carboxylic acid tert-butyl ester

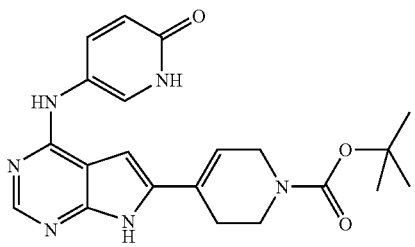

Into the suspension of 4-[4-(6-methoxypyridin-3-ylamino)-7H-pyrrolo[2,3-d]pyrimidin-6-yl]-3,6-dihydro-2H-pyridine-1-carboxylic acid tert-butyl ester (68.4 mg, 79% purity, 0.127 mmol) and NaI (19.1 mg, 0.127 mmol) in CH$_3$CN (10 mL) was added trimethylsilyl chloride (1 M in THF, 0.765 mL, 0.765 mmol) at rt. The mixture was then heated at 80° C. in a flask under N$_2$ for 48 h. After that time, the mixture was cooled at 0° C. and the aqueous solution (H$_2$O, 8 mL) of NaHCO$_3$ (159 mg) and NaS$_2$O$_4$·5H$_2$O (318 mg) was added while stirring. The solid was filtered off and washed with water to obtain a brown-red solid. Boc$_2$O (30.8 mg, 0.140 mmol), DMAP (17.1 mg, 0.140 mmol) and the above solid were dissolved in pyridine and the mixture was stirred at rt for 18 h. After that time, the mixture was concentrated in vacuo to obtain a green-yellow oil that was submitted for MS directed purification. One obtained the title compound as off-white solid. $^1$H NMR (DMSO-$d_6$, 400 MHz): δ=1.44 (s, 9H), 2.46 (brs, 2H), 3.56 (t, 2H, J=5.4 Hz), 4.00 (brs, 2H), 6.38 (s, 1H), 6.40 (s, 1H), 6.67-7.70 (m, 1H), 8.02 (d, 1H, J=2.4 Hz), 8.20 (s, 1H), 9.06 (s, 1H), 11.40 (brs, 1H), 11.92 (s 1H). MS (ES+): m/z 409.05 (100) [MH$^+$]. HPLC: t$_R$=2.33 min (ZQ2000, polar__5 min).

EXAMPLE 241

4-[4-(1-Methyl-6-oxo-1,6-dihydropyridin-3-ylamino)-7H-pyrrolo[2,3-d]pyrimidin-6-yl]-3,6-dihydro-2H-pyridine-1-carboxylic acid tert-butyl ester

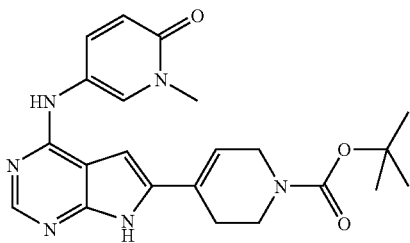

The title compound was obtained following the General method for the reaction of amines with tert-butyl 4-(4-chloro-7H-pyrrolo[2,3-d]pyrimidin-6-yl)-3,6-dihydropyridine-1-(2H)-carboxylate, using 5-amino-1-methyl-1H-pyridin-2-one. $^1$H NMR (DMSO-d$_6$, 400 MHz): δ=1.44 (s, 9H), 2.43 (brs, 2H), 3.46 (s, 3H), 3.56 (t, 2H, J=6.4 Hz), 4.04 (brs, 2H), 6.38 (brs, 1H), 6.43 (d, 1H, J=9.6 Hz), 6.61 (s, 1H), 7.63 (dd, 1H, J=2.8 & 9.6 Hz), 8.18-8.20 (m, 2H), 9.07 (s, 1H), 11.91 (s, 1H). MS (ES+): m/z 423.07 (100) [MH$^+$]. HPLC: t$_R$=2.38 min (ZQ2000, polar__5 min).

5-Amino-1-methyl-1H-pyridin-2-one

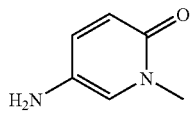

To a suspension of 5-nitro-1-methyl-2(1H)-pyridone (154 mg, 0.999 mmol) in ethyl acetate (3 mL) and ethanol (3 mL) was added 5% Pd—C (36 mg), and the resulting mixture was stirred under hydrogen atmosphere overnight. The reaction mixture was filtered and the filtrate was concentrated in vacuo to obtain the title compound as light-green oil. $^1$H NMR (CD$_3$OD 400 MHz): δ=3.53 (s, 3H), 6.49 (d, 1H, J=9.6 Hz), 7.07 (d, 1H, J=3.2 Hz), 7.28 (dd, 1H, J=2.8 & 9.6 Hz). MS (ES+): m/z 125.04 (100) [MH$^+$]. HPLC: t$_R$=0.43 min (ZQ2000, polar__5 min).

1-Methyl-5-nitro-1H-pyridin-2-one

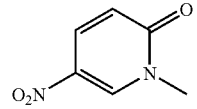

Tetra-N-butylammonium bromide (3220 mg, 10.00 mmol), sodium hydroxide (400.0 mg, 10.00 mmol) and methyl iodide (3113 µL, 50.00 mmol) were sequentially added into the two-phase mixture of 2-hydroxy-5-nitropyridine (700.0 mg, 5.000 mmol) in water (25 mL) and methylene chloride (50 mL). The above mixture was stirred at rt for 1 h and then partitioned between CH$_2$Cl$_2$ (50 mL) and water (75 mL). The aqueous layer was extracted with CH$_2$Cl$_2$ (50 mL). The combined organic phases were dried over MgSO$_4$, filtered, and concentrated in vacuo to obtain a beige solid. Silica gel (134 g) was used to purify the above solid eluting with 2500 mL EtOAc to obtain the title compound as beige powder. $^1$H NMR (CDCl$_3$, 400 MHz): δ=3.66 (s, 3H), 6.57 (d, 1H, J=10.0 Hz), 8.10 (dd, 1H, J=2.8 & 10.0 Hz), 8.63 (d, 1H, J=2.8 Hz). MS (ES+): m/z 155.15 (100) [MH$^+$]. HPLC: t$_R$'1.69 min (ZQ2000, polar__5 min).

EXAMPLE 242

4-[4-(1-Methyl-6-oxo-1,6-dihydropyridin-3-ylamino)-7H-pyrrolo[2,3-d]pyrimidin-6-yl]-3,6-dihydro-2H-pyridine-1-carboxylic acid tert-butylamide

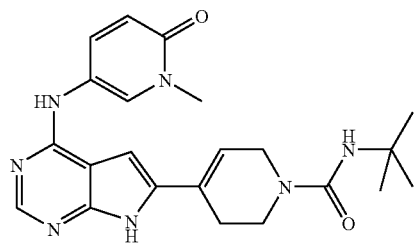

4-[4-(1-Methyl-6-oxo-1,6-dihydropyridin-3-ylamino)-7H-pyrrolo[2,3-d]pyrimidin-6-yl]-3,6-dihydro-2H-pyridine-1-carboxylic acid tert-butyl ester (38.0 mg, 0.0845 mmol), 9M of Hydrogen chloride in Methanol (2 mL) and Methanol (2 mL) were combined, and the above miture was stirred at rt for 3 h. The reaction mixture was concentrated in vacuo to obtain a black solid. DMF (3 mL), NEt$_3$ (58.9 µL, 0.423 mmol) and tert-butyl isocyanate (14.5 µL, 0.127 mol) were added, and the mixture was stirred at rt under N$_2$ for 1.5 h. Another portion of tert-butyl isocyanate was added and the reaction was stirred overnight. The mixture was concentrated in vacuo, and the residue was purified by HPLC to obtain the title compound as pink solid. $^1$H NMR (CD$_3$OD, 400 MHz): δ=1.36 (s, 9H), 2.56 (brs, 2H), 3.61 (m, 2H), 3.62 (s, 3H), 4.07 (brs, 2H), 6.29 (brs, 1H), 6.58 (s, 1H), 6.60 (d, 1H, J=9.6 Hz), 7.71 (dd, 1H, J=2.8 & 9.6 Hz), 8.16 (brs, 2H), 8.19 (s, 1H), 8.25 (d, 1H, J=2.4 Hz). MS (ES+): m/z 422.12 (100) [MH⁺]. HPLC: $t_R$=20.11 min (ZQ2000, polar_5 min).

EXAMPLE 243

4-[4-(4-Carbamoylphenylamino)-7H-pyrrolo[2,3-d]-pyrimidin-6-yl]-3,6-dihydro-2H-pyridine-1-carboxylic acid tert-butyl ester

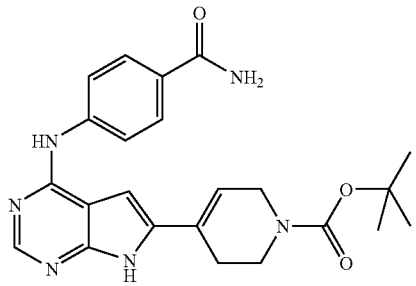

The title compound was obtained following the General method for the reaction of amines with tert-butyl 4-(4-chloro-7H-pyrrolo[2,3-d]pyrimidin-6-yl)-3,6-dihydropyridine-1(2H)-carboxylate, using 4-aminobenzamide. ¹H NMR (DMSO-d₆, 400 MHz): δ=1.44 (s, 9H), 2.50 (m, 2H), 3.58 (t, 2H, J=5.2 Hz), 4.05 (brs, 2H), 6.43 (brs, 1H), 6.84 (s, 1H), 7.21 (brs, 1H), 7.86 (m, 3H), 8.00 (d, 1H, J=8.4 Hz), 8.34 (s, 1H), 9.57 (s, 1H), 12.04 (s, 1H). MS (ES+): m/z 435.09 (100) [MH⁺]. HPLC: $t_R$=2.61 min (ZQ2000, polar_5 min).

EXAMPLE 244

4-[4-(1-Oxo-2,3-dihydro-1H-isoindol-5-ylamino)-7H-pyrrolo[2,3-d]pyrimidin-6-yl]-3,6-dihydro-2H-pyridine-1-carboxylic acid tert-butyl ester

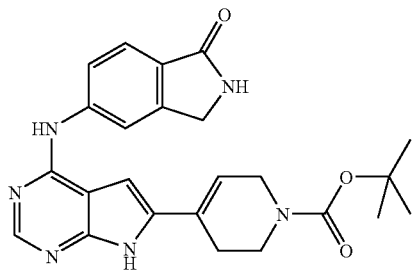

The title compound was obtained following the General method for the reaction of amines with tert-butyl 4-(4-chloro-7H-pyrrolo[2,3-d]pyrimidin-6-yl)-3,6-dihydropyridine-1(2H)-carboxylate, using 5-amino-2,3-dihydroisoindol-1-one. ¹H NMR (DMSO-d₆, 400 MHz): δ 1.47 (s, 9H), 2.50 (m, 2H), 3.61 (t, 2H, J=5.6 Hz), 4.08 (brs, 2H), 4.42 (s, 2H), 6.46 (brs, 1H), 6.89 (s, 1H), 7.65 (d, 1H, J=8.4 Hz), 7.90 (dd, 1H, J=0.8 & 8.4 Hz), 8.37-8.40 (m, 3H), 9.67 (s, 1H), 12.08 (s, 1H). MS (ES+): m/z 447.10 (100) [MH⁺]. HPLC: $t_R$=2.61 min (ZQ2000, polar_5 min).

5-Amino-2,3-dihydroisoindol-1-one

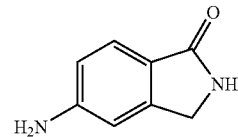

Iron powder (158 mg, 2.83 mmol), water (61 μL), and HCl (37%, 5 μL, 0.566 mmol) were added into the suspension of 5-nitro-2,3-dihydroisoindol-1-one (50.4 mg, 0.283 mmol) in EtOH (754 μL). The above mixture was heated at 95° C. for 2 h. After that time, several drops of 7N NH₃ in MeOH were added to basify the solution, and the solid was filtered off. The filtrate was concentrated in vacuo to obtain a light-yellow solid that was purified by preparative TLC eluting with 10% MeOH/CH₂Cl₂ to give a light-yellow solid of 5-amino-2,3-dihydroisoindol-1-one. ¹H NMR (CD₃OD, 400 MHz): δ=7.48 (s, 1H), 8.08 (s, 2H), 9.91 (s, 1H), 10.66 (d, 1H, J=8.8 Hz). MS (ES+): m/z 149.21 (100) [MH⁺]. HPLC: $t_R$=1.20 min (ZQ2000, polar_5 min).

5-Nitro-2,3-dihydroisoindol-1-one

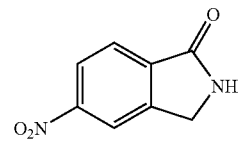

AIBN (58.6 mg, 0.357 mmol), NBS (785 mg, 4.46 mmol), and 2-methyl-4-nitrobenzoic acid methyl ester (696 mg, 3.57 mmol) were suspended in CCl₄ (35 mL) in a sealed tube. The above mixture was flushed with N₂ for 5 min and heated at 80° C. for 22 h. After cooling, the solid was filtered off and the filtrate was concentrated to dryness to obtain a crude light-brown solid. To above solid was added NH₃ (7 N in MeOH, 5 mL), and the mixture was stirred at rt for 2 h and concentrated in vacuo to obtain a yellow solid. This crude solid was triturated with EtOAc (15 mL) and was then cooled at −20° C. The mixture was filtered to obtain the title compound as yellow solid. ¹H NMR (DMSO-d₆, 400 MHz): δ=4.51 (s, 2H), 7.13 (brs, 2H), 7.91 (d, 1H, J=8.4 Hz), 8.25 (dd, 1H, J=2.0 & 8.4 Hz), 8.48 (d, 1H, J=2.0 Hz), 9.04 (brs, 1H). MS (ES+): m/z 179.22 (100) [MH⁺]. HPLC: $t_R$32 2.14 min (ZQ2000, polar_5 min).

2-Methyl-4-nitrobenzoic acid methyl ester

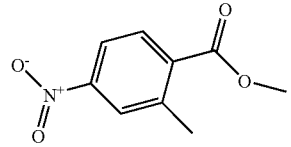

H₂SO₄ (98%, 0.030 mL) was added dropwise into the MeOH (30 mL) solution of 2-methyl-4-nitrobenzoic acid at rt. The mixture was then heated at 55° C. After 50 h, the solvent was removed in vacuo and the residue was partitioned

EXAMPLE 245

4-[4-(4-Benzyloxy-3-chlorophenylamino)-7H-pyrrolo[2,3-d]pyrimidin-6-yl]-3,6-dihydro-2H-pyridine-1-carboxylic acid tert-butyl ester

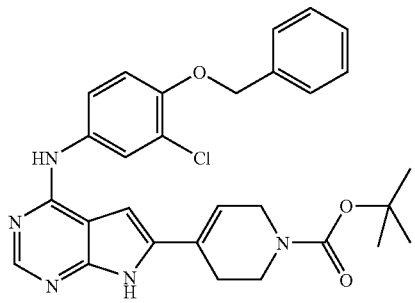

The title compound was obtained following the General method for the reaction of amines with tert-butyl 4-(4-chloro-7H-pyrrolo[2,3-d]pyrimidin-6-yl)-3,6-dihydropyridine-1(2H)-carboxylate, using 4-benzyloxy-3-chlorophenylamine. $^1$H NMR (DMSO-d$_6$, 400 MHz): δ=1.44 (s, 9H), 2.52 (brs, 2H), 3.57 (t, 2H, J=5.6 Hz), 4.05 (brs, 2H), 5.19 (s, 2H), 6.40 (brs, 1H), 6.74 (s, 1H), 7.23 (d, 1H, J=9.2 Hz), 7.33-7.37 (m, 1H), 7.40-7.44 (m, 2H), 7.48-7.50 (m, 2H), 7.68-7.72 (m, 1H), 8.13-8.15 (m, 1H), 8.27 (d, 1H, J=1.2 Hz), 9.34 (s, 1H), 11.96 (s, 1H). MS (ES+): m/z 532.02/533.98 (100/38) [MH$^+$]. HPLC: t$_R$=3.81 min (ZQ2000, polar_5 min).

EXAMPLE 246

4-[4-(2-Aminobenzothiazol-6-ylamino)-7H-pyrrolo[2,3-d]pyrimidin-6-yl]-3,6-dihydro-2H-pyridine-1-carboxylic acid tert-butyl ester

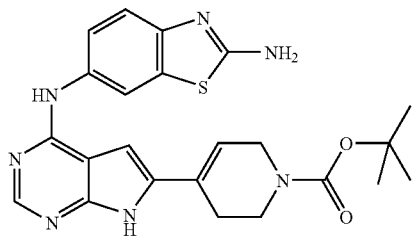

The title compound was obtained following the General method for the reaction of amines with tert-butyl 4-(4-chloro-7H-pyrrolo[2,3-d]pyrimidin-6-yl)-3,6-dihydropyridine-1(2H)-carboxylate, using benzothiazole-2,6-diamine. $^1$H NMR (DMSO-d$_6$, 400 MHz): δ=1.40 (s, 9H), 2.50 (brs, 2H), 3.52 (brs, 2H), 4.00 (brs, 2H), 6.29 (brs, 1H), 6.65 (brs, 1H), 7.21-7.46 (m, 4H), 8.21-8.28 (m, 2H), 9.27 (brs, 1H), 11.88 (brs, 1H). MS (ES+): m/z 464.03 (50) [MH$^+$]. HPLC: t$_R$=2.34 min (ZQ2000, polar_5 min).

EXAMPLE 247

4-[4-(2-Amino-1H-benzimidazol-5-ylamino)-7H-pyrrolo[2,3-d]pyrimidin-6-yl]-3,6-dihydro-2H-pyridine-1-carboxylic acid tert-butyl ester

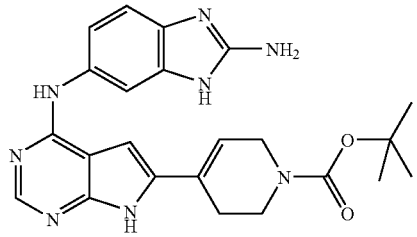

The title compound was obtained following the General method for the reaction of amines with tert-butyl 4-(4-chloro-7H-pyrrolo[2,3-d]pyrimidin-6-yl)-3,6-dihydropyridine-1(2H)-carboxylate, using benzimidazole-2,5-diamine, except that the heating was conducted at 140° C. for 24 h. $^1$H NMR (CD$_3$OD, 400 MHz): δ=1.50 (s, 9H), 2.48 (brs, 2H), 3.61 (brs, 2H), 4.11 (brs, 2H), 6.24 (brs, 1H), 6.36 (brs, 1H), 7.12 (dd, 1H, J=2.0 & 8.8 Hz), 7.19 (d, 1H, J=8.0 Hz), 7.48 (s, 1H), 8.12 (s, 1H). MS (ES+): m/z 447.03 (60) [MH$^+$]. HPLC: t$_R$=1.97 min (ZQ2000, polar_5 min).

EXAMPLE 248

4-{4-[3-(2H-[1,2,3]Triazol-4-yl)-phenylamino]-7H-pyrrolo[2,3-d]pyrimidin-6-yl}-3,6-dihydro-2H-pyridine-1-carboxylic acid tert-butyl ester

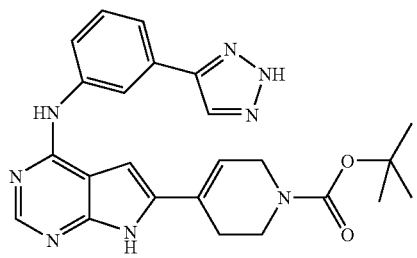

The title compound was obtained following the General method for the reaction of amines with tert-butyl 4-(4-chloro-7H-pyrrolo[2,3-d]pyrimidin-6-yl)-3,6-dihydropyridine-1 (2 h)-carboxylate, using 3-(2H-[1,2,3]triazol-4-yl)phenylamine. $^1$H NMR (DMSO-d$_6$, 400 MHz): δ=1.40 (s, 9H), 2.47 (brs, 2H), 3.54 (t, 2H, J=5.2 Hz), 4.01 (brs, 2H), 6.37 (brs, 1H), 6.80 (s, 1H), 7.37 (t, 1H, J=8.0 Hz), 7.43 (d, 1H, J=8.0 Hz), 7.98 (d, 1H, J=8.4 Hz), 8.19 (s, 1H), 8.26-8.31 (m, 2H), 9.44 (s, 1H), 11.94 (s, 1H). MS (ES+): m/z 458.96 (100) [MH$^+$]. HPLC: t$_R$=2.74 min (ZQ2000, polar_5 min).

3-(2H-[1,2,3]Triazol-4-yl)phenylamine

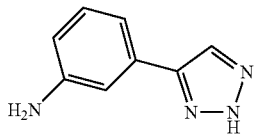

The mixture of azidotrimethylsilane (137 μL, 1.03 mmol) and 3-amino-phenylacetylene (117 mg, 1.00 mmol) was heated in a sealed tube at 150° C. for 16 h. After that time, the mixture was cooled down and triturated by EtOAc/hexane (50%, 10 mL). The mother liquor was purified by TLC eluting with 7% MeOH/CH$_2$Cl$_2$. to give the title compound as brown oil. $^1$H NMR (CD$_3$OD, 400 MHz): δ=6.61-6.64 (m, 1H), 7.01-7.09 (m, 3H), 7.94 (s, 1H). MS (ES+): m/z 161.20 (38) [MH$^+$]. HPLC: t$_R$=1.54 min (ZQ2000, polar_5 min).

EXAMPLE 249

4-[4-(3-Thiophen-2-yl-phenylamino)-7H-pyrrolo[2,3-d]pyrimidin-6-yl]-3,6-dihydro-2H-pyridine-1-carboxylic acid tert-butyl ester

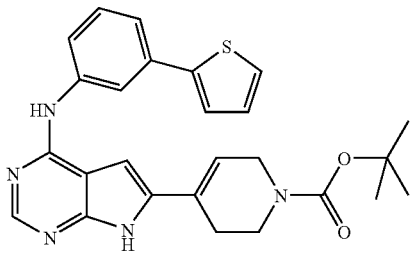

The title compound was obtained following the General method for the reaction of amines with tert-butyl 4-(4-chloro-7H-pyrrolo[2,3-d]pyrimidin-6-yl)-3,6-dihydropyridine-1(2H)-carboxylate, using 3-thiophen-2-ylphenylamine. $^1$H NMR (CD$_3$OD, 400 MHz): δ=1.52 (s, 9H), 2.58 (brs, 2H), 3.68 (brs, 2H), 4.14 (brs, 2H), 6.31 (brs, 1H), 6.69 (s, 1H), 7.11-7.13 (m, 1H), 7.38-7.43 (m, 4H), 7.68-7.71 (m, 1H), 8.07 (s, 1H), 8.26 (s, 1H). MS (ES+): m/z 473.95 (100) [MH$^+$]. HPLC: t$_R$=3.71 min (ZQ2000, polar_5 min).

EXAMPLE 250

4-{4-[3-(4-Methylpiperazin-1-yl)-phenylamino]-7H-pyrrolo[2,3-d]pyrimidin-6-yl}-3,6-dihydro-2H-pyridine-1-carboxylic acid tert-butyl ester

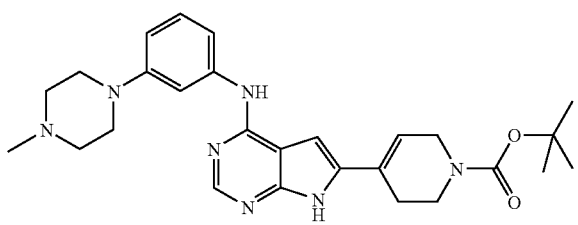

The title compound was obtained following the General method for the reaction of amines with tert-butyl 4-(4-chloro-7H-pyrrolo[2,3-d]pyrimidin-6-yl)-3,6-dihydropyridine-1(2H)-carboxylate, using 3-(4-methylpiperazin-1-yl)-phenylamine. $^1$H NMR (CD$_3$OD, 400 MHz): δ=1.51 (s, 9H), 2.56 (brs, 2H), 2.86 (s, 3H), 3.31 (brs, 4H), 3.54 (brs, 4H), 3.67 (brs, 2H), 4.14 (brs, 2H), 6.29 (brs, 1H), 6.63 (s, 1H), 6.78-6.80 (m, 1H), 7.20 (d, 1H, J=8.0 Hz), 7.26-7.30 (m, 1H), 7.53 (s, 1H), 8.22 (s, 1H), 8.41 (brs, 2H). MS (ES+): m/z 490.08 (100) [MH$^+$]. HPLC: t$_R$=2.15 min (ZQ2000, polar_5 min).

3-(4-Methylpiperazin-1-yl)-phenylamine

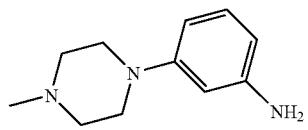

Into the solution of 1-methyl-4-(3-nitrophenyl)-piperazine (123 mg, 0.556 mmol) in ethanol (5 mL) was added Pd (10% on carbon, 12.0 mg). The mixture was degassed for 5 min and was then was stirred under H$_2$ atmosphere (balloon pressure) at rt for 24 h. After that time, the reaction mixture was filtered and the filtrate was concentrated in vacuo to obtain the title compound as light yellow oil. $^1$H NMR (CDCl$_3$, 400 MHz): δ=2.35 (s, 3H), 2.56 (t, 41H, J=5.2 Hz), 3.18 (t, 41H, J=5.0 Hz), 3.60 (brs, 2H), 6.21-6.23 (m, 1H), 6.27 (t, 1H, J=2.2 Hz), 6.36-6.39 (m, 1H), 7.05 (m, 1H). MS (ES+): m/z 192.31 (100) [MH$^+$]. HPLC: t$_R$=0.39 min (ZQ2000, polar_5 min).

1-Methyl-4-(3-nitrophenyl)-piperazine

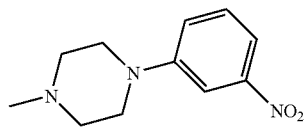

A mixture of 1-fluoro-3-nitrobenzene (282 mg, 2.00 mmol), 1-methylpiperazine (401 mg, 4.00 mmol), potassium carbonate (276 mg, 2.00 mmol), and DMF (3 mL) was stirred and heated at 110° C. for 24 h. After cooling to rt, the mixture was poured into brine (10 mL) and extracted with EtOAc (3×10 mL). The combined organic extracts were extracted with aqueous HCl (1 N, 2×20 mL). The acidic extracts were basified by aqueous NaOH until pH>10. The basified aqueous solution was extracted with EtOAc (2×30 mL). The extracts were then washed with H$_2$O (3×20 mL) and brine (20 mL), dried over MgSO$_4$, filtered and concentrated in vacuo to give the title compound as yellow oil. $^1$H NMR (CD$_3$OD, 400 MHz): δ=2.22 (s, 3H), 2.48 (t, 4H, J=5.0 Hz), 3.16 (t, 4H, J=5.2 Hz), 7.16-7.18 (m, 1H), 7.27 (t, 1H, J=8.2 Hz), 7.46-7.49 (m, 1H), 7.57 (t, 1H, J=2.2 Hz). MS (ES+): m/z 222.26 (100) [MH$^+$]. HPLC: t$_R$=1.55 min (ZQ2000, polar_5 min).

EXAMPLE 251

4-{4-[3-Chloro-5-(4-methylpiperazin-1-yl)-phenyl-amino]-7H-pyrrolo[2,3-d]pyrimidin-6-yl}-3,6-dihydro-2H-pyridine-1-carboxylic acid tert-butyl ester

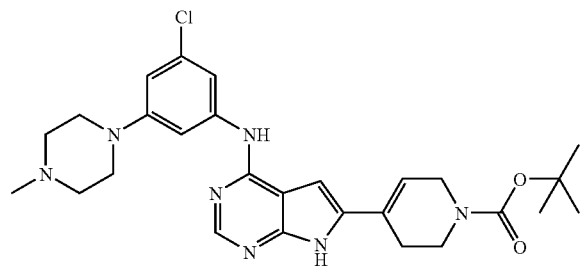

A mixture of 4-(4-chloro-7H-pyrrolo[2,3-d]pyrimidin-6-yl)-3,6-dihydro-2H-pyridine-1-carboxylic acid tert-butyl ester (88.0 mg, 0.263 mmol), 3-chloro-5-(4-methylpiperazin-1-yl)-phenylamine (71.2 mg, 0.316 mmol), trifluoroacetic acid (203 µL, 2.63 mmol), and DMF (2 mL) was stirred in a sealed tube at 70° C. for 18 h. The mixture was concentrated in vacuo, sodium bicarbonate (221 mg, 2.63 mmol), di-tert-butyldicarbonate (86.1 mg, 0.394 mmol), and DMF (2 mL) were added to the residue, and the resulting mixture was stirred at rt under $N_2$ for 16 h. After that time, the mixture was filtered, and the filtrate was concentrated in vacuo and submitted for MS-directed purification. One obtained the title compound as light-brown solid. $^1$H NMR (CD$_3$OD, 400 MHz): δ=1.50 (s, 9H), 2.57 (brs, 2H), 2.86 (s, 3H), 3.29 (brs, 4H), 3.46 (brs, 4H), 3.67 (brs, 2H), 4.13 (brs, 2H), 6.29 (brs, 1H), 6.68 (s, 1H), 6.74 (s 1H), 7.44 (s, 1H), 7.47 (s, 1H), 8.28 (s, 1H). M (ES+): m/z 523.99/525.95(100/40) [MH$^+$]. HPLC: $t_R$ (polar_5 mins)=2.28 min (ZQ2000, polar_5 min).

3-Chloro-5-(4-methylpiperazin-1-yl)-phenylamine

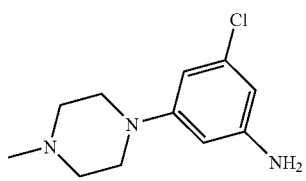

The title compound was obtained by following the procedure for the reduction of 5-nitro-2,3-dihydroisoindol-1-one with iron powder, but using 1-(3-chloro-5-nitrophenyl)-4-methylpiperazine. $^1$H NMR (DMSO-d$_6$, 400 MHz): δ=2.33 (s, 3H), 2.58 (brs, 4H), 3.11 (brs, 4H), 5.21 (brs, 2H), 6.05-6.06 (m, 2H), 6.12-6.13 (m, 1H). MS (ES+): m/z 226.17/228.19 (100/33) [MH$^+$]. HPLC: $t_R$=1.42 min (ZQ2000, polar_5 min).

1-(3-Chloro-5-nitrophenyl)-4-methylpiperazine

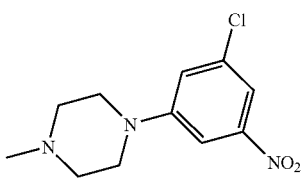

The title compound was obtained by following the procedure for the halide displacement of 3-fluoronitrobenzene with methylpiperazine, but using 1,3-dichloro-5-nitrobenzene and conducting the reaction at 130° C. $^1$H NMR (CDCl$_3$, 400 MHz): δ=2.34-2.40 (m, 3H), 2.56-2.59 (m, 4H), 3.30-3.33(m, 4H), 7.11-7.15 (m, 1H), 7.61-7.64 (m, 2H). MS (ES+): m/z 256.12/258.07 (100/33) [MH$^+$]. HPLC: $t_R$=1.94 min (ZQ2000, polar_5 min).

EXAMPLE 252

4-{4-[3-Chloro-5-(4-methylpiperazin-1-yl)-phenyl-amino]-7H-pyrrolo[2,3-d]pyrimidin-6-yl}-3,6-dihydro-2H-pyridine-1-carboxylic acid tert-butylamide

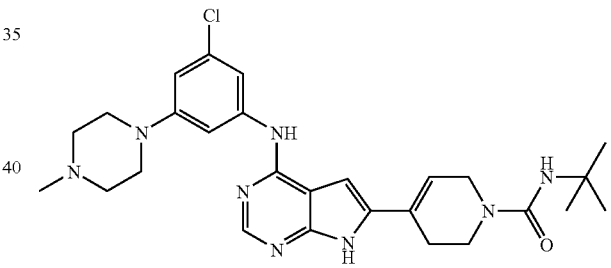

A mixture of 4-(4-chloro-7H-pyrrolo[2,3-d]pyrimidin-6-yl)-3,6-dihydro-2H-pyridine-1-carboxylic acid tert-butyl ester (88.0 mg, 0.263 mmol), 3-chloro-5-(4-methylpiperazin-1-yl)-phenylamine (71.2 mg, 0.316 mmol), trifluoroacetic acid (243 µL, 3.16 mmol), and DMF (2 mL) was stirred in a sealed tube at 80° C. for 16 h. After cooling, N,N-diisopropylethylamine (550 µL, 3.16 mmol) was added, and the mixture turned into a dark clear solution. Into above solution was added tert-butyl isocyanate (36.0 µL, 0.316 mmol) and the solution was stirring at rt for 1 h. After that time, the mixture was concentrated in vacuo to obtain dark-brown oil that was submitted for MS-directed purification to obtain a light-brown oil. Further purification by HPLC gave the title compound as an off-white powder. $^1$H NMR (DMSO-d$_6$, 400 MHz): δ=1.29 (s, 9H), 2.23 (s, 3H), 2.46 (t, 4H, J=4.6 Hz), 3.18 (t, 4H, J=4.8 Hz), 3.53 (t, 2H, J=5.4 Hz), 4.00 (brs, 2H), 5.79 (s, 1H), 6.43 (s, 1H), 6.63 (d, 1H, J=1.6 Hz), 6.78 (s 1H), 7.30 (s, 1H), 7.75 (d, 1H, J=1.6 Hz), 8.32 (s, 1H), 9.27 (s, 1H), 11.98 (s, 1H). MS (ES+): m/z 522.98/525.01(100/33) [MH$^+$]. HPLC: $t_R$=2.13 min (ZQ2000, polar_5 min).

EXAMPLE 253

4-{4-[3-(2-Aminothiazol-4-yl)-phenylamino]-7H-pyrrolo[2,3-d]pyrimidin-6-yl}-3,6-dihydro-2H-pyridine-1-carboxylic acid tert-butyl ester

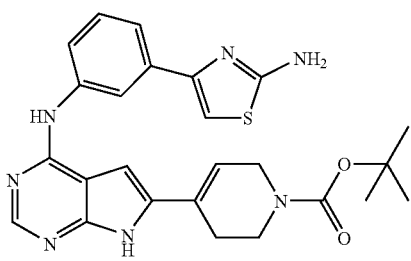

The title compound was obtained following the General method for the reaction of amines with tert-butyl 4-(4-chloro-7H-pyrrolo[2,3-d]pyrimidin-6-yl)-3,6-dihydropyridine-1(2H)-carboxylate, using 4-(3-aminophenyl)-thiazol-2-ylamine. $^1$H NMR (CD$_3$OD, 400 MHz): δ=1.52 (s, 9H), 2.58 (brs, 2H), 3.68 (brs, 2H), 4.13 (brs, 2H), 6.30 (brs, 1H), 6.65 (s, 1H), 6.86 (s, 1H), 7.36-7.40 (m, 1H), 7.52-7.54 (m, 1H), 7.65-7.67 (m, 1H), 8.07-8.08 (m, 1H), 8.24 (s, 1H). MS (ES+): m/z 489.94 (38) [MH$^+$]. HPLC: t$_R$=2.71 min (ZQ2000, polar_5 min).

4-(3-Aminophenyl)-thiazol-2-ylamine

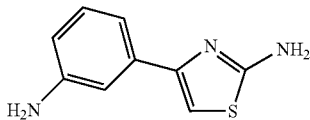

The title compound was obtained by following the procedure for the reduction of 5-nitro-2,3-dihydroisoindol-1-one with iron powder, but using 4-(3-nitrophenyl)-thiazol-2-ylamine. $^1$H NMR (DMSO-d$_6$, 400 MHz): δ=5.03 (brs, 2H), 6.43 (d, 1H, J=7.2 Hz), 6.75 (s, 1H), 6.89-7.00 (m, 5H). MS (ES+): m/z 192.24 (100) [MH$^+$]. HPLC: t$_R$=1.45 min (ZQ2000, polar_5 min).

4-(3-Nitrophenyl)-thiazol-2-ylamine

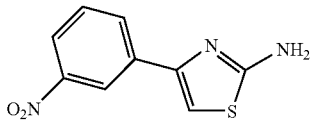

A solution of 3-nitrophenacyl bromide (244 mg, 1.00 mmol) and thiourea (76.1 mg, 1.00 mmol) in DMF (2 mL) was stirred at 60° C. for 16 h. The mixture was concentrated in vacuo to obtain a yellow solid that was then washed with H$_2$O and dried to yield a yellow solid (206 mg). The solid was dissolved in DMSO and purified by SCX column (4×6 mL capacity), eluted with CH$_2$Cl$_2$ (4×6 mL), MeOH (4×12 mL) and then released by NH$_3$ (7 N in MeOH, 4×6 mL) to give a light-yellow solid of 4-(3-aminophenyl)-thiazol-2-ylamine. $^1$H NMR (DMSO-d$_6$, 400 MHz): δ=7.24 (brs, 2H), 7.35 (s, 1H), 7.65-7.69 (m, 1H), 8.10-8.13 (m, 1H), 8.23-8.26 (m, 1H), 8.62 (t, 1H, J=1.8 Hz). MS (ES+): m/z 223.12 (45) [M]+]. HPLC: t$_R$=2.82 min (ZQ2000, polar_5 min). The combined CH$_2$Cl$_2$ and MeOH solution was concentrated in vacuo to give a yellow solid of 4-(3-aminophenyl)-1H-imidazole-2-thiol. $^1$H NMR (DMSO-d$_6$, 400 MHz): δ=7.75 (t, 1H, J=8.0 Hz), 8.01 (d, 1H, J=0.8 Hz), 8.17-8.20 (m, 1H), 8.35-8.37 (m, 1H), 8.56 (d, 1H, J=1.6 Hz), 8.72 (t, 1H, J=1.8 Hz), 12.56 (s, 1H). MS (ES+): m/z 222.12 (15) [MH$^+$]. HPLC: t$_R$=2.97 min (ZQ2000, polar 5 min).

EXAMPLE 254 tert-Butyl 4-[4-(3-iodo-4-methoxyphenylamino)-7H-pyrrolo[2,3-d]pyrimidin-6-yl]-3,6-dihydro-2H-pyridine-1-carboxylate

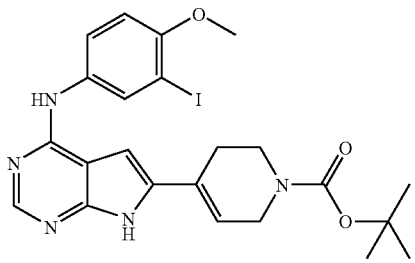

3-Iodo-4-methoxyaniline (0.670 g, 2.0 mmol) was added to a solution of tert-butyl 4-(chloro-7H-pyrrolo[2,3-d]pyrimidin-6-yl)-3,6-dihydro-2H-pyridine-1-carboxylate (0.598 g, 2.4 mmol) in n-butanol (10 mL). The mixture was heated to 95° C. for 15 h. The solvent was removed and the residue was purified by silica gel chromatography (5% MeOH in dichloromethane) to afford the title compound. $^1$H-NMR (DMSO-d$_6$, 400 MHz): δ=1.43 (s, 9H), 2.46 (m, 2H), 3.56 (m, 2H), 3.80 (s, 3H), 4.03 (m, 2H), 6.38 (s, 1H), 6.72 (s, 1H), 7.00 (d, J=9.2 Hz, 1H), 7.85 (dd, J=2.8, 8.8 Hz, 1H), 8.34 (s, 1H), 9.27 (s, 1H), 11.93 (s, 1H). MS (ES+): m/z 547.91 [MH$^+$]. HPLC: t$_R$=3.39 min (ZQ2000, polar_5 min).

EXAMPLE 255 tert-Butyl 4-[4-(3-iodophenylamino)-7H-pyrrolo[2,3-d]pyrimidin-6-yl]-3,6-dihydro-2H-pyridine-1-carboxylate

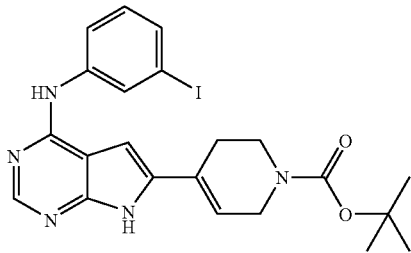

The title compound was prepared following the above procedure, but using 3-iodoaniline. MS (ES+): m/z 517.91. HPLC: t$_R$=3.75 min (ZQ2000, polar_5 min).

EXAMPLE 256 tert-Butyl 4-{4-[3-(1H-pyrrol-2-yl)phenylamino]-7H-pyrrolo[2,3-d]pyrimidin-6-yl}-3,6-dihydro-2H-pyridine-1-carboxylate

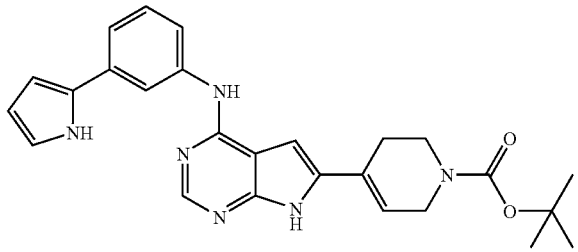

To a stirred solution of tert-butyl 4-[4-(3-iodophenylamino)-7H-pyrrolo[2,3-d]pyrimidin-6-yl]-3,6-dihydro-2H-pyridine-1-carboxylate (77.6 mg, 0.15 mmol), N-Boc-2-pyrrolylboronic acid (47.5 mg, 0.225 mmol) and potassium carbonate (41.5 mg, 0.3 mmol) in dioxane/water (4:1) (11.0 mL) was added PdCl$_2$(dppf).CH$_2$Cl$_2$ (12.2 mg, 0.015 mmol). The mixture was heated at reflux for 18 h. Solvents were removed in vacuo and the residue was dissolved in DMF ($\approx$2 mL). The DMF solution was filtered and purified by HPLC to afford the title compound. $^1$H-NMR(CD$_3$OD, 400 MHz): δ=1.50 (s, 9H), 2.53 (m, 2H), 3.64 (m, 2H), 4.11 (m, 2H), 6.16 (t, J=2.8 Hz, 2H), 6.26 (s, 1H), 6.48 (dd, J=1.2, 3.6 Hz, 1H), 6.60 (s, 1H), 6.81 (dd, J=1.2, 2.8 Hz, 1H), 7.31 (s, 1H), 7.33 (s, 1H), 7.42-7.45 (m, 1H), 7.87 (s, 1H), 8.21 (s, 1H). MS (ES+): m/z 457.08 [MH$^+$]. HPLC: t$_R$=3.15 min (ZQ2000, polar__5 min).

EXAMPLE 257 tert-Butyl 4-[4-(3-thiophen-3-ylphenylamino)-7H-pyrrolo[2,3-d]pyrimidin-6-yl]-3,6-dihydro-2H-pyridine-1-carboxylate

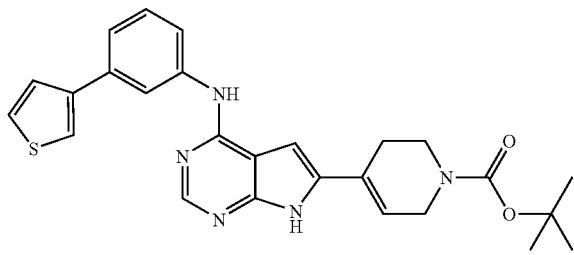

The title compound was prepared following the procedure for tert-butyl 4-{4-[3-(1H-pyrrol-2-yl)phenylamino]-7H-pyrrolo[2,3-d]pyrimidin-6-yl}-3,6-dihydro-2H-pyridine-1-carboxylate, but using 3-thienylboronic acid. $^1$H-NMR (CD$_3$OD, 400 MHz): δ=1.50 (s, 9H), 2.56 (m, 2H), 3.67 (m, 2H), 4.13 (m, 2H), 6.30 (s, br, 1H), 6.66 (s, 1H), 7.37-7.42 (m, 2H), 7.47-7.50 (m, 2H), 7.63-7.66 (m, 2H), 8.01-8.02 (m, 1H), 8.23 (s, 1H). MS (ES+): m/z 474.04 [MH$^+$]. HPLC: t$_R$=3.58 min (ZQ2000, polar__5 min).

EXAMPLE 258 tert-Butyl 4-{4-[3-(1H-pyrazol-4-yl)phenylamino]-7H-pyrrolo[2,3-d]pyrimidin-6-yl}-3,6-dihydro-2H-pyridine-1-carboxylate

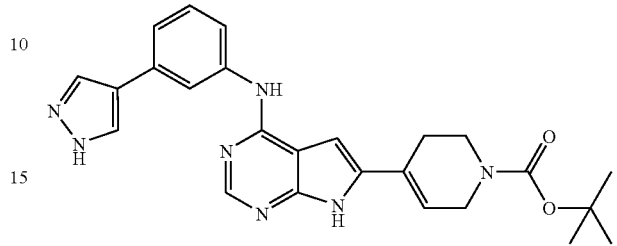

The title compound was prepared following the procedure for tert-butyl 4-{4-[3-(1H-pyrrol-2-yl)phenylamino]-7H-pyrrolo[2,3-d]pyrimidin-6-yl}-3,6-dihydro-2H-pyridine-1-carboxylate, but using 4-(4,4,5,5-tetramethyl-[1,3,2]dioxaborolan-2-yl)-1H-pyrazole. $^1$H-NMR (CD$_3$OD, 400 MHz): δ=1.50 (s, 9H), 2.57 (m, 2H), 3.67 (m, 2H), 4.14 (m, 2H), 6.29 (s, br, 1H), 6.66 (s, 1H), 7.33-7.39 (m, 2H), 7.58 (dt, J=2.0, 7.2 Hz, 1H), 7.92 (d, J=1.2 Hz, 1H), 7.93-8.00 (m, 2H), 8.23 (s, 1H). MS (ES+): m/z 458.03 [MH$^+$]. HPLC: t$_R$=2.70 min (ZQ2000, polar__5 min).

EXAMPLE 259 tert-Butyl 4-{4-[4-methoxy-3-(1H-pyrrol-2-yl)-phenylamino]-7H-pyrrolo[2,3-d]pyrimidin-6-yl}-3,6-dihydro-2H-pyridine-1-carboxylate

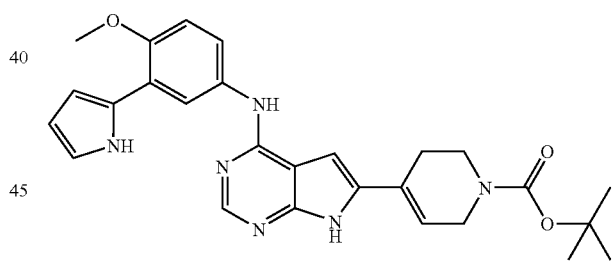

To a stirred solution of tert-butyl 4-[4-(3-iodo-4-methoxyphenylamino)-7H-pyrrolo[2,3-d]pyrimidin-6-yl]-3,6-dihydro-2H-pyridine-1-carboxylate (82.1 mg, 0.15 mmol), N-Boc-2-pyrrolylboronic acid (47.5 mg, 0.225 mmol) and potassium carbonate (41.5 mg, 0.3 mmol) in dioxane/water (4:1) (11.0 mL) was added PdCl$_2$(dppf).CH$_2$Cl$_2$ (12.2 mg, 0.015 mmol). The mixture was heated at reflux for 18 h. Solvents were removed and the residue was dissolved in DMF ($\approx$2 mL). The DMF solution was filtered and sent to mass-directed HPLC purification. The pyrrole-Boc-protected product obtained was stirred with NaOH (s, 369 mg) in 9 mL of methanol at rt for 17 h. The solvent was removed and the residue was dissolved in DMF (1.5 mL) and purified by HPLC purification to give the title compound. $^1$H-NMR (DMSO-d$_6$, 400 MHz): δ=1.43 (s, 9H), 2.46 (m, 2H), 3.56 (m, 2H), 3.87 (s, 3H), 4.03 (m, 2H), 6.11 (q, J=2.4 Hz, 1H), 6.37 (s, br, 1H), 6.49 (s, 1H), 6.71 (s, 1H), 6.81 (q, J=2.4 Hz, 1H), 7.04 (d, J=9.2 Hz, 1H), 7.63 (d, J=6.0 Hz, 1H), 7.92 (d, J=2.4

Hz, 1H), 8.20 (d, J=4.4 Hz, 1H), 9.22 (s, 1H), 10.91 (s, 1H), 11.89 (s, 1H). MS (ES+): m/z 487.04 [MH⁺]. HPLC: t$_R$=2.96 min (ZQ2000, polar__5 min).

EXAMPLE 260 tert-Butyl 4-[4-(4-methoxy-3-thiophen-3-ylphenyl-amino)-7H-pyrrolo[2,3-d]pyrimidin-6-yl]-3,6-dihydro-2H-pyridine-1-carboxylate

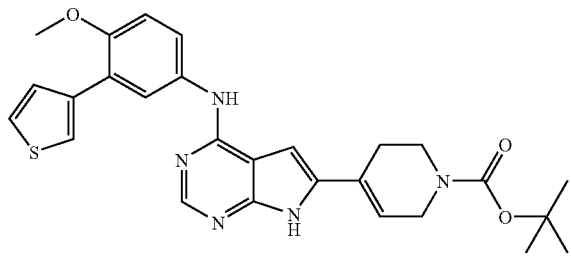

To a stirred solution of tert-butyl 4-[4-(3-iodo-4-methoxyphenylamino)-7H-pyrrolo[2,3-d]pyrimidin-6-yl]-3,6-dihydro-2H-pyridine-1-carboxylate (82.1 mg, 0.15 mmol), 3-thienylboronic acid (28.8 mg, 0.225 mmol) and potassium carbonate (41.5 mg, 0.3 mmol) in dioxane/water (4:1) (1.0 mL) was added [1,1'-bis(diphenylphosphino)ferrocene]dichloro-palladium(II), complex with dichloromethane (1:1) (12 mg, 0.015 mmol). The resulting mixture was bubbled N$_2$ for 5 min and then heated at reflux for 16 h. After cooled to rt, the solvents were removed under reduced pressure. The residue was dissolved in DMF (2 mL). The DMF solution was filtered and purified by HPLC to give the title compound. ¹H-NMR (DMSO-d$_6$, 400 MHz): δ=1.43 (s, 9H), 3.56 (m, 2H), 3.82 (s, 3H), 4.03 (m, 2H), 6.38 (s, br, 1H), 6.73 (s, 1H), 7.09 (d, J=9.2 Hz, 1H), 7.45 (dd, J=0.8, 5.2 Hz, 1H), 7.60 (dd, J=2.8, 4.8 Hz, 1H), 7.76 (m, 1H), 7.80 (dd, J=2.8, 8.8 Hz, 1H), 7.94 (d, J=2.8 Hz, 1H), 8.22 (s, 1H), 9.26 (s, 1H), 11.90 (s, 1H). MS (ES+): m/z 504.05 [MH⁺]. HPLC: t$_R$=3.22 min (ZQ2000, polar__5 min).

EXAMPLE 261 tert-Butyl 4-[4-(4-hydroxy-3-thiazol-5-ylphenylamino)-7H-pyrrolo[2,3-d]pyrimidin-6-yl]-3,6-dihydro-2H-pyridine-1-carboxylate

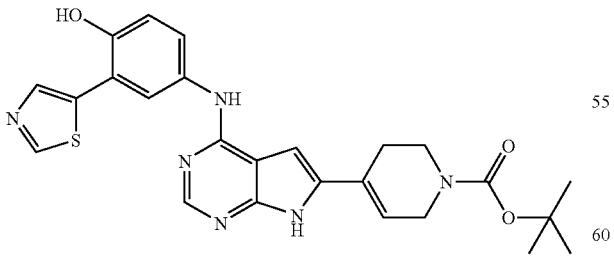

4-Amino-2-thiazol-5-ylphenol (70.0 mg, 0.364 mmol) was added to a solution of tert-butyl 4-(chloro-7H-pyrrolo[2,3-d]pyrimidin-6-yl)-3,6-dihydro-2H-pyridine-1-carboxylate (192 mg, 0.546 mol) in n-butanol (2.0 mL). The reaction was stirred at 120° C. for 14 h. The solvent was removed and the residue was dissolved in DMF. The DMF solution was filtered and purified by HPLC to give the title compound. ¹H-NMR (DMSO-d$_6$, 400 MHz): δ=1.43 (s, 9H), 2.46 (m, 2H), 3.56 (t, J=5.6 Hz, 2H), 4.04 (s, 2H), 6.38 (s, br, 1H), 6.70 (s, 1H), 6.97 (d, J=8.8 Hz, 1H), 7.70 (dd, J=2.4, 8.8 Hz, 1H), 8.07 (d, J=2.4 Hz, 1H), 8.22 (s, 1H), 8.32 (s, 1H), 9.05 (s, 1H), 9.23 (s, 1H), 10.25 (s, br, 1H), 11.88 (s, 1H). MS (ES+): m/z 490.94 (MH⁺). HPLC: t$_R$=2.51 min (ZQ2000, polar__5 min).

4-Amino-2-thiazol-5-ylphenol

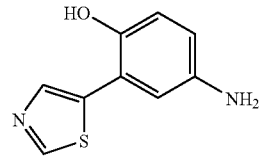

4-Nitro-2-thiazol-5-ylphenol (100 mg, 0.4 mmol) in methanol (5 mL) was hydrogenated in the presence of 10% Pd/C (80 mg) for 16 h. The reaction mixture was filtered through a Celite pad. The filtrate was concentrated in vacuo to afford the title compound, which was used directly in the next step without purification. ¹H-NMR (CD$_3$OD, 400 MHz): δ=7.18 (d, J=8.8 Hz, 1H), 7.39 (dd, J=2.4, 8.8 h z, 1H), 7.91 (d, J=2.8 Hz, 1H), 8.91 (s, 1H), 9.97 (s, 1H). MS (ES+): m/z 193.14 [MH⁺]. HPLC: t$_R$=0.48 min (ZQ2000, polar__5 min).

4-Nitro-2-thiazol-5-ylphenol

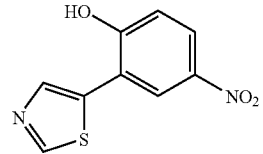

A mixture of 5-(2-methoxy-5-nitrophenyl)thiazole (156 mg, 0.660 mmol) and anhydrous sodium sulfide (309 mg, 3.96 mmol) in N-methylpyrrolidinone (2 mL) was heated at 160° C. for 2 h. After cooling to rt, the solvent was removed in vacuo, and the residue was partitioned between water (5 mL) and dichloromethane (20 mL). The organic phase was separated, dried over MgSO$_4$, and purified by silica gel chromatography (3% MeOH in dichloromethane) to afford the title compound. ¹H-NMR (CDCl$_3$, 400 MHz): δ=7.18 (d, J=9.2 Hz, 1H), 8.08 (dd, J=1.6, 9.2 Hz, 1H), 8.45 (s, 1H), 8.52 (d, J=2.4 Hz, 1H), 8.86 (s, 1H), 11.95 (s, br, 1H). MS (ES+): m/z 223.14 [MH⁺]. HPLC: t$_R$=2.68 min (ZQ2000, polar__5 min).

5-(2-Methoxy-5-nitrophenyl)thiazole

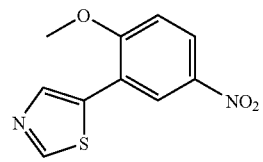

N₂ was bubbled through a solution of 2-iodo-4-nitroanisole (2.8 g, 10.0 mmol), thiazole (2.55 g, 30.0 mmol), potassium acetate (1.47 g, 15.0 mmol), and tetrakis(triphenyl phosphine)palladium(0) (0.81 g, 0.70 mmol) in DMF (15 mL) for 10 min. The mixture was then heated to 100° C. and stirred overnight. Solvent was removed under reduced pressure, and the residue was purified by silica gel chromatography (dichloromethane:MeOH=96:4) to afford the title compound. ¹H-NMR (CDCl₃, 400 MHz): δ=4.08 (s, 3H), 7.09 (d, J=9.2 Hz, 1H), 8.25 (dd, J=2.8, 9.2 Hz, 1H), 8.37 (s, 1H), 8.54 (d, J=3.2 Hz, 1H), 8.88 (s, 1H). MS (ES+): m/z 237.13 [MH⁺]. HPLC: $t_R$=3.07 min (ZQ2000, polar_5 min).

EXAMPLE 262 tert-Butyl 4-[4-(3-chloro-5-thiazol-5-ylphenylamino)-7H-pyrrolo[2,3-d]pyrimidin-6-yl]-3,6-dihydro-2H-pyridine-1-carboxylate

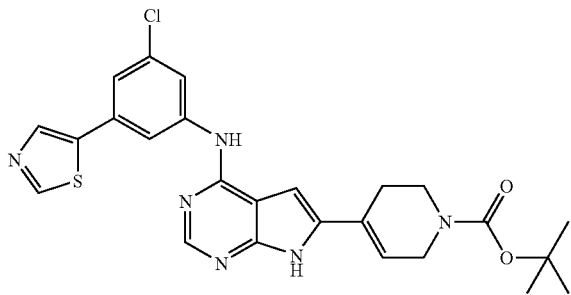

The title compound was obtained following the General method for the reaction of amines with tert-butyl 4-(4-chloro-7H-pyrrolo[2,3-d]pyrimidin-6-yl)-3,6-dihydropyridine-1 (2H)-carboxylate, using 3-chloro-5-thiazol-5-ylphenylamine. ¹H-NMR (CD₃OD, 400 MHz): δ=1.50 (s, 9H), 2.58 (m, 2H), 3.67 (m, 2H), 4.13 (s, 2H), 6.30 (s, br, 1H), 6.72 (s, 1H), 7.35 (t, J=1.6 Hz, 1H), 8.05-8.07 (m, 2H), 8.21 (d, J=0.4 Hz, 1H), 8.33 (s, 1H), 9.00 (d, J=0.8 Hz, 1H). MS (ES+): m/z 508.81 (MH⁺, ³⁵Cl), 510.91 (MH⁺, ³⁷Cl). HPLC: $t_R$=3.75 min (ZQ2000, polar_5 min).

3-Chloro-5-thiazol-5-ylphenylamine

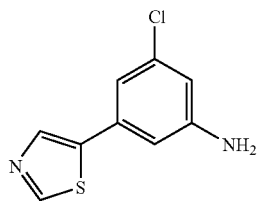

To a solution of 5-(3-chloro-5-nitrophenyl)thiazole (0.120 g, 0.499 mmol) inethanol (5 mL) was added tin dichloride (0.9555 g, 4.986 mmol). The mixture was stirred at 90° C. for 1.5 h. After cooling to rt, sat. NaHCO₃ (aq) was added dropwise to adjust the pH to 9-10. The resulting suspension was filtered through a Celite pad. The filtrate was concentrated to dryness in vacuo to afford the title compound, which was used directly in the next step without purification. ¹H-NMR (CD₃OD, 400 MHz): δ=6.67 (t, J=2.0 Hz, 1H), 6.85 (t, J=1.6 Hz, 1H), 6.88 (t, J=1.6 Hz, 1H), 8.10 (s, 1H), 8.94 (s, 1H). MS (ES+): m/z 211.10 (MH⁺, ³⁵Cl), 213.12 (MH⁺, ³⁷Cl). HPLC: $t_R$=2.92 min (ZQ2000, polar_5 min).

5-(3-Chloro-5-nitrophenyl)thiazole

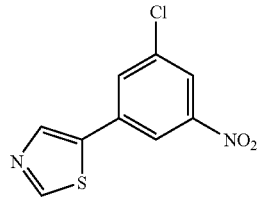

N₂ was bubbled through a solution of 3,5-dichloronitrobenzene (0.384 g, 2.00 mmol), thiazole (0.204 g, 2.40 mmol), potassium acetate (0.294 g, 3.00 mmol), and tetrakis(triphenylphosphine)palladium(0) (0.16 g, 0.14 mol) in DMF (5 mL) for 10 min. The mixture was then heated to 120° C. and stirred for 17 h. The solvents were removed in vacuo. The residue was purified by chromatography on silica gel (MeOH in methylene chloride: 1% to 5%) to afford the title compound. ¹H-NMR (CDCl₃, 400 MHz): δ=7.88 (t, J=2.0 Hz, 1H), 8.20 (t, J=2.4 Hz, 1H), 8.22 (s, 1H), 8.32 (t, J=2.0 Hz, 1H), 8.90 (s, 1H). MS (ES+): m/z 241.04 (³⁵Cl, MH⁺), 243.00 (³⁷Cl, MH⁺). HPLC: $t_R$=3.35 min (ZQ2000, polar_5 min).

EXAMPLE 263 tert-Butyl 4-{4-[3-(4-methyl-4H-[1,2,4]triazol-3-yl)-phenylamino]-7H-pyrrolo[2,3-d]pyrimidin-6-yl}-3,6-dihydro-2H-pyridine-1-carboxylate

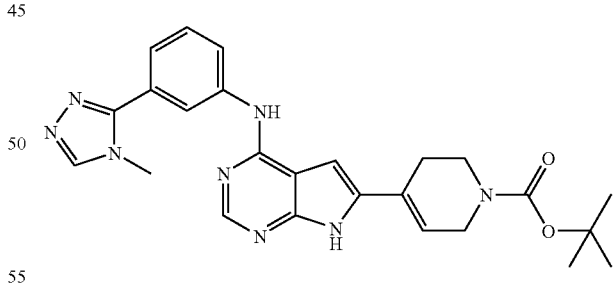

The title compound was obtained following the General method for the reaction of amines with tert-butyl 4-(4-chloro-7H-pyrrolo[2,3-d]pyrimidin-6-yl)-3,6-dihydropyridine-1 (2H)-carboxylate, using 3-(4-methyl-4H-[1,2,4]triazol-3-yl)-phenylamine. ¹H-NMR (CD₃OD, 400 MHz): δ=1.50 (s, 9H), 2.58 (m, 2H), 3.67 (m, 2H), 3.89 (s, 3H), 4.13 (m, 2H), 6.30 (s, br, 1H), 6.73 (s, 1H), 7.41 (dt, J=1.2, 7.6 Hz, 1H), 7.54 (t, J=7.6 Hz, 1H), 7.93 (dq, J=0.8, 8.4 Hz, 1H), 8.26 (s, 1H), 8.30 (t, J=1.6 Hz, 1H), 8.57 (s, 1H). MS (ES+): m/z 473.01 [MH⁺]. HPLC: $t_R$=2.60 min (ZQ2000, polar_5 min).

EXAMPLE 264 tert-Butyl 4-[4-(1H-indol-4-ylamino)-7H-pyrrolo[2,3-d]pyrimidin-6-yl]-3,6-dihydro-2H-pyridine-1-carboxylate

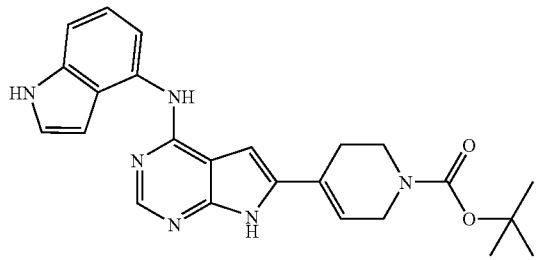

The title compound was obtained following the General method for the reaction of amines with tert-butyl 4-(4-chloro-7H-pyrrolo[2,3-d]pyrimidin-6-yl)-3,6-dihydropyridine-1 (2H)-carboxylate, using 4-aminoindole. $^1$H-NMR (CD$_3$OD, 400 MHz): δ=1.49 (s, 9H), 2.42 (m, 2H), 3.61 (m, 2H), 4.09 (m, 2H), 6.22 (br, 2H), 6.39 (dd, J=1.2, 2.8 Hz, 1H), 7.13-7.18 (m, 2H), 7.21 (d, J=3.2 Hz, 1H), 7.32-7.34 (m, 1H), 8.07 (s, 1H). MS (ES+): m/z 431.09 [MH$^+$]. HPLC: t$_R$=2.47 min (ZQ2000, polar_5 min).

EXAMPLE 265

4-[4-(Naphthalen-1-ylamino)-7H-pyrrolo[2,3-d]-pyrimidin-6-yl]-3,6-dihydro-2H-pyridine-1-carboxylic acid tert-butyl ester

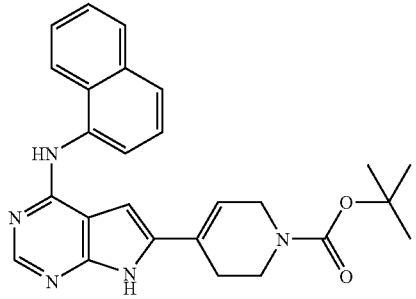

A suspension containing naphthalen-1-yl-[6-(1,2,3,6-tetrahydropyridin-4-yl)-7H-pyrrolo[2,3-d]pyrimidin-4-yl]-amine (120 mg, 0.35 mmol), di-tert-butyldicarbonate (77 mg, 0.35 mmol) and N,N-diisopropylethylamine (122 μL, 0.70 mmol) in anhydrous N,N-dimethylformamide (2 mL) was stirred overnight at rt. The reaction mixture was poured into saturated NaHCO$_3$ solution (50 mL) and extracted with EtOAc (3×40 mL). The combined organics were washed with brine (3×100 mL), dried (MgSO$_4$), filtered and concentrated. Flash chromatography (2 to 4% MeOH in DCM) gave the title compound as a white solid. $^1$H NMR (DMSO-d$_6$, 400 MHz): δ=8.28 (1H, s), 8.14-8.12 (2H, m), 7.94 (1H, d, J=7.5 Hz), 7.87 (1H, d, J=7.4 Hz), 7.67 (1H, d, J=7.1 Hz), 7.56-7.48 (3H, m), 6.13 (1H, s), 5.35 (1H, s), 4.02 (2H, s), 3.52 (2H, s), 2.21 (2H, s), 1.47 (9H, s); MS (ES+): m/z 442.08 [MH$^+$], HPLC: t$_R$=2.96 min (MicromassZQ, polar_5 min).

Naphthalen-1-yl-[6-(1,2,3,6-tetrahydropyridin-4-yl)-7H-pyrrolo[2,3-d]pyrimidin-4-yl]amine

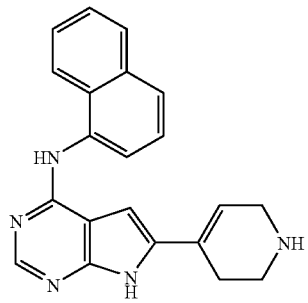

A sealed tube containing a solution of 4-(4-chloro-7H-pyrrolo[2,3-d]-pyrimidin-6-yl)-3,6-dihydro-2H-pyridine-1-carboxylic acid tert-butyl ester (250 mg, 0.75 mmol), 1-naphthylamine (160 mg, 1.12 mmol) and trifluoroacetic acid (287 μL, 3.73 mmol) in 2,2,2-trifluoroethanol (5 mL) was heated at 80° C. and maintained at this temperature overnight. The product was poured into saturated NaHCO$_3$ solution (50 mL) and the precipitate was filtered off, giving the title compound as an off-white solid. $^1$H NMR (DMSO-d$_6$, 400 MHz): δ=9.48 (1H, s), 8.14-7.92 (3H, m), 7.82 (1H, d, J=8.0 Hz), 7.64 (1H, d, J=7.2 Hz), 7.61-7.44 (3H, m), 6.40 (1H, s), 4.02 (2H, brs), 3.51 (2H, brs), 2.89 (2H, brs); MS (ES+): m/z 342.11 [MH$^+$], HPLC: t$_R$=1.71 min (MicromassZQ, polar_5 min).

EXAMPLE 266

4-[4-(Naphthalen-1-ylamino)-7H-pyrrolo[2,3-d]-pyrimidin-6-yl]-3,6-dihydro-2H-pyridine-1-carboxylic acid tert-butylamide

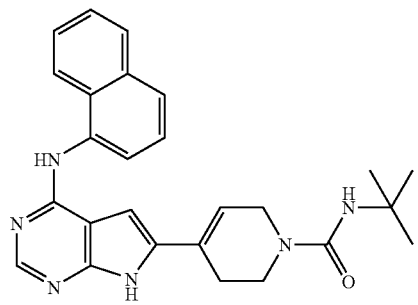

A suspension containing naphthalen-1-yl-[6-(1,2,3,6-tetrahydropyridin-4-yl)-7H-pyrrolo[2,3-d]pyrimidin-4-yl]-amine (120 mg, 0.35 mmol), tert-butyl isocyanate (35 mg, 0.35 mmol) and N,N-diisopropylethylamine (122 μL, 0.70 mmol) in anhydrous N,N-dimethylformamide (2 mL) was stirred overnight at rt. The reaction mixture was poured into saturated NaHCO$_3$ solution (50 mL) and extracted with EtOAc (3×50 ml). The combined organics were washed with brine (3×50 mL), dried (MgSO$_4$), filtered and concentrated. Flash chromatography (2 to 4% MeOH in DCM) gave the title compound as a white solid. $^1$H NMR (DMSO-d$_6$, 400 MHz): δ=8.13 (1H, s), 8.08-8.02 (2H, m), 7.89 (1H, d, J=8.1 Hz), 7.74-7.71 (1H, m), 7.63-7.54 (3H, m), 6.55 (1H, d, J=8.3 Hz), 6.43 (1H, s), 5.83 (1H, s), 4.04 (2H, s), 3.55 (2H, t, J=5.6 Hz),

EXAMPLE 267

4-[4-(6-Oxo-1-phenyl-1,6-dihydropyridin-3-ylamino)-7H-pyrrolo[2,3-d]pyrimidin-6-yl]-3,6-dihydro-2H-pyridine-1-carboxylic acid tert-butyl ester

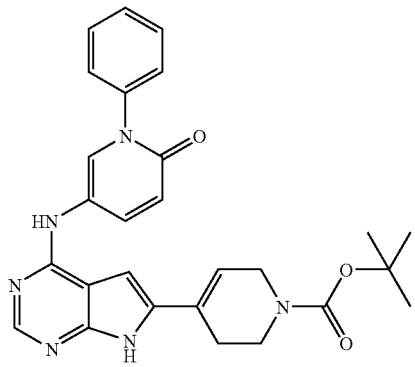

A mixture of 4-(4-chloro-7H-pyrrolo[2,3-d]pyrimidin-6-yl)-3,6-dihydro-2H-pyridine-1-carboxylic acid tert-butyl ester (75 mg, 0.22 mmol) and 5-amino-1-phenyl-1H-pyridin-2-one (50 mg, 0.27 mmol) in 1-butanol (3 mL) was heated at 120° C. overnight, LC-MS showed the desired product together with some de-Boc product. After the mixture was cooled to rt, it was diluted with methylene chloride (3 mL), then N,N-diisopropylethylamine (0.1 mL, 0.6 mmol) and di-tert-butyldicarbonate (49 mg, 0.22 mmol) were added. The resulting mixture was stirred at rt for 30 min. The mixture was diluted with EtOAc (30 mL), then washed with brine (20 mL), and dried over anhydrous sodium sulfate. The solvent was evaporated under reduced pressure, and the residue was crystallized with EtOAc/Hexane to give the title compound as a green solid. LC-MS (ES, Pos.): 485 [MH$^+$], and $^1$H NMR (DMSO-d$_6$, 400 MHz): δ 1.43 (s, 9H), 2.50 (m, 2H), 3.56 (m, 2H), 4.04 (m, 2H), 6.39 (s, 1H), 6.56 (d, J=9.7 Hz, 1H), 6.66 (s, 1H), 7.39-7.57 (m, 5H), 7.81 (dd, J=9.7, 2.7 Hz, 1H), 8.17 (s, 1H), 8.34 (d, J=2.7 Hz, 1H), 9.17 (s, 1H), 11.94 (br s, 1H).

5-Amino-1-phenyl-1H-pyridin-2-one

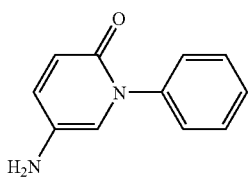

To a suspension of 5-nitro-1-phenyl-1H-pyridin-2-one (60 mg, 0.28 mmol) in ethyl acetate (2 mL) and ethanol (2 mL) was added 5% Pd—C (10 mg), the resulting mixture was stirred under hydrogen atmosphere for 3 h. The catalyst was removed by filtration, and the filtrate was concentrated to give the title compound as a green oil. The product was used to next step without further purification. LC-MS (ES, Pos.): 187 [MH$^+$], and $^1$H NMR (CDCl$_3$, 400 MHz): δ=3.09 (br s, 2H), 6.60 (d, J=9.6 Hz, 1H), 6.82 (d, J=3.0 Hz, 1H), 7.12 (dd, J=9.6, 3.0 Hz, 1H), 7.37-7.41 (m, 3H), 7.45-7.49 (m, 2H).

5-Nitro-1-phenyl-1H-pyridin-2-one

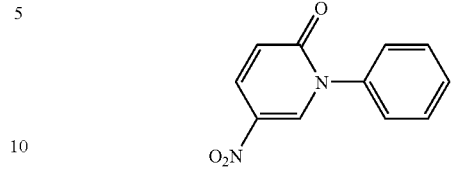

[Ref. Mederski, W. W. K. R., et al. *Tetrahedron*, 1999, 55, 12757-12770.] To a solution of 2-hydroxy-5-nitropyridine (1.07 g, 7.64 mmol) in dry methylene chloride (50 mL) were added phenylboronic acid (1.86 g, 15.3 mmol), cupric acetate (1.71 g, 9.41 mmol), pyridine (1.2 mL, 15.3 mmol), triethylamine (2.1 mL, 15.3 mmol) and activated 4 Å molecular sieves (2 g). The resulting mixture was stirred in air at rt for 2 d. The mixture was then filtered through celite and washed with methylene chloride. The crude material was purified by silica gel chromatography, eluting with CH$_2$Cl$_2$:EtOAc (85:15) to give the title compound as a white solid. LC-MS (ES, Pos.): 217 [MH$^+$], and $^1$H NMR (CDCl$_3$, 400 MHz): δ=6.67 (d, J=10.1 Hz, 1H), 7.39-7.42 (m, 2H), 7.53-7.58 (m, 3H), 8.17 (dd, J=10.1, 3.1 Hz, 1H), 8.67 (d, J=3.1 Hz, 1H).

EXAMPLE 268

4-[4-(6-Oxo-1-phenyl-1,6-dihydropyridin-3-ylamino)-7H-pyrrolo[2,3-d]pyrimidin-6-yl]-3,6-dihydro-2H-pyridine-1-carboxylic acid tert-butylamide

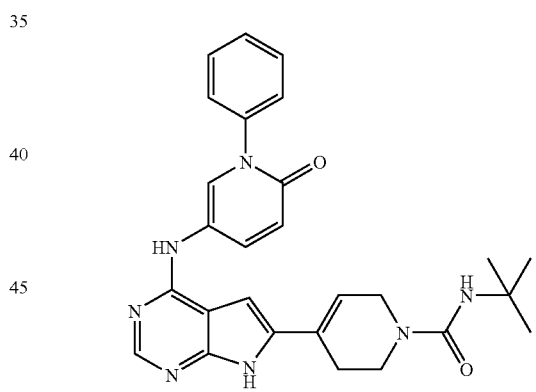

A mixture of 4-(4-chloro-7H-pyrrolo[2,3-d]pyrimidin-6-yl)-3,6-dihydro-2H-pyridine-1-carboxylic acid tert-butyl ester (54.5 mg, 0.163 mmol), 5-amino-1-phenyl-1H-pyridin-2-one hydrochloride (43.5 mg, 0.195 mmol), dimethyl sulfoxide (3 mL) and trifluoroacetic acid (125 μl, 1.63 mmol) in a sealed tube was heated at 100° C. overnight. The mixture was concentrated in vacuo and was charged with N,N-dimethylformamide (2 mL), triethylamine (272 μL, 1.95 mmol) and tert-butyl isocyanate (20.4 μl, 0.179 mmol). The above mixture was stirred at rt for 1.5 h, concentrated in vacuo, and partitioned between water/EtOAc (10 mL/15 mL). The aqueous phase was extracted with EtOAc (2×15 mL), and the combined organic phase was washed with brine (10 mL), concentrated in vacuo, and dissolved in DMSO/MeOH for submission for MS-directed purification, which gave the title compound as beige solid. $^1$H NMR (CD$_3$OD, 400 MHz): δ=1.46 (s, 9H), 2.67 (brs, 2H), 3.69-3.72 (m, 2H), 4.16(brs, 2H), 6.41 (brs, 1H), 6.72 (s, 1H), 6.79 (d, 1H, J=9.6 Hz), 7.56-7.68 (m, 5H), 7.95 (dd, 1H, J=2.8 & 9.6 Hz), 8.27 (s, 1H), 8.39 (d, 1H, J=2.4 Hz), 8.64 (s, 1H). MS (ES+): m/z 484.09 (100) [MH$^+$]. HPLC: $t_R$=2.44 min (ZQ2000polar_5 min).

5-Amino-1-phenyl-1H-pyridin-2-one, hydrochloride

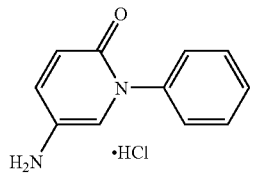

5-(Benzhydrylideneamino)-1-phenyl-1H-pyridin-2-one (72.0 mg) was dissolved in tetrahydrofuran (3 ml), and aqueous HCl (2 M, 1.0 ml) was added while stirring at rt. The yellow color was faded. After 30 min, the reaction mixture was partitioned between aqueous HCl (1 M, 8 ml) and 40% EtOAc/hexane (15 ml). The aqueous layer was extracted with 40% EtOAc/hexane (15 ml), and the aqueous phase was then concentrated in vacuo to the title compound as beige foam. $^1$H NMR (DMSO-d$_6$, 400 MHz): δ=6.62 (d, 1H, J=10.0 Hz), 7.42-7.59 (m, 6H), 7.90 (d, 1H, J=2.8 Hz), 10.34 (brs, 2H). MS(ES+): m/z 187.22 (100) [MH$^+$]. HPLC: $t_R$=0.52 min (ZQ2000, polar_5 min).

5-(Benzhydrylideneamino)-1-phenyl-1H-pyridin-2-one

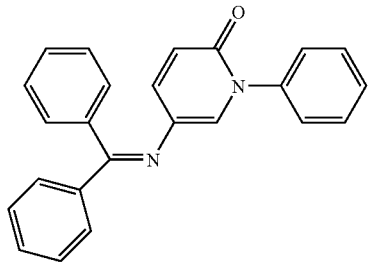

Into a dried flask were added 5-bromo-1-phenyl-1H-pyridin-2-one (125 mg, 0.500 mmol), benzophenone imine (100 µl, 0.600 mmol), tris(dibenzylideneacetone)-dipalladium(0) (1.14 mg, 1.25 µmol), (R)-(+)-2,2'-bis(diphenylphosphino)-1,1'-binaphthyl (2.33 mg, 3.75 µmol), sodium tert-butoxide (67.2 mg, 0.700 mmol), and toluene (3 ml). The above mixture was flushed with N$_2$ for 5 min and was then heated at 80° C. under an atmosphere of nitrogen for 5 h. After that time, the heating was stopped and the reaction mixture was diluted with ethyl ether (30 ml), filtered and concentrated to obtain light-brown oil, which was then purified by chromatography on silica gel (10 g) eluting with 100 ml of 10%, 20%, 30% and 40%, and 300 ml 50% EtOAc/hexane to obtain the title compound as a yellow solid. $^1$H NMR (CDCl$_3$, 400 MHz): δ=6.45 (d, 1H, J=9.6 Hz), 6.89 (d, 1H, J=2.8 Hz), 7.00 (dd, 1H, J=2.8 & 10.4 Hz), 7.13-7.16 (m, 2H), 7.19-7.22 (m, 2H), 7.33-7.48 (m, 9H), 7.69-7.72 (m, 2H). MS(ES+): m/z 351.05 (100) [MH$^+$]. HPLC: $t_R$=3.46 min (ZQ2000, polar_5 min).

5-Bromo-1-phenyl-1H-pyridin-2-one

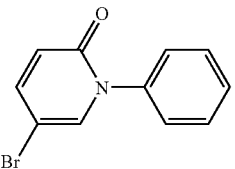

Into a one-neck round-bottom flask were added 5-bromo-1H-pyridin-2-one (696 mg, 4.00 mmol), phenylboronic acid (975 mg, 8.00 mmol), cupric acetate (1450 mg, 8.00 mmol), triethylamine (1120 µl, 8.00 mmol), pyridine (647 µl, 8.00 mmol), 4 Å molecular sieves (1056 mg) and methylene chloride (24 ml). The flask was loosely capped and the above mixture was stirred at rt in the atmosphere of air for 20 h. The mixture was filtered through a celite pad, washed with CH$_2$Cl$_2$. After concentration in vacuo, a green oil (2100 mg) was obtained, which was then purified by chromatography on silica gel (64 g) eluting with 1000 ml 20%, 2000 ml 40% and 1000 ml 50% EtOAc/hexane to obtain the title compound as a light-yellow wax-like material. $^1$H NMR (CDCl$_3$, 400 MHz): δ=5.59 (d, 1H, J=9.6 Hz), 7.35-7.38 (m, 2H), 7.41-7.46 (m, 2H), 7.49-7.52 (m, 3H). MS(ES+): m/z 250.06/252.02 (100/97) [MH$^+$]. HPLC: $t_R$=2.71 min (ZQ2000, polar_5 min).

EXAMPLE 269 tert-Butyl 4-[4-(6-hydroxy-5-thiazol-5-ylpyridin-3-ylamino)-7H-pyrrolo[2,3-d]pyrimidin-6-yl]-3,6-dihydro-2H-pyridine-1-carboxylate

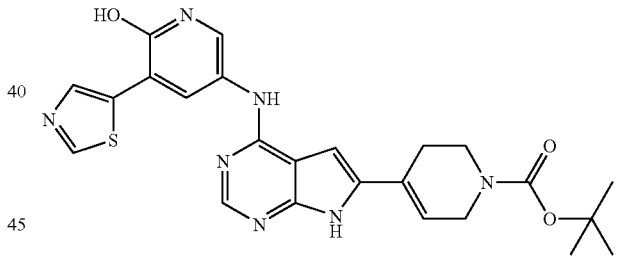

The title compound was obtained following the General method for the reaction of amines with tert-butyl 4-(4-chloro-7H-pyrrolo[2,3-d]pyrimidin-6-yl)-3,6-dihydropyridine-1 (2H)-carboxylate, using 5-amino-3-thiazol-5-ylpyridin-2-ol. $^1$H-NMR (DMSO-d$_6$, 400 MHz): δ=1.43 (s, 9H), 2.47 (m, 2H), 3.57 (t, J=5.6 Hz, 2H), 4.04 (m, 2H), 6.38 (br, 1H), 6.66 (s, 1H), 8.15 (s, 1H), 8.23 (s, 1H), 8.37 (d, J=3.2 Hz, 1H), 8.49 (s, 1H), 9.04 (s, 1H), 9.22 (s, 1H), 11.96 (s, 1H), 12.10 (s, br, 1H). MS (ES+): m/z 491.98 [MH$^+$]. HPLC: $t_R$=2.49 min (ZQ2000, polar_5 min).

5-Amino-3-thiazol-5-ylpyridin-2-ol

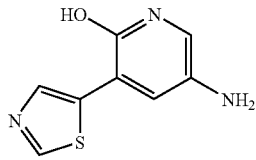

A solution of 5-nitro-3-thiazol-5-ylpyridin-2-ol (218 mg, 0.977 mmol) and 10% Pd/C (100 mg) in methanol (5 mL) was hydrogenated under 1 atm at rt for 5 h. The resulting mixture was filtered through a Celite pad. The filtrate was concentrated under reduced pressure to give 170 mg of the title compound, which was used directly in the next step without purification. $^1$H-NMR (DMSO-$d_6$, 400 MHz): δ=4.38 (s, br, 2H), 6.78 (d, J=2.8 Hz, 1H), 7.80 (d, J=2.8 Hz, 1H), 8.41 (s, 1H), 8.97 (s, 1H), 11.52 (s, br, 1H). MS (ES+): m/z 194.15 [MH$^+$]. HPLC: $t_R$=0.49 and 0.90 min (ZQ2000, polar_5 min).

5-Nitro-3-thiazol-5-ylpyridin-2-ol

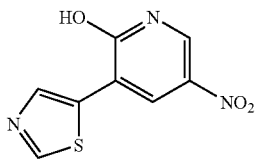

N$_2$ was bubbled through a solution of 3-iodo-5-nitropyridin-2-ol (1.33 g, 5.00 mmol), thiazole (2.13 g, 25.0 mmol), potassium acetate (1.47 g, 15.0 mmol), and tetrakis(triphenylphosphine)palladium(0) (0.4 g, 0.4 mmol) in DMF (10 mL) for 10 min. The mixture was then heated to 120° C. and stirred for 17 h. The solvents were removed in vacuo. The residue was stirred with methanol (5 mL) and dichloromethane (10 mL) for 30 min. The solids were collected by filtration, washed with dichloromethane (2 mL) and water (3×8 mL), and dried in vacuo to afford the title compound as an off-white solid. $^1$H-NMR (DMSO-$d_6$, 400 MHz): δ=8.74 (d, J=2.8 Hz, 1H), 8.77 (s, 1H), 8.79 (d, J=2.8 Hz, 1H), 9.12 (s, 1H), 13.26 (s, br, 1H). MS (ES+): m/z 224.09 [MH$^+$]. HPLC: $t_R$=2.16 min (ZQ2000, polar_5 min).

EXAMPLE 270 tert-Butyl 4-[4-(1-methyl-6-oxo-5-thiazol-5-yl-1,6-dihydropyridin-3-ylamino)-7H-pyrrolo[2,3-d]pyrimidin-6-yl]-3,6-dihydro-2H-pyridine-1-carboxylate

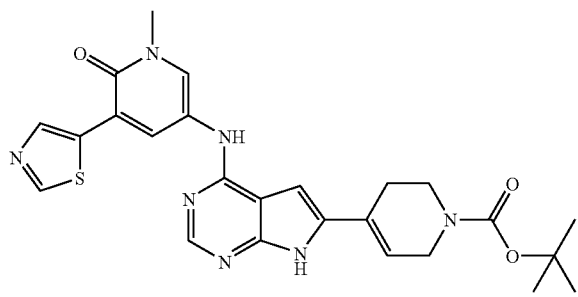

5-Amino-1-methyl-3-thiazol-5-yl-1H-pyridin-2-one (99.0 mg, 0.478 mmol) was added to a solution of tert-butyl 4-(chloro-7H-pyrrolo[2,3-d]pyrimidin-6-yl)-3,6-dihydro-2H-pyridine-1-carboxylate (133 mg, 0.398 mmol) in 1-butanol (2.0 L). The reaction was stirred at 120° C. for 15 h. DMF (1.5 mL) was added and the mixture was filtered. The filtrate was purified by HPLC to yield the title compound.

$^1$H-NMR (CD$_3$OD, 400 MHz): δ=1.50 (s, 9H), 2.57 (m, 2H), 3.67 (m, 2H), 3.73 (s, 3H), 4.13 (m, 2H), 6.30 (s, br, 1H), 6.62 (s, 1H), 8.21 (s, 1H), 8.33 (d, J=2.4 Hz, 1H), 8.34 (d, J=2.4 Hz, 1H), 8.47 (s, 1H), 8.99 (s, 1H). MS (ES+): m/z 506.08 [MH$^+$]. HPLC: $t_R$=2.62 min (ZQ2000, polar_5 min).

5-Amino-1-methyl-3-thiazol-5-yl-1H-pyridin-2-one

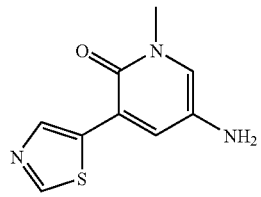

To a solution of 1-methyl-5-nitro-3-thiazol-5-yl-1H-pyridin-2-one (290 mg, 1.22 mmol) in ethanol (10 mL) was added SnCl$_2$ (2.342 g, 12.22 mmol). The mixture was stirred at 90° C. for 15 h. After cooled to rt, sat. NaHCO$_3$ (aq) was added dropwise to the reaction to adjust the pH to 9-10. The resulting solution was filtered through a Celite pad. The filtrate was concentrated to dryness in vacuo to afford the crude product, which was used directly in the next step without purification. MS (ES+): m/z 208.21 [MH$^+$]. HPLC: $t_R$=1.47 min (ZQ2000, polar_5 min).

1-Methyl-5-nitro-3-thiazol-5-yl-1H-pyridin-2-one

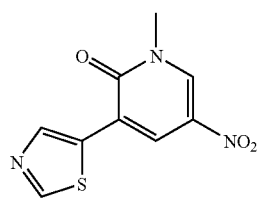

N$_2$ was bubbled through a solution of 3-iodo-1-methyl-5-nitro-1H-pyridin-2-one (840 mg, 3.0 mmol), thiazole (1280 mg, 15.0 mmol), potassium acetate (0.883 g, 9.0 mmol), and tetrakis(triphenylphosphine)palladium(0) (0.243 g, 0.21 mmol) in DMF (8 mL) for 10 min. The mixture was then heated to 120° C. and stirred for 28 h. The solvents were removed in vacuo. The black-colored residue was dissolved in a mixture of methanol (8 mL) and methylene chloride (250 mL). Water (30 mL) and sat. NaHCO$_3$ (aq) (15 mL) were added. Layers were separated and the aqueous phase was extracted with methylene chloride (3×80 mL). The combined organic phases were dried over MgSO$_4$, filtered, and concentrated under reduced pressure to 15 mL. The product precipitated and was collected by filtration to afford the desired product as a black solid. $^1$H-NMR (DMSO-$d_6$, 400 MHz): δ=3.70 (s, 3H), 8.79 (s, 1H), 8.82 (d, J=2.8 Hz, 1H), 9.13 (s, 1H), 9.29 (d, J=3.2 Hz, 1H). MS (ES+): m/z 238.15 [MH$^+$]. HPLC: $t_R$=2.33 min (ZQ2000, polar_5 min).

257

3-Iodo-1-methyl-5-nitro-1H-pyridin-2-one

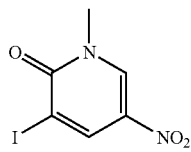

A solution of 3-iodo-5-nitropyridin-2-ol (2.66 g, 10.0 mmol) in THF (30 mL) was cooled to −20° C. NaH (60% dispersion in mineral oil, 0.600 g, 15.0 mmol) was added cautiously in three portions. After being stirred for 30 min at this temperature, methyl iodide (6.23 mL, 100.0 mmol) was added dropwise through a syringe. The resulting mixture was allowed to warm to rt during a 30 min period. Stirring was continued for 18 h at rt. Water (15 mL) was added with caution to quench the reaction. THF was removed under reduced pressure and methylene chloride (80 mL) was added to the aqueous phase. Layers were separated and the aqueous phase was extracted with methylene chloride (2×50 mL). The combined organic phases were dried over $MgSO_4$, filtered, and concentrated to afford the desired product as a yellow crystalline solid. $^1$H-NMR (CDCl$_3$, 400 MHz): δ=3.73 (s, 3H), 8.65 (d, J=2.8 Hz, 1H), 8.74 (d, J=2.8 Hz, 1H). MS (ES+): m/z 280.96 [MH$^+$]. HPLC: $t_R$=2.55 min (ZQ2000, polar__5 min).

EXAMPLE 271 tert-Butyl 4-(4-{3-[1-(2-dimethylaminoethyl)-1H-imidazol-2-yl]phenylamino}-7H-pyrrolo[2,3-d]pyrimidin-6-yl)-3,6-dihydro-2H-pyridine-1-carboxylate

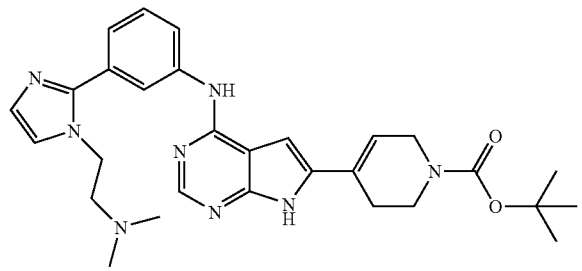

The title compound was obtained following the General method for the reaction of amines with tert-butyl 4-(4-chloro-7H-pyrrolo[2,3-d]pyrimidin-6-yl)-3,6-dihydropyridine-1(2H)-carboxylate, using 3-[1-(2-dimethylaminoethyl)-1H-imidazol-2-yl]phenylamine. $^1$H-NMR (CD$_3$OD, 400 MHz): δ=1.50 (s, 9H), 2.17 (s, 6H), 2.58 (m, 2H), 2.68 (t, J=7.2 Hz, 2H), 3.67 (m, 2H), 4.13 (s, 2H), 4.28 (t, J=6.4 Hz, 2H), 6.30 (s, br, 1H), 6.71 (s, 1H), 7.06 (d, J=2.4 Hz, 1H), 7.29 (dt, J=2.4, 7.6 Hz, 1H), 7.31 (d, J=1.2 Hz, 1H), 7.49 (t, J=8.0 Hz, 1H), 8.24 (dq, J=0.8, 8.0 Hz, 1H), 8.16 (t, J=1.6 Hz, 1H), 8.26 (d, J=1.2 Hz, 1H). MS (ES+): m/z 529.06 [MH$^+$]. HPLC: $t_R$=1.90 min (ZQ2000, polar__5 min).

258

3-[1-(2-Dimethylaminoethyl)-1H-imidazol-2-yl]phenylamine

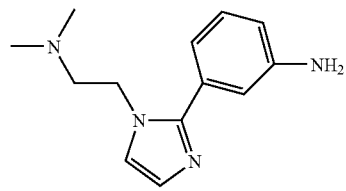

Dimethyl-{2-[2-(3-nitrophenyl)imidazol-1-yl]ethyl}amine (88 mg, 0.34 mmol) in methanol (5 mL) was hydrogenated in the presence of 10% Pd/C (80 mg) for 16 h. The reaction mixture was filtered through a Celite pad. The filtrate was concentrated in vacuo to afford the title compound, which was used directly in the next step without purification. $^1$H-NMR (CDCl$_3$, 400 MHz): δ=2.23 (s, 6H), 2.63 (t, J=7.2 Hz, 2H), 4.13 (d, J=7.2 Hz, 2H), 6.72-6.75 (m, 1H), 6.90-6.92 (m, 1H), 6.96 (t, J=2.0 Hz, 1H), 7.08 (d, J=1.2 Hz, 1H), 7.11 (d, J=1.2 Hz, 1H), 7.22 (t, J=7.6 Hz, 1H). MS (ES+): m/z 231.22 [MH$^+$]. HPLC: $t_R$=0.33 min (ZQ2000, polar__5 min).

Dimethyl-{2-[2-(3-nitrophenyl)imidazol-1-yl]ethyl}amine

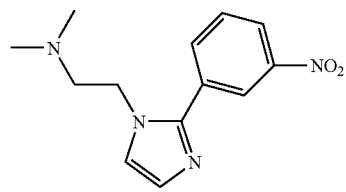

At rt and under $N_2$, to a solution of 2-(3-nitrophenyl)-1H-imidazole (0.189 g, 1.00 mmol) and (2-bromoethyl)dimethylamine hydrobromide (0.280 g, 1.20 mmol) in anhydrous DMF (5 mL) was added NaH (60% in mineral oil, 160 mg, 4.0 mmol) in two portions with caution. The mixture was stirred at rt for 15 h. Water (0.3 mL) was added cautiously to quench the reaction. Solvent was removed in vacuo, and the residue was purified by silica gel chromatography (5% MeOH in dichloromethane) to afford the title compound. $^1$H-NMR (CDCl$_3$, 400 MHz): δ=2.24 (s, 6H), 2.69 (t, J=7.2 Hz, 2H), 4.13 (d, J=6.8 Hz, 2H), 7.17 (d, J=1.2 Hz, 1H), 7.19 (d, J=1.2 Hz, 1H), 7.65 (t, J=8.0 Hz, 1H), 8.04 (dt, J=0.8, 8.0 Hz, 1H), 8.28 (dq, J=1.2, 8.4 Hz, 1H), 8.56 (t, J=1.6 Hz, 1H). MS (ES+): m/z 261.17 [MH$^+$]. HPLC: $t_R$=0.46 min (ZQ2000, polar__5 min).

2-(3-Nitrophenyl)-1H-imidazole

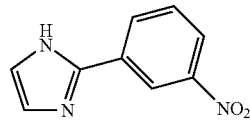

3-Nitrobenzaldehyde (4.53 g, 30.0 mmol), 40% aqueous glyoxal solution (23.9 g, 165 mmol), and sodium acetate (11.6 g, 141 mmol) were dissolved at rt in 90 mL of aqueous ammonium hydroxide solution (28-30 wt %) and 180 mL of methanol. The solution was stirred at rt for 16 h. Solvents were removed in vacuo, and 80 mL of sat. NaHCO$_3$ (aq) was added to the residue. The aqueous solution was extracted with EtOAc (3×300 mL). The combined organic phases were dried over MgSO$_4$, filtered, and concentrated to give a black oily residue, which was purified by silica gel chromatography (5% MeOH in CH$_2$Cl$_2$) to afford the title compound as light brown solid. $^1$H-NMR (DMSO-d$_6$, 400 MHz): δ=7.11 (s, br, 1H), 7.36 (s, br, 1H), 7.75 (t, J=8.0 Hz, 1H), 8.18 (dt, J=0.8, 8.0 Hz, 1H), 8.37 (dd, J=0.8, 7.6 Hz, 1H), 8.79 (s, 1H). MS (ES+): m/z 190.18 [MH$^+$]. HPLC: t$_R$=1.43 min (ZQ2000, polar__5 min).

EXAMPLE 272

4-{4-[3-(1H-Imidazol-2-yl)-phenylamino]-7H-pyrrolo[2,3-d]pyrimidin-6-yl}-3,6-dihydro-2H-pyridine-1-carboxylic acid tert-butyl ester

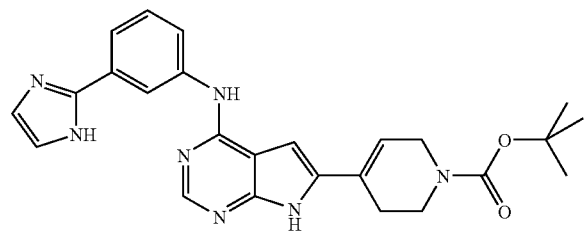

Into a sealed tube were added 4-(4-chloro-7H-pyrrolo[2,3-d]pyrimidin-6-yl)-3,6-dihydro-2H-pyridine-1-carboxylic acid tert-butyl ester (368 mg, 1.0 mmol), 3-(1H-imidazol-2-yl)-phenylamine (210 mg, 1.32 mmol), trifluoroacetic acid (847 μL, 11.0 mmol) and 1-butanol (10 mL). The above mixture was heated at 80° C. for 24 h. After that time, the mixture was concentrated in vacuo, and the residue was dissolved in DMSO for submission for MS-directed purification to obtain brown oil, which was purified again to give the title compound. $^1$H NMR (CD$_3$OD, 400 MHz): δ=1.52 (s, 9H), 2.58 (brs, 2H), 3.68 (brs, 2H), 4.14 (brs, 2H), 6.30 (brs, 1H), 6.68 (s, 1H), 7.16 (s, 2H), 7,45 (t, 1H, J=8.0 Hz), 7.57-7.60 (m, 1H), 7.76-7.79 (m, 1H), 8.21 (t, 1H, J=1.6 Hz), 9.26 (s, 1H). MS (ES+): m/z 458.06 (100) [MH$^+$]. HPLC: t$_R$=2.17 min (ZQ2000, polar__5 min).

3-(1H-Imidazol-2-yl)-phenylamine

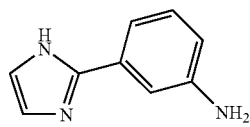

The compound was obtained from 2-(3-nitrophenyl)-1H-imidazole following the procedure for dimethyl-{2-[2-(3-nitrophenyl)imidazol-1-yl]ethyl}amine], except that ethanol was used as solvent. $^1$H NMR (DMSO-d$_6$, 400 MHz): δ=5.14 (s, 2H), 6.52-6.55 (m, 1H), 6.96 (s, 1H), 7.02-7.08 (m, 3H), 7.16-7.21 (m, 2H). MS (ES+): m/z 106.19 (100) [MH$^+$]. HPLC: t$_R$=0.48 min (ZQ2000, polar__5 min).

EXAMPLE 273

4-{4-[3-(1H-Imidazol-2-yl)-phenylamino]-7H-pyrrolo[2,3-d]pyrimidin-6-yl}-3,6-dihydro-2H-pyridine-1-carboxylic acid tert-butylamide

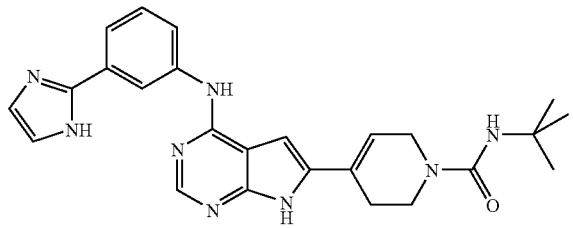

Into the solution of 4-{4-[3-(1H-imidazol-2-yl)-phenylamino]-7H-pyrrolo[2,3-d]pyrimidin-6-yl}-3,6-dihydro-2H-pyridine-1-carboxylic acid tert-butyl ester (59.4 mg, 0.118 mmol) in methanol (1.0 mL) was added HCl in methanol (9 M, 11.0 mL). The above mixture was stirred at rt for 4 h. After that time, the mixture was concentrated in vacuo and was then suspended in DMF (2 mL). Into the above suspension were added triethylamine (159 μL, 1.18 mmol) and tert-butyl isocyanate (14.8 μL, 0.130 mmol). The above mixture was stirred at rt under an atmosphere of N$_2$ for 1 h. After that time, the mixture was concentrated in vacuo to obtain brown oil that was purified by HPLC to yield the title compound. $^1$H NMR (CD$_3$OD, 400 MHz): δ=1.35 (s, 9H), 2.55 (brs, 2H), 3.59 (t, 2H, J=4.2 Hz), 4.05 (brs, 2H), 6.28 (brs, 1H), 6.65 (s, 1H), 7.13 (d, 2H, J=1.2 Hz), 7.42 (t, 1H, J=8.4 Hz), 7.55 (dd, 1H, J=0.8 & 7.6 Hz), 7.74 (dd, 1H, J=0.8 & 8.0 Hz), 7.75-8.19 (m, 1H), 8.23 (d, 1H, J=1.2 Hz). MS (ES+): m/z 457.12 (100) [MH$^+$]. HPLC: t$_R$=2.00 min (ZQ2000, polar__5 min).

EXAMPLE 274 tert-Butyl 4-(4-{3-[3-(2-dimethylaminoethyl)-3H-imidazol-4-yl]phenylamino}-7H-pyrrolo[2,3-d]pyrimidin-6-yl)-3,6-dihydro-2H-pyridine-1-carboxylate

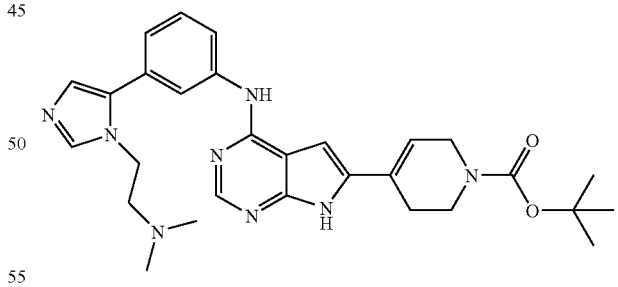

3-[3-(2-Dimethylaminoethyl)-3H-imidazol-4-yl]phenylamine (110 mg, 0.478 mmol) was added to a solution of tert-butyl 4-(chloro-7H-pyrrolo[2,3-d]pyrimidin-6-yl)-3,6-dihydro-2H-pyridine-1-carboxylate (133 mg, 0.398 mmol) in 1-butanol (2.0 mL). The reaction was stirred at 120° C. for 48 h. 0.8 mL of 1 N HCl in ether was then added and the mixture was stirred further at 120° C. for 15 h. LC-MS showed the displacement reaction was complete and the BOC group in the desired product was completely removed. Di-tert-butyl-dicarbonate (347 mg, 1.59 mmol) and N,N-diisopropylethylamine (0.347 mL, 1.99 mmol) were added, and the resulting mixture was stirred at rt for 30 min. DMF (z1.5 mL) was added and the mixture was filtered. The filtrate was purified by HPLC purification to give the title compound. $^1$H-NMR (CD$_3$OD, 400 MHz): δ=1.50 (s, 9H), 2.52 (s, 6H), 2.58 (m, 2H), 3.04 (t, J=6.8 Hz, 2H), 3.67 (m, 2H), 4.13 (m, 2H), 4.53 (t, J=6.8 Hz, 2H), 6.30 (s, br, 1H), 6.72 (s, 1H), 7.18 (s, 1H), 7.19 (d, J=7.6 Hz, 1H), 7.48-7.52 (m, 1H), 7.72 (dd, J=2.4, 8.0 Hz, 1H), 8.06 (s, 1H), 8.12 (m, 1H), 8.26 (s, 1H). MS (ES+): m/z 529 [MH$^+$]. HPLC: t$_R$=2.00 min (ZQ2000, polar__5 min).

3-[3-(2-Dimethylaminoethyl)-3H-imidazol-4-yl]phenylamine

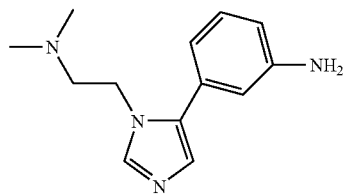

A solution of dimethyl-{2-[5-(3-nitrophenyl)imidazol-1-yl]ethyl}amine (140 mg, 0.54 mmol) and 10% Pd/C (80 mg) in methanol (8 mL) was hydrogenated under 1 atm hydrogen pressure for 5 h. The reaction mixture was filtered through a Celite pad. The filtrate was concentrated to dryness to afford the desired amine, which was used directly in the next step without purification. $^1$H-NMR (CD$_3$OD, 400 MHz): δ=2.15 (s, 6H), 2.49 (t, J=6.8 Hz, 2H), 4.18 (t, J=7.2 Hz, 2H), 6.69-6.77 (m, 3H), 6.91 (d, J=1.2 Hz, 1H), 7.18 (dt, J=1.2, 7.6 Hz, 1H), 7.44 (d, J=0.8 Hz, 1H). MS (ES+): m/z 231.29 [MH$^+$]. HPLC: t$_R$=0.39 min (ZQ2000, polar__5 min).

Dimethyl-{2-[5-(3-nitrophenyl)imidazol-1-yl]ethyl}amine

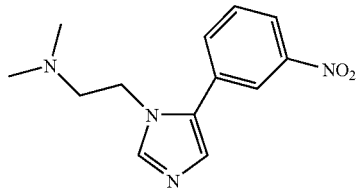

A stirred mixture of 3-[2-(3-nitrophenyl)-2-oxoethyl]-3H-quinazolin-4-one (2.00 g, 6.47 mmol), N,N-dimethyl-1,2-ethanediamine (2.28 g, 25.9 mmol), and p-toluenesulfonic acid (2.23 g, 12.9 mmol) in xylenes (150 mL) was refluxed for 48 h. After cooling to rt, water (20 mL) and sat. NaHCO$_3$ (aq) (15 mL) were added. Layers were separated, and the aqueous phase was extracted with EtOAc (3×50 mL). The combined organic phases were dried over MgSO$_4$, filtered, concentrated, and purified by silica gel chromatography (8% MeOH in CH$_2$Cl$_2$) to afford the desired product. $^1$H-NMR (CD$_3$OD, 400 MHz): δ=2.15 (s, 6H), 2.54 (t, J=7.2 Hz, 2H), 4.22 (t, J=6.8 Hz, 2H), 7.15 (d, J=1.2 Hz, 1H), 7.74 (t, J=8.0 Hz, 1H), 7.89 (dt, J=2.4, 7.6 Hz, 1H), 7.90 (s, 1H), 8.24-8.26 (m, 1H), 8.30 (s, 1H). MS (ES+): m/z 261.24 [MH$^+$]. HPLC: t$_R$=0.49 and 0.71 min (ZQ2000, polar__5 min).

3-[2-(3-Nitrophenyl)-2-oxoethyl]-3H-quinazolin-4-one

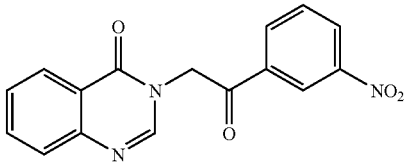

To a solution of 4(3H)-quinazolinone (2.19 g, 15.0 mol) in anhydrous DMF (10 mL) was added NaH (60% dispersion in mineral oil, 0.719 g, 18.0 mmol) in two portions with caution. The mixture was stirred at rt for 30 min. 3-Nitrophenacyl bromide (4.39 g, 18.0 mmol) was added and the resulting suspension was stirred at rt for 16 h. Solvent was removed under reduced pressure. To the residue were added water (10 mL) and 4 N HCl (aq) to adjust the pH to ≈6. The solid material was collected by filtration, washed with water (20 mL) and dichloromethane (3×20 mL) to afford the title compound as a white powder. $^1$H-NMR (CD$_3$OD, 400 MHz): δ=5.70 (d, J=10.0 Hz, 2H), 7.60 (d, J=7.2 Hz, 1H), 7.76 (d, J=8.4 Hz, 1H), 7.86-7.91 (m, 2H), 8.25 (d, J=8.0 Hz, 1H), 8.30 (s, 1H), 8.51-8.58 (m, 2H), 8.90 (t, J=1.2 Hz, 1H). MS (ES+): m/z 310.06 [MH$^+$]. HPLC: t$_R$=2.90 min (ZQ2000, polar__5 min).

EXAMPLE 275 tert-Butyl 4-{4-[3-(1H-benzimidazol-2-yl)phenylamino]-7H-pyrrolo[2,3-d]pyrimidin-6-yl}-3,6-dihydro-2H-pyridine-1-carboxylate

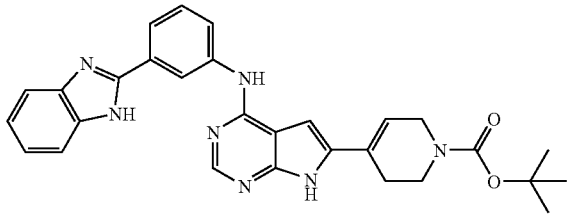

The title compound was obtained following the General method for the reaction of amines with tert-butyl 4-(4-chloro-7H-pyrrolo[2,3-d]pyrimidin-6-yl)-3,6-dihydropyridine-1 (2H)-carboxylate, using 3-(1H-Benzimidazol-2-yl)-phenylamine. $^1$H-NMR (CD$_3$OD, 400 MHz): δ=1.50 (s, 9H), 2.58 (m, 2H), 3.67 (m, 2H), 4.13 (m, 2H), 6.31 (s, br, 1H), 6.72 (s, 1H), 6.26-6.30 (m, 2H), 7.54 (t, J=8.0 Hz, 1H), 7.63 (m, 2H), 7.79 (dt, J=0.8, 8.4 Hz, 1H), 7.88 (dt, J=0.8, 8.0 Hz, 1H), 8.29 (s, 1H), 8.50 (m, 1H). MS (ES+): m/z 508.03 [MH$^+$]. HPLC: t$_R$=2.72 min (ZQ2000, polar__5 min).

EXAMPLE 276 tert-Butyl 4-{4-[3-(1-methylpiperidin-4-yl)phenylamino]-7H-pyrrolo[2,3-d]pyrimidin-6-yl}-3,6-dihydro-2H-pyridine-1-carboxylate

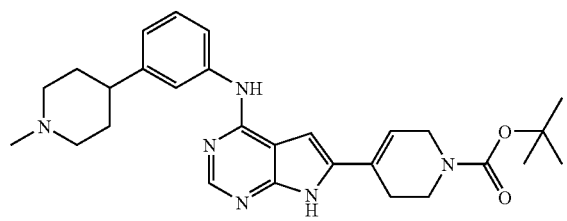

The title compound was obtained following the General method for the reaction of amines with tert-butyl 4-(4-chloro-7H-pyrrolo[2,3-d]pyrimidin-6-yl)-3,6-dihydropyridine-1(2H)-carboxylate, using 3-(1-methylpiperidin-4-yl)phenylamine. $^1$H-NMR (CD$_3$OD, 400 MHz): δ=1.49 (s, 9H), 1.72-1.85 (m, 2H), 1.93-1.97 (m, 2H), 2.56 (m, 2H), 2.74 (s, 3H), 2.81 (m, 1H), 3.21 (t, J=12.8 Hz, 2H), 3.64 (m, 2H), 4.11 (m, 2H), 4.86 (d, J=13.2 Hz, 2H), 6.25 (s, br, 1H), 6.48 (dt, J=2.4, 8.0 Hz, 1H), 6.53-6.59 (m, 3H), 7.05 (t, J=7.6 Hz, 1H), 8.12 (s, 1H). MS (ES+): m/z 489.14 [MH$^+$]. HPLC: t$_R$=2.50 min (ZQ2000, polar_5 min).

3-(1-Methylpiperidin-4-yl)phenylamine

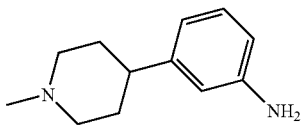

A dried flask was charged with tert-butyl 4-(3-aminophenyl)piperidine-1-carboxylate (0.553 g, 2.00 mmol). Lithium aluminium hydride (1M in THF, 10 mL, 10.0 mmol) was added slowly through a syringe under N$_2$. The resulting mixture was stirred overnight at rt. Water (0.5 mL) was cautiously added to quench the reaction. The resulting mixture was filtered. The filtrate was concentrated to dryness to give the title compound as a white solid, which was used without further purification in the next step. $^1$H-NMR (CDCl$_3$, 400 MHz): δ=1.80-1.85 (m, 2H), 2.04 (dt, J=4.0, 11.6 Hz, 2H), 2.33 (s, 3H), 2.40 (m, 1H), 2.98 (m, 2H), 3.64 (s, br, 2H), 6.54-6.59 (m, 2H), 6.66 (d, J=7.6 Hz, 1H), 7.10 (t, J=7.6 Hz, 1H). MS (ES+): m/z 191.26 [MH$^+$]. HPLC: t$_R$=0.49 min (ZQ2000, polar_5 min).

EXAMPLE 277 tert-Butyl 4-[4-(3-piperidin-4-ylphenylamino)-7H-pyrrolo[2,3-d]pyrimidin-6-yl]-3,6-dihydro-2H-pyridine-1-carboxylate

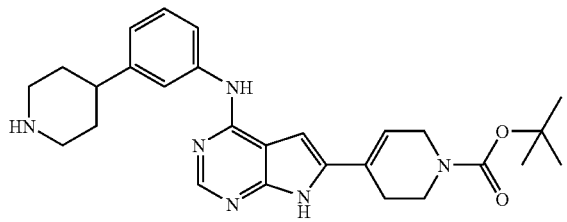

The title compound was also isolated from the above reaction mixture. $^1$H-NMR (CD$_3$OD, 400 MHz): δ=1.50 (s, 9H), 1.71-1.80 (m, 2H), 1.93-1.96 (m, 2H), 2.56 (m, 2H), 2.75-2.81 (m, 1H), 3.21 (dt, J=2.8, 13.2 Hz, 2H), 3.64 (m, 2H), 4.11 (m, 2H), 4.86 (d, J=13.2 Hz, 2H), 6.26 (s, br, 1H), 6.56-6.64 (m, 4H), 7.02 (t, J=7.6 Hz, 1H), 8.12 (s, 1H). MS (ES+): m/z 475.12 [MH$^+$]. HPLC: t$_R$=2.43 min (ZQ2000, polar_5 min).

EXAMPLE 278

4-{4-[4-Fluoro-3-(1-methylpiperidin-4-yl)-phenylamino]-7H-pyrrolo[2,3-d]pyrimidin-6-yl}-3,6-dihydro-2H-pyridine-1-carboxylic acid tert-butyl ester

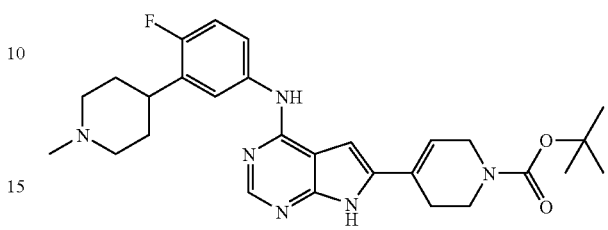

A mixture of 4-(4-chloro-7H-pyrrolo[2,3-d]pyrimidin-6-yl)-3,6-dihydro-2H-pyridine-1-carboxylic acid tert-butyl ester (167 mg, 0.500 mmol), 4-fluoro-3-(1-methylpiperidin-4-yl)-phenylamine (149 mg, 0.600 mmol), N,N-dimethylformamide (3 mL), and trifluoroacetic acid (385 μL, 5.18 mmol) in a sealed tube was heated at 100° C. for 15 h. The mixture was concentrated in vacuo, charged with sodium bicarbonate (504 mg, 6.00 mmol), di-tert-butyldicarbonate (120 mg, 0.550 mmol), and N,N-dimethylformamide (2 mL), and stirred at rt under N$_2$ for 24 h. After that time, the mixture was filtered, and the filtrate was concentrated in vacuo to obtain a brown oil, which was dissolved in EtOAc (30 mL) and washed with water (3×20 mL). The organic phase was concentrated in vacuo to obtain a light-brown oil that was purified by HPLC to give the title compound. $^1$H NMR (CD$_3$OD, 400 MHz): δ=1.51 (s, 9H), 1.87 (brs, 4H), 2.13-2.20 (m, 2H), 2.32 (s, 3H), 2.54 (brs, 2H), 2.83-2.91 (m, 1H), 2.99-3.01 (m, 2H), 3.65 (brs, 2H), 4.12 (brs, 2H), 6.27 (brs, 1H), 6.56 (s, 1H), 7.03 (t, 1H, J=8.8 Hz), 7.57-7.60 (m, 2H), 8.19 (s, 1H). MS (ES+): m/z 507.17 (75) [MH$^+$]. HPLC: t$_R$=2.16 min (ZQ2000, polar_5 min).

4-Fluoro-3-(1-methylpiperidin-4-yl)-phenylamine

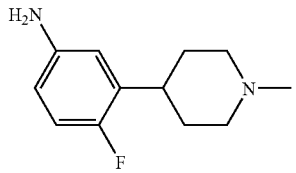

Pd/C (10% w/w, 50% water, 77 mg) was added to the solution of 3-fluoro-4-(1-methyl-1,2,3,6-tetrahydropyridin-4-yl)-phenylamine (386 mg, 1.57 mmol) in methanol (10 mL). The above mixture was degassed and then the H$_2$ balloon was applied. The mixrure was stirred at rt under an atmosphere of H$_2$ overnight. Additional Pd/C (10% w/w, 50% water, 77 mg) was added, and stirring was continued overnight. The mixture was filtered and concentrated in vacuo to give the title compound as brown oil that was used for the next reaction without further purification. $^1$H NMR (DMSO-d$_6$, 400 MHz): δ=1.55-1.64 (m, 4H), 2.05-2.11 (m, 2H), 2.22 (s, 3H), 2.54-2.62 (m, 1H), 2.88-2.97 (m, 2H), 6.29-6.33 (m, 1H), 6.38-6.41 (m, 1H), 6.69-6.73 (m, 1H). MS (ES+): m/z 209.29 (100) [MH$^+$]. HPLC: t$_R$=0.46 min (ZQ2000, polar_5 min).

4-Fluoro-3-(1-methyl-1,2,3,6-tetrahydropyridin-4-yl)-phenylamine

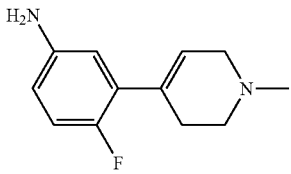

A dried flask was charged with 4-(2-fluoro-5-nitrophenyl)-3,6-dihydro-2H-pyridine-1-carboxylic acid tert-butyl ester (645 mg, 2.00 mmol) and THF (10 mL). Lithium aluminium hydride (1M in THF, 20 mL, 20.0 mmol) was added slowly through a syringe under $N_2$ (the reaction was very exothermic). The resulting mixture was stirred for 16 h at rt. Water was cautiously added to quench the reaction. The resulting mixture was filtered, and the filtrate was concentrated to dryness to give the title compound as a brown oil. $^1$H NMR (DMSO-$d_6$, 400 MHz): δ=2.14 (s, 3H), 2.38-2.44 (m, 2H), 2.89-2.90 (m, 2H), 3.22 (brs, 2H), 5.95 (brs, 1H), 7.24-7.29 (m, 1H), 7.67-7.73 (m, 2H), 8.16 (s, 1H). MS (ES+): m/z 206.26 (100) [MH$^+$]. HPLC: $t_R$=1.68 min (ZQ2000, polar_5 min).

4-(2-fluoro-5-nitrophenyl)-3,6-dihydro-2H-pyridine-1-carboxylic acid tert-butyl ester

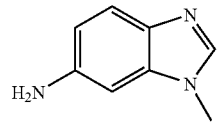

Into a 1-neck round-bottom flask were added 2-bromo-1-fluoro-4-nitrobenzene (1760 mg, 8.000 mmol), potassium carbonate (2210 mg, 16.00 mmol), 4-(4,4,5,5-tetramethyl-[1,3,2]dioxaborolan-2-yl)-3,6-dihydro-2H-pyridine-1-carboxylic acid tert-butyl ester (2720 mg, 8.800 mmol), water (8 mL) and 1,4-dioxane (32 mL). The flask was degassed and filled with $N_2$ for 3 times, and then [1,1'-bis(diphenylphosphino)ferrocene]-dichloropalladium(II) complex with $CH_2Cl_2$ (1:1) (330.0 mg, 0.4000 mmol) was added. The mixture was degassed and filled with $N_2$ for 3 times again and was then heated at 100° C. for 16 h. After that time, the mixture was concentrated in vacuo and was then purified by silica gel (240 g) eluting with 1800 mL of 5%, 1000 mL of 10%, 1000 mL of 15% and 1000 mL of 20% EtOAc/hexane to obtain the title compound as a colorless oil. $^1$H NMR (DMSO-$d_6$, 400 MHz): δ=1.49 (s, 9H), 2.52-2.55 (m, 2H), 3.60 (t, 2H, J=5.6 Hz), 4.09 (brs, 2H), 6.21 (brs, 1H), 7.55-7.60 (m, 1H), 8.21-8.29 (m, 2H). MS (ES+): m/z 223.22 (100) [MH$^+$-Boc]. HPLC: $t_R$=3.83 min (ZQ2000, polar_5 min).

EXAMPLE 279

4-[4-(3-Methyl-3H-benzimidazol-5-ylamino)-7H-pyrrolo[2,3-d]pyrimidin-6-yl]-3,6-dihydro-2H-pyridine-1-carboxylic acid tert-butyl ester

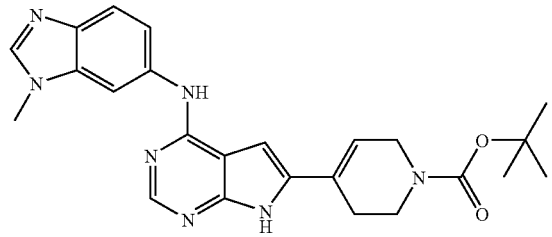

A mixture of 4-(4-chloro-7H-pyrrolo[2,3-d]pyrimidin-6-yl)-3,6-dihydro-2H-pyridine-1-carboxylic acid tert-butyl ester (134 mg, 0.400 mmol) and 3-methyl-3H-benzoimidazol-5-ylamine (70.6 mg, 0.480 mmol) in n-BuOH (3 mL) in a sealed tube was heated at 120° C. for 17 h and concentrated in vacuo to obtain a brown solid that was purified using the mass-directed purification system to yield the title compound as beige solid. $^1$H NMR (CD$_3$OD, 400 MHz): δ=1.52 (s, 9H), 2.57 (brs, 2H), 3.68 (brs, 2H), 3.93 (s, 3H), 4.12 (brs, 2H), 6.31 (brs, 1H), 6.65 (brs, 1H), 7.46 (dd, 1H, J=2.0 & 8.4 Hz), 7.66 (d, 1H, J=8.8 Hz), 8.14-8.15 (m, 2H), 8.23 (s, 1H), 8.24 (brs, 1H). MS (ES+): m/z 464.12 (100) [MH$^+$]. HPLC: $t_R$=2.18 min (ZQ2000, polar_5 min).

3-Methyl-3H-benzimidazol-5-ylamine

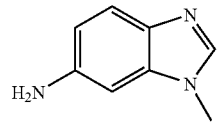

Pd/C (17 mg, 10%, with 50% water) was added into the suspension of 1-methyl-6-nitro-1H-1,3-benzimidazole (85.0 mg, 0.480 mmol) in ethanol (3 mL). The mixture was degassed and filled with $H_2$. The mixture was stirred at rt under balloon pressure for 16 h. After that time, the mixture was filtered and concentrated in vacuo to obtain the title compound as pink crystals. $^1$H NMR (CD$_3$OD, 400 MHz): δ=3.67 (s, 3H), 6.69-6.73 (m, 2H), 7.33 (dd, 1H, J=0.4 & 8.8 Hz), 7.77 (s, 1H). MS (ES+): m/z 148.16 (100) [MH$^+$]. HPLC: $t_R$=0.43 min (ZQ2000, polar_5 min).

EXAMPLE 280

4-[4-(3-Methyl-3H-benzimidazol-5-ylamino)-7H-pyrrolo[2,3-d]pyrimidin-6-yl]-3,6-dihydro-2H-pyridine-1-carboxylic acid tert-butylamide

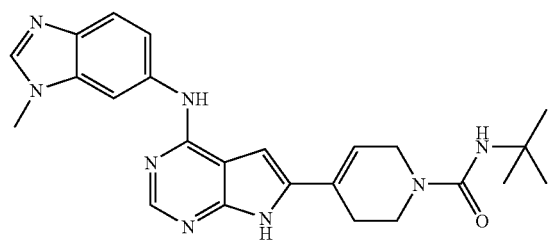

Into the solution of 4-{4-[3-(1H-imidazol-2-yl)-phenylamino]-7H-pyrrolo[2,3-d]pyrimidin-6-yl}-3,6-dihydro-2H-pyridine-1-carboxylic acid tert-butyl ester (EXAMPLE 279) (59.4 mg, 0.118 mmol) in methanol (1.0 mL) was added HCl in methanol (9 M, 1.0 mL). The above mixture was stirred at rt for 4 h. After that time, the mixture was concentrated in vacuo and suspended in DMF (2 mL). Into the above suspension were added triethylamine (159 µL, 1.18 mmol) and tert-butyl isocyanate (14.8 µL, 0.130 mmol). The above mixture was stirred at rt under of $N_2$ for 1 h and concentrated in vacuo to obtain a brown oil that was purified using the mass-directed purification system to yield the title compound. $^1$H NMR (CD$_3$OD, 400 MHz): δ=1.37 (s, 9H), 2.56 (brs, 2H), 3.61 (t, 2H, J=4.8 Hz), 3.90 (s, 3H), 4.07 (brs, 2H), 5.69 (s, 1H), 6.29 (brs, 1H), 6.62 (s, 1H), 7.43 (dd, 1H, J=2.0 & 8.8 Hz), 7.63 (d, 1H, J=8.8 Hz), 8.08 (s, 1H), 8.11 (d, 1H, J=2.0 Hz), 8.22 (s, 1H). MS (ES+): m/z 445.11 (100) [MH$^+$]. HPLC: $t_R$=2.00 min (ZQ2000, polar_5 min).

EXAMPLE 281 tert-Butyl 4-[4-(benzothiazol-5-ylamino)-7H-pyrrolo[2,3-d]pyrimidin-6-yl]-3,6-dihydro-2H-pyridine-1-carboxamide

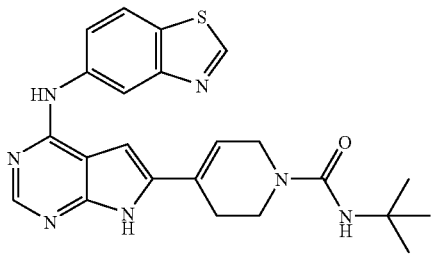

A solution of benzothiazol-5-yl-[6-(1,2,3,6-tetrahydropyridin-4-yl)-7H-pyrrolo[2,3-d]pyrimidin-4-yl]amine trihydrochloride (23 mg, 0.050 mmol) and N,N-diisopropylethylamine (0.07 mL, 0.402 mmol) in DMF (2 mL) was stirred at rt for 30 min. tert-Butyl isocyanate (0.012 mL, 0.0 mmol) was added dropwise through a syringe. The resulting mixture was stirred for 1.5 h at rt. MeOH (0.5 mL) was added to quench the reaction. The whole mixture was filtered and purified by HPLC to afford the desired product. $^1$H-NMR (DMSO-d$_6$, 400 MHz): δ=1.28 (s, 9H), 2.48 (m, 2H), 3.53 (m, 2H), 4.01 (m, 2H), 5.79 (s, 1H), 6.43 (s, br, 1H), 6.84 (s, 1H), 7.92 (d, J=8.4 Hz, 1H), 8.08 (d, J=8.8 Hz, 1H), 8.35 (d, J=1.2 Hz, 1H), 8.88 (s, 1H), 9.37 (d, J=1.2 Hz, 1H), 9.56 (s, 1H), 11.99 (s, 1H). MS (ES+): m/z 448.08 [MH$^+$]. HPLC: $t_R$=2.60 min (ZQ2000, polar_5 min).

Benzothiazol-5-yl-[6-(1,2,3,6-tetrahydropyridin-4-yl)-7H-pyrrolo[2,3-d]pyrimidin-4-yl]amine trihydrochloride

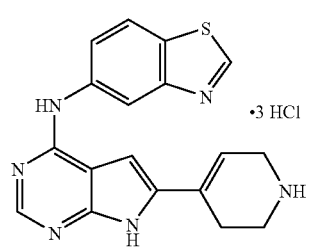

To a suspension of tert-butyl 4-[4-(benzothiazol-5-ylamino)-7H-pyrrolo[2,3-d]pyrimidin-6-yl]-3,6-dihydro-2H-pyridine-1-carboxylate (28.3 mg, 0.063 mmol) in MeOH (3 mL) was added 4 N HCl (aq) (3 mL). The mixture was stirred at 60° C. for 8 h. Solvents were removed under reduced pressure to afford the title compound as yellow solid, which was used directly in the next step without purification. $^1$H-NMR (DMSO-d$_6$, 400 MHz): δ=2.70 (m, 2H), 3.83 (m, 2H), 6.45 (s, 1H), 6.99 (s, 1H), 7.82 (d, J=8.4 Hz, 1H), 8.19 (d, J=8.8 Hz, 1H), 8.36 (s, 1H), 8.68 (s, 1H), 9.07 (s, 1H), 9.44 (s, 1H), 10.32 (s, br, 1H), 12.51 (s, 1H). MS (ES+): m/z 349.06 [MH$^+$]. HPLC: $t_R$=1.73 min (ZQ2000, polar_5 min).

EXAMPLE 282 tert-Butyl 4-[4-(benzothiazol-5-ylamino)-7H-pyrrolo[2,3-d]pyrimidin-6-yl]-3,6-dihydro-2H-pyridine-1-carboxylate

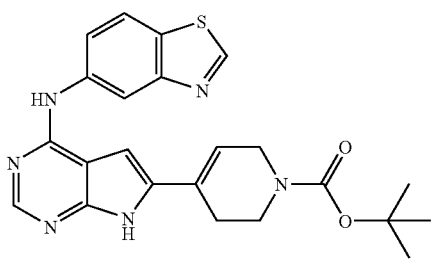

The title compound was obtained following the General method for the reaction of amines with tert-butyl 4-(4-chloro-7H-pyrrolo[2,3-d]pyrimidin-6-yl)-3,6-dihydropyridine-1(2H)-carboxylate, using benzothiazol-5-ylamine. $^1$H-NMR (CD$_3$OD, 400 MHz): δ=1.50 (s, 9H), 2.58 (m, 2H), 3.67 (m, 2H), 4.14 (m, 2H), 6.31 (s, br, 1H), 6.73 (s, 1H), 7.85 (dd, J=2.4, 8.8 Hz, 1H), 8.01 (d, J=8.8 Hz, 1H), 8.27 (s, 1H), 8.67 (d, J=1.6 Hz, 1H), 9.24 (s, 1H). MS (ES+): m/z 449.02 [MH$^+$]. HPLC: $t_R$=3.01 min (ZQ2000, polar_5 min).

EXAMPLE 283

4-[4-(3-Methyl-1H-indazol-5-ylamino)-7H-pyrrolo[2,3-d]pyrimidin-6-yl]-3,6-dihydro-2H-pyridine-1-carboxylic acid tert-butyl ester

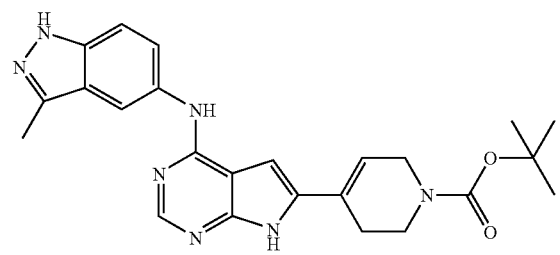

A mixture of 4-(4-chloro-7H-pyrrolo[2,3-d]pyrimidin-6-yl)-3,6-dihydro-2H-pyridine-1-carboxylic acid tert-butyl ester (50.1 mg, 0.150 mmol) and 3-methyl-1H-indazol-5-ylamine (25.0 mg, 0.170 mmol) in iPrOH (2.5 mL) in a sealed tube was heated to 90° C. (bath temp.) for 16 h. The solvent was evaporated, water/NaHCO$_3$ solution was added, the mixture was extracted with CH$_2$Cl$_2$ (3×30 mL), and the combined extracts were washed with brine and dried over MgSO$_4$. The extracts were filtered through a pad of silica gel, washing with 5% MeOH in CH$_2$Cl$_2$ until no more product eluted as indicated by TLC. Concentration in vacuo gave a light brown solid. The solid was triturated with MeOH, filtered, washed with more MeOH, and dried in vacuo overnight. One obtained the title compound as white solid, mp. 245-250° C. (decomp.). $^1$H NMR (DMSO-d$_6$, 400 MHz): δ=1.43 (s, 9H), 2.42-2.50 (brs, 2H), 2.47 (s, 3H), 3.53-3.59 (me, 2H), 3.99-4.08 (m, 2H), 6.38 (brs, 1H), 6.73 (brs, 1H), 7.43 (d, J=8.8 Hz, 1H), 7.69 (dd, J=1.6, 8.8 Hz, 1H), 8.15 (s, 1H), 8.23 (s, 1H), 9.32 (s, 1H), 11.88 (brs, 1H), 12.54 (s, 1H). MS (ES+): m/z 446.0 (100) [MH$^+$]. HPLC: t$_R$=2.4 min (ZQ2000, polar__5 min).

EXAMPLE 284

1-{4-[4-(3-Methyl-1H-indazol-5-ylamino)-7H-pyrrolo[2,3-d]pyrimidin-6-yl]-3,6-dihydro-2H-pyridin-1-yl}-3-piperidin-1-yl-propan-1-one

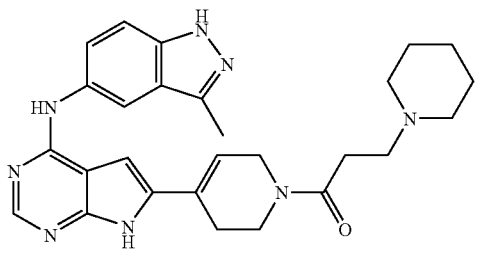

Into the suspension of (3-methyl-1H-indazol-5-yl)-[6-(1,2,3,6-tetrahydro pyridin-4-yl)-7H-pyrrolo[2,3-d]pyrimidin-4-yl]-amine tris-hydrochloride (122 mg, 0.190 mmol), 1-piperidinepropanoic acid (48.4 mg, 0.305 mmol), N-(3-dimethylaminopropyl)-N'-ethylcarbodiimide hydrochloride (EDC·HCl) (76.7 mg, 0.400 mmol) and 1-hydroxy benzotriazole (HOBt·H$_2$O) (30.6 mg, 0.200 mmol) in DMF (4.5 mL) was added N,N-diisopropylethylamine (167 μL, 0.952 mmol) under N$_2$ at rt. The reaction mixture, which became a clear wine-red solution, was stirred at rt for 18 h. After that time, the reaction mixture was treated with water/saturated NaHCO$_3$ (5 mL/5 mL) and extracted with EtOAc (4×20 mL). The combined extracts were washed with water (2×20 mL) and brine (20 mL), dried over MgSO$_4$, filtered and concentrated in vacuo to obtain a light-brown oil that was purified using the mass-directed purification system to yield the title compound as yellow oil. $^1$H NMR (CD$_3$OD, 400 MHz): δ=1.69 (brs, 2H), 1.88 (brs, 4H), 2.57 (s, 3H), 2.66 (brs, 2H), 2.95-3.03 (m, 2H), 3.32 (brs, 4H), 3.41 (t, 2H, J=6.0 Hz), 3.76 (t, 1H, J=5.4 Hz), 3.85 (t, 1H, J=5.6 Hz), 4.28 (brs, 2H), 6.30 (d, 1H, J=2.8 Hz), 6.51-6.55 (m, 1H), 7.49 (d, 1H, J=8.4 Hz), 7.55-7.59 (m, 1H), 7.98-8.00 (m, 1H), 8.19 (s, 1H), 8.42 (s 1H). MS (ES+): m/z 485.00 (70) [MH$^+$]. HPLC: t$_R$=1.70 min (ZQ2000, polar__5 min).

EXAMPLE 285

(3-Methyl-1H-indazol-5-yl)-[6-(1,2,3,6-tetrahydropyridin-4-yl)-7H-pyrrolo[2,3-d]pyrimidin-4-yl]-amine tris-hydrochloride

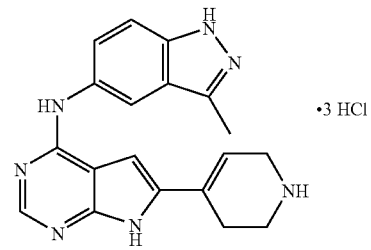

To a suspension of 4-[4-(3-methyl-1H-indazol-5-ylamino)-7H-pyrrolo[2,3-d]pyrimidin-6-yl]-3,6-dihydro-2H-pyridine-1-carboxylic acid tert-butyl ester (488 mg, 1.10 mmol) in MeOH (10 mL) was added hydrogen chloride (9M in MeOH, 2.15 mL, 19.4 mmol), the mixture was stirred at rt for 3 h and concentrated in vacuo. The residue was triturated with Et$_2$O and dried in vacuo to give the title compound. MS (ES+): m/z 347.12 (10) [MH$^+$]. HPLC: t$_R$(polar__5 mins) =1.52 min (ZQ2000, polar__5 min). A purified sample was made by Gilson HPLC to record the $^1$H NMR spectrum. $^1$H NMR (DMSO-d$_6$, 400 MHz): δ=2.34 (s, 3H), 2.47 (brs, 2H), 3.12 (brs, 2H), 3.60 (brs, 2H), 6.29 (s, 1H), 6.92 (s, 1H), 7.07 (s, 1H), 7.19 (s, 1H), 7.25 (d, 1H, J=8.4 Hz), 7.40 (d, 1H, J=8.4 Hz), 7.75 (s, 1H), 8.06 (s, 1H), 9.27 (brs, 1H), 12.73 (brs 1H).

EXAMPLE 286

3-Dimethylamino-1-4-[4-(3-methyl-1H-indazol-5-ylamino)-7H-pyrrolo[2,3-d]pyrimidin-6-yl]-3,6-dihydro-2H-pyridin-1-ylpropan-1-one

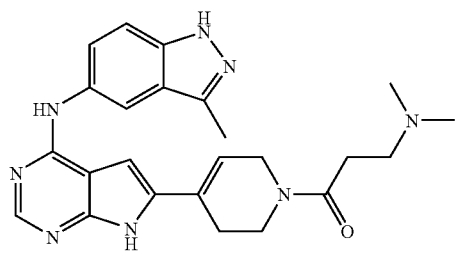

The title compound (yellow solid) was prepared following the procedure for 1-{4-[4-(3-methyl-1H-indazol-5-ylamino)-7H-pyrrolo[2,3-d]pyrimidin-6-yl]-3,6-dihydro-2H-pyridin-1-yl}-3-piperidin-1-yl-propan-1-one, using 3-dimethylaminopropionic acid. $^1$H NMR (400 MHz, MeOH-d$_4$): δ=2.21 & 2.22 (s, rotamers, 6H), 2.47 (s, 4H), 2.49-2.57 (m, 2H), 2.60 (s, 3H), 3.68 & 3.72 (t, J=5.6 Hz, rotamers, 2H), 4.16 & 4.20 (s, rotamers, 2H), 6.20 (s, 1H), 6.40 & 6.45 (s, rotamers, 1H), 7.38 (d, J=8.8 Hz, 1H), 7.47 (d, J=8.8 Hz, 1H), 7.88 (d, J=4.0 Hz, 1H), 8.08 (s, 1H). MS (ES+): m/z 445.03 (50) [MH$^+$]. HPLC: t$_R$=1.63 min (ZQ2000, polar__5 min).

EXAMPLE 287

3-Imidazol-1-yl-1-{4-[4-(3-methyl-1H-indazol-5-ylamino)-7H-pyrrolo[2,3-d]pyrimidin-6-yl]-3,6-dihydro-2H-pyridin-1-yl}-propan-1-one

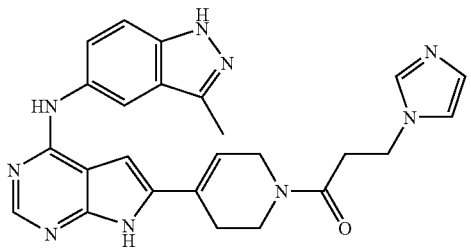

β-Bromopropionic acid (29.1 mg, 0.190 mmol), 1H-imidazole (19.4 mg, 0.286 mmol), potassium carbonate (160 mg, 1.16 mmol) and DMF (3 mL) was combined together and stirred at rt for 20 h. After that time, (3-methyl-1H-indazol-5-yl)-[6-(1,2,3,6-tetrahydropyridin-4-yl)-7H-pyrrolo[2,3-d]pyrimidin-4-yl]-amine hydrogen chloride tri-salt (122 mg, 0.190 mmol), N-(3-dimethylaminopropyl)-N'-ethylcarbodiimide hydrochloride (76.7 mg, 0.400 mmol), and 1-hydroxybenzotriazole (27.0 mg, 0.200 mmol) was added into the above reaction mixture and was stirred at rt under an atmosphere of $N_2$ for 24 h. After that time, the mixture was filtered and the filtrate was concentrated in vacuo. The residue was dissolved in DMSO for submission to MS-directed purification to obtain the title compound as beige oil. $^1$H NMR (DMSO-$d_6$, 400 MHz): δ=2.54-2.56 (m, 2H), 2.59 (s, 3H), 2.97-3.07 (m, 2H), 3.73 (t, 1H, J=5.2 Hz), 3.80 (t, 1H, J=5.6 Hz), 4.25 (brs, 2H), 4.30-4.33 (m, 2H), 6.48 (d, 1H, J=4.0 Hz), 6.80 (d, 1H, J=18.8 Hz), 6.94 (d, 1H, J=0.8 Hz), 7.28-7.30 (m, 1H), 7.52 (d, 1H, J=8.8 Hz), 7.73 (t, 1H, J=0.8 Hz), 7.76-7.80 (m, 1H), 8.23 (dd, 1H, J=1.2 & 6.8 Hz), 8.32 (d, 1H, J=2.0 Hz), 9.40 (s, 1H), 12.01 (brs, 1H), 12.56 (brs, 1H). MS (ES+): m/z 468.11 (10) [MH$^+$]. HPLC: $t_R$=1.62 min (ZQ2000, polar_5 min).

EXAMPLE 288

4-[4-(3-Methoxy-1H-indazol-5-ylamino)-7H-pyrrolo[2,3-d]pyrimidin-6-yl]-3,6-dihydro-2H-pyridine-1-carboxylic acid tert-butyl ester

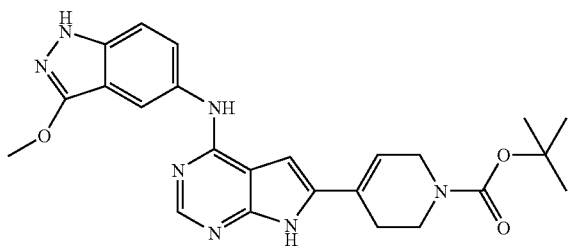

A mixture of 4-(4-chloro-7H-pyrrolo[2,3-d]pyrimidin-6-yl)-3,6-dihydro-2H-pyridine-1-carboxylic acid tert-butyl ester (48.2 mg, 0.144 mmol) and 5-amino-3-methoxyindazole-1-carboxylic acid tert-butyl ester (40.4 mg, 0.153 mmol) in isopropyl alcohol (3.0 mL) in a sealed tube was heated to 85° C. (bath temp.) for 16 h. LC/MS at that time showed the product (minor), indazole-Boc-product (major), de-Boc product (minor), and both starting materials. The bath temperature was increased to 90° C., and heating was continued for 2 d. After reaching rt, di-tert-butyldicarbonate (15 mg, 0.069 mmol) and N,N-diisopropylethylamine (0.1 mL, 0.6 mmol) were added to the reaction mixture, and the now clear solution was stirred at rt for 2 h. LC/MS at that time indicated complete conversion of the de-Boc product to the product. 14.8 M of ammonia in Water (2.0 mL) was added, and the mixture was stirred at rt overnight and heated to 90° C. for 5 h. Sodium hydroxide (6.5 mg, 0.16 mmol) was added, and heating was continued overnight. Water and sat. NH$_4$Cl solution were added, the mixture was extracted with CH$_2$Cl$_2$ (100 mL) and CH$_2$Cl$_2$:MeOH 10:1 (50 mL), and the combined organic layers were dried over MgSO$_4$. The organic solution was filtered through a plug of silica gel (≈1" in a 60 mL glass frit), which was further washed with 5% MeOH in CH$_2$Cl$_2$ until the entire product was eluted. The solution containing the product was concentrated and dried overnight in vacuo. The solid from the aqueous phase was filtered off, washed with water, and dried in vacuo overnight. From the precipitate of the aqueous phase, one obtained the title compound as light brown solid. From the silica gel plug filtration, one obtained a light brown solid that was further purified by MDP to give the title compound as off-white solid. $^1$H NMR (DMSO-$d_6$, 400 MHz): δ=1.44 (s, 9H), 2.42-2.50 (brs, 2H), 3.52-3.60 (m, 2H), 4.00 (s, 3H), 3.98-4.07 (m, 2H), 6.38 (brs, 1H), 6.75 (brs, 1H), 7.34 (d, J=8.8 Hz, 1H), 7.62 (dd, J=2.0, 8.8 Hz, 1H), 8.25 (s, 1H), 8.26 (s, 1H), 9.29 (s, 1H), 11.78 (s, 1H), 11.90 (s, 1H). MS (ES+): m/z 462.0 (100) [MH$^+$]. HPLC: $t_R$=2.5 min (ZQ2000, polar_5 min).

5-Amino-3-methoxyindazole-1-carboxylic acid tert-butyl ester

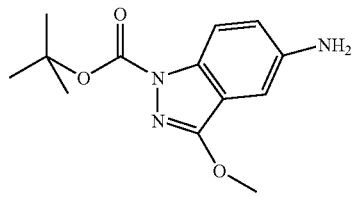

3-Methoxy-5-nitroindazole-1-carboxylic acid tert-butyl ester (0.33 g, 1.11 mmol) and palladium (10% wt) on carbon (0.24 g, 20% wt) were dissolved in EtOAc (25 mL). The flask was evacuated and filled with $N_2$ (×5), then evacuated and filled with hydrogen (×10) and left over a weekend. The mixture was filtered over celite and the solvents removed in vacuo. Purification by column chromatography on silica gel (Jones, 20 g) loading in DCM and eluting in 5:1 Hexanes: EtOAc stepwise to 7:3 Hexanes:EtOAc yielded the title compound as a white powder. $^1$H NMR (400 MHz, CDCl$_3$): δ=1.69 (s, 9H), 3.73 (brs, 2H), 4.15 (s, 3H), 6.85 (d, J=2.0 Hz, 1H), 6.91 (dd, J=8.8, 2.4 Hz, 1H), 7.74 (brs, 1H). MS (ES+): m/z 164.3 (65) [MH$^+$](fragment ion, loss of Boc group).

3-Methoxy-5-nitroindazole-1-carboxylic acid tert-butyl ester

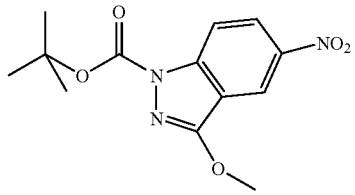

To a pre-dried flask were added 5-nitro-3-oxo-2,3-dihydroindazole-1-carboxylic acid tert-butyl ester (0.65 g, 2.33 mmol), triphenylphosphine (0.92 g, 3.50 mmol), methanol (115 μL, 2.80 mmol) and anhydrous THF (10 mL). The flask was evacuated and purged with N₂ then cooled to 0° C. and diisopropylazodicarboxylate (690 μL, 3.50 mmol) added dropwise over 5 min. The mixture was stirred at rt overnight then diluted with EtOAc and partitioned over water. The organic layer was washed with brine, dried (MgSO₄), filtered and concentrated. Purification by column chromatography on silica gel (Jones, 50 g) loading and eluting in DCM revealed the title compound as a white powder. ¹H NMR (400 MHz, CDCl₃): δ=1.68 (s, 9H), 4.21 (s, 3H), 8.10 (d, J=8.8 Hz, 1H), 8.39 (dd, J=9.2 Hz, 2.4 Hz, 1H), 8.61 (d, J=2.0 Hz, 1H). MS (ES+): m/z 294.3 (20) [MH⁺]. The N-alkylation product methyl-5-nitro-3-oxo-2,3-dihydroindazole-1-carboxylic acid tert-butyl ester was also isolated. ¹H NMR (400 MHz, CDCl₃): δ=1.68 (s, 9H), 3.69 (s, 3H), 8.02 (d, J=9.2 Hz, 1H), 8.48 (dd, J=9.2, 2.4 Hz, 1H), 8.77 (d, J=2.0 Hz, 1H).

5-Nitro-3-oxo-2,3-dihydroindazole-1-carboxylic acid tert-butyl ester

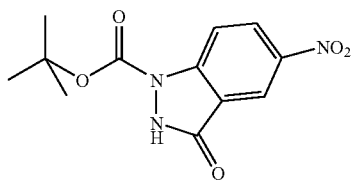

A suspension of 5-nitro-1,2-dihydroindazol-3-one (2.00 g, 11.2 mmol) and di-tert-butyl-dicarbonate (3.17 g, 14.5 mmol) was stirred in anhydrous DCM at 0° C. and DMAP (0.34 g, 2.79 mmol) was added. The mixture turned deep red in color and after 10 minutes a precipitate had formed. This precipitate was filtered and washed with DCM, then dried in vacuo to give the desired product as an off-white powder. ¹H NMR (400 MHz, DMSO-d₆): δ=1.63 (s, 9H), 8.16 (d, J=9.2 Hz, 1H), 8.42 (dd, J=9.2, 2.0 Hz, 1H), 8.61 (d, J=2.4 Hz, 1H), 12.63 (brs, 1H). MS (ES+): m/z 559.3 (100) [MH⁺](dimer).

EXAMPLE 289

4-[4-(1-Methyl-1H-indazol-5-ylamino)-7H-pyrrolo[2,3-d]pyrimidin-6-yl]-3,6-dihydro-2H-pyridine-1-carboxylic acid tert-butyl ester

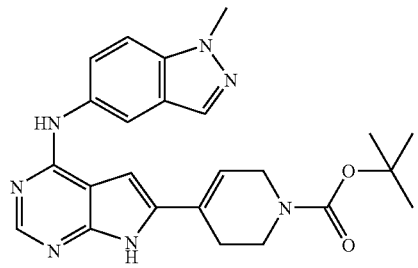

A suspension of 4-(4-chloro-7H-pyrrolo[2,3-d]pyrimidin-6-yl)-3,6-dihydro-2H-pyridine-1-carboxylic acid tert-butyl ester (638.1 mg, 1.906 mmol, 1 eq) and 1-methyl-1H-indazol-5-ylamine (567.4 mg, 3.855 mmol, 2 eq) in n-BuOH (26 mL) was stirred at 120° C. for 15 h. A white precipitate was filtered off, washed several times with MeOH, and dried under high vacuum, giving the title compound, as a white solid. The filtrate was adsorbed onto Hydromatrix, dry loaded, and purified by chromatography on silica gel [Jones Flashmaster, 20 g/70 mL cartridge, eluting with MeOH:DCM 2%→4%→6%]. Fractions containing product were combined and concentrated in vacuo, affording a second batch of the title compound, as a brown solid. ¹H NMR (400 MHz, DMSOd₆): δ=1.44 (s, 9H), 2.43-2.53 (m, 2H), 3.57 (t, J=5.6 Hz, 2H), 4.03 (s, 5H), 6.38 (s, br, 1H), 6.76 (s, br, 1H), 8.60 (d, J=8.8 Hz, 1H), 7.69 (dd, J=8.8, 2.0 Hz, 1H), 8.01 (d, J=0.8 Hz, 1H), 8.26 (s, 1H), 8.39 (d, J=1.6 Hz, 1H), 9.34 (s, —NH), 11.91 (d, J=2.0 Hz, —NH). MS (ES+): m/z 446.07 (100) [MH⁺]. HPLC: t_R=2.59 min (ZQ2000, polar_5 min).

EXAMPLE 290

(1-Methyl-1H-indazol-5-yl)-[6-(1,2,3,6-tetrahydropyridin-4-yl)-7H-pyrrolo[2,3-d]pyrimidin-4-yl]-amine tris-hydrochloride

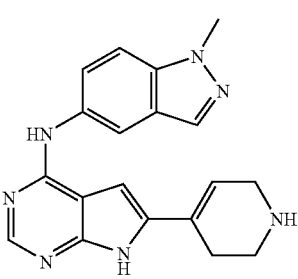

A 4.0 M solution of HCl in 1,4-dioxane (4.7 mL; 20 eq) was added to a suspension of 4-[4-(1-methyl-1H-indazol-5-ylamino)-7H-pyrrolo[2,3-d]pyrimidin-6-yl]-3,6-dihydro- 2H-pyridine-1-carboxylic acid tert-butyl ester (415.4 mg, 0.9324 mmol, 1 eq) in 1,4-dioxane (8 mL) and stirred at rt for 2 h. The solid was filtered off, washed several times with dioxane, and dried under vacuum, yielding the title compound, as a yellow solid. $^1$H NMR (400 MHz, DMSO-$d_6$): δ=2.65 (s, br, 2H), 3.32 (s, br, 2H), 3.80 (s, br, 2H), 4.11 (s, 3H), 6.50 (s, 1H), 7.04 (s, br, 1H), 7.51 (dd, J=8.8, 1.6 Hz, 1H), 7.83 (d, J=9.2 Hz, 1H), 7.98 (s, 1H), 8.15 (s, 1H), 8.26 (s, 1H), 9.43 (s, br, —NH+—NH), 11.56 (s, br, —NH), 13.09 (s, H+). MS (ES+): m/z 346.16 (31) [MH$^+$]. HPLC: $t_R$=1.57 min (ZQ2000, polar_5 min).

EXAMPLE 291

4-[4-(1-Methyl-1H-indazol-5-ylamino)-7H-pyrrolo[2,3-d]pyrimidin-6-yl]-3,6-dihydro-2H-pyridine-1-carboxylic acid tert-butylamide

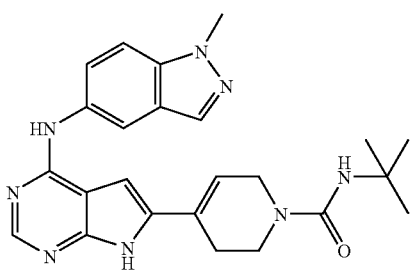

To a suspension of (1-methyl-1H-indazol-5-yl)-[6-(1,2,3,6-tetrahydropyridin-4-yl)-7H-pyrrolo[2,3-d]pyrimidin-4-yl]-amine tris-hydrochloride (166.8 mg, 0.3631 mmol, 1 eq) in anhydrous DMF (17 mL), N,N-diisopropylethylamine (DiPEA) (260 μL, 4.1 eq) was added at rt. The solution was then cooled to −20° C., after which tert-butyl isocyanate (36.5 mg, 0.368 mmol, 1 eq in anhydrous DMF (2 mL) was added. The solution was stirred at rt for 1 h. The reaction was cooled to 0° C., after which additional tert-butyl isocyanate (11.4 mg, 0.115 mmol, 0.3 eq) in anhydrous DMF (1 mL) was added. The reaction was stirred again at rt for 4 h. The reaction was quenched with MeOH, concentrated in vacuo, and dried under vacuum pressure. The crude material was adsorbed onto Hydromatrix, dry loaded, and purified by chromatography on silica gel [Jones Flashmaster, 5 g/25 mL cartridge, eluting with MeOH:DCM 1%→5%]. Fractions containing product were combined and concentrated in vacuo. The material was further purified by trituration in MeOH, yielding the title compound as an off-white solid. $^1$H NMR (400 MHz, DMSOd$_6$): δ=1.28 (s, 9H), 2.44 (s, br, 2H), 3.52 (t, J=5.6 Hz, 2H), 3.99 (d, J=2.0 Hz, 2H), 4.03 (s, 3H), 5.77 (s, —NH), 6.40 (s, br, 1H), 6.75 (s, 1H), 7.60 (d, J=8.8 Hz, 1H), 7.69 (dd, J=8.8, 2.0 Hz, 1H), 8.01 (s, 1H), 8.26 (s, 1H), 8.39 (s, 1H), 9.32 (s, —NH), 11.89 (s, —NH). MS (ES+): m/z 445.07 (100) [MH$^+$]. HPLC: $t_R$=2.29 min (ZQ2000, polar_5 min).

EXAMPLE 292

1-{4-[4-(1-Methyl-1H-indazol-5-ylamino)-7H-pyrrolo[2,3-d]pyrimidin-6-yl]-3,6-dihydro-2H-pyridin-1-yl}-3-piperidin-1-yl-propan-1-one

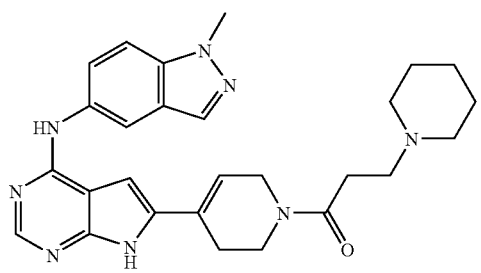

To a suspension of (1-methyl-1H-indazol-5-yl)-[6-(1,2,3,6-tetrahydro-pyridin-4-yl)-7H-pyrrolo[2,3-d]pyrimidin-4-yl]-amine tris-hydrochloride (155.3 mg, 0.3381 mmol, 1 eq), 1-piperidinepropanoic acid (150.1 mg, 0.9548 mmol, 2.8 eq), 1-hydroxybenzotriazole (HOBt) (46.7 mg, 0.346 mmol, 1 eq), and PS-carbodiimide (1.37 mmol/g loading; 1008.7 mg, 1.38 mmol, 4 eq) in anhydrous DMF (10 mL), DiPEA (290 μL, 1.7 mmol, 5 eq) was added and was shaken at rt for 13 h. The resin was filtered off and rinsed several times with DMF. The filtrate was concentrated in vacuo at medium temp (bath temp: max 42° C.), redissolved in MeOH and DCM, and concentrated again under reduced pressure. The crude material was adsorbed onto Hydromatrix, dry loaded, and purified by chromatography on silica gel [Jones Flashmaster, 10 g/70 mL cartridge, eluting with MeOH:DCM 5%→10% →7N NH$_3$(MeOH):DCM 3%→5%]. Fractions containing product were combined and concentrated in vacuo, affording the title compound as an off-white solid. $^1$H NMR (400 MHz, DMSOd$_6$): δ=1.30-1.40 (m$_c$, 2H), 1.45-1.53 (m$_c$, 4H), 2.30-2.41 (s, br, 4H), 2.41-2.63 (m, 6H), 3.69 (t, J=5.6 Hz, 2H), 4.03 (s, 3H), 4.23 & 4.13 (s, br, rotamers, 2H), 6.41 (s, br, 1H), 6.75 & 6.77 (s, br, rotamers, 1H), 7.60 (d, J=9.2 Hz, 1H), 7.69 (dd, J=8.8, 2.0 Hz, 1H), 8.01 (s, 1H), 8.26 (d, J=2.0 Hz, 1H), 8.38 & 8.39 (s, br, rotamers, 1H), 9.34 (s, —NH), 11.90 & 11.93 (s, rotamers, 1H). MS (ES+): m/z 485.11 (45) [MH$^+$]. HPLC: $t_R$=1.72 min (ZQ2000, polar_5 min).

EXAMPLE 293

2-(2-Methoxyethoxy)-1-{4-[4-(1-methyl-1H-indazol-5-ylamino)-7H-pyrrolo[2,3-d]pyrimidin-6-yl]-3,6-dihydro-2H-pyridin-1-yl}-ethanone

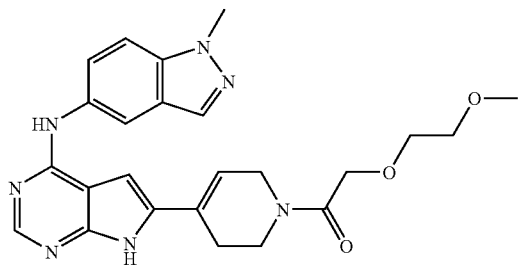

The title compound was obtained following the procedure for 1-{4-[4-(1-methyl-1H-indazol-5-ylamino)-7H-pyrrolo[2,3-d]pyrimidin-6-yl]-3,6-dihydro-2H-pyridin-1-yl}-3-piperidin-1-ylpropan-1-one, using (2-methoxyethoxy)-acetic acid, and triturating the crude material once in MeOH, as an off-white solid. $^1$H NMR (400 MHz, DMSO-d$_6$): δ=2.44-2.61 (s, br, rotamers, 2H), 3.25 (s, 3H), 3.45-3.50 (m, 2H), 3.55-3.60 (m, 2H), 3.64 & 3.70 (t, J=5.2 Hz, rotamers, 2H), 4.03 (s, 3H), 4.13 & 4.16 (s, br, rotamers, 2H), 4.20 & 4.24 (s, rotamers, 2H), 6.40 (s, br, 1H), 6.75 & 6.78 (s, br, rotamers, 1H), 7.60 (d, J=8.8 Hz, 1H), 7.67 (dd, J=8.8, 2.0 Hz, 1H), 8.01 (s, 1H), 8.26 (s, 1H), 8.38 & 8.39 (s, br, rotamers, 1H), 9.34 (s, —NH), 11.91 & 11.94 (s, rotamers, —NH). MS (ES+): m/z 462.08 (100) [MH$^+$]. HPLC: t$_R$=1.99 min (ZQ2000, polar_5 min).

EXAMPLE 294

{4-[4-(1-Methyl-1H-indazol-5-ylamino)-7H-pyrrolo[2,3-d]pyrimidin-6-yl]-3,6-dihydro-2H-pyridin-1-yl}-(4-methylpiperazin-1-yl)-methanone

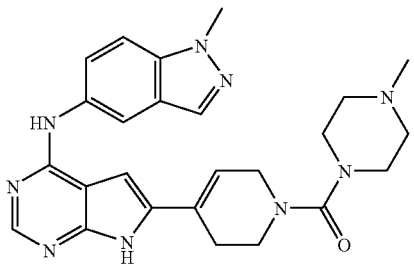

To a suspension of (1-methyl-1H-indazol-5-yl)-[6-(1,2,3,6-tetrahydropyridin-4-yl)-7H-pyrrolo[2,3-d]pyrimidin-4-yl]-amine tris-hydrochloride (78.1 mg, 0.172 mmol, 1 eq) in DMF (5 mL), DiPEA (180 μL, 1.0 mmol, 6 eq) was added. After cooling the suspension to 0° C., 4-methyl-1-piperazinecarbonyl chloride hydrochloride (28.6 mg, 0.170 mmol, 1 eq) in DMF (1.5 mL) was added and the reaction was stirred at 0° C. for 2 h. An additional 0.2 eq of 4-methyl-1-piperazinecarbonyl chloride hydrochloride (6.1 mg, 0.036 mmol) in DMF (1 mL) was added and the suspension was stirred again at 0° C. for 3 h. Still additional acid chloride was needed and 4-methyl-1-piperazinecarbonyl chloride hydrochloride (6.1 mg, 0.036 mmol, 0.2 eq) in DMF (1 mL) was added. After 5 h, the reaction was quenched/worked up as follows: reaction solution was added dropwise into water, filtered (M frit), washed with water and then EtOAc, and dried, giving the title compound as an off-white solid. $^1$H NMR (400 MHz, DMSO-d$_6$): δ=2.19 (s, 3H), 2.31 (s, br, 4H), 2.44-2.55 (m, 2H), 3.17 (s, br, 4H), 3.40 (t, J=5.2 Hz, 2H), 3.92 (s, br, 2H), 4.03 (s, 3H), 6.38 (s, br, 1H), 6.75 (s, 1H), 7.60 (d, J=8.4 Hz, 1H), 7.69 (d, J=8.8 Hz, 1H), 8.01 (s, 1H), 8.25 (s, 1H), 8.38 (s, br, 1H), 9.33 (s, —NH), 11.89 (s, —NH). MS (ES+): m/z 472.14 (9) [MH$^+$]. HPLC: t$_R$=1.68 min (ZQ2000, polar_5 min).

EXAMPLE 295

4-4-[2-(2-Dimethylaminoethylamino)-benzothiazol-6-ylamino]-7H-pyrrolo[2,3-d]pyrimidin-6-yl-3,6-dihydro-2H-pyridine-1-carboxylic acid tert-butyl ester

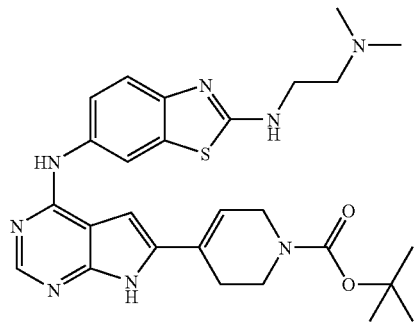

To a suspension of N'2'-(2-dimethylaminoethyl)-N'6'-[6-(1,2,3,6-tetrahydropyridin-4-yl)-7H-pyrrolo[2,3-d]pyrimidin-4-yl]-benzothiazole-2,6-diamine (221.1 mg, 0.346 mmol, 1 eq) in anhydrous DCM (5 mL) and anhydrous DMF (4 mL), DiPEA (425 μL, 2.43 mmol, 7 eq) was added under an atmosphere of N$_2$. A solution of di-tert-butyldicarbonate (78.2 mg, 0.355 mmol, 1 eq) in anhydrous DCM (3 mL) and anhydrous DMF (0.5 mL) was added via syringe. The reaction was allowed to stir at rt for 2 h, after which it was concentrated in vacuo. The crude material (352.4 mg) was adsorbed onto Hydromatrix, dry loaded, and purified by chromatography on silica gel [Jones Flashmaster, 10 g/70 mL cartridge, eluting with neat EtOAc→MeOH:EtOAc 5%→7N NH$_3$/MeOH:EtOAc 2%→5%]. Fractions containing product were combined, concentrated in vacuo, and further purified by HPLC, affording the title compound as a yellow solid. $^1$H NMR (400 MHz, MeOH-d$_4$): δ=1.50 (s, 9H), 2.33 (s, 6H), 2.54 (s, br, 2H), 2.66 (t, J=6.4 Hz, 2H), 3.59 (t, J=6.4 Hz, 2H), 3.65 (s, br, 2H), 4.12 (s, br, 2H), 6.27 (s, br, 1H), 6.55 (s, 1H), 7.42 (d, J=1.2 Hz, 2H), 8.05 (d, J=0.8 Hz, 1H), 8.17 (s, 1H). MS (ES+): m/z 534.92 (95) [MH$^+$]. HPLC: t$_R$=2.07 min (ZQ2000, polar_5 min).

N'2'-(2-Dimethylaminoethyl)-N'6'-[6-(1,2,3,6-tetrahydropyridin-4-yl)-7H-pyrrolo[2,3-d]pyrimidin-4-yl]-benzothiazole-2,6-diamine

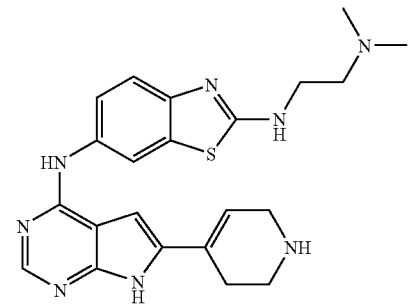

A solution of N'2'-(2-dimethylaminoethyl)-benzothiazole-2,6-diamine (64.4 mg, 0.267 mmol, 1 eq), 4-(4-chloro-7H-pyrrolo[2,3-d]pyrimidin-6-yl)-3,6-dihydro-2H-pyridine-1-carboxylic acid tert-butyl ester (95.8 mg, 0.286 mmol, 1 eq), and trifluoroacetic acid (TFA) (104 µL, 1.34 mmol, 5 eq) in 2,2,2-trifluoroethanol (TFE) (4 ml), in a sealed tube, was stirred at 100° C. for 3.5 h and concentrated in vacuo, giving the crude title compound. No workup or purification was performed prior to N—BOC protection. MS (ES+): m/z 434.92 (15) [MH+]. HPLC: $t_R$=0.49 & 1.40 min (ZQ2000, polar_5 min).

N'2'-(2-Dimethylaminoethyl)-benzothiazole-2,6-diamine

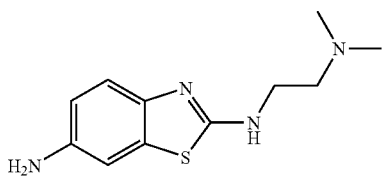

To a suspension of N,N-dimethyl-N'-(6-nitrobenzothiazol-2-yl)-ethane-1,2-diamine (190.3 mg, 0.707 mmol, 1 eq) in MeOH (9 mL) and Pd/C (10%, 50% $H_2O$, 0.06 eq), $H_2$ (g) was introduced into the system and the reaction was allowed to stir for 4 h at rt. Pd/C was filtered over a pad of Celite and rinsed with MeOH. The filtrate was concentrated in vacuo, yielding the title compound as a hard, yellow, plastic-like solid. $^1$H NMR (400 MHz, MeOH-$d_4$): δ=2.34 (s, 6H), 2.65 (t, J=6.4 Hz, 2H), 3.53 (t, J=6.4 Hz, 2H), 6.72 (dd, J=8.4, 2.4 Hz, 1H), 6.98 (d, J=2.4 Hz, 1H), 7.21 (d, J=8.4 Hz, 1H). MS (ES+): m/z 237.20 (89) [MH+]. HPLC: $t_R$=0.33 min (ZQ2000, polar_5 min).

N,N-Dimethyl-N'-(6-nitrobenzothiazol-2-yl)-ethane-1,2-diamine

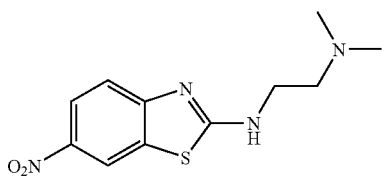

To a solution of 2-bromo-6-nitrobenzothiazole (195.2 mg, 0.7384 mmol, 1 eq) in THF (8 mL) N,N-dimethyl-1,2-ethanediamine (405 µL, 3.69 mmol, 5 eq) was added. The reaction was stirred for 1 h at rt, after which all solvent was evaporated in vacuo. The residue was dissolved in DCM and washed with $NaHCO_3$ (2×) and brine (1×). The filtrate was dried over $Na_2SO_4$, filtered, and concentrated under reduced pressure. The yellow crude material was adsorbed onto Hydromatrix and purified by chromatography on silica gel [Jones Flashmaster, 5 g/25 mL cartridge, eluting with 1:1 EtOAc:DCM→3% MeOH:DCM]. Fractions 19-61 were combined and concentrated in vacuo, affording the title compound as a yellow solid. $^1$H NMR (400 MHz, $CDCl_3$): δ=2.29 (s, 6H), 2.60 (t, J=6.0 Hz, 2H), 3.54 (q, br, J=4.8 Hz, 2H), 6.39 (s, br, —NH), 7.52 (d, J=8.8 Hz, 1H), 8.20 (dd, J=8.8, 2.0 Hz, 1H), 8.50 (d, J=2.0 Hz, 1H). MS (ES+): m/z 267.10 (100) [MH+]. HPLC: $t_R$=1.78 min (ZQ2000, polar_5 min).

2-Bromo-6-nitrobenzothiazole

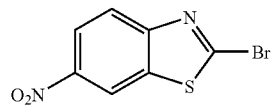

Into a 150 mL beaker, 2-amino-6-nitrobenzothiazole (5.1089 g, 25.39 mmol, 1 eq) was mixed vigorously with phosphoric acid, 85 wt. % (22.6 mL, 13 eq) at 50° C. The solution was then cooled to −20° C., using an acetone/dry ice bath. To this, a solution of $NaNO_2$ (1.943 g, 28.16 mmol, 1.1 eq) in water (5.0 mL), also cooled to −20° C., was added slowly over the course of 15 min. After 1 h, the resulting suspension was poured over a solution of CuBr (4.593 g, 32.02 mmol, 1.3 eq) in 48% HBr (25.3 mL) at rt and was stirred. Additional HBr (≈35 mL) aided in transfer. After 1 h, the mixture was heated at 40° C. for 2 h. After 2 h, the heat was turned off and the reaction continued to stir at rt for 16 h. The crude mixture was diluted with water to a final volume of 200 mL and was extracted with DCM (3×). The organics were dried over anhydrous $mg_2SO_4$, filtered, and concentrated under reduced pressure. The crude material was adsorbed onto silica gel, dry loaded, and purified by chromatography on silica gel [Jones Flashmaster, 50 g/150 mL cartridge, eluting with DCM/Hex 1:1→2:1→neat DCM]. Fractions containing product were combined, concentrated in vacuo, and re-chromatographed to give the title compound as an orange solid. $^1$H NMR (400 MHz, $CDCl_3$): δ=8.11 (d, J=9.2 Hz, 1H), 8.38 (dd, J=9.2, 2.4 Hz, 1H), 8.78 (d, J=2.0 Hz, 1H). MS (ES+): m/z 258.95/260.96 (100/96) [MH+]. HPLC: $t_R$=3.43 min (ZQ2000, polar_5 min).

EXAMPLE 296

4-[4-(2-Benzylaminobenzothiazol-6-ylamino)-7H-pyrrolo[2,3-d]pyrimidin-6-yl]-3,6-dihydro-2H-pyridine-1-carboxylic acid tert-butyl ester

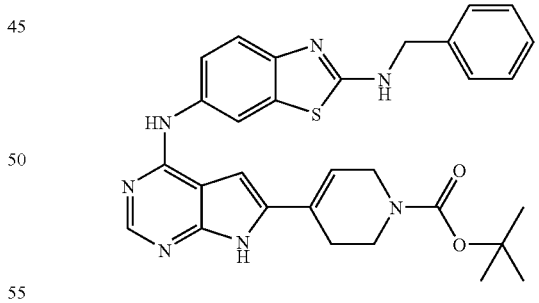

The title compound was prepared following the procedure for 4-4-[2-(2-dimethylaminoethylamino)-benzothiazol-6-ylamino]-7H-pyrrolo[2,3-d]pyrimidin-6-yl-3,6-dihydro-2H-pyridine-1-carboxylic acid tert-butyl ester, using N'2'-benzyl-N'6'-[6-(1,2,3,6-tetrahydropyridin-4-yl)-7H-pyrrolo[2,3-d]pyrimidin-4-yl]-benzothiazole-2,6-diamine, except that additional equivalents (2 eq total) of BOC-anhydride were used, no DiPEA was used, and the material was purified only by column chromatography. Yellow gum. $^1$H NMR (400 MHz, $CDCl_3$): δ=1.49 (s, 9H), 2.42 (br, s, 2H), 3.62 (br, t, J=5.2 Hz, 2H), 4.14 (br, s, 2H), 4.66 (s, 2H), 5.91 (br, s, 1H), 6.04 (br, s, —NH), 6.18 (br, s, 1H), 7.30-7.44 (m, 6H+—NH), 7.54 (d, J=8.4 Hz, 1H), 7.95 (br, s, 1H), 8.30 (br, s, 1H), 11.51 (br, s, —NH). MS (ES+): m/z 553.94 (100) [MH$^+$]. HPLC: t$_R$=3.03 min (ZQ2000, polar__5 min).

N'2'-Benzyl-N'6'-[6-(1,2,3,6-tetrahydropyridin-4-yl)-7H-pyrrolo[2,3-d]pyrimidin-4-yl]-benzothiazole-2,6-diamine

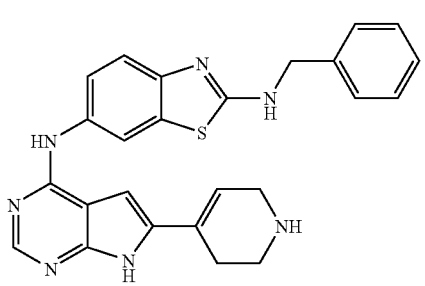

The title compound was prepared following the procedure for N'2'-(2-dimethylaminoethyl)-N'6'-[6-(1,2,3,6-tetrahydropyridin-4-yl)-7H-pyrrolo[2,3-d]pyrimidin-4-yl]-benzothiazole-2,6-diamine, using N'2'-benzylbenzothiazole-2,6-diamine, except for the following modifications: The reaction was heated for 18 h at 100° C. The residue was dissolved in a 5% MeOH:DCM mixture and washed with NaHCO$_3$ (1×) and brine (1×), dried over anhydrous Na$_2$SO$_4$, filtered, and concentrated in vacuo. Any emulsion was dissolved in additional 5% MeOH:DCM and washed in the same manner. The crude material was adsorbed onto Hydromatrix, dry loaded, and purified by chromatography on silica gel [Jones Flashmaster, 2 g/20 mL cartridge, eluting with MeOH:DCM 5% (1-24)→10% (25-41)→7N NH$_3$[MeOH:DCM 5% (42-57)→10% (58+)]. Fractions containing product were combined and concentrated under reduced pressure, affording the title compound. $^1$H NMR (400 MHz, DMSO-d$_6$): δ=2.48 (d, J=2.4 Hz, 2H), 3.06 (t, J=6.0 Hz, 2H), 3.51 (d, J=2.8 Hz, 2H), 4.54 (s, 2H), 6.23 (s, br, 1H), 6.45 (s, br, 1H), 7.13-7.20 (m$_c$, 1H), 7.22-7.28 (m$_c$, 2H), 7.28-7.33 (m, 4H), 7.92-7.97 (m, 1H), 8.07 (s, 1H). MS (ES+): m/z 453.98 (13) [MH$^+$-BOC]. HPLC: t$_R$=2.11 min (MDP [Waters/Micromass], polar__5 min).

N'2'-Benzylbenzothiazole-2,6-diamine

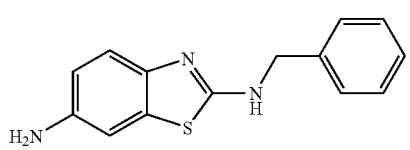

The title compound was prepared following the procedure for N'2'-(2-dimethylaminoethyl)-benzothiazole-2,6-diamine, using benzyl-(6-nitrobenzothiazol-2-yl)-amine. Brown solid. $^1$H NMR (400 MHz, CDCl$_3$): δ=3.56 (s, br, —NH$_2$), 4.61 (s, 2H), 5.25 (s, br, —NH), 6.69 (dd, J=8.4, 2.4 Hz, 1H), 6.93 (d, J=2.4 Hz, 1H), 7.28-7.42 (m, 6H). MS (ES+): m/z 256.19 (100) [MH$^+$]. HPLC: t$_R$=2.01 min (ZQ2000, polar__5 min).

Benzyl-(6-nitrobenzothiazol-2-yl)-amine

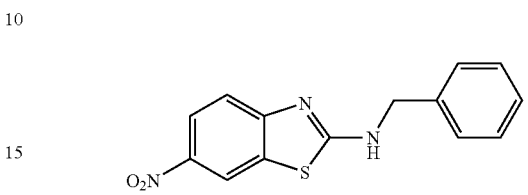

The title compound was prepared following the procedure for N,N-dimethyl-N'-(6-nitrobenzothiazol-2-yl)-ethane-1,2-diamine, using benzylamine. Modified workup: Solid that had precipitated during course of reaction (amine salt) was filtered; no aqueous workup was conducted. $^1$H NMR (400 MHz, CDCl$_3$): δ=4.70 (s, 2H), 6.07 (s, br, —NH), 7.33-7.39 (m, 1H), 7.39-7.42 (m, 4H), 7.51 (d, J=8.8 Hz, 1H), 8.21 (dd, J=8.8, 2.4 Hz, 1H), 8.51 (d, J=2.4 Hz, 1H). MS (ES+): m/z 286.03 (100) [MH$^+$]. HPLC: t$_R$=3.47 min (ZQ2000, polar__5 min).

EXAMPLE 297

4-[4-(2-Phenethylaminobenzothiazol-6-ylamino)-7H-pyrrolo[2,3-d]pyrimidin-6-yl]-3,6-dihydro-2H-pyridine-1-carboxylic acid tert-butyl ester

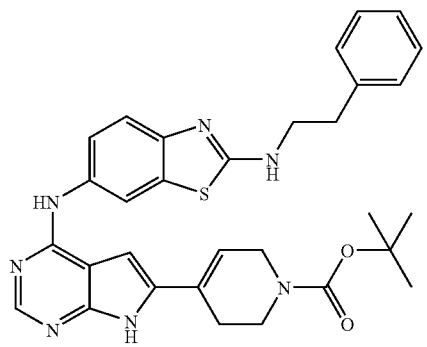

The title compound was prepared following the procedure for 44-[2-(2-dimethylaminoethylamino)-benzothiazol-6-ylamino]-7H-pyrrolo[2,3-d]pyrimidin-6-yl-3,6-dihydro-2H-pyridine-1-carboxylic acid tert-butyl ester, using N'2'-phenethyl-N'6'-[6-(1,2,3,6-tetrahydropyridin-4-yl)-7H-pyrrolo[2,3-d]pyrimidin-4-yl]-benzothiazole-2,6-diamine. Off-white solid. $^1$H NMR (400 MHz, DMSO-d$_6$): δ=1.43 (s, 9H), 2.43-2.48 (s, br, 2H), 2.92 (t, J=6.8 Hz, 2H), 3.53-3.63 (m, 4H), 4.03 (s, br, 2H), 6.38 (s, br, 1H), 6.73 (s, 1H), 7.19-7.24 (m, 1H), 7.26-7.34 (m, 4H), 7.36 (d, J=8.4 Hz, 1H), 7.52 (dd, J=8.8, 2.4 Hz, 1H), 7.99 (t, J=5.2 Hz, —NH), 8.24 (s, 1H), 8.31 (d, J=2.4 Hz, 1H), 9.30 (s, —NH), 11.90 (s, —NH). MS (ES+): m/z 567.98 (77) [MH+]. HPLC: $t_R$=3.02 min (ZQ2000, polar__5 min).

N'2'-Phenethyl-N'6'-[6-(1,2,3,6-tetrahydropyridin-4-yl)-7H-pyrrolo[2,3-d]pyrimidin-4-yl]-benzothiazole-2,6-diamine

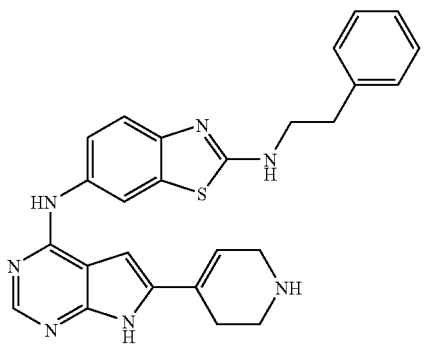

The title compound was prepared following the procedure for N'2'-(2-dimethylaminoethyl)-N'6'-[6-(1,2,3,6-tetrahydropyridin-4-yl)-7H-pyrrolo[2,3-d]pyrimidin-4-yl]-benzothiazole-2,6-diamine, using N'2'-phenethylbenzothiazole-2,6-diamine. MS (ES+): m/z 467.96 (25) [MH+]. HPLC: $t_R$=2.01 min (ZQ2000, polar__5 min).

N'2'-Phenethylbenzothiazole-2,6-diamine

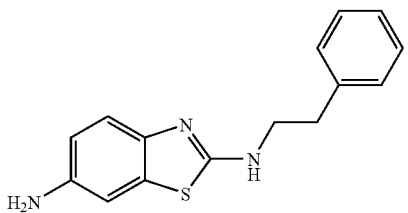

The title compound was prepared following the procedure for N'2'-(2-dimethylaminoethyl)-benzothiazole-2,6-diamine, using (6-nitrobenzothiazol-2-yl)-phenethylamine. Brown gum. ¹H NMR (400 MHz, CDCl₃): δ=2.98 (t, J=6.8 Hz, 2H), 3.58 (s, br, —NH₂), 3.67 (q, J=6.8 Hz, 2H), 4.92 (s, br, —NH), 6.68 (dd, J=8.4, 2.4 Hz, 1H), 6.94 (d, J=2.4 Hz, 1H), 7.21-7.37 (m, 6H). MS (ES+): m/z 270.13 (100) [MH+]. HPLC: $t_R$=2.10 min (ZQ2000, polar__5 min).

(6-Nitrobenzothiazol-2-yl)-phenethylamine

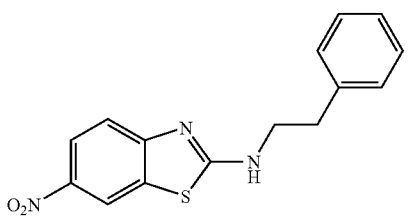

The title compound was prepared following the procedure for N,N-dimethyl-N'-(6-nitrobenzothiazol-2-yl)-ethane-1,2-diamine, using 4 eq of phenethylamine. Modified workup: Solid that had precipitated during course of reaction (amine salt) was filtered; no aqueous workup was conducted. ¹H NMR (400 MHz, CDCl₃): δ=3.03 (t, J=6.4 Hz, 3H), 3.77 (q, J=6.4 Hz, 2H), 7.23-7.30 (m, 3H), 7.33-7.38 (m, 2H), 7.52 (d, J=8.8 Hz, 1H), 8.21 (dd, J=8.8, 2.4 Hz, 1H), 8.51 (d, J=2.4 Hz, 1H). MS (ES+): m/z 300.10 [MH+]. HPLC: $t_R$=3.57 min (ZQ2000, polar__5 min).

EXAMPLE 298

4-4-[2-(2-Methoxyethylamino)-benzothiazol-6-ylamino]-7H-pyrrolo[2,3-d]pyrimidin-6-yl-3,6-dihydro-2H-pyridine-1-carboxylic acid tert-butyl ester

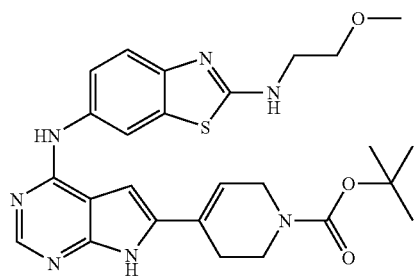

The title compound was prepared following the procedure for 4-4-[2-(2-dimethylaminoethylamino)-benzothiazol-6-ylamino]-7H-pyrrolo[2,3-d]pyrimidin-6-yl-3,6-dihydro-2H-pyridine-1-carboxylic acid tert-butyl ester, using N'2'-(2-methoxyethyl)-N'6'-[6-(1,2,3,6-tetrahydropyridin-4-yl)-7H-pyrrolo[2,3-d]pyrimidin-4-yl]-benzothiazole-2,6-diamine. Tan solid. ¹H NMR (400 MHz, DMSO-d₆): δ=1.43 (s, 9H), 2.43-2.48 (m, 2H), 3.29 (s, 3H), 3.52 (d, J=2.8 Hz, 4H), 3.56 (t, J=5.6 Hz, 2H), 4.00-4.07 (m, 2H), 6.38 (br, s, 1H), 6.73 (s, 1H), 7.34 (d, J=8.4 Hz, 1H), 7.52 (dd, J=8.8, 2.4, 1H), 8.00 (br, s, —NH), 8.23 (s, 1H), 8.29 (d, J=2.0 Hz, 1H), 9.30 (s, —NH), 11.91 (s, —NH). MS (ES+): m/z 521.90 (96) [MH+]. HPLC: $t_R$=2.54 min (ZQ2000, polar__5 min).

N'2'-(2-Methoxyethyl)-N'6'-[6-(1,2,3,6-tetrahydropyridin-4-yl)-7H-pyrrolo[2,3-d]pyrimidin-4-yl]-benzothiazole-2,6-diamine

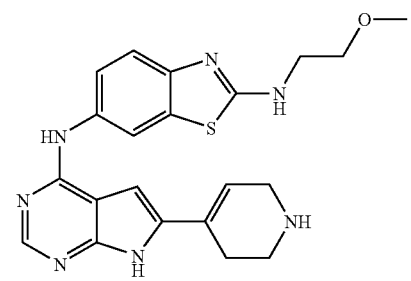

The title compound was prepared following the procedure for N'2'-(2-dimethylaminoethyl)-N'6'-[6-(1,2,3,6-tetrahydropyridin-4-yl)-7H-pyrrolo[2,3-d]pyrimidin-4-yl]-benzothiazole-2,6-diamine, using N'2'-(2-methoxyethyl)-benzothiazole-2,6-diamine, except that the reaction mixture was heated for 45 h to 100° C. MS (ES+): m/z 421.94 (61) [MH+]. HPLC: $t_R$=0.50 & 1.62 min (ZQ2000, polar_5 min).

N'2'-(2-Methoxyethyl)-benzothiazole-2,6-diamine

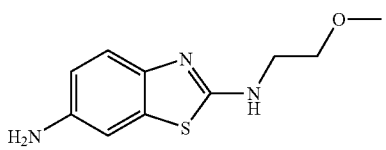

The title compound was prepared following the procedure for N'2'-(2-dimethylaminoethyl)-benzothiazole-2,6-diamine, using (2-methoxyethyl)-(6-nitro-benzothiazol-2-yl)-amine. Pink solid. $^1$H NMR (400 MHz, CDCl$_3$): δ=3.39 (s, 3H), 3.58 (s, br, —NH$_2$), 3.62 (s, 4H), 5.26 (s, br, —NH), 6.68 (dd, J=8.4, 2.4 Hz, 1H), 6.92 (d, J=2.0 Hz, 1H), 7.35 (d, J=8.8 Hz, 1H). MS (ES+): m/z 224.21 (100) [MH+]. HPLC: $t_R$=0.49 & 1.05 min (ZQ2000, polar_5 min).

(2-Methoxyethyl)-(6-nitrobenzothiazol-2-yl)-amine

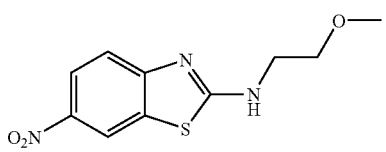

The title compound was prepared following the procedure for N,N-dimethyl-N'-(6-nitrobenzothiazol-2-yl)-ethane-1,2-diamine, using 6.78 eq of 2-methoxyethylamine. $^1$H NMR (400 MHz, CDCl$_3$): δ=3.42 (s, 3H), 3.65 (td, J=4.4, 0.8 Hz, 2H), 3.70 (t, br, J=4.4 Hz, 2H), 5.92 (s, br, —NH), 7.53 (d, J=8.8 Hz, 1H), 8.21 (dd, J=9.2, 2.4 Hz, 1H), 8.51 (d, J=2.4 Hz, 1H). MS (ES+): m/z 254.10 (100) [MH+]. HPLC: $t_R$=2.89 min (ZQ2000, polar_5 min).

EXAMPLE 299 tert-Butyl 4-[4-(4-methoxy-3-thiazol-5-ylphenylamino)-7H-pyrrolo[2,3-d]pyrimidin-6-yl]-3,6-dihydro-2H-pyridine-1-carboxylate

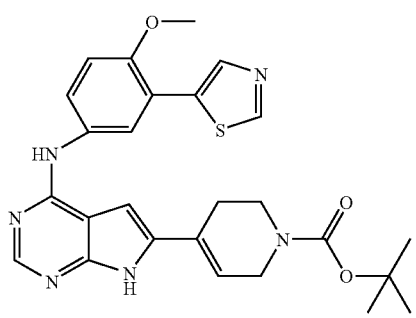

Nitrogen was bubbled through a solution of tert-butyl 4-[4-(3-iodo-4-methoxyphenylamino)-7H-pyrrolo[2,3-d]pyrimidin-6-yl]-3,6-dihydro-2H-pyridine-1-carboxylate (109.5 mg, 0.2 mmol), thiazole (85.1 mg, 1.0 mmol), potassium acetate (39.3 mg, 0.4 mmol), and tetrakis(triphenylphosphine)-palladium (23.1 mg, 0.02 mmol) in DMF (0.8 mL) for 3 min. The mixture was then heated to 100° C. and stirred for 17 h. The solvents were removed in vaccuo and the residue was dissolved in DMF (~2 mL). The DMF solution was filtered and sent to mass-directed HPLC purification to give the title compound. $^1$H-NMR (CD$_3$OD, 400 MHz): δ=1.50 (s, 9H), 2.55 (m, 2H), 3.66 (m, 2H), 3.98 (s, 3H), 4.13 (m, 2H), 6.28 (s, br, 1H), 6.60 (s, 1H), 7.17 (d, J=9.2 Hz, 1H), 7.68 (dd, J=2.4, 8.8 Hz, 1H), 8.06 (d, J=2.8 Hz, 1H), 8.20 (s, 1H), 8.31 (s, 1H), 8.98 (s, 1H). MS (ES+): m/z 504.99 (MH+). HPLC: $t_R$=2.95 min (ZQ2000, polar_5 min). The following EXAMPLES 300-301 are compounds of Formula (I) wherein X=C—CN.

EXAMPLE 300

4-[5-Cyano-4-(1H-indazol-5-ylamino)-1H-pyrrolo[2,3-b]pyridin-2-yl]-3,6-dihydro-2H-pyridine-1-carboxylic acid tert-butyl ester

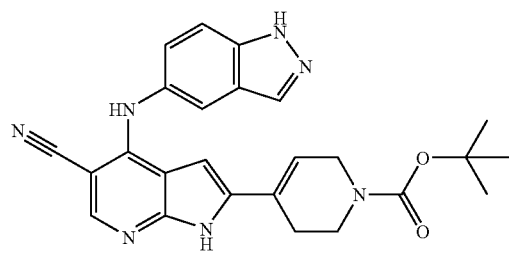

To a mixture of 4-[5-bromo-4-(1H-indazol-5-ylamino)-1H-pyrrolo[2,3-b]pyridin-2-yl]-3,6-dihydro-2H-pyridine-1-carboxylic acid tert-butyl ester (8 mg, 0.015 mmol), DPPF (4.1 mg, 0.007 mmol), water (0.03 mL) and zinc cyanide (3.7 mg, 0.031 mmol) in acetonitrile (3 mL) was added Pd$_2$ dba$_3$ (3.6 mg, 0.004 mmol) and the mixture was heated to reflux under N$_2$ overnight. The reaction mixture was evaporated and the crude product was purified by preparative TLC using 10% methanol in DCM as eluent to afford 4-[5-cyano-4-(1H-indazol-5-ylamino)-1H-pyrrolo[2,3-b]pyridin-2-yl]-3,6-dihydro-2H-pyridine-1-carboxylic acid tert-butyl ester as light gray solid. $^1$H NMR (400 MHz, CD$_3$OD): δ=8.05 (s, 1H), 7.96 (s, 1H), 7.62 (dd, J=1.8, 0.5 Hz, 1H), 7.50 (s, 1H), 7.27 (dd, J=8.8, 1.9 Hz, 1H), 6.05 (bs, 1H), 5.35 (bs, 1H), 3.93-3.97 (m, 2H), 3.40 (t, J=6.2 Hz, 2H), 2.02-2.07 (m, 2H), 1.37 (s, 9H); MS (ES+): m/z 455.99 (100) [MH+]; HPLC: $t_R$=2.97 min (ZQ2000, polar_5 min).

4-[5-Bromo-4-(1H-indazol-5-ylamino)-1H-pyrrolo[2,3-b]pyridin-2-yl]-3,6-dihydro-2H-pyridine-1-carboxylic acid tert-butyl ester

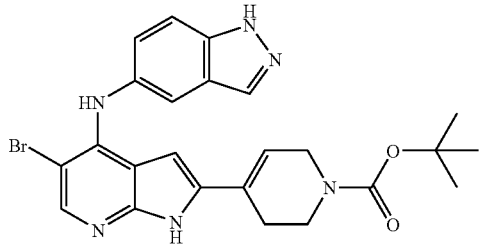

To a mixture of (5-bromo-2-iodo-1H-pyrrolo[2,3-b]pyridin-4-yl)-(1H-indazol-5-yl)-amine (25 mg, 0.069 mmol), potassium carbonate (19 mg, 0.14 mmol), tetrakistriphenylphosphine palladium (10 mg, 0.014 mmol) and 4-(4,4,5,5-tetramethyl-[1,3,2]dioxaborolan-2-yl)-3,6-dihydro-2H-pyridine-1-carboxylic acid tert-butyl ester (21.6 mg, 0.069 mmol) was added degassed DMF (3 mL) and water (0.75 mL) and the mixture was heated to reflux for 5 h. Water was added to the reaction and filtered. The precipitate was washed with water and the filtrate was extracted with DCM. The precipitate was dissolved in DCM/MeOH mixture (9:1) and combined with the DCM extract and evaporated. The crude product was purified by preparative TLC using 8% methanol in DCM as eluent to afford the title compound as beige solid. $^1$H NMR (400 MHz, CD$_3$OD): δ=10.32 (s, 1H), 8.11 (s, 1H), 8.02 (s, 1H), 7.58 (d, J=0.8 Hz, 1H), 7.47 (d, J=8.9 Hz, 1H), 7.26 (dd, J=8.8, 1.9 Hz, 1H), 6.69 (s, 1H), 5.95 (bs, 1H), 5.16 (bs, 1H), 3.99-4.03 (m, 2H), 3.42 (t, J=5.4 Hz, 2H), 2.00-2.07 (m, 2H), 1.39 (s, 9H); MS (ES+): m/z 510.89 (100) [MH$^+$]; HPLC: t$_R$=2.63 min (ZQ2000, polar_5 min).

(5-Bromo-2-iodo-1H-pyrrolo[2,3-b]pyridin-4-yl)-(1H-indazol-5-yl)-amine

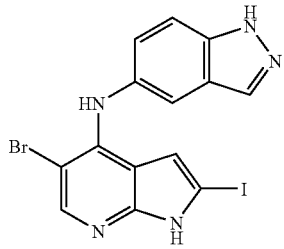

To a slurry of a mixture of 1-benzenesulfonyl-5-bromo-4-chloro-2-iodo-1H-pyrrolo[2,3-b]pyridine and 5-bromo-4-chloro-2-iodo-1-(2-iodobenzenesulfonyl)-1H-pyrrolo[2,3-b]pyridine (560 mg, 1.0 mmol) in trifluoroethanol (6 mL) was added trifluoroacetic acid (0.041 mL, 0.52 mmol) and indazole (266 mg, 2.0 mmol), and the reaction was heated in a sealed tube at 120° C. for 4 d. Additional indazole (67 mg, 0.5 mmol) was added twice to the reaction on the second and third days. The reaction was cooled to RT, diluted with methanol (20 mL), saturated sodium bicarbonate solution was added (1 mL) and evaporated to dryness under reduced pressure. The residue obtained was triturated with methanol:DCM (1:1) mixture and filtered. The filtrate was evaporated and the crude obtained was purified by chromatography on silica gel [Jones Flashmaster, 70 g/150 mL cartridge, eluting with DCM:Methanol 100:0→96:4], yielding the product, which was triturated with 4:1 methanol:DCM mixture and filtered. The precipitate obtained was dried under vacuum to afford the title compound as an off-white solid. The low polar fractions from the column were combined, evaporated and the residue was stirred with 3N NaOH in methanol (2 mL) for 30 min and quenched with saturated ammonium chloride solution (2 mL). Water (10 mL) was added and filtered to afford additional title compound. MS (ES+): m/z 453.63 (100) [MH$^+$]; HPLC: t$_R$=2.58 min (ZQ2000, polar_5 min).

1-Benzenesulfonyl-5-bromo-4-chloro-2-iodo-1H-pyrrolo[2,3-b]pyridine & 5-Bromo-4-chloro-2-iodo-1-(2-iodobenzenesulfonyl)-1H-pyrrolo[2,3-b]pyridine

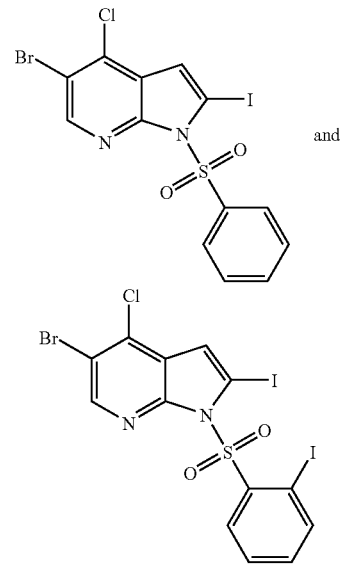

To a solution of 1-benzenesulfonyl-5-bromo-4-chloro-1H-pyrrolo[2,3-b]pyridine (2.585 g, 6.95 mmol) in anhydrous THF (330 mL) at −78° C. was added LDA (11.6 mL, 1.5 M solution, 17.39 mmol), and the mixture was stirred for 30 min. A solution of iodine (4.854 g, 19.12 mmol) in THF (20 mL) was added and stirring was continued for an additional 2 h at −78° C. The reaction was quenched with aqueous sodium thiosulfate solution and extracted with DCM (4×80 mL). The combined DCM layer was washed with brine, dried over anhydrous sodium sulfate and evaporated under reduced pressure. The crude product was purified by chromatography on silica gel [Jones Flashmaster, 70 g/150 mL cartridge, eluting with hexane:ethyl acetate 100:0→99:2], yielding a mixture of the title compounds. 1-Benzenesulfonyl-5-bromo-4-chloro-2-iodo-1H-pyrrolo[2,3-b]pyridine: MS (ES+): m/z 498.58 (100) [MH$^+$], HPLC: t$_R$=7.19 min (ZQ2000, nonpolar_15 min). 5-Bromo-4-chloro-2-iodo-1-(2-iodobenzenesulfonyl)-1H-pyrrolo[2,3-b]pyridine: MS (ES+): m/z 624.41 (100) [MH$^+$], HPLC: t$_R$=7.58 min (ZQ2000, nonpolar_15 min).

1-Benzenesulfonyl-5-bromo-4-chloro-1H-pyrrolo[2,3-b]pyridine

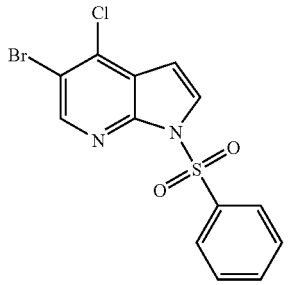

To a solution of 5-bromo-4-chloropyrrolopyridine (248 mg, 1.07 mmol) in THF (5 mL) at 0° C. was added sodium hydride (39 mg, 1.6 mmol) and the mixture was stirred for 15 min. Benzenesulfonyl chloride (227 mg, 1.28 mmol) was added and the mixture was allowed to warm to RT and stirred for 4 h. Water was added to the reaction mixture and extracted with DCM (3×25 mL). The combined DCM layer was washed with brine, dried over anhydrous sodium sulfate and evaporated under reduced pressure. The crude product obtained was purified by chromatography on silica gel [Jones Flashmaster, 50 g/150 mL cartridge, eluting with hexane:ethylacetate 100:0-95:05], yielding the title compound as colorless solid. $^1$H NMR (400 MHz, CDCl$_3$): δ=8.50 (s, 1H), 8.16-8.19 (m, 2H), 7.77 (d, J=4.0 Hz, 1H), 7.59-7.64 (m, 1H), 7.49-7.53 (m, 2H), 6.69 (d, J=4.0 Hz, 1H); MS (ES+): m/z 372.85 (100) [MH$^+$]; HPLC: $t_R$=4.39 min (ZQ2000, nonpolar_7 min).

5-Bromo-4-chloro-1H-pyrrolo[2,3-b]pyridine

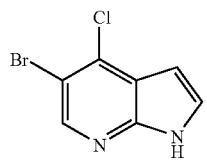

To a solution of 5-bromo-4-chloro-1-triisopropylsilanyl-1H-pyrrolo[2,3-b]pyridine (10.1 g, ≈14.0 mmol; crude material prepared according to *Tetrahedron Lett.*, 2004, 45, 2317-2319) in IPA (250 mL) at 0° C. was added 2N H$_2$SO$_4$ (25 mL) and the mixture was allowed to warm to RT and stirred overnight. IPA was evaporated at 35° C. and water was added to the residue and neutralized with 2N NaOH. The precipitate formed was filtered, washed with water followed by hexane, and dried under vacuum to yield the title compound as off-white solid. MS (ES+): m/z 233.01 (100) [MH$^+$]; HPLC: $t_R$=4.51 min (ZQ2000, polar_15 min).

EXAMPLE 301

4-[4-(Benzothiazol-6-ylamino)-5-cyano-1H-pyrrolo[2,3-b]pyridin-2-yl]-3,6-dihydro-2H-pyridine-1-carboxylicacid tert-butyl ester

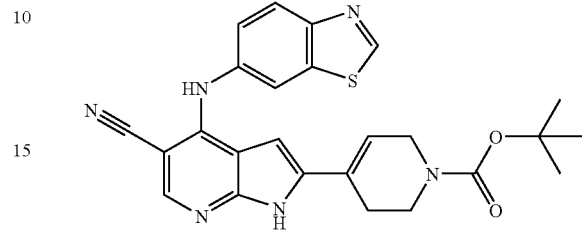

To a mixture of 4-[4-(benzothiazol-6-ylamino)-5-bromo-1H-pyrrolo[2,3-b]pyridin-2-yl]-3,6-dihydro-2H-pyridine-1-carboxylic acid tert-butyl ester (20 mg, 0.038 mmol), DPPF (10.1 mg, 0.018 mmol), water (0.04 mL) and zinc cyanide (8.9 mg, 0.075 mmol) in acetonitrile-(4 mL) was added Pd$_2$dba$_3$ (7.0 mg, 0.007 mmol) and the mixture was heated to reflux under N$_2$ overnight. The reaction mixture was evaporated, and the crude product was purified by preparative TLC using 7% methanol in DCM as eluent to afford the title compound as light gray solid. $^1$H NMR (400 MHz, CDCl$_3$): δ=8.98 (s, 1H), 8.22 (s, 1H), 8.10 (d, J=8.6 Hz, 1H), 7.78 (d, J=2.0 Hz, 1H), 7.36 (dd, J=8.6, 2.1 Hz, 1H), 6.95 (s, 1H), 5.93 (bs, 1H), 5.36 (s, 1H), 3.99-4.02 (m, 2H), 3.44 (t, J=5.7 Hz, 2H), 3.42 (d, J=4.9 Hz, 2H), 2.07-2.12 (m, 2H), 1.39 (s, 9H); MS (ES+): m/z 472.96 (100) [MH$^+$]; HPLC: $t_R$=3.25 min (ZQ2000, polar_5 min).

4-[4-(Benzothiazol-6-ylamino)-5-bromo-1H-pyrrolo[2,3-b]pyridin-2-yl]-3,6-dihydro-2H-pyridine-1-carboxylicacid tert-butyl ester

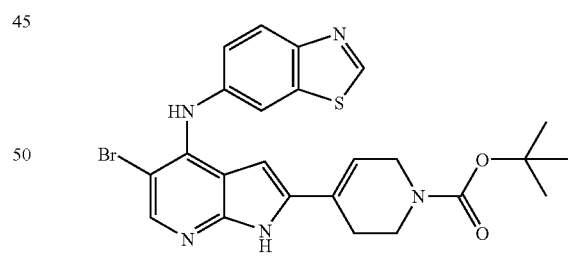

To a mixture (55:45) of benzothiazol-6-yl-[5-bromo-2-(1,2,3,6-tetrahydropyridin-4-yl)-1H-pyrrolo[2,3-b]pyridin-4-yl]-amine and 5-bromo-4-chloro-2-(1,2,3,6-tetrahydropyridin-4-yl)-1H-pyrrolo[2,3-b]pyridine (101 mg, 0.272 mmol) in THF (5 mL) was added triethylamine (83 mg, 0.816 mmol), DMAP (5 mg) and (Boc)$_2$O (47 mg, 0.215 mmol) and the reaction was stirred overnight at RT under N$_2$. The solvent was evaporated and the residue was purified by preparative TLC using 4% methanol in DCM as eluent to afford a mixture of 4-(5-bromo-4-chloro-1H-pyrrolo[2,3-b]pyridin-2-yl)-3,6- dihydro-2H-pyridine-1-carboxylic acid tert-butyl ester and the title compound. 4-[4-(Benzothiazol-6-ylamino)-5-bromo-1H-pyrrolo[2,3-b]pyridin-2-yl]-3,6-dihydro-2H-pyridine-1-carboxylicacid tert-butyl ester: $^1$H NMR (400 MHz, CDCl$_3$): δ=8.98 (s, 1H), 8.19 (s, 1H), 8.11 (d, J=8.6 Hz, 1H), 7.75 (d, J=2.0 Hz, 1H), 7.37 (dd, J=8.7, 2.1 Hz, 1H), 6.81 (s, 1H), 6.15 (bs, 1H), 5.51 (s, 1H), 4.90-4.15 (m, 2H), 3.54 (t, J=5.3 Hz, 2H), 2.95 (s, 1H), 2.88 (s, 1H), 2.17-2.25 (m, 2H), 1.47 (s, 9H); MS (ES+): m/z 527.84 (100) [MH$^+$]; HPLC: t$_R$=3.30 min (ZQ2000, polar__5 min).

Benzothiazol-6-yl-[5-bromo-2-(1,2,3,6-tetrahydropyridin-4-yl)-1H-pyrrolo[2,3-b]pyridin-4-yl]-amine

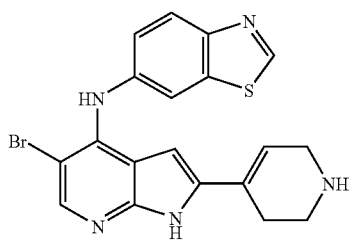

To a slurry of 4-(5-bromo-4-chloro-1H-pyrrolo[2,3-b]pyridin-2-yl)-3,6-dihydro-2H-pyridine-1-carboxylic acid tert-butyl ester (120 mg, 0.29 mmol) in trifluoroethanol (9 mL) were added trifluoroacetic acid (0.112 mL, 1.46 mmol) and 6-benzothiazolamine (58 mg, 1.5 mmol), and the reaction was heated in a sealed tube at 120° C. for 6 d. Additional 6-benzothiazolamine (39 mg, 0.29 mmol) was added twice to the reaction mixture on the third and fifth days. The reaction was cooled to RT, diluted with methanol (20 mL), saturated sodium bicarbonate solution was added (1 mL) and evaporated to dryness under reduced pressure. The residue was triturated with methanol:DCM (1:1) mixture and filtered. The filtrate was evaporated and the crude product was purified by preparative TLC using 25% methanol in DCM to afford a mixture of benzothiazol-6-yl-[5-bromo-2-(1,2,3,6-tetrahydropyridin-4-yl)-1H-pyrrolo[2,3-b]pyridin-4-yl]-amine and 5-bromo-4-chloro-2-(1,2,3,6-tetrahydro-pyridin-4-yl)-1H-pyrrolo[2,3-b]pyridine as beige solid. Benzothiazol-6-yl-[5-bromo-2-(1,2,3,6-tetrahydropyridin-4-yl)-1H-pyrrolo[2,3-b]pyridin-4-yl]-amine: MS (ES+): m/z 427.79 (100) [MH$^+$], HPLC: t$_R$=2.12 min (ZQ2000, polar__5 min). 5-Bromo-4-chloro-2-(1,2,3,6-tetrahydropyridin-4-yl)-1H-pyrrolo[2,3-b]pyridine MS (ES+): m/z 313.85 (100) [MH$^+$], HPLC: t$_R$=2.30 min (ZQ2000, polar__5 min).

4-(5-Bromo-4-chloro-1H-pyrrolo[2,3-b]pyridin-2-yl)-3,6-dihydro-2H-pyridine-1-carboxylic acid tert-butyl ester

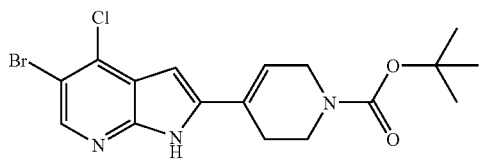

To a mixture of 5-bromo-4-chloro-2-iodo-1H-pyrrolo[2,3-b]pyridine (46 mg, 0.12 mmol), potassium carbonate (36 mg, 0.25 mmol), dichlorobis-(triphenylphosphine)palladium (9 mg, 0.01 mmol) and 4-(4,4,5,5-tetramethyl-[1,3,2]dioxaborolan-2-yl)-3,6-dihydro-2H-pyridine-1-carboxylic acid tert-butyl ester (42 mg, 0.13 mmol) were added degassed dioxane (4 mL) and water (1 mL), and the mixture was heated to reflux for 5 h. The reaction was evaporated under reduced pressure and the residue was dissolved in DCM and filtered. The DCM filtrate was evaporated and the crude product obtained was purified by chromatography on silica gel [Jones Flashmaster, 20 g/70 mL cartridge, eluting with DCM:methanol 100:0→99.5:0.5], yielding the title compound. MS (ES+): m/z 413.84 (100) [MH$^+$]; HPLC: t$_R$=6.95 min (ZQ2000, nonpolar__15 min).

5-Bromo-4-chloro-2-iodo-1H-pyrrolo[2,3-b]pyridine

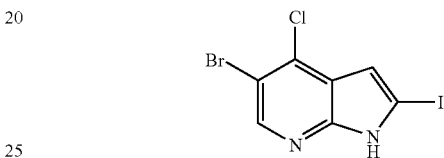

To a solution of a 4:6 mixture of 1-benzenesulfonyl-5-bromo-4-chloro-2-iodo-1H-pyrrolo[2,3-b]pyridine and 5-bromo-4-chloro-2-iodo-1-(2-iodobenzenesulfonyl)-1H-pyrrolo[2,3-b]pyridine (100 mg, 0.178 mmol) in THF (4 mL) was added 3N NaOH in methanol (1 mL), and the mixture was stirred at RT for 30 min. The reaction was quenched with saturated ammonium chloride solution (2 mL), water (5 mL) was added, and the mixture was filtered. The precipitate obtained was washed with water (3×10 mL) followed by hexane (3×10 mL) and dried under vacuum to yield the title compound as white solid. $^1$H NMR (400 MHz, CD$_3$OD): δ=8.21 (s, 1H), 6.74 (s, 1H); MS (ES+): m/z 358.75 (100) [MH$^+$]; HPLC: t$_R$=5.68 min (ZQ2000, nonpolar__15 min).

In vitro Activity

All kinases described in the assays below were recombinant and generated at Upstate (Dundee, UK) except for the KDR assay. Assays were run within 15 μM of the apparent Km for ATP where determined, or at 100 μM ATP. For each enzyme, 1 U activity is defined as the incorporation of 1 nmol phosphate into the appropriate substrate for a given kinase per minute at 30° C. with a final ATP concentration of 100 μM.

Assay ATP concentrations for individual kinases are included in the text.

Abl (human)—45 μM ATP: In a final reaction volume of 25 μL, Abl (h) (5-10 mU) is incubated with 8 mM MOPS pH 7.0, 0.2 mM EDTA, 50 μM EAIYAAPFAKKK, 10 nM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 μL of a 3% phosphoric acid solution. Then, 10 μL of the reaction is spotted onto a P30 filtermat and washed three times for 5 min in 75 mM phosphoric acid and once in methanol prior to drying and scintillation counting.

Aurora-A (human)—15 μM ATP: In a final reaction volume of 25 μL, Aurora-A (h) (5-10 mU) is incubated with 8 mM MOPS pH 7.0, 0.2 mM EDTA, 200 μM LRRASLG (Kemptide), 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 μL of a 3% phosphoric acid solution. 10 μL of the reaction is then spotted onto a P30 filtermat and washed three times for 5 min in 50 mM phosphoric acid and once in methanol prior to drying and scintillation counting.

Blk (mouse)—120 μM ATP: In a final reaction volume of 25 μL, Blk (m) (5-10 mU) is incubated with 50 mM Tris pH 7.5, 0.1 mM EGTA, 0.1 mM Na3 VO4, 0.1% β-mercaptoethanol, 0.1 mg/mL poly(Glu, Tyr) 4:1, 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 μL of a 3% phosphoric acid solution. 10 μL of the reaction is then spotted onto a Filtermat A and washed three times for 5 min in 75 mM phosphoric acid and once in methanol prior to drying and scintillation counting.

Bmx (human)—45 μM ATP: In a final reaction volume of 25 μL, Bmx (h) (5-10 mU) is incubated with 8 mM MOPS pH 7.0, 0.2 mM EDTA, 0.1 mg/ml poly(Glu, Tyr) 4:1, 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 μL of a 3% phosphoric acid solution. 10 μL of the reaction is then spotted onto a Filtermat A and washed three times for 5 min in 75 mM phosphoric acid and once in methanol prior to drying and scintillation counting.

CaMKII (rat)-15 μM ATP: In a final reaction volume of 25 μL, CaMKII (r) (5-10 mU) is incubated with 40 mM HEPES pH 7.4, 5 mM CaCl$_2$, 30 μg/ml calmodulin, 30 μM KKLNRTLSVA, 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 μL of a 3% phosphoric acid solution. 10 μL of the reaction is then spotted onto a P30 filtermat and washed three times for 5 min in 75 mM phosphoric acid and once in methanol prior to drying and scintillation counting.

c-RAF (human)—45 μM ATP: In a final reaction volume of 25 μL, c-RAF (h) (5-10 mU) is incubated with 25 mM Tris pH 7.5, 0.02 mM EGTA, 0.66 mg/mL myelin basic protein, 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 μL of a 3% phosphoric acid solution. 10 μL of the reaction is then spotted onto a P30 filtermat and washed three times for 5 min in 75 mM phosphoric acid and once in methanol prior to drying and scintillation counting.

cSRC (human)—200 μM ATP: In a final reaction volume of 25 μL, cSRC (h) (5-10 mU) is incubated with 8 mM MOPS pH 7.0, 0.2 mM EDTA, 250 μM KVEKIGEGTYGVVYK (Cdc2 peptide), 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 μL of a 3% phosphoric acid solution. 10 μl of the reaction is then spotted onto a P30 filtermat and washed three times for 5 min in 75 mM phosphoric acid and once in methanol prior to drying and scintillation counting.

EGFR (human)—10 μM ATP: In a final reaction volume of 25 μL, EGFR (h) (5-10 mU) is incubated with 8 mM MOPS pH 7.0, 0.2 mM EDTA, 10 mM MnCl$_2$, 0.1 mg/mL poly(Glu, Tyr) 4:1, 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 μL of a 3% phosphoric acid solution. 10 μL of the reaction is then spotted onto a Filtermat A and washed three times for 5 min in 75 mM phosphoric acid and once in methanol prior to drying and scintillation counting.

FGFR3 (human)-15 μM ATP: In a final reaction volume of 25 μL, FGFR3 (h) (5-10 mU) is incubated with 8 mM MOPS pH 7.0, 0.2 mM EDTA, 0.1 mg/mL poly(Glu, Tyr) 4:1, 10 mM MnCl$_2$, 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 μL of a 3% phosphoric acid solution. 10 μL of the reaction is then spotted onto a Filtermat A and washed three times for 5 min in 75 mM phosphoric acid and once in methanol prior to drying and scintillation counting.

Flt3 (human)—200 μM ATP: In a final reaction volume of 25 μL Flt3 (h) (5-10 mU) is incubated with 8 mM MOPS pH 7.0, 0.2 mM EDTA, 50 μM EAIYAAPFAKKK, 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 μL of a 3% phosphoric acid solution. 10 μL of the reaction is then spotted onto a P30 filtermat and washed three times for 5 min in 75 mM phosphoric acid and once in methanol prior to drying and scintillation counting.

GSK3β(human)—15 μM ATP: In a final reaction volume of 25 μL, GSK3β(h) (5-10 mU) is incubated with 8 mM MOPS pH 7.0, 0.2 mM EDTA, 20 μM YRRAAVPPSPSLSRHSSPHQS(p)EDEEE (phospho GS2 peptide), 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 μL of a 3% phosphoric acid solution. 10 μL of the reaction is then spotted onto a P30 filtermat and washed three times for 5 min in 50 mM phosphoric acid and once in methanol prior to drying and scintillation counting.

Lck (human)—90CM ATP: In a final reaction volume of 25 μL, Lck (h) (5-10 mU) is incubated with 50 mM Tris pH 7.5, 0.1 mM EGTA, 0.1 mM Na3VO4, 250 μM KVEKIGEG-TYGVVYK (Cdc2 peptide), 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 μL of a 3% phosphoric acid solution. 10 μL of the reaction is then spotted onto a P30 filtermat and washed three times for 5 min in 75 mM phosphoric acid and once in methanol prior to drying and scintillation counting.

MEK1 (human)—10 μM ATP: In a final reaction volume of 25 μL, MEK1 (h) (1-5 mU) is incubated with 50 mM Tris pH 7.5, 0.2 mM EGTA, 0.1% β-mercaptoethanol, 0.01% Brij-35, 1 μM inactive MAPK2 (m), 10 nM MgAcetate and cold ATP (concentration as required). The reaction is initiated by the addition of themgATP. After incubation for 40 min at rt, 5 μL of this incubation mix is used to initiate a MAPK2 (m) assay. In a final reaction volume of 25 μL, MAPK2 (h) (5-10 mU) is incubated with 25 mM Tris pH 7.5, 0.02 mM EGTA, 0.33 mg/mL myelin basic protein, 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 µL of a 3% phosphoric acid solution. 10 µL of the reaction is then spotted onto a P30 filtermat and washed three times for 5 min in 75 mM phosphoric acid and once in methanol prior to drying and scintillation counting.

PDK1 (human)—10 µM ATP: In a final reaction volume of 25 µL, PDK1 (h) (5-10 mU) is incubated with 50 mM Tris pH 7.5, 100 µM KTFCGTPEYLAPEVRREPRILSEEEQEM-FRDFDYIADWC (PDKtide), 0.1% I mercaptoethanol, 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 µL of a 3% phosphoric acid solution. 10 µL of the reaction is then spotted onto a P30 filtermat and washed three times for 5 min in 75 mM phosphoric acid and once in methanol prior to drying and scintillation counting.

PRK2 (human)—15 µM ATP: In a final reaction volume of 25 µL, PRK2 (h) (5-10 mU) is incubated with 50 mM Tris pH 7.5, 0.1 mM EGTA, 0.1% β-mercaptoethanol, 30 µM AKRRRLSSLRA, 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 µL of a 3% phosphoric acid solution. 10 µL of the reaction is then spotted onto a P30 filtermat and washed three times for 5 min in 75 mM phosphoric acid and once in methanol prior to drying and scintillation counting.

Ret (human)—70 µM ATP: In a final reaction volume of 25 µL, Ret (h) (5-10 mU) is incubated with 8 mM MOPS pH 7.0, 0.2 mM EDTA, 0.25 mM KKKSPGEYVNIEFG, 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 µL of a 3% phosphoric acid solution. 10 µL of the reaction is then spotted onto a P30 filtermat and washed three times for 5 min in 75 mM phosphoric acid and once in methanol prior to drying and scintillation counting.

p70S6K (human)—15 µM ATP: In a final reaction volume of 25 µL, p70S6K (h) (5-10 mU) is incubated with 8 mM MOPS pH 7.0, 0.2 mM EDTA, 100 µM KKRNRTLTV, 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 µL of a 3% phosphoric acid solution. 10 µL of the reaction is then spotted onto a P30 filtermat and washed three times for 5 min in 75 mM phosphoric acid and once in methanol prior to drying and scintillation counting.

SGK (human)-90 µM ATP: In a final reaction volume of 25 µL, SGK (h) (5-10 mU) is incubated with 8 mM MOPS pH 7.0, 0.2 mM EDTA, 30 µM GRPRTSSFAEGKK, 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 µL of a 3% phosphoric acid solution. 10 µL of the reaction is then spotted onto a P30 filtermat and washed three times for 5 min in 75 mM phosphoric acid and once in methanol prior to drying and scintillation counting.

Tie2 (human)—200 µM ATP: In a final reaction volume of 25 µL, Tie2 (h) (5-10 mU) is incubated with 8 mM MOPS pH 7.0, 0.2 mM EDTA, 0.5 mM MnCl$_2$, 0.1 mg/mL poly(Glu, Tyr) 4:1, 10 mM MgAcetate and [γ-33P-ATP] (specific activity approx. 500 cpm/pmol, concentration as required). The reaction is initiated by the addition of themgATP mix. After incubation for 40 min at rt, the reaction is stopped by the addition of 5 µL of a 3% phosphoric acid solution. 10 µL of the reaction is then spotted onto a Filtermat A and washed three times for 5 min in 75 mM phosphoric acid and once in methanol prior to drying and scintillation counting.

KDR (human)—18 µM ATP: 96-well plates are coated with 0.5 µg/75 µL/well poly(Glu, Tyr) over night at 37° C. 50 µL per well of 50 mM Hepes, pH7.4, 125 mM NaCl, 24 mM MgCl2, and 18 µM ATP±compounds are added. The reaction is initiated by the addition of 30 µL (5 ng) KDR (Proqinase) diluted in assay buffer. After incubation for 30 min at rt, the plates are washed and phosphor Tyr detected using pY-20 HRP conjugated antibody with subsequent development using ABTS reagent (KPL) and detection by absorbance at 405 nm.

The EXAMPLES 1-81, except for EXAMPLES 2, 3, 4, 8, 11-14, 21, 22, 24, 32, 34, 78, and 79—for which limited assay results are available—inhibit at least two of the Abl, Aurora-A, Blk, c-Raf, cSRC, Src, PRK2, FGFR3, Flt3, Lck, Mek1, PDK-1, GSK3β, EGFR, p70S6K, BMX, SGK, CaMKII, Tie-2, Ret, and KDR kinases at an $IC_{50}$ of greater than 50% inhibition at 10 µM to 14 nM. It is advantageous that the measured $IC_{50}$ be lower than 10 µM. It is still more advantageous for the $IC_{50}$ to be lower than 5 µM. It is even more advantageous for the $IC_{50}$ to be lower than 0.5 µM. It is yet more advantageous for the $IC_{50}$ to be lower than 0.05 µM.

Someone skilled in the art will appreciate that other assay formats may be used in place of those described above. For example, AlphaScreen (Amplified Luminescent Proximity Homogeneous Assay) technology was used with the kinases described below. Assay ATP concentrations for individual kinases are included in the text.

KDR (human)—100 µM ATP: 9 µL of the reaction mix containing ATP at the desired concentration, biotinylated poly(Glu,Tyr) (84 ng/mL) and 0.334 mM vanadate in assay buffer (50 mM HEPES (pH=7.4), 12.5 mM MgCl$_2$ and 1% glycerol) are added to a well of a 384 well plate along with 1 µL of compound (or vehicle control, usually DMSO). DMSO concentration is controlled at a concentration of 1%. KDR is diluted to the optimized concentration (optimized on a lot-by-lot basis) in an enzyme diluent buffer (50 mM HEPES pH=7.4, 12.5 mM MgCl$_2$ and 1% glycerol, 0.03% Brij35 and 0.3 mM EGTA). 5 µL of this solution are then added to the well, and the complete reaction mixture is incubated for 60 min at RT. In subdued light, 5 µL of PT66 donor and acceptor beads (diluted 1:200 from manufacturers provision in a 25 mM Tris HCl (pH=7.5), 200 mM NaCl, 100 mM EDTA, 0.3% BSA buffer) are added to the wells. The plates are then incubated for 4 h and read on an AlphaQuest plate reader.

IGF-1R (human)—100 µM ATP: To a well of a 384 well plate are added 9 µL of the reaction mix containing ATP at the desired concentration, biotinylated poly(Glu,Tyr) (84 ng/mL) and 0.334 mM vanadate in assay buffer (50 mM HEPES (pH=7.4), 12.5 mM MgCl$_2$ and 1% glycerol) along with 1 µL of compound (or vehicle control, usually DMSO). DMSO concentration is controlled at a concentration of 1%. IGF-1R is diluted to the optimized concentration (optimized on a lot-by-lot basis) in an enzyme diluent buffer (50 mM HEPES pH=7.4, 12.5 mM MgCl$_2$ and 1% glycerol, 0.03% Brij35, 0.3 mM EGTA, 6 mM DTT, and 0.003% BSA). 5 µL of this solution are then added to the well, and the complete reaction mixture is incubated for 60 min at RT. In subdued light, 5 µL of PT66 donor and acceptor beads (diluted 1:200 from manufacturer's provision in a 25 mM Tris HCl (pH=7.5), 200 mM NaCl, 100 mM EDTA, 0.3% BSA buffer) are added to the wells. The plates are then incubated for 4 h and read on an AlphaQuest plate reader.

Ron (human)—100 µM ATP: To a well of a 384 well plate are added 9 µL of the reaction mix containing ATP at the desired concentration, biotinylated poly(Glu,Tyr) (200 ng/mL) and 0.334 mM vanadate in assay buffer (50 mM HEPES (pH=7.4), 12.5 mM $MgCl_2$ and 1% glycerol) along with 1 µL of compound (or vehicle control, usually DMSO). DMSO concentration is controlled at a concentration of 1%. Ron is diluted to the optimized concentration (optimized on a lot-by-lot basis) in an enzyme diluent buffer (50 mM HEPES pH=7.4, 12.5 mM $MgCl_2$ and 1% glycerol, 0.03% Brij35, 0.3 mM EGTA, 1 mM DTT, and 0.003% BSA). 5 µL of this solution are then added to the well, and the complete reaction mixture is incubated for 60 min at RT. In subdued light, 5 µL of PT66 donor and acceptor beads (diluted 1:160 from manufacturer's provision in a 25 mM Tris HCl (pH=7.5), 200 mM NaCl, 100 mM EDTA, 0.3% BSA buffer) are added to the wells. The plates are then incubated for 4 h and read on an AlphaQuest plate reader.

EGFR (human)—4 µM ATP: To a well of a 384 well plate are added 1 µL of compound (or vehicle control, usually DMSO; DMSO concentration is controlled at a concentration of 1%), followed by 9 µL of the reaction mix (ATP, at the desired concentration, is added diluted in assay buffer (50 mM HEPES (pH=7.4), 12.5 mM $MgCl_2$ and 1% glycerol), containing 69.4 mM NaCl, biotinylated poly(Glu,Tyr) (84.5 ng/mL) and 0.334 mM vanadate). EGFR is diluted to the optimized concentration (optimized on a lot-by-lot basis) in an enzyme diluent buffer (50 mM HEPES pH=7.4, 12.5 mM $MgCl_2$ and 1% glycerol, 0.3% Brij35 and 0.3 mM EGTA) and Stablecoat (SurModics), and DTT is also added for a concentration of 3 mM. 5 µL of this solution are then added to the well, and the complete reaction mixture is incubated for 20 min at RT. In subdued light, 5 µl of PT66 donor and acceptor beads (diluted 1:200 from manufacturers provision in a 25 mM Tris HCl (pH=7.5), 200 mM NaCl, 100 mM EDTA, 0.3% BSA buffer) are added to the wells. The plates are then incubated for 4 h and read on an AlphaQuest plate reader.

EGFR (human)—100 µM ATP: To a well of a 384 well plate are added 1 µL of compound (or vehicle control, usually DMSO; DMSO concentration is controlled at a concentration of 1%), followed by 9 µL of the reaction mix (ATP, at the desired concentration, is added diluted in assay buffer (50 mM HEPES (pH=7.4), 12.5 mM $MgCl_2$ and 1% glycerol), containing 69.4 mM NaCl, biotinylated poly(Glu,Tyr) (84.5 ng/mL) and 0.334 mM vanadate). EGFR is diluted to the optimized concentration (optimized on a lot-by-lot basis) in an enzyme diluent buffer (50 mM HEPES pH=7.4, 12.5 mM $MgCl_2$ and 1% glycerol, 0.3% Brij35 and 0.3 mM EGTA) and Stablecoat (SurModics), and DTT is also added for a concentration of 3 mM. 5 µL of this solution are then added to the well, and the complete reaction mixture is incubated for 60 min at RT. In subdued light, 5 µL of PT66 donor and acceptor beads (diluted 1:200 from manufacturer's provision in a 25 mM Tris HCl (pH=7.5), 200 mM NaCl, 100 mM EDTA, 0.3% BSA buffer) are added to the wells. The plates are then incubated for 4 h and read on an AlphaQuest plate reader.

PDK-1 (human)—100 µM ATP: To a well of a 384 well plate are added 1 µL of compound (or vehicle control, usually DMSO; DMSO concentration is controlled at a concentration of 1%), followed by 9 µL of the reaction mix (ATP, at the desired concentration, is added diluted in assay buffer (50 mM Tris pH=7.4, 15 mM $MgCl_2$, 0.1 mg/mL Bovine gamma globulin, 2 mM DTT) containing biotinylated peptide substrate (83.5 nM)). PDK-1 (obtained from Upstate, 200 ng/µL) is diluted 1:25000 in an enzyme diluent buffer (50 mM Tris pH=7.4, 15 mM $MgCl_2$, 0.1 mg/mL Bovine gamma globulin, 2 mM DTT). 5 µL of this solution are then added to the well, and the complete reaction mixture is incubated for 2 h at RT protected from light. 2.5 µL/well of stop buffer (200 mM EDTA in 20 mM Tris/200 nM NaCl) are added, and the mixture is incubated for 1 h at RT protected from light. 2.5 µl/well of antibody/bead complex (antibody diluted 1:1250, donor and acceptor beads diluted 1:200 from manufacturer's provision) are added. The plates are then incubated for 2 h at RT protected from light and read on an AlphaQuest plate reader.

PDK-1 (human)—4.5 µM ATP: Same procedure, except for the different ATP concentration.

The EXAMPLES 82-301, except for EXAMPLES 104, 189, 225, 228, 229, 231, 234, 238, 239, 241, 243, 244, 253, 263, 270, 271, 275, 282, 285, 288, 297, 298, and 299—for which limited assay results are available—inhibit at least two of the IGF-1R, PDK-1, KDR, EGFR, and Ron kinases at greater than 50% inhibition at 10 µM. It is advantageous that the measured $IC_{50}$ be lower than 10 µM. It is still more advantageous for the $IC_{50}$ to be lower than 5 µM. It is even more advantageous for the $IC_{50}$ to be lower than 0.5 µM. It is yet more advantageous for the $IC_{50}$ to be lower than 0.1 µM.

What is claimed is:
1. A compound represented by Formula I:

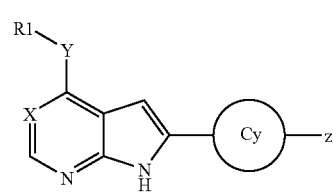

(I)

or a pharmaceutically acceptable salt thereof, wherein
X is C—CN;
Cy is

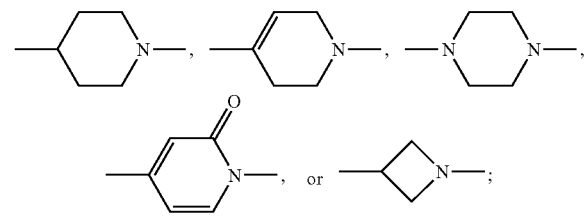

z is hetaryl, —$C_{1-6}$alkyl-O—$C_{1-6}$alkyl-, —$C_{0-6}$alkyl-(heterocyclyl), —$C_{0-6}$alkyl-(hetaryl), —C(O)—$C_{0-6}$alkyl, —C(O)—$C_{0-6}$alkyl-O—$C_{0-6}$alkyl, —C(O)—$C_{0-6}$alkyl-O—$C_{1-6}$alkyl-O—$C_{0-6}$alkyl, —C(O)—$C_{0-6}$alkyl-N($C_{0-6}$ alkyl)($C_{0-6}$alkyl), —C(O)—$C_{0-6}$alkyl-(heterocyclyl), —C(O)—$C_{0-6}$alkyl-(heterocyclyl)-C(O)—$C_{0-6}$alkyl, —C(O)—$C_{0-6}$alkyl-(hetaryl), —S(O)$_2$—$C_{0-6}$alkyl, —S(O)$_2$—N($C_{0-6}$alkyl)($C_{0-6}$alkyl), or —S(O)$_2$—(hetaryl), wherein any of the alkyl, heterocyclyl, or hetaryl optionally is substituted with 1-6 independent halo, OH, —$C_{0-6}$alkyl-O—$C_{0-6}$alkyl, —$C_{0-6}$alkyl-N($C_{0-6}$alkyl)($C_{0-6}$alkyl), —C(O)—$C_{0-6}$alkyl-N($C_{0-6}$ alkyl)($C_{0-6}$alkyl), —C(O)—$C_{0-6}$alkyl-(heterocyclyl), or —$C_{0-6}$alkyl;

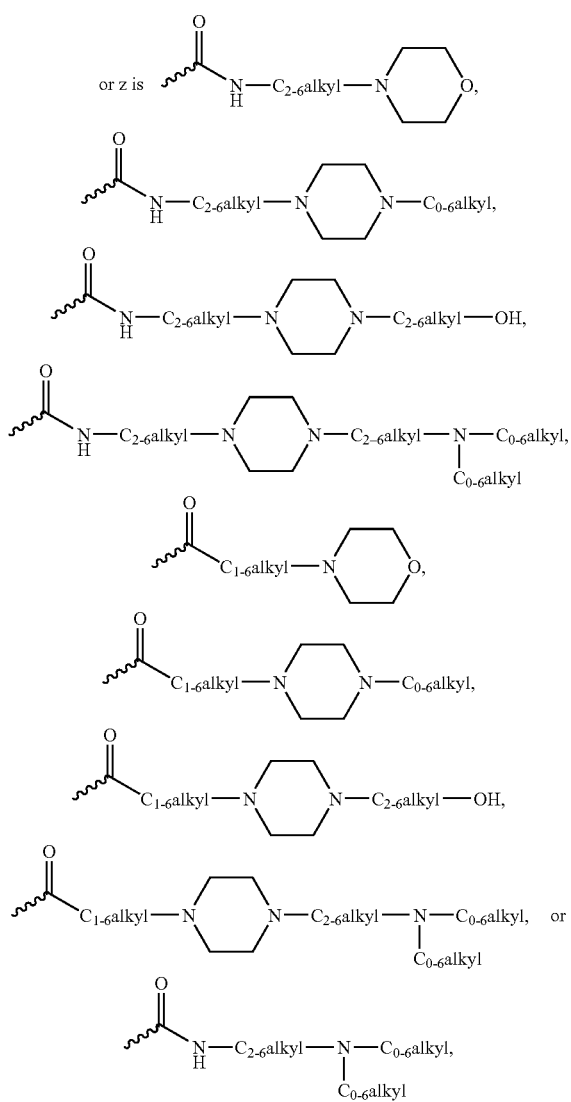

in which the wavy bond is the point of attachment, and wherein the piperazine or morpholine moieties are optionally substituted with 1-6 independent $C_{0-6}$alkyl groups;

Y is —C($C_{0-6}$alkyl)($C_{0-6}$alkyl)-, —N($C_{0-6}$alkyl)-, —N($C_{0-6}$ alkyl)-$C_{1-6}$alkyl-, O, S, >N—$C_{2-6}$alkyl-N—($C_{0-6}$alkyl)($C_{0-6}$alkyl), >N—$C_{2-6}$alkyl-O—$C_{0-6}$alkyl, >N—$C_{1-6}$ alkyl-C(O)—NH—$C_{0-6}$alkyl, or >N—$C_{2-6}$alkyl-N—C(O)—$C_{1-6}$alkyl; and R1 is aryl, hetaryl, or heterocyclyl, optionally substituted with 1-6 independent halo, —CN, —OH, —$C_{0-6}$alkyl, —$C_{3-10}$cycloalkyl, -halo$C_{1-6}$alkyl, —$C_{2-6}$alkynyl, —N($C_{0-6}$alkyl)($C_{0-6}$alkyl), —C(O)—$C_{0-6}$alkyl-N($C_{0-6}$alkyl)($C_{0-6}$alkyl), —C(O)—$C_{0-6}$alkyl-(heterocyclyl), —$C_{1-6}$alkyl-C(O)—$C_{0-6}$alkyl-N($C_{0-6}$alkyl)($C_{0-6}$alkyl), —O—$C_{0-6}$alkyl-(heterocyclyl), —$C_{0-6}$alkyl-O—$C_{0-6}$alkyl, —$C_{0-6}$alkyl-N($C_{0-6}$alkyl)($C_{0-6}$alkyl), —O—$C_{0-6}$alkyl-(hetaryl), —S(O)$_2$—N($C_{0-6}$alkyl)($C_{0-6}$alkyl), aryl, hetaryl, or heterocyclyl substituents, or substituted with an oxo (=O) using a bond from the aryl, hetaryl, or heterocyclyl ring, wherein any of the substituents optionally is substituted with 1-6 independent halo, CN, OH, —$C_{0-6}$alkyl-O—$C_{0-6}$alkyl, —$C_{0-6}$alkyl-N($C_{0-6}$ alkyl)($C_{0-6}$alkyl), —C(O)—$C_{0-6}$alkyl-N($C_{0-6}$alkyl) ($C_{0-6}$ alkyl), —C(O)—$C_{0-6}$alkyl-(heterocyclyl), or $C_{0-6}$alkyl; or a pharmaceutically acceptable salt thereof.

2. The compound according to claim 1, or a pharmaceutically acceptable salt thereof, wherein Cy is

3. The compound according to claim 1, or a pharmaceutically acceptable salt thereof, wherein R1 is aryl optionally substituted with with 1-6 independent halo, —CN, —OH, —$C_{0-6}$alkyl, -halo$C_{1-6}$alkyl, —$C_{2-6}$alkynyl, —N($C_{0-6}$alkyl)($C_{0-6}$alkyl), —C(O)—$C_{0-6}$alkyl-N($C_{0-6}$alkyl)($C_{0-6}$alkyl), —O—$C_{0-6}$alkyl-(heterocyclyl), —O—$C_{0-6}$alkyl-(hetaryl), —S(O)$_2$—N($C_{0-6}$alkyl)($C_{0-6}$alkyl), aryl, hetaryl, or heterocyclyl substituents, or substituted with an oxo (=O) using a bond from the aryl ring, wherein any of the substituents optionally is substituted with 1-6 independent halo or $C_{0-6}$alkyl.

4. The compound according to claim 1, or a pharmaceutically acceptable salt thereof, wherein R1 is aryl optionally substituted with 1-6 independent halo, —CN, —OH, —$C_{0-6}$ alkyl, —$C_{3-10}$cycloalkyl, -halo$C_{1-6}$alkyl, —$C_{2-6}$alkynyl, —N($C_{0-6}$alkyl)($C_{0-6}$alkyl), —C(O)—$C_{0-6}$alkyl-N($C_{0-6}$alkyl) ($C_{0-6}$alkyl), —C(O)—$C_{0-6}$alkyl-(heterocyclyl), —$C_{1-6}$alkyl-C(O)—$C_{0-6}$alkyl-N($C_{0-6}$alkyl)($C_{0-6}$alkyl), —O—$C_{0-6}$alkyl-(heterocyclyl), —$C_{0-6}$alkyl-O—$C_{0-6}$alkyl, —$C_{0-6}$alkyl-N($C_{0-6}$alkyl)($C_{0-6}$alkyl), —O—$C_{0-6}$alkyl-(hetaryl), —S(O)$_2$—N($C_{0-6}$alkyl)($C_{0-6}$alkyl), aryl, hetaryl, or heterocyclyl substituents, or substituted with an oxo (=O) using a bond from the aryl, hetaryl, or heterocyclyl ring, wherein any of the substituents optionally is substituted with 1-6 independent halo, CN, OH, —$C_{0-6}$alkyl-O—$C_{0-6}$alkyl, —$C_{0-6}$alkyl-N ($C_{0-6}$ alkyl)($C_{0-6}$alkyl), —C(O)—$C_{0-6}$alkyl-N($C_{0-6}$alkyl) ($C_{0-6}$ alkyl), —C(O)—$C_{0-6}$alkyl-(heterocyclyl), or $C_6$alkyl.

5. The compound according to claim 1, or a pharmaceutically acceptable salt thereof, wherein R1 is hetaryl optionally substituted with 1-6 independent halo, —CN, —OH, —$C_{0-6}$ alkyl, -halo$C_{1-6}$alkyl, —$C_{2-6}$alkynyl, —N($C_{0-6}$alkyl)($C_{0-6}$ alkyl), —C(O)—$C_{0-6}$alkyl-N($C_{0-6}$alkyl)($C_{0-6}$alkyl), —O—$C_{0-6}$alkyl-(heterocyclyl), —O—$C_{0-6}$alkyl-(hetaryl), —S(O)$_2$—N($C_{0-6}$alkyl)($C_{0-6}$alkyl), aryl, hetaryl, or heterocyclyl substituents, or substituted with an oxo (=O) using a bond from the hetaryl ring, wherein any of the substituents optionally is substituted with 1-6 independent halo or $C_{0-6}$alkyl.

6. The compound according to claim 1, or a pharmaceutically acceptable salt thereof, wherein R1 is hetaryl optionally substituted with 1-6 independent halo, —CN, —OH, —$C_{0-6}$ alkyl, —$C_{3-10}$cycloalkyl, -halo$C_{1-6}$alkyl, —$C_{2-6}$alkynyl, —N($C_{0-6}$alkyl)($C_{0-6}$alkyl), —C(O)—$C_{0-6}$alkyl-N($C_{0-6}$alkyl) ($C_{0-6}$alkyl), —C(O)—$C_{0-6}$alkyl-(heterocyclyl), —$C_{1-6}$alkyl-C(O)—$C_{0-6}$alkyl-N($C_{0-6}$alkyl)($C_{0-6}$alkyl), —O—$C_{0-6}$alkyl-(heterocyclyl), —$C_{0-6}$alkyl-O—$C_{0-6}$alkyl, —$C_{0-6}$alkyl-N ($C_{0-6}$alkyl)($C_{0-6}$alkyl), —O—$C_{0-6}$alkyl-(hetaryl), —S(O)$_2$—N($C_{0-6}$alkyl)($C_{0-6}$alkyl), aryl, hetaryl, or heterocyclyl substituents, or substituted with an oxo (=O) using a bond from the aryl, hetaryl, or heterocyclyl ring, wherein any of the substituents optionally is substituted with 1-6 independent halo, CN, OH, —$C_{0-6}$alkyl-O—$C_{0-6}$alkyl, —$C_{0-6}$alkyl-N ($C_{0-6}$ alkyl)($C_{0-6}$alkyl), —C(O)—$C_{0-6}$alkyl-N($C_{0-6}$alkyl) ($C_{0-6}$ alkyl), —C(O)—$C_{0-6}$alkyl-(heterocyclyl), or $C_{0-6}$alkyl.

7. The compound according to claim 1, or a pharmaceutically acceptable salt thereof, wherein R1 is heterocyclyl optionally substituted with 1-6 independent halo, —CN, —OH, —C$_{0-6}$alkyl, -haloC$_{1-6}$alkyl, —C$_{2-6}$alkynyl, —N(C$_{0-6}$alkyl)(C$_{0-6}$alkyl), —C(O)—C$_{0-6}$alkyl-N(C$_{0-6}$alkyl)(C$_{0-6}$alkyl), —O—C$_{0-6}$alkyl-(heterocyclyl), —O—C$_{0-6}$alkyl-(hetaryl), —S(O)$_2$—N(C$_{0-6}$alkyl)(C$_{0-6}$alkyl), aryl, hetaryl, or heterocyclyl substituents, or substituted with an oxo (=O) using a bond from the heterocyclyl ring, wherein any of the substituents optionally is substituted with 1-6 independent halo or C$_{0-6}$alkyl.

8. The compound according to claim 1, or a pharmaceutically acceptable salt thereof, wherein R1 is heterocyclyl optionally substituted with 1-6 independent halo, —CN, —OH, —C$_{0-6}$alkyl, —C$_{3-10}$cycloalkyl, -haloC$_{1-6}$alkyl, —C$_{2-6}$alkynyl, —N(C$_{0-6}$alkyl)(C$_{0-6}$alkyl), —C(O)—C$_{0-6}$alkyl-N(C$_{0-6}$alkyl)(C$_{0-6}$alkyl), —C(O)—C$_{0-6}$alkyl-(heterocyclyl), —C$_{1-6}$alkyl-C(O)—C$_{0-6}$alkyl-N(C$_{0-6}$alkyl)(C$_{0-6}$alkyl), —O—C$_{0-6}$alkyl-(heterocyclyl), —C$_{0-6}$alkyl-O—C$_{0-6}$alkyl, —C$_{0-6}$alkyl-N(C$_{0-6}$alkyl)(C$_{0-6}$alkyl), —O—C$_{0-6}$alkyl-(hetaryl), —S(O)$_2$—N(C$_{0-6}$alkyl)(C$_{0-6}$alkyl), aryl, hetaryl, or heterocyclyl substituents, or substituted with an oxo (=O) using a bond from the aryl, hetaryl, or heterocyclyl ring, wherein any of the substituents optionally is substituted with 1-6 independent halo, CN, OH, —C$_{0-6}$alkyl-O—C$_{0-6}$alkyl, —C$_{0-6}$alkyl-N(C$_{0-6}$alkyl)(C$_{0-6}$alkyl), —C(O)—C$_{0-6}$alkyl-N(C$_{0-6}$alkyl)(C$_{0-6}$alkyl), —C(O)—C$_{0-6}$alkyl-(heterocyclyl), or C$_{0-6}$alkyl.

9. The compound according to claim 1 or a pharmaceutically acceptable salt thereof, wherein Y—R1 is

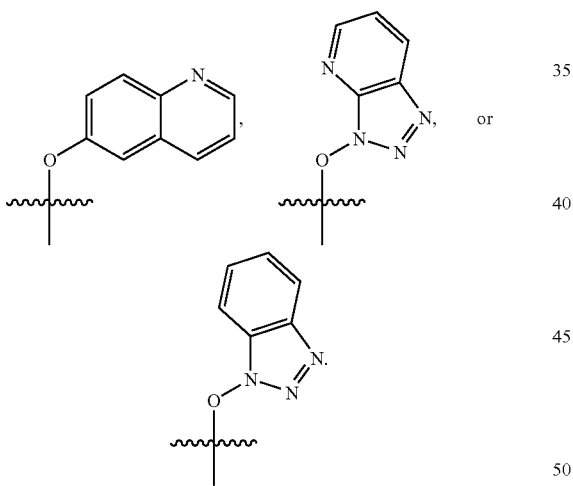

10. The compound according to claim 1 or a pharmaceutically acceptable salt thereof, wherein Y is —N(C$_{0-6}$alkyl)-.

11. A compound represented by Formula I:

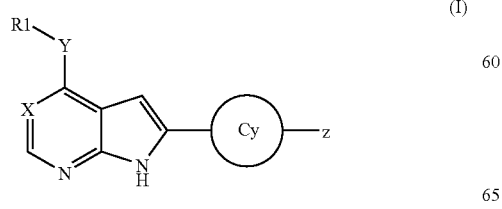

(I)

a pharmaceutically acceptable salt thereof, wherein

X is C—CN;

Cy is

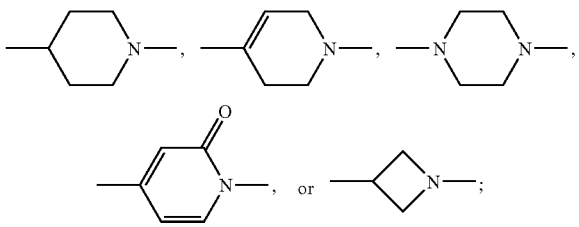

Z is hetaryl, —C$_{1-6}$alkyl-O—C$_{1-6}$alkyl-, —C$_{0-6}$alkyl-(heterocyclyl), —C$_{0-6}$alkyl-(hetaryl), —C(O)—C$_{0-6}$alkyl, —C(O)—C$_{0-6}$alkyl-O—C$_{0-6}$alkyl, —C(O)—C$_{0-6}$alkyl-O—C$_{1-6}$alkyl-O—C$_{0-6}$alkyl, —C(O)—C$_{0-6}$alkyl-N(C$_{0-6}$ alkyl)(C$_{0-6}$alkyl), —C(O)—C$_{0-6}$alkyl-(heterocyclyl), —C(O)—C$_{0-6}$alkyl-(heterocyclyl)-C(O)—C$_{0-6}$alkyl, —C(O)—C$_{0-6}$alkyl-(hetaryl), —S(O)$_2$—C$_{0-6}$alkyl, —S(O)$_2$—N(C$_{0-6}$alkyl)(C$_{0-6}$alkyl), or —S(O)$_2$—(hetaryl), wherein any of the alkyl, heterocyclyl, or hetaryl optionally is substituted with 1-6 independent halo, OH, —C$_{0-6}$alkyl-O—C$_{0-6}$alkyl, —C$_{0-6}$alkyl-N (C$_{0-6}$alkyl)(C$_{0-6}$alkyl), —C(O)—C$_{0-6}$alkyl-N(C$_{0-6}$alkyl)(C$_{0-6}$alkyl), —C(O)—C$_{0-6}$alkyl-(heterocyclyl), or —C$_{0-6}$alkyl;

or z is

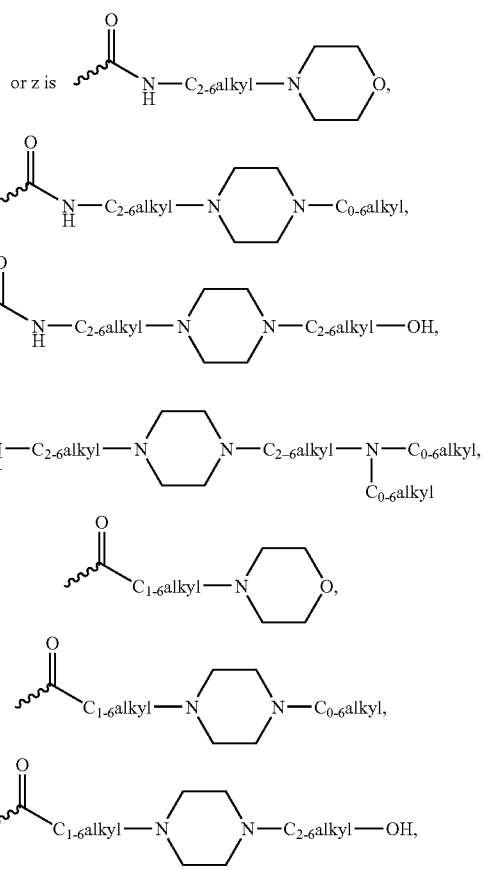

-continued

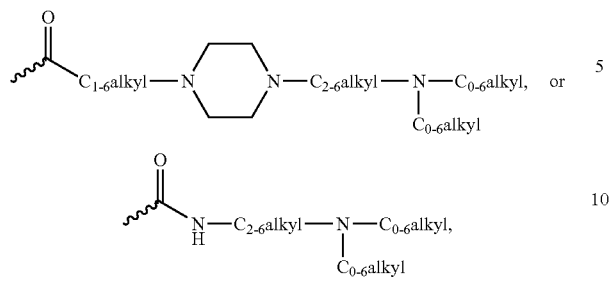

in which the wavy bond is the point of attachment, and wherein the piperazine or morpholine moieties are optionally substituted with 1-6 independent $C_{0-6}$alkyl groups;

Y is —C($C_{0-6}$alkyl)($C_{0-6}$alkyl)-, —N($C_{0-6}$alkyl)-, —N($C_{0-6}$ alkyl)-$C_{1-6}$alkyl-, O, S, >N—$C_{2-6}$alkyl-N—($C_{0-6}$alkyl)($C_{0-6}$alkyl), >N—$C_{2-6}$alkyl-O—$C_{0-6}$alkyl, >N—$C_{1-6}$ alkyl-C(O)—NH—$C_{0-6}$alkyl, or >N—$C_{2-6}$alkyl-N—C(O)—$C_{1-6}$alkyl;

wherein R1 is selected from the following table:

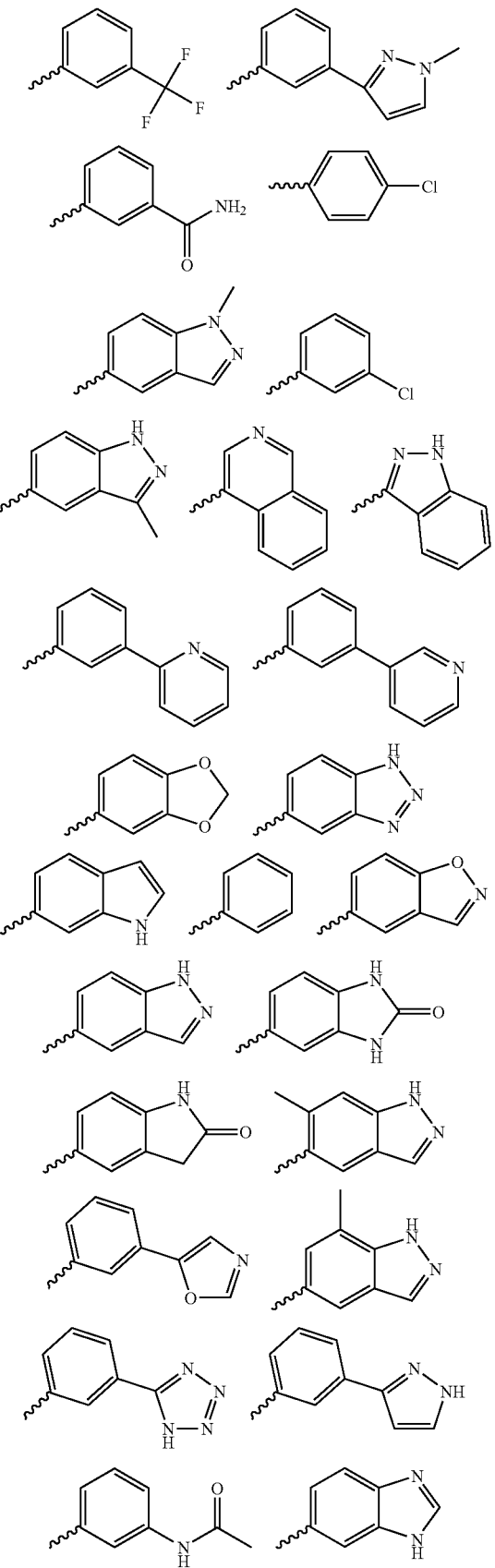

-continued
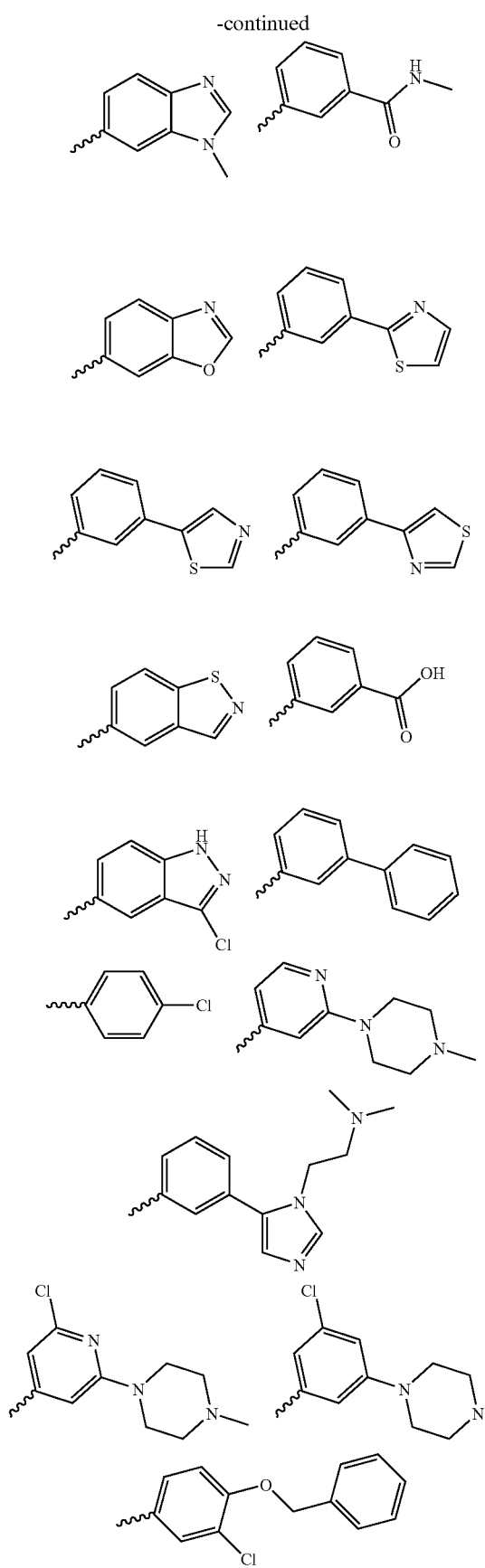
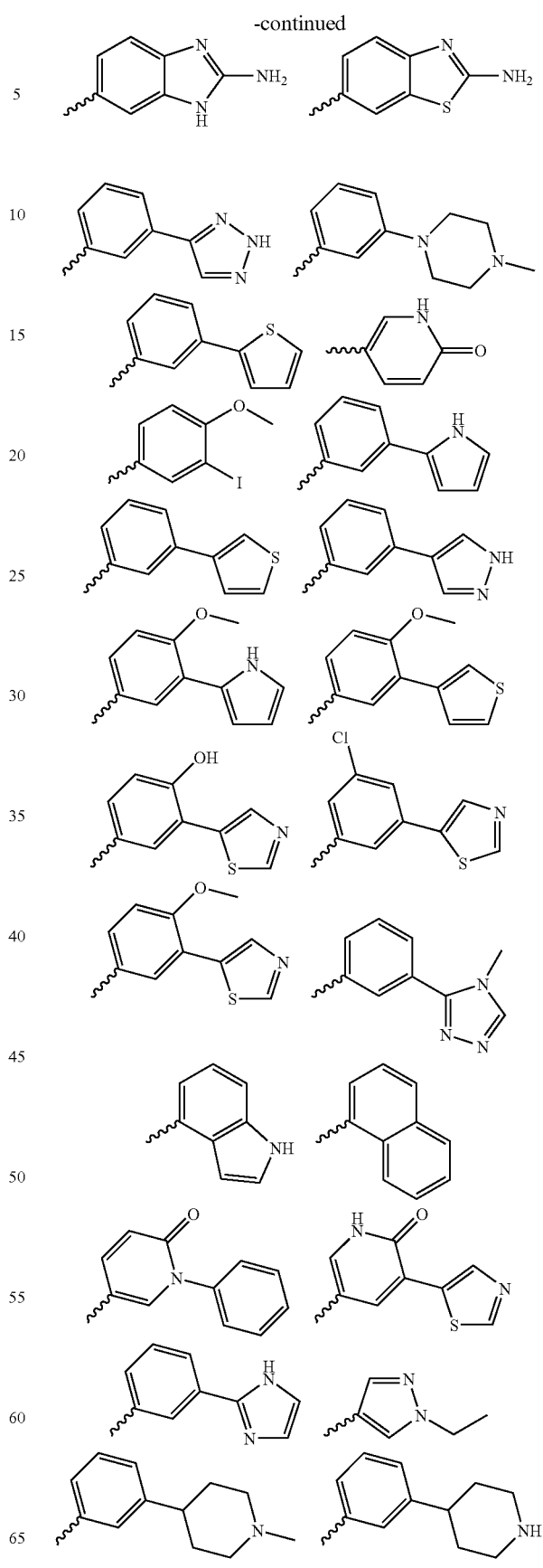

-continued

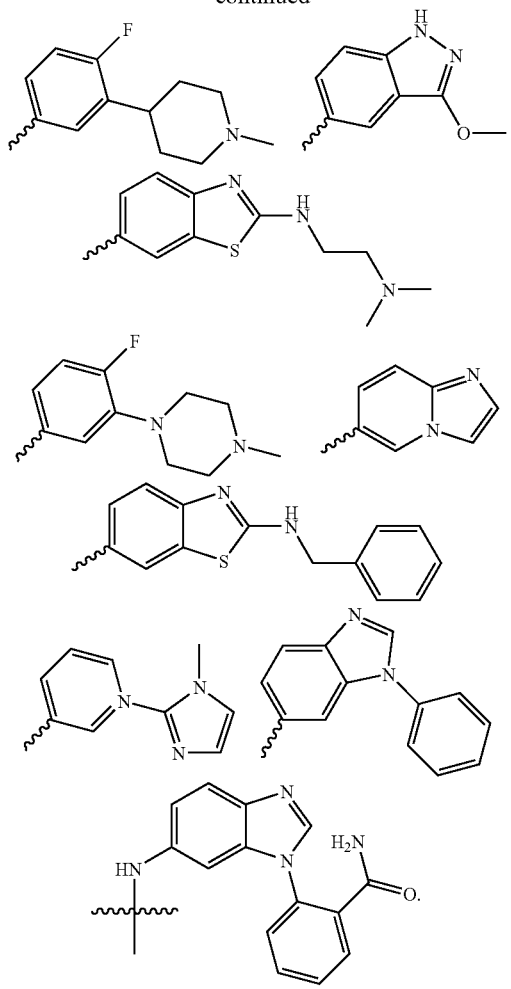

12. A compound represented by Formula I:

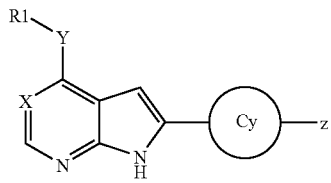

or a pharmaceutically acceptable salt thereof, wherein
X is C—CN;
Cy is

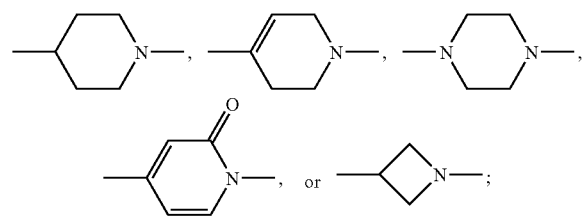

Y is —C($C_{0-6}$alkyl)($C_{0-6}$alkyl)-, —N($C_{0-6}$alkyl)-, —N($C_{0-6}$ alkyl)-$C_{1-6}$alkyl-, O, S, >N—$C_{2-6}$alkyl-N—($C_{0-6}$alkyl)($C_{0-6}$alkyl), >N—$C_{2-6}$alkyl-O—$C_{0-6}$alkyl, >N—$C_{1-6}$ alkyl-C(O)—NH—$C_{0-6}$alkyl, or >N—$C_{2-6}$ alkyl-N—C(O)—$C_{1-6}$alkyl; and R1 is aryl, hetaryl, or heterocyclyl, optionally substituted with 1-6 independent halo, —CN, —OH, —$C_{0-6}$alkyl, —$C_{3-10}$cycloalkyl, -halo$C_{1-6}$alkyl, —$C_{2-6}$alkynyl, —N($C_{0-6}$alkyl)($C_{0-6}$alkyl), —C(O)—$C_{0-6}$alkyl-N($C_{0-6}$alkyl)($C_{0-6}$alkyl), —C(O)—$C_{0-6}$alkyl-(heterocyclyl), —$C_{1-6}$alkyl-C(O)—$C_{0-6}$alkyl-N($C_{0-6}$alkyl)($C_{0-6}$alkyl), —O—$C_{0-6}$alkyl-(heterocyclyl), —$C_{0-6}$alkyl-O—$C_{0-6}$alkyl, —$C_{0-6}$alkyl-N($C_{0-6}$alkyl)($C_{0-6}$alkyl), —O—$C_{0-6}$alkyl-(hetaryl), —S(O)$_2$—N($C_{0-6}$alkyl)($C_{0-6}$alkyl), aryl, hetaryl, or heterocyclyl substituents, or substituted with an oxo (=O) using a bond from the aryl, hetaryl, or heterocyclyl ring, wherein any of the substituents optionally is substituted with 1-6 independent halo, CN, OH, —$C_{0-6}$alkyl-O—$C_{0-6}$alkyl, —$C_{0-6}$alkyl-N($C_{0-6}$alkyl)($C_{0-6}$alkyl), —C(O)—$C_{0-6}$alkyl-N($C_{0-6}$alkyl)($C_{0-6}$alkyl), —C(O)—$C_{0-6}$alkyl-(heterocyclyl), or $C_{0-6}$alkyl;

wherein z is selected from the following table:

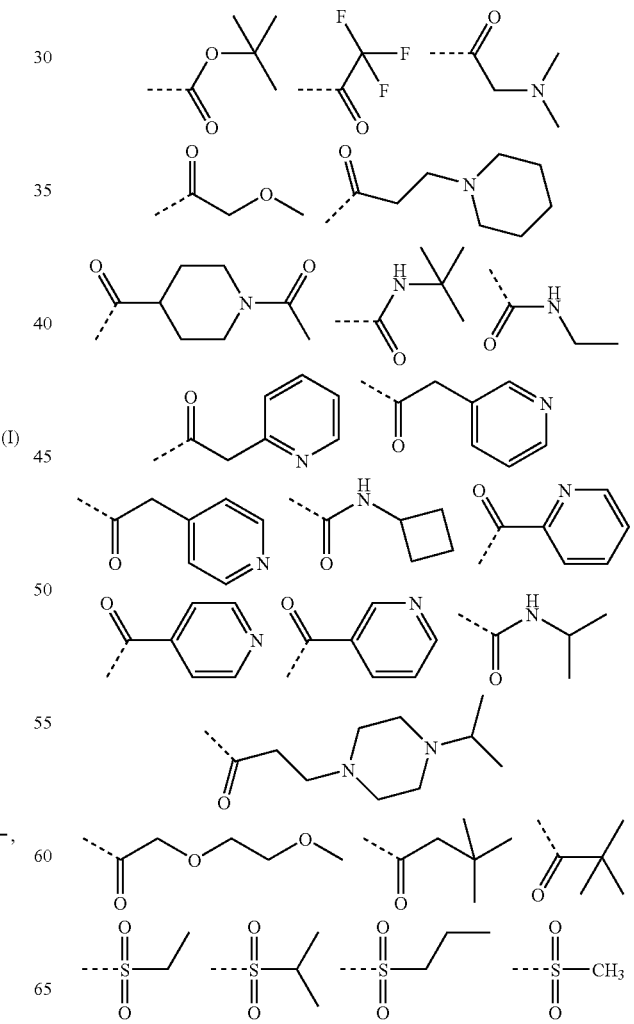

-continued
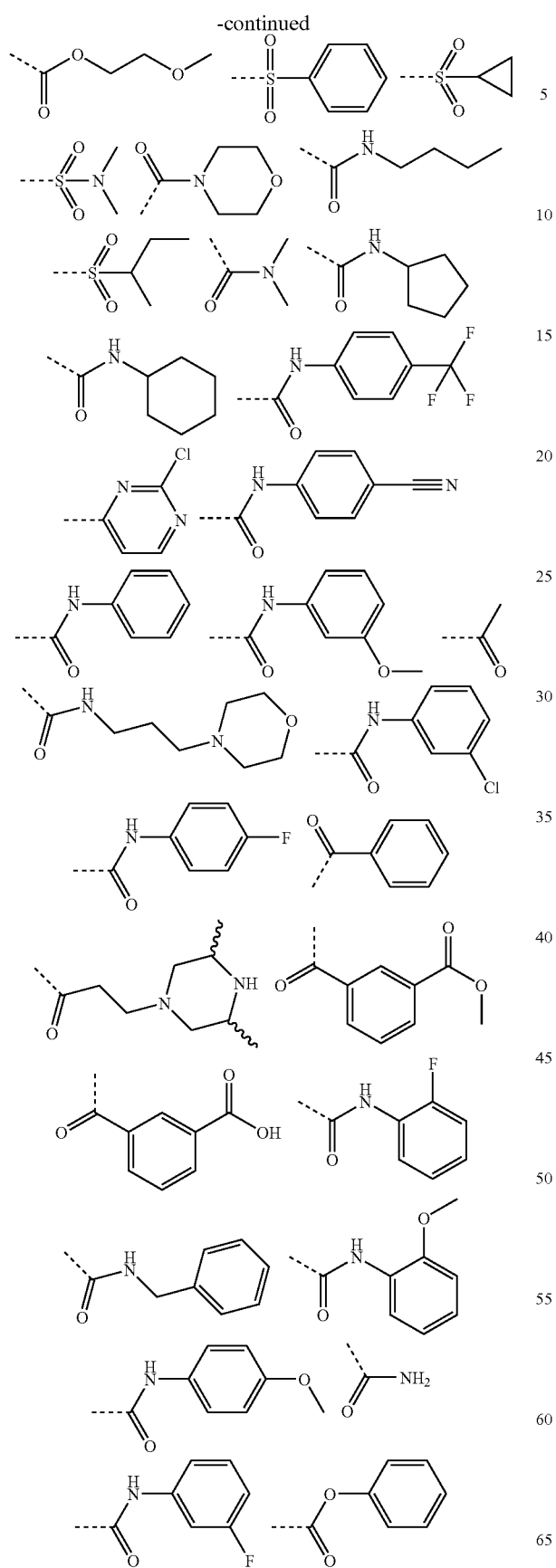
-continued
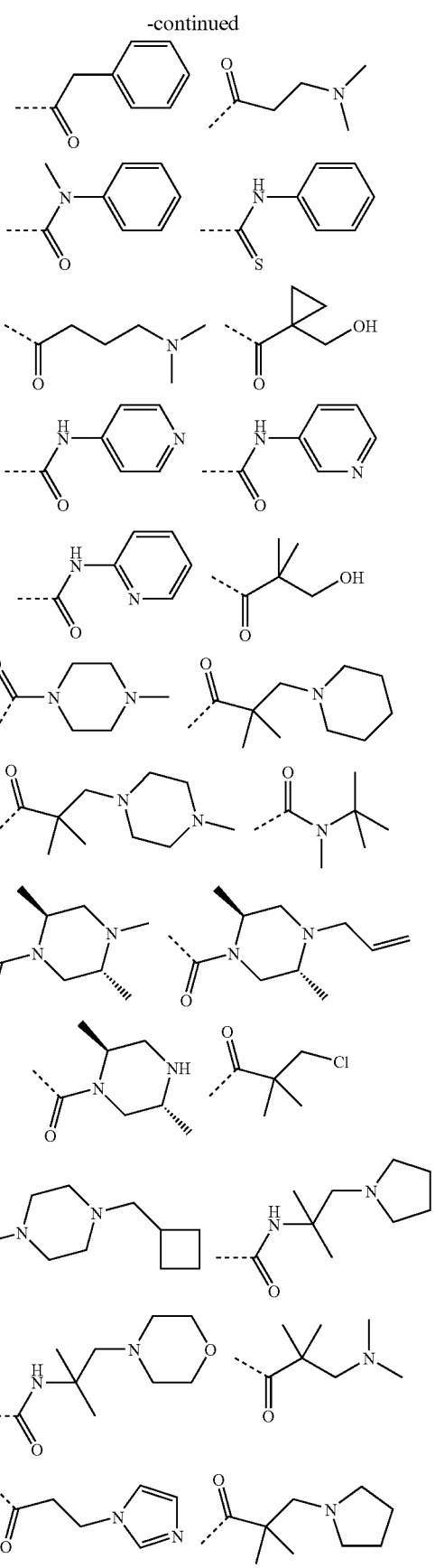

-continued
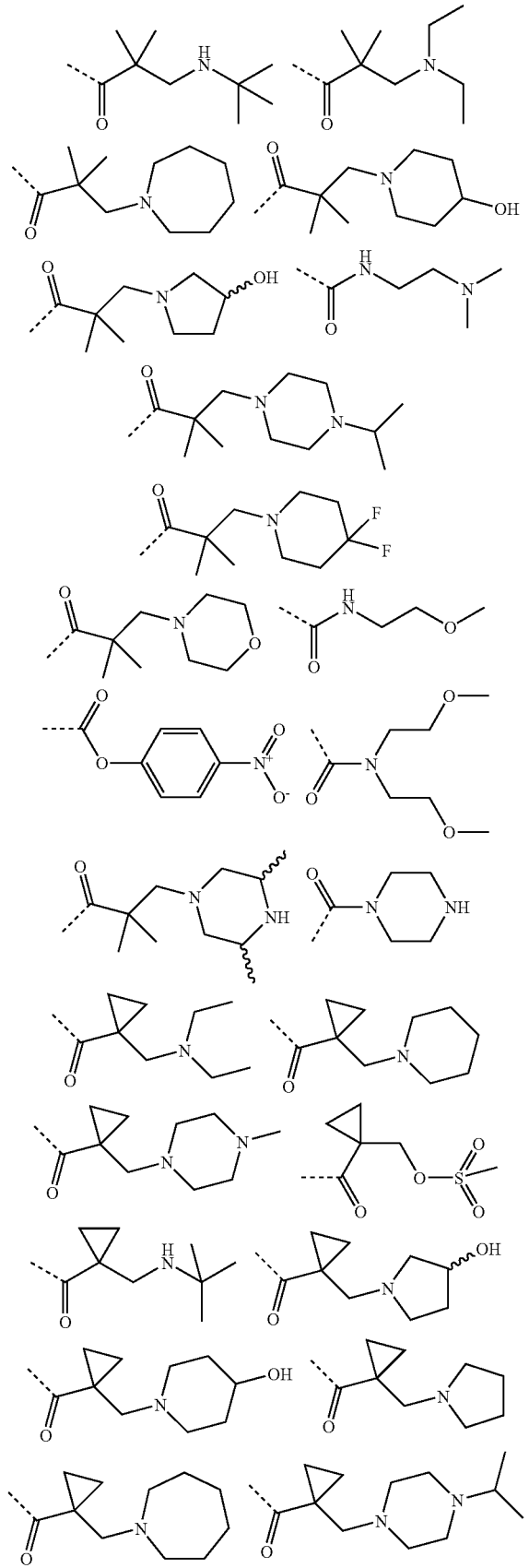
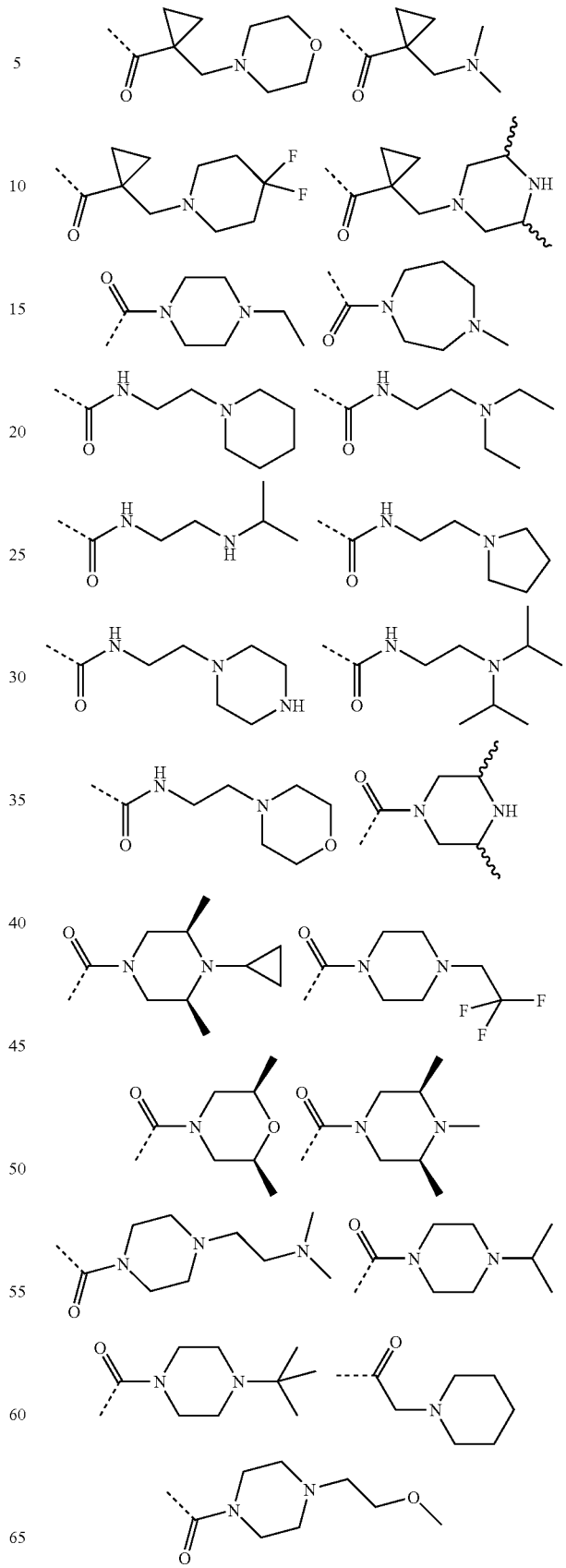

313
-continued
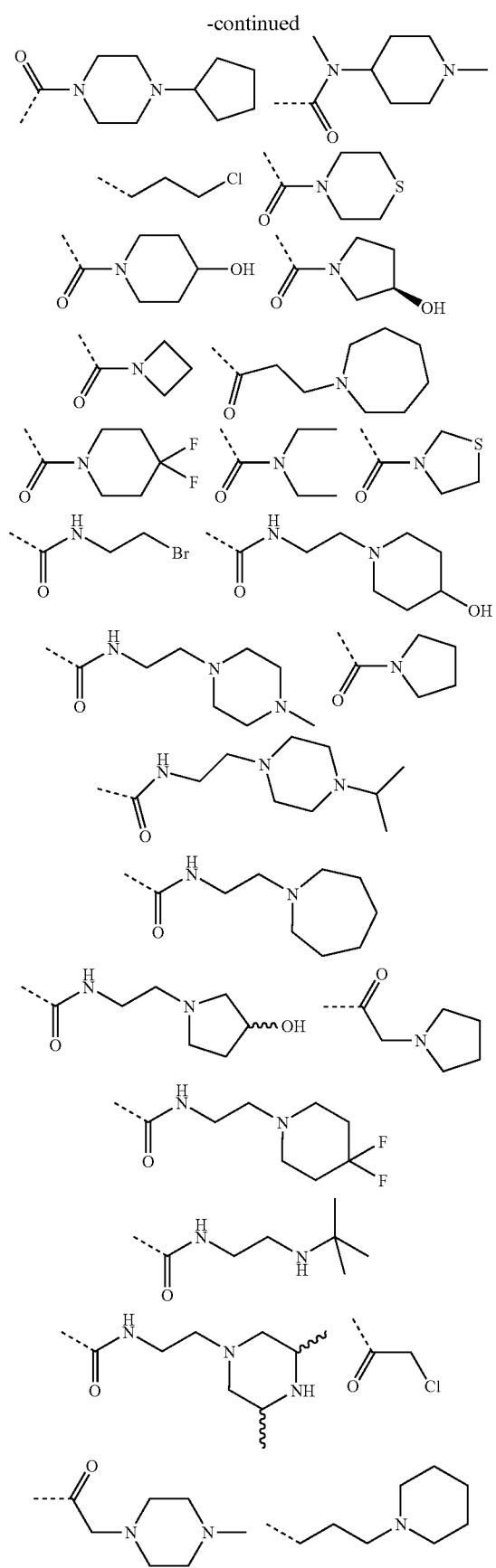
314
-continued
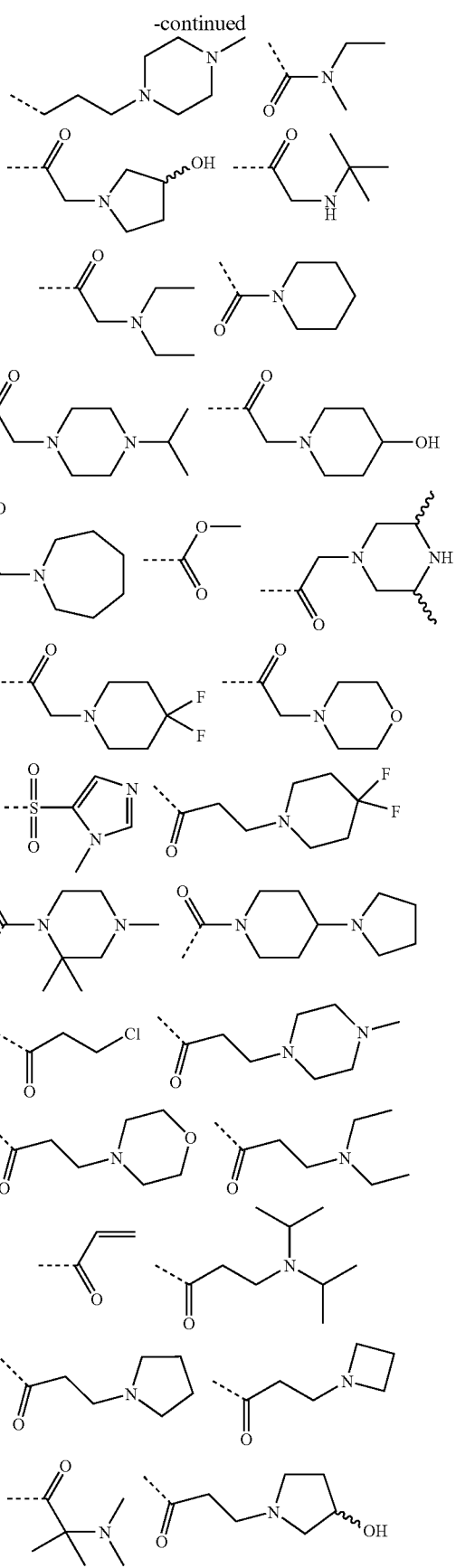

-continued
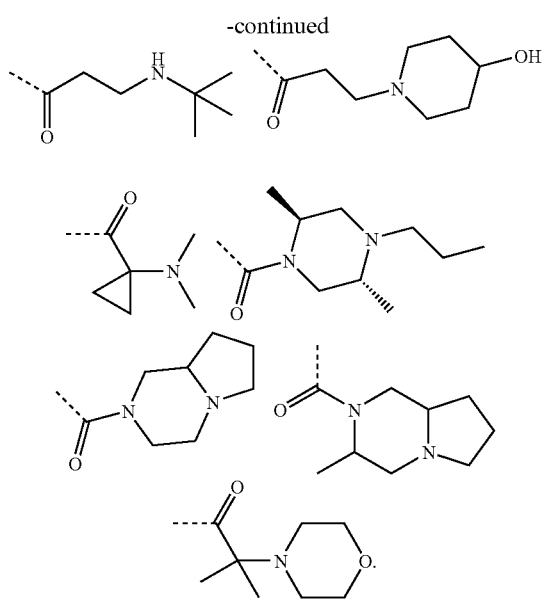
13. The compound according to claim 1 or a pharmaceutically acceptable salt thereof, wherein Y—R1 is
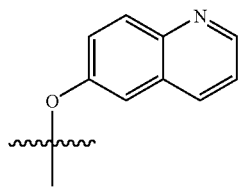
14. A pharmaceutical composition comprising a compound according to claim 1 or a pharmaceutically acceptable salt thereof and a pharmaceutically acceptable carrier.
* * * * *